United States Patent [19]
Akhtar et al.

[11] Patent Number: 6,057,156
[45] Date of Patent: May 2, 2000

[54] ENZYMATIC NUCLEIC ACID TREATMENT OF DISEASES OR CONDITIONS RELATED TO LEVELS OF EPIDERMAL GROWTH FACTOR RECEPTORS

[75] Inventors: Saghir Akhtar, Birmingham; Patricia Fell, Wythall, both of United Kingdom; James A. McSwiggen, Boulder, Colo.

[73] Assignee: Robozyme Pharmaceuticals, Inc., Boulder, Colo.

[21] Appl. No.: 08/985,162

[22] Filed: Dec. 4, 1997

Related U.S. Application Data

[60] Provisional application No. 60/036,476, Jan. 31, 1997.

[51] Int. Cl.[7] ............................. C12Q 1/68; C12N 15/85; C12N 15/63; C07H 21/04
[52] U.S. Cl. ........................... 435/366; 435/6; 435/320.1; 435/325; 536/23.1; 536/24.5
[58] Field of Search ........................... 435/6, 320.1, 325, 435/366; 536/23.1, 24.5

[56] References Cited

U.S. PATENT DOCUMENTS

| | | | |
|---|---|---|---|
| 4,987,071 | 1/1991 | Cech et al. | 435/91 |
| 5,334,711 | 8/1994 | Sproat et al. | 536/24.5 |
| 5,525,468 | 6/1996 | McSwiggen | 435/6 |

FOREIGN PATENT DOCUMENTS

| | | |
|---|---|---|
| 2012312 | 9/1990 | Canada . |
| 0 360 257 A2 | 3/1990 | European Pat. Off. . |
| 0 387 775 | 9/1990 | European Pat. Off. . |
| 91/03162 | 3/1991 | WIPO . |
| 91/15580 | 10/1991 | WIPO . |
| 92/07065 | 4/1992 | WIPO . |
| 93/15187 | 8/1993 | WIPO . |
| 93/23057 | 11/1993 | WIPO . |
| 93/23569 | 11/1993 | WIPO . |
| 94/02595 | 2/1994 | WIPO . |
| 94/11499 | 5/1994 | WIPO . |
| 94/16738 | 8/1994 | WIPO . |
| 95/04818 | 2/1995 | WIPO . |
| 96/22689 | 8/1996 | WIPO . |

OTHER PUBLICATIONS

Aurup et al., "Chapter 10: Stabilized RNA Analogs for Antisense and Ribozyme Applications," *Delivery Strategies for Antisense Oligonucleotide Therapeutics*, 161–177 (1995).
Ayers et al., "Polyacrylic acid mediated ocular delivery of ribozymes," *Journal of Controlled Release*, 38:167–175 (1996).
Bacchetti et al., "Telomerers and Telomerase in Human Cancer (Review)," *International Journal of Oncology* 7:423–432 (1995).
Barinaga, "Ribozymes: Killing the Messenger," *Science*, 262:1512–1514 (1993).
Bassi et al., "Ionic interactions and the global conformations of the hammerhead ribozyme," *Nature Structural Biol.*, 2(1):45–55 (1995).
Beck, et al, (1996).
Beck, et al., (1997).
Beigelman et al., "Alternate Approaches to the Synthesis of 2'–O–Me Nucleosides," *Nucleosides and Nucleotides*, 14(3–5):421–425 (1995).
Beigelman et al., "Chemical Modification of Hammerhead Ribozynes," *Journal of Biological Chemistry*, 270(43):25702–25708 (1995).
Beigelman et al., "Synthesis of 1–Deoxy–D–Ribofuranose Phosphoramidite & the Incorporation of Abasic Nucleotides in Stem–Loop II of A Hammerhead Ribozyme," *Biorg. Med. Chem. Lett.* 4(14):1715–1720 (1994).
Beigelman et al., "Synthesis of 2'–modified nucleotides and their incorporation into hammerhead ribozymes," *Nucleic Acids Research*, 23(21):4434–4442 (1995).
Beltinger et al., "Binding, Uptake, and Intracellular Trafficking of Phosphorothioate–modified Oligodeoxynucleotides," *J. Clin. Invest.*, 95:1814–1823 (1995).
Bertrand et al., "Anti–HIV Therapeutic Hammerhead Ribozymes: Targeting Strategies and Optimization of Intracellular Function," *Nucleic Acids and Molecular Biology* 10:301–313 (1996).
Bertrand et al., "Can hammerhead ribozymes be efficient tools to inactivate gene function?" *Nucleic Acids Research* 22(3):293–300 (1994).
Bertrand et al., "Facilitation of hammerhead ribozyme catalysis by the nucleocapsid protein of HIV–1 and the heterogeneous nuclear ribonucleoprotein A1," *EMBO Journal*, 13(12):2904–2912 (1994).
Bigner et al., "Cytogenetics and Molecular Genetics of Malignant Gliomas and Medulloblastoma," *Brain Pathol.*, 1:12–18 (1990).
Black et al., "Brain Tumors," *New England Journal of Medicine* 324(21):1471–1476 & (22):1555–1564 (1991).
Blackburn et al., (1990).
Bratty et al., "The Hammerhead RNA Domain, a Model Ribozyme," *Biochimica et Biophysica Acta.* 1216:345–359 (1993).
Brem, et al., "Interstitial chemotherapy with drug polymer implants for the treatment of recurrent gliomas," *Journal of Neurosurgery*, 74:441–446 (1991).
Bruner, "Neuropathology of Malignant Gliomas," *Seminars in Oncology*, 21(2):126–138 (1994).
Cech et al., "Biological Catalysis By RNA," *Annual Review of Biochemistry*, 55:599–629 (1986).
Cech et al., "Hammerhead Nailed Down," *Nature*, 372:39–40 (1994).
Cech et al., "In Vitro Splicing of the Ribosomal RNA Precursor of Tetrahymena: Involvement of a Guanosine Nucleotide in the Excision of the Intervening Sequence," *Cell*, 27:487–496 (1981).
Cech, "Ribozymes and Their Medical Implications," *JAMA* 260(20):3030–3034 (1988).
Chadeneau et al., "Telomerase Activity in Normal and Malignant Murine Tissues," *Oncogene* 11:893–898 (1995).

(List continued on next page.)

*Primary Examiner*—Nancy Degen
*Assistant Examiner*—Andrew Wang
*Attorney, Agent, or Firm*—Lyon & Lyon LLP

[57] ABSTRACT

Enzymatic nucleic acid molecules which cleave EGFR RNA.

44 Claims, 12 Drawing Sheets

OTHER PUBLICATIONS

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20(17):4581–4589 (1992).

Chen et al., "Effects on Tumor Cells of Ribozymes that Cleave the RNA Transcripts of Human Papillomavirus Type 18," *Cancer Gene Therapy* 3(1):18–23 (1996).

Chowrira et al., "Extensive Phosphorothioate Substitution Yields Highly Active and Nuclease–Resistant Hairpin Ribozymes," *Nucleic Acids Research* 20(11):2835–2840 (1992).

Chowrira et al., "In Vitro and in Vivo Comparison of Hammerhead, Hairpin, and Hepatitis Delta Virus Self–Processing Ribozyme Cassettes," *J. Biol. Chem.* 269(41):25856–25864 (1994).

Christoffersen and Marr, "Ribozymes as Human Therapeutic Agents," *J. Med. Chem.* 38(12):2023–2037 (1995).

Christoffersen et al., "Application of Computational Technologies to Ribozyme Biotechnology Products," *Journal of Molecular Structure (Theochem)* 311:273–284 (1994).

Collins et al., "Reaction Conditions and Kinetics of Self–Cleavage of a Ribozyme Derived From Neurospora VS RNA," *Biochemistry* 32:2795–2799 (1993).

Couture and Stinchcomb, "Anti–gene Therapy: the Use of Ribozymes to Inhibit Gene Function," *TIG*, 12(12):510 (1996).

Crooke, "Therapeutic Applications of Oligonucleotides," *Annual Review of Pharmacology and Toxicology*, 32:329–379 (1992).

Denman, "Biocomputing: Using RNAFOLD to Predict the Activity of Small Catalytic RNAs," *BioTechniques*, 15(6):1090–1094 (1993).

Denman, "Facilitator Oligonucleotides Increase Ribozyme RNA binding to full–length RNA Substrates in vitro," *FEBS Letters* 382:116–120 (1996).

Downward, "Close similarity of Epidermal Growth Factor Receptor and v–erb–B Oncogene Protein Sequences," *Nature* 307(5951):521–527 (1984).

Dreyfus, "Restriction Ribozymes?" *Einstein Quarterly Journal of Biology and Medicine* 6(2):92–93 (1988).

Dropulic et al., "Functional Characterization of a U5 Ribozyme: Intracellular Suppression of Human Immunodeficiency Virus Type I Expression," *Journal of Virology* 66(3):1432–1441 (1992).

Dropulic et al., "Meeting Report–Ribozymes: Use as Anti–HIV Therapeutic Molecules," *Antisense Research and Development*, 3:87–94 (1993).

Eckstein, "Nucleoside Phoshorothioates," *Annual Review of Biochemistry* 54:367–402 (1985).

Ekstrand et al., "Genes for Epidermal Growth Factor Receptor, Transforming Growth Factor α, and Epidermal Growth Factor and Their Expression in Human Gliomas in Vivo," *Cancer Research* 51:2164–2172 (1991).

Elkins et al., "Cellular Delivery of Ribozymes," *Delivery Strategies for Antisense Oligonucleotide Therapeutics*, London, CRC Press, 17–37 (1995).

Ellis et al., "Design and Specificity of Hammerhead Ribozymes Against Calretinin mRNA," *Nucleic Acids Research* 21(22):5171–5178 (1993).

Elroy–Stein et al., "Cytoplasmic Expression System Based on Constitutive Synthesis of Bacteriophage T7 RNA Polymerase in Mammalian Cells," *Proc. Natl. Acad. Sci. USA* 87:6743–6747 (1990).

Fedor et al., "Kinetics of Intermolecular Cleavage by Hammerhead Ribozymes," *Biochemistry* 31:12042–12054 (1992).

Fedor et al., "Substrate sequence effects on "hammerhead" RNA catalytic efficiency," *Proc. Natl. Acad. Sci. USA* 87:1668–1672 (1990).

Feldstein et al., "Two Sequences Participating in the Autolytic Processing of Satellite Tobacco Ringspot Virus Complementary RNA," *Gene* 82:53–61 (1989).

Felgner et al., "Enhanced Gene Delivery and Mechanism Studies with a Novel Series of Cationic Lipid Formulations," *Journal of Biological Chemistry* 269(4):2550–2561 (1994).

Feng et al., "The RNA Component of Human Telomerase," *Science* 269:1236–1241 (1995).

Fine, et al., "Meta–Analysis of Radiation Therapy with and without Adjuvant Chemotherapy for Malignant Gliomas in Adults," *Cancer*, 71(8):2585–2597, (1993).

Flory et al., "Nuclease–resistant ribozymes decrease stromelysin mRNA levels in rabbit synovium following exogenous delivery to the knee joint," *Proc. Natl. Acad. Sci. USA*, 93:754–758 (1996).

Forster and Altman, "External Guide Sequences for an RNA Enzyme," *Science* 249:783–786 (1990).

Forster et al., "Self–cleavage of Plus and Minus RNAs of a Virusoid and a Structural Model for the Active Sites," *Cell* 49:211–220 (1987).

Fu et al., "Importance of specific purine amino and hydroxyl groups for efficient cleavage by a hammerhead ribozyme," *Proc. Natl. Acad Sci. USA*, 89:3985–3989 (1992).

Gait et al., "Synthetic Ribonucleotide Analogues for RNA Structure–Function Studies," *Nucleosides and Nucleotides* 14(3–5):1133–1144 (1995).

Gao et al., "Ctyoplasmic Expression of a Receptor Gene by Co–Delivery of T7 RNA Polymerase and T7 Promoter Sequence with Cationic Liposomes," *Nucleic Acids Research* 21(12):2867–2872 (1993).

Gish et al., "Phosphorothioates in Molecular Biology," *Trends in Biochemical Sciences* 14:97–100 (1989).

Goodarzi, et al., "Binding of Oligonucleotides to Cell Membranes at Acidic pH," *Biochem. Biophys. Res. Comm.* 181(3):1343–1351, (1991).

Goodchild et al., "Enhancement of Ribozyme Catalytic Activity by a Contiguous Oligodeoxynucleotide (Facilitator) and By 2'–O–Methylation," *Nucleic Acids Research*, 20(17):4607–4612 (1990).

Griffin, Jr., et al., "Group II Intron Ribozymes that Cleave DNA and RNA Linkages with Similar Efficiency, and Lack Contacts with Substrate 2'–Hydroxyl Groups," *Chemistry & Biology* 2(11):761–770 (1995).

Griffiths et al., "Stereospecificity of Nucleases Towards Phosphorothioate–Substituted RNA: Stereochemistry of Transcription by T7 RNA Polymerase," *Nucleic Acids Research* 15(10):4145–4162 (1987).

Guerrier–Takada et al., "The RNA Moiety of Ribonuclease P Is the Catalytic Subunit of the Enzyme," *Cell* 35:849–857 (1983).

Guo et al., "Efficient Trans–Cleavage of a Stem–Loop RNA Substrate by a Ribozyme Derived from Neurospora VS RNA," *EMBO J.* 14(2):368–376 (1995).

Gutierrez et al, "Gene Therapy for Cancer," *The Lancet* 339:715–719 (1992).

Hampel et al., "'Hairpin' Catalytic RNA Model: Evidence for Helices and Sequence Requirement for Substrate RNA," *Nucleic Acids Research* 18(2):299–304 (1990).

Hampel et al., "RNA Catalytic Properties of the Minimum (−)sTRSV Sequence," *Biochemistry* 28:4929–4933 (1989).

Haseloff et al., "Sequences Required for Self–Catalysed Cleavage of the Satellite RNA of Tobacco Ringspot Virus," *Gene* 82:43–52 (1989).

Haseloff et al., "Simple RNA Enzymes with New and Highly Specific Endoribonuclease Activities," *Nature* 334:585–591 (1988).

Healy, "Telomere Dynamics and Telomerase Activation in Tumor Progression: Prospects for Prognosis and Therapy," *Oncology Research* 7(3/4):121–130 (1995).

Heidenreich et al., "Chemically Modified RNA: Approaches and Applications," *FASEB Journal* 7(1):90–96 (1993).

Heidenreich et al., "High Activity and Stability of Hammerhead Ribozymes Containing 2'–Modified Pyrimidine Nucleosides and Phosphorothioates," *Journal of Biological Chemistry* 269(3):2131–2138 (1994).

Hendry et al., "A Comparison of the in vitro activity of DNA–Armed and all–RNA Hammerhead Ribozymes," *Nucleic Acids Research* 23(19):3928–3936 (1995).

Herschlag et al., "An RNA chaperone activity of non–specific RNA binding proteins in hammerheads ribozymes catalysis," *EMBO Journal* 13(12):2913–2924 (1994).

Hertel et al., "Numbering System for the Hammerhead," *Nucleic Acids Research* 20(12):3252 (1992).

Hertel et al., "A Kinetic and Thermodynamic Framework for the Hammerhead Ribozyme Reaction," *Biochemistry* 33(11):3374–3385 (1994).

Homann et al., "Extension of helix II of an HIV–1–directed hammerhead ribozyme with long antisense flanks does not alter kinetic parameters in vitro but causes loss of the inhibitory potential in living cells," *Nucleic Acids Research* 22(19):3951–3957 (1994).

Inoue, T., "Time to Change Partners," *Nature* 370:99–100 (1994).

Izant et al., "Constitutive and Conditional Suppression of Exogenous and Endogenous Genes by Anti–Sense RNA," *Science* 229:345–352 (1985).

Jaeger et al., "Improved Predictions of Secondary Structures for RNA," *Proc. Natl. Acad. Sci. USA* 86:7706–7710 (1989).

Jaroszewski et al., (1990).

Jarvis et al., "Inhibition of Vascular Smooth Muscle Cell proliferation by Ribozymes that Cleave c–myb mRNA," *RNA* 2:419–428 (1996).

Jeffries et al., "A Catalytic 13–mer Ribozyme," *Nucleic Acids Research* 17(4):1371–1377 (1989).

Juliano et al., "Liposomes as a Drug Delivery System for Antisense Oligonucleotides," *Antisense Research and Development* 2:165–176 (1992).

Kanazawa et al., "Hammerhead Ribozyme–Mediated Inhibition of Telomerase Activity in Extracts of Human Hepatocellular Carcinoma Cells," *Biochemical and Biophysical Research Communication* 225:570–576 (1996).

Kariko et al., "Lipofectin–aided Cell Delivery of Ribozyme Targeted to Human Urokinase Receptor mRNA," *FEBS Letters* 352:41–44 (1994).

Kashani–Sabet et al., "Reversal of the Malignant Phenotype by an Anti–ras Ribozyme," *Antisense Research & Development* 2:3–15 (1992).

Khazaie et al., "EGF Receptor in Neoplasia and Metastasis," *Cancer and Metastasis Reviews*, 12:255–274 (1993).

Kiehntopf et al., "Clinical Applications of Ribozymes," *The Lancet* 345:1027–1031 (1995).

Kiehntopf et al., "Ribozyme–Mediated Cleavage of the MDR–1 Transcript Restores Chemosensitivity in Previously Resistant Cancer Cells," *EMBO Journal* 13(19):4645–4652 (1994).

Kiehntopf et al., "Ribozymes: Biology, Biochemistry, and Implications for Clinical Medicine," *Journal of Molecular Medicine* 73:65–71 (1995).

Kim et al., "Three–dimensional Model of the Active Site of the Self–Splicing rRNA Precursor of Tetrahymena," *Proc. Natl. Acad. Sci. USA* 84:8788–8792 (1987).

Kim et al., "Specific Association of Human Telomerase Activity with Immortal Cells and Cancer," *Science* 266:2011–2015 (1994).

Kisich et al., "Inhibition of TNF–α Secretion by Murine Macrophages Folowing In Vivo and In Vitro Ribozyme Treatment," *Journal of Cellular Biochemistry* 328(19a):221 (1995).

Koizumi et al., "Inhibition of c–Ha–ras Gene Expression by Hammerhead Ribozymes Containing a Stable C(UUCG)G Hairpin Loop," *Biol. Pharm. Bull.*, 16(9):879–883 (1993).

Kornblith, et al., "The Future of Therapy for Glioblastoma," *Surg. Neurol.* 39:538–543, (1993).

Kumar et al., "Mechanistic Studies on Hammerhead Ribozymes," *Nucleic Acids and Molecular Biology* 10:217–230 (1996).

Kung et al., "Structural Basis of Oncogenic Activation of Epidermal Growth Factor Receptor," *Biochemical And Molecular Aspects of Selected Cancers* 2:19–45 (1994).

Lamond et al., "Antisense Oligonucleotides Made of 2'–O–alkyl1RNA: their Properties and Applications in RNA Biochemistry," *FEBS Letters* 325(1,2):123–127 (1993).

Lange et al., "In Vitro and In Vivo Effects of Synthetic Ribozymes Targeted against BCR/ABL mRNA," *Leukemia* 7(11):1786–1794 (1994).

Leopold et al., "Multi–Unit Ribozyme–Mediated Cleavage of bcr–abl mRNA in Myeloid Leukemias," *Blood* 85(8):2162–2170 (1995).

Lesser et al., "The Chemotherapy of High Grade Astocytomas," *Seminars in Oncology* 21(2):220–235 (1994).

Lewis et al., "Biodegradable Polymer Devices for the Sustained Exogenous Delivery of Ribozymes," *Journal of Cellular Biochemistry* 328(19a):227 (1995).

L'Huillier et al., "Cytoplasmic Delivery of Ribozymes Leads to Efficient Reduction in α–Lactalbumin mRNA Levels in C1271 Mouse Cells," *EMBO J.* 11(12):4411–4418 (1992).

L'Huillier et al., "Efficacy of Hammerhead Ribozymes Targeting α–Lactalbumin Transcripts: Experiments in Cells and Transgenic Mice," *Nucleic Acids and Molecular Biology* 10:283–299 (1996).

Li and Altman, "Cleavage by RNase P of gene N mRNA reduces bacteriophage λ burst size," *Nucleic Acids Research* 24(5):835–842 (1996).

Liebel et al., "Contemporary Approaches to the Treatment of Malignant Gliomas with Radiation Therapy," *Seminars in Oncology*, 21(2):198–219 (1994).

Lieber et al., "Stable High–Level Gene Expression in Mammalian Cells by T7 Phage RNA Polymerase," *Methods Enzymol.* 217:47–66 (1993).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Loke, et al., "Characterization of Oligonucleotide Transport into Living Cells," *Proceedings of the National Academy of Sciences, USA,* 86:3474–3478, (1989).

Lyngstadaas et al., "A Synthetic, Chemically Modified Ribozyme Eliminates Amelogenin, the Major Translation Product in Developing Mouse Enamel In Vivo," *EMBO Journal* 14(21):5224–5229 (1995).

Marschall et al., "Inhibition of Gene Expression with Ribozymes," *Cellular and Molecular Neurobiology* 14(5):523–538 (1994).

Marschall et al., "Phosphorodithioate DNA as a Potential Therapeutic Drug," *Science* 259:1564–1569 (1993).

Martuza, "Experimental Therapy of Human Glioma by Means of a Genetically Engineered Virus Mutant," *Science* 252:854–855 (1991).

McGarry et al., "Inhibition of Heat Shock Protein Synthesis by Heat–Inducible Antisense RNA," *Proc. Natl. Acad. Sci. USA* 83:399–403 (1986).

Michels and Pyle, "Conversion of a Group II Intron into a New Multiple–Turnover Ribozyme that Selectively Cleaves Oligonucleotides: Elucidation of Reaction Mechanism and Structure/Function Relationships," *Biochemistry* 34:2965–2977 (1995).

Miller et al., "A Satellite RNA of Barley Yellow Dwarf Virus Contains a Novel Hammerhead Structure in the Self–Cleavage Domain," *Virology* 183:711–720 (1991).

Milligan et al., "Synthesis of Small RNAs Using T7 RNA Polymerase," *Methods Enzymol.* 180:51–62 (1989).

Milligan et al., "Current Concepts in Antisense Drug Design," *Journal of Medicinal Chemistry* 36(14):1923–1937 (1993).

Modjtahedi et al., *International Journal of Cancer,* 4:277–296 (1994).

Morvan et al., "Modified Oligonucleotides: IV Solid Phase Synthesis and Preliminary Evaluation of Phosphorothioate RNA as Potential Antisense Agents." *Tetrahedron Letters* 31(49):7149–7152 (1990).

Ohkawa et al., "Activities of HIV–RNA Targeted Ribozymes Transcribed From a 'Shot–Gun' Type Ribozyme–Trimming Plasmid," *Nucleic Acids Symp. Ser.* 27:15–16 (1992).

Ohkawa et al., "Ribozymes: From Mechanistic Studies to Applications In Vivo," *Journal of Biochemistry* 118:251–258 (1995).

Ojwang et al., "Inhibition of Human Immunodeficiency Virus Type 1 Expression by a Hairpin Ribozyme," *Proc. Natl. Acad. Sci. USA* 89:10802–10806 (1992).

Olsen et al., "Study of Hammerhead Ribozyme Containing 2'–Modified Adenosine Residues," *Biochemistry* 30:9735–9741 (1991).

Ostrowski et al., "Genetic Alterations and Gene Expression In Human Malignant Glioma," *Biochemical and Molecular Aspects of Selected Cancers* 2:143–168 (1994).

Paolella et al., "Nuclease resistant ribozymes with high catalytic activity," *EMBO Journal* 11(5):1913–1919 (1992).

Perreault et al., "Mixed Deoxyribo– and Ribo–Oligonucleotides with Catalytic Activity," *Nature* 344:565–567 (1990).

Perriman et al., "Effective Ribozyme Delivery in Plant Cells (Abstract)," *Proc. Natl. Acad. Sci. USA* 92:6175–79 (1995).

Perriman et al., "Extended Target–Site Specifically for a Hammerhead Ribozyme," *Gene* 113:157–163 (1992).

Perrotta et al., "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Pley et al., Three Dimensional Structure of a Hammerhead Ribozyme *Nature* 372:68–74 (1994).

Ponten, et al., "Long Term Culture of Normal and Neoplastic Human GLIA," *Acta Path. Microbiol. Scandinav.,* 74:465–486 (1968).

Puttaraju et al., "A Circular Trans–Acting Hepatitis Delta Virus Ribozyme," *Nucleic Acids Research* 21(18):4253–4258 (1993).

Rawls, "Ribozymes Move Closer to Applications for AIDS Therapy," *Chemical and Engineering News* 74(5):26–28 (1996).

Reddy, "Antisense Oligonucleotides: A New Class of Potential Anti–AIDS and Anticancer Drugs," *Drugs of Today* 32(2):113–137 (1996).

Rhyu, "Telomeres, Telomerase, and Immortality," *Journal of the National Cancer Institute* 87(12):884–894 (1995).

Ringertz, "Grading of Gliomas," *Acta. Pathol. Microbiol. Scand.,* 27:51–64, (1950).

Rossi et al., "Ribozymes as Anti–HIV–1 Therapeutic Agents: Principles, Applications, and Problems," *AIDS Research and Human Retroviruses* 8(2):183–189 (1992).

Rossi, "Controlled, Targeted, Intracellular Expression of Ribozymes: Progress and Problems," *TIBTECH* 13:301–305 (1995).

Rossi, "Making Ribozymes Work in Cells," *Current Biology* 4(5):469–471 (1994).

Ruffner et al., "Sequence Requirements of the Hammerhead RNA Self–Cleavage Reaction," *Biochemistry* 29:10695–10702 (1990).

Ruffner et al., "Thiophosphate Interference Experiments Locate Phosphates Important for the Hammerhead RNA Self–Cleavage Reaction," *Nucleic Acids Research* 18(20):6025–6029 (1990).

Sambrook, *Molecular Cloning: A Laboratory Manual,* Second Edition, vols. 1,2 & 3. Cold Springs Harbor, Laboratory Press (1989).

Sarver et al., "Ribozymes as Potential Anti–HIV–1 Therapeutic Agents" *Science* 247:1222–1225 (1990).

Saville et al., "A Site–Specific Self–Cleavage Reaction Performed by a Novel RNA In Neurospora Mitochondria," *Cell* 61:685–696 (1990).

Saville et al., "RNA–Mediated Ligation of Self–Cleavage Products of a Neurospora Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical Synthesis of Biologically Active Oligoribonucleotides using β–cyanoethyl Protected Ribonucleoside Phosphoramidites," *Nucl Acids Res.* 18(18):5433–5441 (1990).

Scott et al., "The Crystal Structure of an All–RNA Hammerhead Ribozyme: A Proposed Mechanism for RNA Catalytic Cleavage," *Cell* 81:991–1002 (1995).

Sczakiel et al., "Antisense Principle or Ribozyme Action?" *Biol. Chem. Hoppe–Seyler* 375:745–746 (1994).

Sczakiel et al., "Computer–Aided Search for Effective Antisense RNA Target Ssequences of the Human Immunodeficiency Virus Type 1," *Antisense Research and Development* 3:45–52 (1993).

Sczakiel, "Hammerhead Ribozymes with Long Flanking Sequences: a Structural and Kinetic View," *Nucleic Acids and Molecular Biology* 10:231–241 (1996).

Shaw et al., "Modified deoxyoligonucleotides Stable to Exonuclease Degradation in Serum," *Nucleic Acids Research* 19(4):747–750 (1991).

Shibahara et al., "Inhibition of Human Immunodeficiency Virus (HIV–1) Replication by Synthetic Oligo–RNA Derivatives," *Nucleic Acids Research* 17(1):239–252 (1989).

Shimayama et al., "Generality of the NUX Rule: Kinetic Analysis of the Results of Systematic Mutations in the Trinucleotide at the Cleavage Site of Hammerhead Ribozymes," *Biochemistry* 34:3649–3654 (1995).

Shimayama et al., "Nuclease–resistant chimeric ribozymes containing deoxyribonucleotides and phosphorothioate linkages," *Nucleic Acids Research* 21(11):2605–2611 (1993).

Shoji, et al., "Cellular Uptake and Biological Effects of Antisense Oligodeoxynucleotide Analogs Targeted to Herpes Simplex Virus," *Antimicrobial Agents and Chemotherapy*, 40(7):1670–1675 (1996).

Shoji, et al., "Mechanism of Cellular Uptake of Modified Oligodeoxynucleotides Containing Methylphosphonate Linkages," *Nucleic Acids Research* 19(20):5543–5550 (1991).

Sioud et al., "Preformed Ribozyme Destroys Tumour Necrosis Factor mRNA in Human Cells," *Journal of Molecular Biology* 223:831–835 (1992).

Snyder et al., "Ribozyme–Mediated Inhibition of bcr–abl Gene Expression in a Philadelphia Chromosome–Positive Cell Line," *Blood* 82(2):600–605 (1993).

Sporn et al., "Autocrine Growth Factors and Cancer," *Nature* 313:745–747 (1985).

Sproat, "Synthetic Catalytic Oligonucleotides Based on the Hammerhead Ribozyme," *Nucleic Acids and Molecular Biology* 10:265–281 (1996).

Stein et al., "Antisense Oligonucleotides as Therapeutic Agents—Is the Bullet Really Magical?," *Science* 261:1004–1012 (1993).

Stein et al., "Phosphorothioate and Normal Oligodeoxyribonucleotides with 5' –linked acridine: characterization and preliminary kinetics of cellular uptake," *Gene* 72(1–2):333–341 (1988).

Suh et al., "Systematic Substitution of Individual Bases in Two Important Single–Stranded Regions of the HDV Ribozyme for Evaluation of the Role Specific Bases," *FEBS Letters* 326(1,2,3):158–162 (1993).

Sullenger et al., "Tethering Ribozymes to a Retroviral Packaging Signal for Destruction of Viral RNA," *Science* 262:1566–1569 (1993).

Sullivan, "Development of Ribozymes for Gene Therapy," *Journal of Investigative Dermatology* 103(5):85S–89S (1994).

Sullivan, "Liposome–Mediated Uptake of Ribozymes," *A Companion to Methods in Enzymology* 5(1):61–66 (1993).

Symons, "Ribozymes," *Current Opinion in Structural Biology* 4(3):322–330 (1994).

Symons, "Small Catalytic RNA's," *Annual Review of Biochemistry* 61:641–671 (1992).

Szostak, "Evolution ex vivo," *Nature* 361(6408):119–120 (1993).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19(19):5125–5130 (1991).

Tayler et al., "Chimeric DNA–RNA hammerhead ribozymes have enhanced in vitro catalytic efficiency and increased stability in vivo," *Nucleic Acids Research* 20(17):4559–4565 (1992).

Theirry et al., "Liposomes as a Delivery System for Antisense and Ribozyme Compounds," *Delivery Strategies for Antisense Oligonucleotide Therapeutics*, pp. 199–220, London CRC Press.

Thompson et al., "Improved Accumulation and Activity of Ribozymes Expressed from a tRNA–based RNA Polymerase III Promoter," *Nucleic Acids Research* 23(12):2259–2268 (1995).

Thompson et al., "Ribozymes in Gene Therapy," *Nature Medicine* 1(3):277–278 (1995).

Thomson et al., "Activity of hammerhead ribozymes containing non–nucleotides linkers," *Nucleic Acids Research* 21:5600–5603 (1993).

Thomson et al., "The Hammerhead Ribozyme," *Nucleic Acids and Molecular Biology* 10:172–196 (1996).

Tidd et al., "Partial Protection of Oncogene, Anti–sense Oligodeoxynucleotides Against Serum Nuclease Degradation Using Terminal Methylphosphonate Groups," *British Journal of Cancer* 60:343–350 (1989).

Tsuchihashi et al., "Protein Enhancement of Hammerhead Ribozyme Catalysis," *Science* 262:99–102 (1993).

Tuschl et al., "A Three Dimensional Model for the Hammerhead Ribozyme based on Fluorescence Measurements" *Science* 266:785–788 (1995).

Tuschl et al., "Hammerhead Ribozymes: Importance of Stem–loop II for Activity," *Proc. Natl Acad. Sci. USA* 90:6991–6994 (1993).

Uhlenbeck, "A Small Catalytic Oligoribonucleotide," *Nature* 328:596–600 (1987).

Usman and McSwiggen, "Ch. 30—Catalytic RNA (Ribozymes) as Drugs," *Annual Reports in Medicinal Chemistry* 30:285–294 (1995).

Usman et al., "Automated Chemical Synthesis of Long Oligonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethionine tRNA," *J. Am. Chem. Soc.* 109(25):7845–7854 (1987).

Usman et al., "Chemical Modification of Hammerhead Ribozymes: Activity and Nuclease Resistance," *Nucleic Acids Symposium Series* 31:163–164 (1994).

Usman et al., "Exploiting the Chemical Synthesis of RNA," *TIBS* 17:334–339 (1992).

Usman et al., "Design, Synthesis, and Function of Therapeutic Hammerhead Ribozymes," *Nucleic Acids and Molecular Biology* 10:243–263 (1996).

Ventura et al., "Activation of HIV–Specific Ribozyme Activity by Self–Cleavage," *Nucleic Acids Research* 21(14):3249–3255 (1993).

Weerasinghe et al., "Resistance to Human Immunodeficiency Virus Type 1 (HIV–1) Infection in Human CD4[+] Lymphocyte–Derived Cell Lines Conferred by Using Retroviral Vectors Expressing an HIV–1 RNA–Specific Ribozyme," *Journal of Virology* 65(10):5531–5534 (1991).

Werner et al., "The Effect of Base Mismatches in the Substrate Recognition Helices of Hammerhead Ribozymes on Binding and Catalysis," *Nucleic Acids Research* 23(12):2092–2096 (1995).

Williams et al., "Function of specific 2'–hydroxyl groups of guanosines in a hammerhead ribozyme probed by 2' modifications," *Proc. Natl. Acad. Sci. USA* 89:918–921 (1992).

Wincott et al., "Synthesis, Deprotection, Analysis and Purification of RNA and Ribozymes," *Nucleic Acids Research* 23(14):2677–2684 (1995).

Wong et al., "The Molecular Biology and Molecular Genetics of Astrocytic Neoplasms," *Seminars in Oncology,* 21(2):139–148 (1994).

Wu et al., "Human hepatitis δ virus RNA subfragments contain an autocleavage activity," *Proc. Natl. Acad. Sci. USA* 86:1831–1835 (1989).

Wu–Pong et al., "Antisense c–myc Oligonucleotide Cellular Uptake and Activity," *Antisense Research and Development,* 4:155–163 (1994).

Yakubov et al., "Mechanism of Oligonucleotide Uptake by Cells: Involvement of Specific Receptors?" *Proc. Natl. Acad. Sci. USA* 86:6454–6458 (1989).

Yang et al., "Minimum Ribonucleotide Requirements for Catalysis by the RNA Hammerhead Domain," *Biochemistry* 31:5005–5009 (1992).

Young et al., "Systematic Substitution of the Individual Bases in two Important Single–Stranded Regions of the HDV Ribozyme for the Evaluation of the Role Specific Bases," *FEBS Letters* 326(1,2,3):158–162 (1993).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zaug et al., "The Tetrahymena Ribozyme Acts Like an RNA Restriction Endonuclease," *Nature* 324:429–433 (1986).

Zhou et al., "Synthesis of Functional mRNA in Mammalian Cells by Bacteriophage T3 RNA Polymerase," *Mol. Cell. Biol.* 10(9):4529–4537 (1990).

Zuker et al., "A Comparison of Optimal and Suboptimal RNA Secondary Structures Predicted by Free Energy Minimization with Structures Determined by Phylogenetic Comparison," *Nucleic Acids Research* 19(10):2707–2714 (1991).

Adams et al., "A Convenient Synthesis Of S–Cyanoethyl–Protected 4–Thiouridine and Its Incorporation Into Oligorobonucleotides," *Tetrahedron Letters* 35(5):765–768 (1994).

Akhtar et al., "Cellular uptake and intracellular fate of antisense oligonnucleotides," *Trends in Cell Biology* 2:139–144 (1992).

Akhtar et al., "Molecular DIY with Hairpins and Hammerheads," *Nature Medicine* 1(4):300–302 (1995).

Akhtar et al., "Stability of Antisense DNA Oligodeoxynucleotide Analogs in Cellular Extracts and Sera," *Life Sciences,* 49:1793–1801 (1991).

Ali et al., "The Use of DNA Viruses as Vectors for Gene Therapy," *Gene Therapy* 1(6):367–384 (1994).

Altman, "RNA Enzyme–Directed Gene Therapy," *Proc. Natl. Acad. Sci. USA,* 90:10898–10900 (1993).

Amiri et al., "Global Conformation of a Self–Cleaving Hammerhead RNA," *Biochemistry* 33:13172–13177 (1994).

Fell et al., "Cellular Uptake Properties of a 2'–amino/ 2'–O–Methyl–Modified Chimeric Hammerhead Ribozyme Targeted to the Epidermal Growth Factor Receptor mRNA," *Antisense Nucleic Acid Drug Development* 7(4):319–326 (1997).

Kijima et al., "Therapeutic Applications of Ribozymes," *Pharmacology and Therapeutics* 68(2):247–267 (1995).

Ullrich et al., "Human Epidermal Growth Factor Receptor CDNA Sequence and Aberrant Expression of the Amplified Gene in A431 Epidermoid Carcinoma Cells," *Nature* 309:418–425 (1984).

Yamazaki et al., "Cleavage of Glioma–Specific Aberrant mRNA of Epidermal Growth Factor Receptor (EGFR) by Ribozyme In Vitro," *Proc. Amer. Assoc. for Cancer Research Annual Meeting* 36:429 (1995).

10nM ribozyme : 300nM substrate

10nM ribozyme : 1μM substrate

SEQUENCE LISTING (1) GENERAL INFORMATION:

(iii) NUMBER OF SEQUENCES: 1877

(2) INFORMATION FOR SEQ ID NO: 1:

(i) SEQUENCE CHARACTERISTICS:

(A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO: 1:

GCCGGAGUCC CGAGCUA                       17

(2) INFORMATION FOR SEQ ID NO: 2:

(i) SEQUENCE CHARACTERISTICS:

(A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO: 2:

CCCGAGCUAG CCCCGGC                       17

(2) INFORMATION FOR SEQ ID NO: 3:

(i) SEQUENCE CHARACTERISTICS:

(A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO: 3:

GGCCACCUCG UCGGCGU                       17

(2) INFORMATION FOR SEQ ID NO: 4:

(i) SEQUENCE CHARACTERISTICS:

```
            (A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 4:

CACCUCGUCG GCGUCCG                                                        17

(2)  INFORMATION FOR SEQ ID NO: 5:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 5:

GUCGGCGUCC GCCCGAG                                                        17

(2)  INFORMATION FOR SEQ ID NO: 6:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 6:

GCCCGAGUCC CCGCCUC                                                        17

(2)  INFORMATION FOR SEQ ID NO: 7:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 7:

CCCCGCCUCG CCGCCAA                                                        17

(2)  INFORMATION FOR SEQ ID NO: 8:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 8:

CCCUGACUCC GUCCAGU                                                        17

(2)  INFORMATION FOR SEQ ID NO: 9:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 9:

GACUCCGUCC AGUAUUG                                                        17
```

(2) INFORMATION FOR SEQ ID NO: 10:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 10:

CGUCCAGUAU UGAUCGG                              17

(2) INFORMATION FOR SEQ ID NO: 11:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 11:

UCCAGUAUUG AUCGGGA                              17

(2) INFORMATION FOR SEQ ID NO: 12:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 12:

GUAUUGAUCG GGAGAGC                              17

(2) INFORMATION FOR SEQ ID NO: 13:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 13:

AGCGAGCUCU UCGGGGA                              17

(2) INFORMATION FOR SEQ ID NO: 14:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 14:

CGAGCUCUUC GGGGAGC                              17

(2) INFORMATION FOR SEQ ID NO: 15:

(i) SEQUENCE CHARACTERISTICS:

(A) LENGTH:        17 base pairs
        (B) TYPE:          nucleic acid
        (C) STRANDEDNESS:  single

```
        (D) TOPOLOGY:           linear (xi) SEQUENCE DESCRIPTION: SEQ ID NO: 15:

GAGCUCUUCG GGGAGCA                                                        17

(2) INFORMATION FOR SEQ ID NO: 16:

(i) SEQUENCE CHARACTERISTICS:

(A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 16:

GCGACCCUCC GGGACGG                                                        17

(2) INFORMATION FOR SEQ ID NO: 17:

(i) SEQUENCE CHARACTERISTICS:

(A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 17:

GCAGCGCUCC UGGCGCU                                                        17

(2) INFORMATION FOR SEQ ID NO: 18:

(i) SEQUENCE CHARACTERISTICS:

(A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 18:

GCUGCGCUCU GCCCGGC                                                        17

(2) INFORMATION FOR SEQ ID NO: 19:

(i) SEQUENCE CHARACTERISTICS:

(A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 19:

CGGCGAGUCG GGCUCUG                                                        17

(2) INFORMATION FOR SEQ ID NO: 20:

(i) SEQUENCE CHARACTERISTICS:

(A) LENGTH:             17 base pairs
        (B) TYPE:               nucleic acid
        (C) STRANDEDNESS:       single
        (D) TOPOLOGY:           linear (xi) SEQUENCE DESCRIPTION: SEQ ID NO: 20:

GUCGGGCUCU GGAGGAA                                                        17

(2) INFORMATION FOR SEQ ID NO: 21:
```

```
        (i)  SEQUENCE CHARACTERISTICS:

(A)  LENGTH:           17 base pairs
             (B)  TYPE:             nucleic acid
             (C)  STRANDEDNESS:     single
             (D)  TOPOLOGY:         linear (xi)  SEQUENCE DESCRIPTION: SEQ ID NO: 21:

AAGAAAGUUU GCCAAGG                                                      17

(2) INFORMATION FOR SEQ ID NO: 22:

(i)  SEQUENCE CHARACTERISTICS:

(A)  LENGTH:           17 base pairs
             (B)  TYPE:             nucleic acid
             (C)  STRANDEDNESS:     single
             (D)  TOPOLOGY:         linear (xi)  SEQUENCE DESCRIPTION: SEQ ID NO: 22:

AGAAAGUUUG CCAAGGC                                                      17

(2) INFORMATION FOR SEQ ID NO: 23:

(i)  SEQUENCE CHARACTERISTICS:

(A)  LENGTH:           17 base pairs
             (B)  TYPE:             nucleic acid
             (C)  STRANDEDNESS:     single
             (D)  TOPOLOGY:         linear (xi)  SEQUENCE DESCRIPTION: SEQ ID NO: 23:

GCACGAGUAA CAAGCUC                                                      17

(2) INFORMATION FOR SEQ ID NO: 24:

(i)  SEQUENCE CHARACTERISTICS:

(A)  LENGTH:           17 base pairs
             (B)  TYPE:             nucleic acid
             (C)  STRANDEDNESS:     single
             (D)  TOPOLOGY:         linear (xi)  SEQUENCE DESCRIPTION: SEQ ID NO: 24:

AACAAGCUCA CGCAGUU                                                      17

(2) INFORMATION FOR SEQ ID NO: 25:

(i)  SEQUENCE CHARACTERISTICS:

(A)  LENGTH:           17 base pairs
             (B)  TYPE:             nucleic acid
             (C)  STRANDEDNESS:     single
             (D)  TOPOLOGY:         linear (xi)  SEQUENCE DESCRIPTION: SEQ ID NO: 25:

CACGCAGUUG GGCACUU                                                      17

(2) INFORMATION FOR SEQ ID NO: 26:

(i)  SEQUENCE CHARACTERISTICS:

(A)  LENGTH:           17 base pairs
             (B)  TYPE:             nucleic acid
             (C)  STRANDEDNESS:     single
             (D)  TOPOLOGY:         linear (xi)  SEQUENCE DESCRIPTION: SEQ ID NO: 26:
```

```
UGGGCACUUU UGAAGAU                                                        17

(2) INFORMATION FOR SEQ ID NO: 27:

(i) SEQUENCE CHARACTERISTICS:

(A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 27:

GGGCACUUUU GAAGAUC                                                        17

(2) INFORMATION FOR SEQ ID NO: 28:

(i) SEQUENCE CHARACTERISTICS:

(A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 28:

GGCACUUUUG AAGAUCA                                                        17

(2) INFORMATION FOR SEQ ID NO: 29:

(i) SEQUENCE CHARACTERISTICS:

(A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 29:

UUGAAGAUCA UUUUCUC                                                        17

(2) INFORMATION FOR SEQ ID NO: 30:

(i) SEQUENCE CHARACTERISTICS:

(A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 30:

AAGAUCAUUU UCUCAGC                                                        17

(2) INFORMATION FOR SEQ ID NO: 31:

(i) SEQUENCE CHARACTERISTICS:

(A) LENGTH:              17 base pairs
        (B) TYPE:                nucleic acid
        (C) STRANDEDNESS:        single
        (D) TOPOLOGY:            linear (xi) SEQUENCE DESCRIPTION: SEQ ID NO: 31:

AGAUCAUUUU CUCAGCC                                                        17

(2) INFORMATION FOR SEQ ID NO: 32:

(i) SEQUENCE CHARACTERISTICS:

(A) LENGTH:              17 base pairs
        (B) TYPE:                nucleic acid
```

```
            (C) STRANDEDNESS:           single
            (D) TOPOLOGY:               linear (xi) SEQUENCE DESCRIPTION: SEQ ID NO: 32:

GAUCAUUUUC UCAGCCU                                                          17

(2) INFORMATION FOR SEQ ID NO: 33:

(i) SEQUENCE CHARACTERISTICS:

(A) LENGTH:                 17 base pairs
            (B) TYPE:                   nucleic acid
            (C) STRANDEDNESS:           single
            (D) TOPOLOGY:               linear (xi) SEQUENCE DESCRIPTION: SEQ ID NO: 33:

AUCAUUUUCU CAGCCUC                                                          17

(2) INFORMATION FOR SEQ ID NO: 34:

(i) SEQUENCE CHARACTERISTICS:

(A) LENGTH:                 17 base pairs
            (B) TYPE:                   nucleic acid
            (C) STRANDEDNESS:           single
            (D) TOPOLOGY:               linear (xi) SEQUENCE DESCRIPTION: SEQ ID NO: 34:

CAUUUCUCA GCCUCCA                                                           17

(2) INFORMATION FOR SEQ ID NO: 35:

(i) SEQUENCE CHARACTERISTICS:

(A) LENGTH:                 17 base pairs
            (B) TYPE:                   nucleic acid
            (C) STRANDEDNESS:           single
            (D) TOPOLOGY:               linear (xi) SEQUENCE DESCRIPTION: SEQ ID NO: 35:

CUCAGCCUCC AGAGGAU                                                          17

(2) INFORMATION FOR SEQ ID NO: 36:

(i) SEQUENCE CHARACTERISTICS:

(A) LENGTH:                 17 base pairs
            (B) TYPE:                   nucleic acid
            (C) STRANDEDNESS:           single
            (D) TOPOLOGY:               linear (xi) SEQUENCE DESCRIPTION: SEQ ID NO: 36:

GAGGAUGUUC AAUAACU                                                          17

(2) INFORMATION FOR SEQ ID NO: 37:

(i) SEQUENCE CHARACTERISTICS:

(A) LENGTH:                 17 base pairs
            (B) TYPE:                   nucleic acid
            (C) STRANDEDNESS:           single
            (D) TOPOLOGY:               linear (xi) SEQUENCE DESCRIPTION: SEQ ID NO: 37:

AGGAUGUUCA AUAACUG                                                          17

(2) INFORMATION FOR SEQ ID NO: 38:
```

```
    (i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 38:

UGUUCAAUAA CUGUGAG                                              17

(2) INFORMATION FOR SEQ ID NO: 39:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 39:

GAGGUGGUCC UUGGGAA                                              17

(2) INFORMATION FOR SEQ ID NO: 40:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 40:

GUGGUCCUUG GGAAUUU                                              17

(2) INFORMATION FOR SEQ ID NO: 41:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 41:

UUGGGAAUUU GGAAAUU                                              17

(2) INFORMATION FOR SEQ ID NO: 42:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 42:

UGGGAAUUUG GAAAUUA                                              17

(2) INFORMATION FOR SEQ ID NO: 43:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 43:
```

UUGGAAAUUA CCUAUGU                                                    17

(2) INFORMATION FOR SEQ ID NO: 44:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 44:

UGGAAAUUAC CUAUGUG                                                    17

(2) INFORMATION FOR SEQ ID NO: 45:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 45:

AAUUACCUAU GUGCAGA                                                    17

(2) INFORMATION FOR SEQ ID NO: 46:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 46:

AGAGGAAUUA UGAUCUU                                                    17

(2) INFORMATION FOR SEQ ID NO: 47:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 47:

GAGGAAUUAU GAUCUUU                                                    17

(2) INFORMATION FOR SEQ ID NO: 48:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 48:

AUUAUGAUCU UUCCUUC                                                    17

(2) INFORMATION FOR SEQ ID NO: 49:

(i) SEQUENCE CHARACTERISTICS:

(A) LENGTH:           17 base pairs

```
            (B)  TYPE:             nucleic acid
            (C)  STRANDEDNESS:     single
            (D)  TOPOLOGY:         linear (xi)  SEQUENCE DESCRIPTION: SEQ ID NO: 49:

UAUGAUCUUU CCUUCUU                                                  17

(2)  INFORMATION FOR SEQ ID NO: 50:

(i)  SEQUENCE CHARACTERISTICS:
            (A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 50:

AUGAUCUUUC CUUCUUA                                                  17

(2)  INFORMATION FOR SEQ ID NO: 51:

(i)  SEQUENCE CHARACTERISTICS:
            (A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 51:

UGAUCUUUCC UUCUUAA                                                  17

(2)  INFORMATION FOR SEQ ID NO: 52:

(i)  SEQUENCE CHARACTERISTICS:
            (A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 52:

UCUUUCCUUC UUAAAGA                                                  17

(2)  INFORMATION FOR SEQ ID NO: 53:

(i)  SEQUENCE CHARACTERISTICS:
            (A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 53:

CUUUCCUUCU UAAAGAC                                                  17

(2)  INFORMATION FOR SEQ ID NO: 54:

(i)  SEQUENCE CHARACTERISTICS:
            (A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 54:

UUCCUUCUUA AAGACCA                                                  17
```

(2) INFORMATION FOR SEQ ID NO: 55:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 55:

UCCUUCUUAA AGACCAU                                        17

(2) INFORMATION FOR SEQ ID NO: 56:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 56:

AAGACCAUCC AGGAGGU                                        17

(2) INFORMATION FOR SEQ ID NO: 57:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 57:

UGGCUGGUUA UGUCCUC                                        17

(2) INFORMATION FOR SEQ ID NO: 58:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 58:

GGCUGGUUAU GUCCUCA                                        17

(2) INFORMATION FOR SEQ ID NO: 59:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 59:

GGUUAUGUCC UCAUUGC                                        17

(2) INFORMATION FOR SEQ ID NO: 60:

(i) SEQUENCE CHARACTERISTICS:

(A) LENGTH: 17 base pairs
        (B) TYPE: nucleic acid
        (C) STRANDEDNESS: single
        (D) TOPOLOGY: linear -continued (xi) SEQUENCE DESCRIPTION: SEQ ID NO: 60:

UAUGUCCUCA UUGCCCU                                                                17

(2) INFORMATION FOR SEQ ID NO: 61:

(i) SEQUENCE CHARACTERISTICS:

(A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 61:

GUCCUCAUUG CCCUCAA                                                                17

(2) INFORMATION FOR SEQ ID NO: 62:

(i) SEQUENCE CHARACTERISTICS:

(A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 62:

AUUGCCCUCA ACACAGU                                                                17

(2) INFORMATION FOR SEQ ID NO: 63:

(i) SEQUENCE CHARACTERISTICS:

(A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 63:

GAGCGAAUUC CUUUGGA                                                                17

(2) INFORMATION FOR SEQ ID NO: 64:

(i) SEQUENCE CHARACTERISTICS:

(A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 64:

AGCGAAUUCC UUUGGAA                                                                17

(2) INFORMATION FOR SEQ ID NO: 65:

(i) SEQUENCE CHARACTERISTICS:

(A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 65:

GAAUUCCUUU GGAAAAC                                                                17

(2) INFORMATION FOR SEQ ID NO: 66:

(i) SEQUENCE CHARACTERISTICS:

```
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 66:

AAUUCCUUUG GAAAACC                                                    17

(2) INFORMATION FOR SEQ ID NO: 67:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 67:

CUGCAGAUCA UCAGAGG                                                    17

(2) INFORMATION FOR SEQ ID NO: 68:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 68:

CAGAUCAUCA GAGGAAA                                                    17

(2) INFORMATION FOR SEQ ID NO: 69:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 69:

GAGGAAAUAU GUACUAC                                                    17

(2) INFORMATION FOR SEQ ID NO: 70:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 70:

AAAUAUGUAC UACGAAA                                                    17

(2) INFORMATION FOR SEQ ID NO: 71:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 71:

UAUGUACUAC GAAAAUU                                                    17
```

(2) INFORMATION FOR SEQ ID NO: 72:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 72:

ACGAAAAUUC CUAUGCC                                    17

(2) INFORMATION FOR SEQ ID NO: 73:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 73:

CGAAAAUUCC UAUGCCU                                    17

(2) INFORMATION FOR SEQ ID NO: 74:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 74:

AAAUUCCUAU GCCUUAG                                    17

(2) INFORMATION FOR SEQ ID NO: 75:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 75:

CUAUGCCUUA GCAGUCU                                    17

(2) INFORMATION FOR SEQ ID NO: 76:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 76:

UAUGCCUUAG CAGUCUU                                    17

(2) INFORMATION FOR SEQ ID NO: 77:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear

```
        (xi) SEQUENCE DESCRIPTION: SEQ ID NO: 77:

UUAGCAGUCU UAUCUAA                                                17

(2) INFORMATION FOR SEQ ID NO: 78:

(i) SEQUENCE CHARACTERISTICS:
                (A) LENGTH:         17 base pairs
                (B) TYPE:           nucleic acid
                (C) STRANDEDNESS:   single
                (D) TOPOLOGY:       linear (xi) SEQUENCE DESCRIPTION: SEQ ID NO: 78:

AGCAGUCUUA UCUAACU                                                17

(2) INFORMATION FOR SEQ ID NO: 79:

(i) SEQUENCE CHARACTERISTICS:
                (A) LENGTH:         17 base pairs
                (B) TYPE:           nucleic acid
                (C) STRANDEDNESS:   single
                (D) TOPOLOGY:       linear (xi) SEQUENCE DESCRIPTION: SEQ ID NO: 79:

GCAGUCUUAU CUAACUA                                                17

(2) INFORMATION FOR SEQ ID NO: 80:

(i) SEQUENCE CHARACTERISTICS:
                (A) LENGTH:         17 base pairs
                (B) TYPE:           nucleic acid
                (C) STRANDEDNESS:   single
                (D) TOPOLOGY:       linear (xi) SEQUENCE DESCRIPTION: SEQ ID NO: 80:

AGUCUUAUCU AACUAUG                                                17

(2) INFORMATION FOR SEQ ID NO: 81:

(i) SEQUENCE CHARACTERISTICS:
                (A) LENGTH:         17 base pairs
                (B) TYPE:           nucleic acid
                (C) STRANDEDNESS:   single
                (D) TOPOLOGY:       linear (xi) SEQUENCE DESCRIPTION: SEQ ID NO: 81:

UCUUAUCUAA CUAUGAU                                                17

(2) INFORMATION FOR SEQ ID NO: 82:

(i) SEQUENCE CHARACTERISTICS:
                (A) LENGTH:         17 base pairs
                (B) TYPE:           nucleic acid
                (C) STRANDEDNESS:   single
                (D) TOPOLOGY:       linear (xi) SEQUENCE DESCRIPTION: SEQ ID NO: 82:

AUCUAACUAU GAUGCAA                                                17

(2) INFORMATION FOR SEQ ID NO: 83:

(i) SEQUENCE CHARACTERISTICS:
```

```
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 83:

AUGCAAAUAA AACCGGA                                                17

(2) INFORMATION FOR SEQ ID NO: 84:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 84:

UGAGAAAUUU ACAGGAA                                                17

(2) INFORMATION FOR SEQ ID NO: 85:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 85:

GAGAAAUUUA CAGGAAA                                                17

(2) INFORMATION FOR SEQ ID NO: 86:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 86:

AGAAAUUUAC AGGAAAU                                                17

(2) INFORMATION FOR SEQ ID NO: 87:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 87:

CAGGAAAUCC UGCAUGG                                                17

(2) INFORMATION FOR SEQ ID NO: 88:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 88:

CGUGCGGUUC AGCAACA                                                17
```

(2) INFORMATION FOR SEQ ID NO: 89:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 89:

GUGCGGUUCA GCAACAA          17

(2) INFORMATION FOR SEQ ID NO: 90:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 90:

GAGAGCAUCC AGUGGCG          17

(2) INFORMATION FOR SEQ ID NO: 91:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 91:

CGGGACAUAG UCAGCAG          17

(2) INFORMATION FOR SEQ ID NO: 92:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 92:

GACAUAGUCA GCAGUGA          17

(2) INFORMATION FOR SEQ ID NO: 93:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 93:

CAGUGACUUU CUCAGCA          17

(2) INFORMATION FOR SEQ ID NO: 94:

(i) SEQUENCE CHARACTERISTICS:

(A) LENGTH: 17 base pairs
        (B) TYPE: nucleic acid
        (C) STRANDEDNESS: single -continued (D) TOPOLOGY:            linear (xi) SEQUENCE DESCRIPTION: SEQ ID NO: 94:

AGUGACUUUC UCAGCAA                                                17

(2) INFORMATION FOR SEQ ID NO: 95:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 95:

GUGACUUUCU CAGCAAC                                                17

(2) INFORMATION FOR SEQ ID NO: 96:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 96:

GACUUUCUCA GCAACAU                                                17

(2) INFORMATION FOR SEQ ID NO: 97:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 97:

CAACAUGUCG AUGGACU                                                17

(2) INFORMATION FOR SEQ ID NO: 98:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 98:

GAUGGACUUC CAGAACC                                                17

(2) INFORMATION FOR SEQ ID NO: 99:

(i) SEQUENCE CHARACTERISTICS:
            (A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 99:

AUGGACUUCC AGAACCA                                                17

(2) INFORMATION FOR SEQ ID NO: 100:

```
        (i) SEQUENCE CHARACTERISTICS:

(A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 100:

AGUGUGAUCC AAGCUGU                                                17

(2) INFORMATION FOR SEQ ID NO: 101:

(i) SEQUENCE CHARACTERISTICS:

(A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 101:

CAAGCUGUCC CAAUGGG                                                17

(2) INFORMATION FOR SEQ ID NO: 102:

(i) SEQUENCE CHARACTERISTICS:

(A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 102:

ACCAAAAUCA UCUGUGC                                                17

(2) INFORMATION FOR SEQ ID NO: 103:

(i) SEQUENCE CHARACTERISTICS:

(A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 103:

AAAAUCAUCU GUGCCCA                                                17

(2) INFORMATION FOR SEQ ID NO: 104:

(i) SEQUENCE CHARACTERISTICS:

(A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 104:

GCAGUGCUCC GGGCGCU                                                17

(2) INFORMATION FOR SEQ ID NO: 105:

(i) SEQUENCE CHARACTERISTICS:

(A) LENGTH:           17 base pairs
            (B) TYPE:             nucleic acid
            (C) STRANDEDNESS:     single
            (D) TOPOLOGY:         linear (xi) SEQUENCE DESCRIPTION: SEQ ID NO: 105:
```

```
UGGCAAGUCC CCCAGUG                                           17
```

(2) INFORMATION FOR SEQ ID NO: 106:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 106:

```
UGCCUGGUCU GCCGCAA                                           17
```

(2) INFORMATION FOR SEQ ID NO: 107:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 107:

```
CCGCAAAUUC CGAGACG                                           17
```

(2) INFORMATION FOR SEQ ID NO: 108:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 108:

```
CGCAAAUUCC GAGACGA                                           17
```

(2) INFORMATION FOR SEQ ID NO: 109:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 109:

```
CCCCCACUCA UGCUCUA                                           17
```

(2) INFORMATION FOR SEQ ID NO: 110:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 110:

```
CUCAUGCUCU ACAACCC                                           17
```

(2) INFORMATION FOR SEQ ID NO: 111:

(i) SEQUENCE CHARACTERISTICS:

(A) LENGTH:           17 base pairs
        (B) TYPE:             nucleic acid

```
            (C)  STRANDEDNESS:       single
            (D)  TOPOLOGY:           linear (xi) SEQUENCE DESCRIPTION: SEQ ID NO: 111:

CAUGCUCUAC AACCCCA                                                      17

(2)  INFORMATION FOR SEQ ID NO: 112:

(i)  SEQUENCE CHARACTERISTICS:
            (A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 112:

CACCACGUAC CAGAUGG                                                      17

(2)  INFORMATION FOR SEQ ID NO: 113:

(i)  SEQUENCE CHARACTERISTICS:
            (A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 113:

GGGCAAAUAC AGCUUUG                                                      17

(2)  INFORMATION FOR SEQ ID NO: 114:

(i)  SEQUENCE CHARACTERISTICS:
            (A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 114:

AUACAGCUUU GGUGCCA                                                      17

(2)  INFORMATION FOR SEQ ID NO: 115:

(i)  SEQUENCE CHARACTERISTICS:
            (A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 115:

UACAGCUUUG GUGCCAC                                                      17

(2)  INFORMATION FOR SEQ ID NO: 116:

(i)  SEQUENCE CHARACTERISTICS:
            (A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 116:

AGAAGUGUCC CCGUAAU                                                      17

(2)  INFORMATION FOR SEQ ID NO: 117:
```

```
    (i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 117:

GUCCCCGUAA UUAUGUG                                                  17

(2) INFORMATION FOR SEQ ID NO: 118:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 118:

CCCGUAAUUA UGUGGUG                                                  17

(2) INFORMATION FOR SEQ ID NO: 119:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 119:

CCGUAAUUAU GUGGUGA                                                  17

(2) INFORMATION FOR SEQ ID NO: 120:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 120:

UGACAGAUCA CGGCUCG                                                  17

(2) INFORMATION FOR SEQ ID NO: 121:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 121:

UCACGGCUCG UGCGUCC                                                  17

(2) INFORMATION FOR SEQ ID NO: 122:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 122:
```

UCGUGCGUCC GAGCCUG                                                              17

(2) INFORMATION FOR SEQ ID NO: 123:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 123:

CGACAGCUAU GAGAUGG                                                              17

(2) INFORMATION FOR SEQ ID NO: 124:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 124:

GACGGCGUCC GCAAGUG                                                              17

(2) INFORMATION FOR SEQ ID NO: 125:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 125:

GCAAGUGUAA GAAGUGC                                                              17

(2) INFORMATION FOR SEQ ID NO: 126:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 126:

AAGGGCCUUG CCGCAAA                                                              17

(2) INFORMATION FOR SEQ ID NO: 127:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 127:

AAGUGUGUAA CGGAAUA                                                              17

(2) INFORMATION FOR SEQ ID NO: 128:

(i) SEQUENCE CHARACTERISTICS:

(A) LENGTH: 17 base pairs

```
            (B)  TYPE:              nucleic acid
            (C)  STRANDEDNESS:      single
            (D)  TOPOLOGY:          linear (xi)  SEQUENCE DESCRIPTION: SEQ ID NO: 128:

AACGGAAUAG GUAUUGG                                                    17

(2)  INFORMATION FOR SEQ ID NO: 129:

(i)   SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 129:

GAAUAGGUAU UGGUGAA                                                    17

(2)  INFORMATION FOR SEQ ID NO: 130:

(i)   SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 130:

AUAGGUAUUG GUGAAUU                                                    17

(2)  INFORMATION FOR SEQ ID NO: 131:

(i)   SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 131:

UGGUGAAUUU AAAGACU                                                    17

(2)  INFORMATION FOR SEQ ID NO: 132:

(i)   SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 132:

GGUGAAUUUA AAGACUC                                                    17

(2)  INFORMATION FOR SEQ ID NO: 133:

(i)   SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 133:

GUGAAUUUAA AGACUCA                                                    17
```

```
(2) INFORMATION FOR SEQ ID NO: 134:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 134:

UAAAGACUCA CUCUCCA                                                      17

(2) INFORMATION FOR SEQ ID NO: 135:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 135:

GACUCACUCU CCAUAAA                                                      17

(2) INFORMATION FOR SEQ ID NO: 136:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 136:

CUCACUCUCC AUAAAUG                                                      17

(2) INFORMATION FOR SEQ ID NO: 137:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 137:

CUCUCCAUAA AUGCUAC                                                      17

(2) INFORMATION FOR SEQ ID NO: 138:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 138:

UAAAUGCUAC GAAUAUU                                                      17

(2) INFORMATION FOR SEQ ID NO: 139:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear
```

(xi) SEQUENCE DESCRIPTION: SEQ ID NO: 139:

CUACGAAUAU UAAACAC                                                              17

(2) INFORMATION FOR SEQ ID NO: 140:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 140:

ACGAAUAUUA AACACUU                                                              17

(2) INFORMATION FOR SEQ ID NO: 141:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 141:

CGAAUAUUAA ACACUUC                                                              17

(2) INFORMATION FOR SEQ ID NO: 142:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 142:

UAAACACUUC AAAAACU                                                              17

(2) INFORMATION FOR SEQ ID NO: 143:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 143:

AAACACUUCA AAAACUG                                                              17

(2) INFORMATION FOR SEQ ID NO: 144:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 144:

CUGCACCUCC AUCAGUG                                                              17

(2) INFORMATION FOR SEQ ID NO: 145:

(i) SEQUENCE CHARACTERISTICS:

```
            (A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 145:

ACCUCCAUCA GUGGCGA                                                         17

(2)  INFORMATION FOR SEQ ID NO: 146:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 146:

GUGGCGAUCU CCACAUC                                                         17

(2)  INFORMATION FOR SEQ ID NO: 147:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 147:

GGCGAUCUCC ACAUCCU                                                         17

(2)  INFORMATION FOR SEQ ID NO: 148:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 148:

CUCCACAUCC UGCCGGU                                                         17

(2)  INFORMATION FOR SEQ ID NO: 149:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 149:

GGUGGCAUUU AGGGGUG                                                         17

(2)  INFORMATION FOR SEQ ID NO: 150:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 150:

GUGGCAUUUA GGGGUGA                                                         17
```

(2) INFORMATION FOR SEQ ID NO: 151:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 151:

UGGCAUUUAG GGGUGAC     17

(2) INFORMATION FOR SEQ ID NO: 152:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 152:

GGGUGACUCC UUCACAC     17

(2) INFORMATION FOR SEQ ID NO: 153:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 153:

UGACUCCUUC ACACAUA     17

(2) INFORMATION FOR SEQ ID NO: 154:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 154:

GACUCCUUCA CACAUAC     17

(2) INFORMATION FOR SEQ ID NO: 155:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 155:

UCACACAUAC UCCUCCU     17

(2) INFORMATION FOR SEQ ID NO: 156:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 156:

CACAUACUCC UCCUCUG                                                    17

(2) INFORMATION FOR SEQ ID NO: 157:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 157:

AUACUCCUCC UCUGGAU                                                    17

(2) INFORMATION FOR SEQ ID NO: 158:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 158:

CUCCUCCUCU GGAUCCA                                                    17

(2) INFORMATION FOR SEQ ID NO: 159:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 159:

CUCUGGAUCC ACAGGAA                                                    17

(2) INFORMATION FOR SEQ ID NO: 160:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 160:

AACUGGAUAU UCUGAAA                                                    17

(2) INFORMATION FOR SEQ ID NO: 161:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 161:

CUGGAUAUUC UGAAAAC                                                    17

(2) INFORMATION FOR SEQ ID NO: 162:

(i) SEQUENCE CHARACTERISTICS:

```
            (A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 162:

UGGAUAUUCU GAAAACC                                                        17

(2)  INFORMATION FOR SEQ ID NO: 163:

(i)   SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 163:

AAAACCGUAA AGGAAAU                                                        17

(2)  INFORMATION FOR SEQ ID NO: 164:

(i)   SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 164:

AAGGAAAUCA CAGGGUU                                                        17

(2)  INFORMATION FOR SEQ ID NO: 165:

(i)   SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 165:

CACAGGGUUU UUGCUGA                                                        17

(2)  INFORMATION FOR SEQ ID NO: 166:

(i)   SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 166:

ACAGGGUUUU UGCUGAU                                                        17

(2)  INFORMATION FOR SEQ ID NO: 167:

(i)   SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 167:

CAGGGUUUUU GCUGAUU                                                        17
```

(2) INFORMATION FOR SEQ ID NO: 168:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 168:

AGGGUUUUUG CUGAUUC                                        17

(2) INFORMATION FOR SEQ ID NO: 169:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 169:

UUGCUGAUUC AGGCUUG                                        17

(2) INFORMATION FOR SEQ ID NO: 170:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 170:

UGCUGAUUCA GGCUUGG                                        17

(2) INFORMATION FOR SEQ ID NO: 171:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 171:

UUCAGGCUUG GCCUGAA                                        17

(2) INFORMATION FOR SEQ ID NO: 172:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 172:

ACGGACCUCC AUGCCUU                                        17

(2) INFORMATION FOR SEQ ID NO: 173:

(i) SEQUENCE CHARACTERISTICS:

(A) LENGTH: 17 base pairs
        (B) TYPE: nucleic acid
        (C) STRANDEDNESS: single (D) TOPOLOGY:           linear (xi) SEQUENCE DESCRIPTION: SEQ ID NO: 173:

CCAUGCCUUU GAGAACC                                                17

(2) INFORMATION FOR SEQ ID NO: 174:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 174:

CAUGCCUUUG AGAACCU                                                17

(2) INFORMATION FOR SEQ ID NO: 175:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 175:

GAGAACCUAG AAAUCAU                                                17

(2) INFORMATION FOR SEQ ID NO: 176:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 176:

CUAGAAAUCA UACGCGG                                                17

(2) INFORMATION FOR SEQ ID NO: 177:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 177:

GAAAUCAUAC GCGGCAG                                                17

(2) INFORMATION FOR SEQ ID NO: 178:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 178:

AACAUGGUCA GUUUUCU                                                17

(2) INFORMATION FOR SEQ ID NO: 179:

```
    (i) SEQUENCE CHARACTERISTICS:

(A) LENGTH:           17 base pairs
         (B) TYPE:             nucleic acid
         (C) STRANDEDNESS:     single
         (D) TOPOLOGY:         linear (xi) SEQUENCE DESCRIPTION: SEQ ID NO: 179:

UGGUCAGUUU UCUCUUG                                                 17

(2) INFORMATION FOR SEQ ID NO: 180:

(i) SEQUENCE CHARACTERISTICS:

(A) LENGTH:           17 base pairs
         (B) TYPE:             nucleic acid
         (C) STRANDEDNESS:     single
         (D) TOPOLOGY:         linear (xi) SEQUENCE DESCRIPTION: SEQ ID NO: 180:

GGUCAGUUUU CUCUUGC                                                 17

(2) INFORMATION FOR SEQ ID NO: 181:

(i) SEQUENCE CHARACTERISTICS:

(A) LENGTH:           17 base pairs
         (B) TYPE:             nucleic acid
         (C) STRANDEDNESS:     single
         (D) TOPOLOGY:         linear (xi) SEQUENCE DESCRIPTION: SEQ ID NO: 181:

GUCAGUUUUC UCUUGCA                                                 17

(2) INFORMATION FOR SEQ ID NO: 182:

(i) SEQUENCE CHARACTERISTICS:

(A) LENGTH:           17 base pairs
         (B) TYPE:             nucleic acid
         (C) STRANDEDNESS:     single
         (D) TOPOLOGY:         linear (xi) SEQUENCE DESCRIPTION: SEQ ID NO: 182:

UCAGUUUUCU CUUGCAG                                                 17

(2) INFORMATION FOR SEQ ID NO: 183:

(i) SEQUENCE CHARACTERISTICS:

(A) LENGTH:           17 base pairs
         (B) TYPE:             nucleic acid
         (C) STRANDEDNESS:     single
         (D) TOPOLOGY:         linear (xi) SEQUENCE DESCRIPTION: SEQ ID NO: 183:

AGUUUUCUCU UGCAGUC                                                 17

(2) INFORMATION FOR SEQ ID NO: 184:

(i) SEQUENCE CHARACTERISTICS:

(A) LENGTH:           17 base pairs
         (B) TYPE:             nucleic acid
         (C) STRANDEDNESS:     single
         (D) TOPOLOGY:         linear (xi) SEQUENCE DESCRIPTION: SEQ ID NO: 184:
```

```
UUUUCUCUUG CAGUCGU                                                          17
```

(2) INFORMATION FOR SEQ ID NO: 185:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 185:

```
CUUGCAGUCG UCAGCCU                                                          17
```

(2) INFORMATION FOR SEQ ID NO: 186:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 186:

```
GCAGUCGUCA GCCUGAA                                                          17
```

(2) INFORMATION FOR SEQ ID NO: 187:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 187:

```
CUGAACAUAA CAUCCUU                                                          17
```

(2) INFORMATION FOR SEQ ID NO: 188:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 188:

```
CAUAACAUCC UUGGGAU                                                          17
```

(2) INFORMATION FOR SEQ ID NO: 189:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 189:

```
AACAUCCUUG GGAUUAC                                                          17
```

(2) INFORMATION FOR SEQ ID NO: 190:

(i) SEQUENCE CHARACTERISTICS:

(A) LENGTH:        17 base pairs
        (B) TYPE:          nucleic acid

```
            (C) STRANDEDNESS:       single
            (D) TOPOLOGY:           linear (xi) SEQUENCE DESCRIPTION: SEQ ID NO: 190:

CUUGGGAUUA CGCUCCC                                                  17

(2) INFORMATION FOR SEQ ID NO: 191:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 191:

UUGGGAUUAC GCUCCCU                                                  17

(2) INFORMATION FOR SEQ ID NO: 192:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 192:

AUUACGCUCC CUCAAGG                                                  17

(2) INFORMATION FOR SEQ ID NO: 193:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 193:

CGCUCCCUCA AGGAGAU                                                  17

(2) INFORMATION FOR SEQ ID NO: 194:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 194:

AAGGAGAUAA GUGAUGG                                                  17

(2) INFORMATION FOR SEQ ID NO: 195:

(i) SEQUENCE CHARACTERISTICS:
            (A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 195:

GAUGUGAUAA UUUCAGG                                                  17

(2) INFORMATION FOR SEQ ID NO: 196:
```

```
        (i) SEQUENCE CHARACTERISTICS:
            (A) LENGTH:         17 base pairs
            (B) TYPE:           nucleic acid
            (C) STRANDEDNESS:   single
            (D) TOPOLOGY:       linear (xi) SEQUENCE DESCRIPTION: SEQ ID NO: 196:

GUGAUAAUUU CAGGAAA                                                      17

(2) INFORMATION FOR SEQ ID NO: 197:

(i) SEQUENCE CHARACTERISTICS:
            (A) LENGTH:         17 base pairs
            (B) TYPE:           nucleic acid
            (C) STRANDEDNESS:   single
            (D) TOPOLOGY:       linear (xi) SEQUENCE DESCRIPTION: SEQ ID NO: 197:

UGAUAAUUUC AGGAAAC                                                      17

(2) INFORMATION FOR SEQ ID NO: 198:

(i) SEQUENCE CHARACTERISTICS:
            (A) LENGTH:         17 base pairs
            (B) TYPE:           nucleic acid
            (C) STRANDEDNESS:   single
            (D) TOPOLOGY:       linear (xi) SEQUENCE DESCRIPTION: SEQ ID NO: 198:

GAUAAUUUCA GGAAACA                                                      17

(2) INFORMATION FOR SEQ ID NO: 199:

(i) SEQUENCE CHARACTERISTICS:
            (A) LENGTH:         17 base pairs
            (B) TYPE:           nucleic acid
            (C) STRANDEDNESS:   single
            (D) TOPOLOGY:       linear (xi) SEQUENCE DESCRIPTION: SEQ ID NO: 199:

ACAAAAAUUU GUGCUAU                                                      17

(2) INFORMATION FOR SEQ ID NO: 200:

(i) SEQUENCE CHARACTERISTICS:
            (A) LENGTH:         17 base pairs
            (B) TYPE:           nucleic acid
            (C) STRANDEDNESS:   single
            (D) TOPOLOGY:       linear (xi) SEQUENCE DESCRIPTION: SEQ ID NO: 200:

CAAAAAUUUG UGCUAUG                                                      17

(2) INFORMATION FOR SEQ ID NO: 201:

(i) SEQUENCE CHARACTERISTICS:
            (A) LENGTH:         17 base pairs
            (B) TYPE:           nucleic acid
            (C) STRANDEDNESS:   single
            (D) TOPOLOGY:       linear (xi) SEQUENCE DESCRIPTION: SEQ ID NO: 201:
```

UUUGUGCUAU GCAAAUA                                                              17

(2) INFORMATION FOR SEQ ID NO: 202:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 202:

AUGCAAAUAC AAUAAAC                                                              17

(2) INFORMATION FOR SEQ ID NO: 203:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 203:

AAUACAAUAA ACUGGAA                                                              17

(2) INFORMATION FOR SEQ ID NO: 204:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 204:

AAAACUGUUU GGGACCU                                                              17

(2) INFORMATION FOR SEQ ID NO: 205:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 205:

AAACUGUUUG GACCUC                                                               17

(2) INFORMATION FOR SEQ ID NO: 206:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 206:

UGGGACCUCC GGUCAGA                                                              17

(2) INFORMATION FOR SEQ ID NO: 207:

(i) SEQUENCE CHARACTERISTICS:

(A) LENGTH:           17 base pairs

```
            (B)  TYPE:              nucleic acid
            (C)  STRANDEDNESS:      single
            (D)  TOPOLOGY:          linear (xi) SEQUENCE DESCRIPTION: SEQ ID NO: 207:

CCUCCGGUCA GAAAACC                                                  17

(2) INFORMATION FOR SEQ ID NO: 208:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 208:

ACCAAAAUUA UAAGCAA                                                  17

(2) INFORMATION FOR SEQ ID NO: 209:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 209:

CCAAAAUUAU AAGCAAC                                                  17

(2) INFORMATION FOR SEQ ID NO: 210:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 210:

AAAAUUAUAA GCAACAG                                                  17

(2) INFORMATION FOR SEQ ID NO: 211:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 211:

GGCCAGGUCU GCCAUGC                                                  17

(2) INFORMATION FOR SEQ ID NO: 212:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 212:

CCAUGCCUUG UGCUCCC                                                  17
```

```
(2)  INFORMATION FOR SEQ ID NO: 213:

(i)  SEQUENCE CHARACTERISTICS:
          (A)  LENGTH:            17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 213:

CUUGUGCUCC CCCGAGG                                                    17

(2)  INFORMATION FOR SEQ ID NO: 214:

(i)  SEQUENCE CHARACTERISTICS:
          (A)  LENGTH:            17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 214:

GACUGCGUCU CUUGCCG                                                    17

(2)  INFORMATION FOR SEQ ID NO: 215:

(i)  SEQUENCE CHARACTERISTICS:
          (A)  LENGTH:            17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 215:

CUGCGUCUCU UGCCGGA                                                    17

(2)  INFORMATION FOR SEQ ID NO: 216:

(i)  SEQUENCE CHARACTERISTICS:
          (A)  LENGTH:            17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 216:

GCGUCUCUUG CCGGAAU                                                    17

(2)  INFORMATION FOR SEQ ID NO: 217:

(i)  SEQUENCE CHARACTERISTICS:
          (A)  LENGTH:            17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 217:

CGGAAUGUCA GCCGAGG                                                    17

(2)  INFORMATION FOR SEQ ID NO: 218:

(i)  SEQUENCE CHARACTERISTICS:
          (A)  LENGTH:            17 base pairs
          (B)  TYPE:               nucleic acid
          (C)  STRANDEDNESS:       single
          (D)  TOPOLOGY:           linear
```

(xi) SEQUENCE DESCRIPTION: SEQ ID NO: 218:

UGCAAGCUUC UGGAGGG                                                17

(2) INFORMATION FOR SEQ ID NO: 219:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 219:

GCAAGCUUCU GGAGGGU                                                17

(2) INFORMATION FOR SEQ ID NO: 220:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 220:

AAGGGAGUUU GUGGAGA                                                17

(2) INFORMATION FOR SEQ ID NO: 221:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 221:

AGGGAGUUUG UGGAGAA                                                17

(2) INFORMATION FOR SEQ ID NO: 222:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 222:

GGAGAACUCU GAGUGCA                                                17

(2) INFORMATION FOR SEQ ID NO: 223:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 223:

GAGUGCAUAC AGUGCCA                                                17

(2) INFORMATION FOR SEQ ID NO: 224:

(i) SEQUENCE CHARACTERISTICS:

(A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 224:

GCCUGCCUCA GGCCAUG                                                      17

(2)  INFORMATION FOR SEQ ID NO: 225:

(i)  SEQUENCE CHARACTERISTICS:

(A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 225:

AUGAACAUCA CCUGCAC                                                      17

(2)  INFORMATION FOR SEQ ID NO: 226:

(i)  SEQUENCE CHARACTERISTICS:

(A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 226:

ACAACUGUAU CCAGUGU                                                      17

(2)  INFORMATION FOR SEQ ID NO: 227:

(i)  SEQUENCE CHARACTERISTICS:

(A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 227:

AACUGUAUCC AGUGUGC                                                      17

(2)  INFORMATION FOR SEQ ID NO: 228:

(i)  SEQUENCE CHARACTERISTICS:

(A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 228:

UGCCCACUAC AUUGACG                                                      17

(2)  INFORMATION FOR SEQ ID NO: 229:

(i)  SEQUENCE CHARACTERISTICS:

(A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 229:

CACUACAUUG ACGGCCC                                                      17

(2) INFORMATION FOR SEQ ID NO: 230:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 230:

CACUGCGUCA AGACCUG                                  17

(2) INFORMATION FOR SEQ ID NO: 231:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 231:

GCAGGAGUCA UGGGAGA                                  17

(2) INFORMATION FOR SEQ ID NO: 232:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 232:

ACCCUGGUCU GGAAGUA                                  17

(2) INFORMATION FOR SEQ ID NO: 233:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 233:

CUGGAAGUAC GCAGACG                                  17

(2) INFORMATION FOR SEQ ID NO: 234:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 234:

UGUGCCAUCC AAACUGC                                  17

(2) INFORMATION FOR SEQ ID NO: 235:

(i) SEQUENCE CHARACTERISTICS:

(A) LENGTH:        17 base pairs
        (B) TYPE:          nucleic acid
        (C) STRANDEDNESS:  single
        (D) TOPOLOGY:     linear (xi) SEQUENCE DESCRIPTION: SEQ ID NO: 235:

CUGCACCUAC GGAUGCA                                                17

(2) INFORMATION FOR SEQ ID NO: 236:

(i) SEQUENCE CHARACTERISTICS:

(A) LENGTH:           17 base pairs
      (B) TYPE:             nucleic acid
      (C) STRANDEDNESS:     single
      (D) TOPOLOGY:         linear (xi) SEQUENCE DESCRIPTION: SEQ ID NO: 236:

GGCCAGGUCU UGAAGGC                                                17

(2) INFORMATION FOR SEQ ID NO: 237:

(i) SEQUENCE CHARACTERISTICS:

(A) LENGTH:           17 base pairs
      (B) TYPE:             nucleic acid
      (C) STRANDEDNESS:     single
      (D) TOPOLOGY:         linear (xi) SEQUENCE DESCRIPTION: SEQ ID NO: 237:

CCAGGUCUUG AAGGCUG                                                17

(2) INFORMATION FOR SEQ ID NO: 238:

(i) SEQUENCE CHARACTERISTICS:

(A) LENGTH:           17 base pairs
      (B) TYPE:             nucleic acid
      (C) STRANDEDNESS:     single
      (D) TOPOLOGY:         linear (xi) SEQUENCE DESCRIPTION: SEQ ID NO: 238:

AAGGCUGUCC AACGAAU                                                17

(2) INFORMATION FOR SEQ ID NO: 239:

(i) SEQUENCE CHARACTERISTICS:

(A) LENGTH:           17 base pairs
      (B) TYPE:             nucleic acid
      (C) STRANDEDNESS:     single
      (D) TOPOLOGY:         linear (xi) SEQUENCE DESCRIPTION: SEQ ID NO: 239:

AUGGGCCUAA GAUCCCG                                                17

(2) INFORMATION FOR SEQ ID NO: 240:

(i) SEQUENCE CHARACTERISTICS:

(A) LENGTH:           17 base pairs
      (B) TYPE:             nucleic acid
      (C) STRANDEDNESS:     single
      (D) TOPOLOGY:         linear (xi) SEQUENCE DESCRIPTION: SEQ ID NO: 240:

CCUAAGAUCC CGUCCAU                                                17

(2) INFORMATION FOR SEQ ID NO: 241:

(i) SEQUENCE CHARACTERISTICS:

```
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 241:

GAUCCCGUCC AUCGCCA                                                    17

(2) INFORMATION FOR SEQ ID NO: 242:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 242:

CCGUCCAUCG CCACUGG                                                    17

(2) INFORMATION FOR SEQ ID NO: 243:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 243:

GGGGCCCUCC UCUUGCU                                                    17

(2) INFORMATION FOR SEQ ID NO: 244:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 244:

GCCCUCCUCU UGCUGCU                                                    17

(2) INFORMATION FOR SEQ ID NO: 245:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 245:

CCUCCUCUUG CUGCUGG                                                    17

(2) INFORMATION FOR SEQ ID NO: 246:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 246:

CUGGGGAUCG GCCUCUU                                                    17
```

(2) INFORMATION FOR SEQ ID NO: 247:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 247:

AUCGGCCUCU UCAUGCG                                       17

(2) INFORMATION FOR SEQ ID NO: 248:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 248:

CGGCCUCUUC AUGCGAA                                       17

(2) INFORMATION FOR SEQ ID NO: 249:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 249:

GGCCUCUUCA UGCGAAG                                       17

(2) INFORMATION FOR SEQ ID NO: 250:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 250:

CGCCACAUCG UUCGGAA                                       17

(2) INFORMATION FOR SEQ ID NO: 251:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 251:

CACAUCGUUC GGAAGCG                                     17

(2) INFORMATION FOR SEQ ID NO: 252:

(i) SEQUENCE CHARACTERISTICS:

(A) LENGTH:         17 base pairs
        (B) TYPE:           nucleic acid
        (C) STRANDEDNESS:   single

```
            (D) TOPOLOGY:           linear (xi) SEQUENCE DESCRIPTION: SEQ ID NO: 252:

ACAUCGUUCG GAAGCGC                                                    17

(2) INFORMATION FOR SEQ ID NO: 253:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 253:

AGGGAGCUUG UGGAGCC                                                    17

(2) INFORMATION FOR SEQ ID NO: 254:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 254:

UGGAGCCUCU UACACCC                                                    17

(2) INFORMATION FOR SEQ ID NO: 255:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 255:

GAGCCUCUUA CACCCAG                                                    17

(2) INFORMATION FOR SEQ ID NO: 256:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 256:

AGCCUCUUAC ACCCAGU                                                    17

(2) INFORMATION FOR SEQ ID NO: 257:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 257:

GAGAAGCUCC CAACCAA                                                    17

(2) INFORMATION FOR SEQ ID NO: 258:
```

```
       (i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 258:

ACCAAGCUCU CUUGAGG                                                17

(2)  INFORMATION FOR SEQ ID NO: 259:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 259:

CAAGCUCUCU UGAGGAU                                                17

(2)  INFORMATION FOR SEQ ID NO: 260:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 260:

AGCUCUCUUG AGGAUCU                                                17

(2)  INFORMATION FOR SEQ ID NO: 261:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 261:

UUGAGGAUCU UGAAGGA                                                17

(2)  INFORMATION FOR SEQ ID NO: 262:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 262:

GAGGAUCUUG AAGGAAA                                                17

(2)  INFORMATION FOR SEQ ID NO: 263:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 263:
```

```
      AACUGAAUUC AAAAAGA                                                    17

(2)   INFORMATION FOR SEQ ID NO: 264:

(i)  SEQUENCE CHARACTERISTICS:
           (A)  LENGTH:            17 base pairs
           (B)  TYPE:              nucleic acid
           (C)  STRANDEDNESS:      single
           (D)  TOPOLOGY:          linear (xi) SEQUENCE DESCRIPTION: SEQ ID NO: 264:

ACUGAAUUCA AAAAGAU                                                    17

(2)   INFORMATION FOR SEQ ID NO: 265:

(i)  SEQUENCE CHARACTERISTICS:
           (A)  LENGTH:            17 base pairs
           (B)  TYPE:              nucleic acid
           (C)  STRANDEDNESS:      single
           (D)  TOPOLOGY:          linear (xi) SEQUENCE DESCRIPTION: SEQ ID NO: 265:

AAAAAGAUCA AAGUGCU                                                    17

(2)   INFORMATION FOR SEQ ID NO: 266:

(i)  SEQUENCE CHARACTERISTICS:
           (A)  LENGTH:            17 base pairs
           (B)  TYPE:              nucleic acid
           (C)  STRANDEDNESS:      single
           (D)  TOPOLOGY:          linear (xi) SEQUENCE DESCRIPTION: SEQ ID NO: 266:

GCUGGGCUCC GGUGCGU                                                    17

(2)   INFORMATION FOR SEQ ID NO: 267:

(i)  SEQUENCE CHARACTERISTICS:
           (A)  LENGTH:            17 base pairs
           (B)  TYPE:              nucleic acid
           (C)  STRANDEDNESS:      single
           (D)  TOPOLOGY:          linear (xi) SEQUENCE DESCRIPTION: SEQ ID NO: 267:

CGGUGCGUUC GGCACGG                                                    17

(2)   INFORMATION FOR SEQ ID NO: 268:

(i)  SEQUENCE CHARACTERISTICS:
           (A)  LENGTH:            17 base pairs
           (B)  TYPE:              nucleic acid
           (C)  STRANDEDNESS:      single
           (D)  TOPOLOGY:          linear (xi) SEQUENCE DESCRIPTION: SEQ ID NO: 268:

GGUGCGUUCG GCACGGU                                                    17

(2)   INFORMATION FOR SEQ ID NO: 269:

(i)  SEQUENCE CHARACTERISTICS:
           (A)  LENGTH:            17 base pairs
           (B)  TYPE:              nucleic acid
```

(C)  STRANDEDNESS:       single
          (D)  TOPOLOGY:           linear (xi) SEQUENCE DESCRIPTION: SEQ ID NO: 269:

CACGGUGUAU AAGGGAC                                                  17

(2) INFORMATION FOR SEQ ID NO: 270:

(i) SEQUENCE CHARACTERISTICS:
          (A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 270:

CGGUGUAUAA GGGACUC                                                  17

(2) INFORMATION FOR SEQ ID NO: 271:

(i) SEQUENCE CHARACTERISTICS:
          (A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 271:

AAGGGACUCU GGAUCCC                                                  17

(2) INFORMATION FOR SEQ ID NO: 272:

(i) SEQUENCE CHARACTERISTICS:
          (A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 272:

CUCUGGAUCC CAGAAGG                                                  17

(2) INFORMATION FOR SEQ ID NO: 273:

(i) SEQUENCE CHARACTERISTICS:
          (A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 273:

GAGAAAGUUA AAAUUCC                                                  17

(2) INFORMATION FOR SEQ ID NO: 274:

(i) SEQUENCE CHARACTERISTICS:
          (A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 274:

AGAAAGUUAA AAUUCCC                                                  17

(2) INFORMATION FOR SEQ ID NO: 275:

```
    (i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 275:

GUUAAAAUUC CCGUCGC                                              17

(2) INFORMATION FOR SEQ ID NO: 276:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 276:

UUAAAAUUCC CGUCGCU                                              17

(2) INFORMATION FOR SEQ ID NO: 277:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 277:

AUUCCCGUCG CUAUCAA                                              17

(2) INFORMATION FOR SEQ ID NO: 278:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 278:

CCGUCGCUAU CAAGGAA                                              17

(2) INFORMATION FOR SEQ ID NO: 279:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 279:

GUCGCUAUCA AGGAAUU                                              17

(2) INFORMATION FOR SEQ ID NO: 280:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 280:
```

```
CAAGGAAUUA AGAGAAG                                              17

(2) INFORMATION FOR SEQ ID NO: 281:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 281:

AAGGAAUUAA GAGAAGC                                              17

(2) INFORMATION FOR SEQ ID NO: 282:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 282:

AGCAACAUCU CCGAAAG                                              17

(2) INFORMATION FOR SEQ ID NO: 283:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 283:

CAACAUCUCC GAAAGCC                                              17

(2) INFORMATION FOR SEQ ID NO: 284:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 284:

AAGGAAAUCC UCGAUGA                                              17

(2) INFORMATION FOR SEQ ID NO: 285:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 285:

GAAAUCCUCG AUGAAGC                                              17

(2) INFORMATION FOR SEQ ID NO: 286:

(i) SEQUENCE CHARACTERISTICS:

(A) LENGTH:           17 base pairs
```

```
            (B)  TYPE:              nucleic acid
            (C)  STRANDEDNESS:      single
            (D)  TOPOLOGY:          linear (xi) SEQUENCE DESCRIPTION: SEQ ID NO: 286:

UGAAGCCUAC GUGAUGG                                                17

(2)  INFORMATION FOR SEQ ID NO: 287:

(i)  SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 287:

CUGGGCAUCU GCCUCAC                                                17

(2)  INFORMATION FOR SEQ ID NO: 288:

(i)  SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 288:

AUCUGCCUCA CCUCCAC                                                17

(2)  INFORMATION FOR SEQ ID NO: 289:

(i)  SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 289:

CCUCACCUCC ACCGUGC                                                17

(2)  INFORMATION FOR SEQ ID NO: 290:

(i)  SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 290:

GUGCAACUCA UCACGCA                                                17

(2)  INFORMATION FOR SEQ ID NO: 291:

(i)  SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 291:

CAACUCAUCA CGCAGCU                                                17
```

```
(2) INFORMATION FOR SEQ ID NO: 292:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 292:

ACGCAGCUCA UGCCCUU                                                17

(2) INFORMATION FOR SEQ ID NO: 293:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 293:

CAUGCCCUUC GGCUGCC                                                17

(2) INFORMATION FOR SEQ ID NO: 294:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 294:

AUGCCCUUCG GCUGCCU                                                17

(2) INFORMATION FOR SEQ ID NO: 295:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 295:

GGCUGCCUCC UGGACUA                                                17

(2) INFORMATION FOR SEQ ID NO: 296:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 296:

CCUGGACUAU GUCCGGG                                                17

(2) INFORMATION FOR SEQ ID NO: 297:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear
```

```
    (xi) SEQUENCE DESCRIPTION: SEQ ID NO: 297:

GACUAUGUCC GGGAACA                                                          17

(2) INFORMATION FOR SEQ ID NO: 298:

(i) SEQUENCE CHARACTERISTICS:

(A) LENGTH:         17 base pairs
            (B) TYPE:           nucleic acid
            (C) STRANDEDNESS:   single
            (D) TOPOLOGY:       linear (xi) SEQUENCE DESCRIPTION: SEQ ID NO: 298:

AAGACAAUAU UGGCUCC                                                          17

(2) INFORMATION FOR SEQ ID NO: 299:

(i) SEQUENCE CHARACTERISTICS:

(A) LENGTH:         17 base pairs
            (B) TYPE:           nucleic acid
            (C) STRANDEDNESS:   single
            (D) TOPOLOGY:       linear (xi) SEQUENCE DESCRIPTION: SEQ ID NO: 299:

GACAAUAUUG GCUCCCA                                                          17

(2) INFORMATION FOR SEQ ID NO: 300:

(i) SEQUENCE CHARACTERISTICS:

(A) LENGTH:         17 base pairs
            (B) TYPE:           nucleic acid
            (C) STRANDEDNESS:   single
            (D) TOPOLOGY:       linear (xi) SEQUENCE DESCRIPTION: SEQ ID NO: 300:

UAUUGGCUCC CAGUACC                                                          17

(2) INFORMATION FOR SEQ ID NO: 301:

(i) SEQUENCE CHARACTERISTICS:

(A) LENGTH:         17 base pairs
            (B) TYPE:           nucleic acid
            (C) STRANDEDNESS:   single
            (D) TOPOLOGY:       linear (xi) SEQUENCE DESCRIPTION: SEQ ID NO: 301:

CUCCCAGUAC CUGCUCA                                                          17

(2) INFORMATION FOR SEQ ID NO: 302:

(i) SEQUENCE CHARACTERISTICS:

(A) LENGTH:         17 base pairs
            (B) TYPE:           nucleic acid
            (C) STRANDEDNESS:   single
            (D) TOPOLOGY:       linear (xi) SEQUENCE DESCRIPTION: SEQ ID NO: 302:

UACCUGCUCA ACUGGUG                                                          17

(2) INFORMATION FOR SEQ ID NO: 303:

(i) SEQUENCE CHARACTERISTICS:
```

```
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 303:

GUGCAGAUCG CAAAGGG                                                      17

(2) INFORMATION FOR SEQ ID NO: 304:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 304:

CAUGAACUAC UUGGAGG                                                      17

(2) INFORMATION FOR SEQ ID NO: 305:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 305:

GAACUACUUG GAGGACC                                                      17

(2) INFORMATION FOR SEQ ID NO: 306:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 306:

AGGACCGUCG CUUGGUG                                                      17

(2) INFORMATION FOR SEQ ID NO: 307:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 307:

CCGUCGCUUG GUGCACC                                                      17

(2) INFORMATION FOR SEQ ID NO: 308:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 308:

AGGAACGUAC UGGUGAA                                                      17
```

(2) INFORMATION FOR SEQ ID NO: 309:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 309:

CAGCAUGUCA AGAUCAC                                      17

(2) INFORMATION FOR SEQ ID NO: 310:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 310:

GUCAAGAUCA CAGAUUU                                      17

(2) INFORMATION FOR SEQ ID NO: 311:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 311:

UCACAGAUUU UGGGCUG                                      17

(2) INFORMATION FOR SEQ ID NO: 312:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 312:

CACAGAUUUU GGGCUGG                                      17

(2) INFORMATION FOR SEQ ID NO: 313:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 313:

ACAGAUUUUG GGCUGGC                                      17

(2) INFORMATION FOR SEQ ID NO: 314:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 314:

GAAAGAAUAC CAUGCAG                                                17

(2) INFORMATION FOR SEQ ID NO: 315:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 315:

AAGUGCCUAU CAAGUGG                                                17

(2) INFORMATION FOR SEQ ID NO: 316:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 316:

GUGCCUAUCA AGUGGAU                                                17

(2) INFORMATION FOR SEQ ID NO: 317:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 317:

GAUGGCAUUG GAAUCAA                                                17

(2) INFORMATION FOR SEQ ID NO: 318:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 318:

AUUGGAAUCA AUUUAC                                                 17

(2) INFORMATION FOR SEQ ID NO: 319:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 319:

GAAUCAAUUU UACACAG                                                17

(2) INFORMATION FOR SEQ ID NO: 320:

(i) SEQUENCE CHARACTERISTICS:

```
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 320:

AAUCAAUUUU ACACAGA                                                  17

(2) INFORMATION FOR SEQ ID NO: 321:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 321:

AUCAAUUUUA CACAGAA                                                  17

(2) INFORMATION FOR SEQ ID NO: 322:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 322:

UCAAUUUUAC ACAGAAU                                                  17

(2) INFORMATION FOR SEQ ID NO: 323:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 323:

CACAGAAUCU AUACCCA                                                  17

(2) INFORMATION FOR SEQ ID NO: 324:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 324:

CAGAAUCUAU ACCCACC                                                  17

(2) INFORMATION FOR SEQ ID NO: 325:

(i) SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 325:

GAAUCUAUAC CCACCAG                                                  17
```

(2) INFORMATION FOR SEQ ID NO: 326:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 326:

AGUGAUGUCU GGAGCUA      17

(2) INFORMATION FOR SEQ ID NO: 327:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 327:

CUGGAGCUAC GGGGUGA      17

(2) INFORMATION FOR SEQ ID NO: 328:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 328:

GUGACCGUUU GGGAGUU      17

(2) INFORMATION FOR SEQ ID NO: 329:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 329:

UGACCGUUUG GGAGUUG      17

(2) INFORMATION FOR SEQ ID NO: 330:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 330:

UUGGGAGUUG AUGACCU      17

(2) INFORMATION FOR SEQ ID NO: 331:

(i) SEQUENCE CHARACTERISTICS:

(A) LENGTH: 17 base pairs
        (B) TYPE: nucleic acid
        (C) STRANDEDNESS: single (D)  TOPOLOGY:           linear (xi)  SEQUENCE DESCRIPTION: SEQ ID NO: 331:

GAUGACCUUU GGAUCCA                                                17

(2)  INFORMATION FOR SEQ ID NO: 332:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 332:

AUGACCUUUG GAUCCAA                                                17

(2)  INFORMATION FOR SEQ ID NO: 333:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 333:

CUUUGGAUCC AAGCCAU                                                17

(2)  INFORMATION FOR SEQ ID NO: 334:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 334:

CAAGCCAUAU GACGGAA                                                17

(2)  INFORMATION FOR SEQ ID NO: 335:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 335:

GACGGAAUCC CUGCCAG                                                17

(2)  INFORMATION FOR SEQ ID NO: 336:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 336:

AGCGAGAUCU CCUCCAU                                                17

(2)  INFORMATION FOR SEQ ID NO: 337:

(i) SEQUENCE CHARACTERISTICS:

(A) LENGTH:           17 base pairs
    (B) TYPE:             nucleic acid
    (C) STRANDEDNESS:    single
    (D) TOPOLOGY:        linear (xi) SEQUENCE DESCRIPTION: SEQ ID NO: 337:

CGAGAUCUCC UCCAUCC                                   17

(2) INFORMATION FOR SEQ ID NO: 338:

(i) SEQUENCE CHARACTERISTICS:

(A) LENGTH:           17 base pairs
    (B) TYPE:              nucleic acid
    (C) STRANDEDNESS:    single
    (D) TOPOLOGY:        linear (xi) SEQUENCE DESCRIPTION: SEQ ID NO: 338:

GAUCUCCUCC AUCCUGG                                   17

(2) INFORMATION FOR SEQ ID NO: 339:

(i) SEQUENCE CHARACTERISTICS:

(A) LENGTH:           17 base pairs
    (B) TYPE:              nucleic acid
    (C) STRANDEDNESS:    single
    (D) TOPOLOGY:        linear (xi) SEQUENCE DESCRIPTION: SEQ ID NO: 339:

UCCUCCAUCC UGGAGAA                                   17

(2) INFORMATION FOR SEQ ID NO: 340:

(i) SEQUENCE CHARACTERISTICS:

(A) LENGTH:           17 base pairs
    (B) TYPE:              nucleic acid
    (C) STRANDEDNESS:    single
    (D) TOPOLOGY:        linear (xi) SEQUENCE DESCRIPTION: SEQ ID NO: 340:

GAACGCCUCC CUCAGCC                                   17

(2) INFORMATION FOR SEQ ID NO: 341:

(i) SEQUENCE CHARACTERISTICS:

(A) LENGTH:           17 base pairs
    (B) TYPE:              nucleic acid
    (C) STRANDEDNESS:    single
    (D) TOPOLOGY:        linear (xi) SEQUENCE DESCRIPTION: SEQ ID NO: 341:

GCCUCCCUCA GCCACCC                                   17

(2) INFORMATION FOR SEQ ID NO: 342:

(i) SEQUENCE CHARACTERISTICS:

(A) LENGTH:           17 base pairs
    (B) TYPE:              nucleic acid
    (C) STRANDEDNESS:    single
    (D) TOPOLOGY:        linear (xi) SEQUENCE DESCRIPTION: SEQ ID NO: 342:

```
CCACCCAUAU GUACCAU                                                   17

(2) INFORMATION FOR SEQ ID NO: 343:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 343:

CCAUAUGUAC CAUCGAU                                                   17

(2) INFORMATION FOR SEQ ID NO: 344:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 344:

UGUACCAUCG AUGUCUA                                                   17

(2) INFORMATION FOR SEQ ID NO: 345:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 345:

AUCGAUGUCU ACAUGAU                                                   17

(2) INFORMATION FOR SEQ ID NO: 346:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 346:

CGAUGUCUAC AUGAUCA                                                   17

(2) INFORMATION FOR SEQ ID NO: 347:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 347:

UACAUGAUCA UGGUCAA                                                   17

(2) INFORMATION FOR SEQ ID NO: 348:

(i) SEQUENCE CHARACTERISTICS:

(A) LENGTH:         17 base pairs
        (B) TYPE:           nucleic acid
```

```
            (C)  STRANDEDNESS:       single
            (D)  TOPOLOGY:           linear (xi) SEQUENCE DESCRIPTION: SEQ ID NO: 348:

AUCAUGGUCA AGUGCUG                                                    17

(2) INFORMATION FOR SEQ ID NO: 349:

(i) SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 349:

UGGAUGAUAG ACGCAGA                                                    17

(2) INFORMATION FOR SEQ ID NO: 350:

(i) SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 350:

ACGCAGAUAG UCGCCCA                                                    17

(2) INFORMATION FOR SEQ ID NO: 351:

(i) SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 351:

CAGAUAGUCG CCCAAAG                                                    17

(2) INFORMATION FOR SEQ ID NO: 352:

(i) SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 352:

CCCAAAGUUC CGUGAGU                                                    17

(2) INFORMATION FOR SEQ ID NO: 353:

(i) SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi) SEQUENCE DESCRIPTION: SEQ ID NO: 353:

CCAAAGUUCC GUGAGUU                                                    17

(2) INFORMATION FOR SEQ ID NO: 354:
```

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 354:

CCGUGAGUUG AUCAUCG                                                  17

(2) INFORMATION FOR SEQ ID NO: 355:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 355:

GAGUUGAUCA UCGAAUU                                                  17

(2) INFORMATION FOR SEQ ID NO: 356:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 356:

UUGAUCAUCG AAUUCUC                                                  17

(2) INFORMATION FOR SEQ ID NO: 357:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 357:

CAUCGAAUUC UCCAAAA                                                  17

(2) INFORMATION FOR SEQ ID NO: 358:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 358:

AUCGAAUUCU CCAAAAU                                                  17

(2) INFORMATION FOR SEQ ID NO: 359:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 359:

```
CGAAUUCUCC AAAAUGG                                                      17

(2) INFORMATION FOR SEQ ID NO: 360:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 360:

CCAGCGCUAC CUUGUCA                                                      17

(2) INFORMATION FOR SEQ ID NO: 361:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 361:

CGCUACCUUG UCAUUCA                                                      17

(2) INFORMATION FOR SEQ ID NO: 362:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 362:

UACCUUGUCA UUCAGGG                                                      17

(2) INFORMATION FOR SEQ ID NO: 363:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 363:

CUUGUCAUUC AGGGGGA                                                      17

(2) INFORMATION FOR SEQ ID NO: 364:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 364:

UUGUCAUUCA GGGGGAU                                                      17

(2) INFORMATION FOR SEQ ID NO: 365:

(i) SEQUENCE CHARACTERISTICS:

(A) LENGTH:          17 base pairs
```

```
          (B)  TYPE:               nucleic acid
          (C)  STRANDEDNESS:       single
          (D)  TOPOLOGY:           linear (xi) SEQUENCE DESCRIPTION: SEQ ID NO: 365:

GAAUGCAUUU GCCAAGU                                              17

(2) INFORMATION FOR SEQ ID NO: 366:

(i)  SEQUENCE CHARACTERISTICS:
          (A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 366:

AAUGCAUUUG CCAAGUC                                              17

(2) INFORMATION FOR SEQ ID NO: 367:

(i)  SEQUENCE CHARACTERISTICS:
          (A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 367:

UGCCAAGUCC UACAGAC                                              17

(2) INFORMATION FOR SEQ ID NO: 368:

(i)  SEQUENCE CHARACTERISTICS:
          (A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 368:

CAAGUCCUAC AGACUCC                                              17

(2) INFORMATION FOR SEQ ID NO: 369:

(i)  SEQUENCE CHARACTERISTICS:
          (A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 369:

UACAGACUCC AACUUCU                                              17

(2) INFORMATION FOR SEQ ID NO: 370:

(i)  SEQUENCE CHARACTERISTICS:
          (A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 370:

CUCCAACUUC UACCGUG                                              17
```

(2) INFORMATION FOR SEQ ID NO: 371:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 371:

UCCAACUUCU ACCGUGC        17

(2) INFORMATION FOR SEQ ID NO: 372:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 372:

CAACUUCUAC CGUGCCC        17

(2) INFORMATION FOR SEQ ID NO: 373:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 373:

CGACGAGUAC CUCAUCC        17

(2) INFORMATION FOR SEQ ID NO: 374:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 374:

GAGUACCUCA UCCCACA        17

(2) INFORMATION FOR SEQ ID NO: 375:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 375:

UACCUCAUCC CACAGCA        17

(2) INFORMATION FOR SEQ ID NO: 376:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 376:

GCAGGGCUUC UUCAGCA                                                              17

(2) INFORMATION FOR SEQ ID NO: 377:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 377:

CAGGGCUUCU UCAGCAG                                                              17

(2) INFORMATION FOR SEQ ID NO: 378:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 378:

GGGCUUCUUC AGCAGCC                                                              17

(2) INFORMATION FOR SEQ ID NO: 379:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 379:

GGCUUCUUCA GCAGCCC                                                              17

(2) INFORMATION FOR SEQ ID NO: 380:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 380:

CAGCCCCUCC ACGUCAC                                                              17

(2) INFORMATION FOR SEQ ID NO: 381:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 381:

CUCCACGUCA CGGACUC                                                              17

(2) INFORMATION FOR SEQ ID NO: 382:

(i) SEQUENCE CHARACTERISTICS:

```
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 382:

CACGGACUCC CCUCCUG                                                    17

(2) INFORMATION FOR SEQ ID NO: 383:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 383:

ACUCCCCUCC UGAGCUC                                                    17

(2) INFORMATION FOR SEQ ID NO: 384:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 384:

CCUGAGCUCU CUGAGUG                                                    17

(2) INFORMATION FOR SEQ ID NO: 385:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 385:

UGAGCUCUCU GAGUGCA                                                    17

(2) INFORMATION FOR SEQ ID NO: 386:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 386:

GCAACAAUUC CACCGUG                                                    17

(2) INFORMATION FOR SEQ ID NO: 387:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 387:

CAACAAUUCC ACCGUGG                                                    17
```

(2) INFORMATION FOR SEQ ID NO: 388:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 388:

CCGUGGCUUG CAUUGAU                                17

(2) INFORMATION FOR SEQ ID NO: 389:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 389:

GCUUGCAUUG AUAGAAA                                17

(2) INFORMATION FOR SEQ ID NO: 390:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 390:

GCAUUGAUAG AAAUGGG                                17

(2) INFORMATION FOR SEQ ID NO: 391:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 391:

AAAGCUGUCC CAUCAAG                                17

(2) INFORMATION FOR SEQ ID NO: 392:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 392:

UGUCCCAUCA AGGAAGA                                17

(2) INFORMATION FOR SEQ ID NO: 393:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 393:

AGACAGCUUC UUGCAGC                                                17

(2) INFORMATION FOR SEQ ID NO: 394:

(i) SEQUENCE CHARACTERISTICS:

(A) LENGTH:         17 base pairs
      (B) TYPE:           nucleic acid
      (C) STRANDEDNESS:   single
      (D) TOPOLOGY:       linear (xi) SEQUENCE DESCRIPTION: SEQ ID NO: 394:

GACAGCUUCU UGCAGCG                                                17

(2) INFORMATION FOR SEQ ID NO: 395:

(i) SEQUENCE CHARACTERISTICS:

(A) LENGTH:         17 base pairs
      (B) TYPE:           nucleic acid
      (C) STRANDEDNESS:   single
      (D) TOPOLOGY:       linear (xi) SEQUENCE DESCRIPTION: SEQ ID NO: 395:

CAGCUUCUUG CAGCGAU                                                17

(2) INFORMATION FOR SEQ ID NO: 396:

(i) SEQUENCE CHARACTERISTICS:

(A) LENGTH:         17 base pairs
      (B) TYPE:           nucleic acid
      (C) STRANDEDNESS:   single
      (D) TOPOLOGY:       linear (xi) SEQUENCE DESCRIPTION: SEQ ID NO: 396:

GCAGCGAUAC AGCUCAG                                                17

(2) INFORMATION FOR SEQ ID NO: 397:

(i) SEQUENCE CHARACTERISTICS:

(A) LENGTH:         17 base pairs
      (B) TYPE:           nucleic acid
      (C) STRANDEDNESS:   single
      (D) TOPOLOGY:       linear (xi) SEQUENCE DESCRIPTION: SEQ ID NO: 397:

AUACAGCUCA GACCCCA                                                17

(2) INFORMATION FOR SEQ ID NO: 398:

(i) SEQUENCE CHARACTERISTICS:

(A) LENGTH:         17 base pairs
      (B) TYPE:           nucleic acid
      (C) STRANDEDNESS:   single
      (D) TOPOLOGY:       linear (xi) SEQUENCE DESCRIPTION: SEQ ID NO: 398:

AGGCGCCUUG ACUGAGG                                                17

(2) INFORMATION FOR SEQ ID NO: 399:

(i) SEQUENCE CHARACTERISTICS:

```
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 399:

GACAGCAUAG ACGACAC                                                      17

(2) INFORMATION FOR SEQ ID NO: 400:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 400:

CGACACCUUC CUCCCAG                                                      17

(2) INFORMATION FOR SEQ ID NO: 401:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 401:

GACACCUUCC UCCCAGU                                                      17

(2) INFORMATION FOR SEQ ID NO: 402:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 402:

ACCUUCCUCC CAGUGCC                                                      17

(2) INFORMATION FOR SEQ ID NO: 403:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 403:

GCCUGAAUAC AUAAACC                                                      17

(2) INFORMATION FOR SEQ ID NO: 404:

(i) SEQUENCE CHARACTERISTICS:
            (A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 404:

GAAUACAUAA ACCAGUC                                                      17
```

```
(2)  INFORMATION FOR SEQ ID NO: 405:

(i)  SEQUENCE CHARACTERISTICS:

(A)  LENGTH:           17 base pairs
          (B)  TYPE:              nucleic acid
          (C)  STRANDEDNESS:      single
          (D)  TOPOLOGY:          linear (xi) SEQUENCE DESCRIPTION: SEQ ID NO: 405:

AAACCAGUCC GUUCCCA                                                  17

(2)  INFORMATION FOR SEQ ID NO: 406:

(i)  SEQUENCE CHARACTERISTICS:

(A)  LENGTH:           17 base pairs
          (B)  TYPE:              nucleic acid
          (C)  STRANDEDNESS:      single
          (D)  TOPOLOGY:          linear (xi) SEQUENCE DESCRIPTION: SEQ ID NO: 406:

CAGUCCGUUC CCAAAAG                                                  17

(2)  INFORMATION FOR SEQ ID NO: 407:

(i)  SEQUENCE CHARACTERISTICS:

(A)  LENGTH:           17 base pairs
          (B)  TYPE:              nucleic acid
          (C)  STRANDEDNESS:      single
          (D)  TOPOLOGY:          linear (xi) SEQUENCE DESCRIPTION: SEQ ID NO: 407:

AGUCCGUUCC CAAAAGG                                                  17

(2)  INFORMATION FOR SEQ ID NO: 408:

(i)  SEQUENCE CHARACTERISTICS:

(A)  LENGTH:           17 base pairs
          (B)  TYPE:              nucleic acid
          (C)  STRANDEDNESS:      single
          (D)  TOPOLOGY:          linear (xi) SEQUENCE DESCRIPTION: SEQ ID NO: 408:

CGCUGGCUCU GUGCAGA                                                  17

(2)  INFORMATION FOR SEQ ID NO: 409:

(i)  SEQUENCE CHARACTERISTICS:

(A)  LENGTH:           17 base pairs
          (B)  TYPE:              nucleic acid
          (C)  STRANDEDNESS:      single
          (D)  TOPOLOGY:          linear (xi) SEQUENCE DESCRIPTION: SEQ ID NO: 409:

UGCAGAAUCC UGUCUAU                                                  17

(2)  INFORMATION FOR SEQ ID NO: 410:

(i)  SEQUENCE CHARACTERISTICS:

(A)  LENGTH:           17 base pairs
          (B)  TYPE:              nucleic acid
          (C)  STRANDEDNESS:      single
```

(D) TOPOLOGY:          linear (xi) SEQUENCE DESCRIPTION: SEQ ID NO: 410:

AAUCCUGUCU AUCACAA                                                      17

(2) INFORMATION FOR SEQ ID NO: 411:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 411:

UCCUGUCUAU CACAAUC                                                      17

(2) INFORMATION FOR SEQ ID NO: 412:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 412:

CUGUCUAUCA CAAUCAG                                                      17

(2) INFORMATION FOR SEQ ID NO: 413:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 413:

AUCACAAUCA GCCUCUG                                                      17

(2) INFORMATION FOR SEQ ID NO: 414:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 414:

AUCAGCCUCU GAACCCC                                                      17

(2) INFORMATION FOR SEQ ID NO: 415:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 415:

CCCACACUAC CAGGACC                                                      17

(2) INFORMATION FOR SEQ ID NO: 416:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 416:

CCCCGAGUAU CUCAACA                                                          17

(2) INFORMATION FOR SEQ ID NO: 417:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 417:

CCGAGUAUCU CAACACU                                                          17

(2) INFORMATION FOR SEQ ID NO: 418:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 418:

GAGUAUCUCA ACACUGU                                                          17

(2) INFORMATION FOR SEQ ID NO: 419:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 419:

AACACUGUCC AGCCCAC                                                          17

(2) INFORMATION FOR SEQ ID NO: 420:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 420:

ACCUGUGUCA ACAGCAC                                                          17

(2) INFORMATION FOR SEQ ID NO: 421:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 421:

```
CAGCACAUUC GACAGCC                                                    17

(2) INFORMATION FOR SEQ ID NO: 422:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 422:

AGCACAUUCG ACAGCCC                                                    17

(2) INFORMATION FOR SEQ ID NO: 423:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 423:

CACCAAAUUA GCCUGGA                                                    17

(2) INFORMATION FOR SEQ ID NO: 424:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 424:

ACCAAAUUAG CCUGGAC                                                    17

(2) INFORMATION FOR SEQ ID NO: 425:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 425:

CCCUGACUAC CAGCAGG                                                    17

(2) INFORMATION FOR SEQ ID NO: 426:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 426:

GCAGGACUUC UUUCCCA                                                    17

(2) INFORMATION FOR SEQ ID NO: 427:

(i) SEQUENCE CHARACTERISTICS:

(A) LENGTH:          17 base pairs
         (B) TYPE:            nucleic acid
```

```
            (C) STRANDEDNESS:        single
            (D) TOPOLOGY:            linear (xi) SEQUENCE DESCRIPTION: SEQ ID NO: 427:

CAGGACUUCU UUCCCAA                                              17

(2) INFORMATION FOR SEQ ID NO: 428:

(i) SEQUENCE CHARACTERISTICS:

(A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 428:

GGACUUCUUU CCCAAGG                                              17

(2) INFORMATION FOR SEQ ID NO: 429:

(i) SEQUENCE CHARACTERISTICS:

(A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 429:

GACUUCUUUC CCAAGGA                                              17

(2) INFORMATION FOR SEQ ID NO: 430:

(i) SEQUENCE CHARACTERISTICS:

(A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 430:

ACUUCUUUCC CAAGGAA                                              17

(2) INFORMATION FOR SEQ ID NO: 431:

(i) SEQUENCE CHARACTERISTICS:

(A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 431:

AAUGGCAUCU UUAAGGG                                              17

(2) INFORMATION FOR SEQ ID NO: 432:

(i) SEQUENCE CHARACTERISTICS:

(A) LENGTH:              17 base pairs
            (B) TYPE:                nucleic acid
            (C) STRANDEDNESS:        single
            (D) TOPOLOGY:            linear (xi) SEQUENCE DESCRIPTION: SEQ ID NO: 432:

UGGCAUCUUU AAGGGCU                                              17

(2) INFORMATION FOR SEQ ID NO: 433:
```

```
    (i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 433:

GGCAUCUUUA AGGGCUC                                              17

(2) INFORMATION FOR SEQ ID NO: 434:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 434:

GCAUCUUUAA GGGCUCC                                              17

(2) INFORMATION FOR SEQ ID NO: 435:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 435:

UAAGGGCUCC ACAGCUG                                              17

(2) INFORMATION FOR SEQ ID NO: 436:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 436:

UGCAGAAUAC CUAAGGG                                              17

(2) INFORMATION FOR SEQ ID NO: 437:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 437:

GAAUACCUAA GGGUCGC                                              17

(2) INFORMATION FOR SEQ ID NO: 438:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 438:
```

CUAAGGGUCG CGCCACA					17

(2) INFORMATION FOR SEQ ID NO: 439:

(i) SEQUENCE CHARACTERISTICS:

(A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO: 439:

CAGUGAAUUU AUUGGAG					17

(2) INFORMATION FOR SEQ ID NO: 440:

(i) SEQUENCE CHARACTERISTICS:

(A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO: 440:

AGUGAAUUUA UUGGAGC					17

(2) INFORMATION FOR SEQ ID NO: 441:

(i) SEQUENCE CHARACTERISTICS:

(A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO: 441:

GUGAAUUUAU UGGAGCA					17

(2) INFORMATION FOR SEQ ID NO: 442:

(i) SEQUENCE CHARACTERISTICS:

(A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO: 442:

GAAUUUAUUG GAGCAUG					17

(2) INFORMATION FOR SEQ ID NO: 443:

(i) SEQUENCE CHARACTERISTICS:

(A) LENGTH: 17 base pairs
      (B) TYPE: nucleic acid
      (C) STRANDEDNESS: single
      (D) TOPOLOGY: linear (xi) SEQUENCE DESCRIPTION: SEQ ID NO: 443:

CGGAGGAUAG UAUGAGC					17

(2) INFORMATION FOR SEQ ID NO: 444:

(i) SEQUENCE CHARACTERISTICS:

(A) LENGTH: 17 base pairs

```
            (B)  TYPE:              nucleic acid
            (C)  STRANDEDNESS:      single
            (D)  TOPOLOGY:          linear (xi)  SEQUENCE DESCRIPTION: SEQ ID NO: 444:

AGGAUAGUAU GAGCCCU                                           17

(2)  INFORMATION FOR SEQ ID NO: 445:

(i)  SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 445:

UGAGCCCUAA AAAUCCA                                           17

(2)  INFORMATION FOR SEQ ID NO: 446:

(i)  SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 446:

CUAAAAAUCC AGACUCU                                           17

(2)  INFORMATION FOR SEQ ID NO: 447:

(i)  SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 447:

UCCAGACUCU UUCGAUA                                           17

(2)  INFORMATION FOR SEQ ID NO: 448:

(i)  SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 448:

CAGACUCUUU CGAUACC                                           17

(2)  INFORMATION FOR SEQ ID NO: 449:

(i)  SEQUENCE CHARACTERISTICS:
            (A)  LENGTH:            17 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 449:

AGACUCUUUC GAUACCC                                           17
```

(2) INFORMATION FOR SEQ ID NO: 450:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 450:

GACUCUUUCG AUACCCA    17

(2) INFORMATION FOR SEQ ID NO: 451:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 451:

CUUUCGAUAC CCAGGAC    17

(2) INFORMATION FOR SEQ ID NO: 452:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 452:

CAGCAGGUCC UCCAUCC    17

(2) INFORMATION FOR SEQ ID NO: 453:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 453:

CAGGUCCUCC AUCCCAA    17

(2) INFORMATION FOR SEQ ID NO: 454:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 454:

UCCUCCAUCC CAACAGC    17

(2) INFORMATION FOR SEQ ID NO: 455:

(i) SEQUENCE CHARACTERISTICS:

(A) LENGTH: 17 base pairs
        (B) TYPE: nucleic acid
        (C) STRANDEDNESS: single
        (D) TOPOLOGY: linear

```
    (xi) SEQUENCE DESCRIPTION: SEQ ID NO: 455:

GCCCGCAUUA GCUCUUA                                                    17

(2) INFORMATION FOR SEQ ID NO: 456:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 456:

CCCGCAUUAG CUCUUAG                                                    17

(2) INFORMATION FOR SEQ ID NO: 457:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 457:

CAUUAGCUCU UAGACCC                                                    17

(2) INFORMATION FOR SEQ ID NO: 458:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 458:

UUAGCUCUUA GACCCAC                                                    17

(2) INFORMATION FOR SEQ ID NO: 459:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 459:

UAGCUCUUAG ACCCACA                                                    17

(2) INFORMATION FOR SEQ ID NO: 460:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 460:

AGACUGGUUU UGCAACG                                                    17

(2) INFORMATION FOR SEQ ID NO: 461:

(i) SEQUENCE CHARACTERISTICS:
```

-continued

```
          (A)  LENGTH:              17 base pairs
          (B)  TYPE:                nucleic acid
          (C)  STRANDEDNESS:        single
          (D)  TOPOLOGY:            linear (xi) SEQUENCE DESCRIPTION: SEQ ID NO: 461:

GACUGGUUUU GCAACGU                                                  17

(2)  INFORMATION FOR SEQ ID NO: 462:

(i)  SEQUENCE CHARACTERISTICS:

(A)  LENGTH:              17 base pairs
          (B)  TYPE:                nucleic acid
          (C)  STRANDEDNESS:        single
          (D)  TOPOLOGY:            linear (xi) SEQUENCE DESCRIPTION: SEQ ID NO: 462:

ACUGGUUUUG CAACGUU                                                  17

(2)  INFORMATION FOR SEQ ID NO: 463:

(i)  SEQUENCE CHARACTERISTICS:

(A)  LENGTH:              17 base pairs
          (B)  TYPE:                nucleic acid
          (C)  STRANDEDNESS:        single
          (D)  TOPOLOGY:            linear (xi) SEQUENCE DESCRIPTION: SEQ ID NO: 463:

UGCAACGUUU ACACCGA                                                  17

(2)  INFORMATION FOR SEQ ID NO: 464:

(i)  SEQUENCE CHARACTERISTICS:

(A)  LENGTH:              17 base pairs
          (B)  TYPE:                nucleic acid
          (C)  STRANDEDNESS:        single
          (D)  TOPOLOGY:            linear (xi) SEQUENCE DESCRIPTION: SEQ ID NO: 464:

GCAACGUUUA CACCGAC                                                  17

(2)  INFORMATION FOR SEQ ID NO: 465:

(i)  SEQUENCE CHARACTERISTICS:

(A)  LENGTH:              17 base pairs
          (B)  TYPE:                nucleic acid
          (C)  STRANDEDNESS:        single
          (D)  TOPOLOGY:            linear (xi) SEQUENCE DESCRIPTION: SEQ ID NO: 465:

CAACGUUUAC ACCGACU                                                  17

(2)  INFORMATION FOR SEQ ID NO: 466:

(i)  SEQUENCE CHARACTERISTICS:

(A)  LENGTH:              17 base pairs
          (B)  TYPE:                nucleic acid
          (C)  STRANDEDNESS:        single
          (D)  TOPOLOGY:            linear (xi) SEQUENCE DESCRIPTION: SEQ ID NO: 466:

CACCGACUAG CCAGGAA                                                  17
```

(2) INFORMATION FOR SEQ ID NO: 467:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 467:

CAGGAAGUAC UUCCACC                                       17

(2) INFORMATION FOR SEQ ID NO: 468:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 468:

GAAGUACUUC CACCUCG                                       17

(2) INFORMATION FOR SEQ ID NO: 469:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 469:

AAGUACUUCC ACCUCGG                                       17

(2) INFORMATION FOR SEQ ID NO: 470:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 470:

UUCCACCUCG GGCACAU                                       17

(2) INFORMATION FOR SEQ ID NO: 471:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 471:

GGGCACAUUU UGGGAAG                                     17

(2) INFORMATION FOR SEQ ID NO: 472:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 472:

GGCACAUUUU GGGAAGU                                                    17

(2) INFORMATION FOR SEQ ID NO: 473:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 473:

GCACAUUUUG GGAAGUU                                                    17

(2) INFORMATION FOR SEQ ID NO: 474:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 474:

UGGGAAGUUG CAUUCCU                                                    17

(2) INFORMATION FOR SEQ ID NO: 475:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 475:

AGUUGCAUUC CUUUGUC                                                    17

(2) INFORMATION FOR SEQ ID NO: 476:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 476:

GUUGCAUUCC UUUGUCU                                                    17

(2) INFORMATION FOR SEQ ID NO: 477:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 477:

GCAUUCCUUU GUCUUCA                                                    17

(2) INFORMATION FOR SEQ ID NO: 478:

(i) SEQUENCE CHARACTERISTICS:

```
        (A)  LENGTH:            17 base pairs
        (B)  TYPE:              nucleic acid
        (C)  STRANDEDNESS:      single
        (D)  TOPOLOGY:          linear (xi) SEQUENCE DESCRIPTION: SEQ ID NO: 478:

CAUUCCUUUG UCUUCAA                                                     17

(2) INFORMATION FOR SEQ ID NO: 479:

(i) SEQUENCE CHARACTERISTICS:
        (A)  LENGTH:            17 base pairs
        (B)  TYPE:              nucleic acid
        (C)  STRANDEDNESS:      single
        (D)  TOPOLOGY:          linear (xi) SEQUENCE DESCRIPTION: SEQ ID NO: 479:

UCCUUUGUCU UCAAACU                                                     17

(2) INFORMATION FOR SEQ ID NO: 480:

(i) SEQUENCE CHARACTERISTICS:
        (A)  LENGTH:            17 base pairs
        (B)  TYPE:              nucleic acid
        (C)  STRANDEDNESS:      single
        (D)  TOPOLOGY:          linear (xi) SEQUENCE DESCRIPTION: SEQ ID NO: 480:

CUUUGUCUUC AAACUGU                                                     17

(2) INFORMATION FOR SEQ ID NO: 481:

(i) SEQUENCE CHARACTERISTICS:
        (A)  LENGTH:            17 base pairs
        (B)  TYPE:              nucleic acid
        (C)  STRANDEDNESS:      single
        (D)  TOPOLOGY:          linear (xi) SEQUENCE DESCRIPTION: SEQ ID NO: 481:

UUUGUCUUCA AACUGUG                                                     17

(2) INFORMATION FOR SEQ ID NO: 482:

(i) SEQUENCE CHARACTERISTICS:
        (A)  LENGTH:            17 base pairs
        (B)  TYPE:              nucleic acid
        (C)  STRANDEDNESS:      single
        (D)  TOPOLOGY:          linear (xi) SEQUENCE DESCRIPTION: SEQ ID NO: 482:

UGAAGCAUUU ACAGAAA                                                     17

(2) INFORMATION FOR SEQ ID NO: 483:

(i) SEQUENCE CHARACTERISTICS:
        (A)  LENGTH:            17 base pairs
        (B)  TYPE:              nucleic acid
        (C)  STRANDEDNESS:      single
        (D)  TOPOLOGY:          linear (xi) SEQUENCE DESCRIPTION: SEQ ID NO: 483:

GAAGCAUUUA CAGAAAC                                                     17
```

(2) INFORMATION FOR SEQ ID NO: 484:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 484:

AAGCAUUUAC AGAAACG                  17

(2) INFORMATION FOR SEQ ID NO: 485:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 485:

AAACGCAUCC AGCAAGA                  17

(2) INFORMATION FOR SEQ ID NO: 486:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 486:

GCAAGAAUAU UGUCCCU                  17

(2) INFORMATION FOR SEQ ID NO: 487:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 487:

AAGAAUAUUG UCCCUUU                  17

(2) INFORMATION FOR SEQ ID NO: 488:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 488:

AAUAUUGUCC CUUUGAG                  17

(2) INFORMATION FOR SEQ ID NO: 489:

(i) SEQUENCE CHARACTERISTICS:

(A) LENGTH: 17 base pairs
        (B) TYPE: nucleic acid
        (C) STRANDEDNESS: single (D) TOPOLOGY:          linear (xi) SEQUENCE DESCRIPTION: SEQ ID NO: 489:

UUGUCCCUUU GAGCAGA                                                      17

(2) INFORMATION FOR SEQ ID NO: 490:

(i) SEQUENCE CHARACTERISTICS:
              (A) LENGTH:            17 base pairs
              (B) TYPE:              nucleic acid
              (C) STRANDEDNESS:      single
              (D) TOPOLOGY:          linear (xi) SEQUENCE DESCRIPTION: SEQ ID NO: 490:

UGUCCCUUUG AGCAGAA                                                      17

(2) INFORMATION FOR SEQ ID NO: 491:

(i) SEQUENCE CHARACTERISTICS:
              (A) LENGTH:            17 base pairs
              (B) TYPE:              nucleic acid
              (C) STRANDEDNESS:      single
              (D) TOPOLOGY:          linear (xi) SEQUENCE DESCRIPTION: SEQ ID NO: 491:

GCAGAAAUUU AUCUUUC                                                      17

(2) INFORMATION FOR SEQ ID NO: 492:

(i) SEQUENCE CHARACTERISTICS:
              (A) LENGTH:            17 base pairs
              (B) TYPE:              nucleic acid
              (C) STRANDEDNESS:      single
              (D) TOPOLOGY:          linear (xi) SEQUENCE DESCRIPTION: SEQ ID NO: 492:

CAGAAAUUUA UCUUUCA                                                      17

(2) INFORMATION FOR SEQ ID NO: 493:

(i) SEQUENCE CHARACTERISTICS:
              (A) LENGTH:            17 base pairs
              (B) TYPE:              nucleic acid
              (C) STRANDEDNESS:      single
              (D) TOPOLOGY:          linear (xi) SEQUENCE DESCRIPTION: SEQ ID NO: 493:

AGAAAUUUAU CUUUCAA                                                      17

(2) INFORMATION FOR SEQ ID NO: 494:

(i) SEQUENCE CHARACTERISTICS:
              (A) LENGTH:            17 base pairs
              (B) TYPE:              nucleic acid
              (C) STRANDEDNESS:      single
              (D) TOPOLOGY:          linear (xi) SEQUENCE DESCRIPTION: SEQ ID NO: 494:

AAAUUUAUCU UUCAAAG                                                      17

(2) INFORMATION FOR SEQ ID NO: 495:

(i) SEQUENCE CHARACTERISTICS:

(A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 495:

AUUUAUCUUU CAAAGAG        17

(2) INFORMATION FOR SEQ ID NO: 496:

(i) SEQUENCE CHARACTERISTICS:

(A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 496:

UUUAUCUUUC AAAGAGG        17

(2) INFORMATION FOR SEQ ID NO: 497:

(i) SEQUENCE CHARACTERISTICS:

(A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 497:

UUAUCUUUCA AAGAGGU        17

(2) INFORMATION FOR SEQ ID NO: 498:

(i) SEQUENCE CHARACTERISTICS:

(A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 498:

AAAGAGGUAU AUUUGAA        17

(2) INFORMATION FOR SEQ ID NO: 499:

(i) SEQUENCE CHARACTERISTICS:

(A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 499:

AGAGGUAUAU UUGAAAA        17

(2) INFORMATION FOR SEQ ID NO: 500:

(i) SEQUENCE CHARACTERISTICS:

(A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 500:

```
AGGUAUAUUU GAAAAAA                                                    17

(2) INFORMATION FOR SEQ ID NO: 501:

(i) SEQUENCE CHARACTERISTICS:
          (A) LENGTH:          17 base pairs
          (B) TYPE:            nucleic acid
          (C) STRANDEDNESS:    single
          (D) TOPOLOGY:        linear (xi) SEQUENCE DESCRIPTION: SEQ ID NO: 501:

GGUAUAUUUG AAAAAAA                                                    17

(2) INFORMATION FOR SEQ ID NO: 502:

(i) SEQUENCE CHARACTERISTICS:
          (A) LENGTH:          17 base pairs
          (B) TYPE:            nucleic acid
          (C) STRANDEDNESS:    single
          (D) TOPOLOGY:        linear (xi) SEQUENCE DESCRIPTION: SEQ ID NO: 502:

AAAAAGUAU AUGUGAG                                                     17

(2) INFORMATION FOR SEQ ID NO: 503:

(i) SEQUENCE CHARACTERISTICS:
          (A) LENGTH:          17 base pairs
          (B) TYPE:            nucleic acid
          (C) STRANDEDNESS:    single
          (D) TOPOLOGY:        linear (xi) SEQUENCE DESCRIPTION: SEQ ID NO: 503:

AAAAGUAUAU GUGAGGA                                                    17

(2) INFORMATION FOR SEQ ID NO: 504:

(i) SEQUENCE CHARACTERISTICS:
          (A) LENGTH:          17 base pairs
          (B) TYPE:            nucleic acid
          (C) STRANDEDNESS:    single
          (D) TOPOLOGY:        linear (xi) SEQUENCE DESCRIPTION: SEQ ID NO: 504:

GUGAGGAUUU UUAUUGA                                                    17

(2) INFORMATION FOR SEQ ID NO: 505:

(i) SEQUENCE CHARACTERISTICS:
          (A) LENGTH:          17 base pairs
          (B) TYPE:            nucleic acid
          (C) STRANDEDNESS:    single
          (D) TOPOLOGY:        linear (xi) SEQUENCE DESCRIPTION: SEQ ID NO: 505:

UGAGGAUUUU UAUUGAU                                                    17

(2) INFORMATION FOR SEQ ID NO: 506:

(i) SEQUENCE CHARACTERISTICS:
          (A) LENGTH:          17 base pairs
          (B) TYPE:            nucleic acid
```

```
            (C)  STRANDEDNESS:      single
            (D)  TOPOLOGY:          linear (xi) SEQUENCE DESCRIPTION: SEQ ID NO: 506:

GAGGAUUUUU AUUGAUU                                                17

(2) INFORMATION FOR SEQ ID NO: 507:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 507:

AGGAUUUUUA UUGAUUG                                                17

(2) INFORMATION FOR SEQ ID NO: 508:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 508:

GGAUUUUUAU UGAUUGG                                                17

(2) INFORMATION FOR SEQ ID NO: 509:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 509:

AUUUUUAUUG AUUGGGG                                                17

(2) INFORMATION FOR SEQ ID NO: 510:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 510:

UUAUUGAUUG GGGAUCU                                                17

(2) INFORMATION FOR SEQ ID NO: 511:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 511:

UUGGGGAUCU UGGAGUU                                                17

(2) INFORMATION FOR SEQ ID NO: 512:
```

```
    (i) SEQUENCE CHARACTERISTICS:
         (A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 512:

GGGGAUCUUG GAGUUUU                                                  17

(2) INFORMATION FOR SEQ ID NO: 513:

(i) SEQUENCE CHARACTERISTICS:
         (A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 513:

CUUGGAGUUU UUCAUUG                                                  17

(2) INFORMATION FOR SEQ ID NO: 514:

(i) SEQUENCE CHARACTERISTICS:
         (A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 514:

UUGGAGUUUU UCAUUGU                                                  17

(2) INFORMATION FOR SEQ ID NO: 515:

(i) SEQUENCE CHARACTERISTICS:
         (A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 515:

UGGAGUUUUU CAUUGUC                                                  17

(2) INFORMATION FOR SEQ ID NO: 516:

(i) SEQUENCE CHARACTERISTICS:
         (A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 516:

GGAGUUUUUC AUUGUCG                                                  17

(2) INFORMATION FOR SEQ ID NO: 517:

(i) SEQUENCE CHARACTERISTICS:
         (A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 517:
```

```
GAGUUUUUCA UUGUCGC                                                          17

(2) INFORMATION FOR SEQ ID NO: 518:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 518:

UUUUUCAUUG UCGCUAU                                                          17

(2) INFORMATION FOR SEQ ID NO: 519:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 519:

UUCAUUGUCG CUAUUGA                                                          17

(2) INFORMATION FOR SEQ ID NO: 520:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 520:

UUGUCGCUAU UGAUUUU                                                          17

(2) INFORMATION FOR SEQ ID NO: 521:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 521:

GUCGCUAUUG AUUUUUA                                                          17

(2) INFORMATION FOR SEQ ID NO: 522:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 522:

CUAUUGAUUU UUACUUC                                                          17

(2) INFORMATION FOR SEQ ID NO: 523:

(i) SEQUENCE CHARACTERISTICS:

(A) LENGTH:          17 base pairs
```

```
            (B)  TYPE:             nucleic acid
            (C)  STRANDEDNESS:     single
            (D)  TOPOLOGY:         linear (xi)  SEQUENCE DESCRIPTION: SEQ ID NO: 523:

UAUUGAUUUU UACUUCA                                                    17

(2)   INFORMATION FOR SEQ ID NO: 524:

(i)  SEQUENCE CHARACTERISTICS:
            (A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 524:

AUUGAUUUUU ACUUCAA                                                    17

(2)   INFORMATION FOR SEQ ID NO: 525:

(i)  SEQUENCE CHARACTERISTICS:
            (A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 525:

UUGAUUUUUA CUUCAAU                                                    17

(2)   INFORMATION FOR SEQ ID NO: 526:

(i)  SEQUENCE CHARACTERISTICS:
            (A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 526:

UGAUUUUUAC UUCAAUG                                                    17

(2)   INFORMATION FOR SEQ ID NO: 527:

(i)  SEQUENCE CHARACTERISTICS:
            (A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 527:

UUUUUACUUC AAUGGGC                                                    17

(2)   INFORMATION FOR SEQ ID NO: 528:

(i)  SEQUENCE CHARACTERISTICS:
            (A)  LENGTH:           17 base pairs
            (B)  TYPE:             nucleic acid
            (C)  STRANDEDNESS:     single
            (D)  TOPOLOGY:         linear (xi)  SEQUENCE DESCRIPTION: SEQ ID NO: 528:

UUUUACUUCA AUGGGCU                                                    17
```

```
(2) INFORMATION FOR SEQ ID NO: 529:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 529:

AAUGGGCUCU UCCAACA                                                  17

(2) INFORMATION FOR SEQ ID NO: 530:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 530:

UGGGCUCUUC CAACAAG                                                  17

(2) INFORMATION FOR SEQ ID NO: 531:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 531:

GGGCUCUUCC AACAAGG                                                  17

(2) INFORMATION FOR SEQ ID NO: 532:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 532:

AAGAAGCUUG CUGGUAG                                                  17

(2) INFORMATION FOR SEQ ID NO: 533:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 533:

UUGCUGGUAG CACUUGC                                                  17

(2) INFORMATION FOR SEQ ID NO: 534:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear
```

(xi) SEQUENCE DESCRIPTION: SEQ ID NO: 534:

GUAGCACUUG CUACCCU                                                              17

(2) INFORMATION FOR SEQ ID NO: 535:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 535:

CACUUGCUAC CCUGAGU                                                              17

(2) INFORMATION FOR SEQ ID NO: 536:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 536:

CCCUGAGUUC AUCCAGG                                                              17

(2) INFORMATION FOR SEQ ID NO: 537:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 537:

CCUGAGUUCA UCCAGGC                                                              17

(2) INFORMATION FOR SEQ ID NO: 538:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 538:

GAGUUCAUCC AGGCCCA                                                              17

(2) INFORMATION FOR SEQ ID NO: 539:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 539:

CCACAAGUCU UCCAGAG                                                              17

(2) INFORMATION FOR SEQ ID NO: 540:

(i) SEQUENCE CHARACTERISTICS:

```
            (A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 540:

ACAAGUCUUC CAGAGGA                                                     17

(2)  INFORMATION FOR SEQ ID NO: 541:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 541:

CAAGUCUUCC AGAGGAU                                                     17

(2)  INFORMATION FOR SEQ ID NO: 542:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 542:

AGGAUGCUUG AUUCCAG                                                     17

(2)  INFORMATION FOR SEQ ID NO: 543:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 543:

UGCUUGAUUC CAGUGGU                                                     17

(2)  INFORMATION FOR SEQ ID NO: 544:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 544:

GCUUGAUUCC AGUGGUU                                                     17

(2)  INFORMATION FOR SEQ ID NO: 545:

(i)   SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 545:

CCAGUGGUUC UGCUUCA                                                     17
```

(2) INFORMATION FOR SEQ ID NO: 546:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 546:

CAGUGGUUCU GCUUCAA                                     17

(2) INFORMATION FOR SEQ ID NO: 547:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 547:

GUUCUGCUUC AAGGCUU                                     17

(2) INFORMATION FOR SEQ ID NO: 548:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 548:

UUCUGCUUCA AGGCUUC                                   17

(2) INFORMATION FOR SEQ ID NO: 549:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 549:

UCAAGGCUUC CACUGCA                                   17

(2) INFORMATION FOR SEQ ID NO: 550:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 550:

CAAGGCUUCC ACUGCAA                                   17

(2) INFORMATION FOR SEQ ID NO: 551:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 551:

AAAACACUAA AGAUCCA                                                   17

(2) INFORMATION FOR SEQ ID NO: 552:

(i) SEQUENCE CHARACTERISTICS:

(A) LENGTH:          17 base pairs
      (B) TYPE:            nucleic acid
      (C) STRANDEDNESS:    single
      (D) TOPOLOGY:        linear (xi) SEQUENCE DESCRIPTION: SEQ ID NO: 552:

CUAAAGAUCC AAGAAGG                                                   17

(2) INFORMATION FOR SEQ ID NO: 553:

(i) SEQUENCE CHARACTERISTICS:

(A) LENGTH:          17 base pairs
      (B) TYPE:            nucleic acid
      (C) STRANDEDNESS:    single
      (D) TOPOLOGY:        linear (xi) SEQUENCE DESCRIPTION: SEQ ID NO: 553:

GAAGGCCUUC AUGGCCC                                                   17

(2) INFORMATION FOR SEQ ID NO: 554:

(i) SEQUENCE CHARACTERISTICS:

(A) LENGTH:          17 base pairs
      (B) TYPE:            nucleic acid
      (C) STRANDEDNESS:    single
      (D) TOPOLOGY:        linear (xi) SEQUENCE DESCRIPTION: SEQ ID NO: 554:

AAGGCCUUCA UGGCCCC                                                   17

(2) INFORMATION FOR SEQ ID NO: 555:

(i) SEQUENCE CHARACTERISTICS:

(A) LENGTH:          17 base pairs
      (B) TYPE:            nucleic acid
      (C) STRANDEDNESS:    single
      (D) TOPOLOGY:        linear (xi) SEQUENCE DESCRIPTION: SEQ ID NO: 555:

GGCCGGAUCG GUACUGU                                                   17

(2) INFORMATION FOR SEQ ID NO: 556:

(i) SEQUENCE CHARACTERISTICS:

(A) LENGTH:          17 base pairs
      (B) TYPE:            nucleic acid
      (C) STRANDEDNESS:    single
      (D) TOPOLOGY:        linear (xi) SEQUENCE DESCRIPTION: SEQ ID NO: 556:

GGAUCGGUAC UGUAUCA                                                   17

(2) INFORMATION FOR SEQ ID NO: 557:

(i) SEQUENCE CHARACTERISTICS:

```
          (A)  LENGTH:              17 base pairs
          (B)  TYPE:                nucleic acid
          (C)  STRANDEDNESS:        single
          (D)  TOPOLOGY:            linear (xi) SEQUENCE DESCRIPTION: SEQ ID NO: 557:

GGUACUGUAU CAAGUCA                                                    17

(2)  INFORMATION FOR SEQ ID NO: 558:

(i)  SEQUENCE CHARACTERISTICS:

(A)  LENGTH:              17 base pairs
          (B)  TYPE:                nucleic acid
          (C)  STRANDEDNESS:        single
          (D)  TOPOLOGY:            linear (xi) SEQUENCE DESCRIPTION: SEQ ID NO: 558:

UACUGUAUCA AGUCAUG                                                    17

(2)  INFORMATION FOR SEQ ID NO: 559:

(i)  SEQUENCE CHARACTERISTICS:

(A)  LENGTH:              17 base pairs
          (B)  TYPE:                nucleic acid
          (C)  STRANDEDNESS:        single
          (D)  TOPOLOGY:            linear (xi) SEQUENCE DESCRIPTION: SEQ ID NO: 559:

UAUCAAGUCA UGGCAGG                                                    17

(2)  INFORMATION FOR SEQ ID NO: 560:

(i)  SEQUENCE CHARACTERISTICS:

(A)  LENGTH:              17 base pairs
          (B)  TYPE:                nucleic acid
          (C)  STRANDEDNESS:        single
          (D)  TOPOLOGY:            linear (xi) SEQUENCE DESCRIPTION: SEQ ID NO: 560:

UGGCAGGUAC AGUAGGA                                                    17

(2)  INFORMATION FOR SEQ ID NO: 561:

(i)  SEQUENCE CHARACTERISTICS:

(A)  LENGTH:              17 base pairs
          (B)  TYPE:                nucleic acid
          (C)  STRANDEDNESS:        single
          (D)  TOPOLOGY:            linear (xi) SEQUENCE DESCRIPTION: SEQ ID NO: 561:

GGUACAGUAG GAUAAGC                                                    17

(2)  INFORMATION FOR SEQ ID NO: 562:

(i)  SEQUENCE CHARACTERISTICS:

(A)  LENGTH:              17 base pairs
          (B)  TYPE:                nucleic acid
          (C)  STRANDEDNESS:        single
          (D)  TOPOLOGY:            linear (xi) SEQUENCE DESCRIPTION: SEQ ID NO: 562:

AGUAGGAUAA GCCACUC                                                    17
```

(2) INFORMATION FOR SEQ ID NO: 563:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 563:

AAGCCACUCU GUCCCUU      17

(2) INFORMATION FOR SEQ ID NO: 564:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 564:

CACUCUGUCC CUUCCUG      17

(2) INFORMATION FOR SEQ ID NO: 565:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 565:

CUGUCCCUUC CUGGGCA      17

(2) INFORMATION FOR SEQ ID NO: 566:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 566:

UGUCCCUUCC UGGGCAA      17

(2) INFORMATION FOR SEQ ID NO: 567:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 567:

GGAUGAAUUC UUCCUUA      17

(2) INFORMATION FOR SEQ ID NO: 568:

(i) SEQUENCE CHARACTERISTICS:

(A) LENGTH: 17 base pairs
        (B) TYPE: nucleic acid
        (C) STRANDEDNESS: single (D) TOPOLOGY:          linear (xi) SEQUENCE DESCRIPTION: SEQ ID NO: 568:

GAUGAAUUCU UCCUUAG                                                      17

(2) INFORMATION FOR SEQ ID NO: 569:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 569:

UGAAUUCUUC CUUAGAC                                                      17

(2) INFORMATION FOR SEQ ID NO: 570:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 570:

GAAUUCUUCC UUAGACU                                                      17

(2) INFORMATION FOR SEQ ID NO: 571:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 571:

UUCUUCCUUA GACUUAC                                                      17

(2) INFORMATION FOR SEQ ID NO: 572:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 572:

UCUUCCUUAG ACUUACU                                                      17

(2) INFORMATION FOR SEQ ID NO: 573:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 573:

CUUAGACUUA CUUUUGU                                                      17

(2) INFORMATION FOR SEQ ID NO: 574:

```
          (i) SEQUENCE CHARACTERISTICS:

(A) LENGTH:          17 base pairs
               (B) TYPE:            nucleic acid
               (C) STRANDEDNESS:    single
               (D) TOPOLOGY:        linear (xi) SEQUENCE DESCRIPTION: SEQ ID NO: 574:

UUAGACUUAC UUUUGUA                                                      17

(2)  INFORMATION FOR SEQ ID NO: 575:

(i) SEQUENCE CHARACTERISTICS:

(A) LENGTH:          17 base pairs
               (B) TYPE:            nucleic acid
               (C) STRANDEDNESS:    single
               (D) TOPOLOGY:        linear (xi) SEQUENCE DESCRIPTION: SEQ ID NO: 575:

GACUUACUUU UGUAAAA                                                      17

(2)  INFORMATION FOR SEQ ID NO: 576:

(i) SEQUENCE CHARACTERISTICS:

(A) LENGTH:          17 base pairs
               (B) TYPE:            nucleic acid
               (C) STRANDEDNESS:    single
               (D) TOPOLOGY:        linear (xi) SEQUENCE DESCRIPTION: SEQ ID NO: 576:

ACUUACUUUU GUAAAAA                                                      17

(2)  INFORMATION FOR SEQ ID NO: 577:

(i) SEQUENCE CHARACTERISTICS:

(A) LENGTH:          17 base pairs
               (B) TYPE:            nucleic acid
               (C) STRANDEDNESS:    single
               (D) TOPOLOGY:        linear (xi) SEQUENCE DESCRIPTION: SEQ ID NO: 577:

CUUACUUUUG UAAAAAU                                                      17

(2)  INFORMATION FOR SEQ ID NO: 578:

(i) SEQUENCE CHARACTERISTICS:

(A) LENGTH:          17 base pairs
               (B) TYPE:            nucleic acid
               (C) STRANDEDNESS:    single
               (D) TOPOLOGY:        linear (xi) SEQUENCE DESCRIPTION: SEQ ID NO: 578:

ACUUUUGUAA AAAUGUC                                                      17

(2)  INFORMATION FOR SEQ ID NO: 579:

(i) SEQUENCE CHARACTERISTICS:

(A) LENGTH:          17 base pairs
               (B) TYPE:            nucleic acid
               (C) STRANDEDNESS:    single
               (D) TOPOLOGY:        linear (xi) SEQUENCE DESCRIPTION: SEQ ID NO: 579:
```

-continued

```
AAAAAUGUCC CCACGGU                                            17

(2) INFORMATION FOR SEQ ID NO: 580:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 580:

CCCACGGUAC UUACUCC                                            17

(2) INFORMATION FOR SEQ ID NO: 581:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 581:

ACGGUACUUA CUCCCCA                                            17

(2) INFORMATION FOR SEQ ID NO: 582:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 582:

CGGUACUUAC UCCCCAC                                            17

(2) INFORMATION FOR SEQ ID NO: 583:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 583:

UACUUACUCC CCACUGA                                            17

(2) INFORMATION FOR SEQ ID NO: 584:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 584:

CCAGUGGUUU CCAGUCA                                            17

(2) INFORMATION FOR SEQ ID NO: 585:

(i) SEQUENCE CHARACTERISTICS:

(A) LENGTH:           17 base pairs
        (B) TYPE:             nucleic acid
```

```
            (C) STRANDEDNESS:       single
            (D) TOPOLOGY:           linear (xi) SEQUENCE DESCRIPTION: SEQ ID NO: 585:

CAGUGGUUUC CAGUCAU                                                    17

(2) INFORMATION FOR SEQ ID NO: 586:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 586:

AGUGGUUUCC AGUCAUG                                                    17

(2) INFORMATION FOR SEQ ID NO: 587:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 587:

UUUCCAGUCA UGAGCGU                                                    17

(2) INFORMATION FOR SEQ ID NO: 588:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 588:

AUGAGCGUUA GACUGAC                                                    17

(2) INFORMATION FOR SEQ ID NO: 589:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 589:

UGAGCGUUAG ACUGACU                                                    17

(2) INFORMATION FOR SEQ ID NO: 590:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 590:

GACUGACUUG UUUGUCU                                                    17

(2) INFORMATION FOR SEQ ID NO: 591:
```

```
    (i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 591:

UGACUUGUUU GUCUUCC                                                  17

(2) INFORMATION FOR SEQ ID NO: 592:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 592:

GACUUGUUUG UCUUCCA                                                  17

(2) INFORMATION FOR SEQ ID NO: 593:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 593:

UUGUUUGUCU UCCAUUC                                                  17

(2) INFORMATION FOR SEQ ID NO: 594:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 594:

GUUUGUCUUC CAUUCCA                                                  17

(2) INFORMATION FOR SEQ ID NO: 595:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 595:

UUUGUCUUCC AUUCCAU                                                  17

(2) INFORMATION FOR SEQ ID NO: 596:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 596:
```

UCUUCCAUUC CAUUGUU                                              17

(2) INFORMATION FOR SEQ ID NO: 597:

(i) SEQUENCE CHARACTERISTICS:

(A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 597:

CUUCCAUUCC AUUGUUU                                              17

(2) INFORMATION FOR SEQ ID NO: 598:

(i) SEQUENCE CHARACTERISTICS:

(A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 598:

CAUUCCAUUG UUUUGAA                                              17

(2) INFORMATION FOR SEQ ID NO: 599:

(i) SEQUENCE CHARACTERISTICS:

(A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 599:

UCCAUUGUUU UGAAACU                                              17

(2) INFORMATION FOR SEQ ID NO: 600:

(i) SEQUENCE CHARACTERISTICS:

(A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 600:

CCAUUGUUUU GAAACUC                                              17

(2) INFORMATION FOR SEQ ID NO: 601:

(i) SEQUENCE CHARACTERISTICS:

(A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 601:

CAUUGUUUUG AAACUCA                                              17

(2) INFORMATION FOR SEQ ID NO: 602:

(i) SEQUENCE CHARACTERISTICS:

(A) LENGTH:        17 base pairs

```
            (B) TYPE:              nucleic acid
            (C) STRANDEDNESS:      single
            (D) TOPOLOGY:          linear (xi) SEQUENCE DESCRIPTION: SEQ ID NO: 602:

UUGAAACUCA GUAUGCC                                             17

(2) INFORMATION FOR SEQ ID NO: 603:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 603:

AACUCAGUAU GCCGCCC                                             17

(2) INFORMATION FOR SEQ ID NO: 604:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 604:

GCCCCUGUCU UGCUGUC                                             17

(2) INFORMATION FOR SEQ ID NO: 605:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 605:

CCCUGUCUUG CUGUCAU                                             17

(2) INFORMATION FOR SEQ ID NO: 606:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 606:

CUUGCUGUCA UGAAAUC                                             17

(2) INFORMATION FOR SEQ ID NO: 607:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 607:

CAUGAAAUCA GCAAGAG                                             17
```

```
(2) INFORMATION FOR SEQ ID NO: 608:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 608:

UGACACAUCA AAUAAUA                                                17

(2) INFORMATION FOR SEQ ID NO: 609:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 609:

CAUCAAAUAA UAACUCG                                                17

(2) INFORMATION FOR SEQ ID NO: 610:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 610:

CAAAUAAUAA CUCGGAU                                                17

(2) INFORMATION FOR SEQ ID NO: 611:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 611:

UAAUAACUCG GAUUCCA                                                17

(2) INFORMATION FOR SEQ ID NO: 612:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 612:

ACUCGGAUUC CAGCCCA                                                17

(2) INFORMATION FOR SEQ ID NO: 613:

(i) SEQUENCE CHARACTERISTICS:
        (A) LENGTH:         17 base pairs
        (B) TYPE:           nucleic acid
        (C) STRANDEDNESS:   single
        (D) TOPOLOGY:       linear
```

```
    (xi) SEQUENCE DESCRIPTION: SEQ ID NO: 613:

CUCGGAUUCC AGCCCAC                                                      17

(2) INFORMATION FOR SEQ ID NO: 614:

(i) SEQUENCE CHARACTERISTICS:

(A) LENGTH:              17 base pairs
         (B) TYPE:                nucleic acid
         (C) STRANDEDNESS:        single
         (D) TOPOLOGY:            linear (xi) SEQUENCE DESCRIPTION: SEQ ID NO: 614:

GCCCACAUUG GAUUCAU                                                      17

(2) INFORMATION FOR SEQ ID NO: 615:

(i) SEQUENCE CHARACTERISTICS:

(A) LENGTH:              17 base pairs
         (B) TYPE:                nucleic acid
         (C) STRANDEDNESS:        single
         (D) TOPOLOGY:            linear (xi) SEQUENCE DESCRIPTION: SEQ ID NO: 615:

CAUUGGAUUC AUCAGCA                                                      17

(2) INFORMATION FOR SEQ ID NO: 616:

(i) SEQUENCE CHARACTERISTICS:

(A) LENGTH:              17 base pairs
         (B) TYPE:                nucleic acid
         (C) STRANDEDNESS:        single
         (D) TOPOLOGY:            linear (xi) SEQUENCE DESCRIPTION: SEQ ID NO: 616:

AUUGGAUUCA UCAGCAU                                                      17

(2) INFORMATION FOR SEQ ID NO: 617:

(i) SEQUENCE CHARACTERISTICS:

(A) LENGTH:              17 base pairs
         (B) TYPE:                nucleic acid
         (C) STRANDEDNESS:        single
         (D) TOPOLOGY:            linear (xi) SEQUENCE DESCRIPTION: SEQ ID NO: 617:

GGAUUCAUCA GCAUUUG                                                      17

(2) INFORMATION FOR SEQ ID NO: 618:

(i) SEQUENCE CHARACTERISTICS:

(A) LENGTH:              17 base pairs
         (B) TYPE:                nucleic acid
         (C) STRANDEDNESS:        single
         (D) TOPOLOGY:            linear (xi) SEQUENCE DESCRIPTION: SEQ ID NO: 618:

AUCAGCAUUU GGACCAA                                                      17

(2) INFORMATION FOR SEQ ID NO: 619:

(i) SEQUENCE CHARACTERISTICS:
```

```
            (A)  LENGTH:              17 base pairs
            (B)  TYPE:                nucleic acid
            (C)  STRANDEDNESS:        single
            (D)  TOPOLOGY:            linear (xi) SEQUENCE DESCRIPTION: SEQ ID NO: 619:

UCAGCAUUUG GACCAAU                                              17

(2) INFORMATION FOR SEQ ID NO: 620:

(i) SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi) SEQUENCE DESCRIPTION: SEQ ID NO: 620:

GGACCAAUAG CCCACAG                                              17

(2) INFORMATION FOR SEQ ID NO: 621:

(i) SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi) SEQUENCE DESCRIPTION: SEQ ID NO: 621:

UGUGGAAUAC CUAAGGA                                              17

(2) INFORMATION FOR SEQ ID NO: 622:

(i) SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi) SEQUENCE DESCRIPTION: SEQ ID NO: 622:

GAAUACCUAA GGAUAAC                                              17

(2) INFORMATION FOR SEQ ID NO: 623:

(i) SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi) SEQUENCE DESCRIPTION: SEQ ID NO: 623:

CUAAGGAUAA CACCGCU                                              17

(2) INFORMATION FOR SEQ ID NO: 624:

(i) SEQUENCE CHARACTERISTICS:

(A)  LENGTH:              17 base pairs
            (B)  TYPE:                nucleic acid
            (C)  STRANDEDNESS:        single
            (D)  TOPOLOGY:            linear (xi) SEQUENCE DESCRIPTION: SEQ ID NO: 624:

ACACCGCUUU UGUUCUC                                              17
```

-continued (2) INFORMATION FOR SEQ ID NO: 625:

(i) SEQUENCE CHARACTERISTICS:

(A) LENGTH:          17 base pairs
        (B) TYPE:            nucleic acid
        (C) STRANDEDNESS:   single
        (D) TOPOLOGY:       linear (xi) SEQUENCE DESCRIPTION: SEQ ID NO: 625:

CACCGCUUUU GUUCUCG                                 17

(2) INFORMATION FOR SEQ ID NO: 626:

(i) SEQUENCE CHARACTERISTICS:

(A) LENGTH:          17 base pairs
        (B) TYPE:            nucleic acid
        (C) STRANDEDNESS:   single
        (D) TOPOLOGY:       linear (xi) SEQUENCE DESCRIPTION: SEQ ID NO: 626:

ACCGCUUUUG UUCUCGC                                 17

(2) INFORMATION FOR SEQ ID NO: 627:

(i) SEQUENCE CHARACTERISTICS:

(A) LENGTH:          17 base pairs
        (B) TYPE:            nucleic acid
        (C) STRANDEDNESS:   single
        (D) TOPOLOGY:       linear (xi) SEQUENCE DESCRIPTION: SEQ ID NO: 627:

GCUUUUGUUC UCGCAAA                                 17

(2) INFORMATION FOR SEQ ID NO: 628:

(i) SEQUENCE CHARACTERISTICS:

(A) LENGTH:          17 base pairs
        (B) TYPE:            nucleic acid
        (C) STRANDEDNESS:   single
        (D) TOPOLOGY:       linear (xi) SEQUENCE DESCRIPTION: SEQ ID NO: 628:

CUUUUGUUCU CGCAAAA                                 17

(2) INFORMATION FOR SEQ ID NO: 629:

(i) SEQUENCE CHARACTERISTICS:

(A) LENGTH:          17 base pairs
        (B) TYPE:            nucleic acid
        (C) STRANDEDNESS:   single
        (D) TOPOLOGY:       linear (xi) SEQUENCE DESCRIPTION: SEQ ID NO: 629:

UUUGUUCUCG CAAAAAC                                 17

(2) INFORMATION FOR SEQ ID NO: 630:

(i) SEQUENCE CHARACTERISTICS:

(A) LENGTH:          17 base pairs
        (B) TYPE:            nucleic acid
        (C) STRANDEDNESS:   single
        (D) TOPOLOGY:       linear (xi) SEQUENCE DESCRIPTION: SEQ ID NO: 630:

AAAAACGUAU CUCCUAA                                                17

(2) INFORMATION FOR SEQ ID NO: 631:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 631:

AAACGUAUCU CCUAAUU                                                17

(2) INFORMATION FOR SEQ ID NO: 632:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 632:

ACGUAUCUCC UAAUUUG                                                17

(2) INFORMATION FOR SEQ ID NO: 633:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 633:

UAUCUCCUAA UUUGAGG                                                17

(2) INFORMATION FOR SEQ ID NO: 634:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 634:

CUCCUAAUUU GAGGCUC                                                17

(2) INFORMATION FOR SEQ ID NO: 635:

(i) SEQUENCE CHARACTERISTICS:

(A) LENGTH:         17 base pairs
        (B) TYPE:           nucleic acid
        (C) STRANDEDNESS:   single
        (D) TOPOLOGY:       linear (xi) SEQUENCE DESCRIPTION: SEQ ID NO: 635:

UCCUAAUUUG AGGCUCA                                                17

(2) INFORMATION FOR SEQ ID NO: 636:

(i) SEQUENCE CHARACTERISTICS:

```
        (A)  LENGTH:            17 base pairs
        (B)  TYPE:              nucleic acid
        (C)  STRANDEDNESS:      single
        (D)  TOPOLOGY:          linear (xi) SEQUENCE DESCRIPTION: SEQ ID NO: 636:

UUGAGGCUCA GAUGAAA                                                  17

(2) INFORMATION FOR SEQ ID NO: 637:

(i) SEQUENCE CHARACTERISTICS:

(A)  LENGTH:            17 base pairs
        (B)  TYPE:              nucleic acid
        (C)  STRANDEDNESS:      single
        (D)  TOPOLOGY:          linear (xi) SEQUENCE DESCRIPTION: SEQ ID NO: 637:

AAAUGCAUCA GGUCCUU                                                  17

(2) INFORMATION FOR SEQ ID NO: 638:

(i) SEQUENCE CHARACTERISTICS:

(A)  LENGTH:            17 base pairs
        (B)  TYPE:              nucleic acid
        (C)  STRANDEDNESS:      single
        (D)  TOPOLOGY:          linear (xi) SEQUENCE DESCRIPTION: SEQ ID NO: 638:

CAUCAGGUCC UUUGGGG                                                  17

(2) INFORMATION FOR SEQ ID NO: 639:

(i) SEQUENCE CHARACTERISTICS:

(A)  LENGTH:            17 base pairs
        (B)  TYPE:              nucleic acid
        (C)  STRANDEDNESS:      single
        (D)  TOPOLOGY:          linear (xi) SEQUENCE DESCRIPTION: SEQ ID NO: 639:

CAGGUCCUUU GGGGCAU                                                  17

(2) INFORMATION FOR SEQ ID NO: 640:

(i) SEQUENCE CHARACTERISTICS:

(A)  LENGTH:            17 base pairs
        (B)  TYPE:              nucleic acid
        (C)  STRANDEDNESS:      single
        (D)  TOPOLOGY:          linear (xi) SEQUENCE DESCRIPTION: SEQ ID NO: 640:

AGGUCCUUUG GGGCAUA                                                  17

(2) INFORMATION FOR SEQ ID NO: 641:

(i) SEQUENCE CHARACTERISTICS:

(A)  LENGTH:            17 base pairs
        (B)  TYPE:              nucleic acid
        (C)  STRANDEDNESS:      single
        (D)  TOPOLOGY:          linear (xi) SEQUENCE DESCRIPTION: SEQ ID NO: 641:

UGGGGCAUAG AUCAGAA                                                  17
```

(2) INFORMATION FOR SEQ ID NO: 642:

(i) SEQUENCE CHARACTERISTICS:

(A) LENGTH:          17 base pairs
　　　　(B) TYPE:            nucleic acid
　　　　(C) STRANDEDNESS:    single
　　　　(D) TOPOLOGY:        linear (xi) SEQUENCE DESCRIPTION: SEQ ID NO: 642:

GCAUAGAUCA GAAGACU                                            17

(2) INFORMATION FOR SEQ ID NO: 643:

(i) SEQUENCE CHARACTERISTICS:

(A) LENGTH:          17 base pairs
　　　　(B) TYPE:            nucleic acid
　　　　(C) STRANDEDNESS:    single
　　　　(D) TOPOLOGY:        linear (xi) SEQUENCE DESCRIPTION: SEQ ID NO: 643:

AGAAGACUAC AAAAAUG                                            17

(2) INFORMATION FOR SEQ ID NO: 644:

(i) SEQUENCE CHARACTERISTICS:

(A) LENGTH:          17 base pairs
　　　　(B) TYPE:            nucleic acid
　　　　(C) STRANDEDNESS:    single
　　　　(D) TOPOLOGY:        linear (xi) SEQUENCE DESCRIPTION: SEQ ID NO: 644:

AAGCUGCUCU GAAAUCU                                            17

(2) INFORMATION FOR SEQ ID NO: 645:

(i) SEQUENCE CHARACTERISTICS:

(A) LENGTH:          17 base pairs
　　　　(B) TYPE:            nucleic acid
　　　　(C) STRANDEDNESS:    single
　　　　(D) TOPOLOGY:        linear (xi) SEQUENCE DESCRIPTION: SEQ ID NO: 645:

UCUGAAAUCU CCUUUAG                                            17

(2) INFORMATION FOR SEQ ID NO: 646:

(i) SEQUENCE CHARACTERISTICS:

(A) LENGTH:          17 base pairs
　　　　(B) TYPE:            nucleic acid
　　　　(C) STRANDEDNESS:    single
　　　　(D) TOPOLOGY:        linear (xi) SEQUENCE DESCRIPTION: SEQ ID NO: 646:

UGAAAUCUCC UUUAGCC                                            17

(2) INFORMATION FOR SEQ ID NO: 647:

(i) SEQUENCE CHARACTERISTICS:

(A) LENGTH:          17 base pairs
　　　　(B) TYPE:            nucleic acid
　　　　(C) STRANDEDNESS:    single

```
          (D) TOPOLOGY:           linear (xi) SEQUENCE DESCRIPTION: SEQ ID NO: 647:

AAUCUCCUUU AGCCAUC                                                17

(2) INFORMATION FOR SEQ ID NO: 648:

(i) SEQUENCE CHARACTERISTICS:

(A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 648:

AUCUCCUUUA GCCAUCA                                                17

(2) INFORMATION FOR SEQ ID NO: 649:

(i) SEQUENCE CHARACTERISTICS:

(A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 649:

UCUCCUUUAG CCAUCAC                                                17

(2) INFORMATION FOR SEQ ID NO: 650:

(i) SEQUENCE CHARACTERISTICS:

(A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 650:

UUAGCCAUCA CCCCAAC                                                17

(2) INFORMATION FOR SEQ ID NO: 651:

(i) SEQUENCE CHARACTERISTICS:

(A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 651:

CCCAAAAUUA GUUUGUG                                                17

(2) INFORMATION FOR SEQ ID NO: 652:

(i) SEQUENCE CHARACTERISTICS:

(A) LENGTH:             17 base pairs
          (B) TYPE:               nucleic acid
          (C) STRANDEDNESS:       single
          (D) TOPOLOGY:           linear (xi) SEQUENCE DESCRIPTION: SEQ ID NO: 652:

CCAAAAUUAG UUUGUGU                                                17

(2) INFORMATION FOR SEQ ID NO: 653:
```

```
        (i) SEQUENCE CHARACTERISTICS:

(A) LENGTH:         17 base pairs
              (B) TYPE:           nucleic acid
              (C) STRANDEDNESS:   single
              (D) TOPOLOGY:       linear (xi) SEQUENCE DESCRIPTION: SEQ ID NO: 653:

AAAUUAGUUU GUGUUAC                                                  17

(2) INFORMATION FOR SEQ ID NO: 654:

(i) SEQUENCE CHARACTERISTICS:

(A) LENGTH:         17 base pairs
              (B) TYPE:           nucleic acid
              (C) STRANDEDNESS:   single
              (D) TOPOLOGY:       linear (xi) SEQUENCE DESCRIPTION: SEQ ID NO: 654:

AAUUAGUUUG UGUUACU                                                  17

(2) INFORMATION FOR SEQ ID NO: 655:

(i) SEQUENCE CHARACTERISTICS:

(A) LENGTH:         17 base pairs
              (B) TYPE:           nucleic acid
              (C) STRANDEDNESS:   single
              (D) TOPOLOGY:       linear (xi) SEQUENCE DESCRIPTION: SEQ ID NO: 655:

GUUUGUGUUA CUUAUGG                                                  17

(2) INFORMATION FOR SEQ ID NO: 656:

(i) SEQUENCE CHARACTERISTICS:

(A) LENGTH:         17 base pairs
              (B) TYPE:           nucleic acid
              (C) STRANDEDNESS:   single
              (D) TOPOLOGY:       linear (xi) SEQUENCE DESCRIPTION: SEQ ID NO: 656:

UUUGUGUUAC UUAUGGA                                                  17

(2) INFORMATION FOR SEQ ID NO: 657:

(i) SEQUENCE CHARACTERISTICS:

(A) LENGTH:         17 base pairs
              (B) TYPE:           nucleic acid
              (C) STRANDEDNESS:   single
              (D) TOPOLOGY:       linear (xi) SEQUENCE DESCRIPTION: SEQ ID NO: 657:

GUGUUACUUA UGGAAGA                                                  17

(2) INFORMATION FOR SEQ ID NO: 658:

(i) SEQUENCE CHARACTERISTICS:

(A) LENGTH:         17 base pairs
              (B) TYPE:           nucleic acid
              (C) STRANDEDNESS:   single
              (D) TOPOLOGY:       linear (xi) SEQUENCE DESCRIPTION: SEQ ID NO: 658:
```

```
UGUUACUUAU GGAAGAU                                                        17

(2) INFORMATION FOR SEQ ID NO: 659:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 659:

UGGAAGAUAG UUUUCUC                                                        17

(2) INFORMATION FOR SEQ ID NO: 660:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 660:

AAGAUAGUUU UCUCCUU                                                        17

(2) INFORMATION FOR SEQ ID NO: 661:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 661:

AGAUAGUUUU CUCCUUU                                                        17

(2) INFORMATION FOR SEQ ID NO: 662:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 662:

GAUAGUUUUC UCCUUUU                                                        17

(2) INFORMATION FOR SEQ ID NO: 663:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 663:

AUAGUUUUCU CCUUUUA                                                        17

(2) INFORMATION FOR SEQ ID NO: 664:

(i) SEQUENCE CHARACTERISTICS:

(A) LENGTH:            17 base pairs
        (B) TYPE:              nucleic acid
```

```
          (C)  STRANDEDNESS:       single
          (D)  TOPOLOGY:           linear (xi) SEQUENCE DESCRIPTION: SEQ ID NO: 664:

AGUUUUCUCC UUUUACU                                                17

(2)  INFORMATION FOR SEQ ID NO: 665:

(i)  SEQUENCE CHARACTERISTICS:

(A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 665:

UUUCUCCUUU UACUUCA                                                17

(2)  INFORMATION FOR SEQ ID NO: 666:

(i)  SEQUENCE CHARACTERISTICS:

(A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 666:

UUCUCCUUUU ACUUCAC                                                17

(2)  INFORMATION FOR SEQ ID NO: 667:

(i)  SEQUENCE CHARACTERISTICS:

(A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 667:

UCUCCUUUUA CUUCACU                                                17

(2)  INFORMATION FOR SEQ ID NO: 668:

(i)  SEQUENCE CHARACTERISTICS:

(A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 668:

CUCCUUUUAC UUCACUU                                                17

(2)  INFORMATION FOR SEQ ID NO: 669:

(i)  SEQUENCE CHARACTERISTICS:

(A)  LENGTH:             17 base pairs
          (B)  TYPE:               nucleic acid
          (C)  STRANDEDNESS:       single
          (D)  TOPOLOGY:           linear (xi) SEQUENCE DESCRIPTION: SEQ ID NO: 669:

CUUUUACUUC ACUUCAA                                                17

(2)  INFORMATION FOR SEQ ID NO: 670:
```

```
    (i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 670:

UUUUACUUCA CUUCAAA                                              17

(2) INFORMATION FOR SEQ ID NO: 671:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 671:

ACUUCACUUC AAAAGCU                                              17

(2) INFORMATION FOR SEQ ID NO: 672:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 672:

CUUCACUUCA AAAGCUU                                              17

(2) INFORMATION FOR SEQ ID NO: 673:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 673:

CAAAAGCUUU UUACUCA                                              17

(2) INFORMATION FOR SEQ ID NO: 674:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 674:

AAAAGCUUUU UACUCAA                                              17

(2) INFORMATION FOR SEQ ID NO: 675:

(i) SEQUENCE CHARACTERISTICS:
        (A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 675:
```

```
AAAGCUUUUU ACUCAAA                                              17

(2) INFORMATION FOR SEQ ID NO: 676:

(i)  SEQUENCE CHARACTERISTICS:

(A)  LENGTH:           17 base pairs
         (B)  TYPE:             nucleic acid
         (C)  STRANDEDNESS:     single
         (D)  TOPOLOGY:         linear (xi) SEQUENCE DESCRIPTION: SEQ ID NO: 676:

AAGCUUUUUA CUCAAAG                                              17

(2) INFORMATION FOR SEQ ID NO: 677:

(i)  SEQUENCE CHARACTERISTICS:

(A)  LENGTH:           17 base pairs
         (B)  TYPE:             nucleic acid
         (C)  STRANDEDNESS:     single
         (D)  TOPOLOGY:         linear (xi) SEQUENCE DESCRIPTION: SEQ ID NO: 677:

AGCUUUUUAC UCAAAGA                                              17

(2) INFORMATION FOR SEQ ID NO: 678:

(i)  SEQUENCE CHARACTERISTICS:

(A)  LENGTH:           17 base pairs
         (B)  TYPE:             nucleic acid
         (C)  STRANDEDNESS:     single
         (D)  TOPOLOGY:         linear (xi) SEQUENCE DESCRIPTION: SEQ ID NO: 678:

UUUUUACUCA AAGAGUA                                              17

(2) INFORMATION FOR SEQ ID NO: 679:

(i)  SEQUENCE CHARACTERISTICS:

(A)  LENGTH:           17 base pairs
         (B)  TYPE:             nucleic acid
         (C)  STRANDEDNESS:     single
         (D)  TOPOLOGY:         linear (xi) SEQUENCE DESCRIPTION: SEQ ID NO: 679:

CAAAGAGUAU AUGUUCC                                              17

(2) INFORMATION FOR SEQ ID NO: 680:

(i)  SEQUENCE CHARACTERISTICS:

(A)  LENGTH:           17 base pairs
         (B)  TYPE:             nucleic acid
         (C)  STRANDEDNESS:     single
         (D)  TOPOLOGY:         linear (xi) SEQUENCE DESCRIPTION: SEQ ID NO: 680:

AAGAGUAUAU GUUCCCU                                              17

(2) INFORMATION FOR SEQ ID NO: 681:

(i)  SEQUENCE CHARACTERISTICS:

(A)  LENGTH:           17 base pairs
```

```
            (B)  TYPE:            nucleic acid
            (C)  STRANDEDNESS:    single
            (D)  TOPOLOGY:        linear (xi)  SEQUENCE DESCRIPTION: SEQ ID NO: 681:

GUAUAUGUUC CCUCCAG                                                  17

(2)  INFORMATION FOR SEQ ID NO: 682:

(i)  SEQUENCE CHARACTERISTICS:
            (A)  LENGTH:          17 base pairs
            (B)  TYPE:            nucleic acid
            (C)  STRANDEDNESS:    single
            (D)  TOPOLOGY:        linear (xi)  SEQUENCE DESCRIPTION: SEQ ID NO: 682:

UAUAUGUUCC CUCCAGG                                                  17

(2)  INFORMATION FOR SEQ ID NO: 683:

(i)  SEQUENCE CHARACTERISTICS:
            (A)  LENGTH:          17 base pairs
            (B)  TYPE:            nucleic acid
            (C)  STRANDEDNESS:    single
            (D)  TOPOLOGY:        linear (xi)  SEQUENCE DESCRIPTION: SEQ ID NO: 683:

UGUUCCCUCC AGGUCAG                                                  17

(2)  INFORMATION FOR SEQ ID NO: 684:

(i)  SEQUENCE CHARACTERISTICS:
            (A)  LENGTH:          17 base pairs
            (B)  TYPE:            nucleic acid
            (C)  STRANDEDNESS:    single
            (D)  TOPOLOGY:        linear (xi)  SEQUENCE DESCRIPTION: SEQ ID NO: 684:

CUCCAGGUCA GCUGCCC                                                  17

(2)  INFORMATION FOR SEQ ID NO: 685:

(i)  SEQUENCE CHARACTERISTICS:
            (A)  LENGTH:          17 base pairs
            (B)  TYPE:            nucleic acid
            (C)  STRANDEDNESS:    single
            (D)  TOPOLOGY:        linear (xi)  SEQUENCE DESCRIPTION: SEQ ID NO: 685:

AACCCCCUCC UUACGCU                                                  17

(2)  INFORMATION FOR SEQ ID NO: 686:

(i)  SEQUENCE CHARACTERISTICS:
            (A)  LENGTH:          17 base pairs
            (B)  TYPE:            nucleic acid
            (C)  STRANDEDNESS:    single
            (D)  TOPOLOGY:        linear (xi)  SEQUENCE DESCRIPTION: SEQ ID NO: 686:

CCCCUCCUUA CGCUUUG                                                  17
```

(2) INFORMATION FOR SEQ ID NO: 687:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 687:

CCCUCCUUAC GCUUUGU                                                17

(2) INFORMATION FOR SEQ ID NO: 688:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 688:

CUUACGCUUU GUCACAC                                                17

(2) INFORMATION FOR SEQ ID NO: 689:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 689:

UUACGCUUUG UCACACA                                                17

(2) INFORMATION FOR SEQ ID NO: 690:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 690:

CGCUUUGUCA CACAAAA                                                17

(2) INFORMATION FOR SEQ ID NO: 691:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear (xi) SEQUENCE DESCRIPTION: SEQ ID NO: 691:

AAAAGUGUCU CUGCCUU                                                17

(2) INFORMATION FOR SEQ ID NO: 692:

(i) SEQUENCE CHARACTERISTICS:
        (A) LENGTH:        17 base pairs
        (B) TYPE:          nucleic acid
        (C) STRANDEDNESS:  single
        (D) TOPOLOGY:      linear

```
        (xi) SEQUENCE DESCRIPTION: SEQ ID NO: 692:

AAGUGUCUCU GCCUUGA                                                    17

(2) INFORMATION FOR SEQ ID NO: 693:

(i) SEQUENCE CHARACTERISTICS:

(A) LENGTH:            17 base pairs
                (B) TYPE:              nucleic acid
                (C) STRANDEDNESS:      single
                (D) TOPOLOGY:          linear (xi) SEQUENCE DESCRIPTION: SEQ ID NO: 693:

CUCUGCCUUG AGUCAUC                                                    17

(2) INFORMATION FOR SEQ ID NO: 694:

(i) SEQUENCE CHARACTERISTICS:

(A) LENGTH:            17 base pairs
                (B) TYPE:              nucleic acid
                (C) STRANDEDNESS:      single
                (D) TOPOLOGY:          linear (xi) SEQUENCE DESCRIPTION: SEQ ID NO: 694:

CCUUGAGUCA UCUAUUC                                                    17

(2) INFORMATION FOR SEQ ID NO: 695:

(i) SEQUENCE CHARACTERISTICS:

(A) LENGTH:            17 base pairs
                (B) TYPE:              nucleic acid
                (C) STRANDEDNESS:      single
                (D) TOPOLOGY:          linear (xi) SEQUENCE DESCRIPTION: SEQ ID NO: 695:

UGAGUCAUCU AUUCAAG                                                    17

(2) INFORMATION FOR SEQ ID NO: 696:

(i) SEQUENCE CHARACTERISTICS:

(A) LENGTH:            17 base pairs
                (B) TYPE:              nucleic acid
                (C) STRANDEDNESS:      single
                (D) TOPOLOGY:          linear (xi) SEQUENCE DESCRIPTION: SEQ ID NO: 696:

AGUCAUCUAU UCAAGCA                                                    17

(2) INFORMATION FOR SEQ ID NO: 697:

(i) SEQUENCE CHARACTERISTICS:

(A) LENGTH:            17 base pairs
                (B) TYPE:              nucleic acid
                (C) STRANDEDNESS:      single
                (D) TOPOLOGY:          linear (xi) SEQUENCE DESCRIPTION: SEQ ID NO: 697:

UCAUCUAUUC AAGCACU                                                    17

(2) INFORMATION FOR SEQ ID NO: 698:

(i) SEQUENCE CHARACTERISTICS:
```

```
            (A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 698:

CAUCUAUUCA AGCACUU                                                           17

(2)  INFORMATION FOR SEQ ID NO: 699:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 699:

CAAGCACUUA CAGCUCU                                                           17

(2)  INFORMATION FOR SEQ ID NO: 700:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 700:

AAGCACUUAC AGCUCUG                                                           17

(2)  INFORMATION FOR SEQ ID NO: 701:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 701:

UUACAGCUCU GGCCACA                                                           17

(2)  INFORMATION FOR SEQ ID NO: 702:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 702:

CAGGGCAUUU UACAGGU                                                           17

(2)  INFORMATION FOR SEQ ID NO: 703:

(i)  SEQUENCE CHARACTERISTICS:

(A)  LENGTH:             17 base pairs
            (B)  TYPE:               nucleic acid
            (C)  STRANDEDNESS:       single
            (D)  TOPOLOGY:           linear (xi)  SEQUENCE DESCRIPTION: SEQ ID NO: 703:

AGGGCAUUUU ACAGGUG                                                           17
```

-continued (2) INFORMATION FOR SEQ ID NO: 704:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 704:

GGGCAUUUUA CAGGUGC                                        17

(2) INFORMATION FOR SEQ ID NO: 705:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 705:

GGCAUUUUAC AGGUGCG                                        17

(2) INFORMATION FOR SEQ ID NO: 706:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 706:

AUGACAGUAG CAUUAUG                                        17

(2) INFORMATION FOR SEQ ID NO: 707:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 707:

AGUAGCAUUA UGAGUAG                                        17

(2) INFORMATION FOR SEQ ID NO: 708:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 708:

GUAGCAUUAU GAGUAGU                                        17

(2) INFORMATION FOR SEQ ID NO: 709:

(i) SEQUENCE CHARACTERISTICS:

(A) LENGTH: 17 base pairs
        (B) TYPE: nucleic acid
        (C) STRANDEDNESS: single
        (D) TOPOLOGY: linear -continued

```
    (xi) SEQUENCE DESCRIPTION: SEQ ID NO: 709:

UUAUGAGUAG UGUGAAU                                              17

(2) INFORMATION FOR SEQ ID NO: 710:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 710:

GUGUGAAUUC AGGUAGU                                              17

(2) INFORMATION FOR SEQ ID NO: 711:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 711:

UGUGAAUUCA GGUAGUA                                              17

(2) INFORMATION FOR SEQ ID NO: 712:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 712:

AUUCAGGUAG UAAAUAU                                              17

(2) INFORMATION FOR SEQ ID NO: 713:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 713:

CAGGUAGUAA AUAUGAA                                              17

(2) INFORMATION FOR SEQ ID NO: 714:

(i) SEQUENCE CHARACTERISTICS:

(A) LENGTH:          17 base pairs
         (B) TYPE:            nucleic acid
         (C) STRANDEDNESS:    single
         (D) TOPOLOGY:        linear (xi) SEQUENCE DESCRIPTION: SEQ ID NO: 714:

UAGUAAAUAU GAAACUA                                              17

(2) INFORMATION FOR SEQ ID NO: 715:

(i) SEQUENCE CHARACTERISTICS:
```

```
        (A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 715:

AUGAAACUAG GGUUUGA                                                    17

(2) INFORMATION FOR SEQ ID NO: 716:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 716:

ACUAGGGUUU GAAAUUG                                                    17

(2) INFORMATION FOR SEQ ID NO: 717:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 717:

CUAGGGUUUG AAAUUGA                                                    17

(2) INFORMATION FOR SEQ ID NO: 718:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 718:

UUUGAAAUUG AUAAUGC                                                    17

(2) INFORMATION FOR SEQ ID NO: 719:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 719:

AAAUUGAUAA UGCUUUC                                                    17

(2) INFORMATION FOR SEQ ID NO: 720:

(i) SEQUENCE CHARACTERISTICS:

(A) LENGTH:           17 base pairs
        (B) TYPE:             nucleic acid
        (C) STRANDEDNESS:     single
        (D) TOPOLOGY:         linear (xi) SEQUENCE DESCRIPTION: SEQ ID NO: 720:

AUAAUGCUUU CACAACA                                                    17
```

(2) INFORMATION FOR SEQ ID NO: 721:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 721:

UAAUGCUUUC ACAACAU                                    17

(2) INFORMATION FOR SEQ ID NO: 722:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 722:

AAUGCUUUCA CAACAUU                                    17

(2) INFORMATION FOR SEQ ID NO: 723:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 723:

CACAACAUUU GCAGAUG                                    17

(2) INFORMATION FOR SEQ ID NO: 724:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 724:

ACAACAUUUG CAGAUGU                                    17

(2) INFORMATION FOR SEQ ID NO: 725:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 725:

GCAGAUGUUU UAGAAGG                                    17

(2) INFORMATION FOR SEQ ID NO: 726:

(i) SEQUENCE CHARACTERISTICS:

(A) LENGTH: 17 base pairs
        (B) TYPE: nucleic acid
        (C) STRANDEDNESS: single

```
            (D) TOPOLOGY:           linear (xi) SEQUENCE DESCRIPTION: SEQ ID NO: 726:

CAGAUGUUUU AGAAGGA                                                      17

(2) INFORMATION FOR SEQ ID NO: 727:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 727:

AGAUGUUUUA GAAGGAA                                                      17

(2) INFORMATION FOR SEQ ID NO: 728:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 728:

GAUGUUUUAG AAGGAAA                                                      17

(2) INFORMATION FOR SEQ ID NO: 729:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 729:

AAAAAAGUUC CUUCCUA                                                      17

(2) INFORMATION FOR SEQ ID NO: 730:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 730:

AAAAAGUUCC UUCCUAA                                                      17

(2) INFORMATION FOR SEQ ID NO: 731:

(i) SEQUENCE CHARACTERISTICS:

(A) LENGTH:             17 base pairs
            (B) TYPE:               nucleic acid
            (C) STRANDEDNESS:       single
            (D) TOPOLOGY:           linear (xi) SEQUENCE DESCRIPTION: SEQ ID NO: 731:

AAGUUCCUUC CUAAAAU                                                      17

(2) INFORMATION FOR SEQ ID NO: 732:
```

```
        (i) SEQUENCE CHARACTERISTICS:

(A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 732:

AGUUCCUUCC UAAAAUA                                                      17

(2) INFORMATION FOR SEQ ID NO: 733:

(i) SEQUENCE CHARACTERISTICS:

(A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 733:

UCCUUCCUAA AAUAAUU                                                      17

(2) INFORMATION FOR SEQ ID NO: 734:

(i) SEQUENCE CHARACTERISTICS:

(A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 734:

CCUAAAAUAA UUUCUCU                                                      17

(2) INFORMATION FOR SEQ ID NO: 735:

(i) SEQUENCE CHARACTERISTICS:

(A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 735:

AAAAUAAUUU CUCUACA                                                      17

(2) INFORMATION FOR SEQ ID NO: 736:

(i) SEQUENCE CHARACTERISTICS:

(A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 736:

AAAUAAUUUC UCUACAA                                                      17

(2) INFORMATION FOR SEQ ID NO: 737:

(i) SEQUENCE CHARACTERISTICS:

(A) LENGTH:          17 base pairs
            (B) TYPE:            nucleic acid
            (C) STRANDEDNESS:    single
            (D) TOPOLOGY:        linear (xi) SEQUENCE DESCRIPTION: SEQ ID NO: 737:
```

AAUAAUUUCU CUACAAU                                                        17

(2) INFORMATION FOR SEQ ID NO: 738:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 738:

UAAUUCUCU ACAAUUG                                                         17

(2) INFORMATION FOR SEQ ID NO: 739:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 739:

AUUUCUCUAC AAUUGGA                                                        17

(2) INFORMATION FOR SEQ ID NO: 740:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 740:

UCUACAAUUG GAAGAUU                                                        17

(2) INFORMATION FOR SEQ ID NO: 741:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 741:

UGGAAGAUUG GAAGAUU                                                        17

(2) INFORMATION FOR SEQ ID NO: 742:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 742:

UGGAAGAUUC AGCUAGU                                                        17

(2) INFORMATION FOR SEQ ID NO: 743:

(i) SEQUENCE CHARACTERISTICS:

(A) LENGTH:          17 base pairs
        (B) TYPE:            nucleic acid

```
          (C)  STRANDEDNESS:          single
          (D)  TOPOLOGY:              linear (xi) SEQUENCE DESCRIPTION: SEQ ID NO: 743:

GGAAGAUUCA GCUAGUU                                              17

(2)  INFORMATION FOR SEQ ID NO: 744:

(i)  SEQUENCE CHARACTERISTICS:
          (A)  LENGTH:                17 base pairs
          (B)  TYPE:                  nucleic acid
          (C)  STRANDEDNESS:          single
          (D)  TOPOLOGY:              linear (xi) SEQUENCE DESCRIPTION: SEQ ID NO: 744:

AUUCAGCUAG UUAGGAG                                              17

(2)  INFORMATION FOR SEQ ID NO: 745:

(i)  SEQUENCE CHARACTERISTICS:
          (A)  LENGTH:                17 base pairs
          (B)  TYPE:                  nucleic acid
          (C)  STRANDEDNESS:          single
          (D)  TOPOLOGY:              linear (xi) SEQUENCE DESCRIPTION: SEQ ID NO: 745:

CAGCUAGUUA GGAGCCC                                              17

(2)  INFORMATION FOR SEQ ID NO: 746:

(i)  SEQUENCE CHARACTERISTICS:
          (A)  LENGTH:                17 base pairs
          (B)  TYPE:                  nucleic acid
          (C)  STRANDEDNESS:          single
          (D)  TOPOLOGY:              linear (xi) SEQUENCE DESCRIPTION: SEQ ID NO: 746:

AGCUAGUUAG GAGCCCA                                              17

(2)  INFORMATION FOR SEQ ID NO: 747:

(i)  SEQUENCE CHARACTERISTICS:
          (A)  LENGTH:                17 base pairs
          (B)  TYPE:                  nucleic acid
          (C)  STRANDEDNESS:          single
          (D)  TOPOLOGY:              linear (xi) SEQUENCE DESCRIPTION: SEQ ID NO: 747:

GAGCCCAUUU UUUCCUA                                              17

(2)  INFORMATION FOR SEQ ID NO: 748:

(i)  SEQUENCE CHARACTERISTICS:
          (A)  LENGTH:                17 base pairs
          (B)  TYPE:                  nucleic acid
          (C)  STRANDEDNESS:          single
          (D)  TOPOLOGY:              linear (xi) SEQUENCE DESCRIPTION: SEQ ID NO: 748:

AGCCCAUUUU UUCCUAA                                              17

(2)  INFORMATION FOR SEQ ID NO: 749:
```

```
    (i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 749:

GCCCAUUUUU UCCUAAU                                                    17

(2) INFORMATION FOR SEQ ID NO: 750:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 750:

CCCAUUUUUU CCUAAUC                                                    17

(2) INFORMATION FOR SEQ ID NO: 751:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 751:

CCAUUUUUUC CUAAUCU                                                    17

(2) INFORMATION FOR SEQ ID NO: 752:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 752:

CAUUUUUUCC UAAUCUG                                                    17

(2) INFORMATION FOR SEQ ID NO: 753:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 753:

UUUUUCCUAA UCUGUGU                                                    17

(2) INFORMATION FOR SEQ ID NO: 754:

(i) SEQUENCE CHARACTERISTICS:

(A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 754:
```

UUCCUAAUCU GUGUGUG                                                                17

(2) INFORMATION FOR SEQ ID NO: 755:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 755:

UGCCCUGUAA CCUGACU                                                                17

(2) INFORMATION FOR SEQ ID NO: 756:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 756:

UGACUGGUUA ACAGCAG                                                                17

(2) INFORMATION FOR SEQ ID NO: 757:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 757:

GACUGGUUAA CAGCAGU                                                                17

(2) INFORMATION FOR SEQ ID NO: 758:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 758:

ACAGCAGUCC UUUGUAA                                                                17

(2) INFORMATION FOR SEQ ID NO: 759:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 759:

GCAGUCCUUU GUAAACA                                                                17

(2) INFORMATION FOR SEQ ID NO: 760:

(i) SEQUENCE CHARACTERISTICS:

(A) LENGTH:          17 base pairs

```
        (B) TYPE:              nucleic acid
        (C) STRANDEDNESS:      single
        (D) TOPOLOGY:          linear (xi) SEQUENCE DESCRIPTION: SEQ ID NO: 760:

CAGUCCUUUG UAAACAG                                               17

(2) INFORMATION FOR SEQ ID NO: 761:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 761:

UCCUUUGUAA ACAGUGU                                               17

(2) INFORMATION FOR SEQ ID NO: 762:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 762:

AACAGUGUUU UAAACUC                                               17

(2) INFORMATION FOR SEQ ID NO: 763:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 763:

ACAGUGUUUU AAACUCU                                               17

(2) INFORMATION FOR SEQ ID NO: 764:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 764:

CAGUGUUUUA AACUCUC                                               17

(2) INFORMATION FOR SEQ ID NO: 765:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (xi) SEQUENCE DESCRIPTION: SEQ ID NO: 765:

AGUGUUUUAA ACUCUCC                                               17
```

(2) INFORMATION FOR SEQ ID NO: 766:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 766:

UUUAAACUCU CCUAGUC            17

(2) INFORMATION FOR SEQ ID NO: 767:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 767:

UAAACUCUCC UAGUCAA            17

(2) INFORMATION FOR SEQ ID NO: 768:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 768:

ACUCUCCUAG UCAAUAU            17

(2) INFORMATION FOR SEQ ID NO: 769:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 769:

CUCCUAGUCA AUAUCCA            17

(2) INFORMATION FOR SEQ ID NO: 770:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 770:

UAGUCAAUAU CCACCCC            17

(2) INFORMATION FOR SEQ ID NO: 771:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 771:

GUCAAUAUCC ACCCCAU                                                          17

(2) INFORMATION FOR SEQ ID NO: 772:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 772:

CACCCCAUCC AAUUUAU                                                          17

(2) INFORMATION FOR SEQ ID NO: 773:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 773:

CAUCCAAUUU AUCAAGG                                                          17

(2) INFORMATION FOR SEQ ID NO: 774:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 774:

AUCCAAUUUA UCAAGGA                                                          17

(2) INFORMATION FOR SEQ ID NO: 775:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 775:

UCCAAUUUAU CAAGGAA                                                          17

(2) INFORMATION FOR SEQ ID NO: 776:

(i) SEQUENCE CHARACTERISTICS:

(A) LENGTH:          17 base pairs
        (B) TYPE:            nucleic acid
        (C) STRANDEDNESS:    single
        (D) TOPOLOGY:        linear (xi) SEQUENCE DESCRIPTION: SEQ ID NO: 776:

CAAUUUAUCA AGGAAGA                                                          17

(2) INFORMATION FOR SEQ ID NO: 777:

(i) SEQUENCE CHARACTERISTICS:

```
            (A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 777:

GAAAUGGUUC AGAAAAU                                                  17

(2) INFORMATION FOR SEQ ID NO: 778:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 778:

AAAUGGUUCA GAAAAUA                                                  17

(2) INFORMATION FOR SEQ ID NO: 779:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 779:

CAGAAAAUAU UUUCAGC                                                  17

(2) INFORMATION FOR SEQ ID NO: 780:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 780:

GAAAAUAUUU UCAGCCU                                                  17

(2) INFORMATION FOR SEQ ID NO: 781:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 781:

AAAAUAUUUU CAGCCUA                                                  17

(2) INFORMATION FOR SEQ ID NO: 782:

(i) SEQUENCE CHARACTERISTICS:

(A)  LENGTH:            17 base pairs
            (B)  TYPE:              nucleic acid
            (C)  STRANDEDNESS:      single
            (D)  TOPOLOGY:          linear (xi) SEQUENCE DESCRIPTION: SEQ ID NO: 782:

AAAUAUUUUC AGCCUAC                                                  17
```

(2) INFORMATION FOR SEQ ID NO: 783:

(i) SEQUENCE CHARACTERISTICS:

(A) LENGTH:           17 base pairs
        (B) TYPE:             nucleic acid
        (C) STRANDEDNESS:    single
        (D) TOPOLOGY:        linear (xi) SEQUENCE DESCRIPTION: SEQ ID NO: 783:

AAUAUUUUCA GCCUACA                                    17

(2) INFORMATION FOR SEQ ID NO: 784:

(i) SEQUENCE CHARACTERISTICS:

(A) LENGTH:           17 base pairs
        (B) TYPE:             nucleic acid
        (C) STRANDEDNESS:    single
        (D) TOPOLOGY:        linear (xi) SEQUENCE DESCRIPTION: SEQ ID NO: 784:

UUCAGCCUAC AGUUAUG                                    17

(2) INFORMATION FOR SEQ ID NO: 785:

(i) SEQUENCE CHARACTERISTICS:

(A) LENGTH:           17 base pairs
        (B) TYPE:             nucleic acid
        (C) STRANDEDNESS:    single
        (D) TOPOLOGY:        linear (xi) SEQUENCE DESCRIPTION: SEQ ID NO: 785:

CCUACAGUUA UGUUCAG                                    17

(2) INFORMATION FOR SEQ ID NO: 786:

(i) SEQUENCE CHARACTERISTICS:

(A) LENGTH:           17 base pairs
        (B) TYPE:             nucleic acid
        (C) STRANDEDNESS:    single
        (D) TOPOLOGY:        linear (xi) SEQUENCE DESCRIPTION: SEQ ID NO: 786:

CUACAGUUAU GUUCAGU                                    17

(2) INFORMATION FOR SEQ ID NO: 787:

(i) SEQUENCE CHARACTERISTICS:

(A) LENGTH:           17 base pairs
        (B) TYPE:             nucleic acid
        (C) STRANDEDNESS:    single
        (D) TOPOLOGY:        linear (xi) SEQUENCE DESCRIPTION: SEQ ID NO: 787:

AGUUAUGUUC AGUCACA                                    17

(2) INFORMATION FOR SEQ ID NO: 788:

(i) SEQUENCE CHARACTERISTICS:

(A) LENGTH:           17 base pairs
        (B) TYPE:             nucleic acid
        (C) STRANDEDNESS:    single
        (D) TOPOLOGY:        linear (xi) SEQUENCE DESCRIPTION: SEQ ID NO: 788:

GUUAUGUUCA GUCACAC                          17

(2) INFORMATION FOR SEQ ID NO: 789:

(i) SEQUENCE CHARACTERISTICS:
      (A) LENGTH:         17 base pairs
      (B) TYPE:            nucleic acid
      (C) STRANDEDNESS:    single
      (D) TOPOLOGY:        linear (xi) SEQUENCE DESCRIPTION: SEQ ID NO: 789:

UGUUCAGUCA CACACAC                          17

(2) INFORMATION FOR SEQ ID NO: 790:

(i) SEQUENCE CHARACTERISTICS:
      (A) LENGTH:         17 base pairs
      (B) TYPE:            nucleic acid
      (C) STRANDEDNESS:    single
      (D) TOPOLOGY:        linear (xi) SEQUENCE DESCRIPTION: SEQ ID NO: 790:

ACACACAUAC AAAAUGU                          17

(2) INFORMATION FOR SEQ ID NO: 791:

(i) SEQUENCE CHARACTERISTICS:
      (A) LENGTH:         17 base pairs
      (B) TYPE:            nucleic acid
      (C) STRANDEDNESS:    single
      (D) TOPOLOGY:        linear (xi) SEQUENCE DESCRIPTION: SEQ ID NO: 791:

CAAAAUGUUC CUUUUGC                          17

(2) INFORMATION FOR SEQ ID NO: 792:

(i) SEQUENCE CHARACTERISTICS:
      (A) LENGTH:         17 base pairs
      (B) TYPE:            nucleic acid
      (C) STRANDEDNESS:    single
      (D) TOPOLOGY:        linear (xi) SEQUENCE DESCRIPTION: SEQ ID NO: 792:

AAAAUGUUCC UUUUGCU                          17

(2) INFORMATION FOR SEQ ID NO: 793:

(i) SEQUENCE CHARACTERISTICS:
      (A) LENGTH:         17 base pairs
      (B) TYPE:            nucleic acid
      (C) STRANDEDNESS:    single
      (D) TOPOLOGY:        linear (xi) SEQUENCE DESCRIPTION: SEQ ID NO: 793:

AUGUUCCUUU UGCUUUU                          17

(2) INFORMATION FOR SEQ ID NO: 794:

(i) SEQUENCE CHARACTERISTICS:

(A) LENGTH:           17 base pairs
              (B) TYPE:             nucleic acid
              (C) STRANDEDNESS:     single
              (D) TOPOLOGY:         linear (xi) SEQUENCE DESCRIPTION: SEQ ID NO: 794:

UGUUCCUUUU GCUUUUA                                                   17

(2)   INFORMATION FOR SEQ ID NO: 795:

(i) SEQUENCE CHARACTERISTICS:

(A) LENGTH:           17 base pairs
              (B) TYPE:             nucleic acid
              (C) STRANDEDNESS:     single
              (D) TOPOLOGY:         linear (xi) SEQUENCE DESCRIPTION: SEQ ID NO: 795:

GUUCCUUUUG CUUUUAA                                                   17

(2)   INFORMATION FOR SEQ ID NO: 796:

(i) SEQUENCE CHARACTERISTICS:

(A) LENGTH:           17 base pairs
              (B) TYPE:             nucleic acid
              (C) STRANDEDNESS:     single
              (D) TOPOLOGY:         linear (xi) SEQUENCE DESCRIPTION: SEQ ID NO: 796:

CUUUUGCUUU UAAAGUA                                                   17

(2)   INFORMATION FOR SEQ ID NO: 797:

(i) SEQUENCE CHARACTERISTICS:

(A) LENGTH:           17 base pairs
              (B) TYPE:             nucleic acid
              (C) STRANDEDNESS:     single
              (D) TOPOLOGY:         linear (xi) SEQUENCE DESCRIPTION: SEQ ID NO: 797:

UUUUGCUUUU AAAGUAA                                                   17

(2)   INFORMATION FOR SEQ ID NO: 798:

(i) SEQUENCE CHARACTERISTICS:

(A) LENGTH:           17 base pairs
              (B) TYPE:             nucleic acid
              (C) STRANDEDNESS:     single
              (D) TOPOLOGY:         linear (xi) SEQUENCE DESCRIPTION: SEQ ID NO: 798:

UUUGCUUUUA AAGUAAU                                                   17

(2)   INFORMATION FOR SEQ ID NO: 799:

(i) SEQUENCE CHARACTERISTICS:

(A) LENGTH:           17 base pairs
              (B) TYPE:             nucleic acid
              (C) STRANDEDNESS:     single
              (D) TOPOLOGY:         linear (xi) SEQUENCE DESCRIPTION: SEQ ID NO: 799:

UUGCUUUUAA AGUAAUU                                                   17

(2) INFORMATION FOR SEQ ID NO: 800:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 800:

UUUAAAGUAA UUUUUGA    17

(2) INFORMATION FOR SEQ ID NO: 801:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 801:

AAAGUAAUUU UUGACUC    17

(2) INFORMATION FOR SEQ ID NO: 802:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 802:

AAGUAAUUUU UGACUCC    17

(2) INFORMATION FOR SEQ ID NO: 803:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 803:

AGUAAUUUUU GACUCCC    17

(2) INFORMATION FOR SEQ ID NO: 804:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 804:

GUAAUUUUUG ACUCCCA    17

(2) INFORMATION FOR SEQ ID NO: 805:

(i) SEQUENCE CHARACTERISTICS:

(A) LENGTH: 17 base pairs
        (B) TYPE: nucleic acid
        (C) STRANDEDNESS: single (D) TOPOLOGY:          linear (xi) SEQUENCE DESCRIPTION: SEQ ID NO: 805:

UUUUGACUCC CAGAUCA                                                    17

(2) INFORMATION FOR SEQ ID NO: 806:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 806:

UCCCAGAUCA GUCAGAG                                                    17

(2) INFORMATION FOR SEQ ID NO: 807:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 807:

AGAUCAGUCA GAGCCCC                                                    17

(2) INFORMATION FOR SEQ ID NO: 808:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 808:

GAGCCCCUAC AGCAUUG                                                    17

(2) INFORMATION FOR SEQ ID NO: 809:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 809:

UACAGCAUUG UUAAGAA                                                    17

(2) INFORMATION FOR SEQ ID NO: 810:

(i) SEQUENCE CHARACTERISTICS:
            (A) LENGTH:            17 base pairs
            (B) TYPE:              nucleic acid
            (C) STRANDEDNESS:      single
            (D) TOPOLOGY:          linear (xi) SEQUENCE DESCRIPTION: SEQ ID NO: 810:

AGCAUUGUUA AGAAAGU                                                    17

(2) INFORMATION FOR SEQ ID NO: 811:

```
       (i) SEQUENCE CHARACTERISTICS:

(A) LENGTH:          17 base pairs
           (B) TYPE:            nucleic acid
           (C) STRANDEDNESS:    single
           (D) TOPOLOGY:        linear (xi) SEQUENCE DESCRIPTION: SEQ ID NO: 811:

GCAUUGUUAA GAAAGUA                                                    17

(2) INFORMATION FOR SEQ ID NO: 812:

(i) SEQUENCE CHARACTERISTICS:

(A) LENGTH:          17 base pairs
           (B) TYPE:            nucleic acid
           (C) STRANDEDNESS:    single
           (D) TOPOLOGY:        linear (xi) SEQUENCE DESCRIPTION: SEQ ID NO: 812:

AAGAAAGUAU UUGAUUU                                                    17

(2) INFORMATION FOR SEQ ID NO: 813:

(i) SEQUENCE CHARACTERISTICS:

(A) LENGTH:          17 base pairs
           (B) TYPE:            nucleic acid
           (C) STRANDEDNESS:    single
           (D) TOPOLOGY:        linear (xi) SEQUENCE DESCRIPTION: SEQ ID NO: 813:

GAAAGUAUUU GAUUUUU                                                    17

(2) INFORMATION FOR SEQ ID NO: 814:

(i) SEQUENCE CHARACTERISTICS:

(A) LENGTH:          17 base pairs
           (B) TYPE:            nucleic acid
           (C) STRANDEDNESS:    single
           (D) TOPOLOGY:        linear (xi) SEQUENCE DESCRIPTION: SEQ ID NO: 814:

AAAGUAUUUG AUUUUUG                                                    17

(2) INFORMATION FOR SEQ ID NO: 815:

(i) SEQUENCE CHARACTERISTICS:

(A) LENGTH:          17 base pairs
           (B) TYPE:            nucleic acid
           (C) STRANDEDNESS:    single
           (D) TOPOLOGY:        linear (xi) SEQUENCE DESCRIPTION: SEQ ID NO: 815:

UAUUUGAUUU UUGUCUC                                                    17

(2) INFORMATION FOR SEQ ID NO: 816:

(i) SEQUENCE CHARACTERISTICS:

(A) LENGTH:          17 base pairs
           (B) TYPE:            nucleic acid
           (C) STRANDEDNESS:    single
           (D) TOPOLOGY:        linear (xi) SEQUENCE DESCRIPTION: SEQ ID NO: 816:
```

```
AUUUGAUUUU UGUCUCA                                                17
```

(2) INFORMATION FOR SEQ ID NO: 817:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 817:

```
UUUGAUUUUU GUCUCAA                                                17
```

(2) INFORMATION FOR SEQ ID NO: 818:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 818:

```
UUGAUUUUUG UCUCAAU                                                17
```

(2) INFORMATION FOR SEQ ID NO: 819:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 819:

```
AUUUUGUCU CAAUGAA                                                 17
```

(2) INFORMATION FOR SEQ ID NO: 820:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 820:

```
UUUUGUCUCA AUGAAAA                                                17
```

(2) INFORMATION FOR SEQ ID NO: 821:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 821:

```
AUGAAAAUAA AACUAUA                                                17
```

(2) INFORMATION FOR SEQ ID NO: 822:

(i) SEQUENCE CHARACTERISTICS:

(A) LENGTH: 17 base pairs
        (B) TYPE: nucleic acid

```
        (C)  STRANDEDNESS:       single
        (D)  TOPOLOGY:           linear (xi)  SEQUENCE DESCRIPTION: SEQ ID NO: 822:

AUAAAACUAU AUUCAUU                                                    17

(2)  INFORMATION FOR SEQ ID NO: 823:

(i)  SEQUENCE CHARACTERISTICS:

(A)  LENGTH:             17 base pairs
        (B)  TYPE:               nucleic acid
        (C)  STRANDEDNESS:       single
        (D)  TOPOLOGY:           linear (xi)  SEQUENCE DESCRIPTION: SEQ ID NO: 823:

AAAACUAUAU UCAUUUC                                                    17

(2)  INFORMATION FOR SEQ ID NO: 824:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear

FEATURE:

(D)  OTHER INFORMATION: The letter "N" stands for the stem
             II region of a HH ribozyme.

(xi)  SEQUENCE DESCRIPTION: SEQ ID NO: 824:

UAGCUCGGCU GAUGANGAAA CUCCGGC                                         27

(2)  INFORMATION FOR SEQ ID NO: 825:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear (ix)  FEATURE:

(D)  OTHER INFORMATION:  The letter "N" stands for the stem
             II region of a HH ribozyme.

(xi)  SEQUENCE DESCRIPTION: SEQ ID NO: 825:

GCCGGGGCCU GAUGANGAAA GCUCGGG                                         27

(2)  INFORMATION FOR SEQ ID NO: 826:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear (ix)  FEATURE:

(D)  OTHER INFORMATION:  The letter "N" stands for the stem
             II region of a HH ribozyme.

(xi)  SEQUENCE DESCRIPTION: SEQ ID NO: 826:

ACGCCGACCU GAUGANGAAA GGUGGCC                                         27
```

```
(2)  INFORMATION FOR SEQ ID NO: 827:

(i)  SEQUENCE CHARACTERISTICS:

(A)  LENGTH:           27 base pairs
          (B)  TYPE:              nucleic acid
          (C)  STRANDEDNESS:      single
          (D)  TOPOLOGY:          linear

FEATURE:

(D)  OTHER INFORMATION:  The letter "N" stands for the stem
               II region of a HH ribozyme.

(xi) SEQUENCE DESCRIPTION: SEQ ID NO: 827:

CGGACGCCCU GAUGANGAAA CGAGGUG                                               27

(2)  INFORMATION FOR SEQ ID NO: 828:

(i)  SEQUENCE CHARACTERISTICS:

(A)  LENGTH:           27 base pairs
          (B)  TYPE:              nucleic acid
          (C)  STRANDEDNESS:      single
          (D)  TOPOLOGY:          linear (ix) FEATURE:

(D)  OTHER INFORMATION:  The letter "N" stands for the stem
               II region of a HH ribozyme.

(xi) SEQUENCE DESCRIPTION: SEQ ID NO: 828:

CUCGGGCGCU GAUGANGAAA CGCCGAC                                               27

(2)  INFORMATION FOR SEQ ID NO: 829:

(i)  SEQUENCE CHARACTERISTICS:

(A)  LENGTH:           27 base pairs
          (B)  TYPE:              nucleic acid
          (C)  STRANDEDNESS:      single
          (D)  TOPOLOGY:          linear (ix) FEATURE:

(D)  OTHER INFORMATION:  The letter "N" stands for the stem
               II region of a HH ribozyme.

(xi) SEQUENCE DESCRIPTION: SEQ ID NO: 829:

GAGGCGGGCU GAUGANGAAA CUCGGGC                                               27

(2)  INFORMATION FOR SEQ ID NO: 830:

(i)  SEQUENCE CHARACTERISTICS:

(A)  LENGTH:           27 base pairs
          (B)  TYPE:              nucleic acid
          (C)  STRANDEDNESS:      single
          (D)  TOPOLOGY:          linear (ix) FEATURE:

(D)  OTHER INFORMATION:  The letter "N" stands for the stem
               II region of a HH ribozyme.

(xi) SEQUENCE DESCRIPTION: SEQ ID NO: 830:

UUGGCGGCCU GAUGANGAAA GGCGGGG                                               27

(2)  INFORMATION FOR SEQ ID NO: 831:

(i)  SEQUENCE CHARACTERISTICS:
```

```
          (A)  LENGTH:            27 base pairs
          (B)  TYPE:              nucleic acid
          (C)  STRANDEDNESS:      single
          (D)  TOPOLOGY:          linear (ix) FEATURE:

(D)  OTHER INFORMATION:  The letter "N" stands for the stem
               II region of a HH ribozyme.

(xi) SEQUENCE DESCRIPTION: SEQ ID NO: 831:

ACUGGACGCU GAUGANGAAA GUCAGGG                                              27

(2) INFORMATION FOR SEQ ID NO: 832:

(i)  SEQUENCE CHARACTERISTICS:

(A)  LENGTH:            27 base pairs
          (B)  TYPE:              nucleic acid
          (C)  STRANDEDNESS:      single
          (D)  TOPOLOGY:          linear (ix) FEATURE:

(D)  OTHER INFORMATION:  The letter "N" stands for the stem
               II region of a HH ribozyme.

(xi) SEQUENCE DESCRIPTION: SEQ ID NO: 832:

CAAUACUGCU GAUGANGAAA CGGAGUC                                              27

(2) INFORMATION FOR SEQ ID NO: 833:

(i)  SEQUENCE CHARACTERISTICS:

(A)  LENGTH:            27 base pairs
          (B)  TYPE:              nucleic acid
          (C)  STRANDEDNESS:      single
          (D)  TOPOLOGY:          linear (ix) FEATURE:

(D)  OTHER INFORMATION:  The letter "N" stands for the stem
               II region of a HH ribozyme.

(xi) SEQUENCE DESCRIPTION: SEQ ID NO: 833:

CCGAUCAACU GAUGANGAAA CUGGACG                                              27

(2) INFORMATION FOR SEQ ID NO: 834:

(i)  SEQUENCE CHARACTERISTICS:

(A)  LENGTH:            27 base pairs
          (B)  TYPE:              nucleic acid
          (C)  STRANDEDNESS:      single
          (D)  TOPOLOGY:          linear (ix) FEATURE:

(D)  OTHER INFORMATION:  The letter "N" stands for the stem
               II region of a HH ribozyme.

(xi) SEQUENCE DESCRIPTION: SEQ ID NO: 834:

UCCCGAUCCU GAUGANGAAA UACUGGA                                              27

(2) INFORMATION FOR SEQ ID NO: 835:

(i)  SEQUENCE CHARACTERISTICS:

(A)  LENGTH:            27 base pairs
          (B)  TYPE:              nucleic acid
```

(C)  STRANDEDNESS:       single
                    (D)  TOPOLOGY:           linear (ix) FEATURE:

(D)  OTHER INFORMATION:  The letter "N" stands for the stem
                         II region of a HH ribozyme.

(xi) SEQUENCE DESCRIPTION: SEQ ID NO: 835:

GCUCUCCCCU GAUGANGAAA UCAAUAC                                                27

(2)  INFORMATION FOR SEQ ID NO: 836:

(i)  SEQUENCE CHARACTERISTICS:

(A)  LENGTH:             27 base pairs
                    (B)  TYPE:               nucleic acid
                    (C)  STRANDEDNESS:       single
                    (D)  TOPOLOGY:           linear (ix) FEATURE:

(D)  OTHER INFORMATION:  The letter "N" stands for the stem
                         II region of a HH ribozyme.

(xi) SEQUENCE DESCRIPTION: SEQ ID NO: 836:

UCCCCGAACU GAUGANGAAA GCUCGCU                                                27

(2)  INFORMATION FOR SEQ ID NO: 837:

(i)  SEQUENCE CHARACTERISTICS:

(A)  LENGTH:             27 base pairs
                    (B)  TYPE:               nucleic acid
                    (C)  STRANDEDNESS:       single
                    (D)  TOPOLOGY:           linear (ix) FEATURE:

(D)  OTHER INFORMATION:  The letter "N" stands for the stem
                         II region of a HH ribozyme.

(xi) SEQUENCE DESCRIPTION: SEQ ID NO: 837:

GCUCCCCGCU GAUGANGAAA GAGCUCG                                                27

(2)  INFORMATION FOR SEQ ID NO: 838:

(i)  SEQUENCE CHARACTERISTICS:

(A)  LENGTH:             27 base pairs
                    (B)  TYPE:               nucleic acid
                    (C)  STRANDEDNESS:       single
                    (D)  TOPOLOGY:           linear (ix) FEATURE:

(D)  OTHER INFORMATION:  The letter "N" stands for the stem
                         II region of a HH ribozyme.

(xi) SEQUENCE DESCRIPTION: SEQ ID NO: 838:

UGCUCCCCCU GAUGANGAAA AGAGCUC                                                27

(2)  INFORMATION FOR SEQ ID NO: 839:

(i)  SEQUENCE CHARACTERISTICS:

(A)  LENGTH:             27 base pairs
                    (B)  TYPE:               nucleic acid
                    (C)  STRANDEDNESS:       single
                    (D)  TOPOLOGY:           linear (ix) FEATURE:

(D) OTHER INFORMATION:   The letter "N" stands for the stem
                  II region of a HH ribozyme.

(xi) SEQUENCE DESCRIPTION: SEQ ID NO: 839:

CCGUCCCGCU GAUGANGAAA GGGUCGC                                          27

(2) INFORMATION FOR SEQ ID NO: 840:

(i) SEQUENCE CHARACTERISTICS:

(A) LENGTH:            27 base pairs
              (B) TYPE:              nucleic acid
              (C) STRANDEDNESS:      single
              (D) TOPOLOGY:          linear (ix) FEATURE:

(D) OTHER INFORMATION:   The letter "N" stands for the stem
                  II region of a HH ribozyme.

(xi) SEQUENCE DESCRIPTION: SEQ ID NO: 840:

AGCGCCAGCU GAUGANGAAA GCGCUGC                                          27

(2) INFORMATION FOR SEQ ID NO: 841:

(i) SEQUENCE CHARACTERISTICS:

(A) LENGTH:            27 base pairs
              (B) TYPE:              nucleic acid
              (C) STRANDEDNESS:      single
              (D) TOPOLOGY:          linear (ix) FEATURE:

(D) OTHER INFORMATION:   The letter "N" stands for the stem
                  II region of a HH ribozyme.

(xi) SEQUENCE DESCRIPTION: SEQ ID NO: 841:

GCCGGGCACU GAUGANGAAA GCGCAGC                                          27

(2) INFORMATION FOR SEQ ID NO: 842:

(i) SEQUENCE CHARACTERISTICS:

(A) LENGTH:            27 base pairs
              (B) TYPE:              nucleic acid
              (C) STRANDEDNESS:      single
              (D) TOPOLOGY:          linear (ix) FEATURE:

(D) OTHER INFORMATION:   The letter "N" stands for the stem
                  II region of a HH ribozyme.

(xi) SEQUENCE DESCRIPTION: SEQ ID NO: 842:

CAGAGCCCCU GAUGANGAAA CUCGCCG                                          27

(2) INFORMATION FOR SEQ ID NO: 843:

(i) SEQUENCE CHARACTERISTICS:

(A) LENGTH:            27 base pairs
              (B) TYPE:              nucleic acid
              (C) STRANDEDNESS:      single
              (D) TOPOLOGY:          linear (ix) FEATURE:

(D) OTHER INFORMATION:   The letter "N" stands for the stem

II region of a HH ribozyme.

(xi) SEQUENCE DESCRIPTION: SEQ ID NO: 843:

UUCCUCCACU GAUGANGAAA GCCCGAC                                              27

(2) INFORMATION FOR SEQ ID NO: 844:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 844:

CCUUGGCACU GAUGANGAAA CUUUCUU                                              27

(2) INFORMATION FOR SEQ ID NO: 845:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 845:

GCCUUGGCCU GAUGANGAAA ACUUUCU                                              27

(2) INFORMATION FOR SEQ ID NO: 846:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 846:

GAGCUUGUCU GAUGANGAAA CUCGUGC                                              27

(2) INFORMATION FOR SEQ ID NO: 847:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 847:

AACUGCGUCU GAUGANGAAA GCUUGUU                                              27

(2) INFORMATION FOR SEQ ID NO: 848:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem II region of a HH ribozyme.

(xi) SEQUENCE DESCRIPTION: SEQ ID NO: 848:

AAGUGCCCCU GAUGANGAAA CUGCGUG                                              27

(2) INFORMATION FOR SEQ ID NO: 849:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem II region of a HH ribozyme.

(xi) SEQUENCE DESCRIPTION: SEQ ID NO: 849:

AUCUUCAACU GAUGANGAAA GUGCCCA                                              27

(2) INFORMATION FOR SEQ ID NO: 850:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem II region of a HH ribozyme.

(xi) SEQUENCE DESCRIPTION: SEQ ID NO: 850:

GAUCUUCACU GAUGANGAAA AGUGCCC                                              27

(2) INFORMATION FOR SEQ ID NO: 851:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem II region of a HH ribozyme.

(xi) SEQUENCE DESCRIPTION: SEQ ID NO: 851:

UGAUCUUCCU GAUGANGAAA AAGUGCC                                              27

(2) INFORMATION FOR SEQ ID NO: 852:

(i) SEQUENCE CHARACTERISTICS:

(A) LENGTH:          27 base pairs
        (B) TYPE:            nucleic acid
        (C) STRANDEDNESS:   single
        (D) TOPOLOGY:       linear (ix) FEATURE:

(D) OTHER INFORMATION: The letter "N" stands for the stem II region of a HH ribozyme.

(xi) SEQUENCE DESCRIPTION: SEQ ID NO: 852:

GAGAAAAUCU GAUGANGAAA UCUUCAA                                27

(2) INFORMATION FOR SEQ ID NO: 853:

(i) SEQUENCE CHARACTERISTICS:

(A) LENGTH:          27 base pairs
        (B) TYPE:            nucleic acid
        (C) STRANDEDNESS:   single
        (D) TOPOLOGY:       linear (ix) FEATURE:

(D) OTHER INFORMATION: The letter "N" stands for the stem II region of a HH ribozyme.

(xi) SEQUENCE DESCRIPTION: SEQ ID NO: 853:

GCUGAGAACU GAUGANGAAA UGAUCUU                                27

(2) INFORMATION FOR SEQ ID NO: 854:

(i) SEQUENCE CHARACTERISTICS:

(A) LENGTH:          27 base pairs
        (B) TYPE:            nucleic acid
        (C) STRANDEDNESS:   single
        (D) TOPOLOGY:       linear (ix) FEATURE:

(D) OTHER INFORMATION: The letter "N" stands for the stem II region of a HH ribozyme.

(xi) SEQUENCE DESCRIPTION: SEQ ID NO: 854:

GGCUGAGACU GAUGANGAAA AUGAUCU                                27

(2) INFORMATION FOR SEQ ID NO: 855:

(i) SEQUENCE CHARACTERISTICS:

(A) LENGTH:          27 base pairs
        (B) TYPE:            nucleic acid
        (C) STRANDEDNESS:   single
        (D) TOPOLOGY:       linear (ix) FEATURE:

(D) OTHER INFORMATION: The letter "N" stands for the stem II region of a HH ribozyme.

(xi) SEQUENCE DESCRIPTION: SEQ ID NO: 855:

AGGCUGAGCU GAUGANGAAA AAUGAUC                                27

(2) INFORMATION FOR SEQ ID NO: 856:

(i) SEQUENCE CHARACTERISTICS:

(A) LENGTH:           27 base pairs
           (B) TYPE:             nucleic acid
           (C) STRANDEDNESS:     single
           (D) TOPOLOGY:         linear (ix) FEATURE:

(D) OTHER INFORMATION:  The letter "N" stands for the stem
               II region of a HH ribozyme.

(xi) SEQUENCE DESCRIPTION: SEQ ID NO: 856:

GAGGCUGACU GAUGANGAAA AAAUGAU                                            27

(2) INFORMATION FOR SEQ ID NO: 857:

(i) SEQUENCE CHARACTERISTICS:

(A) LENGTH:           27 base pairs
           (B) TYPE:             nucleic acid
           (C) STRANDEDNESS:     single
           (D) TOPOLOGY:         linear (ix) FEATURE:

(D) OTHER INFORMATION:  The letter "N" stands for the stem
               II region of a HH ribozyme.

(xi) SEQUENCE DESCRIPTION: SEQ ID NO: 857:

UGGAGGCUCU GAUGANGAAA GAAAAUG                                            27

(2) INFORMATION FOR SEQ ID NO: 858:

(i) SEQUENCE CHARACTERISTICS:

(A) LENGTH:           27 base pairs
           (B) TYPE:             nucleic acid
           (C) STRANDEDNESS:     single
           (D) TOPOLOGY:         linear (ix) FEATURE:

(D) OTHER INFORMATION:  The letter "N" stands for the stem
               II region of a HH ribozyme.

(xi) SEQUENCE DESCRIPTION: SEQ ID NO: 858:

AUCCUCUGCU GAUGANGAAA GGCUGAG                                            27

(2) INFORMATION FOR SEQ ID NO: 859:

(i) SEQUENCE CHARACTERISTICS:

(A) LENGTH:           27 base pairs
           (B) TYPE:             nucleic acid
           (C) STRANDEDNESS:     single
           (D) TOPOLOGY:         linear (ix) FEATURE:

(D) OTHER INFORMATION:  The letter "N" stands for the stem
               II region of a HH ribozyme.

(xi) SEQUENCE DESCRIPTION: SEQ ID NO: 859:

AGUUAUUGCU GAUGANGAAA CAUCCUC                                            27

(2) INFORMATION FOR SEQ ID NO: 860:

(i) SEQUENCE CHARACTERISTICS:

(A) LENGTH:           27 base pairs

```
            (B)  TYPE:              nucleic acid
            (C)  STRANDEDNESS:      single
            (D)  TOPOLOGY:          linear (ix)  FEATURE:

(D)  OTHER INFORMATION:  The letter "N" stands for the stem
                 II region of a HH ribozyme.

(xi)  SEQUENCE DESCRIPTION: SEQ ID NO: 860:

CAGUUAUUCU GAUGANGAAA ACAUCCU                                        27

(2)  INFORMATION FOR SEQ ID NO: 861:

(i)  SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix)  FEATURE:

(D)  OTHER INFORMATION:  The letter "N" stands for the stem
                 II region of a HH ribozyme.

(xi)  SEQUENCE DESCRIPTION: SEQ ID NO: 861:

CUCACAGUCU GAUGANGAAA UUGAACA                                        27

(2)  INFORMATION FOR SEQ ID NO: 862:

(i)  SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix)  FEATURE:

(D)  OTHER INFORMATION:  The letter "N" stands for the stem
                 II region of a HH ribozyme.

(xi)  SEQUENCE DESCRIPTION: SEQ ID NO: 862:

UUCCCAAGCU GAUGANGAAA CCACCUC                                        27

(2)  INFORMATION FOR SEQ ID NO: 863:

(i)  SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix)  FEATURE:

(D)  OTHER INFORMATION:  The letter "N" stands for the stem
                 II region of a HH ribozyme.

(xi)  SEQUENCE DESCRIPTION: SEQ ID NO: 863:

AAAUUCCCCU GAUGANGAAA GGACCAC                                        27

(2)  INFORMATION FOR SEQ ID NO: 864:

(i)  SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear
```

-continued (ix) FEATURE:

(D) OTHER INFORMATION: The letter "N" stands for the stem
II region of a HH ribozyme.

(xi) SEQUENCE DESCRIPTION: SEQ ID NO: 864:

AAUUUCCACU GAUGANGAAA UUCCCAA                                           27

(2) INFORMATION FOR SEQ ID NO: 865:

(i) SEQUENCE CHARACTERISTICS:

(A) LENGTH:           27 base pairs
(B) TYPE:             nucleic acid
(C) STRANDEDNESS:     single
(D) TOPOLOGY:         linear (ix) FEATURE:

(D) OTHER INFORMATION: The letter "N" stands for the stem
II region of a HH ribozyme.

(xi) SEQUENCE DESCRIPTION: SEQ ID NO: 865:

UAAUUUCCCU GAUGANGAAA AUUCCCA                                           27

(2) INFORMATION FOR SEQ ID NO: 866:

(i) SEQUENCE CHARACTERISTICS:

(A) LENGTH:           27 base pairs
(B) TYPE:             nucleic acid
(C) STRANDEDNESS:     single
(D) TOPOLOGY:         linear (ix) FEATURE:

(D) OTHER INFORMATION: The letter "N" stands for the stem
II region of a HH ribozyme.

(xi) SEQUENCE DESCRIPTION: SEQ ID NO: 866:

ACAUAGGUCU GAUGANGAAA UUUCCAA                                           27

(2) INFORMATION FOR SEQ ID NO: 867:

(i) SEQUENCE CHARACTERISTICS:

(A) LENGTH:           27 base pairs
(B) TYPE:             nucleic acid
(C) STRANDEDNESS:     single
(D) TOPOLOGY:         linear (ix) FEATURE:

(D) OTHER INFORMATION: The letter "N" stands for the stem
II region of a HH ribozyme.

(xi) SEQUENCE DESCRIPTION: SEQ ID NO: 867:

CACAUAGGCU GAUGANGAAA AUUCCA                                            27

(2) INFORMATION FOR SEQ ID NO: 868:

(i) SEQUENCE CHARACTERISTICS:

(A) LENGTH:           27 base pairs
(B) TYPE:             nucleic acid
(C) STRANDEDNESS:     single
(D) TOPOLOGY:         linear (ix) FEATURE:

(D) OTHER INFORMATION:   The letter "N" stands for the stem
               II region of a HH ribozyme.

(xi) SEQUENCE DESCRIPTION: SEQ ID NO: 868:

UCUGCACACU GAUGANGAAA GGUAAUU                                              27

(2) INFORMATION FOR SEQ ID NO: 869:

(i) SEQUENCE CHARACTERISTICS:

(A) LENGTH:              27 base pairs
           (B) TYPE:                nucleic acid
           (C) STRANDEDNESS:        single
           (D) TOPOLOGY:            linear (ix) FEATURE:

(D) OTHER INFORMATION:   The letter "N" stands for the stem
               II region of a HH ribozyme.

(xi) SEQUENCE DESCRIPTION: SEQ ID NO: 869:

AAGAUCAUCU GAUGANGAAA UUCCUCU                                              27

(2) INFORMATION FOR SEQ ID NO: 870:

(i) SEQUENCE CHARACTERISTICS:

(A) LENGTH:              27 base pairs
           (B) TYPE:                nucleic acid
           (C) STRANDEDNESS:        single
           (D) TOPOLOGY:            linear (ix) FEATURE:

(D) OTHER INFORMATION:   The letter "N" stands for the stem
               II region of a HH ribozyme.

(xi) SEQUENCE DESCRIPTION: SEQ ID NO: 870:

AAAGAUCACU GAUGANGAAA AUUCCUC                                              27

(2) INFORMATION FOR SEQ ID NO: 871:

(i) SEQUENCE CHARACTERISTICS:

(A) LENGTH:              27 base pairs
           (B) TYPE:                nucleic acid
           (C) STRANDEDNESS:        single
           (D) TOPOLOGY:            linear (ix) FEATURE:

(D) OTHER INFORMATION:   The letter "N" stands for the stem
               II region of a HH ribozyme.

(xi) SEQUENCE DESCRIPTION: SEQ ID NO: 871:

GAAGGAAACU GAUGANGAAA UCAUAAU                                              27

(2) INFORMATION FOR SEQ ID NO: 872:

(i) SEQUENCE CHARACTERISTICS:

(A) LENGTH:              27 base pairs
           (B) TYPE:                nucleic acid
           (C) STRANDEDNESS:        single
           (D) TOPOLOGY:            linear (ix) FEATURE:

(D) OTHER INFORMATION:   The letter "N" stands for the stem
               II region of a HH ribozyme.

(xi) SEQUENCE DESCRIPTION: SEQ ID NO: 872:

AAGAAGGACU GAUGANGAAA GAUCAUA                                               27

(2) INFORMATION FOR SEQ ID NO: 873:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 873:

UAAGAAGGCU GAUGANGAAA AGAUCAU                                               27

(2) INFORMATION FOR SEQ ID NO: 874:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 874:

UUAAGAAGCU GAUGANGAAA AAGAUCA                                               27

(2) INFORMATION FOR SEQ ID NO: 875:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 875:

UCUUUAAGCU GAUGANGAAA GGAAAGA                                               27

(2) INFORMATION FOR SEQ ID NO: 876:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 876:

GUCUUUAACU GAUGANGAAA AGGAAAG                                               27

(2) INFORMATION FOR SEQ ID NO: 877:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 877:

UGGUCUUUCU GAUGANGAAA GAAGGAA                     27

(2) INFORMATION FOR SEQ ID NO: 878:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 878:

AUGGUCUUCU GAUGANGAAA AGAAGGA                     27

(2) INFORMATION FOR SEQ ID NO: 879:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 879:

ACCUCCUGCU GAUGANGAAA UGGUCUU                     27

(2) INFORMATION FOR SEQ ID NO: 880:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 880:

GAGGACAUCU GAUGANGAAA CCAGCCA                     27

(2) INFORMATION FOR SEQ ID NO: 881:

```
    (i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 881:

UGAGGACACU GAUGANGAAA ACCAGCC                                           27

(2) INFORMATION FOR SEQ ID NO: 882:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 882:

GCAAUGAGCU GAUGANGAAA CAUAACC                                           27

(2) INFORMATION FOR SEQ ID NO: 883:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 883:

AGGGCAAUCU GAUGANGAAA GGACAUA                                           27

(2) INFORMATION FOR SEQ ID NO: 884:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 884:

UUGAGGGCCU GAUGANGAAA UGAGGAC                                           27

(2) INFORMATION FOR SEQ ID NO: 885:

(i) SEQUENCE CHARACTERISTICS:
```

```
            (A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 885:

ACUGUGUUCU GAUGANGAAA GGGCAAU                                               27

(2) INFORMATION FOR SEQ ID NO: 886:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 886:

UCCAAAGGCU GAUGANGAAA UUCGCUC                                               27

(2) INFORMATION FOR SEQ ID NO: 887:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 887:

UUCCAAAGCU GAUGANGAAA AUUCGCU                                               27

(2) INFORMATION FOR SEQ ID NO: 888:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 888:

GUUUUCCACU GAUGANGAAA GGAAUUC                                               27

(2) INFORMATION FOR SEQ ID NO: 889:

(i) SEQUENCE CHARACTERISTICS:

(A) LENGTH:            27 base pairs
            (B) TYPE:              nucleic acid
            (C) STRANDEDNESS:      single
```

(D) TOPOLOGY: linear (ix) FEATURE:

(D) OTHER INFORMATION: The letter "N" stands for the stem
II region of a HH ribozyme.

(xi) SEQUENCE DESCRIPTION: SEQ ID NO: 889:

GGUUUUCCCU GAUGANGAAA AGGAAUU                                   27

(2) INFORMATION FOR SEQ ID NO: 890:

(i) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:

(D) OTHER INFORMATION: The letter "N" stands for the stem
II region of a HH ribozyme.

(xi) SEQUENCE DESCRIPTION: SEQ ID NO: 890:

CCUCUGAUCU GAUGANGAAA UCUGCAG                                   27

(2) INFORMATION FOR SEQ ID NO: 891:

(i) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:

(D) OTHER INFORMATION: The letter "N" stands for the stem
II region of a HH ribozyme.

(xi) SEQUENCE DESCRIPTION: SEQ ID NO: 891:

UUUCCUCUCU GAUGANGAAA UGAUCUG                                   27

(2) INFORMATION FOR SEQ ID NO: 892:

(i) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:

(D) OTHER INFORMATION: The letter "N" stands for the stem
II region of a HH ribozyme.

(xi) SEQUENCE DESCRIPTION: SEQ ID NO: 892:

GUAGUACACU GAUGANGAAA UUUCCUC                                   27

(2) INFORMATION FOR SEQ ID NO: 893:

(i) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:

(D) OTHER INFORMATION: The letter "N" stands for the stem
            II region of a HH ribozyme.

(xi) SEQUENCE DESCRIPTION: SEQ ID NO: 893:

UUUCGUAGCU GAUGANGAAA CAUAUUU                                         27

(2) INFORMATION FOR SEQ ID NO: 894:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 894:

AAUUUUCGCU GAUGANGAAA GUACAUA                                         27

(2) INFORMATION FOR SEQ ID NO: 895:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 895:

GGCAUAGGCU GAUGANGAAA UUUUCGU                                         27

(2) INFORMATION FOR SEQ ID NO: 896:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 896:

AGGCAUAGCU GAUGANGAAA AUUUUCG                                         27

(2) INFORMATION FOR SEQ ID NO: 897:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 897:

CUAAGGCACU GAUGANGAAA GGAAUUU                    27

(2) INFORMATION FOR SEQ ID NO: 898:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION: The letter "N" stands for the stem II region of a HH ribozyme.

(xi) SEQUENCE DESCRIPTION: SEQ ID NO: 898:

AGACUGCUCU GAUGANGAAA GGCAUAG                    27

(2) INFORMATION FOR SEQ ID NO: 899:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION: The letter "N" stands for the stem II region of a HH ribozyme.

(xi) SEQUENCE DESCRIPTION: SEQ ID NO: 899:

AAGACUGCCU GAUGANGAAA AGGCAUA                    27

(2) INFORMATION FOR SEQ ID NO: 900:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION: The letter "N" stands for the stem II region of a HH ribozyme.

(xi) SEQUENCE DESCRIPTION: SEQ ID NO: 900:

UUAGAUAACU GAUGANGAAA CUGCUAA                    27

(2) INFORMATION FOR SEQ ID NO: 901:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION: The letter "N" stands for the stem II region of a HH ribozyme.

(xi) SEQUENCE DESCRIPTION: SEQ ID NO: 901:

AGUUAGAUCU GAUGANGAAA GACUGCU                27

(2) INFORMATION FOR SEQ ID NO: 902:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION: The letter "N" stands for the stem
         II region of a HH ribozyme.

(xi) SEQUENCE DESCRIPTION: SEQ ID NO: 902:

UAGUUAGACU GAUGANGAAA AGACUGC                 27

(2) INFORMATION FOR SEQ ID NO: 903:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION: The letter "N" stands for the stem
         II region of a HH ribozyme.

(xi) SEQUENCE DESCRIPTION: SEQ ID NO: 903:

CAUAGUUACU GAUGANGAAA UAAGACU                 27

(2) INFORMATION FOR SEQ ID NO: 904:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION: The letter "N" stands for the stem
         II region of a HH ribozyme.

(xi) SEQUENCE DESCRIPTION: SEQ ID NO: 904:

AUCAUAGUCU GAUGANGAAA GAUAAGA                 27

(2) INFORMATION FOR SEQ ID NO: 905:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION: The letter "N" stands for the stem
         II region of a HH ribozyme.

(xi) SEQUENCE DESCRIPTION: SEQ ID NO: 905:

UUGCAUCACU GAUGANGAAA GUUAGAU                 27

(2) INFORMATION FOR SEQ ID NO: 906:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 906:

UCCGGUUUCU GAUGANGAAA UUUGCAU                          27

(2) INFORMATION FOR SEQ ID NO: 907:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 907:

UUCCUGUACU GAUGANGAAA UUUCUCA                          27

(2) INFORMATION FOR SEQ ID NO: 908:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 908:

UUUCCUGUCU GAUGANGAAA AUUUCUC                          27

(2) INFORMATION FOR SEQ ID NO: 909:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 909:

AUUUCCUGCU GAUGANGAAA AAUUUCU                          27

(2) INFORMATION FOR SEQ ID NO: 910:

(i) SEQUENCE CHARACTERISTICS:

```
            (A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 910:

CCAUGCAGCU GAUGANGAAA UUUCCUG                                        27

(2) INFORMATION FOR SEQ ID NO: 911:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 911:

UGUUGCUGCU GAUGANGAAA CCGCACG                                        27

(2) INFORMATION FOR SEQ ID NO: 912:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 912:

UUGUUGCUCU GAUGANGAAA ACCGCAC                                        27

(2) INFORMATION FOR SEQ ID NO: 913:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 913:

CGCCACUGCU GAUGANGAAA UGCUCUC                                        27

(2) INFORMATION FOR SEQ ID NO: 914:

(i) SEQUENCE CHARACTERISTICS:

(A) LENGTH:            27 base pairs
            (B) TYPE:              nucleic acid
```

(C)  STRANDEDNESS:       single
        (D)  TOPOLOGY:           linear (ix) FEATURE:

(D)  OTHER INFORMATION:   The letter "N" stands for the stem
             II region of a HH ribozyme.

(xi) SEQUENCE DESCRIPTION: SEQ ID NO: 914:

CUGCUGACCU GAUGANGAAA UGUCCCG                                            27

(2) INFORMATION FOR SEQ ID NO: 915:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear (ix) FEATURE:

(D)  OTHER INFORMATION:   The letter "N" stands for the stem
             II region of a HH ribozyme.

(xi) SEQUENCE DESCRIPTION: SEQ ID NO: 915:

UCACUGCUCU GAUGANGAAA CUAUGUC                                            27

(2) INFORMATION FOR SEQ ID NO: 916:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear (ix) FEATURE:

(D)  OTHER INFORMATION:   The letter "N" stands for the stem
             II region of a HH ribozyme.

(xi) SEQUENCE DESCRIPTION: SEQ ID NO: 916:

UGCUGAGACU GAUGANGAAA GUCACUG                                            27

(2) INFORMATION FOR SEQ ID NO: 917:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear (ix) FEATURE:

(D)  OTHER INFORMATION:   The letter "N" stands for the stem
             II region of a HH ribozyme.

(xi) SEQUENCE DESCRIPTION: SEQ ID NO: 917:

UUGCUGAGCU GAUGANGAAA AGUCACU                                            27

(2) INFORMATION FOR SEQ ID NO: 918:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear (ix) FEATURE:

(D) OTHER INFORMATION:   The letter "N" stands for the stem
        II region of a HH ribozyme.

(xi) SEQUENCE DESCRIPTION: SEQ ID NO: 918:

GUUGCUGACU GAUGANGAAA AAGUCAC                                                27

(2) INFORMATION FOR SEQ ID NO: 919:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 919:

AUGUUGCUCU GAUGANGAAA GAAAGUC                                                27

(2) INFORMATION FOR SEQ ID NO: 920:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 920:

AGUCCAUCCU GAUGANGAAA CAUGUUG                                                27

(2) INFORMATION FOR SEQ ID NO: 921:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 921:

GGUUCUGGCU GAUGANGAAA GUCCAUC                                                27

(2) INFORMATION FOR SEQ ID NO: 922:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem

II region of a HH ribozyme.

(xi) SEQUENCE DESCRIPTION: SEQ ID NO: 922:

UGGUUCUGCU GAUGANGAAA AGUCCAU                                          27

(2) INFORMATION FOR SEQ ID NO: 923:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem
         II region of a HH ribozyme.

(xi) SEQUENCE DESCRIPTION: SEQ ID NO: 923:

ACAGCUUGCU GAUGANGAAA UCACACU                                          27

(2) INFORMATION FOR SEQ ID NO: 924:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem
         II region of a HH ribozyme.

(xi) SEQUENCE DESCRIPTION: SEQ ID NO: 924:

CCCAUUGGCU GAUGANGAAA CAGCUUG                                          27

(2) INFORMATION FOR SEQ ID NO: 925:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem
         II region of a HH ribozyme.

(xi) SEQUENCE DESCRIPTION: SEQ ID NO: 925:

GCACAGAUCU GAUGANGAAA UUUUGGU                                          27

(2) INFORMATION FOR SEQ ID NO: 926:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem
         II region of a HH ribozyme.

(xi) SEQUENCE DESCRIPTION: SEQ ID NO: 926:

UGGGCACACU GAUGANGAAA UGAUUUU                                              27

(2) INFORMATION FOR SEQ ID NO: 927:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION:  The letter "N" stands for the stem
            II region of a HH ribozyme.

(xi) SEQUENCE DESCRIPTION: SEQ ID NO: 927:

AGCGCCCGCU GAUGANGAAA GCACUGC                                              27

(2) INFORMATION FOR SEQ ID NO: 928:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION:  The letter "N" stands for the stem
            II region of a HH ribozyme.

(xi) SEQUENCE DESCRIPTION: SEQ ID NO: 928:

CACUGGGGCU GAUGANGAAA CUUGCCA                                              27

(2) INFORMATION FOR SEQ ID NO: 929:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION:  The letter "N" stands for the stem
            II region of a HH ribozyme.

(xi) SEQUENCE DESCRIPTION: SEQ ID NO: 929:

UUGCGGCACU GAUGANGAAA CCAGGCA                                              27

(2) INFORMATION FOR SEQ ID NO: 930:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION:  The letter "N" stands for the stem
            II region of a HH ribozyme.

(xi) SEQUENCE DESCRIPTION: SEQ ID NO: 930:

CGUCUCGGCU GAUGANGAAA UUUGCGG                                              27

(2) INFORMATION FOR SEQ ID NO: 931:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 931:

UCGUCUCGCU GAUGANGAAA AUUUGCG        27

(2) INFORMATION FOR SEQ ID NO: 932:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 932:

UAGAGCAUCU GAUGANGAAA GUGGGGG        27

(2) INFORMATION FOR SEQ ID NO: 933:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 933:

GGGUUGUACU GAUGANGAAA GCAUGAG        27

(2) INFORMATION FOR SEQ ID NO: 934:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 934:

UGGGGUUGCU GAUGANGAAA GAGCAUG        27

(2) INFORMATION FOR SEQ ID NO: 935:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:  The letter "N" stands for the stem
                II region of a HH ribozyme.

(xi) SEQUENCE DESCRIPTION: SEQ ID NO: 935:

CCAUCUGGCU GAUGANGAAA CGUGGUG                                              27

(2) INFORMATION FOR SEQ ID NO: 936:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:  The letter "N" stands for the stem
                II region of a HH ribozyme.

(xi) SEQUENCE DESCRIPTION: SEQ ID NO: 936:

CAAAGCUGCU GAUGANGAAA UUUGCCC                                              27

(2) INFORMATION FOR SEQ ID NO: 937:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:  The letter "N" stands for the stem
                II region of a HH ribozyme.

(xi) SEQUENCE DESCRIPTION: SEQ ID NO: 937:

UGGCACCACU GAUGANGAAA GCUGUAU                                              27

(2) INFORMATION FOR SEQ ID NO: 938:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:  The letter "N" stands for the stem
                II region of a HH ribozyme.

(xi) SEQUENCE DESCRIPTION: SEQ ID NO: 938:

GUGGCACCCU GAUGANGAAA AGCUGUA                                              27

(2) INFORMATION FOR SEQ ID NO: 939:

(i) SEQUENCE CHARACTERISTICS:

(A) LENGTH:             27 base pairs

```
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 939:

AUUACGGGCU GAUGANGAAA CACUUCU                                         27

(2) INFORMATION FOR SEQ ID NO: 940:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 940:

CACAUAAUCU GAUGANGAAA CGGGGAC                                         27

(2) INFORMATION FOR SEQ ID NO: 941:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 941:

CACCACAUCU GAUGANGAAA UUACGGG                                         27

(2) INFORMATION FOR SEQ ID NO: 942:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 942:

UCACCACACU GAUGANGAAA AUUACGG                                         27

(2) INFORMATION FOR SEQ ID NO: 943:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear
```

(ix) FEATURE:

(D) OTHER INFORMATION: The letter "N" stands for the stem
II region of a HH ribozyme.

(xi) SEQUENCE DESCRIPTION: SEQ ID NO: 943:

CGAGCCGUCU GAUGANGAAA UCUGUCA                                27

(2) INFORMATION FOR SEQ ID NO: 944:

(i) SEQUENCE CHARACTERISTICS:

(A) LENGTH:           27 base pairs
(B) TYPE:             nucleic acid
(C) STRANDEDNESS:     single
(D) TOPOLOGY:         linear (ix) FEATURE:

(D) OTHER INFORMATION: The letter "N" stands for the stem
II region of a HH ribozyme.

(xi) SEQUENCE DESCRIPTION: SEQ ID NO: 944:

GGACGCACCU GAUGANGAAA GCCGUGA                                27

(2) INFORMATION FOR SEQ ID NO: 945:

(i) SEQUENCE CHARACTERISTICS:

(A) LENGTH:           27 base pairs
(B) TYPE:             nucleic acid
(C) STRANDEDNESS:     single
(D) TOPOLOGY:         linear (ix) FEATURE:

(D) OTHER INFORMATION: The letter "N" stands for the stem
II region of a HH ribozyme.

(xi) SEQUENCE DESCRIPTION: SEQ ID NO: 945:

CAGGCUCGCU GAUGANGAAA CGCACGA                                27

(2) INFORMATION FOR SEQ ID NO: 946:

(i) SEQUENCE CHARACTERISTICS:

(A) LENGTH:           27 base pairs
(B) TYPE:             nucleic acid
(C) STRANDEDNESS:     single
(D) TOPOLOGY:         linear (ix) FEATURE:

(D) OTHER INFORMATION: The letter "N" stands for the stem
II region of a HH ribozyme.

(xi) SEQUENCE DESCRIPTION: SEQ ID NO: 946:

CCAUCUCACU GAUGANGAAA GCUGUCG                                27

(2) INFORMATION FOR SEQ ID NO: 947:

(i) SEQUENCE CHARACTERISTICS:

(A) LENGTH:           27 base pairs
(B) TYPE:             nucleic acid
(C) STRANDEDNESS:     single
(D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 947:

CACUUGCGCU GAUGANGAAA CGCCGUC                                          27

(2) INFORMATION FOR SEQ ID NO: 948:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 948:

GCACUUCUCU GAUGANGAAA CACUUGC                                          27

(2) INFORMATION FOR SEQ ID NO: 949:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 949:

UUUGCGGCCU GAUGANGAAA GGCCCUU                                          27

(2) INFORMATION FOR SEQ ID NO: 950:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 950:

UAUUCCGUCU GAUGANGAAA CACACUU                                          27

(2) INFORMATION FOR SEQ ID NO: 951:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 951:

CCAAUACCCU GAUGANGAAA UUCCGUU                                    27

(2) INFORMATION FOR SEQ ID NO: 952:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 952:

UUCACCAACU GAUGANGAAA CCUAUUC                                    27

(2) INFORMATION FOR SEQ ID NO: 953:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 953:

AAUUCACCCU GAUGANGAAA UACCUAU                                    27

(2) INFORMATION FOR SEQ ID NO: 954:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 954:

AGUCUUUACU GAUGANGAAA UUCACCA                                    27

(2) INFORMATION FOR SEQ ID NO: 955:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 955:

GAGUCUUUCU GAUGANGAAA AUUCACC                                    27

(2) INFORMATION FOR SEQ ID NO: 956:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION:  The letter "N" stands for the stem
          II region of a HH ribozyme.

(xi) SEQUENCE DESCRIPTION: SEQ ID NO: 956:

UGAGUCUUCU GAUGANGAAA AAUUCAC                                              27

(2) INFORMATION FOR SEQ ID NO: 957:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION:  The letter "N" stands for the stem
          II region of a HH ribozyme.

(xi) SEQUENCE DESCRIPTION: SEQ ID NO: 957:

UGGAGAGUCU GAUGANGAAA GUCUUUA                                              27

(2) INFORMATION FOR SEQ ID NO: 958:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION:  The letter "N" stands for the stem
          II region of a HH ribozyme.

(xi) SEQUENCE DESCRIPTION: SEQ ID NO: 958:

UUUAUGGACU GAUGANGAAA GUGAGUC                                              27

(2) INFORMATION FOR SEQ ID NO: 959:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION:  The letter "N" stands for the stem
          II region of a HH ribozyme.

(xi) SEQUENCE DESCRIPTION: SEQ ID NO: 959:

CAUUUAUGCU GAUGANGAAA GAGUGAG                                              27

(2) INFORMATION FOR SEQ ID NO: 960:

```
        (i)  SEQUENCE CHARACTERISTICS:

(A)  LENGTH:            27 base pairs
              (B)  TYPE:              nucleic acid
              (C)  STRANDEDNESS:      single
              (D)  TOPOLOGY:          linear (ix)  FEATURE:

(D)  OTHER INFORMATION:  The letter "N" stands for the stem
                   II region of a HH ribozyme.

(xi)  SEQUENCE DESCRIPTION: SEQ ID NO: 960:

GUAGCAUUCU GAUGANGAAA UGGAGAG                                            27

(2)  INFORMATION FOR SEQ ID NO: 961:

(i)  SEQUENCE CHARACTERISTICS:

(A)  LENGTH:            27 base pairs
              (B)  TYPE:              nucleic acid
              (C)  STRANDEDNESS:      single
              (D)  TOPOLOGY:          linear (ix)  FEATURE:

(D)  OTHER INFORMATION:  The letter "N" stands for the stem
                   II region of a HH ribozyme.

(xi)  SEQUENCE DESCRIPTION: SEQ ID NO: 961:

AAUAUUCGCU GAUGANGAAA GCAUUUA                                            27

(2)  INFORMATION FOR SEQ ID NO: 962:

(i)  SEQUENCE CHARACTERISTICS:

(A)  LENGTH:            27 base pairs
              (B)  TYPE:              nucleic acid
              (C)  STRANDEDNESS:      single
              (D)  TOPOLOGY:          linear (ix)  FEATURE:

(D)  OTHER INFORMATION:  The letter "N" stands for the stem
                   II region of a HH ribozyme.

(xi)  SEQUENCE DESCRIPTION: SEQ ID NO: 962:

GUGUUUAACU GAUGANGAAA UUCGUAG                                            27

(2)  INFORMATION FOR SEQ ID NO: 963:

(i)  SEQUENCE CHARACTERISTICS:

(A)  LENGTH:            27 base pairs
              (B)  TYPE:              nucleic acid
              (C)  STRANDEDNESS:      single
              (D)  TOPOLOGY:          linear (ix)  FEATURE:

(D)  OTHER INFORMATION:  The letter "N" stands for the stem
                   II region of a HH ribozyme.

(xi)  SEQUENCE DESCRIPTION: SEQ ID NO: 963:

AAGUGUUUCU GAUGANGAAA UAUUCGU                                            27

(2)  INFORMATION FOR SEQ ID NO: 964:

(i)  SEQUENCE CHARACTERISTICS:
```

```
            (A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 964:

GAAGUGUUCU GAUGANGAAA AUAUUCG                                              27

(2)  INFORMATION FOR SEQ ID NO: 965:

(i)  SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 965:

AGUUUUUGCU GAUGANGAAA GUGUUUA                                              27

(2)  INFORMATION FOR SEQ ID NO: 966:

(i)  SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 966:

CAGUUUUUCU GAUGANGAAA AGUGUUU                                              27

(2)  INFORMATION FOR SEQ ID NO: 967:

(i)  SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 967:

CACUGAUGCU GAUGANGAAA GGUGCAG                                              27

(2)  INFORMATION FOR SEQ ID NO: 968:

(i)  SEQUENCE CHARACTERISTICS:

(A)  LENGTH:             27 base pairs
            (B)  TYPE:               nucleic acid
            (C)  STRANDEDNESS:       single
```

(D)  TOPOLOGY:         linear (ix) FEATURE:

(D)  OTHER INFORMATION:  The letter "N" stands for the stem
                 II region of a HH ribozyme.

(xi) SEQUENCE DESCRIPTION: SEQ ID NO: 968:

UCGCCACUCU GAUGANGAAA UGGAGGU                                              27

(2) INFORMATION FOR SEQ ID NO: 969:

(i) SEQUENCE CHARACTERISTICS:

(A)  LENGTH:           27 base pairs
            (B)  TYPE:             nucleic acid
            (C)  STRANDEDNESS:     single
            (D)  TOPOLOGY:         linear (ix) FEATURE:

(D)  OTHER INFORMATION:  The letter "N" stands for the stem
                 II region of a HH ribozyme.

(xi) SEQUENCE DESCRIPTION: SEQ ID NO: 969:

GAUGUGGACU GAUGANGAAA UCGCCAC                                              27

(2) INFORMATION FOR SEQ ID NO: 970:

(i) SEQUENCE CHARACTERISTICS:

(A)  LENGTH:           27 base pairs
            (B)  TYPE:             nucleic acid
            (C)  STRANDEDNESS:     single
            (D)  TOPOLOGY:         linear (ix) FEATURE:

(D)  OTHER INFORMATION:  The letter "N" stands for the stem
                 II region of a HH ribozyme.

(xi) SEQUENCE DESCRIPTION: SEQ ID NO: 970:

AGGAUGUGCU GAUGANGAAA GAUCGCC                                              27

(2) INFORMATION FOR SEQ ID NO: 971:

(i) SEQUENCE CHARACTERISTICS:

(A)  LENGTH:           27 base pairs
            (B)  TYPE:             nucleic acid
            (C)  STRANDEDNESS:     single
            (D)  TOPOLOGY:         linear (ix) FEATURE:

(D)  OTHER INFORMATION:  The letter "N" stands for the stem
                 II region of a HH ribozyme.

(xi) SEQUENCE DESCRIPTION: SEQ ID NO: 971:

ACCGGCAGCU GAUGANGAAA UGUGGAG                                              27

(2) INFORMATION FOR SEQ ID NO: 972:

(i) SEQUENCE CHARACTERISTICS:

(A)  LENGTH:           27 base pairs
            (B)  TYPE:             nucleic acid
            (C)  STRANDEDNESS:     single
            (D)  TOPOLOGY:         linear (ix) FEATURE:

(D) OTHER INFORMATION:    The letter "N" stands for the stem
                II region of a HH ribozyme.

(xi) SEQUENCE DESCRIPTION: SEQ ID NO: 972:

CACCCCUACU GAUGANGAAA UGCCACC                                              27

(2) INFORMATION FOR SEQ ID NO: 973:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:    The letter "N" stands for the stem
                II region of a HH ribozyme.

(xi) SEQUENCE DESCRIPTION: SEQ ID NO: 973:

UCACCCCUCU GAUGANGAAA AUGCCAC                                              27

(2) INFORMATION FOR SEQ ID NO: 974:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:    The letter "N" stands for the stem
                II region of a HH ribozyme.

(xi) SEQUENCE DESCRIPTION: SEQ ID NO: 974:

GUCACCCCU GAUGANGAAA AAUGCCA                                               27

(2) INFORMATION FOR SEQ ID NO: 975:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:    The letter "N" stands for the stem
                II region of a HH ribozyme.

(xi) SEQUENCE DESCRIPTION: SEQ ID NO: 975:

GUGUGAAGCU GAUGANGAAA GUCACCC                                              27

(2) INFORMATION FOR SEQ ID NO: 976:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:    The letter "N" stands for the stem
                II region of a HH ribozyme.

```
      (xi) SEQUENCE DESCRIPTION: SEQ ID NO: 976:

UAUGUGUGCU GAUGANGAAA GGAGUCA                                          27

(2) INFORMATION FOR SEQ ID NO: 977:

(i) SEQUENCE CHARACTERISTICS:

(A) LENGTH:         27 base pairs
              (B) TYPE:           nucleic acid
              (C) STRANDEDNESS:   single
              (D) TOPOLOGY:       linear (ix) FEATURE:

(D) OTHER INFORMATION:   The letter "N" stands for the stem
                  II region of a HH ribozyme.

(xi) SEQUENCE DESCRIPTION: SEQ ID NO: 977:

GUAUGUGUCU GAUGANGAAA AGGAGUC                                          27

(2) INFORMATION FOR SEQ ID NO: 978:

(i) SEQUENCE CHARACTERISTICS:

(A) LENGTH:         27 base pairs
              (B) TYPE:           nucleic acid
              (C) STRANDEDNESS:   single
              (D) TOPOLOGY:       linear (ix) FEATURE:

(D) OTHER INFORMATION:   The letter "N" stands for the stem
                  II region of a HH ribozyme.

(xi) SEQUENCE DESCRIPTION: SEQ ID NO: 978:

AGGAGGAGCU GAUGANGAAA UGUGUGA                                          27

(2) INFORMATION FOR SEQ ID NO: 979:

(i) SEQUENCE CHARACTERISTICS:

(A) LENGTH:         27 base pairs
              (B) TYPE:           nucleic acid
              (C) STRANDEDNESS:   single
              (D) TOPOLOGY:       linear (ix) FEATURE:

(D) OTHER INFORMATION:   The letter "N" stands for the stem
                  II region of a HH ribozyme.

(xi) SEQUENCE DESCRIPTION: SEQ ID NO: 979:

CAGAGGAGCU GAUGANGAAA GUAUGUG                                          27

(2) INFORMATION FOR SEQ ID NO: 980:

(i) SEQUENCE CHARACTERISTICS:

(A) LENGTH:         27 base pairs
              (B) TYPE:           nucleic acid
              (C) STRANDEDNESS:   single
              (D) TOPOLOGY:       linear (ix) FEATURE:

(D) OTHER INFORMATION:   The letter "N" stands for the stem
                  II region of a HH ribozyme.

(xi) SEQUENCE DESCRIPTION: SEQ ID NO: 980:
```

```
AUCCAGAGCU GAUGANGAAA GGAGUAU                                            27
```

(2) INFORMATION FOR SEQ ID NO: 981:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION: The letter "N" stands for the stem II region of a HH ribozyme.

(xi) SEQUENCE DESCRIPTION: SEQ ID NO: 981:

```
UGGAUCCACU GAUGANGAAA GGAGGAG                                            27
```

(2) INFORMATION FOR SEQ ID NO: 982:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION: The letter "N" stands for the stem II region of a HH ribozyme.

(xi) SEQUENCE DESCRIPTION: SEQ ID NO: 982:

```
UUCCUGUGCU GAUGANGAAA UCCAGAG                                            27
```

(2) INFORMATION FOR SEQ ID NO: 983:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION: The letter "N" stands for the stem II region of a HH ribozyme.

(xi) SEQUENCE DESCRIPTION: SEQ ID NO: 983:

```
UUUCAGAACU GAUGANGAAA UCCAGUU                                            27
```

(2) INFORMATION FOR SEQ ID NO: 984:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION: The letter "N" stands for the stem II region of a HH ribozyme.

(xi) SEQUENCE DESCRIPTION: SEQ ID NO: 984:

```
GUUUUCAGCU GAUGANGAAA UAUCCAG                                            27
```

(2) INFORMATION FOR SEQ ID NO: 985:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem II region of a HH ribozyme.

(xi) SEQUENCE DESCRIPTION: SEQ ID NO: 985:

GGUUUUCACU GAUGANGAAA AUAUCCA                                    27

(2) INFORMATION FOR SEQ ID NO: 986:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem II region of a HH ribozyme.

(xi) SEQUENCE DESCRIPTION: SEQ ID NO: 986:

AUUUCCUUCU GAUGANGAAA CGGUUUU                                    27

(2) INFORMATION FOR SEQ ID NO: 987:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem II region of a HH ribozyme.

(xi) SEQUENCE DESCRIPTION: SEQ ID NO: 987:

AACCCUGUCU GAUGANGAAA UUUCCUU                                    27

(2) INFORMATION FOR SEQ ID NO: 988:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem II region of a HH ribozyme.

(xi) SEQUENCE DESCRIPTION: SEQ ID NO: 988:

UCAGCAAACU GAUGANGAAA CCCUGUG                                    27

(2) INFORMATION FOR SEQ ID NO: 989:

(i) SEQUENCE CHARACTERISTICS:

```
            (A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 989:

AUCAGCAACU GAUGANGAAA ACCCUGU                                       27

(2) INFORMATION FOR SEQ ID NO: 990:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 990:

AAUCAGCACU GAUGANGAAA AACCCUG                                       27

(2) INFORMATION FOR SEQ ID NO: 991:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 991:

GAAUCAGCCU GAUGANGAAA AAACCCU                                       27

(2) INFORMATION FOR SEQ ID NO: 992:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 992:

CAAGCCUGCU GAUGANGAAA UCAGCAA                                       27

(2) INFORMATION FOR SEQ ID NO: 993:

(i) SEQUENCE CHARACTERISTICS:

(A)  LENGTH:             27 base pairs
            (B)  TYPE:               nucleic acid
```

(C)  STRANDEDNESS:      single
              (D)  TOPOLOGY:          linear (ix)  FEATURE:

(D)  OTHER INFORMATION:  The letter "N" stands for the stem
                   II region of a HH ribozyme.

(xi)  SEQUENCE DESCRIPTION: SEQ ID NO: 993:

CCAAGCCUCU GAUGANGAAA AUCAGCA                                              27

(2)  INFORMATION FOR SEQ ID NO: 994:

(i)  SEQUENCE CHARACTERISTICS:

(A)  LENGTH:            27 base pairs
              (B)  TYPE:              nucleic acid
              (C)  STRANDEDNESS:      single
              (D)  TOPOLOGY:          linear (ix)  FEATURE:

(D)  OTHER INFORMATION:  The letter "N" stands for the stem
                   II region of a HH ribozyme.

(xi)  SEQUENCE DESCRIPTION: SEQ ID NO: 994:

UUCAGGCCCU GAUGANGAAA GCCUGAA                                              27

(2)  INFORMATION FOR SEQ ID NO: 995:

(i)  SEQUENCE CHARACTERISTICS:

(A)  LENGTH:            27 base pairs
              (B)  TYPE:              nucleic acid
              (C)  STRANDEDNESS:      single
              (D)  TOPOLOGY:          linear (ix)  FEATURE:

(D)  OTHER INFORMATION:  The letter "N" stands for the stem
                   II region of a HH ribozyme.

(xi)  SEQUENCE DESCRIPTION: SEQ ID NO: 995:

AAGGCAUGCU GAUGANGAAA GGUCCGU                                              27

(2)  INFORMATION FOR SEQ ID NO: 996:

(i)  SEQUENCE CHARACTERISTICS:

(A)  LENGTH:            27 base pairs
              (B)  TYPE:              nucleic acid
              (C)  STRANDEDNESS:      single
              (D)  TOPOLOGY:          linear (ix)  FEATURE:

(D)  OTHER INFORMATION:  The letter "N" stands for the stem
                   II region of a HH ribozyme.

(xi)  SEQUENCE DESCRIPTION: SEQ ID NO: 996:

GGUUCUCACU GAUGANGAAA GGCAUGG                                              27

(2)  INFORMATION FOR SEQ ID NO: 997:

(i)  SEQUENCE CHARACTERISTICS:

(A)  LENGTH:            27 base pairs
              (B)  TYPE:              nucleic acid
              (C)  STRANDEDNESS:      single
              (D)  TOPOLOGY:          linear (ix) FEATURE:

(D) OTHER INFORMATION:   The letter "N" stands for the stem
            II region of a HH ribozyme.

(xi) SEQUENCE DESCRIPTION: SEQ ID NO: 997:

AGGUUCUCCU GAUGANGAAA AGGCAUG                                              27

(2) INFORMATION FOR SEQ ID NO: 998:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for the stem
            II region of a HH ribozyme.

(xi) SEQUENCE DESCRIPTION: SEQ ID NO: 998:

AUGAUUUCCU GAUGANGAAA GGUUCUC                                              27

(2) INFORMATION FOR SEQ ID NO: 999:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for the stem
            II region of a HH ribozyme.

(xi) SEQUENCE DESCRIPTION: SEQ ID NO: 999:

CCGCGUAUCU GAUGANGAAA UUUCUAG                                              27

(2) INFORMATION FOR SEQ ID NO: 1000:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for the stem
            II region of a HH ribozyme.

(xi) SEQUENCE DESCRIPTION: SEQ ID NO: 1000:

CUGCCGCGCU GAUGANGAAA UGAUUUC                                              27

(2) INFORMATION FOR SEQ ID NO: 1001:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for the stem

II region of a HH ribozyme.

(xi) SEQUENCE DESCRIPTION: SEQ ID NO: 1001:

AGAAAACUCU GAUGANGAAA CCAUGUU                                              27

(2) INFORMATION FOR SEQ ID NO: 1002:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION: The letter "N" stands for the stem
            II region of a HH ribozyme.

(xi) SEQUENCE DESCRIPTION: SEQ ID NO: 1002:

CAAGAGAACU GAUGANGAAA CUGACCA                                              27

(2) INFORMATION FOR SEQ ID NO: 1003:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION: The letter "N" stands for the stem
            II region of a HH ribozyme.

(xi) SEQUENCE DESCRIPTION: SEQ ID NO: 1003:

GCAAGAGACU GAUGANGAAA ACUGACC                                              27

(2) INFORMATION FOR SEQ ID NO: 1004:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION: The letter "N" stands for the stem
            II region of a HH ribozyme.

(xi) SEQUENCE DESCRIPTION: SEQ ID NO: 1004:

UGCAAGAGCU GAUGANGAAA AACUGAC                                              27

(2) INFORMATION FOR SEQ ID NO: 1005:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION: The letter "N" stands for the stem
            II region of a HH ribozyme.

(xi) SEQUENCE DESCRIPTION: SEQ ID NO: 1005:

CUGCAAGACU GAUGANGAAA AAACUGA                                27

(2) INFORMATION FOR SEQ ID NO: 1006:

(i) SEQUENCE CHARACTERISTICS:

(A) LENGTH:   27 base pairs
  (B) TYPE:    nucleic acid
  (C) STRANDEDNESS: single
  (D) TOPOLOGY:  linear (ix) FEATURE:

(D) OTHER INFORMATION: The letter "N" stands for the stem
   II region of a HH ribozyme.

(xi) SEQUENCE DESCRIPTION: SEQ ID NO: 1006:

GACUGCAACU GAUGANGAAA GAAAACU                                27

(2) INFORMATION FOR SEQ ID NO: 1007:

(i) SEQUENCE CHARACTERISTICS:

(A) LENGTH:   27 base pairs
  (B) TYPE:    nucleic acid
  (C) STRANDEDNESS: single
  (D) TOPOLOGY:  linear (ix) FEATURE:

(D) OTHER INFORMATION: The letter "N" stands for the stem
   II region of a HH ribozyme.

(xi) SEQUENCE DESCRIPTION: SEQ ID NO: 1007:

ACGACUGCCU GAUGANGAAA GAGAAAA                                27

(2) INFORMATION FOR SEQ ID NO: 1008:

(i) SEQUENCE CHARACTERISTICS:

(A) LENGTH:   27 base pairs
  (B) TYPE:    nucleic acid
  (C) STRANDEDNESS: single
  (D) TOPOLOGY:  linear (ix) FEATURE:

(D) OTHER INFORMATION: The letter "N" stands for the stem
   II region of a HH ribozyme.

(xi) SEQUENCE DESCRIPTION: SEQ ID NO: 1008:

AGGCUGACCU GAUGANGAAA CUGCAAG                                27

(2) INFORMATION FOR SEQ ID NO: 1009:

(i) SEQUENCE CHARACTERISTICS:

(A) LENGTH:   27 base pairs
  (B) TYPE:    nucleic acid
  (C) STRANDEDNESS: single
  (D) TOPOLOGY:  linear (ix) FEATURE:

(D) OTHER INFORMATION: The letter "N" stands for the stem
   II region of a HH ribozyme.

(xi) SEQUENCE DESCRIPTION: SEQ ID NO: 1009:

UUCAGGCUCU GAUGANGAAA CGACUGC                                27

(2) INFORMATION FOR SEQ ID NO: 1010:

(i) SEQUENCE CHARACTERISTICS:

(A) LENGTH:         27 base pairs
       (B) TYPE:           nucleic acid
       (C) STRANDEDNESS:   single
       (D) TOPOLOGY:       linear (ix) FEATURE:

(D) OTHER INFORMATION:  The letter "N" stands for the stem
           II region of a HH ribozyme.

(xi) SEQUENCE DESCRIPTION: SEQ ID NO: 1010:

AAGGAUGUCU GAUGANGAAA UGUUCAG                                    27

(2) INFORMATION FOR SEQ ID NO: 1011:

(i) SEQUENCE CHARACTERISTICS:

(A) LENGTH:         27 base pairs
       (B) TYPE:           nucleic acid
       (C) STRANDEDNESS:   single
       (D) TOPOLOGY:       linear (ix) FEATURE:

(D) OTHER INFORMATION:  The letter "N" stands for the stem
           II region of a HH ribozyme.

(xi) SEQUENCE DESCRIPTION: SEQ ID NO: 1011:

AUCCCAAGCU GAUGANGAAA UGUUAUG                                    27

(2) INFORMATION FOR SEQ ID NO: 1012:

(i) SEQUENCE CHARACTERISTICS:

(A) LENGTH:         27 base pairs
       (B) TYPE:           nucleic acid
       (C) STRANDEDNESS:   single
       (D) TOPOLOGY:       linear (ix) FEATURE:

(D) OTHER INFORMATION:  The letter "N" stands for the stem
           II region of a HH ribozyme.

(xi) SEQUENCE DESCRIPTION: SEQ ID NO: 1012:

GUAAUCCCCU GAUGANGAAA GGAUGUU                                    27

(2) INFORMATION FOR SEQ ID NO: 1013:

(i) SEQUENCE CHARACTERISTICS:

(A) LENGTH:         27 base pairs
       (B) TYPE:           nucleic acid
       (C) STRANDEDNESS:   single
       (D) TOPOLOGY:       linear (ix) FEATURE:

(D) OTHER INFORMATION:  The letter "N" stands for the stem
           II region of a HH ribozyme.

(xi) SEQUENCE DESCRIPTION: SEQ ID NO: 1013:

GGGAGCGUCU GAUGANGAAA UCCCAAG                                    27

(2) INFORMATION FOR SEQ ID NO: 1014:

```
    (i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1014:

AGGGAGCGCU GAUGANGAAA AUCCCAA                                           27

(2) INFORMATION FOR SEQ ID NO: 1015:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1015:

CCUUGAGGCU GAUGANGAAA GCGUAAU                                           27

(2) INFORMATION FOR SEQ ID NO: 1016:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1016:

AUCUCCUUCU GAUGANGAAA GGGAGCG                                           27

(2) INFORMATION FOR SEQ ID NO: 1017:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1017:

CCAUCACUCU GAUGANGAAA UCUCCUU                                           27

(2) INFORMATION FOR SEQ ID NO: 1018:

(i) SEQUENCE CHARACTERISTICS:

(A) LENGTH:             27 base pairs
```

```
            (B)  TYPE:               nucleic acid
            (C)  STRANDEDNESS:       single
            (D)  TOPOLOGY:           linear (ix)  FEATURE:

(D)  OTHER INFORMATION:  The letter "N" stands for the stem
                 II region of a HH ribozyme.

(xi)  SEQUENCE DESCRIPTION: SEQ ID NO: 1018:

CCUGAAAUCU GAUGANGAAA UCACAUC                                              27

(2)   INFORMATION FOR SEQ ID NO: 1019:

(i)   SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix)  FEATURE:

(D)  OTHER INFORMATION:  The letter "N" stands for the stem
                 II region of a HH ribozyme.

(xi)  SEQUENCE DESCRIPTION: SEQ ID NO: 1019:

UUUCCUGACU GAUGANGAAA UUAUCAC                                              27

(2)   INFORMATION FOR SEQ ID NO: 1020:

(i)   SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix)  FEATURE:

(D)  OTHER INFORMATION:  The letter "N" stands for the stem
                 II region of a HH ribozyme.

(xi)  SEQUENCE DESCRIPTION: SEQ ID NO: 1020:

GUUUCCUGCU GAUGANGAAA AUUAUCA                                              27

(2)   INFORMATION FOR SEQ ID NO: 1021:

(i)   SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix)  FEATURE:

(D)  OTHER INFORMATION:  The letter "N" stands for the stem
                 II region of a HH ribozyme.

(xi)  SEQUENCE DESCRIPTION: SEQ ID NO: 1021:

UGUUUCCUCU GAUGANGAAA AAUUAUC                                              27

(2)   INFORMATION FOR SEQ ID NO: 1022:

(i)   SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear
```

(ix) FEATURE:

(D) OTHER INFORMATION: The letter "N" stands for the stem
        II region of a HH ribozyme.

(xi) SEQUENCE DESCRIPTION: SEQ ID NO: 1022:

AUAGCACACU GAUGANGAAA UUUUUGU                    27

(2) INFORMATION FOR SEQ ID NO: 1023:

(i) SEQUENCE CHARACTERISTICS:

(A) LENGTH:        27 base pairs
    (B) TYPE:          nucleic acid
    (C) STRANDEDNESS:  single
    (D) TOPOLOGY:     linear (ix) FEATURE:

(D) OTHER INFORMATION: The letter "N" stands for the stem
        II region of a HH ribozyme.

(xi) SEQUENCE DESCRIPTION: SEQ ID NO: 1023:

CAUAGCACCU GAUGANGAAA AUUUUUG                    27

(2) INFORMATION FOR SEQ ID NO: 1024:

(i) SEQUENCE CHARACTERISTICS:

(A) LENGTH:        27 base pairs
    (B) TYPE:          nucleic acid
    (C) STRANDEDNESS:  single
    (D) TOPOLOGY:     linear (ix) FEATURE:

(D) OTHER INFORMATION: The letter "N" stands for the stem
        II region of a HH ribozyme.

(xi) SEQUENCE DESCRIPTION: SEQ ID NO: 1024:

UAUUUGCACU GAUGANGAAA GCACAAA                    27

(2) INFORMATION FOR SEQ ID NO: 1025:

(i) SEQUENCE CHARACTERISTICS:

(A) LENGTH:        27 base pairs
    (B) TYPE:          nucleic acid
    (C) STRANDEDNESS:  single
    (D) TOPOLOGY:     linear (ix) FEATURE:

(D) OTHER INFORMATION: The letter "N" stands for the stem
        II region of a HH ribozyme.

(xi) SEQUENCE DESCRIPTION: SEQ ID NO: 1025:

GUUUAUUGCU GAUGANGAAA UUUGCAU                    27

(2) INFORMATION FOR SEQ ID NO: 1026:

(i) SEQUENCE CHARACTERISTICS:

(A) LENGTH:        27 base pairs
    (B) TYPE:          nucleic acid
    (C) STRANDEDNESS:  single
    (D) TOPOLOGY:     linear (ix) FEATURE:

(D) OTHER INFORMATION: The letter "N" stands for the stem
            II region of a HH ribozyme.

(xi) SEQUENCE DESCRIPTION: SEQ ID NO: 1026:

UUCCAGUUCU GAUGANGAAA UUGUAUU                                              27

(2) INFORMATION FOR SEQ ID NO: 1027:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION: The letter "N" stands for the stem
            II region of a HH ribozyme.

(xi) SEQUENCE DESCRIPTION: SEQ ID NO: 1027:

AGGUCCCACU GAUGANGAAA CAGUUUU                                              27

(2) INFORMATION FOR SEQ ID NO: 1028:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION: The letter "N" stands for the stem
            II region of a HH ribozyme.

(xi) SEQUENCE DESCRIPTION: SEQ ID NO: 1028:

GAGGUCCCCU GAUGANGAAA ACAGUUU                                              27

(2) INFORMATION FOR SEQ ID NO: 1029:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION: The letter "N" stands for the stem
            II region of a HH ribozyme.

(xi) SEQUENCE DESCRIPTION: SEQ ID NO: 1029:

UCUGACCGCU GAUGANGAAA GGUCCCA                                              27

(2) INFORMATION FOR SEQ ID NO: 1030:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION: The letter "N" stands for the stem
            II region of a HH ribozyme.

(xi) SEQUENCE DESCRIPTION: SEQ ID NO: 1030:

GGUUUUCUCU GAUGANGAAA CCGGAGG                                           27

(2) INFORMATION FOR SEQ ID NO: 1031:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 1031:

UUGCUUAUCU GAUGANGAAA UUUUGGU                                           27

(2) INFORMATION FOR SEQ ID NO: 1032:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 1032:

GUUGCUUACU GAUGANGAAA AUUUUGG                                           27

(2) INFORMATION FOR SEQ ID NO: 1033:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 1033:

CUGUUGCUCU GAUGANGAAA UAAUUUU                                           27

(2) INFORMATION FOR SEQ ID NO: 1034:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 1034:

GCAUGGCACU GAUGANGAAA CCUGGCC                                           27

(2) INFORMATION FOR SEQ ID NO: 1035:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1035:

GGGAGCACCU GAUGANGAAA GGCAUGG        27

(2) INFORMATION FOR SEQ ID NO: 1036:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1036:

CCUCGGGGCU GAUGANGAAA GCACAAG        27

(2) INFORMATION FOR SEQ ID NO: 1037:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1037:

CGGCAAGACU GAUGANGAAA CGCAGUC        27

(2) INFORMATION FOR SEQ ID NO: 1038:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1038:

UCCGGCAACU GAUGANGAAA GACGCAG        27

(2) INFORMATION FOR SEQ ID NO: 1039:

```
        (i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:   The letter "N" stands for the stem
                II region of a HH ribozyme.

(xi) SEQUENCE DESCRIPTION: SEQ ID NO: 1039:

AUUCCGGCCU GAUGANGAAA GAGACGC                                              27

(2) INFORMATION FOR SEQ ID NO: 1040:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:   The letter "N" stands for the stem
                II region of a HH ribozyme.

(xi) SEQUENCE DESCRIPTION: SEQ ID NO: 1040:

CCUCGGCUCU GAUGANGAAA CAUUCCG                                              27

(2) INFORMATION FOR SEQ ID NO: 1041:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:   The letter "N" stands for the stem
                II region of a HH ribozyme.

(xi) SEQUENCE DESCRIPTION: SEQ ID NO: 1041:

CCCUCCAGCU GAUGANGAAA GCUUGCA                                              27

(2) INFORMATION FOR SEQ ID NO: 1042:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:   The letter "N" stands for the stem
                II region of a HH ribozyme.

(xi) SEQUENCE DESCRIPTION: SEQ ID NO: 1042:

ACCCUCCACU GAUGANGAAA AGCUUGC                                              27

(2) INFORMATION FOR SEQ ID NO: 1043:

(i) SEQUENCE CHARACTERISTICS:
```

```
        (A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:  The letter "N" stands for the stem
            II region of a HH ribozyme.

(xi) SEQUENCE DESCRIPTION: SEQ ID NO: 1043:

UCUCCACACU GAUGANGAAA CUCCCUU                                              27

(2) INFORMATION FOR SEQ ID NO: 1044:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:  The letter "N" stands for the stem
            II region of a HH ribozyme.

(xi) SEQUENCE DESCRIPTION: SEQ ID NO: 1044:

UUCUCCACCU GAUGANGAAA ACUCCCU                                              27

(2) INFORMATION FOR SEQ ID NO: 1045:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:  The letter "N" stands for the stem
            II region of a HH ribozyme.

(xi) SEQUENCE DESCRIPTION: SEQ ID NO: 1045:

UGCACUCACU GAUGANGAAA GUUCUCC                                              27

(2) INFORMATION FOR SEQ ID NO: 1046:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:  The letter "N" stands for the stem
            II region of a HH ribozyme.

(xi) SEQUENCE DESCRIPTION: SEQ ID NO: 1046:

UGGCACUGCU GAUGANGAAA UGCACUC                                              27

(2) INFORMATION FOR SEQ ID NO: 1047:

(i) SEQUENCE CHARACTERISTICS:

(A) LENGTH:            27 base pairs
        (B) TYPE:              nucleic acid
        (C) STRANDEDNESS:      single
```

```
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1047:

CAUGGCCUCU GAUGANGAAA GGCAGGC                                            27

(2) INFORMATION FOR SEQ ID NO: 1048:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1048:

GUGCAGGUCU GAUGANGAAA UGUUCAU                                            27

(2) INFORMATION FOR SEQ ID NO: 1049:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1049:

ACACUGGACU GAUGANGAAA CAGUUGU                                            27

(2) INFORMATION FOR SEQ ID NO: 1050:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1050:

GCACACUGCU GAUGANGAAA UACAGUU                                            27

(2) INFORMATION FOR SEQ ID NO: 1051:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:
```

(D) OTHER INFORMATION:    The letter "N" stands for the stem
                II region of a HH ribozyme.

(xi) SEQUENCE DESCRIPTION: SEQ ID NO: 1051:

CGUCAAUGCU GAUGANGAAA GUGGGCA                                               27

(2) INFORMATION FOR SEQ ID NO: 1052:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:    The letter "N" stands for the stem
            II region of a HH ribozyme.

(xi) SEQUENCE DESCRIPTION: SEQ ID NO: 1052:

GGGCCGUCCU GAUGANGAAA UGUAGUG                                               27

(2) INFORMATION FOR SEQ ID NO: 1053:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:    The letter "N" stands for the stem
            II region of a HH ribozyme.

(xi) SEQUENCE DESCRIPTION: SEQ ID NO: 1053:

CAGGUCUUCU GAUGANGAAA CGCAGUG                                               27

(2) INFORMATION FOR SEQ ID NO: 1054:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:    The letter "N" stands for the stem
            II region of a HH ribozyme.

(xi) SEQUENCE DESCRIPTION: SEQ ID NO: 1054:

UCUCCCAUCU GAUGANGAAA CUCCUGC                                               27

(2) INFORMATION FOR SEQ ID NO: 1055:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:    The letter "N" stands for the stem
            II region of a HH ribozyme.

(xi) SEQUENCE DESCRIPTION: SEQ ID NO: 1055:

UACUUCCACU GAUGANGAAA CCAGGGU                                           27

(2) INFORMATION FOR SEQ ID NO: 1056:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1056:

CGUCUGCGCU GAUGANGAAA CUUCCAG                                           27

(2) INFORMATION FOR SEQ ID NO: 1057:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1057:

GCAGUUUGCU GAUGANGAAA UGGCACA                                           27

(2) INFORMATION FOR SEQ ID NO: 1058:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1058:

UGCAUCCGCU GAUGANGAAA GGUGCAG                                           27

(2) INFORMATION FOR SEQ ID NO: 1059:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1059:

```
GCCUUCAACU GAUGANGAAA CCUGGCC                                              27
```

(2) INFORMATION FOR SEQ ID NO: 1060:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION: The letter "N" stands for the stem II region of a HH ribozyme.

(xi) SEQUENCE DESCRIPTION: SEQ ID NO: 1060:

```
CAGCCUUCCU GAUGANGAAA GACCUGG                                              27
```

(2) INFORMATION FOR SEQ ID NO: 1061:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION: The letter "N" stands for the stem II region of a HH ribozyme.

(xi) SEQUENCE DESCRIPTION: SEQ ID NO: 1061:

```
AUUCGUUGCU GAUGANGAAA CAGCCUU                                              27
```

(2) INFORMATION FOR SEQ ID NO: 1062:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION: The letter "N" stands for the stem II region of a HH ribozyme.

(xi) SEQUENCE DESCRIPTION: SEQ ID NO: 1062:

```
CGGGAUCUCU GAUGANGAAA GGCCCAU                                              27
```

(2) INFORMATION FOR SEQ ID NO: 1063:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION: The letter "N" stands for the stem II region of a HH ribozyme.

(xi) SEQUENCE DESCRIPTION: SEQ ID NO: 1063:

```
AUGGACGGCU GAUGANGAAA UCUUAGG                                              27
```

(2) INFORMATION FOR SEQ ID NO: 1064:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION:   The letter "N" stands for the stem
          II region of a HH ribozyme.

(xi) SEQUENCE DESCRIPTION: SEQ ID NO: 1064:

UGGCGAUGCU GAUGANGAAA CGGGAUC                                      27

(2) INFORMATION FOR SEQ ID NO: 1065:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION:   The letter "N" stands for the stem
          II region of a HH ribozyme.

(xi) SEQUENCE DESCRIPTION: SEQ ID NO: 1065:

CCAGUGGCCU GAUGANGAAA UGGACGG                                      27

(2) INFORMATION FOR SEQ ID NO: 1066:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION:   The letter "N" stands for the stem
          II region of a HH ribozyme.

(xi) SEQUENCE DESCRIPTION: SEQ ID NO: 1066:

AGCAAGAGCU GAUGANGAAA GGGCCCC                                      27

(2) INFORMATION FOR SEQ ID NO: 1067:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION:   The letter "N" stands for the stem
          II region of a HH ribozyme.

(xi) SEQUENCE DESCRIPTION: SEQ ID NO: 1067:

AGCAGCAACU GAUGANGAAA GGAGGGC                                      27

(2) INFORMATION FOR SEQ ID NO: 1068:

(i) SEQUENCE CHARACTERISTICS:

```
            (A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION:  The letter "N" stands for the stem
                II region of a HH ribozyme.

(xi) SEQUENCE DESCRIPTION: SEQ ID NO: 1068:

CCAGCAGCCU GAUGANGAAA GAGGAGG                                           27

(2) INFORMATION FOR SEQ ID NO: 1069:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION:  The letter "N" stands for the stem
                II region of a HH ribozyme.

(xi) SEQUENCE DESCRIPTION: SEQ ID NO: 1069:

AAGAGGCCCU GAUGANGAAA UCCCCAG                                           27

(2) INFORMATION FOR SEQ ID NO: 1070:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION:  The letter "N" stands for the stem
                II region of a HH ribozyme.

(xi) SEQUENCE DESCRIPTION: SEQ ID NO: 1070:

CGCAUGAACU GAUGANGAAA GGCCGAU                                           27

(2) INFORMATION FOR SEQ ID NO: 1071:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION:  The letter "N" stands for the stem
                II region of a HH ribozyme.

(xi) SEQUENCE DESCRIPTION: SEQ ID NO: 1071:

UUCGCAUGCU GAUGANGAAA GAGGCCG                                           27

(2) INFORMATION FOR SEQ ID NO: 1072:

(i) SEQUENCE CHARACTERISTICS:

(A) LENGTH:           27 base pairs
            (B) TYPE:             nucleic acid
```

(C)  STRANDEDNESS:     single
        (D)  TOPOLOGY:         linear (ix) FEATURE:

(D)  OTHER INFORMATION: The letter "N" stands for the stem
             II region of a HH ribozyme.

(xi) SEQUENCE DESCRIPTION: SEQ ID NO: 1072:

CUUCGCAUCU GAUGANGAAA AGAGGCC                                      27

(2) INFORMATION FOR SEQ ID NO: 1073:

(i) SEQUENCE CHARACTERISTICS:

(A)  LENGTH:           27 base pairs
        (B)  TYPE:             nucleic acid
        (C)  STRANDEDNESS:     single
        (D)  TOPOLOGY:         linear (ix) FEATURE:

(D)  OTHER INFORMATION: The letter "N" stands for the stem
             II region of a HH ribozyme.

(xi) SEQUENCE DESCRIPTION: SEQ ID NO: 1073:

UUCCGAACCU GAUGANGAAA UGUGGCG                                      27

(2) INFORMATION FOR SEQ ID NO: 1074:

(i) SEQUENCE CHARACTERISTICS:

(A)  LENGTH:           27 base pairs
        (B)  TYPE:             nucleic acid
        (C)  STRANDEDNESS:     single
        (D)  TOPOLOGY:         linear (ix) FEATURE:

(D)  OTHER INFORMATION: The letter "N" stands for the stem
             II region of a HH ribozyme.

(xi) SEQUENCE DESCRIPTION: SEQ ID NO: 1074:

CGCUUCCGCU GAUGANGAAA CGAUGUG                                      27

(2) INFORMATION FOR SEQ ID NO: 1075:

(i) SEQUENCE CHARACTERISTICS:

(A)  LENGTH:           27 base pairs
        (B)  TYPE:             nucleic acid
        (C)  STRANDEDNESS:     single
        (D)  TOPOLOGY:         linear (ix) FEATURE:

(D)  OTHER INFORMATION: The letter "N" stands for the stem
             II region of a HH ribozyme.

(xi) SEQUENCE DESCRIPTION: SEQ ID NO: 1075:

GCGCUUCCCU GAUGANGAAA ACGAUGU                                      27

(2) INFORMATION FOR SEQ ID NO: 1076:

(i) SEQUENCE CHARACTERISTICS:

(A)  LENGTH:           27 base pairs
        (B)  TYPE:             nucleic acid
        (C)  STRANDEDNESS:     single
        (D)  TOPOLOGY:         linear (ix) FEATURE:

(D) OTHER INFORMATION: The letter "N" stands for the stem
            II region of a HH ribozyme.

(xi) SEQUENCE DESCRIPTION: SEQ ID NO: 1076:

GGCUCCACCU GAUGANGAAA GCUCCCU                                              27

(2) INFORMATION FOR SEQ ID NO: 1077:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION: The letter "N" stands for the stem
            II region of a HH ribozyme.

(xi) SEQUENCE DESCRIPTION: SEQ ID NO: 1077:

GGGUGUAACU GAUGANGAAA GGCUCCA                                              27

(2) INFORMATION FOR SEQ ID NO: 1078:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION: The letter "N" stands for the stem
            II region of a HH ribozyme.

(xi) SEQUENCE DESCRIPTION: SEQ ID NO: 1078:

CUGGGUGUCU GAUGANGAAA GAGGCUC                                              27

(2) INFORMATION FOR SEQ ID NO: 1079:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION: The letter "N" stands for the stem
            II region of a HH ribozyme.

(xi) SEQUENCE DESCRIPTION: SEQ ID NO: 1079:

ACUGGGUGCU GAUGANGAAA AGAGGCU                                              27

(2) INFORMATION FOR SEQ ID NO: 1080:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION: The letter "N" stands for the stem

II region of a HH ribozyme.

(xi) SEQUENCE DESCRIPTION: SEQ ID NO: 1080:

UUGGUUGGCU GAUGANGAAA GCUUCUC                                           27

(2) INFORMATION FOR SEQ ID NO: 1081:

(i) SEQUENCE CHARACTERISTICS:

(A) LENGTH:          27 base pairs
       (B) TYPE:            nucleic acid
       (C) STRANDEDNESS:    single
       (D) TOPOLOGY:        linear (ix) FEATURE:

(D) OTHER INFORMATION:  The letter "N" stands for the stem
           II region of a HH ribozyme.

(xi) SEQUENCE DESCRIPTION: SEQ ID NO: 1081:

CCUCAAGACU GAUGANGAAA GCUUGGU                                           27

(2) INFORMATION FOR SEQ ID NO: 1082:

(i) SEQUENCE CHARACTERISTICS:

(A) LENGTH:          27 base pairs
       (B) TYPE:            nucleic acid
       (C) STRANDEDNESS:    single
       (D) TOPOLOGY:        linear (ix) FEATURE:

(D) OTHER INFORMATION:  The letter "N" stands for the stem
           II region of a HH ribozyme.

(xi) SEQUENCE DESCRIPTION: SEQ ID NO: 1082:

AUCCUCAACU GAUGANGAAA GAGCUUG                                           27

(2) INFORMATION FOR SEQ ID NO: 1083:

(i) SEQUENCE CHARACTERISTICS:

(A) LENGTH:          27 base pairs
       (B) TYPE:            nucleic acid
       (C) STRANDEDNESS:    single
       (D) TOPOLOGY:        linear (ix) FEATURE:

(D) OTHER INFORMATION:  The letter "N" stands for the stem
           II region of a HH ribozyme.

(xi) SEQUENCE DESCRIPTION: SEQ ID NO: 1083:

AGAUCCUCCU GAUGANGAAA GAGAGCU                                           27

(2) INFORMATION FOR SEQ ID NO: 1084:

(i) SEQUENCE CHARACTERISTICS:

(A) LENGTH:          27 base pairs
       (B) TYPE:            nucleic acid
       (C) STRANDEDNESS:    single
       (D) TOPOLOGY:        linear (ix) FEATURE:

(D) OTHER INFORMATION:  The letter "N" stands for the stem
           II region of a HH ribozyme.

(xi) SEQUENCE DESCRIPTION: SEQ ID NO: 1084:

UCCUUCAACU GAUGANGAAA UCCUCAA                                              27

(2) INFORMATION FOR SEQ ID NO: 1085:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 1085:

UUUCCUUCCU GAUGANGAAA GAUCCUC                                              27

(2) INFORMATION FOR SEQ ID NO: 1086:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 1086:

UCUUUUUGCU GAUGANGAAA UUCAGUU                                              27

(2) INFORMATION FOR SEQ ID NO: 1087:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 1087:

AUCUUUUUCU GAUGANGAAA AUUCAGU                                              27

(2) INFORMATION FOR SEQ ID NO: 1088:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 1088:

AGCACUUUCU GAUGANGAAA UCUUUUU                                              27

(2) INFORMATION FOR SEQ ID NO: 1089:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1089:

ACGCACCGCU GAUGANGAAA GCCCAGC                              27

(2) INFORMATION FOR SEQ ID NO: 1090:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1090:

CCGUGCCGCU GAUGANGAAA CGCACCG                              27

(2) INFORMATION FOR SEQ ID NO: 1091:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1091:

ACCGUGCCCU GAUGANGAAA ACGCACC                              27

(2) INFORMATION FOR SEQ ID NO: 1092:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1092:

GUCCCUUACU GAUGANGAAA CACCGUG                              27

(2) INFORMATION FOR SEQ ID NO: 1093:

```
            (i) SEQUENCE CHARACTERISTICS:

(A) LENGTH:             27 base pairs
                (B) TYPE:               nucleic acid
                (C) STRANDEDNESS:       single
                (D) TOPOLOGY:           linear (ix) FEATURE:

(D) OTHER INFORMATION:  The letter "N" stands for the stem
                    II region of a HH ribozyme.

(xi) SEQUENCE DESCRIPTION: SEQ ID NO: 1093:

GAGUCCCUCU GAUGANGAAA UACACCG                                          27

(2) INFORMATION FOR SEQ ID NO: 1094:

(i) SEQUENCE CHARACTERISTICS:

(A) LENGTH:             27 base pairs
                (B) TYPE:               nucleic acid
                (C) STRANDEDNESS:       single
                (D) TOPOLOGY:           linear (ix) FEATURE:

(D) OTHER INFORMATION:  The letter "N" stands for the stem
                    II region of a HH ribozyme.

(xi) SEQUENCE DESCRIPTION: SEQ ID NO: 1094:

GGGAUCCACU GAUGANGAAA GUCCCUU                                          27

(2) INFORMATION FOR SEQ ID NO: 1095:

(i) SEQUENCE CHARACTERISTICS:

(A) LENGTH:             27 base pairs
                (B) TYPE:               nucleic acid
                (C) STRANDEDNESS:       single
                (D) TOPOLOGY:           linear (ix) FEATURE:

(D) OTHER INFORMATION:  The letter "N" stands for the stem
                    II region of a HH ribozyme.

(xi) SEQUENCE DESCRIPTION: SEQ ID NO: 1095:

CCUUCUGGCU GAUGANGAAA UCCAGAG                                          27

(2) INFORMATION FOR SEQ ID NO: 1096:

(i) SEQUENCE CHARACTERISTICS:

(A) LENGTH:             27 base pairs
                (B) TYPE:               nucleic acid
                (C) STRANDEDNESS:       single
                (D) TOPOLOGY:           linear (ix) FEATURE:

(D) OTHER INFORMATION:  The letter "N" stands for the stem
                    II region of a HH ribozyme.

(xi) SEQUENCE DESCRIPTION: SEQ ID NO: 1096:

GGAAUUUUCU GAUGANGAAA CUUUCUC                                          27

(2) INFORMATION FOR SEQ ID NO: 1097:

(i) SEQUENCE CHARACTERISTICS:

(A) LENGTH:             27 base pairs
```

```
          (B)  TYPE:               nucleic acid
          (C)  STRANDEDNESS:       single
          (D)  TOPOLOGY:           linear (ix) FEATURE:

(D)  OTHER INFORMATION:  The letter "N" stands for the stem
               II region of a HH ribozyme.

(xi) SEQUENCE DESCRIPTION: SEQ ID NO: 1097:

GGGAAUUUCU GAUGANGAAA ACUUUCU                                             27

(2) INFORMATION FOR SEQ ID NO: 1098:

(i)  SEQUENCE CHARACTERISTICS:

(A)  LENGTH:             27 base pairs
          (B)  TYPE:               nucleic acid
          (C)  STRANDEDNESS:       single
          (D)  TOPOLOGY:           linear (ix) FEATURE:

(D)  OTHER INFORMATION:  The letter "N" stands for the stem
               II region of a HH ribozyme.

(xi) SEQUENCE DESCRIPTION: SEQ ID NO: 1098:

GCGACGGGCU GAUGANGAAA UUUUAAC                                             27

(2) INFORMATION FOR SEQ ID NO: 1099:

(i)  SEQUENCE CHARACTERISTICS:

(A)  LENGTH:             27 base pairs
          (B)  TYPE:               nucleic acid
          (C)  STRANDEDNESS:       single
          (D)  TOPOLOGY:           linear (ix) FEATURE:

(D)  OTHER INFORMATION:  The letter "N" stands for the stem
               II region of a HH ribozyme.

(xi) SEQUENCE DESCRIPTION: SEQ ID NO: 1099:

AGCGACGGCU GAUGANGAAA AUUUUAA                                             27

(2) INFORMATION FOR SEQ ID NO: 1100:

(i)  SEQUENCE CHARACTERISTICS:

(A)  LENGTH:             27 base pairs
          (B)  TYPE:               nucleic acid
          (C)  STRANDEDNESS:       single
          (D)  TOPOLOGY:           linear (ix) FEATURE:

(D)  OTHER INFORMATION:  The letter "N" stands for the stem
               II region of a HH ribozyme.

(xi) SEQUENCE DESCRIPTION: SEQ ID NO: 1100:

UUGAUAGCCU GAUGANGAAA CGGGAAU                                             27

(2) INFORMATION FOR SEQ ID NO: 1101:

(i)  SEQUENCE CHARACTERISTICS:

(A)  LENGTH:             27 base pairs
          (B)  TYPE:               nucleic acid
          (C)  STRANDEDNESS:       single
          (D)  TOPOLOGY:           linear
```

(ix) FEATURE:

(D) OTHER INFORMATION:   The letter "N" stands for the stem
                   II region of a HH ribozyme.

(xi) SEQUENCE DESCRIPTION: SEQ ID NO: 1101:

UUCCUUGACU GAUGANGAAA GCGACGG                                            27

(2) INFORMATION FOR SEQ ID NO: 1102:

(i) SEQUENCE CHARACTERISTICS:

(A) LENGTH:              27 base pairs
              (B) TYPE:                nucleic acid
              (C) STRANDEDNESS:        single
              (D) TOPOLOGY:            linear (ix) FEATURE:

(D) OTHER INFORMATION:   The letter "N" stands for the stem
                   II region of a HH ribozyme.

(xi) SEQUENCE DESCRIPTION: SEQ ID NO: 1102:

AAUUCCUUCU GAUGANGAAA UAGCGAC                                            27

(2) INFORMATION FOR SEQ ID NO: 1103:

(i) SEQUENCE CHARACTERISTICS:

(A) LENGTH:              27 base pairs
              (B) TYPE:                nucleic acid
              (C) STRANDEDNESS:        single
              (D) TOPOLOGY:            linear (ix) FEATURE:

(D) OTHER INFORMATION:   The letter "N" stands for the stem
                   II region of a HH ribozyme.

(xi) SEQUENCE DESCRIPTION: SEQ ID NO: 1103:

CUUCUCUUCU GAUGANGAAA UUCCUUG                                            27

(2) INFORMATION FOR SEQ ID NO: 1104:

(i) SEQUENCE CHARACTERISTICS:

(A) LENGTH:              27 base pairs
              (B) TYPE:                nucleic acid
              (C) STRANDEDNESS:        single
              (D) TOPOLOGY:            linear (ix) FEATURE:

(D) OTHER INFORMATION:   The letter "N" stands for the stem
                   II region of a HH ribozyme.

(xi) SEQUENCE DESCRIPTION: SEQ ID NO: 1104:

GCUUCUCUCU GAUGANGAAA AUUCCUU                                            27

(2) INFORMATION FOR SEQ ID NO: 1105:

(i) SEQUENCE CHARACTERISTICS:

(A) LENGTH:              27 base pairs
              (B) TYPE:                nucleic acid
              (C) STRANDEDNESS:        single
              (D) TOPOLOGY:            linear (ix) FEATURE:

```
            (D) OTHER INFORMATION:  The letter "N" stands for the stem
                II region of a HH ribozyme.

(xi) SEQUENCE DESCRIPTION: SEQ ID NO: 1105:

CUUUCGGACU GAUGANGAAA UGUUGCU                                           27

(2) INFORMATION FOR SEQ ID NO: 1106:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:  The letter "N" stands for the stem
                II region of a HH ribozyme.

(xi) SEQUENCE DESCRIPTION: SEQ ID NO: 1106:

GGCUUUCGCU GAUGANGAAA GAUGUUG                                           27

(2) INFORMATION FOR SEQ ID NO: 1107:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:  The letter "N" stands for the stem
                II region of a HH ribozyme.

(xi) SEQUENCE DESCRIPTION: SEQ ID NO: 1107:

UCAUCGAGCU GAUGANGAAA UUUCCUU                                           27

(2) INFORMATION FOR SEQ ID NO: 1108:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:  The letter "N" stands for the stem
                II region of a HH ribozyme.

(xi) SEQUENCE DESCRIPTION: SEQ ID NO: 1108:

GCUUCAUCCU GAUGANGAAA GGAUUUC                                           27

(2) INFORMATION FOR SEQ ID NO: 1109:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:  The letter "N" stands for the stem
                II region of a HH ribozyme.
```

(xi)  SEQUENCE DESCRIPTION: SEQ ID NO: 1109:

CCAUCACGCU GAUGANGAAA GGCUUCA                                                  27

(2)  INFORMATION FOR SEQ ID NO: 1110:

(i)  SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi)  SEQUENCE DESCRIPTION: SEQ ID NO: 1110:

GUGAGGCACU GAUGANGAAA UGCCCAG                                                  27

(2)  INFORMATION FOR SEQ ID NO: 1111:

(i)  SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi)  SEQUENCE DESCRIPTION: SEQ ID NO: 1111:

GUGGAGGUCU GAUGANGAAA GGCAGAU                                                  27

(2)  INFORMATION FOR SEQ ID NO: 1112:

(i)  SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi)  SEQUENCE DESCRIPTION: SEQ ID NO: 1112:

GCACGGUGCU GAUGANGAAA GGUGAGG                                                  27

(2)  INFORMATION FOR SEQ ID NO: 1113:

(i)  SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi)  SEQUENCE DESCRIPTION: SEQ ID NO: 1113:

UGCGUGAUCU GAUGANGAAA GUUGCAC                                                  27

(2) INFORMATION FOR SEQ ID NO: 1114:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1114:

AGCUGCGUCU GAUGANGAAA UGAGUUG 27

(2) INFORMATION FOR SEQ ID NO: 1115:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1115:

AAGGGCAUCU GAUGANGAAA GCUGCGU 27

(2) INFORMATION FOR SEQ ID NO: 1116:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1116:

GGCAGCCGCU GAUGANGAAA GGGCAUG 27

(2) INFORMATION FOR SEQ ID NO: 1117:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1117:

AGGCAGCCCU GAUGANGAAA AGGGCAU 27

(2) INFORMATION FOR SEQ ID NO: 1118:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 1118:

UAGUCCAGCU GAUGANGAAA GGCAGCC                                              27

(2) INFORMATION FOR SEQ ID NO: 1119:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 1119:

CCCGGACACU GAUGANGAAA GUCCAGG                                              27

(2) INFORMATION FOR SEQ ID NO: 1120:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 1120:

UGUUCCCGCU GAUGANGAAA CAUAGUC                                              27

(2) INFORMATION FOR SEQ ID NO: 1121:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 1121:

GGAGCCAACU GAUGANGAAA UUGUCUU                                              27

(2) INFORMATION FOR SEQ ID NO: 1122:

(i) SEQUENCE CHARACTERISTICS:

```
            (A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1122:

UGGGAGCCCU GAUGANGAAA UAUUGUC                                            27

(2) INFORMATION FOR SEQ ID NO: 1123:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1123:

GGUACUGGCU GAUGANGAAA GCCAAUA                                            27

(2) INFORMATION FOR SEQ ID NO: 1124:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1124:

UGAGCAGGCU GAUGANGAAA CUGGGAG                                            27

(2) INFORMATION FOR SEQ ID NO: 1125:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1125:

CACCAGUUCU GAUGANGAAA GCAGGUA                                            27

(2) INFORMATION FOR SEQ ID NO: 1126:

(i) SEQUENCE CHARACTERISTICS:

(A)  LENGTH:             27 base pairs
            (B)  TYPE:               nucleic acid
            (C)  STRANDEDNESS:       single
```

(D)  TOPOLOGY:          linear (ix) FEATURE:

(D)  OTHER INFORMATION:  The letter "N" stands for the stem
             II region of a HH ribozyme.

(xi) SEQUENCE DESCRIPTION: SEQ ID NO: 1126:

CCCUUUGCCU GAUGANGAAA UCUGCAC                                              27

(2) INFORMATION FOR SEQ ID NO: 1127:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear (ix) FEATURE:

(D)  OTHER INFORMATION:  The letter "N" stands for the stem
             II region of a HH ribozyme.

(xi) SEQUENCE DESCRIPTION: SEQ ID NO: 1127:

CCUCCAAGCU GAUGANGAAA GUUCAUG                                              27

(2) INFORMATION FOR SEQ ID NO: 1128:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear (ix) FEATURE:

(D)  OTHER INFORMATION:  The letter "N" stands for the stem
             II region of a HH ribozyme.

(xi) SEQUENCE DESCRIPTION: SEQ ID NO: 1128:

GGUCCUCCCU GAUGANGAAA GUAGUUC                                              27

(2) INFORMATION FOR SEQ ID NO: 1129:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear (ix) FEATURE:

(D)  OTHER INFORMATION:  The letter "N" stands for the stem
             II region of a HH ribozyme.

(xi) SEQUENCE DESCRIPTION: SEQ ID NO: 1129:

CACCAAGCCU GAUGANGAAA CGGUCCU                                              27

(2) INFORMATION FOR SEQ ID NO: 1130:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear (ix) FEATURE:

(D) OTHER INFORMATION:   The letter "N" stands for the stem
                II region of a HH ribozyme.

(xi) SEQUENCE DESCRIPTION: SEQ ID NO: 1130:

GGUGCACCCU GAUGANGAAA GCGACGG                                              27

(2) INFORMATION FOR SEQ ID NO: 1131:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 1131:

UUCACCAGCU GAUGANGAAA CGUUCCU                                              27

(2) INFORMATION FOR SEQ ID NO: 1132:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 1132:

GUGAUCUUCU GAUGANGAAA CAUGCUG                                              27

(2) INFORMATION FOR SEQ ID NO: 1133:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 1133:

AAAUCUGUCU GAUGANGAAA UCUUGAC                                              27

(2) INFORMATION FOR SEQ ID NO: 1134:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 1134:

CAGCCCAACU GAUGANGAAA UCUGUGA                                27

(2) INFORMATION FOR SEQ ID NO: 1135:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION:  The letter "N" stands for the stem II region of a HH ribozyme.

(xi) SEQUENCE DESCRIPTION: SEQ ID NO: 1135:

CCAGCCCACU GAUGANGAAA AUCUGUG                                27

(2) INFORMATION FOR SEQ ID NO: 1136:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION:  The letter "N" stands for the stem II region of a HH ribozyme.

(xi) SEQUENCE DESCRIPTION: SEQ ID NO: 1136:

GCCAGCCCCU GAUGANGAAA AAUCUGU                                27

(2) INFORMATION FOR SEQ ID NO: 1137:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION:  The letter "N" stands for the stem II region of a HH ribozyme.

(xi) SEQUENCE DESCRIPTION: SEQ ID NO: 1137:

CUGCAUGGCU GAUGANGAAA UUCUUUC                                27

(2) INFORMATION FOR SEQ ID NO: 1138:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION:  The letter "N" stands for the stem II region of a HH ribozyme.

(xi) SEQUENCE DESCRIPTION: SEQ ID NO: 1138:

CCACUUGACU GAUGANGAAA GGCACUU         27

(2) INFORMATION FOR SEQ ID NO: 1139:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem II region of a HH ribozyme.

(xi) SEQUENCE DESCRIPTION: SEQ ID NO: 1139:

AUCCACUUCU GAUGANGAAA UAGGCAC         27

(2) INFORMATION FOR SEQ ID NO: 1140:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem II region of a HH ribozyme.

(xi) SEQUENCE DESCRIPTION: SEQ ID NO: 1140:

UUGAUUCCCU GAUGANGAAA UGCCAUC         27

(2) INFORMATION FOR SEQ ID NO: 1141:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem II region of a HH ribozyme.

(xi) SEQUENCE DESCRIPTION: SEQ ID NO: 1141:

GUAAAAUUCU GAUGANGAAA UUCCAAU         27

(2) INFORMATION FOR SEQ ID NO: 1142:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem II region of a HH ribozyme.

(xi) SEQUENCE DESCRIPTION: SEQ ID NO: 1142:

CUGUGUAACU GAUGANGAAA UUGAUUC         27

-continued (2) INFORMATION FOR SEQ ID NO: 1143:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1143:

UCUGUGUACU GAUGANGAAA AUUGAUU     27

(2) INFORMATION FOR SEQ ID NO: 1144:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1144:

UUCUGUGUCU GAUGANGAAA AAUUGAU     27

(2) INFORMATION FOR SEQ ID NO: 1145:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1145:

AUUCUGUGCU GAUGANGAAA AAAUUGA     27

(2) INFORMATION FOR SEQ ID NO: 1146:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1146:

UGGGUAUACU GAUGANGAAA UUCUGUG     27

(2) INFORMATION FOR SEQ ID NO: 1147:

(i) SEQUENCE CHARACTERISTICS:

```
            (A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:  The letter "N" stands for the stem
                II region of a HH ribozyme.

(xi) SEQUENCE DESCRIPTION: SEQ ID NO: 1147:

GGUGGGUACU GAUGANGAAA GAUUCUG                                              27

(2) INFORMATION FOR SEQ ID NO: 1148:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:  The letter "N" stands for the stem
                II region of a HH ribozyme.

(xi) SEQUENCE DESCRIPTION: SEQ ID NO: 1148:

CUGGUGGGCU GAUGANGAAA UAGAUUC                                              27

(2) INFORMATION FOR SEQ ID NO: 1149:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:  The letter "N" stands for the stem
                II region of a HH ribozyme.

(xi) SEQUENCE DESCRIPTION: SEQ ID NO: 1149:

UAGCUCCACU GAUGANGAAA CAUCACU                                              27

(2) INFORMATION FOR SEQ ID NO: 1150:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:  The letter "N" stands for the stem
                II region of a HH ribozyme.

(xi) SEQUENCE DESCRIPTION: SEQ ID NO: 1150:

UCACCCCGCU GAUGANGAAA GCUCCAG                                              27

(2) INFORMATION FOR SEQ ID NO: 1151:

(i) SEQUENCE CHARACTERISTICS:

(A) LENGTH:          27 base pairs
            (B) TYPE:            nucleic acid
```

```
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1151:

AACUCCCACU GAUGANGAAA CGGUCAC                                          27

(2) INFORMATION FOR SEQ ID NO: 1152:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1152:

CAACUCCCCU GAUGANGAAA ACGGUCA                                          27

(2) INFORMATION FOR SEQ ID NO: 1153:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1153:

AGGUCAUCCU GAUGANGAAA CUCCCAA                                          27

(2) INFORMATION FOR SEQ ID NO: 1154:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1154:

UGGAUCCACU GAUGANGAAA GGUCAUC                                          27

(2) INFORMATION FOR SEQ ID NO: 1155:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear
```

531

532

-continued (ix) FEATURE:

(D) OTHER INFORMATION: The letter "N" stands for the stem
                II region of a HH ribozyme.

(xi) SEQUENCE DESCRIPTION: SEQ ID NO: 1155:

UUGGAUCCCU GAUGANGAAA AGGUCAU                                              27

(2) INFORMATION FOR SEQ ID NO: 1156:

(i) SEQUENCE CHARACTERISTICS:

(A) LENGTH:         27 base pairs
            (B) TYPE:           nucleic acid
            (C) STRANDEDNESS:   single
            (D) TOPOLOGY:       linear (ix) FEATURE:

(D) OTHER INFORMATION: The letter "N" stands for the stem
                II region of a HH ribozyme.

(xi) SEQUENCE DESCRIPTION: SEQ ID NO: 1156:

AUGGCUUGCU GAUGANGAAA UCCAAAG                                              27

(2) INFORMATION FOR SEQ ID NO: 1157:

(i) SEQUENCE CHARACTERISTICS:

(A) LENGTH:         27 base pairs
            (B) TYPE:           nucleic acid
            (C) STRANDEDNESS:   single
            (D) TOPOLOGY:       linear (ix) FEATURE:

(D) OTHER INFORMATION: The letter "N" stands for the stem
                II region of a HH ribozyme.

(xi) SEQUENCE DESCRIPTION: SEQ ID NO: 1157:

UUCCGUCACU GAUGANGAAA UGGCUUG                                              27

(2) INFORMATION FOR SEQ ID NO: 1158:

(i) SEQUENCE CHARACTERISTICS:

(A) LENGTH:         27 base pairs
            (B) TYPE:           nucleic acid
            (C) STRANDEDNESS:   single
            (D) TOPOLOGY:       linear (ix) FEATURE:

(D) OTHER INFORMATION: The letter "N" stands for the stem
                II region of a HH ribozyme.

(xi) SEQUENCE DESCRIPTION: SEQ ID NO: 1158:

CUGGCAGGCU GAUGANGAAA UUCCGUC                                              27

(2) INFORMATION FOR SEQ ID NO: 1159:

(i) SEQUENCE CHARACTERISTICS:

(A) LENGTH:         27 base pairs
            (B) TYPE:           nucleic acid
            (C) STRANDEDNESS:   single
            (D) TOPOLOGY:       linear (ix) FEATURE:

(D) OTHER INFORMATION: The letter "N" stands for the stem

II region of a HH ribozyme.

(xi) SEQUENCE DESCRIPTION: SEQ ID NO: 1159:

AUGGAGGACU GAUGANGAAA UCUCGCU                                                   27

(2) INFORMATION FOR SEQ ID NO: 1160:

(i) SEQUENCE CHARACTERISTICS:

(A) LENGTH:          27 base pairs
        (B) TYPE:            nucleic acid
        (C) STRANDEDNESS:   single
        (D) TOPOLOGY:       linear (ix) FEATURE:

(D) OTHER INFORMATION:   The letter "N" stands for the stem
            II region of a HH ribozyme.

(xi) SEQUENCE DESCRIPTION: SEQ ID NO: 1160:

GGAUGGAGCU GAUGANGAAA GAUCUCG                                                   27

(2) INFORMATION FOR SEQ ID NO: 1161:

(i) SEQUENCE CHARACTERISTICS:

(A) LENGTH:          27 base pairs
        (B) TYPE:            nucleic acid
        (C) STRANDEDNESS:   single
        (D) TOPOLOGY:       linear (ix) FEATURE:

(D) OTHER INFORMATION:   The letter "N" stands for the stem
            II region of a HH ribozyme.

(xi) SEQUENCE DESCRIPTION: SEQ ID NO: 1161:

CCAGGAUGCU GAUGANGAAA GGAGAUC                                                   27

(2) INFORMATION FOR SEQ ID NO: 1162:

(i) SEQUENCE CHARACTERISTICS:

(A) LENGTH:          27 base pairs
        (B) TYPE:            nucleic acid
        (C) STRANDEDNESS:   single
        (D) TOPOLOGY:       linear (ix) FEATURE:

(D) OTHER INFORMATION:   The letter "N" stands for the stem
            II region of a HH ribozyme.

(xi) SEQUENCE DESCRIPTION: SEQ ID NO: 1162:

UUCUCCAGCU GAUGANGAAA UGGAGGA                                                   27

(2) INFORMATION FOR SEQ ID NO: 1163:

(i) SEQUENCE CHARACTERISTICS:

(A) LENGTH:          27 base pairs
        (B) TYPE:            nucleic acid
        (C) STRANDEDNESS:   single
        (D) TOPOLOGY:       linear (ix) FEATURE:

(D) OTHER INFORMATION:   The letter "N" stands for the stem
            II region of a HH ribozyme.

(xi) SEQUENCE DESCRIPTION: SEQ ID NO: 1163:

GGCUGAGGCU GAUGANGAAA GGCGUUC                                              27

(2) INFORMATION FOR SEQ ID NO: 1164:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION: The letter "N" stands for the stem
            II region of a HH ribozyme.

(xi) SEQUENCE DESCRIPTION: SEQ ID NO: 1164:

GGGUGGCUCU GAUGANGAAA GGGAGGC                                              27

(2) INFORMATION FOR SEQ ID NO: 1165:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION: The letter "N" stands for the stem
            II region of a HH ribozyme.

(xi) SEQUENCE DESCRIPTION: SEQ ID NO: 1165:

AUGGUACACU GAUGANGAAA UGGGUGG                                              27

(2) INFORMATION FOR SEQ ID NO: 1166:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION: The letter "N" stands for the stem
            II region of a HH ribozyme.

(xi) SEQUENCE DESCRIPTION: SEQ ID NO: 1166:

AUCGAUGGCU GAUGANGAAA CAUAUGG                                              27

(2) INFORMATION FOR SEQ ID NO: 1167:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION: The letter "N" stands for the stem
            II region of a HH ribozyme.

(xi) SEQUENCE DESCRIPTION: SEQ ID NO: 1167:

UAGACAUCCU GAUGANGAAA UGGUACA                                              27

(2) INFORMATION FOR SEQ ID NO: 1168:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1168:

AUCAUGUACU GAUGANGAAA CAUCGAU                               27

(2) INFORMATION FOR SEQ ID NO: 1169:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1169:

UGAUCAUGCU GAUGANGAAA GACAUCG                               27

(2) INFORMATION FOR SEQ ID NO: 1170:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1170:

UUGACCAUCU GAUGANGAAA UCAUGUA                               27

(2) INFORMATION FOR SEQ ID NO: 1171:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1171:

CAGCACUUCU GAUGANGAAA CCAUGAU                               27

(2) INFORMATION FOR SEQ ID NO: 1172:

```
           (i) SEQUENCE CHARACTERISTICS:

(A) LENGTH:           27 base pairs
                (B) TYPE:             nucleic acid
                (C) STRANDEDNESS:     single
                (D) TOPOLOGY:         linear (ix) FEATURE:

(D) OTHER INFORMATION:   The letter "N" stands for the stem
                    II region of a HH ribozyme.

(xi) SEQUENCE DESCRIPTION: SEQ ID NO: 1172:

UCUGCGUCCU GAUGANGAAA UCAUCCA                                              27

(2) INFORMATION FOR SEQ ID NO: 1173:

(i) SEQUENCE CHARACTERISTICS:

(A) LENGTH:           27 base pairs
                (B) TYPE:             nucleic acid
                (C) STRANDEDNESS:     single
                (D) TOPOLOGY:         linear (ix) FEATURE:

(D) OTHER INFORMATION:   The letter "N" stands for the stem
                    II region of a HH ribozyme.

(xi) SEQUENCE DESCRIPTION: SEQ ID NO: 1173:

UGGGCGACCU GAUGANGAAA UCUGCGU                                              27

(2) INFORMATION FOR SEQ ID NO: 1174:

(i) SEQUENCE CHARACTERISTICS:

(A) LENGTH:           27 base pairs
                (B) TYPE:             nucleic acid
                (C) STRANDEDNESS:     single
                (D) TOPOLOGY:         linear (ix) FEATURE:

(D) OTHER INFORMATION:   The letter "N" stands for the stem
                    II region of a HH ribozyme.

(xi) SEQUENCE DESCRIPTION: SEQ ID NO: 1174:

CUUUGGGCCU GAUGANGAAA CUAUCUG                                              27

(2) INFORMATION FOR SEQ ID NO: 1175:

(i) SEQUENCE CHARACTERISTICS:

(A) LENGTH:           27 base pairs
                (B) TYPE:             nucleic acid
                (C) STRANDEDNESS:     single
                (D) TOPOLOGY:         linear (ix) FEATURE:

(D) OTHER INFORMATION:   The letter "N" stands for the stem
                    II region of a HH ribozyme.

(xi) SEQUENCE DESCRIPTION: SEQ ID NO: 1175:

ACUCACGGCU GAUGANGAAA CUUUGGG                                              27

(2) INFORMATION FOR SEQ ID NO: 1176:

(i) SEQUENCE CHARACTERISTICS:

(A) LENGTH:           27 base pairs
```

```
            (B)  TYPE:              nucleic acid
            (C)  STRANDEDNESS:      single
            (D)  TOPOLOGY:          linear (ix) FEATURE:

(D)  OTHER INFORMATION:   The letter "N" stands for the stem
                 II region of a HH ribozyme.

(xi) SEQUENCE DESCRIPTION: SEQ ID NO: 1176:

AACUCACGCU GAUGANGAAA ACUUUGG                                              27

(2) INFORMATION FOR SEQ ID NO: 1177:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:   The letter "N" stands for the stem
                 II region of a HH ribozyme.

(xi) SEQUENCE DESCRIPTION: SEQ ID NO: 1177:

CGAUGAUCCU GAUGANGAAA CUCACGG                                              27

(2) INFORMATION FOR SEQ ID NO: 1178:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:   The letter "N" stands for the stem
                 II region of a HH ribozyme.

(xi) SEQUENCE DESCRIPTION: SEQ ID NO: 1178:

AAUUCGAUCU GAUGANGAAA UCAACUC                                              27

(2) INFORMATION FOR SEQ ID NO: 1179:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:   The letter "N" stands for the stem
                 II region of a HH ribozyme.

(xi) SEQUENCE DESCRIPTION: SEQ ID NO: 1179:

GAGAAUUCCU GAUGANGAAA UGAUCAA                                              27

(2) INFORMATION FOR SEQ ID NO: 1180:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear
```

(ix) FEATURE:

(D) OTHER INFORMATION: The letter "N" stands for the stem
        II region of a HH ribozyme.

(xi) SEQUENCE DESCRIPTION: SEQ ID NO: 1180:

UUUUGGAGCU GAUGANGAAA UUCGAUG                                27

(2) INFORMATION FOR SEQ ID NO: 1181:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 1181:

AUUUUGGACU GAUGANGAAA AUUCGAU                               27

(2) INFORMATION FOR SEQ ID NO: 1182:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 1182:

CCAUUUUGCU GAUGANGAAA GAAUUCG                               27

(2) INFORMATION FOR SEQ ID NO: 1183:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 1183:

UGACAAGGCU GAUGANGAAA GCGCUGG                               27

(2) INFORMATION FOR SEQ ID NO: 1184:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
                II region of a HH ribozyme.

(xi) SEQUENCE DESCRIPTION: SEQ ID NO: 1184:

UGAAUGACCU GAUGANGAAA GGUAGCG                                          27

(2) INFORMATION FOR SEQ ID NO: 1185:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 1185:

CCCUGAAUCU GAUGANGAAA CAAGGUA                                          27

(2) INFORMATION FOR SEQ ID NO: 1186:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 1186:

UCCCCCUGCU GAUGANGAAA UGACAAG                                          27

(2) INFORMATION FOR SEQ ID NO: 1187:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 1187:

AUCCCCCUCU GAUGANGAAA AUGACAA                                          27

(2) INFORMATION FOR SEQ ID NO: 1188:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 1188:

ACUUGGCACU GAUGANGAAA UGCAUUC                27

(2) INFORMATION FOR SEQ ID NO: 1189:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION: The letter "N" stands for the stem
         II region of a HH ribozyme.

(xi) SEQUENCE DESCRIPTION: SEQ ID NO: 1189:

GACUUGGCCU GAUGANGAAA AUGCAUU                27

(2) INFORMATION FOR SEQ ID NO: 1190:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION: The letter "N" stands for the stem
         II region of a HH ribozyme.

(xi) SEQUENCE DESCRIPTION: SEQ ID NO: 1190:

GUCUGUAGCU GAUGANGAAA CUUGGCA                27

(2) INFORMATION FOR SEQ ID NO: 1191:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION: The letter "N" stands for the stem
         II region of a HH ribozyme.

(xi) SEQUENCE DESCRIPTION: SEQ ID NO: 1191:

GGAGUCUGCU GAUGANGAAA GGACUUG                27

(2) INFORMATION FOR SEQ ID NO: 1192:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION: The letter "N" stands for the stem
         II region of a HH ribozyme.

(xi) SEQUENCE DESCRIPTION: SEQ ID NO: 1192:

AGAAGUUGCU GAUGANGAAA GUCUGUA                27

(2) INFORMATION FOR SEQ ID NO: 1193:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1193:

CACGGUAGCU GAUGANGAAA GUUGGAG                                  27

(2) INFORMATION FOR SEQ ID NO: 1194:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1194:

GCACGGUACU GAUGANGAAA AGUUGGA                                  27

(2) INFORMATION FOR SEQ ID NO: 1195:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1195:

GGGCACGGCU GAUGANGAAA GAAGUUG                                  27

(2) INFORMATION FOR SEQ ID NO: 1196:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1196:

GGAUGAGGCU GAUGANGAAA CUCGUCG                                  27

(2) INFORMATION FOR SEQ ID NO: 1197:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION:  The letter "N" stands for the stem
                II region of a HH ribozyme.

(xi) SEQUENCE DESCRIPTION: SEQ ID NO: 1197:

UGUGGGAUCU GAUGANGAAA GGUACUC                                               27

(2) INFORMATION FOR SEQ ID NO: 1198:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION:  The letter "N" stands for the stem
                II region of a HH ribozyme.

(xi) SEQUENCE DESCRIPTION: SEQ ID NO: 1198:

UGCUGUGGCU GAUGANGAAA UGAGGUA                                               27

(2) INFORMATION FOR SEQ ID NO: 1199:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION:  The letter "N" stands for the stem
                II region of a HH ribozyme.

(xi) SEQUENCE DESCRIPTION: SEQ ID NO: 1199:

UGCUGAAGCU GAUGANGAAA GCCCUGC                                               27

(2) INFORMATION FOR SEQ ID NO: 1200:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION:  The letter "N" stands for the stem
                II region of a HH ribozyme.

(xi) SEQUENCE DESCRIPTION: SEQ ID NO: 1200:

CUGCUGAACU GAUGANGAAA AGCCCUG                                               27

(2) INFORMATION FOR SEQ ID NO: 1201:

(i) SEQUENCE CHARACTERISTICS:

-continued

```
          (A)  LENGTH:              27 base pairs
          (B)  TYPE:                nucleic acid
          (C)  STRANDEDNESS:        single
          (D)  TOPOLOGY:            linear (ix) FEATURE:

(D)  OTHER INFORMATION:   The letter "N" stands for the stem
               II region of a HH ribozyme.

(xi) SEQUENCE DESCRIPTION: SEQ ID NO: 1201:

GGCUGCUGCU GAUGANGAAA GAAGCCC                                              27

(2) INFORMATION FOR SEQ ID NO: 1202:

(i)  SEQUENCE CHARACTERISTICS:

(A)  LENGTH:              27 base pairs
          (B)  TYPE:                nucleic acid
          (C)  STRANDEDNESS:        single
          (D)  TOPOLOGY:            linear (ix) FEATURE:

(D)  OTHER INFORMATION:   The letter "N" stands for the stem
               II region of a HH ribozyme.

(xi) SEQUENCE DESCRIPTION: SEQ ID NO: 1202:

GGGCUGCUCU GAUGANGAAA AGAAGCC                                              27

(2) INFORMATION FOR SEQ ID NO: 1203:

(i)  SEQUENCE CHARACTERISTICS:

(A)  LENGTH:              27 base pairs
          (B)  TYPE:                nucleic acid
          (C)  STRANDEDNESS:        single
          (D)  TOPOLOGY:            linear (ix) FEATURE:

(D)  OTHER INFORMATION:   The letter "N" stands for the stem
               II region of a HH ribozyme.

(xi) SEQUENCE DESCRIPTION: SEQ ID NO: 1203:

GUGACGUGCU GAUGANGAAA GGGGCUG                                              27

(2) INFORMATION FOR SEQ ID NO: 1204:

(i)  SEQUENCE CHARACTERISTICS:

(A)  LENGTH:              27 base pairs
          (B)  TYPE:                nucleic acid
          (C)  STRANDEDNESS:        single
          (D)  TOPOLOGY:            linear (ix) FEATURE:

(D)  OTHER INFORMATION:   The letter "N" stands for the stem
               II region of a HH ribozyme.

(xi) SEQUENCE DESCRIPTION: SEQ ID NO: 1204:

GAGUCCGUCU GAUGANGAAA CGUGGAG                                              27

(2) INFORMATION FOR SEQ ID NO: 1205:

(i)  SEQUENCE CHARACTERISTICS:

(A)  LENGTH:              27 base pairs
          (B)  TYPE:                nucleic acid
          (C)  STRANDEDNESS:        single
```

```
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 1205:

CAGGAGGGCU GAUGANGAAA GUCCGUG                                              27

(2) INFORMATION FOR SEQ ID NO: 1206:

(i)  SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 1206:

GAGCUCAGCU GAUGANGAAA GGGGAGU                                              27

(2) INFORMATION FOR SEQ ID NO: 1207:

(i)  SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 1207:

CACUCAGACU GAUGANGAAA GCUCAGG                                              27

(2) INFORMATION FOR SEQ ID NO: 1208:

(i)  SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 1208:

UGCACUCACU GAUGANGAAA GAGCUCA                                              27

(2) INFORMATION FOR SEQ ID NO: 1209:

(i)  SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:
```

```
        (D) OTHER INFORMATION:  The letter "N" stands for the stem
            II region of a HH ribozyme.

(xi) SEQUENCE DESCRIPTION: SEQ ID NO: 1209:

CACGGUGGCU GAUGANGAAA UUGUUGC                                              27

(2) INFORMATION FOR SEQ ID NO: 1210:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 1210:

CCACGGUGCU GAUGANGAAA AUUGUUG                                              27

(2) INFORMATION FOR SEQ ID NO: 1211:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 1211:

AUCAAUGCCU GAUGANGAAA GCCACGG                                              27

(2) INFORMATION FOR SEQ ID NO: 1212:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 1212:

UUUCUAUCCU GAUGANGAAA UGCAAGC                                              27

(2) INFORMATION FOR SEQ ID NO: 1213:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.
```

(xi) SEQUENCE DESCRIPTION: SEQ ID NO: 1213:

CCCAUUUCCU GAUGANGAAA UCAAUGC  27

(2) INFORMATION FOR SEQ ID NO: 1214:

(i) SEQUENCE CHARACTERISTICS:

(A) LENGTH: 27 base pairs
      (B) TYPE: nucleic acid
      (C) STRANDEDNESS: single
      (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1214:

CUUGAUGGCU GAUGANGAAA CAGCUUU  27

(2) INFORMATION FOR SEQ ID NO: 1215:

(i) SEQUENCE CHARACTERISTICS:

(A) LENGTH: 27 base pairs
      (B) TYPE: nucleic acid
      (C) STRANDEDNESS: single
      (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1215:

UCUUCCUUCU GAUGANGAAA UGGGACA  27

(2) INFORMATION FOR SEQ ID NO: 1216:

(i) SEQUENCE CHARACTERISTICS:

(A) LENGTH: 27 base pairs
      (B) TYPE: nucleic acid
      (C) STRANDEDNESS: single
      (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1216:

GCUGCAAGCU GAUGANGAAA GCUGUCU  27

(2) INFORMATION FOR SEQ ID NO: 1217:

(i) SEQUENCE CHARACTERISTICS:

(A) LENGTH: 27 base pairs
      (B) TYPE: nucleic acid
      (C) STRANDEDNESS: single
      (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1217:

```
CGCUGCAACU GAUGANGAAA AGCUGUC                                                27
```

(2) INFORMATION FOR SEQ ID NO: 1218:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION: The letter "N" stands for the stem
            II region of a HH ribozyme.

(xi) SEQUENCE DESCRIPTION: SEQ ID NO: 1218:

```
AUCGCUGCCU GAUGANGAAA GAAGCUG                                                27
```

(2) INFORMATION FOR SEQ ID NO: 1219:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION: The letter "N" stands for the stem
            II region of a HH ribozyme.

(xi) SEQUENCE DESCRIPTION: SEQ ID NO: 1219:

```
CUGAGCUGCU GAUGANGAAA UCGCUGC                                                27
```

(2) INFORMATION FOR SEQ ID NO: 1220:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION: The letter "N" stands for the stem
            II region of a HH ribozyme.

(xi) SEQUENCE DESCRIPTION: SEQ ID NO: 1220:

```
UGGGGUCUCU GAUGANGAAA GCUGUAU                                                27
```

(2) INFORMATION FOR SEQ ID NO: 1221:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION: The letter "N" stands for the stem
            II region of a HH ribozyme.

(xi) SEQUENCE DESCRIPTION: SEQ ID NO: 1221:

```
CCUCAGUCCU GAUGANGAAA GGCGCCU                                                27
```

```
(2) INFORMATION FOR SEQ ID NO: 1222:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 1222:

GUGUCGUCCU GAUGANGAAA UGCUGUC                                       27

(2) INFORMATION FOR SEQ ID NO: 1223:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 1223:

CUGGGAGGCU GAUGANGAAA GGUGUCG                                       27

(2) INFORMATION FOR SEQ ID NO: 1224:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 1224:

ACUGGGAGCU GAUGANGAAA AGGUGUC                                       27

(2) INFORMATION FOR SEQ ID NO: 1225:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 1225:

GGCACUGGCU GAUGANGAAA GGAAGGU                                       27

(2) INFORMATION FOR SEQ ID NO: 1226:

(i) SEQUENCE CHARACTERISTICS:
```

```
            (A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1226:

GGUUUAUGCU GAUGANGAAA UUCAGGC                                              27

(2) INFORMATION FOR SEQ ID NO: 1227:

(i) SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1227:

GACUGGUUCU GAUGANGAAA UGUAUUC                                              27

(2) INFORMATION FOR SEQ ID NO: 1228:

(i) SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1228:

UGGGAACGCU GAUGANGAAA CUGGUUU                                              27

(2) INFORMATION FOR SEQ ID NO: 1229:

(i) SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1229:

CUUUUGGGCU GAUGANGAAA CGGACUG                                              27

(2) INFORMATION FOR SEQ ID NO: 1230:

(i) SEQUENCE CHARACTERISTICS:

(A)  LENGTH:              27 base pairs
            (B)  TYPE:                nucleic acid
```

(C) STRANDEDNESS:      single
        (D) TOPOLOGY:          linear (ix) FEATURE:

(D) OTHER INFORMATION: The letter "N" stands for the stem
            II region of a HH ribozyme.

(xi) SEQUENCE DESCRIPTION: SEQ ID NO: 1230:

CCUUUUGGCU GAUGANGAAA ACGGACU                                          27

(2) INFORMATION FOR SEQ ID NO: 1231:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION: The letter "N" stands for the stem
            II region of a HH ribozyme.

(xi) SEQUENCE DESCRIPTION: SEQ ID NO: 1231:

UCUGCACACU GAUGANGAAA GCCAGCG                                          27

(2) INFORMATION FOR SEQ ID NO: 1232:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION: The letter "N" stands for the stem
            II region of a HH ribozyme.

(xi) SEQUENCE DESCRIPTION: SEQ ID NO: 1232:

AUAGACAGCU GAUGANGAAA UUCUGCA                                          27

(2) INFORMATION FOR SEQ ID NO: 1233:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION: The letter "N" stands for the stem
            II region of a HH ribozyme.

(xi) SEQUENCE DESCRIPTION: SEQ ID NO: 1233:

UUGUGAUACU GAUGANGAAA CAGGAUU                                          27

(2) INFORMATION FOR SEQ ID NO: 1234:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION: The letter "N" stands for the stem
          II region of a HH ribozyme.

(xi) SEQUENCE DESCRIPTION: SEQ ID NO: 1234:

GAUUGUGACU GAUGANGAAA GACAGGA                         27

(2) INFORMATION FOR SEQ ID NO: 1235:

(i) SEQUENCE CHARACTERISTICS:

(A) LENGTH:          27 base pairs
      (B) TYPE:            nucleic acid
      (C) STRANDEDNESS:   single
      (D) TOPOLOGY:       linear (ix) FEATURE:

(D) OTHER INFORMATION: The letter "N" stands for the stem
          II region of a HH ribozyme.

(xi) SEQUENCE DESCRIPTION: SEQ ID NO: 1235:

CUGAUUGUCU GAUGANGAAA UAGACAG                         27

(2) INFORMATION FOR SEQ ID NO: 1236:

(i) SEQUENCE CHARACTERISTICS:

(A) LENGTH:          27 base pairs
      (B) TYPE:            nucleic acid
      (C) STRANDEDNESS:   single
      (D) TOPOLOGY:       linear (ix) FEATURE:

(D) OTHER INFORMATION: The letter "N" stands for the stem
          II region of a HH ribozyme.

(xi) SEQUENCE DESCRIPTION: SEQ ID NO: 1236:

CAGAGGCUCU GAUGANGAAA UUGUGAU                         27

(2) INFORMATION FOR SEQ ID NO: 1237:

(i) SEQUENCE CHARACTERISTICS:

(A) LENGTH:          27 base pairs
      (B) TYPE:            nucleic acid
      (C) STRANDEDNESS:   single
      (D) TOPOLOGY:       linear (ix) FEATURE:

(D) OTHER INFORMATION: The letter "N" stands for the stem
          II region of a HH ribozyme.

(xi) SEQUENCE DESCRIPTION: SEQ ID NO: 1237:

GGGGUUCACU GAUGANGAAA GGCUGAU                         27

(2) INFORMATION FOR SEQ ID NO: 1238:

(i) SEQUENCE CHARACTERISTICS:

(A) LENGTH:          27 base pairs
      (B) TYPE:            nucleic acid
      (C) STRANDEDNESS:   single
      (D) TOPOLOGY:       linear (ix) FEATURE:

(D) OTHER INFORMATION: The letter "N" stands for the stem

II region of a HH ribozyme.

(xi) SEQUENCE DESCRIPTION: SEQ ID NO: 1238:

GGUCCUGGCU GAUGANGAAA GUGUGGG                                              27

(2) INFORMATION FOR SEQ ID NO: 1239:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 1239:

UGUUGAGACU GAUGANGAAA CUCGGGG                                              27

(2) INFORMATION FOR SEQ ID NO: 1240:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 1240:

AGUGUUGACU GAUGANGAAA UACUCGG                                              27

(2) INFORMATION FOR SEQ ID NO: 1241:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 1241:

ACAGUGUUCU GAUGANGAAA GAUACUC                                              27

(2) INFORMATION FOR SEQ ID NO: 1242:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 1242:

GUGGGCUGCU GAUGANGAAA CAGUGUU        27

(2) INFORMATION FOR SEQ ID NO: 1243:

(i) SEQUENCE CHARACTERISTICS:
       (A) LENGTH:        27 base pairs
       (B) TYPE:          nucleic acid
       (C) STRANDEDNESS:  single
       (D) TOPOLOGY:      linear (ix) FEATURE:
       (D) OTHER INFORMATION: The letter "N" stands for the stem
           II region of a HH ribozyme.

(xi) SEQUENCE DESCRIPTION: SEQ ID NO: 1243:

GUGCUGUUCU GAUGANGAAA CACAGGU        27

(2) INFORMATION FOR SEQ ID NO: 1244:

(i) SEQUENCE CHARACTERISTICS:
       (A) LENGTH:        27 base pairs
       (B) TYPE:          nucleic acid
       (C) STRANDEDNESS:  single
       (D) TOPOLOGY:      linear (ix) FEATURE:
       (D) OTHER INFORMATION: The letter "N" stands for the stem
           II region of a HH ribozyme.

(xi) SEQUENCE DESCRIPTION: SEQ ID NO: 1244:

GGCUGUCGCU GAUGANGAAA UGUGCUG        27

(2) INFORMATION FOR SEQ ID NO: 1245:

(i) SEQUENCE CHARACTERISTICS:
       (A) LENGTH:        27 base pairs
       (B) TYPE:          nucleic acid
       (C) STRANDEDNESS:  single
       (D) TOPOLOGY:      linear (ix) FEATURE:
       (D) OTHER INFORMATION: The letter "N" stands for the stem
           II region of a HH ribozyme.

(xi) SEQUENCE DESCRIPTION: SEQ ID NO: 1245:

GGGCUGUCCU GAUGANGAAA AUGUGCU        27

(2) INFORMATION FOR SEQ ID NO: 1246:

(i) SEQUENCE CHARACTERISTICS:
       (A) LENGTH:        27 base pairs
       (B) TYPE:          nucleic acid
       (C) STRANDEDNESS:  single
       (D) TOPOLOGY:      linear (ix) FEATURE:
       (D) OTHER INFORMATION: The letter "N" stands for the stem
           II region of a HH ribozyme.

(xi) SEQUENCE DESCRIPTION: SEQ ID NO: 1246:

UCCAGGCUCU GAUGANGAAA UUUGGUG        27

(2) INFORMATION FOR SEQ ID NO: 1247:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1247:

GUCCAGGCCU GAUGANGAAA AUUUGGU          27

(2) INFORMATION FOR SEQ ID NO: 1248:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1248:

CCUGCUGGCU GAUGANGAAA GUCAGGG          27

(2) INFORMATION FOR SEQ ID NO: 1249:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1249:

UGGGAAAGCU GAUGANGAAA GUCCUGC          27

(2) INFORMATION FOR SEQ ID NO: 1250:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1250:

UUGGGAAACU GAUGANGAAA AGUCCUG          27

(2) INFORMATION FOR SEQ ID NO: 1251:

```
        (i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:   The letter "N" stands for the stem
                II region of a HH ribozyme.

(xi) SEQUENCE DESCRIPTION: SEQ ID NO: 1251:

CCUUGGGACU GAUGANGAAA GAAGUCC                                             27

(2) INFORMATION FOR SEQ ID NO: 1252:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:   The letter "N" stands for the stem
                II region of a HH ribozyme.

(xi) SEQUENCE DESCRIPTION: SEQ ID NO: 1252:

UCCUUGGGCU GAUGANGAAA AGAAGUC                                             27

(2) INFORMATION FOR SEQ ID NO: 1253:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:   The letter "N" stands for the stem
                II region of a HH ribozyme.

(xi) SEQUENCE DESCRIPTION: SEQ ID NO: 1253:

UUCCUUGGCU GAUGANGAAA AAGAAGU                                             27

(2) INFORMATION FOR SEQ ID NO: 1254:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:   The letter "N" stands for the stem
                II region of a HH ribozyme.

(xi) SEQUENCE DESCRIPTION: SEQ ID NO: 1254:

CCCUUAAACU GAUGANGAAA UGCCAUU                                             27

(2) INFORMATION FOR SEQ ID NO: 1255:

(i) SEQUENCE CHARACTERISTICS:

(A) LENGTH:          27 base pairs
```

```
              (B)  TYPE:              nucleic acid
              (C)  STRANDEDNESS:      single
              (D)  TOPOLOGY:          linear (ix)  FEATURE:

(D)  OTHER INFORMATION:  The letter "N" stands for the stem
                   II region of a HH ribozyme.

(xi)  SEQUENCE DESCRIPTION: SEQ ID NO: 1255:

AGCCCUUACU GAUGANGAAA GAUGCCA                                          27

(2)  INFORMATION FOR SEQ ID NO: 1256:

(i)  SEQUENCE CHARACTERISTICS:

(A)  LENGTH:            27 base pairs
              (B)  TYPE:              nucleic acid
              (C)  STRANDEDNESS:      single
              (D)  TOPOLOGY:          linear (ix)  FEATURE:

(D)  OTHER INFORMATION:  The letter "N" stands for the stem
                   II region of a HH ribozyme.

(xi)  SEQUENCE DESCRIPTION: SEQ ID NO: 1256:

GAGCCCUUCU GAUGANGAAA AGAUGCC                                          27

(2)  INFORMATION FOR SEQ ID NO: 1257:

(i)  SEQUENCE CHARACTERISTICS:

(A)  LENGTH:            27 base pairs
              (B)  TYPE:              nucleic acid
              (C)  STRANDEDNESS:      single
              (D)  TOPOLOGY:          linear (ix)  FEATURE:

(D)  OTHER INFORMATION:  The letter "N" stands for the stem
                   II region of a HH ribozyme.

(xi)  SEQUENCE DESCRIPTION: SEQ ID NO: 1257:

GGAGCCCUCU GAUGANGAAA AAGAUGC                                          27

(2)  INFORMATION FOR SEQ ID NO: 1258:

(i)  SEQUENCE CHARACTERISTICS:

(A)  LENGTH:            27 base pairs
              (B)  TYPE:              nucleic acid
              (C)  STRANDEDNESS:      single
              (D)  TOPOLOGY:          linear (ix)  FEATURE:

(D)  OTHER INFORMATION:  The letter "N" stands for the stem
                   II region of a HH ribozyme.

(xi)  SEQUENCE DESCRIPTION: SEQ ID NO: 1258:

CAGCUGUGCU GAUGANGAAA GCCCUUA                                          27

(2)  INFORMATION FOR SEQ ID NO: 1259:

(i)  SEQUENCE CHARACTERISTICS:

(A)  LENGTH:            27 base pairs
              (B)  TYPE:              nucleic acid
              (C)  STRANDEDNESS:      single
              (D)  TOPOLOGY:          linear
```

(ix) FEATURE:

(D) OTHER INFORMATION:   The letter "N" stands for the stem
            II region of a HH ribozyme.

(xi) SEQUENCE DESCRIPTION: SEQ ID NO: 1259:

CCCUUAGGCU GAUGANGAAA UUCUGCA                                         27

(2) INFORMATION FOR SEQ ID NO: 1260:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:   The letter "N" stands for the stem
            II region of a HH ribozyme.

(xi) SEQUENCE DESCRIPTION: SEQ ID NO: 1260:

GCGACCCUCU GAUGANGAAA GGUAUUC                                         27

(2) INFORMATION FOR SEQ ID NO: 1261:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:   The letter "N" stands for the stem
            II region of a HH ribozyme.

(xi) SEQUENCE DESCRIPTION: SEQ ID NO: 1261:

UGUGGCGCCU GAUGANGAAA CCCUUAG                                         27

(2) INFORMATION FOR SEQ ID NO: 1262:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:   The letter "N" stands for the stem
            II region of a HH ribozyme.

(xi) SEQUENCE DESCRIPTION: SEQ ID NO: 1262:

CUCCAAUACU GAUGANGAAA UUCACUG                                         27

(2) INFORMATION FOR SEQ ID NO: 1263:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION: The letter "N" stands for the stem
    II region of a HH ribozyme.

(xi) SEQUENCE DESCRIPTION: SEQ ID NO: 1263:

GCUCCAAUCU GAUGANGAAA AUUCACU                27

(2) INFORMATION FOR SEQ ID NO: 1264:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION: The letter "N" stands for the stem
            II region of a HH ribozyme.

(xi) SEQUENCE DESCRIPTION: SEQ ID NO: 1264:

UGCUCCAACU GAUGANGAAA AAUUCAC                27

(2) INFORMATION FOR SEQ ID NO: 1265:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION: The letter "N" stands for the stem
            II region of a HH ribozyme.

(xi) SEQUENCE DESCRIPTION: SEQ ID NO: 1265:

CAUGCUCCCU GAUGANGAAA UAAAUUC                27

(2) INFORMATION FOR SEQ ID NO: 1266:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION: The letter "N" stands for the stem
            II region of a HH ribozyme.

(xi) SEQUENCE DESCRIPTION: SEQ ID NO: 1266:

GCUCAUACCU GAUGANGAAA UCCUCCG                27

(2) INFORMATION FOR SEQ ID NO: 1267:

(i) SEQUENCE CHARACTERISTICS:

(A) LENGTH:        27 base pairs
        (B) TYPE:          nucleic acid
        (C) STRANDEDNESS:  single
        (D) TOPOLOGY:      linear (ix) FEATURE:

(D) OTHER INFORMATION: The letter "N" stands for the stem
            II region of a HH ribozyme.

```
      (xi) SEQUENCE DESCRIPTION: SEQ ID NO: 1267:

AGGGCUCACU GAUGANGAAA CUAUCCU                                             27

(2) INFORMATION FOR SEQ ID NO: 1268:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION: The letter "N" stands for the stem
                II region of a HH ribozyme.

(xi) SEQUENCE DESCRIPTION: SEQ ID NO: 1268:

UGGAUUUUCU GAUGANGAAA GGGCUCA                                             27

(2) INFORMATION FOR SEQ ID NO: 1269:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION: The letter "N" stands for the stem
                II region of a HH ribozyme.

(xi) SEQUENCE DESCRIPTION: SEQ ID NO: 1269:

AGAGUCUGCU GAUGANGAAA UUUUUAG                                             27

(2) INFORMATION FOR SEQ ID NO: 1270:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION: The letter "N" stands for the stem
                II region of a HH ribozyme.

(xi) SEQUENCE DESCRIPTION: SEQ ID NO: 1270:

UAUCGAAACU GAUGANGAAA GUCUGGA                                             27

(2) INFORMATION FOR SEQ ID NO: 1271:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION: The letter "N" stands for the stem
                II region of a HH ribozyme.

(xi) SEQUENCE DESCRIPTION: SEQ ID NO: 1271:

GGUAUCGACU GAUGANGAAA GAGUCUG                                             27
```

(2) INFORMATION FOR SEQ ID NO: 1272:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1272:

GGGUAUCGCU GAUGANGAAA AGAGUCU     27

(2) INFORMATION FOR SEQ ID NO: 1273:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1273:

UGGGUAUCCU GAUGANGAAA AAGAGUC     27

(2) INFORMATION FOR SEQ ID NO: 1274:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1274:

GUCCUGGGCU GAUGANGAAA UCGAAAG     27

(2) INFORMATION FOR SEQ ID NO: 1275:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1275:

GGAUGGAGCU GAUGANGAAA CCUGCUG     27

(2) INFORMATION FOR SEQ ID NO: 1276:

(i) SEQUENCE CHARACTERISTICS:

(A) LENGTH:            27 base pairs
           (B) TYPE:              nucleic acid
           (C) STRANDEDNESS:      single
           (D) TOPOLOGY:          linear (ix) FEATURE:

(D) OTHER INFORMATION: The letter "N" stands for the stem
               II region of a HH ribozyme.

(xi) SEQUENCE DESCRIPTION: SEQ ID NO: 1276:

UUGGGAUGCU GAUGANGAAA GGACCUG                                              27

(2) INFORMATION FOR SEQ ID NO: 1277:

(i) SEQUENCE CHARACTERISTICS:

(A) LENGTH:            27 base pairs
           (B) TYPE:              nucleic acid
           (C) STRANDEDNESS:      single
           (D) TOPOLOGY:          linear (ix) FEATURE:

(D) OTHER INFORMATION: The letter "N" stands for the stem
               II region of a HH ribozyme.

(xi) SEQUENCE DESCRIPTION: SEQ ID NO: 1277:

GCUGUUGGCU GAUGANGAAA UGGAGGA                                              27

(2) INFORMATION FOR SEQ ID NO: 1278:

(i) SEQUENCE CHARACTERISTICS:

(A) LENGTH:            27 base pairs
           (B) TYPE:              nucleic acid
           (C) STRANDEDNESS:      single
           (D) TOPOLOGY:          linear (ix) FEATURE:

(D) OTHER INFORMATION: The letter "N" stands for the stem
               II region of a HH ribozyme.

(xi) SEQUENCE DESCRIPTION: SEQ ID NO: 1278:

UAAGAGCUCU GAUGANGAAA UGCGGGC                                              27

(2) INFORMATION FOR SEQ ID NO: 1279:

(i) SEQUENCE CHARACTERISTICS:

(A) LENGTH:            27 base pairs
           (B) TYPE:              nucleic acid
           (C) STRANDEDNESS:      single
           (D) TOPOLOGY:          linear (ix) FEATURE:

(D) OTHER INFORMATION: The letter "N" stands for the stem
               II region of a HH ribozyme.

(xi) SEQUENCE DESCRIPTION: SEQ ID NO: 1279:

CUAAGAGCCU GAUGANGAAA AUGCGGG                                              27

(2) INFORMATION FOR SEQ ID NO: 1280:

(i) SEQUENCE CHARACTERISTICS:

```
            (A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1280:

GGGUCUAACU GAUGANGAAA GCUAAUG                                               27

(2) INFORMATION FOR SEQ ID NO: 1281:

(i)  SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1281:

GUGGGUCUCU GAUGANGAAA GAGCUAA                                               27

(2) INFORMATION FOR SEQ ID NO: 1282:

(i)  SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1282:

UGUGGGUCCU GAUGANGAAA AGAGCUA                                               27

(2) INFORMATION FOR SEQ ID NO: 1283:

(i)  SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1283:

CGUUGCAACU GAUGANGAAA CCAGUCU                                               27

(2) INFORMATION FOR SEQ ID NO: 1284:

(i)  SEQUENCE CHARACTERISTICS:

(A)  LENGTH:              27 base pairs
            (B)  TYPE:                nucleic acid
            (C)  STRANDEDNESS:        single
```

```
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1284:

ACGUUGCACU GAUGANGAAA ACCAGUC                                          27

(2) INFORMATION FOR SEQ ID NO: 1285:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1285:

AACGUUGCCU GAUGANGAAA AACCAGU                                          27

(2) INFORMATION FOR SEQ ID NO: 1286:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1286:

UCGGUGUACU GAUGANGAAA CGUUGCA                                          27

(2) INFORMATION FOR SEQ ID NO: 1287:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1287:

GUCGGUGUCU GAUGANGAAA ACGUUGC                                          27

(2) INFORMATION FOR SEQ ID NO: 1288:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:
```

(D) OTHER INFORMATION:   The letter "N" stands for the stem
                II region of a HH ribozyme.

(xi) SEQUENCE DESCRIPTION: SEQ ID NO: 1288:

AGUCGGUGCU GAUGANGAAA AACGUUG                                            27

(2) INFORMATION FOR SEQ ID NO: 1289:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:   The letter "N" stands for the stem
            II region of a HH ribozyme.

(xi) SEQUENCE DESCRIPTION: SEQ ID NO: 1289:

UUCCUGGCCU GAUGANGAAA GUCGGUG                                            27

(2) INFORMATION FOR SEQ ID NO: 1290:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:   The letter "N" stands for the stem
            II region of a HH ribozyme.

(xi) SEQUENCE DESCRIPTION: SEQ ID NO: 1290:

GGUGGAAGCU GAUGANGAAA CUUCCUG                                            27

(2) INFORMATION FOR SEQ ID NO: 1291:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:   The letter "N" stands for the stem
            II region of a HH ribozyme.

(xi) SEQUENCE DESCRIPTION: SEQ ID NO: 1291:

CGAGGUGGCU GAUGANGAAA GUACUUC                                            27

(2) INFORMATION FOR SEQ ID NO: 1292:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:   The letter "N" stands for the stem
            II region of a HH ribozyme.

(xi) SEQUENCE DESCRIPTION: SEQ ID NO: 1292:

CCGAGGUGCU GAUGANGAAA AGUACUU                               27

(2) INFORMATION FOR SEQ ID NO: 1293:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem II region of a HH ribozyme.

(xi) SEQUENCE DESCRIPTION: SEQ ID NO: 1293:

AUGUGCCCCU GAUGANGAAA GGUGGAA                               27

(2) INFORMATION FOR SEQ ID NO: 1294:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem II region of a HH ribozyme.

(xi) SEQUENCE DESCRIPTION: SEQ ID NO: 1294:

CUUCCCAACU GAUGANGAAA UGUGCCC                               27

(2) INFORMATION FOR SEQ ID NO: 1295:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem II region of a HH ribozyme.

(xi) SEQUENCE DESCRIPTION: SEQ ID NO: 1295:

ACUUCCCACU GAUGANGAAA AUGUGCC                               27

(2) INFORMATION FOR SEQ ID NO: 1296:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem II region of a HH ribozyme.

(xi) SEQUENCE DESCRIPTION: SEQ ID NO: 1296:

```
AACUUCCCCU GAUGANGAAA AAUGUGC                                              27
```

(2) INFORMATION FOR SEQ ID NO: 1297:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION: The letter "N" stands for the stem
         II region of a HH ribozyme.

(xi) SEQUENCE DESCRIPTION: SEQ ID NO: 1297:

```
AGGAAUGCCU GAUGANGAAA CUUCCCA                                              27
```

(2) INFORMATION FOR SEQ ID NO: 1298:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION: The letter "N" stands for the stem
         II region of a HH ribozyme.

(xi) SEQUENCE DESCRIPTION: SEQ ID NO: 1298:

```
GACAAAGGCU GAUGANGAAA UGCAACU                                              27
```

(2) INFORMATION FOR SEQ ID NO: 1299:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION: The letter "N" stands for the stem
         II region of a HH ribozyme.

(xi) SEQUENCE DESCRIPTION: SEQ ID NO: 1299:

```
AGACAAAGCU GAUGANGAAA AUGCAAC                                              27
```

(2) INFORMATION FOR SEQ ID NO: 1300:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION: The letter "N" stands for the stem
         II region of a HH ribozyme.

(xi) SEQUENCE DESCRIPTION: SEQ ID NO: 1300:

```
UGAAGACACU GAUGANGAAA GGAAUGC                                              27
```

```
(2) INFORMATION FOR SEQ ID NO: 1301:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 1301:

UUGAAGACCU GAUGANGAAA AGGAAUG                                              27

(2) INFORMATION FOR SEQ ID NO: 1302:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 1302:

AGUUUGAACU GAUGANGAAA CAAAGGA                                              27

(2) INFORMATION FOR SEQ ID NO: 1303:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 1303:

ACAGUUUGCU GAUGANGAAA GACAAAG                                              27

(2) INFORMATION FOR SEQ ID NO: 1304:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 1304:

CACAGUUUCU GAUGANGAAA AGACAAA                                              27

(2) INFORMATION FOR SEQ ID NO: 1305:

(i) SEQUENCE CHARACTERISTICS:
```

```
            (A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 1305:

UUUCUGUACU GAUGANGAAA UGCUUCA                                            27

(2) INFORMATION FOR SEQ ID NO: 1306:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 1306:

GUUUCUGUCU GAUGANGAAA AUGCUUC                                            27

(2) INFORMATION FOR SEQ ID NO: 1307:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 1307:

CGUUUCUGCU GAUGANGAAA AAUGCUU                                            27

(2) INFORMATION FOR SEQ ID NO: 1308:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 1308:

UCUUGCUGCU GAUGANGAAA UGCGUUU                                            27

(2) INFORMATION FOR SEQ ID NO: 1309:

(i) SEQUENCE CHARACTERISTICS:

(A)  LENGTH:            27 base pairs
            (B)  TYPE:              nucleic acid
```

```
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 1309:

AGGGACAACU GAUGANGAAA UUCUUGC                                          27

(2) INFORMATION FOR SEQ ID NO: 1310:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 1310:

AAAGGGACCU GAUGANGAAA UAUUCUU                                          27

(2) INFORMATION FOR SEQ ID NO: 1311:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 1311:

CUCAAAGGCU GAUGANGAAA CAAUAUU                                          27

(2) INFORMATION FOR SEQ ID NO: 1312:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix) FEATURE:

(D)  OTHER INFORMATION:  The letter "N" stands for the stem
                 II region of a HH ribozyme.

(xi) SEQUENCE DESCRIPTION: SEQ ID NO: 1312:

UCUGCUCACU GAUGANGAAA GGGACAA                                          27

(2) INFORMATION FOR SEQ ID NO: 1313:

(i) SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear
```

(ix) FEATURE:

(D) OTHER INFORMATION: The letter "N" stands for the stem
       II region of a HH ribozyme.

(xi) SEQUENCE DESCRIPTION: SEQ ID NO: 1313:

UUCUGCUCCU GAUGANGAAA AGGGACA                                              27

(2) INFORMATION FOR SEQ ID NO: 1314:

(i) SEQUENCE CHARACTERISTICS:

(A) LENGTH:         27 base pairs
       (B) TYPE:           nucleic acid
       (C) STRANDEDNESS:   single
       (D) TOPOLOGY:       linear (ix) FEATURE:

(D) OTHER INFORMATION: The letter "N" stands for the stem
           II region of a HH ribozyme.

(xi) SEQUENCE DESCRIPTION: SEQ ID NO: 1314:

GAAAGAUACU GAUGANGAAA UUUCUGC                                              27

(2) INFORMATION FOR SEQ ID NO: 1315:

(i) SEQUENCE CHARACTERISTICS:

(A) LENGTH:         27 base pairs
       (B) TYPE:           nucleic acid
       (C) STRANDEDNESS:   single
       (D) TOPOLOGY:       linear (ix) FEATURE:

(D) OTHER INFORMATION: The letter "N" stands for the stem
           II region of a HH ribozyme.

(xi) SEQUENCE DESCRIPTION: SEQ ID NO: 1315:

UGAAAGAUCU GAUGANGAAA AUUUCUG                                              27

(2) INFORMATION FOR SEQ ID NO: 1316:

(i) SEQUENCE CHARACTERISTICS:

(A) LENGTH:         27 base pairs
       (B) TYPE:           nucleic acid
       (C) STRANDEDNESS:   single
       (D) TOPOLOGY:       linear (ix) FEATURE:

(D) OTHER INFORMATION: The letter "N" stands for the stem
           II region of a HH ribozyme.

(xi) SEQUENCE DESCRIPTION: SEQ ID NO: 1316:

UUGAAAGACU GAUGANGAAA AAUUUCU                                              27

(2) INFORMATION FOR SEQ ID NO: 1317:

(i) SEQUENCE CHARACTERISTICS:

(A) LENGTH:         27 base pairs
       (B) TYPE:           nucleic acid
       (C) STRANDEDNESS:   single
       (D) TOPOLOGY:       linear (ix) FEATURE:

(D) OTHER INFORMATION: The letter "N" stands for the stem

II region of a HH ribozyme.

(xi) SEQUENCE DESCRIPTION: SEQ ID NO: 1317:

CUUUGAAACU GAUGANGAAA UAAAUUU                                              27

(2) INFORMATION FOR SEQ ID NO: 1318:

(i) SEQUENCE CHARACTERISTICS:

(A) LENGTH:          27 base pairs
       (B) TYPE:            nucleic acid
       (C) STRANDEDNESS:    single
       (D) TOPOLOGY:        linear (ix) FEATURE:

(D) OTHER INFORMATION:  The letter "N" stands for the stem
           II region of a HH ribozyme.

(xi) SEQUENCE DESCRIPTION: SEQ ID NO: 1318:

CUCUUUGACU GAUGANGAAA GAUAAAU                                              27

(2) INFORMATION FOR SEQ ID NO: 1319:

(i) SEQUENCE CHARACTERISTICS:

(A) LENGTH:          27 base pairs
       (B) TYPE:            nucleic acid
       (C) STRANDEDNESS:    single
       (D) TOPOLOGY:        linear (ix) FEATURE:

(D) OTHER INFORMATION:  The letter "N" stands for the stem
           II region of a HH ribozyme.

(xi) SEQUENCE DESCRIPTION: SEQ ID NO: 1319:

CCUCUUUGCU GAUGANGAAA AGAUAAA                                              27

(2) INFORMATION FOR SEQ ID NO: 1320:

(i) SEQUENCE CHARACTERISTICS:

(A) LENGTH:          27 base pairs
       (B) TYPE:            nucleic acid
       (C) STRANDEDNESS:    single
       (D) TOPOLOGY:        linear (ix) FEATURE:

(D) OTHER INFORMATION:  The letter "N" stands for the stem
           II region of a HH ribozyme.

(xi) SEQUENCE DESCRIPTION: SEQ ID NO: 1320:

ACCUCUUUCU GAUGANGAAA AAGAUAA                                              27

(2) INFORMATION FOR SEQ ID NO: 1321:

(i) SEQUENCE CHARACTERISTICS:

(A) LENGTH:          27 base pairs
       (B) TYPE:            nucleic acid
       (C) STRANDEDNESS:    single
       (D) TOPOLOGY:        linear (ix) FEATURE:

(D) OTHER INFORMATION:  The letter "N" stands for the stem
           II region of a HH ribozyme.

(xi) SEQUENCE DESCRIPTION: SEQ ID NO: 1321:

UUCAAAUACU GAUGANGAAA CCUCUUU	27

(2) INFORMATION FOR SEQ ID NO: 1322:

(i) SEQUENCE CHARACTERISTICS:

(A) LENGTH: 27 base pairs
      (B) TYPE: nucleic acid
      (C) STRANDEDNESS: single
      (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1322:

UUUUCAAACU GAUGANGAAA UACCUCU	27

(2) INFORMATION FOR SEQ ID NO: 1323:

(i) SEQUENCE CHARACTERISTICS:

(A) LENGTH: 27 base pairs
      (B) TYPE: nucleic acid
      (C) STRANDEDNESS: single
      (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1323:

UUUUUUCACU GAUGANGAAA UAUACCU	27

(2) INFORMATION FOR SEQ ID NO: 1324:

(i) SEQUENCE CHARACTERISTICS:

(A) LENGTH: 27 base pairs
      (B) TYPE: nucleic acid
      (C) STRANDEDNESS: single
      (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1324:

UUUUUUUCCU GAUGANGAAA AUAUACC	27

(2) INFORMATION FOR SEQ ID NO: 1325:

(i) SEQUENCE CHARACTERISTICS:

(A) LENGTH: 27 base pairs
      (B) TYPE: nucleic acid
      (C) STRANDEDNESS: single
      (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1325:

CUCACAUACU GAUGANGAAA CUUUUUU	27

(2) INFORMATION FOR SEQ ID NO: 1326:

(i) SEQUENCE CHARACTERISTICS:

(A) LENGTH: 27 base pairs
      (B) TYPE: nucleic acid
      (C) STRANDEDNESS: single
      (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1326:

UCCUCACACU GAUGANGAAA UACUUUU                     27

(2) INFORMATION FOR SEQ ID NO: 1327:

(i) SEQUENCE CHARACTERISTICS:

(A) LENGTH: 27 base pairs
      (B) TYPE: nucleic acid
      (C) STRANDEDNESS: single
      (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1327:

UCAAUAAACU GAUGANGAAA UCCUCAC                     27

(2) INFORMATION FOR SEQ ID NO: 1328:

(i) SEQUENCE CHARACTERISTICS:

(A) LENGTH: 27 base pairs
      (B) TYPE: nucleic acid
      (C) STRANDEDNESS: single
      (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1328:

AUCAAUAACU GAUGANGAAA AUCCUCA                     27

(2) INFORMATION FOR SEQ ID NO: 1329:

(i) SEQUENCE CHARACTERISTICS:

(A) LENGTH: 27 base pairs
      (B) TYPE: nucleic acid
      (C) STRANDEDNESS: single
      (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1329:

AAUCAAUACU GAUGANGAAA AAUCCUC                     27

(2) INFORMATION FOR SEQ ID NO: 1330:

```
           (i) SEQUENCE CHARACTERISTICS:

(A) LENGTH:         27 base pairs
                 (B) TYPE:           nucleic acid
                 (C) STRANDEDNESS:   single
                 (D) TOPOLOGY:       linear (ix) FEATURE:

(D) OTHER INFORMATION:  The letter "N" stands for the stem
                     II region of a HH ribozyme.

(xi) SEQUENCE DESCRIPTION: SEQ ID NO: 1330:

CAAUCAAUCU GAUGANGAAA AAAUCCU                                         27

(2) INFORMATION FOR SEQ ID NO: 1331:

(i) SEQUENCE CHARACTERISTICS:

(A) LENGTH:         27 base pairs
                 (B) TYPE:           nucleic acid
                 (C) STRANDEDNESS:   single
                 (D) TOPOLOGY:       linear (ix) FEATURE:

(D) OTHER INFORMATION:  The letter "N" stands for the stem
                     II region of a HH ribozyme.

(xi) SEQUENCE DESCRIPTION: SEQ ID NO: 1331:

CCAAUCAACU GAUGANGAAA AAAAUCC                                         27

(2) INFORMATION FOR SEQ ID NO: 1332:

(i) SEQUENCE CHARACTERISTICS:

(A) LENGTH:         27 base pairs
                 (B) TYPE:           nucleic acid
                 (C) STRANDEDNESS:   single
                 (D) TOPOLOGY:       linear (ix) FEATURE:

(D) OTHER INFORMATION:  The letter "N" stands for the stem
                     II region of a HH ribozyme.

(xi) SEQUENCE DESCRIPTION: SEQ ID NO: 1332:

CCCCAAUCCU GAUGANGAAA UAAAAAU                                         27

(2) INFORMATION FOR SEQ ID NO: 1333:

(i) SEQUENCE CHARACTERISTICS:

(A) LENGTH:         27 base pairs
                 (B) TYPE:           nucleic acid
                 (C) STRANDEDNESS:   single
                 (D) TOPOLOGY:       linear (ix) FEATURE:

(D) OTHER INFORMATION:  The letter "N" stands for the stem
                     II region of a HH ribozyme.

(xi) SEQUENCE DESCRIPTION: SEQ ID NO: 1333:

AGAUCCCCU GAUGANGAAA UCAAUAA                                          27

(2) INFORMATION FOR SEQ ID NO: 1334:

(i) SEQUENCE CHARACTERISTICS:

(A) LENGTH:         27 base pairs
```

```
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1334:

AACUCCAACU GAUGANGAAA UCCCCAA                                               27

(2) INFORMATION FOR SEQ ID NO: 1335:

(i)  SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1335:

AAAACUCCCU GAUGANGAAA GAUCCCC                                               27

(2) INFORMATION FOR SEQ ID NO: 1336:

(i)  SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1336:

CAAUGAAACU GAUGANGAAA CUCCAAG                                               27

(2) INFORMATION FOR SEQ ID NO: 1337:

(i)  SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1337:

ACAAUGAACU GAUGANGAAA ACUCCAA                                               27

(2) INFORMATION FOR SEQ ID NO: 1338:

(i)  SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear
```

-continued

```
    (ix) FEATURE:

(D) OTHER INFORMATION:   The letter "N" stands for the stem
             II region of a HH ribozyme.

(xi) SEQUENCE DESCRIPTION: SEQ ID NO: 1338:

GACAAUGACU GAUGANGAAA AACUCCA                                          27

(2) INFORMATION FOR SEQ ID NO: 1339:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:   The letter "N" stands for the stem
             II region of a HH ribozyme.

(xi) SEQUENCE DESCRIPTION: SEQ ID NO: 1339:

CGACAAUGCU GAUGANGAAA AAACUCC                                          27

(2) INFORMATION FOR SEQ ID NO: 1340:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:   The letter "N" stands for the stem
             II region of a HH ribozyme.

(xi) SEQUENCE DESCRIPTION: SEQ ID NO: 1340:

GCGACAAUCU GAUGANGAAA AAAACUC                                          27

(2) INFORMATION FOR SEQ ID NO: 1341:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:   The letter "N" stands for the stem
             II region of a HH ribozyme.

(xi) SEQUENCE DESCRIPTION: SEQ ID NO: 1341:

AUAGCGACCU GAUGANGAAA UGAAAAA                                          27

(2) INFORMATION FOR SEQ ID NO: 1342:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:
```

(D) OTHER INFORMATION:    The letter "N" stands for the stem
                II region of a HH ribozyme.

(xi) SEQUENCE DESCRIPTION: SEQ ID NO: 1342:

UCAAUAGCCU GAUGANGAAA CAAUGAA                                              27

(2) INFORMATION FOR SEQ ID NO: 1343:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:    The letter "N" stands for the stem
                II region of a HH ribozyme.

(xi) SEQUENCE DESCRIPTION: SEQ ID NO: 1343:

AAAAUCAACU GAUGANGAAA GCGACAA                                              27

(2) INFORMATION FOR SEQ ID NO: 1344:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:    The letter "N" stands for the stem
                II region of a HH ribozyme.

(xi) SEQUENCE DESCRIPTION: SEQ ID NO: 1344:

UAAAAAUCCU GAUGANGAAA UAGCGAC                                              27

(2) INFORMATION FOR SEQ ID NO: 1345:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:    The letter "N" stands for the stem
                II region of a HH ribozyme.

(xi) SEQUENCE DESCRIPTION: SEQ ID NO: 1345:

GAAGUAAACU GAUGANGAAA UCAAUAG                                              27

(2) INFORMATION FOR SEQ ID NO: 1346:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:    The letter "N" stands for the stem
                II region of a HH ribozyme.

(xi) SEQUENCE DESCRIPTION: SEQ ID NO: 1346:

UGAAGUAACU GAUGANGAAA AUCAAUA                                27

(2) INFORMATION FOR SEQ ID NO: 1347:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION: The letter "N" stands for the stem
         II region of a HH ribozyme.

(xi) SEQUENCE DESCRIPTION: SEQ ID NO: 1347:

UUGAAGUACU GAUGANGAAA AAUCAAU                                27

(2) INFORMATION FOR SEQ ID NO: 1348:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION: The letter "N" stands for the stem
         II region of a HH ribozyme.

(xi) SEQUENCE DESCRIPTION: SEQ ID NO: 1348:

AUUGAAGUCU GAUGANGAAA AAAUCAA                                27

(2) INFORMATION FOR SEQ ID NO: 1349:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION: The letter "N" stands for the stem
         II region of a HH ribozyme.

(xi) SEQUENCE DESCRIPTION: SEQ ID NO: 1349:

CAUUGAAGCU GAUGANGAAA AAAAUCA                                27

(2) INFORMATION FOR SEQ ID NO: 1350:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION: The letter "N" stands for the stem
         II region of a HH ribozyme.

(xi) SEQUENCE DESCRIPTION: SEQ ID NO: 1350:

GCCCAUUGCU GAUGANGAAA GUAAAAA                                27

(2) INFORMATION FOR SEQ ID NO: 1351:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1351:

AGCCCAUUCU GAUGANGAAA AGUAAAA     27

(2) INFORMATION FOR SEQ ID NO: 1352:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1352:

UGUUGGAACU GAUGANGAAA GCCCAUU     27

(2) INFORMATION FOR SEQ ID NO: 1353:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1353:

CUUGUUGGCU GAUGANGAAA GAGCCCA     27

(2) INFORMATION FOR SEQ ID NO: 1354:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1354:

CCUUGUUGCU GAUGANGAAA AGAGCCC     27

(2) INFORMATION FOR SEQ ID NO: 1355:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION: The letter "N" stands for the stem
            II region of a HH ribozyme.

(xi) SEQUENCE DESCRIPTION: SEQ ID NO: 1355:

CUACCAGCCU GAUGANGAAA GCUUCUU                                        27

(2) INFORMATION FOR SEQ ID NO: 1356:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION: The letter "N" stands for the stem
            II region of a HH ribozyme.

(xi) SEQUENCE DESCRIPTION: SEQ ID NO: 1356:

GCAAGUGCCU GAUGANGAAA CCAGCAA                                        27

(2) INFORMATION FOR SEQ ID NO: 1357:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION: The letter "N" stands for the stem
            II region of a HH ribozyme.

(xi) SEQUENCE DESCRIPTION: SEQ ID NO: 1357:

AGGGUAGCCU GAUGANGAAA GUGCUAC                                        27

(2) INFORMATION FOR SEQ ID NO: 1358:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION: The letter "N" stands for the stem
            II region of a HH ribozyme.

(xi) SEQUENCE DESCRIPTION: SEQ ID NO: 1358:

ACUCAGGGCU GAUGANGAAA GCAAGUG                                        27

(2) INFORMATION FOR SEQ ID NO: 1359:

(i) SEQUENCE CHARACTERISTICS:

```
          (A)  LENGTH:              27 base pairs
          (B)  TYPE:                nucleic acid
          (C)  STRANDEDNESS:        single
          (D)  TOPOLOGY:            linear (ix)  FEATURE:

(D)  OTHER INFORMATION:   The letter "N" stands for the stem
               II region of a HH ribozyme.

(xi)  SEQUENCE DESCRIPTION: SEQ ID NO: 1359:

CCUGGAUGCU GAUGANGAAA CUCAGGG                                              27

(2)  INFORMATION FOR SEQ ID NO: 1360:

(i)  SEQUENCE CHARACTERISTICS:

(A)  LENGTH:              27 base pairs
          (B)  TYPE:                nucleic acid
          (C)  STRANDEDNESS:        single
          (D)  TOPOLOGY:            linear (ix)  FEATURE:

(D)  OTHER INFORMATION:   The letter "N" stands for the stem
               II region of a HH ribozyme.

(xi)  SEQUENCE DESCRIPTION: SEQ ID NO: 1360:

GCCUGGAUCU GAUGANGAAA ACUCAGG                                              27

(2)  INFORMATION FOR SEQ ID NO: 1361:

(i)  SEQUENCE CHARACTERISTICS:

(A)  LENGTH:              27 base pairs
          (B)  TYPE:                nucleic acid
          (C)  STRANDEDNESS:        single
          (D)  TOPOLOGY:            linear (ix)  FEATURE:

(D)  OTHER INFORMATION:   The letter "N" stands for the stem
               II region of a HH ribozyme.

(xi)  SEQUENCE DESCRIPTION: SEQ ID NO: 1361:

UGGGCCUGCU GAUGANGAAA UGAACUC                                              27

(2)  INFORMATION FOR SEQ ID NO: 1362:

(i)  SEQUENCE CHARACTERISTICS:

(A)  LENGTH:              27 base pairs
          (B)  TYPE:                nucleic acid
          (C)  STRANDEDNESS:        single
          (D)  TOPOLOGY:            linear (ix)  FEATURE:

(D)  OTHER INFORMATION:   The letter "N" stands for the stem
               II region of a HH ribozyme.

(xi)  SEQUENCE DESCRIPTION: SEQ ID NO: 1362:

CUCUGGAACU GAUGANGAAA CUUGUGG                                              27

(2)  INFORMATION FOR SEQ ID NO: 1363:

(i)  SEQUENCE CHARACTERISTICS:

(A)  LENGTH:              27 base pairs
          (B)  TYPE:                nucleic acid
          (C)  STRANDEDNESS:        single
```

(D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1363:

UCCUCUGGCU GAUGANGAAA GACUUGU                                           27

(2) INFORMATION FOR SEQ ID NO: 1364:

(i)  SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1364:

AUCCUCUGCU GAUGANGAAA AGACUUG                                           27

(2) INFORMATION FOR SEQ ID NO: 1365:

(i)  SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1365:

CUGGAAUCCU GAUGANGAAA GCAUCCU                                           27

(2) INFORMATION FOR SEQ ID NO: 1366:

(i)  SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1366:

ACCACUGGCU GAUGANGAAA UCAAGCA                                           27

(2) INFORMATION FOR SEQ ID NO: 1367:

(i)  SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D) OTHER INFORMATION:  The letter "N" stands for the stem
                II region of a HH ribozyme.

(xi) SEQUENCE DESCRIPTION: SEQ ID NO: 1367:

AACCACUGCU GAUGANGAAA AUCAAGC                                          27

(2) INFORMATION FOR SEQ ID NO: 1368:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 1368:

UGAAGCAGCU GAUGANGAAA CCACUGG                                          27

(2) INFORMATION FOR SEQ ID NO: 1369:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 1369:

UUGAAGCACU GAUGANGAAA ACCACUG                                          27

(2) INFORMATION FOR SEQ ID NO: 1370:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 1370:

AAGCCUUGCU GAUGANGAAA GCAGAAC                                          27

(2) INFORMATION FOR SEQ ID NO: 1371:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 1371:

GAAGCCUUCU GAUGANGAAA AGCAGAA                                                27

(2) INFORMATION FOR SEQ ID NO: 1372:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION:  The letter "N" stands for the stem
         II region of a HH ribozyme.

(xi) SEQUENCE DESCRIPTION: SEQ ID NO: 1372:

UGCAGUGGCU GAUGANGAAA GCCUUGA                                                27

(2) INFORMATION FOR SEQ ID NO: 1373:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION:  The letter "N" stands for the stem
         II region of a HH ribozyme.

(xi) SEQUENCE DESCRIPTION: SEQ ID NO: 1373:

UUGCAGUGCU GAUGANGAAA AGCCUUG                                                27

(2) INFORMATION FOR SEQ ID NO: 1374:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION:  The letter "N" stands for the stem
         II region of a HH ribozyme.

(xi) SEQUENCE DESCRIPTION: SEQ ID NO: 1374:

UGGAUCUUCU GAUGANGAAA GUGUUUU                                                27

(2) INFORMATION FOR SEQ ID NO: 1375:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION:  The letter "N" stands for the stem
         II region of a HH ribozyme.

(xi) SEQUENCE DESCRIPTION: SEQ ID NO: 1375:

CCUUCUUGCU GAUGANGAAA UCUUUAG 27

(2) INFORMATION FOR SEQ ID NO: 1376:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1376:

GGGCCAUGCU GAUGANGAAA GGCCUUC 27

(2) INFORMATION FOR SEQ ID NO: 1377:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1377:

GGGGCCAUCU GAUGANGAAA AGGCCUU 27

(2) INFORMATION FOR SEQ ID NO: 1378:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1378:

ACAGUACCCU GAUGANGAAA UCCGGCC 27

(2) INFORMATION FOR SEQ ID NO: 1379:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1379:

UGAUACAGCU GAUGANGAAA CCGAUCC 27

(2) INFORMATION FOR SEQ ID NO: 1380:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION:   The letter "N" stands for the stem
          II region of a HH ribozyme.

(xi) SEQUENCE DESCRIPTION: SEQ ID NO: 1380:

UGACUUGACU GAUGANGAAA CAGUACC                                              27

(2) INFORMATION FOR SEQ ID NO: 1381:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION:   The letter "N" stands for the stem
          II region of a HH ribozyme.

(xi) SEQUENCE DESCRIPTION: SEQ ID NO: 1381:

CAUGACUUCU GAUGANGAAA UACAGUA                                              27

(2) INFORMATION FOR SEQ ID NO: 1382:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION:   The letter "N" stands for the stem
          II region of a HH ribozyme.

(xi) SEQUENCE DESCRIPTION: SEQ ID NO: 1382:

CCUGCCAUCU GAUGANGAAA CUUGAUA                                              27

(2) INFORMATION FOR SEQ ID NO: 1383:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION:   The letter "N" stands for the stem
          II region of a HH ribozyme.

(xi) SEQUENCE DESCRIPTION: SEQ ID NO: 1383:

UCCUACUGCU GAUGANGAAA CCUGCCA                                              27

(2) INFORMATION FOR SEQ ID NO: 1384:

(i) SEQUENCE CHARACTERISTICS:

```
            (A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION:  The letter "N" stands for the stem
                II region of a HH ribozyme.

(xi) SEQUENCE DESCRIPTION: SEQ ID NO: 1384:

GCUUAUCCCU GAUGANGAAA CUGUACC                                           27

(2) INFORMATION FOR SEQ ID NO: 1385:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION:  The letter "N" stands for the stem
                II region of a HH ribozyme.

(xi) SEQUENCE DESCRIPTION: SEQ ID NO: 1385:

GAGUGGCUCU GAUGANGAAA UCCUACU                                           27

(2) INFORMATION FOR SEQ ID NO: 1386:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION:  The letter "N" stands for the stem
                II region of a HH ribozyme.

(xi) SEQUENCE DESCRIPTION: SEQ ID NO: 1386:

AAGGGACACU GAUGANGAAA GUGGCUU                                           27

(2) INFORMATION FOR SEQ ID NO: 1387:

(i) SEQUENCE CHARACTERISTICS:

(A) LENGTH:           27 base pairs
            (B) TYPE:             nucleic acid
            (C) STRANDEDNESS:     single
            (D) TOPOLOGY:         linear (ix) FEATURE:

(D) OTHER INFORMATION:  The letter "N" stands for the stem
                II region of a HH ribozyme.

(xi) SEQUENCE DESCRIPTION: SEQ ID NO: 1387:

CAGGAAGGCU GAUGANGAAA CAGAGUG                                           27

(2) INFORMATION FOR SEQ ID NO: 1388:

(i) SEQUENCE CHARACTERISTICS:

(A) LENGTH:           27 base pairs
            (B) TYPE:             nucleic acid
```

```
            (C)  STRANDEDNESS:         single
            (D)  TOPOLOGY:             linear (ix)  FEATURE:

(D)  OTHER INFORMATION:    The letter "N" stands for the stem
                 II region of a HH ribozyme.

(xi)  SEQUENCE DESCRIPTION: SEQ ID NO: 1388:

UGCCCAGGCU GAUGANGAAA GGGACAG                                             27

(2)  INFORMATION FOR SEQ ID NO: 1389:

(i)  SEQUENCE CHARACTERISTICS:

(A)  LENGTH:               27 base pairs
            (B)  TYPE:                 nucleic acid
            (C)  STRANDEDNESS:         single
            (D)  TOPOLOGY:             linear (ix)  FEATURE:

(D)  OTHER INFORMATION:    The letter "N" stands for the stem
                 II region of a HH ribozyme.

(xi)  SEQUENCE DESCRIPTION: SEQ ID NO: 1389:

UUGCCCAGCU GAUGANGAAA AGGGACA                                             27

(2)  INFORMATION FOR SEQ ID NO: 1390:

(i)  SEQUENCE CHARACTERISTICS:

(A)  LENGTH:               27 base pairs
            (B)  TYPE:                 nucleic acid
            (C)  STRANDEDNESS:         single
            (D)  TOPOLOGY:             linear (ix)  FEATURE:

(D)  OTHER INFORMATION:    The letter "N" stands for the stem
                 II region of a HH ribozyme.

(xi)  SEQUENCE DESCRIPTION: SEQ ID NO: 1390:

UAAGGAAGCU GAUGANGAAA UUCAUCC                                             27

(2)  INFORMATION FOR SEQ ID NO: 1391:

(i)  SEQUENCE CHARACTERISTICS:

(A)  LENGTH:               27 base pairs
            (B)  TYPE:                 nucleic acid
            (C)  STRANDEDNESS:         single
            (D)  TOPOLOGY:             linear (ix)  FEATURE:

(D)  OTHER INFORMATION:    The letter "N" stands for the stem
                 II region of a HH ribozyme.

(xi)  SEQUENCE DESCRIPTION: SEQ ID NO: 1391:

CUAAGGAACU GAUGANGAAA AUUCAUC                                             27

(2)  INFORMATION FOR SEQ ID NO: 1392:

(i)  SEQUENCE CHARACTERISTICS:

(A)  LENGTH:               27 base pairs
            (B)  TYPE:                 nucleic acid
            (C)  STRANDEDNESS:         single
            (D)  TOPOLOGY:             linear
```

(ix) FEATURE:

(D) OTHER INFORMATION: The letter "N" stands for the stem
            II region of a HH ribozyme.

(xi) SEQUENCE DESCRIPTION: SEQ ID NO: 1392:

GUCUAAGGCU GAUGANGAAA GAAUUCA                                                27

(2) INFORMATION FOR SEQ ID NO: 1393:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION: The letter "N" stands for the stem
            II region of a HH ribozyme.

(xi) SEQUENCE DESCRIPTION: SEQ ID NO: 1393:

AGUCUAAGCU GAUGANGAAA AGAAUUC                                                27

(2) INFORMATION FOR SEQ ID NO: 1394:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION: The letter "N" stands for the stem
            II region of a HH ribozyme.

(xi) SEQUENCE DESCRIPTION: SEQ ID NO: 1394:

GUAAGUCUCU GAUGANGAAA GGAAGAA                                                27

(2) INFORMATION FOR SEQ ID NO: 1395:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION: The letter "N" stands for the stem
            II region of a HH ribozyme.

(xi) SEQUENCE DESCRIPTION: SEQ ID NO: 1395:

AGUAAGUCCU GAUGANGAAA AGGAAGA                                                27

(2) INFORMATION FOR SEQ ID NO: 1396:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION: The letter "N" stands for the stem

-continued

II region of a HH ribozyme.

(xi) SEQUENCE DESCRIPTION: SEQ ID NO: 1396:

ACAAAAGUCU GAUGANGAAA GUCUAAG                                    27

(2) INFORMATION FOR SEQ ID NO: 1397:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION:  The letter "N" stands for the stem
          II region of a HH ribozyme.

(xi) SEQUENCE DESCRIPTION: SEQ ID NO: 1397:

UACAAAAGCU GAUGANGAAA AGUCUAA                                    27

(2) INFORMATION FOR SEQ ID NO: 1398:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION:  The letter "N" stands for the stem
          II region of a HH ribozyme.

(xi) SEQUENCE DESCRIPTION: SEQ ID NO: 1398:

UUUUACAACU GAUGANGAAA GUAAGUC                                    27

(2) INFORMATION FOR SEQ ID NO: 1399:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION:  The letter "N" stands for the stem
          II region of a HH ribozyme.

(xi) SEQUENCE DESCRIPTION: SEQ ID NO: 1399:

UUUUUACACU GAUGANGAAA AGUAAGU                                    27

(2) INFORMATION FOR SEQ ID NO: 1400:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION:  The letter "N" stands for the stem
          II region of a HH ribozyme.

(xi) SEQUENCE DESCRIPTION: SEQ ID NO: 1400:

AUUUUUACCU GAUGANGAAA AAGUAAG                                              27

(2) INFORMATION FOR SEQ ID NO: 1401:

(i) SEQUENCE CHARACTERISTICS:

(A) LENGTH:        27 base pairs
        (B) TYPE:          nucleic acid
        (C) STRANDEDNESS:  single
        (D) TOPOLOGY:     linear (ix) FEATURE:

(D) OTHER INFORMATION: The letter "N" stands for the stem
            II region of a HH ribozyme.

(xi) SEQUENCE DESCRIPTION: SEQ ID NO: 1401:

GACAUUUUCU GAUGANGAAA CAAAAGU                                              27

(2) INFORMATION FOR SEQ ID NO: 1402:

(i) SEQUENCE CHARACTERISTICS:

(A) LENGTH:        27 base pairs
        (B) TYPE:          nucleic acid
        (C) STRANDEDNESS:  single
        (D) TOPOLOGY:     linear (ix) FEATURE:

(D) OTHER INFORMATION: The letter "N" stands for the stem
            II region of a HH ribozyme.

(xi) SEQUENCE DESCRIPTION: SEQ ID NO: 1402:

ACCGUGGGCU GAUGANGAAA CAUUUUU                                              27

(2) INFORMATION FOR SEQ ID NO: 1403:

(i) SEQUENCE CHARACTERISTICS:

(A) LENGTH:        27 base pairs
        (B) TYPE:          nucleic acid
        (C) STRANDEDNESS:  single
        (D) TOPOLOGY:     linear (ix) FEATURE:

(D) OTHER INFORMATION: The letter "N" stands for the stem
            II region of a HH ribozyme.

(xi) SEQUENCE DESCRIPTION: SEQ ID NO: 1403:

GGAGUAAGCU GAUGANGAAA CCGUGGG                                              27

(2) INFORMATION FOR SEQ ID NO: 1404:

(i) SEQUENCE CHARACTERISTICS:

(A) LENGTH:        27 base pairs
        (B) TYPE:          nucleic acid
        (C) STRANDEDNESS:  single
        (D) TOPOLOGY:     linear (ix) FEATURE:

(D) OTHER INFORMATION: The letter "N" stands for the stem
            II region of a HH ribozyme.

(xi) SEQUENCE DESCRIPTION: SEQ ID NO: 1404:

UGGGGAGUCU GAUGANGAAA GUACCGU                                              27

(2) INFORMATION FOR SEQ ID NO: 1405:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1405:

GUGGGGAGCU GAUGANGAAA AGUACCG                         27

(2) INFORMATION FOR SEQ ID NO: 1406:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1406:

UCAGUGGGCU GAUGANGAAA GUAAGUA                         27

(2) INFORMATION FOR SEQ ID NO: 1407:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1407:

UGACUGGACU GAUGANGAAA CCACUGG                         27

(2) INFORMATION FOR SEQ ID NO: 1408:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1408:

AUGACUGGCU GAUGANGAAA ACCACUG                         27

(2) INFORMATION FOR SEQ ID NO: 1409:

```
    (i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:  The letter "N" stands for the stem
            II region of a HH ribozyme.

(xi) SEQUENCE DESCRIPTION: SEQ ID NO: 1409:

CAUGACUGCU GAUGANGAAA AACCACU                                             27

(2) INFORMATION FOR SEQ ID NO: 1410:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:  The letter "N" stands for the stem
            II region of a HH ribozyme.

(xi) SEQUENCE DESCRIPTION: SEQ ID NO: 1410:

ACGCUCAUCU GAUGANGAAA CUGGAAA                                             27

(2) INFORMATION FOR SEQ ID NO: 1411:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:  The letter "N" stands for the stem
            II region of a HH ribozyme.

(xi) SEQUENCE DESCRIPTION: SEQ ID NO: 1411:

GUCAGUCUCU GAUGANGAAA CGCUCAU                                             27

(2) INFORMATION FOR SEQ ID NO: 1412:

(i) SEQUENCE CHARACTERISTICS:

(A) LENGTH:            27 base pairs
        (B) TYPE:              nucleic acid
        (C) STRANDEDNESS:      single
        (D) TOPOLOGY:          linear (ix) FEATURE:

(D) OTHER INFORMATION:  The letter "N" stands for the stem
            II region of a HH ribozyme.

(xi) SEQUENCE DESCRIPTION: SEQ ID NO: 1412:

AGUCAGUCCU GAUGANGAAA ACGCUCA                                             27

(2) INFORMATION FOR SEQ ID NO: 1413:

(i) SEQUENCE CHARACTERISTICS:

(A) LENGTH:            27 base pairs
```

```
             (B)  TYPE:              nucleic acid
             (C)  STRANDEDNESS:      single
             (D)  TOPOLOGY:          linear (ix) FEATURE:

(D)  OTHER INFORMATION:   The letter "N" stands for the stem
                  II region of a HH ribozyme.

(xi) SEQUENCE DESCRIPTION: SEQ ID NO: 1413:

AGACAAACCU GAUGANGAAA GUCAGUC                                               27

(2)  INFORMATION FOR SEQ ID NO: 1414:

(i) SEQUENCE CHARACTERISTICS:

(A)  LENGTH:            27 base pairs
             (B)  TYPE:              nucleic acid
             (C)  STRANDEDNESS:      single
             (D)  TOPOLOGY:          linear (ix) FEATURE:

(D)  OTHER INFORMATION:   The letter "N" stands for the stem
                  II region of a HH ribozyme.

(xi) SEQUENCE DESCRIPTION: SEQ ID NO: 1414:

GGAAGACACU GAUGANGAAA CAAGUCA                                               27

(2)  INFORMATION FOR SEQ ID NO: 1415:

(i) SEQUENCE CHARACTERISTICS:

(A)  LENGTH:            27 base pairs
             (B)  TYPE:              nucleic acid
             (C)  STRANDEDNESS:      single
             (D)  TOPOLOGY:          linear (ix) FEATURE:

(D)  OTHER INFORMATION:   The letter "N" stands for the stem
                  II region of a HH ribozyme.

(xi) SEQUENCE DESCRIPTION: SEQ ID NO: 1415:

UGGAAGACCU GAUGANGAAA ACAAGUC                                               27

(2)  INFORMATION FOR SEQ ID NO: 1416:

(i) SEQUENCE CHARACTERISTICS:

(A)  LENGTH:            27 base pairs
             (B)  TYPE:              nucleic acid
             (C)  STRANDEDNESS:      single
             (D)  TOPOLOGY:          linear (ix) FEATURE:

(D)  OTHER INFORMATION:   The letter "N" stands for the stem
                  II region of a HH ribozyme.

(xi) SEQUENCE DESCRIPTION: SEQ ID NO: 1416:

GAAUGGAACU GAUGANGAAA CAAACAA                                               27

(2)  INFORMATION FOR SEQ ID NO: 1417:

(i) SEQUENCE CHARACTERISTICS:

(A)  LENGTH:            27 base pairs
             (B)  TYPE:              nucleic acid
             (C)  STRANDEDNESS:      single
             (D)  TOPOLOGY:          linear
```

(ix) FEATURE:

(D) OTHER INFORMATION: The letter "N" stands for the stem
    II region of a HH ribozyme.

(xi) SEQUENCE DESCRIPTION: SEQ ID NO: 1417:

UGGAAUGGCU GAUGANGAAA GACAAAC                27

(2) INFORMATION FOR SEQ ID NO: 1418:

(i) SEQUENCE CHARACTERISTICS:

(A) LENGTH:     27 base pairs
  (B) TYPE:      nucleic acid
  (C) STRANDEDNESS:  single
  (D) TOPOLOGY:    linear (ix) FEATURE:

(D) OTHER INFORMATION: The letter "N" stands for the stem
    II region of a HH ribozyme.

(xi) SEQUENCE DESCRIPTION: SEQ ID NO: 1418:

AUGGAAUGCU GAUGANGAAA AGACAAA                27

(2) INFORMATION FOR SEQ ID NO: 1419:

(i) SEQUENCE CHARACTERISTICS:

(A) LENGTH:     27 base pairs
  (B) TYPE:      nucleic acid
  (C) STRANDEDNESS:  single
  (D) TOPOLOGY:    linear (ix) FEATURE:

(D) OTHER INFORMATION: The letter "N" stands for the stem
    II region of a HH ribozyme.

(xi) SEQUENCE DESCRIPTION: SEQ ID NO: 1419:

AACAAUGGCU GAUGANGAAA UGGAAGA                27

(2) INFORMATION FOR SEQ ID NO: 1420:

(i) SEQUENCE CHARACTERISTICS:

(A) LENGTH:     27 base pairs
  (B) TYPE:      nucleic acid
  (C) STRANDEDNESS:  single
  (D) TOPOLOGY:    linear (ix) FEATURE:

(D) OTHER INFORMATION: The letter "N" stands for the stem
    II region of a HH ribozyme.

(xi) SEQUENCE DESCRIPTION: SEQ ID NO: 1420:

AAACAAUGCU GAUGANGAAA AUGGAAG                27

(2) INFORMATION FOR SEQ ID NO: 1421:

(i) SEQUENCE CHARACTERISTICS:

(A) LENGTH:     27 base pairs
  (B) TYPE:      nucleic acid
  (C) STRANDEDNESS:  single
  (D) TOPOLOGY:    linear (ix) FEATURE:

(D)  OTHER INFORMATION:    The letter "N" stands for the stem
                 II region of a HH ribozyme.

(xi)  SEQUENCE DESCRIPTION: SEQ ID NO: 1421:

UUCAAAACCU GAUGANGAAA UGGAAUG                                           27

(2) INFORMATION FOR SEQ ID NO: 1422:

(i)  SEQUENCE CHARACTERISTICS:

(A)  LENGTH:            27 base pairs
         (B)  TYPE:              nucleic acid
         (C)  STRANDEDNESS:      single
         (D)  TOPOLOGY:          linear (ix) FEATURE:

(D)  OTHER INFORMATION:    The letter "N" stands for the stem
              II region of a HH ribozyme.

(xi)  SEQUENCE DESCRIPTION: SEQ ID NO: 1422:

AGUUUCAACU GAUGANGAAA CAAUGGA                                           27

(2) INFORMATION FOR SEQ ID NO: 1423:

(i)  SEQUENCE CHARACTERISTICS:

(A)  LENGTH:            27 base pairs
         (B)  TYPE:              nucleic acid
         (C)  STRANDEDNESS:      single
         (D)  TOPOLOGY:          linear (ix) FEATURE:

(D)  OTHER INFORMATION:    The letter "N" stands for the stem
              II region of a HH ribozyme.

(xi)  SEQUENCE DESCRIPTION: SEQ ID NO: 1423:

GAGUUUCACU GAUGANGAAA ACAAUGG                                           27

(2) INFORMATION FOR SEQ ID NO: 1424:

(i)  SEQUENCE CHARACTERISTICS:

(A)  LENGTH:            27 base pairs
         (B)  TYPE:              nucleic acid
         (C)  STRANDEDNESS:      single
         (D)  TOPOLOGY:          linear (ix) FEATURE:

(D)  OTHER INFORMATION:    The letter "N" stands for the stem
              II region of a HH ribozyme.

(xi)  SEQUENCE DESCRIPTION: SEQ ID NO: 1424:

UGAGUUUCCU GAUGANGAAA AACAAUG                                           27

(2) INFORMATION FOR SEQ ID NO: 1425:

(i)  SEQUENCE CHARACTERISTICS:

(A)  LENGTH:            27 base pairs
         (B)  TYPE:              nucleic acid
         (C)  STRANDEDNESS:      single
         (D)  TOPOLOGY:          linear (ix) FEATURE:

(D)  OTHER INFORMATION:    The letter "N" stands for the stem
              II region of a HH ribozyme.

(xi) SEQUENCE DESCRIPTION: SEQ ID NO: 1425:

GGCAUACUCU GAUGANGAAA GUUUCAA                                                    27

(2)  INFORMATION FOR SEQ ID NO: 1426:

(i) SEQUENCE CHARACTERISTICS:

(A)  LENGTH:          27 base pairs
          (B)  TYPE:            nucleic acid
          (C)  STRANDEDNESS:    single
          (D)  TOPOLOGY:        linear (ix) FEATURE:

(D)  OTHER INFORMATION:  The letter "N" stands for the stem
               II region of a HH ribozyme.

(xi) SEQUENCE DESCRIPTION: SEQ ID NO: 1426:

GGGCGGCACU GAUGANGAAA CUGAGUU                                                    27

(2)  INFORMATION FOR SEQ ID NO: 1427:

(i) SEQUENCE CHARACTERISTICS:

(A)  LENGTH:          27 base pairs
          (B)  TYPE:            nucleic acid
          (C)  STRANDEDNESS:    single
          (D)  TOPOLOGY:        linear (ix) FEATURE:

(D)  OTHER INFORMATION:  The letter "N" stands for the stem
               II region of a HH ribozyme.

(xi) SEQUENCE DESCRIPTION: SEQ ID NO: 1427:

GACAGCAACU GAUGANGAAA CAGGGGC                                                    27

(2)  INFORMATION FOR SEQ ID NO: 1428:

(i) SEQUENCE CHARACTERISTICS:

(A)  LENGTH:          27 base pairs
          (B)  TYPE:            nucleic acid
          (C)  STRANDEDNESS:    single
          (D)  TOPOLOGY:        linear (ix) FEATURE:

(D)  OTHER INFORMATION:  The letter "N" stands for the stem
               II region of a HH ribozyme.

(xi) SEQUENCE DESCRIPTION: SEQ ID NO: 1428:

AUGACAGCCU GAUGANGAAA GACAGGG                                                    27

(2)  INFORMATION FOR SEQ ID NO: 1429:

(i) SEQUENCE CHARACTERISTICS:

(A)  LENGTH:          27 base pairs
          (B)  TYPE:            nucleic acid
          (C)  STRANDEDNESS:    single
          (D)  TOPOLOGY:        linear (ix) FEATURE:

(D)  OTHER INFORMATION:  The letter "N" stands for the stem
               II region of a HH ribozyme.

(xi) SEQUENCE DESCRIPTION: SEQ ID NO: 1429:

GAUUUCAUCU GAUGANGAAA CAGCAAG                                                    27

(2) INFORMATION FOR SEQ ID NO: 1430:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 1430:

CUCUUGCUCU GAUGANGAAA UUUCAUG                                       27

(2) INFORMATION FOR SEQ ID NO: 1431:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 1431:

UAUUAUUUCU GAUGANGAAA UGUGUCA                                       27

(2) INFORMATION FOR SEQ ID NO: 1432:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 1432:

CGAGUUAUCU GAUGANGAAA UUUGAUG                                       27

(2) INFORMATION FOR SEQ ID NO: 1433:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 1433:

AUCCGAGUCU GAUGANGAAA UUAUUUG                                       27

(2) INFORMATION FOR SEQ ID NO: 1434:

(i) SEQUENCE CHARACTERISTICS:

(A) LENGTH: 27 base pairs
    (B) TYPE: nucleic acid
    (C) STRANDEDNESS: single
    (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1434:

UGGAAUCCCU GAUGANGAAA GUUAUUA    27

(2) INFORMATION FOR SEQ ID NO: 1435:

(i) SEQUENCE CHARACTERISTICS:

(A) LENGTH: 27 base pairs
    (B) TYPE: nucleic acid
    (C) STRANDEDNESS: single
    (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1435:

UGGGCUGGCU GAUGANGAAA UCCGAGU    27

(2) INFORMATION FOR SEQ ID NO: 1436:

(i) SEQUENCE CHARACTERISTICS:

(A) LENGTH: 27 base pairs
    (B) TYPE: nucleic acid
    (C) STRANDEDNESS: single
    (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1436:

GUGGGCUGCU GAUGANGAAA AUCCGAG    27

(2) INFORMATION FOR SEQ ID NO: 1437:

(i) SEQUENCE CHARACTERISTICS:

(A) LENGTH: 27 base pairs
    (B) TYPE: nucleic acid
    (C) STRANDEDNESS: single
    (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1437:

AUGAAUCCCU GAUGANGAAA UGUGGGC    27

(2) INFORMATION FOR SEQ ID NO: 1438:

(i) SEQUENCE CHARACTERISTICS:

```
              (A)  LENGTH:           27 base pairs
              (B)  TYPE:             nucleic acid
              (C)  STRANDEDNESS:     single
              (D)  TOPOLOGY:         linear (ix)  FEATURE:

(D)  OTHER INFORMATION:   The letter "N" stands for the stem
                   II region of a HH ribozyme.

(xi)  SEQUENCE DESCRIPTION: SEQ ID NO: 1438:

UGCUGAUGCU GAUGANGAAA UCCAAUG                                              27

(2)  INFORMATION FOR SEQ ID NO: 1439:

(i)  SEQUENCE CHARACTERISTICS:

(A)  LENGTH:           27 base pairs
              (B)  TYPE:             nucleic acid
              (C)  STRANDEDNESS:     single
              (D)  TOPOLOGY:         linear (ix)  FEATURE:

(D)  OTHER INFORMATION:   The letter "N" stands for the stem
                   II region of a HH ribozyme.

(xi)  SEQUENCE DESCRIPTION: SEQ ID NO: 1439:

AUGCUGAUCU GAUGANGAAA AUCCAAU                                              27

(2)  INFORMATION FOR SEQ ID NO: 1440:

(i)  SEQUENCE CHARACTERISTICS:

(A)  LENGTH:           27 base pairs
              (B)  TYPE:             nucleic acid
              (C)  STRANDEDNESS:     single
              (D)  TOPOLOGY:         linear (ix)  FEATURE:

(D)  OTHER INFORMATION:   The letter "N" stands for the stem
                   II region of a HH ribozyme.

(xi)  SEQUENCE DESCRIPTION: SEQ ID NO: 1440:

CAAAUGCUCU GAUGANGAAA UGAAUCC                                              27

(2)  INFORMATION FOR SEQ ID NO: 1441:

(i)  SEQUENCE CHARACTERISTICS:

(A)  LENGTH:           27 base pairs
              (B)  TYPE:             nucleic acid
              (C)  STRANDEDNESS:     single
              (D)  TOPOLOGY:         linear (ix)  FEATURE:

(D)  OTHER INFORMATION:   The letter "N" stands for the stem
                   II region of a HH ribozyme.

(xi)  SEQUENCE DESCRIPTION: SEQ ID NO: 1441:

UUGGUCCACU GAUGANGAAA UGCUGAU                                              27

(2)  INFORMATION FOR SEQ ID NO: 1442:

(i)  SEQUENCE CHARACTERISTICS:

(A)  LENGTH:           27 base pairs
              (B)  TYPE:             nucleic acid
              (C)  STRANDEDNESS:     single
```

```
            (D) TOPOLOGY:           linear (ix) FEATURE:

(D) OTHER INFORMATION:  The letter "N" stands for the stem
                II region of a HH ribozyme.

(xi) SEQUENCE DESCRIPTION: SEQ ID NO: 1442:

AUUGGUCCCU GAUGANGAAA AUGCUGA                                          27

(2) INFORMATION FOR SEQ ID NO: 1443:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:  The letter "N" stands for the stem
                II region of a HH ribozyme.

(xi) SEQUENCE DESCRIPTION: SEQ ID NO: 1443:

CUGUGGGCCU GAUGANGAAA UUGGUCC                                          27

(2) INFORMATION FOR SEQ ID NO: 1444:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:  The letter "N" stands for the stem
                II region of a HH ribozyme.

(xi) SEQUENCE DESCRIPTION: SEQ ID NO: 1444:

UCCUUAGGCU GAUGANGAAA UUCCACA                                          27

(2) INFORMATION FOR SEQ ID NO: 1445:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:

(D) OTHER INFORMATION:  The letter "N" stands for the stem
                II region of a HH ribozyme.

(xi) SEQUENCE DESCRIPTION: SEQ ID NO: 1445:

GUUAUCCUCU GAUGANGAAA GGUAUUC                                          27

(2) INFORMATION FOR SEQ ID NO: 1446:

(i) SEQUENCE CHARACTERISTICS:

(A) LENGTH:             27 base pairs
            (B) TYPE:               nucleic acid
            (C) STRANDEDNESS:       single
            (D) TOPOLOGY:           linear (ix) FEATURE:
```

(D) OTHER INFORMATION:  The letter "N" stands for the stem
            II region of a HH ribozyme.

(xi) SEQUENCE DESCRIPTION: SEQ ID NO: 1446:

AGCGGUGUCU GAUGANGAAA UCCUUAG                                         27

(2) INFORMATION FOR SEQ ID NO: 1447:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1447:

GAGAACAACU GAUGANGAAA GCGGUGU                                         27

(2) INFORMATION FOR SEQ ID NO: 1448:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1448:

CGAGAACACU GAUGANGAAA AGCGGUG                                         27

(2) INFORMATION FOR SEQ ID NO: 1449:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1449:

GCGAGAACCU GAUGANGAAA AAGCGGU                                         27

(2) INFORMATION FOR SEQ ID NO: 1450:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1450:

UUUGCGAGCU GAUGANGAAA CAAAAGC                                                27

(2) INFORMATION FOR SEQ ID NO: 1451:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 1451:

UUUUGCGACU GAUGANGAAA ACAAAAG                                                27

(2) INFORMATION FOR SEQ ID NO: 1452:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 1452:

GUUUUUGCCU GAUGANGAAA GAACAAA                                                27

(2) INFORMATION FOR SEQ ID NO: 1453:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 1453:

UUAGGAGACU GAUGANGAAA CGUUUUU                                                27

(2) INFORMATION FOR SEQ ID NO: 1454:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION:  The letter "N" stands for the stem
            II region of a HH ribozyme.

(xi) SEQUENCE DESCRIPTION: SEQ ID NO: 1454:

```
AAUUAGGACU GAUGANGAAA UACGUUU                                                27
```

(2) INFORMATION FOR SEQ ID NO: 1455:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION:  The letter "N" stands for the stem II region of a HH ribozyme.

(xi) SEQUENCE DESCRIPTION: SEQ ID NO: 1455:

```
CAAAUUAGCU GAUGANGAAA GAUACGU                                                27
```

(2) INFORMATION FOR SEQ ID NO: 1456:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION:  The letter "N" stands for the stem II region of a HH ribozyme.

(xi) SEQUENCE DESCRIPTION: SEQ ID NO: 1456:

```
CCUCAAAUCU GAUGANGAAA GGAGAUA                                                27
```

(2) INFORMATION FOR SEQ ID NO: 1457:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION:  The letter "N" stands for the stem II region of a HH ribozyme.

(xi) SEQUENCE DESCRIPTION: SEQ ID NO: 1457:

```
GAGCCUCACU GAUGANGAAA UUAGGAG                                                27
```

(2) INFORMATION FOR SEQ ID NO: 1458:

(i) SEQUENCE CHARACTERISTICS:

(A) LENGTH:        27 base pairs
      (B) TYPE:          nucleic acid
      (C) STRANDEDNESS:  single
      (D) TOPOLOGY:      linear (ix) FEATURE:

(D) OTHER INFORMATION:  The letter "N" stands for the stem II region of a HH ribozyme.

(xi) SEQUENCE DESCRIPTION: SEQ ID NO: 1458:

```
UGAGCCUCCU GAUGANGAAA AUUAGGA                                                27
```

(2) INFORMATION FOR SEQ ID NO: 1459:

(i) SEQUENCE CHARACTERISTICS:

(A) LENGTH:        27 base pairs
        (B) TYPE:          nucleic acid
        (C) STRANDEDNESS:  single
        (D) TOPOLOGY:     linear (ix) FEATURE:

(D) OTHER INFORMATION: The letter "N" stands for the stem
            II region of a HH ribozyme.

(xi) SEQUENCE DESCRIPTION: SEQ ID NO: 1459:

UUUCAUCUCU GAUGANGAAA GCCUCAA                             27

(2) INFORMATION FOR SEQ ID NO: 1460:

(i) SEQUENCE CHARACTERISTICS:

(A) LENGTH:        27 base pairs
        (B) TYPE:          nucleic acid
        (C) STRANDEDNESS:  single
        (D) TOPOLOGY:     linear (ix) FEATURE:

(D) OTHER INFORMATION: The letter "N" stands for the stem
            II region of a HH ribozyme.

(xi) SEQUENCE DESCRIPTION: SEQ ID NO: 1460:

AAGGACCUCU GAUGANGAAA UGCAUUU                             27

(2) INFORMATION FOR SEQ ID NO: 1461:

(i) SEQUENCE CHARACTERISTICS:

(A) LENGTH:        27 base pairs
        (B) TYPE:          nucleic acid
        (C) STRANDEDNESS:  single
        (D) TOPOLOGY:     linear (ix) FEATURE:

(D) OTHER INFORMATION: The letter "N" stands for the stem
            II region of a HH ribozyme.

(xi) SEQUENCE DESCRIPTION: SEQ ID NO: 1461:

CCCCAAAGCU GAUGANGAAA CCUGAUG                             27

(2) INFORMATION FOR SEQ ID NO: 1462:

(i) SEQUENCE CHARACTERISTICS:

(A) LENGTH:        27 base pairs
        (B) TYPE:          nucleic acid
        (C) STRANDEDNESS:  single
        (D) TOPOLOGY:     linear (ix) FEATURE:

(D) OTHER INFORMATION: The letter "N" stands for the stem
            II region of a HH ribozyme.

(xi) SEQUENCE DESCRIPTION: SEQ ID NO: 1462:

AUGCCCCACU GAUGANGAAA GGACCUG                             27

(2) INFORMATION FOR SEQ ID NO: 1463:

(i) SEQUENCE CHARACTERISTICS:

```
            (A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1463:

UAUGCCCCCU GAUGANGAAA AGGACCU                                          27

(2) INFORMATION FOR SEQ ID NO: 1464:

(i) SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1464:

UUCUGAUCCU GAUGANGAAA UGCCCCA                                          27

(2) INFORMATION FOR SEQ ID NO: 1465:

(i) SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1465:

AGUCUUCUCU GAUGANGAAA UCUAUGC                                          27

(2) INFORMATION FOR SEQ ID NO: 1466:

(i) SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1466:

CAUUUUUGCU GAUGANGAAA GUCUUCU                                          27

(2) INFORMATION FOR SEQ ID NO: 1467:

(i) SEQUENCE CHARACTERISTICS:

(A)  LENGTH:              27 base pairs
            (B)  TYPE:                nucleic acid
```

```
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1467:

AGAUUUCACU GAUGANGAAA GCAGCUU                                              27

(2) INFORMATION FOR SEQ ID NO: 1468:

(i) SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1468:

CUAAAGGACU GAUGANGAAA UUUCAGA                                              27

(2) INFORMATION FOR SEQ ID NO: 1469:

(i) SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1469:

GGCUAAAGCU GAUGANGAAA GAUUUCA                                              27

(2) INFORMATION FOR SEQ ID NO: 1470:

(i) SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1470:

GAUGGCUACU GAUGANGAAA GGAGAUU                                              27

(2) INFORMATION FOR SEQ ID NO: 1471:

(i) SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear
```

(ix) FEATURE:

(D) OTHER INFORMATION: The letter "N" stands for the stem
            II region of a HH ribozyme.

(xi) SEQUENCE DESCRIPTION: SEQ ID NO: 1471:

UGAUGGCUCU GAUGANGAAA AGGAGAU                                              27

(2) INFORMATION FOR SEQ ID NO: 1472:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION: The letter "N" stands for the stem
            II region of a HH ribozyme.

(xi) SEQUENCE DESCRIPTION: SEQ ID NO: 1472:

GUGAUGGCCU GAUGANGAAA AAGGAGA                                              27

(2) INFORMATION FOR SEQ ID NO: 1473:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION: The letter "N" stands for the stem
            II region of a HH ribozyme.

(xi) SEQUENCE DESCRIPTION: SEQ ID NO: 1473:

GUUGGGGUCU GAUGANGAAA UGGCUAA                                              27

(2) INFORMATION FOR SEQ ID NO: 1474:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION: The letter "N" stands for the stem
            II region of a HH ribozyme.

(xi) SEQUENCE DESCRIPTION: SEQ ID NO: 1474:

CACAAACUCU GAUGANGAAA UUUUGGG                                              27

(2) INFORMATION FOR SEQ ID NO: 1475:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION: The letter "N" stands for the stem

II region of a HH ribozyme.

(xi) SEQUENCE DESCRIPTION: SEQ ID NO: 1475:

ACACAAACCU GAUGANGAAA AUUUUGG                                    27

(2) INFORMATION FOR SEQ ID NO: 1476:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION: The letter "N" stands for the stem
         II region of a HH ribozyme.

(xi) SEQUENCE DESCRIPTION: SEQ ID NO: 1476:

GUAACACACU GAUGANGAAA CUAAUUU                                    27

(2) INFORMATION FOR SEQ ID NO: 1477:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION: The letter "N" stands for the stem
         II region of a HH ribozyme.

(xi) SEQUENCE DESCRIPTION: SEQ ID NO: 1477:

AGUAACACCU GAUGANGAAA ACUAAUU                                    27

(2) INFORMATION FOR SEQ ID NO: 1478:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION: The letter "N" stands for the stem
         II region of a HH ribozyme.

(xi) SEQUENCE DESCRIPTION: SEQ ID NO: 1478:

CCAUAAGUCU GAUGANGAAA CACAAAC                                    27

(2) INFORMATION FOR SEQ ID NO: 1479:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION: The letter "N" stands for the stem
         II region of a HH ribozyme.

(xi) SEQUENCE DESCRIPTION: SEQ ID NO: 1479:

UCCAUAAGCU GAUGANGAAA ACACAAA                                                27

(2) INFORMATION FOR SEQ ID NO: 1480:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1480:

UCUUCCAUCU GAUGANGAAA GUAACAC                                                27

(2) INFORMATION FOR SEQ ID NO: 1481:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1481:

AUCUUCCACU GAUGANGAAA AGUAACA                                                27

(2) INFORMATION FOR SEQ ID NO: 1482:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1482:

GAGAAAACCU GAUGANGAAA UCUUCCA                                                27

(2) INFORMATION FOR SEQ ID NO: 1483:

(i) SEQUENCE CHARACTERISTICS:

(A) LENGTH:             27 base pairs
        (B) TYPE:               nucleic acid
        (C) STRANDEDNESS:       single
        (D) TOPOLOGY:           linear (ix) FEATURE:

(D) OTHER INFORMATION:  The letter "N" stands for the stem
            II region of a HH ribozyme.

(xi) SEQUENCE DESCRIPTION: SEQ ID NO: 1483:

AAGGAGAACU GAUGANGAAA CUAUCUU                                                27

(2) INFORMATION FOR SEQ ID NO: 1484:

(i) SEQUENCE CHARACTERISTICS:

(A) LENGTH: 27 base pairs  
        (B) TYPE: nucleic acid  
        (C) STRANDEDNESS: single  
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1484:

AAAGGAGACU GAUGANGAAA ACUAUCU                       27

(2) INFORMATION FOR SEQ ID NO: 1485:

(i) SEQUENCE CHARACTERISTICS:

(A) LENGTH: 27 base pairs  
        (B) TYPE: nucleic acid  
        (C) STRANDEDNESS: single  
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1485:

AAAAGGAGCU GAUGANGAAA AACUAUC                       27

(2) INFORMATION FOR SEQ ID NO: 1486:

(i) SEQUENCE CHARACTERISTICS:

(A) LENGTH: 27 base pairs  
        (B) TYPE: nucleic acid  
        (C) STRANDEDNESS: single  
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1486:

UAAAAGGACU GAUGANGAAA AAACUAU                       27

(2) INFORMATION FOR SEQ ID NO: 1487:

(i) SEQUENCE CHARACTERISTICS:

(A) LENGTH: 27 base pairs  
        (B) TYPE: nucleic acid  
        (C) STRANDEDNESS: single  
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1487:

AGUAAAAGCU GAUGANGAAA GAAAACU                       27

(2) INFORMATION FOR SEQ ID NO: 1488:

```
        (i) SEQUENCE CHARACTERISTICS:

(A) LENGTH:             27 base pairs
                (B) TYPE:               nucleic acid
                (C) STRANDEDNESS:       single
                (D) TOPOLOGY:           linear (ix) FEATURE:

(D) OTHER INFORMATION:  The letter "N" stands for the stem
                    II region of a HH ribozyme.

(xi) SEQUENCE DESCRIPTION: SEQ ID NO: 1488:

UGAAGUAACU GAUGANGAAA GGAGAAA                                              27

(2) INFORMATION FOR SEQ ID NO: 1489:

(i) SEQUENCE CHARACTERISTICS:

(A) LENGTH:             27 base pairs
                (B) TYPE:               nucleic acid
                (C) STRANDEDNESS:       single
                (D) TOPOLOGY:           linear (ix) FEATURE:

(D) OTHER INFORMATION:  The letter "N" stands for the stem
                    II region of a HH ribozyme.

(xi) SEQUENCE DESCRIPTION: SEQ ID NO: 1489:

GUGAAGUACU GAUGANGAAA AGGAGAA                                              27

(2) INFORMATION FOR SEQ ID NO: 1490:

(i) SEQUENCE CHARACTERISTICS:

(A) LENGTH:             27 base pairs
                (B) TYPE:               nucleic acid
                (C) STRANDEDNESS:       single
                (D) TOPOLOGY:           linear (ix) FEATURE:

(D) OTHER INFORMATION:  The letter "N" stands for the stem
                    II region of a HH ribozyme.

(xi) SEQUENCE DESCRIPTION: SEQ ID NO: 1490:

AGUGAAGUCU GAUGANGAAA AAGGAGA                                              27

(2) INFORMATION FOR SEQ ID NO: 1491:

(i) SEQUENCE CHARACTERISTICS:

(A) LENGTH:             27 base pairs
                (B) TYPE:               nucleic acid
                (C) STRANDEDNESS:       single
                (D) TOPOLOGY:           linear (ix) FEATURE:

(D) OTHER INFORMATION:  The letter "N" stands for the stem
                    II region of a HH ribozyme.

(xi) SEQUENCE DESCRIPTION: SEQ ID NO: 1491:

AAGUGAAGCU GAUGANGAAA AAAGGAG                                              27

(2) INFORMATION FOR SEQ ID NO: 1492:

(i) SEQUENCE CHARACTERISTICS:

(A) LENGTH:             27 base pairs
```

```
            (B)  TYPE:                nucleic acid
            (C)  STRANDEDNESS:        single
            (D)  TOPOLOGY:            linear (ix) FEATURE:

(D) OTHER INFORMATION:  The letter "N" stands for the stem
                II region of a HH ribozyme.

(xi) SEQUENCE DESCRIPTION: SEQ ID NO: 1492:

UUGAAGUGCU GAUGANGAAA GUAAAAG                                              27

(2) INFORMATION FOR SEQ ID NO: 1493:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D) OTHER INFORMATION:  The letter "N" stands for the stem
                II region of a HH ribozyme.

(xi) SEQUENCE DESCRIPTION: SEQ ID NO: 1493:

UUUGAAGUCU GAUGANGAAA AGUAAAA                                              27

(2) INFORMATION FOR SEQ ID NO: 1494:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D) OTHER INFORMATION:  The letter "N" stands for the stem
                II region of a HH ribozyme.

(xi) SEQUENCE DESCRIPTION: SEQ ID NO: 1494:

AGCUUUUGCU GAUGANGAAA GUGAAGU                                              27

(2) INFORMATION FOR SEQ ID NO: 1495:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D) OTHER INFORMATION:  The letter "N" stands for the stem
                II region of a HH ribozyme.

(xi) SEQUENCE DESCRIPTION: SEQ ID NO: 1495:

AAGCUUUUCU GAUGANGAAA AGUGAAG                                              27

(2) INFORMATION FOR SEQ ID NO: 1496:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear
```

(ix) FEATURE:

(D) OTHER INFORMATION: The letter "N" stands for the stem
        II region of a HH ribozyme.

(xi) SEQUENCE DESCRIPTION: SEQ ID NO: 1496:

UGAGUAAACU GAUGANGAAA GCUUUG                                  27

(2) INFORMATION FOR SEQ ID NO: 1497:

(i) SEQUENCE CHARACTERISTICS:

(A) LENGTH:        27 base pairs
        (B) TYPE:          nucleic acid
        (C) STRANDEDNESS:  single
        (D) TOPOLOGY:     linear (ix) FEATURE:

(D) OTHER INFORMATION: The letter "N" stands for the stem
        II region of a HH ribozyme.

(xi) SEQUENCE DESCRIPTION: SEQ ID NO: 1497:

UUGAGUAACU GAUGANGAAA AGCUUUU                               27

(2) INFORMATION FOR SEQ ID NO: 1498:

(i) SEQUENCE CHARACTERISTICS:

(A) LENGTH:        27 base pairs
        (B) TYPE:          nucleic acid
        (C) STRANDEDNESS:  single
        (D) TOPOLOGY:     linear (ix) FEATURE:

(D) OTHER INFORMATION: The letter "N" stands for the stem
        II region of a HH ribozyme.

(xi) SEQUENCE DESCRIPTION: SEQ ID NO: 1498:

UUUGAGUACU GAUGANGAAA AAGCUUU                               27

(2) INFORMATION FOR SEQ ID NO: 1499:

(i) SEQUENCE CHARACTERISTICS:

(A) LENGTH:        27 base pairs
        (B) TYPE:          nucleic acid
        (C) STRANDEDNESS:  single
        (D) TOPOLOGY:     linear (ix) FEATURE:

(D) OTHER INFORMATION: The letter "N" stands for the stem
        II region of a HH ribozyme.

(xi) SEQUENCE DESCRIPTION: SEQ ID NO: 1499:

CUUUGAGUCU GAUGANGAAA AAAGCUU                               27

(2) INFORMATION FOR SEQ ID NO: 1500:

(i) SEQUENCE CHARACTERISTICS:

(A) LENGTH:        27 base pairs
        (B) TYPE:          nucleic acid
        (C) STRANDEDNESS:  single
        (D) TOPOLOGY:     linear (ix) FEATURE:

(D) OTHER INFORMATION: The letter "N" stands for the stem
                II region of a HH ribozyme.

(xi) SEQUENCE DESCRIPTION: SEQ ID NO: 1500:

UCUUUGAGCU GAUGANGAAA AAAAGCU                                    27

(2) INFORMATION FOR SEQ ID NO: 1501:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 1501:

UACUCUUUCU GAUGANGAAA GUAAAAA                                    27

(2) INFORMATION FOR SEQ ID NO: 1502:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 1502:

GGAACAUACU GAUGANGAAA CUCUUUG                                    27

(2) INFORMATION FOR SEQ ID NO: 1503:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 1503:

AGGGAACACU GAUGANGAAA UACUCUU                                    27

(2) INFORMATION FOR SEQ ID NO: 1504:

(i) SEQUENCE CHARACTERISTICS:

(A) LENGTH:         27 base pairs
        (B) TYPE:           nucleic acid
        (C) STRANDEDNESS:   single
        (D) TOPOLOGY:       linear (ix) FEATURE:

(D) OTHER INFORMATION: The letter "N" stands for the stem
            II region of a HH ribozyme.

(xi) SEQUENCE DESCRIPTION: SEQ ID NO: 1504:

CUGGAGGGCU GAUGANGAAA CAUAUAC                                                    27

(2) INFORMATION FOR SEQ ID NO: 1505:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for the stem
            II region of a HH ribozyme.

(xi) SEQUENCE DESCRIPTION: SEQ ID NO: 1505:

CCUGGAGGCU GAUGANGAAA ACAUAUA                                                    27

(2) INFORMATION FOR SEQ ID NO: 1506:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for the stem
            II region of a HH ribozyme.

(xi) SEQUENCE DESCRIPTION: SEQ ID NO: 1506:

CUGACCUGCU GAUGANGAAA GGGAACA                                                    27

(2) INFORMATION FOR SEQ ID NO: 1507:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for the stem
            II region of a HH ribozyme.

(xi) SEQUENCE DESCRIPTION: SEQ ID NO: 1507:

GGGCAGCUCU GAUGANGAAA CCUGGAG                                                    27

(2) INFORMATION FOR SEQ ID NO: 1508:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for the stem
            II region of a HH ribozyme.

(xi) SEQUENCE DESCRIPTION: SEQ ID NO: 1508:

AGCGUAAGCU GAUGANGAAA GGGGGUU                                                    27

(2) INFORMATION FOR SEQ ID NO: 1509:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1509:

CAAAGCGUCU GAUGANGAAA GGAGGGG                        27

(2) INFORMATION FOR SEQ ID NO: 1510:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1510:

ACAAAGCGCU GAUGANGAAA AGGAGGG                        27

(2) INFORMATION FOR SEQ ID NO: 1511:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1511:

GUGUGACACU GAUGANGAAA GCGUAAG                        27

(2) INFORMATION FOR SEQ ID NO: 1512:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1512:

UGUGUGACCU GAUGANGAAA AGCGUAA                        27

(2) INFORMATION FOR SEQ ID NO: 1513:

```
        (i)  SEQUENCE CHARACTERISTICS:

(A)  LENGTH:              27 base pairs
             (B)  TYPE:                nucleic acid
             (C)  STRANDEDNESS:        single
             (D)  TOPOLOGY:            linear (ix)  FEATURE:

(D)  OTHER INFORMATION:   The letter "N" stands for the stem
                  II region of a HH ribozyme.

(xi)  SEQUENCE DESCRIPTION: SEQ ID NO: 1513:

UUUUGUGUCU GAUGANGAAA CAAAGCG                                          27

(2)  INFORMATION FOR SEQ ID NO: 1514:

(i)  SEQUENCE CHARACTERISTICS:

(A)  LENGTH:              27 base pairs
             (B)  TYPE:                nucleic acid
             (C)  STRANDEDNESS:        single
             (D)  TOPOLOGY:            linear (ix)  FEATURE:

(D)  OTHER INFORMATION:   The letter "N" stands for the stem
                  II region of a HH ribozyme.

(xi)  SEQUENCE DESCRIPTION: SEQ ID NO: 1514:

AAGGCAGACU GAUGANGAAA CACUUUU                                          27

(2)  INFORMATION FOR SEQ ID NO: 1515:

(i)  SEQUENCE CHARACTERISTICS:

(A)  LENGTH:              27 base pairs
             (B)  TYPE:                nucleic acid
             (C)  STRANDEDNESS:        single
             (D)  TOPOLOGY:            linear (ix)  FEATURE:

(D)  OTHER INFORMATION:   The letter "N" stands for the stem
                  II region of a HH ribozyme.

(xi)  SEQUENCE DESCRIPTION: SEQ ID NO: 1515:

UCAAGGCACU GAUGANGAAA GACACUU                                          27

(2)  INFORMATION FOR SEQ ID NO: 1516:

(i)  SEQUENCE CHARACTERISTICS:

(A)  LENGTH:              27 base pairs
             (B)  TYPE:                nucleic acid
             (C)  STRANDEDNESS:        single
             (D)  TOPOLOGY:            linear (ix)  FEATURE:

(D)  OTHER INFORMATION:   The letter "N" stands for the stem
                  II region of a HH ribozyme.

(xi)  SEQUENCE DESCRIPTION: SEQ ID NO: 1516:

GAUGACUCCU GAUGANGAAA GGCAGAG                                          27

(2)  INFORMATION FOR SEQ ID NO: 1517:

(i)  SEQUENCE CHARACTERISTICS:
```

```
            (A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1517:

GAAUAGAUCU GAUGANGAAA CUCAAGG                                              27

(2) INFORMATION FOR SEQ ID NO: 1518:

(i) SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1518:

CUUGAAUACU GAUGANGAAA UGACUCA                                              27

(2) INFORMATION FOR SEQ ID NO: 1519:

(i) SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1519:

UGCUUGAACU GAUGANGAAA GAUGACU                                              27

(2) INFORMATION FOR SEQ ID NO: 1520:

(i) SEQUENCE CHARACTERISTICS:

(A)  LENGTH:              27 base pairs
            (B)  TYPE:                nucleic acid
            (C)  STRANDEDNESS:        single
            (D)  TOPOLOGY:            linear (ix) FEATURE:

(D)  OTHER INFORMATION:   The letter "N" stands for the stem
                 II region of a HH ribozyme.

(xi) SEQUENCE DESCRIPTION: SEQ ID NO: 1520:

AGUGCUUGCU GAUGANGAAA UAGAUGA                                              27

(2) INFORMATION FOR SEQ ID NO: 1521:

(i) SEQUENCE CHARACTERISTICS:

(A)  LENGTH:              27 base pairs
            (B)  TYPE:                nucleic acid
            (C)  STRANDEDNESS:        single
```

```
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 1521:

AAGUGCUUCU GAUGANGAAA AUAGAUG                                         27

(2) INFORMATION FOR SEQ ID NO: 1522:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 1522:

AGAGCUGUCU GAUGANGAAA GUGCUUG                                         27

(2) INFORMATION FOR SEQ ID NO: 1523:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 1523:

CAGAGCUGCU GAUGANGAAA AGUGCUU                                         27

(2) INFORMATION FOR SEQ ID NO: 1524:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:

(D) OTHER INFORMATION:  The letter "N" stands for the stem
                II region of a HH ribozyme.

(xi) SEQUENCE DESCRIPTION: SEQ ID NO: 1524:

UGUGGCCACU GAUGANGAAA GCUGUAA                                         27

(2) INFORMATION FOR SEQ ID NO: 1525:

(i) SEQUENCE CHARACTERISTICS:

(A) LENGTH:            27 base pairs
            (B) TYPE:              nucleic acid
            (C) STRANDEDNESS:      single
            (D) TOPOLOGY:          linear (ix) FEATURE:
```

(D) OTHER INFORMATION:   The letter "N" stands for the stem
                II region of a HH ribozyme.

(xi) SEQUENCE DESCRIPTION: SEQ ID NO: 1525:

ACCUGUAACU GAUGANGAAA UGCCCUG                                              27

(2) INFORMATION FOR SEQ ID NO: 1526:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1526:

CACCUGUACU GAUGANGAAA AUGCCCU                                              27

(2) INFORMATION FOR SEQ ID NO: 1527:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1527:

GCACCUGUCU GAUGANGAAA AAUGCCC                                              27

(2) INFORMATION FOR SEQ ID NO: 1528:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1528:

CGCACCUGCU GAUGANGAAA AAAUGCC                                              27

(2) INFORMATION FOR SEQ ID NO: 1529:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1529:

CAUAAUGCCU GAUGANGAAA CUGUCAU                                    27

(2) INFORMATION FOR SEQ ID NO: 1530:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION:   The letter "N" stands for the stem
         II region of a HH ribozyme.

(xi) SEQUENCE DESCRIPTION: SEQ ID NO: 1530:

CUACUCAUCU GAUGANGAAA UGCUACU                                    27

(2) INFORMATION FOR SEQ ID NO: 1531:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION:   The letter "N" stands for the stem
         II region of a HH ribozyme.

(xi) SEQUENCE DESCRIPTION: SEQ ID NO: 1531:

ACUACUCACU GAUGANGAAA AUGCUAC                                    27

(2) INFORMATION FOR SEQ ID NO: 1532:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION:   The letter "N" stands for the stem
         II region of a HH ribozyme.

(xi) SEQUENCE DESCRIPTION: SEQ ID NO: 1532:

AUUCACACCU GAUGANGAAA CUCAUAA                                    27

(2) INFORMATION FOR SEQ ID NO: 1533:

(i) SEQUENCE CHARACTERISTICS:

(A) LENGTH:           27 base pairs
      (B) TYPE:             nucleic acid
      (C) STRANDEDNESS:     single
      (D) TOPOLOGY:         linear (ix) FEATURE:

(D) OTHER INFORMATION:   The letter "N" stands for the stem
         II region of a HH ribozyme.

(xi) SEQUENCE DESCRIPTION: SEQ ID NO: 1533:

```
ACUACCUGCU GAUGANGAAA UUCACAC                                              27
```

(2) INFORMATION FOR SEQ ID NO: 1534:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1534:

```
UACUACCUCU GAUGANGAAA AUUCACA                                              27
```

(2) INFORMATION FOR SEQ ID NO: 1535:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1535:

```
AUAUUUACCU GAUGANGAAA CCUGAAU                                              27
```

(2) INFORMATION FOR SEQ ID NO: 1536:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1536:

```
UUCAUAUUCU GAUGANGAAA CUACCUG                                              27
```

(2) INFORMATION FOR SEQ ID NO: 1537:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1537:

```
UAGUUUCACU GAUGANGAAA UUUACUA                                              27
```

(2) INFORMATION FOR SEQ ID NO: 1538:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1538:

UCAAACCCCU GAUGANGAAA GUUUCAU                          27

(2) INFORMATION FOR SEQ ID NO: 1539:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1539:

CAAUUUCACU GAUGANGAAA CCCUAGU                          27

(2) INFORMATION FOR SEQ ID NO: 1540:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1540:

UCAAUUUCCU GAUGANGAAA ACCCUAG                          27

(2) INFORMATION FOR SEQ ID NO: 1541:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1541:

GCAUUAUCCU GAUGANGAAA UUUCAAA                          27

(2) INFORMATION FOR SEQ ID NO: 1542:

(i) SEQUENCE CHARACTERISTICS:

```
            (A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:   The letter "N" stands for the stem
                II region of a HH ribozyme.

(xi) SEQUENCE DESCRIPTION: SEQ ID NO: 1542:

GAAAGCAUCU GAUGANGAAA UCAAUUU                                        27

(2) INFORMATION FOR SEQ ID NO: 1543:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:   The letter "N" stands for the stem
                II region of a HH ribozyme.

(xi) SEQUENCE DESCRIPTION: SEQ ID NO: 1543:

UGUUGUGACU GAUGANGAAA GCAUUAU                                        27

(2) INFORMATION FOR SEQ ID NO: 1544:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:   The letter "N" stands for the stem
                II region of a HH ribozyme.

(xi) SEQUENCE DESCRIPTION: SEQ ID NO: 1544:

AUGUUGUGCU GAUGANGAAA AGCAUUA                                        27

(2) INFORMATION FOR SEQ ID NO: 1545:

(i) SEQUENCE CHARACTERISTICS:

(A) LENGTH:          27 base pairs
            (B) TYPE:            nucleic acid
            (C) STRANDEDNESS:    single
            (D) TOPOLOGY:        linear (ix) FEATURE:

(D) OTHER INFORMATION:   The letter "N" stands for the stem
                II region of a HH ribozyme.

(xi) SEQUENCE DESCRIPTION: SEQ ID NO: 1545:

AAUGUUGUCU GAUGANGAAA AAGCAUU                                        27

(2) INFORMATION FOR SEQ ID NO: 1546:

(i) SEQUENCE CHARACTERISTICS:

(A) LENGTH:          27 base pairs
            (B) TYPE:            nucleic acid
```

```
        (C)  STRANDEDNESS:       single
        (D)  TOPOLOGY:           linear (ix) FEATURE:

(D)  OTHER INFORMATION:  The letter "N" stands for the stem
             II region of a HH ribozyme.

(xi) SEQUENCE DESCRIPTION: SEQ ID NO: 1546:

CAUCUGCACU GAUGANGAAA UGUUGUG                                        27

(2) INFORMATION FOR SEQ ID NO: 1547:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear (ix) FEATURE:

(D)  OTHER INFORMATION:  The letter "N" stands for the stem
             II region of a HH ribozyme.

(xi) SEQUENCE DESCRIPTION: SEQ ID NO: 1547:

ACAUCUGCCU GAUGANGAAA AUGUUGU                                        27

(2) INFORMATION FOR SEQ ID NO: 1548:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear (ix) FEATURE:

(D)  OTHER INFORMATION:  The letter "N" stands for the stem
             II region of a HH ribozyme.

(xi) SEQUENCE DESCRIPTION: SEQ ID NO: 1548:

CCUUCUAACU GAUGANGAAA CAUCUGC                                        27

(2) INFORMATION FOR SEQ ID NO: 1549:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear (ix) FEATURE:

(D)  OTHER INFORMATION:  The letter "N" stands for the stem
             II region of a HH ribozyme.

(xi) SEQUENCE DESCRIPTION: SEQ ID NO: 1549:

UCCUUCUACU GAUGANGAAA ACAUCUG                                        27

(2) INFORMATION FOR SEQ ID NO: 1550:

(i)  SEQUENCE CHARACTERISTICS:

(A)  LENGTH:             27 base pairs
        (B)  TYPE:               nucleic acid
        (C)  STRANDEDNESS:       single
        (D)  TOPOLOGY:           linear
```

(ix) FEATURE:

(D) OTHER INFORMATION:    The letter "N" stands for the stem
                 II region of a HH ribozyme.

(xi) SEQUENCE DESCRIPTION: SEQ ID NO: 1550:

UUCCUUCUCU GAUGANGAAA AACAUCU                                              27

(2) INFORMATION FOR SEQ ID NO: 1551:

(i) SEQUENCE CHARACTERISTICS:

(A) LENGTH:           27 base pairs
             (B) TYPE:             nucleic acid
             (C) STRANDEDNESS:     single
             (D) TOPOLOGY:         linear (ix) FEATURE:

(D) OTHER INFORMATION:    The letter "N" stands for the stem
                 II region of a HH ribozyme.

(xi) SEQUENCE DESCRIPTION: SEQ ID NO: 1551:

UUUCCUUCCU GAUGANGAAA AAACAUC                                              27

(2) INFORMATION FOR SEQ ID NO: 1552:

(i) SEQUENCE CHARACTERISTICS:

(A) LENGTH:           27 base pairs
             (B) TYPE:             nucleic acid
             (C) STRANDEDNESS:     single
             (D) TOPOLOGY:         linear (ix) FEATURE:

(D) OTHER INFORMATION:    The letter "N" stands for the stem
                 II region of a HH ribozyme.

(xi) SEQUENCE DESCRIPTION: SEQ ID NO: 1552:

UAGGAAGGCU GAUGANGAAA CUUUUUU                                              27

(2) INFORMATION FOR SEQ ID NO: 1553:

(i) SEQUENCE CHARACTERISTICS:

(A) LENGTH:           27 base pairs
             (B) TYPE:             nucleic acid
             (C) STRANDEDNESS:     single
             (D) TOPOLOGY:         linear (ix) FEATURE:

(D) OTHER INFORMATION:    The letter "N" stands for the stem
                 II region of a HH ribozyme.

(xi) SEQUENCE DESCRIPTION: SEQ ID NO: 1553:

UUAGGAAGCU GAUGANGAAA ACUUUUU                                              27

(2) INFORMATION FOR SEQ ID NO: 1554:

(i) SEQUENCE CHARACTERISTICS:

(A) LENGTH:           27 base pairs
             (B) TYPE:             nucleic acid
             (C) STRANDEDNESS:     single
             (D) TOPOLOGY:         linear (ix) FEATURE:

(D) OTHER INFORMATION:    The letter "N" stands for the stem

II region of a HH ribozyme.

(xi) SEQUENCE DESCRIPTION: SEQ ID NO: 1554:

AUUUUAGGCU GAUGANGAAA GGAACUU                                           27

(2) INFORMATION FOR SEQ ID NO: 1555:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 1555:

UAUUUUAGCU GAUGANGAAA AGGAACU                                           27

(2) INFORMATION FOR SEQ ID NO: 1556:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 1556:

AAUUAUUUCU GAUGANGAAA GGAAGGA                                           27

(2) INFORMATION FOR SEQ ID NO: 1557:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 1557:

AGAGAAAUCU GAUGANGAAA UUUUAGG                                           27

(2) INFORMATION FOR SEQ ID NO: 1558:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:  The letter "N" stands for the stem
            II region of a HH ribozyme.

(xi) SEQUENCE DESCRIPTION: SEQ ID NO: 1558:

UGUAGAGACU GAUGANGAAA UUAUUUU                                              27

(2) INFORMATION FOR SEQ ID NO: 1559:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for the stem
            II region of a HH ribozyme.

(xi) SEQUENCE DESCRIPTION: SEQ ID NO: 1559:

UUGUAGAGCU GAUGANGAAA AUUAUUU                                              27

(2) INFORMATION FOR SEQ ID NO: 1560:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for the stem
            II region of a HH ribozyme.

(xi) SEQUENCE DESCRIPTION: SEQ ID NO: 1560:

AUUGUAGACU GAUGANGAAA AAUUAUU                                              27

(2) INFORMATION FOR SEQ ID NO: 1561:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for the stem
            II region of a HH ribozyme.

(xi) SEQUENCE DESCRIPTION: SEQ ID NO: 1561:

CAAUUGUACU GAUGANGAAA GAAAUUA                                              27

(2) INFORMATION FOR SEQ ID NO: 1562:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for the stem
            II region of a HH ribozyme.

(xi) SEQUENCE DESCRIPTION: SEQ ID NO: 1562:

UCCAAUUGCU GAUGANGAAA GAGAAAU                                              27

(2) INFORMATION FOR SEQ ID NO: 1563:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION: The letter "N" stands for the stem
            II region of a HH ribozyme.

(xi) SEQUENCE DESCRIPTION: SEQ ID NO: 1563:

AAUCUUCCCU GAUGANGAAA UUGUAGA                          27

(2) INFORMATION FOR SEQ ID NO: 1564:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION: The letter "N" stands for the stem
            II region of a HH ribozyme.

(xi) SEQUENCE DESCRIPTION: SEQ ID NO: 1564:

AAUCUUCCCU GAUGANGAAA UCUUCCA                          27

(2) INFORMATION FOR SEQ ID NO: 1565:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION: The letter "N" stands for the stem
            II region of a HH ribozyme.

(xi) SEQUENCE DESCRIPTION: SEQ ID NO: 1565:

ACUAGCUGCU GAUGANGAAA UCUUCCA                          27

(2) INFORMATION FOR SEQ ID NO: 1566:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION: The letter "N" stands for the stem
            II region of a HH ribozyme.

(xi) SEQUENCE DESCRIPTION: SEQ ID NO: 1566:

AACUAGCUCU GAUGANGAAA AUCUUCC                          27

(2) INFORMATION FOR SEQ ID NO: 1567:

```
        (i)  SEQUENCE CHARACTERISTICS:

(A)  LENGTH:              27 base pairs
             (B)  TYPE:                nucleic acid
             (C)  STRANDEDNESS:        single
             (D)  TOPOLOGY:            linear (ix)  FEATURE:

(D)  OTHER INFORMATION:   The letter "N" stands for the stem
                  II region of a HH ribozyme.

(xi)  SEQUENCE DESCRIPTION: SEQ ID NO: 1567:

CUCCUAACCU GAUGANGAAA GCUGAAU                                               27

(2)  INFORMATION FOR SEQ ID NO: 1568:

(i)  SEQUENCE CHARACTERISTICS:

(A)  LENGTH:              27 base pairs
             (B)  TYPE:                nucleic acid
             (C)  STRANDEDNESS:        single
             (D)  TOPOLOGY:            linear (ix)  FEATURE:

(D)  OTHER INFORMATION:   The letter "N" stands for the stem
                  II region of a HH ribozyme.

(xi)  SEQUENCE DESCRIPTION: SEQ ID NO: 1568:

GGGCUCCUCU GAUGANGAAA CUAGCUG                                               27

(2)  INFORMATION FOR SEQ ID NO: 1569:

(i)  SEQUENCE CHARACTERISTICS:

(A)  LENGTH:              27 base pairs
             (B)  TYPE:                nucleic acid
             (C)  STRANDEDNESS:        single
             (D)  TOPOLOGY:            linear (ix)  FEATURE:

(D)  OTHER INFORMATION:   The letter "N" stands for the stem
                  II region of a HH ribozyme.

(xi)  SEQUENCE DESCRIPTION: SEQ ID NO: 1569:

UGGGCUCCCU GAUGANGAAA ACUAGCU                                               27

(2)  INFORMATION FOR SEQ ID NO: 1570:

(i)  SEQUENCE CHARACTERISTICS:

(A)  LENGTH:              27 base pairs
             (B)  TYPE:                nucleic acid
             (C)  STRANDEDNESS:        single
             (D)  TOPOLOGY:            linear (ix)  FEATURE:

(D)  OTHER INFORMATION:   The letter "N" stands for the stem
                  II region of a HH ribozyme.

(xi)  SEQUENCE DESCRIPTION: SEQ ID NO: 1570:

UAGGAAAACU GAUGANGAAA UGGGCUC                                               27

(2)  INFORMATION FOR SEQ ID NO: 1571:

(i)  SEQUENCE CHARACTERISTICS:

(A)  LENGTH:              27 base pairs
```

```
            (B)  TYPE:              nucleic acid
            (C)  STRANDEDNESS:      single
            (D)  TOPOLOGY:          linear (ix)  FEATURE:

(D)  OTHER INFORMATION:   The letter "N" stands for the stem
                 II region of a HH ribozyme.

(xi)  SEQUENCE DESCRIPTION: SEQ ID NO: 1571:

UUAGGAAACU GAUGANGAAA AUGGGCU                                          27

(2)  INFORMATION FOR SEQ ID NO: 1572:

(i)  SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix)  FEATURE:

(D)  OTHER INFORMATION:   The letter "N" stands for the stem
                 II region of a HH ribozyme.

(xi)  SEQUENCE DESCRIPTION: SEQ ID NO: 1572:

AUUAGGAACU GAUGANGAAA AAUGGGC                                          27

(2)  INFORMATION FOR SEQ ID NO: 1573:

(i)  SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix)  FEATURE:

(D)  OTHER INFORMATION:   The letter "N" stands for the stem
                 II region of a HH ribozyme.

(xi)  SEQUENCE DESCRIPTION: SEQ ID NO: 1573:

GAUUAGGACU GAUGANGAAA AAAUGGG                                          27

(2)  INFORMATION FOR SEQ ID NO: 1574:

(i)  SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear (ix)  FEATURE:

(D)  OTHER INFORMATION:   The letter "N" stands for the stem
                 II region of a HH ribozyme.

(xi)  SEQUENCE DESCRIPTION: SEQ ID NO: 1574:

AGAUUAGGCU GAUGANGAAA AAAAUGG                                          27

(2)  INFORMATION FOR SEQ ID NO: 1575:

(i)  SEQUENCE CHARACTERISTICS:

(A)  LENGTH:            27 base pairs
            (B)  TYPE:              nucleic acid
            (C)  STRANDEDNESS:      single
            (D)  TOPOLOGY:          linear
```

(ix) FEATURE:

(D) OTHER INFORMATION:   The letter "N" stands for the stem
                  II region of a HH ribozyme.

(xi) SEQUENCE DESCRIPTION: SEQ ID NO: 1575:

CAGAUUAGCU GAUGANGAAA AAAAAUG                                              27

(2) INFORMATION FOR SEQ ID NO: 1576:

(i) SEQUENCE CHARACTERISTICS:

(A) LENGTH:             27 base pairs
              (B) TYPE:               nucleic acid
              (C) STRANDEDNESS:       single
              (D) TOPOLOGY:           linear (ix) FEATURE:

(D) OTHER INFORMATION:   The letter "N" stands for the stem
                  II region of a HH ribozyme.

(xi) SEQUENCE DESCRIPTION: SEQ ID NO: 1576:

ACACAGAUCU GAUGANGAAA GGAAAAA                                              27

(2) INFORMATION FOR SEQ ID NO: 1577:

(i) SEQUENCE CHARACTERISTICS:

(A) LENGTH:             27 base pairs
              (B) TYPE:               nucleic acid
              (C) STRANDEDNESS:       single
              (D) TOPOLOGY:           linear (ix) FEATURE:

(D) OTHER INFORMATION:   The letter "N" stands for the stem
                  II region of a HH ribozyme.

(xi) SEQUENCE DESCRIPTION: SEQ ID NO: 1577:

CACACACACU GAUGANGAAA UUAGGAA                                              27

(2) INFORMATION FOR SEQ ID NO: 1578:

(i) SEQUENCE CHARACTERISTICS:

(A) LENGTH:             27 base pairs
              (B) TYPE:               nucleic acid
              (C) STRANDEDNESS:       single
              (D) TOPOLOGY:           linear (ix) FEATURE:

(D) OTHER INFORMATION:   The letter "N" stands for the stem
                  II region of a HH ribozyme.

(xi) SEQUENCE DESCRIPTION: SEQ ID NO: 1578:

AGUCAGGUCU GAUGANGAAA CAGGGCA                                              27

(2) INFORMATION FOR SEQ ID NO: 1579:

(i) SEQUENCE CHARACTERISTICS:

(A) LENGTH:             27 base pairs
              (B) TYPE:               nucleic acid
              (C) STRANDEDNESS:       single
              (D) TOPOLOGY:           linear (ix) FEATURE:

(D) OTHER INFORMATION:    The letter "N" stands for the stem
               II region of a HH ribozyme.

(xi) SEQUENCE DESCRIPTION: SEQ ID NO: 1579:

CUGCUGUUCU GAUGANGAAA CCAGUCA                                              27

(2) INFORMATION FOR SEQ ID NO: 1580:

(i) SEQUENCE CHARACTERISTICS:

(A) LENGTH:              27 base pairs
           (B) TYPE:                nucleic acid
           (C) STRANDEDNESS:        single
           (D) TOPOLOGY:            linear (ix) FEATURE:

(D) OTHER INFORMATION:    The letter "N" stands for the stem
               II region of a HH ribozyme.

(xi) SEQUENCE DESCRIPTION: SEQ ID NO: 1580:

ACUGCUGUCU GAUGANGAAA ACCAGUC                                              27

(2) INFORMATION FOR SEQ ID NO: 1581:

(i) SEQUENCE CHARACTERISTICS:

(A) LENGTH:              27 base pairs
           (B) TYPE:                nucleic acid
           (C) STRANDEDNESS:        single
           (D) TOPOLOGY:            linear (ix) FEATURE:

(D) OTHER INFORMATION:    The letter "N" stands for the stem
               II region of a HH ribozyme.

(xi) SEQUENCE DESCRIPTION: SEQ ID NO: 1581:

UUACAAAGCU GAUGANGAAA CUGCUGU                                              27

(2) INFORMATION FOR SEQ ID NO: 1582:

(i) SEQUENCE CHARACTERISTICS:

(A) LENGTH:              27 base pairs
           (B) TYPE:                nucleic acid
           (C) STRANDEDNESS:        single
           (D) TOPOLOGY:            linear (ix) FEATURE:

(D) OTHER INFORMATION:    The letter "N" stands for the stem
               II region of a HH ribozyme.

(xi) SEQUENCE DESCRIPTION: SEQ ID NO: 1582:

UGUUUACACU GAUGANGAAA GGACUGC                                              27

(2) INFORMATION FOR SEQ ID NO: 1583:

(i) SEQUENCE CHARACTERISTICS:

(A) LENGTH:              27 base pairs
           (B) TYPE:                nucleic acid
           (C) STRANDEDNESS:        single
           (D) TOPOLOGY:            linear (ix) FEATURE:

(D) OTHER INFORMATION:    The letter "N" stands for the stem
               II region of a HH ribozyme.

(xi) SEQUENCE DESCRIPTION: SEQ ID NO: 1583:

CUGUUUACCU GAUGANGAAA AGGACUG                27

(2) INFORMATION FOR SEQ ID NO: 1584:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION: The letter "N" stands for the stem
        II region of a HH ribozyme.

(xi) SEQUENCE DESCRIPTION: SEQ ID NO: 1584:

ACACUGUUCU GAUGANGAAA CAAAGGA                27

(2) INFORMATION FOR SEQ ID NO: 1585:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION: The letter "N" stands for the stem
        II region of a HH ribozyme.

(xi) SEQUENCE DESCRIPTION: SEQ ID NO: 1585:

GAGUUUAACU GAUGANGAAA CACUGUU                27

(2) INFORMATION FOR SEQ ID NO: 1586:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION: The letter "N" stands for the stem
        II region of a HH ribozyme.

(xi) SEQUENCE DESCRIPTION: SEQ ID NO: 1586:

AGAGUUUACU GAUGANGAAA ACACUGU                27

(2) INFORMATION FOR SEQ ID NO: 1587:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION: The letter "N" stands for the stem
        II region of a HH ribozyme.

(xi) SEQUENCE DESCRIPTION: SEQ ID NO: 1587:

GAGAGUUUCU GAUGANGAAA AACACUG                27

(2) INFORMATION FOR SEQ ID NO: 1588:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1588:

GGAGAGUUCU GAUGANGAAA AAACACU                                              27

(2) INFORMATION FOR SEQ ID NO: 1589:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1589:

GACUAGGACU GAUGANGAAA GUUUAAA                                              27

(2) INFORMATION FOR SEQ ID NO: 1590:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1590:

UUGACUAGCU GAUGANGAAA GAGUUUA                                              27

(2) INFORMATION FOR SEQ ID NO: 1591:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1591:

AUAUUGACCU GAUGANGAAA GGAGAGU                                              27

(2) INFORMATION FOR SEQ ID NO: 1592:

```
        (i)  SEQUENCE CHARACTERISTICS:

(A)  LENGTH:              27 base pairs
             (B)  TYPE:                nucleic acid
             (C)  STRANDEDNESS:        single
             (D)  TOPOLOGY:            linear (ix)  FEATURE:

(D)  OTHER INFORMATION:   The letter "N" stands for the stem
                  II region of a HH ribozyme.

(xi)  SEQUENCE DESCRIPTION: SEQ ID NO: 1592:

UGGAUAUUCU GAUGANGAAA CUAGGAG                                              27

(2)  INFORMATION FOR SEQ ID NO: 1593:

(i)  SEQUENCE CHARACTERISTICS:

(A)  LENGTH:              27 base pairs
             (B)  TYPE:                nucleic acid
             (C)  STRANDEDNESS:        single
             (D)  TOPOLOGY:            linear (ix)  FEATURE:

(D)  OTHER INFORMATION:   The letter "N" stands for the stem
                  II region of a HH ribozyme.

(xi)  SEQUENCE DESCRIPTION: SEQ ID NO: 1593:

GGGGUGGACU GAUGANGAAA UUGACUA                                              27

(2)  INFORMATION FOR SEQ ID NO: 1594:

(i)  SEQUENCE CHARACTERISTICS:

(A)  LENGTH:              27 base pairs
             (B)  TYPE:                nucleic acid
             (C)  STRANDEDNESS:        single
             (D)  TOPOLOGY:            linear (ix)  FEATURE:

(D)  OTHER INFORMATION:   The letter "N" stands for the stem
                  II region of a HH ribozyme.

(xi)  SEQUENCE DESCRIPTION: SEQ ID NO: 1594:

AUGGGGUGCU GAUGANGAAA UAUUGAC                                              27

(2)  INFORMATION FOR SEQ ID NO: 1595:

(i)  SEQUENCE CHARACTERISTICS:

(A)  LENGTH:              27 base pairs
             (B)  TYPE:                nucleic acid
             (C)  STRANDEDNESS:        single
             (D)  TOPOLOGY:            linear (ix)  FEATURE:

(D)  OTHER INFORMATION:   The letter "N" stands for the stem
                  II region of a HH ribozyme.

(xi)  SEQUENCE DESCRIPTION: SEQ ID NO: 1595:

AUAAAUUGCU GAUGANGAAA UGGGGUG                                              27

(2)  INFORMATION FOR SEQ ID NO: 1596:

(i)  SEQUENCE CHARACTERISTICS:
```

```
            (A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1596:

CCUUGAUACU GAUGANGAAA UUGGAUG                                            27

(2) INFORMATION FOR SEQ ID NO: 1597:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1597:

UCCUUGAUCU GAUGANGAAA AUUGGAU                                            27

(2) INFORMATION FOR SEQ ID NO: 1598:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1598:

UUCCUUGACU GAUGANGAAA AAUUGGA                                            27

(2) INFORMATION FOR SEQ ID NO: 1599:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1599:

UCUUCCUUCU GAUGANGAAA UAAAUUG                                            27

(2) INFORMATION FOR SEQ ID NO: 1600:

(i) SEQUENCE CHARACTERISTICS:

(A)  LENGTH:             27 base pairs
            (B)  TYPE:               nucleic acid
            (C)  STRANDEDNESS:       single
```

(D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1600:

AUUUUCUGCU GAUGANGAAA CCAUUUC                                              27

(2) INFORMATION FOR SEQ ID NO: 1601:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1601:

UAUUUUCUCU GAUGANGAAA ACCAUUU                                              27

(2) INFORMATION FOR SEQ ID NO: 1602:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1602:

GCUGAAAACU GAUGANGAAA UUUUCUG                                              27

(2) INFORMATION FOR SEQ ID NO: 1603:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D)  OTHER INFORMATION:  The letter "N" stands for the stem
                 II region of a HH ribozyme.

(xi) SEQUENCE DESCRIPTION: SEQ ID NO: 1603:

AGGCUGAACU GAUGANGAAA UAUUUUC                                              27

(2) INFORMATION FOR SEQ ID NO: 1604:

(i) SEQUENCE CHARACTERISTICS:

(A)  LENGTH:             27 base pairs
            (B)  TYPE:               nucleic acid
            (C)  STRANDEDNESS:       single
            (D)  TOPOLOGY:           linear (ix) FEATURE:

(D) OTHER INFORMATION:   The letter "N" stands for the stem
            II region of a HH ribozyme.

(xi) SEQUENCE DESCRIPTION: SEQ ID NO: 1604:

UAGGCUGACU GAUGANGAAA AUAUUUU                                           27

(2) INFORMATION FOR SEQ ID NO: 1605:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 1605:

GUAGGCUGCU GAUGANGAAA AAUAUUU                                           27

(2) INFORMATION FOR SEQ ID NO: 1606:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 1606:

UGUAGGCUCU GAUGANGAAA AAAUAUU                                           27

(2) INFORMATION FOR SEQ ID NO: 1607:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 1607:

CAUAACUGCU GAUGANGAAA GGCUGAA                                           27

(2) INFORMATION FOR SEQ ID NO: 1608:

(i) SEQUENCE CHARACTERISTICS:

(A) LENGTH:              27 base pairs
        (B) TYPE:                nucleic acid
        (C) STRANDEDNESS:        single
        (D) TOPOLOGY:            linear (ix) FEATURE:

(D) OTHER INFORMATION:   The letter "N" stands for the stem
            II region of a HH ribozyme.

(xi) SEQUENCE DESCRIPTION: SEQ ID NO: 1608:

CUGAACAUCU GAUGANGAAA CUGUAGG                                              27

(2) INFORMATION FOR SEQ ID NO: 1609:

(i) SEQUENCE CHARACTERISTICS:

(A) LENGTH:          27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 1609:

ACUGAACACU GAUGANGAAA ACUGUAG                                              27

(2) INFORMATION FOR SEQ ID NO: 1610:

(i) SEQUENCE CHARACTERISTICS:

(A) LENGTH:          27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 1610:

UGUGACUGCU GAUGANGAAA CAUAACU                                              27

(2) INFORMATION FOR SEQ ID NO: 1611:

(i) SEQUENCE CHARACTERISTICS:

(A) LENGTH:          27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 1611:

GUGUGACUCU GAUGANGAAA ACAUAAC                                              27

(2) INFORMATION FOR SEQ ID NO: 1612:

(i) SEQUENCE CHARACTERISTICS:

(A) LENGTH:          27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 1612:

```
GUGUGUGUCU GAUGANGAAA CUGAACA                                                27
```

(2) INFORMATION FOR SEQ ID NO: 1613:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem
         II region of a HH ribozyme.

(xi) SEQUENCE DESCRIPTION: SEQ ID NO: 1613:

```
ACAUUUUGCU GAUGANGAAA UGUGUGU                                                27
```

(2) INFORMATION FOR SEQ ID NO: 1614:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem
         II region of a HH ribozyme.

(xi) SEQUENCE DESCRIPTION: SEQ ID NO: 1614:

```
GCAAAAGGCU GAUGANGAAA CAUUUUG                                                27
```

(2) INFORMATION FOR SEQ ID NO: 1615:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem
         II region of a HH ribozyme.

(xi) SEQUENCE DESCRIPTION: SEQ ID NO: 1615:

```
AGCAAAAGCU GAUGANGAAA ACAUUUU                                                27
```

(2) INFORMATION FOR SEQ ID NO: 1616:

(i) SEQUENCE CHARACTERISTICS:

(A) LENGTH:          27 base pairs
      (B) TYPE:            nucleic acid
      (C) STRANDEDNESS:    single
      (D) TOPOLOGY:        linear (ix) FEATURE:

(D) OTHER INFORMATION: The letter "N" stands for the stem
         II region of a HH ribozyme.

(xi) SEQUENCE DESCRIPTION: SEQ ID NO: 1616:

```
AAAAGCAACU GAUGANGAAA GGAACAU                                                27
```

(2) INFORMATION FOR SEQ ID NO: 1617:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 1617:

UAAAAGCACU GAUGANGAAA AGGAACA                                          27

(2) INFORMATION FOR SEQ ID NO: 1618:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 1618:

UUAAAAGCCU GAUGANGAAA AAGGAAC                                          27

(2) INFORMATION FOR SEQ ID NO: 1619:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 1619:

UACUUUAACU GAUGANGAAA GCAAAAG                                          27

(2) INFORMATION FOR SEQ ID NO: 1620:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:   The letter "N" stands for the stem
            II region of a HH ribozyme.

(xi) SEQUENCE DESCRIPTION: SEQ ID NO: 1620:

UUACUUUACU GAUGANGAAA AGCAAAA                                          27

(2) INFORMATION FOR SEQ ID NO: 1621:

(i) SEQUENCE CHARACTERISTICS:

```
            (A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1621:

AUUACUUUCU GAUGANGAAA AAGCAAA                                       27

(2) INFORMATION FOR SEQ ID NO: 1622:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1622:

AAUUACUUCU GAUGANGAAA AAAGCAA                                       27

(2) INFORMATION FOR SEQ ID NO: 1623:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1623:

UCAAAAAUCU GAUGANGAAA CUUUAAA                                       27

(2) INFORMATION FOR SEQ ID NO: 1624:

(i) SEQUENCE CHARACTERISTICS:

(A) LENGTH:              27 base pairs
            (B) TYPE:                nucleic acid
            (C) STRANDEDNESS:        single
            (D) TOPOLOGY:            linear (ix) FEATURE:

(D) OTHER INFORMATION:   The letter "N" stands for the stem
                II region of a HH ribozyme.

(xi) SEQUENCE DESCRIPTION: SEQ ID NO: 1624:

GAGUCAAACU GAUGANGAAA UUACUUU                                       27

(2) INFORMATION FOR SEQ ID NO: 1625:

(i) SEQUENCE CHARACTERISTICS:

(A) LENGTH:              27 base pairs
            (B) TYPE:                nucleic acid
```

```
              (C)  STRANDEDNESS:        single
              (D)  TOPOLOGY:            linear (ix) FEATURE:

(D)  OTHER INFORMATION:   The letter "N" stands for the stem
                   II region of a HH ribozyme.

(xi) SEQUENCE DESCRIPTION: SEQ ID NO: 1625:

GGAGUCAACU GAUGANGAAA AUUACUU                                         27

(2)  INFORMATION FOR SEQ ID NO: 1626:

(i)  SEQUENCE CHARACTERISTICS:

(A)  LENGTH:              27 base pairs
              (B)  TYPE:                nucleic acid
              (C)  STRANDEDNESS:        single
              (D)  TOPOLOGY:            linear (ix) FEATURE:

(D)  OTHER INFORMATION:   The letter "N" stands for the stem
                   II region of a HH ribozyme.

(xi) SEQUENCE DESCRIPTION: SEQ ID NO: 1626:

GGGAGUCACU GAUGANGAAA AAUUACU                                         27

(2)  INFORMATION FOR SEQ ID NO: 1627:

(i)  SEQUENCE CHARACTERISTICS:

(A)  LENGTH:              27 base pairs
              (B)  TYPE:                nucleic acid
              (C)  STRANDEDNESS:        single
              (D)  TOPOLOGY:            linear (ix) FEATURE:

(D)  OTHER INFORMATION:   The letter "N" stands for the stem
                   II region of a HH ribozyme.

(xi) SEQUENCE DESCRIPTION: SEQ ID NO: 1627:

UGGGAGUCCU GAUGANGAAA AAAUUAC                                         27

(2)  INFORMATION FOR SEQ ID NO: 1628:

(i)  SEQUENCE CHARACTERISTICS:

(A)  LENGTH:              27 base pairs
              (B)  TYPE:                nucleic acid
              (C)  STRANDEDNESS:        single
              (D)  TOPOLOGY:            linear (ix) FEATURE:

(D)  OTHER INFORMATION:   The letter "N" stands for the stem
                   II region of a HH ribozyme.

(xi) SEQUENCE DESCRIPTION: SEQ ID NO: 1628:

UGAUCUGGCU GAUGANGAAA GUCAAAA                                         27

(2)  INFORMATION FOR SEQ ID NO: 1629:

(i)  SEQUENCE CHARACTERISTICS:

(A)  LENGTH:              27 base pairs
              (B)  TYPE:                nucleic acid
              (C)  STRANDEDNESS:        single
              (D)  TOPOLOGY:            linear
```

(ix) FEATURE:

(D) OTHER INFORMATION:   The letter "N" stands for the stem
                  II region of a HH ribozyme.

(xi) SEQUENCE DESCRIPTION: SEQ ID NO: 1629:

CUCUGACUCU GAUGANGAAA UCUGGGA                                              27

(2) INFORMATION FOR SEQ ID NO: 1630:

(i) SEQUENCE CHARACTERISTICS:

(A) LENGTH:              27 base pairs
              (B) TYPE:                nucleic acid
              (C) STRANDEDNESS:        single
              (D) TOPOLOGY:            linear (ix) FEATURE:

(D) OTHER INFORMATION:   The letter "N" stands for the stem
                  II region of a HH ribozyme.

(xi) SEQUENCE DESCRIPTION: SEQ ID NO: 1630:

GGGGCUCUCU GAUGANGAAA CUGAUCU                                              27

(2) INFORMATION FOR SEQ ID NO: 1631:

(i) SEQUENCE CHARACTERISTICS:

(A) LENGTH:              27 base pairs
              (B) TYPE:                nucleic acid
              (C) STRANDEDNESS:        single
              (D) TOPOLOGY:            linear (ix) FEATURE:

(D) OTHER INFORMATION:   The letter "N" stands for the stem
                  II region of a HH ribozyme.

(xi) SEQUENCE DESCRIPTION: SEQ ID NO: 1631:

CAAUGCUGCU GAUGANGAAA GGGGCUC                                              27

(2) INFORMATION FOR SEQ ID NO: 1632:

(i) SEQUENCE CHARACTERISTICS:

(A) LENGTH:              27 base pairs
              (B) TYPE:                nucleic acid
              (C) STRANDEDNESS:        single
              (D) TOPOLOGY:            linear (ix) FEATURE:

(D) OTHER INFORMATION:   The letter "N" stands for the stem
                  II region of a HH ribozyme.

(xi) SEQUENCE DESCRIPTION: SEQ ID NO: 1632:

UUCUUAACCU GAUGANGAAA UGCUGUA                                              27

(2) INFORMATION FOR SEQ ID NO: 1633:

(i) SEQUENCE CHARACTERISTICS:

(A) LENGTH:              27 base pairs
              (B) TYPE:                nucleic acid
              (C) STRANDEDNESS:        single
              (D) TOPOLOGY:            linear (ix) FEATURE:

(D) OTHER INFORMATION:   The letter "N" stands for the stem

-continued

II region of a HH ribozyme.

(xi) SEQUENCE DESCRIPTION: SEQ ID NO: 1633:

ACUUCUUCU GAUGANGAAA CAAUGCU                                              27

(2) INFORMATION FOR SEQ ID NO: 1634:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION: The letter "N" stands for the stem
            II region of a HH ribozyme.

(xi) SEQUENCE DESCRIPTION: SEQ ID NO: 1634:

UACUUUCUCU GAUGANGAAA ACAAUGC                                             27

(2) INFORMATION FOR SEQ ID NO: 1635:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION: The letter "N" stands for the stem
            II region of a HH ribozyme.

FEATURE:

(D) OTHER INFORMATION: The letter "N" stands for the stem
            II region of a HH ribozyme.

(xi) SEQUENCE DESCRIPTION: SEQ ID NO: 1635:

AAAUCAAACU GAUGANGAAA CUUUCUU                                             27

2) INFORMATION FOR SEQ ID NO: 1636:

(i) SEQUENCE CHARACTERISTICS:

(A) LENGTH:          27 base pairs
        (B) TYPE:            nucleic acid
        (C) STRANDEDNESS:    single
        (D) TOPOLOGY:        linear (ix) FEATURE:

(D) OTHER INFORMATION: The letter "N" stands for the stem
            II region of a HH ribozyme.

(ix) FEATURE:

(D) OTHER INFORMATION: The letter "N" stands for the stem
            II region of a HH ribozyme.

(xi) SEQUENCE DESCRIPTION: SEQ ID NO: 1636:

AAAAAUCACU GAUGANGAAA UACUUUC                                         27

(2) INFORMATION FOR SEQ ID NO: 1637:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 1637:

CAAAAAUCCU GAUGANGAAA AUACUUU                                          27

(2) INFORMATION FOR SEQ ID NO: 1638:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 1638:

GAGACAAACU GAUGANGAAA UCAAAUA                                          27

(2) INFORMATION FOR SEQ ID NO: 1639:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 1639:

UGAGACAACU GAUGANGAAA AUCAAAU                                          27

(2) INFORMATION FOR SEQ ID NO: 1640:

(i) SEQUENCE CHARACTERISTICS:

(A) LENGTH:           27 base pairs
        (B) TYPE:             nucleic acid
        (C) STRANDEDNESS:     single
        (D) TOPOLOGY:         linear (ix) FEATURE:

(D) OTHER INFORMATION:  The letter "N" stands for the stem
            II region of a HH ribozyme.

(xi) SEQUENCE DESCRIPTION: SEQ ID NO: 1640:

UUGAGACACU GAUGANGAAA AAUCAAA                                          27

(2) INFORMATION FOR SEQ ID NO: 1641:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1641:

AUUGAGACCU GAUGANGAAA AAAUCAA                           27

(2) INFORMATION FOR SEQ ID NO: 1642:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1642:

UUCAUUGACU GAUGANGAAA CAAAAAU                           27

(2) INFORMATION FOR SEQ ID NO: 1643:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1643:

UUUUCAUUCU GAUGANGAAA GACAAAA                           27

(2) INFORMATION FOR SEQ ID NO: 1644:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:

(D) OTHER INFORMATION: The letter "N" stands for the stem II region of a HH ribozyme.

(xi) SEQUENCE DESCRIPTION: SEQ ID NO: 1644:

UAUAGUUUCU GAUGANGAAA UUUUCAU                           27

(2) INFORMATION FOR SEQ ID NO: 1645:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION:  The letter "N" stands for the stem
          II region of a HH ribozyme.

(xi) SEQUENCE DESCRIPTION: SEQ ID NO: 1645:

AAUGAAUACU GAUGANGAAA GUUUUAU                                            27

(2) INFORMATION FOR SEQ ID NO: 1646:

(i) SEQUENCE CHARACTERISTICS:

(A) LENGTH:         27 base pairs
      (B) TYPE:           nucleic acid
      (C) STRANDEDNESS:   single
      (D) TOPOLOGY:       linear (ix) FEATURE:

(D) OTHER INFORMATION:  The letter "N" stands for the stem
          II region of a HH ribozyme.

(xi) SEQUENCE DESCRIPTION: SEQ ID NO: 1646:

GAAAUGAACU GAUGANGAAA UAGUUUU                                            27

(2) INFORMATION FOR SEQ ID NO: 1647:

(i) SEQUENCE CHARACTERISTICS:

(A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1647:

GGCGGCAGAA GCGCACCAGA GAAACACACG UUGUGGUACA UUACCUGGUA                   50

(2) INFORMATION FOR SEQ ID NO: 1648:

(i) SEQUENCE CHARACTERISTICS:

(A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1648:

CUGGGCAGAA GCGGACCAGA GAAACACACG UUGUGGUACA UUACCUGGUA                   50

(2) INFORMATION FOR SEQ ID NO: 1649:

(i) SEQUENCE CHARACTERISTICS:

(A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1649:

GGUCUGAGAA GCGGACCAGA GAAACACACG UUGUGGUACA UUACCUGGUA                   50

(2) INFORMATION FOR SEQ ID NO: 1650:

```
    (i) SEQUENCE CHARACTERISTICS:
         (A) LENGTH:          50 base pairs
         (B) TYPE:             nucleic acid
         (C) STRANDEDNESS:    single
         (D) TOPOLOGY:        linear (xi) SEQUENCE DESCRIPTION: SEQ ID NO: 1650:

CGUCCGAGAA GGGCACCAGA GAAACACACG UUGUGGUACA UUACCUGGUA          50

(2) INFORMATION FOR SEQ ID NO: 1651:

(i) SEQUENCE CHARACTERISTICS:
         (A) LENGTH:          50 base pairs
         (B) TYPE:             nucleic acid
         (C) STRANDEDNESS:    single
         (D) TOPOLOGY:        linear (xi) SEQUENCE DESCRIPTION: SEQ ID NO: 1651:

CCUGUCAGAA GGUCACCAGA GAAACACACG UUGUGGUACA UUACCUGGUA          50

(2) INFORMATION FOR SEQ ID NO: 1652:

(i) SEQUENCE CHARACTERISTICS:
         (A) LENGTH:          50 base pairs
         (B) TYPE:             nucleic acid
         (C) STRANDEDNESS:    single
         (D) TOPOLOGY:        linear (xi) SEQUENCE DESCRIPTION: SEQ ID NO: 1652:

GACUCGAGAA GACGACCAGA GAAACACACG UUGUGGUACA UUACCUGGUA          50

(2) INFORMATION FOR SEQ ID NO: 1653:

(i) SEQUENCE CHARACTERISTICS:
         (A) LENGTH:          50 base pairs
         (B) TYPE:             nucleic acid
         (C) STRANDEDNESS:    single
         (D) TOPOLOGY:        linear (xi) SEQUENCE DESCRIPTION: SEQ ID NO: 1653:

CGGCGAAGAA GGGAACCAGA GAAACACACG UUGUGGUACA UUACCUGGUA          50

(2) INFORMATION FOR SEQ ID NO: 1654:

(i) SEQUENCE CHARACTERISTICS:
         (A) LENGTH:          50 base pairs
         (B) TYPE:             nucleic acid
         (C) STRANDEDNESS:    single
         (D) TOPOLOGY:        linear (xi) SEQUENCE DESCRIPTION: SEQ ID NO: 1654:

UCAGGGAGAA GUGCACCAGA GAAACACACG UUGUGGUACA UUACCUGGUA          50

(2) INFORMATION FOR SEQ ID NO: 1655:

(i) SEQUENCE CHARACTERISTICS:
         (A) LENGTH:          50 base pairs
         (B) TYPE:             nucleic acid
         (C) STRANDEDNESS:    single
         (D) TOPOLOGY:        linear
```

(xi) SEQUENCE DESCRIPTION: SEQ ID NO: 1655:

GACGGAAGAA GGGGACCAGA GAAACACACG UUGUGGUACA UUACCUGGUA          50

(2) INFORMATION FOR SEQ ID NO: 1656:

(i) SEQUENCE CHARACTERISTICS:
        (A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1656:

GAUACUGAGAA GAGUACCAGA GAAACACACG UUGUGGUACA UUACCUGGUA         50

(2) INFORMATION FOR SEQ ID NO: 1657:

(i) SEQUENCE CHARACTERISTICS:
        (A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1657:

UGCCCCAGAA GUCCACCAGA GAAACACACG UUGUGGUACA UUACCUGGUA          50

(2) INFORMATION FOR SEQ ID NO: 1658:

(i) SEQUENCE CHARACTERISTICS:
        (A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1658:

GCAGCCAGAA GCGCACCAGA GAAACACACG UUGUGGUACA UUACCUGGUA          50

(2) INFORMATION FOR SEQ ID NO: 1659:

(i) SEQUENCE CHARACTERISTICS:
        (A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1659:

UCGCCGAGAA GAGCACCAGA GAAACACACG UUGUGGUACA UUACCUGGUA          50

(2) INFORMATION FOR SEQ ID NO: 1660:

(i) SEQUENCE CHARACTERISTICS:
        (A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1660:

GUGCCCAGAA GCGUACCAGA GAAACACACG UUGUGGUACA UUACCUGGUA          50

```
(2) INFORMATION FOR SEQ ID NO: 1661:

(i) SEQUENCE CHARACTERISTICS:

(A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1661:

UCUGGAAGAA GAGAACCAGA GAAACACACG UUGUGGUACA UUACCUGGUA              50

(2) INFORMATION FOR SEQ ID NO: 1662:

(i) SEQUENCE CHARACTERISTICS:

(A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1662:

CUGAUGAGAA GCAGACCAGA GAAACACACG UUGUGGUACA UUACCUGGUA              50

(2) INFORMATION FOR SEQ ID NO: 1663:

(i) SEQUENCE CHARACTERISTICS:

(A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1663:

AGAUAAAGAA GCUAACCAGA GAAACACACG UUGUGGUACA UUACCUGGUA              50

(2) INFORMATION FOR SEQ ID NO: 1664:

(i) SEQUENCE CHARACTERISTICS:

(A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1664:

CCUUCAAGAA GGUUACCAGA GAAACACACG UUGUGGUACA UUACCUGGUA              50

(2) INFORMATION FOR SEQ ID NO: 1665:

(i) SEQUENCE CHARACTERISTICS:

(A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1665:

CUCAUGAGAA GCUCACCAGA GAAACACACG UUGUGGUACA UUACCUGGUA              50

(2) INFORMATION FOR SEQ ID NO: 1666:

(i) SEQUENCE CHARACTERISTICS:

(A) LENGTH:         50 base pairs
        (B) TYPE:           nucleic acid
        (C) STRANDEDNESS:   single
        (D) TOPOLOGY:       linear
```

(xi) SEQUENCE DESCRIPTION: SEQ ID NO: 1666:

UUGCUGAGAA GCACACCAGA GAAACACACG UUGUGGUACA UUACCUGGUA                50

(2) INFORMATION FOR SEQ ID NO: 1667:

(i) SEQUENCE CHARACTERISTICS:

(A) LENGTH:        50 base pairs
      (B) TYPE:          nucleic acid
      (C) STRANDEDNESS:  single
      (D) TOPOLOGY:      linear (xi) SEQUENCE DESCRIPTION: SEQ ID NO: 1667:

GCACAGAGAA GGGUACCAGA GAAACACACG UUGUGGUACA UUACCUGGUA                50

(2) INFORMATION FOR SEQ ID NO: 1668:

(i) SEQUENCE CHARACTERISTICS:

(A) LENGTH:        50 base pairs
      (B) TYPE:          nucleic acid
      (C) STRANDEDNESS:  single
      (D) TOPOLOGY:      linear (xi) SEQUENCE DESCRIPTION: SEQ ID NO: 1668:

UUUGGCAGAA GCCCACCAGA GAAACACACG UUGUGGUACA UUACCUGGUA                50

(2) INFORMATION FOR SEQ ID NO: 1669:

(i) SEQUENCE CHARACTERISTICS:

(A) LENGTH:        50 base pairs
      (B) TYPE:          nucleic acid
      (C) STRANDEDNESS:  single
      (D) TOPOLOGY:      linear (xi) SEQUENCE DESCRIPTION: SEQ ID NO: 1669:

CAUUGGAGAA GCUUACCAGA GAAACACACG UUGUGGUACA UUACCUGGUA                50

(2) INFORMATION FOR SEQ ID NO: 1670:

(i) SEQUENCE CHARACTERISTICS:

(A) LENGTH:        50 base pairs
      (B) TYPE:          nucleic acid
      (C) STRANDEDNESS:  single
      (D) TOPOLOGY:      linear (xi) SEQUENCE DESCRIPTION: SEQ ID NO: 1670:

CACCCCAGAA GCUCACCAGA GAAACACACG UUGUGGUACA UUACCUGGUA                50

(2) INFORMATION FOR SEQ ID NO: 1671:

(i) SEQUENCE CHARACTERISTICS:

(A) LENGTH:        50 base pairs
      (B) TYPE:          nucleic acid
      (C) STRANDEDNESS:  single
      (D) TOPOLOGY:      linear (xi) SEQUENCE DESCRIPTION: SEQ ID NO: 1671:

AUUUUGAGAA GUUUACCAGA GAAACACACG UUGUGGUACA UUACCUGGUA                50

(2) INFORMATION FOR SEQ ID NO: 1672:

(i) SEQUENCE CHARACTERISTICS:

```
        (A) LENGTH:           50 base pairs
        (B) TYPE:             nucleic acid
        (C) STRANDEDNESS:     single
        (D) TOPOLOGY:         linear (xi) SEQUENCE DESCRIPTION: SEQ ID NO: 1672:

UGCCACAGAA GCGCACCAGA GAAACACACG UUGUGGUACA UUACCUGGUA              50

(2) INFORMATION FOR SEQ ID NO: 1673:

(i) SEQUENCE CHARACTERISTICS:

(A) LENGTH:           50 base pairs
        (B) TYPE:             nucleic acid
        (C) STRANDEDNESS:     single
        (D) TOPOLOGY:         linear (xi) SEQUENCE DESCRIPTION: SEQ ID NO: 1673:

UGUGGCAGAA GUCAACCAGA GAAACACACG UUGUGGUACA UUACCUGGUA              50

(2) INFORMATION FOR SEQ ID NO: 1674:

(i) SEQUENCE CHARACTERISTICS:

(A) LENGTH:           50 base pairs
        (B) TYPE:             nucleic acid
        (C) STRANDEDNESS:     single
        (D) TOPOLOGY:         linear (xi) SEQUENCE DESCRIPTION: SEQ ID NO: 1674:

AGACCAAGAA GUCGACCAGA GAAACACACG UUGUGGUACA UUACCUGGUA              50

(2) INFORMATION FOR SEQ ID NO: 1675:

(i) SEQUENCE CHARACTERISTICS:

(A) LENGTH:           50 base pairs
        (B) TYPE:             nucleic acid
        (C) STRANDEDNESS:     single
        (D) TOPOLOGY:         linear (xi) SEQUENCE DESCRIPTION: SEQ ID NO: 1675:

AUUUGCAGAA GACCACCAGA GAAACACACG UUGUGGUACA UUACCUGGUA              50

(2) INFORMATION FOR SEQ ID NO: 1676:

(i) SEQUENCE CHARACTERISTICS:

(A) LENGTH:           50 base pairs
        (B) TYPE:             nucleic acid
        (C) STRANDEDNESS:     single
        (D) TOPOLOGY:         linear (xi) SEQUENCE DESCRIPTION: SEQ ID NO: 1676:

GUGGGGAGAA GGUGACCAGA GAAACACACG UUGUGGUACA UUACCUGGUA              50

(2) INFORMATION FOR SEQ ID NO: 1677:

(i) SEQUENCE CHARACTERISTICS:

(A) LENGTH:           50 base pairs
        (B) TYPE:             nucleic acid
        (C) STRANDEDNESS:     single
        (D) TOPOLOGY:         linear (xi) SEQUENCE DESCRIPTION: SEQ ID NO: 1677:

ACAUCCAGAA GGUAACCAGA GAAACACACG UUGUGGUACA UUACCUGGUA              50
```

(2) INFORMATION FOR SEQ ID NO: 1678:

(i) SEQUENCE CHARACTERISTICS:

(A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 1678:

CACCAAAGAA GUAUACCAGA GAAACACACG UUGUGGUACA UUACCUGGUA      50

(2) INFORMATION FOR SEQ ID NO: 1679:

(i) SEQUENCE CHARACTERISTICS:

(A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 1679:

GCCGUGAGAA GUCAACCAGA GAAACACACG UUGUGGUACA UUACCUGGUA      50

(2) INFORMATION FOR SEQ ID NO: 1680:

(i) SEQUENCE CHARACTERISTICS:

(A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 1680:

CGCACGAGAA GUGAACCAGA GAAACACACG UUGUGGUACA UUACCUGGUA      50

(2) INFORMATION FOR SEQ ID NO: 1681:

(i) SEQUENCE CHARACTERISTICS:

(A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 1681:

GCCACCAGAA GGAUACCAGA GAAACACACG UUGUGGUACA UUACCUGGUA      50

(2) INFORMATION FOR SEQ ID NO: 1682:

(i) SEQUENCE CHARACTERISTICS:

(A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 1682:

GCCUGAAGAA GCAAACCAGA GAAACACACG UUGUGGUACA UUACCUGGUA      50

(2) INFORMATION FOR SEQ ID NO: 1683:

(i) SEQUENCE CHARACTERISTICS:

(A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 1683:

AUGGAGAGAA GUCCACCAGA GAAACACACG UUGUGGUACA UUACCUGGUA        50

(2) INFORMATION FOR SEQ ID NO: 1684:

(i) SEQUENCE CHARACTERISTICS:

(A) LENGTH:            50 base pairs
      (B) TYPE:              nucleic acid
      (C) STRANDEDNESS:      single
      (D) TOPOLOGY:          linear (xi) SEQUENCE DESCRIPTION: SEQ ID NO: 1684:

AGAGAAAGAA GACCACCAGA GAAACACACG UUGUGGUACA UUACCUGGUA        50

(2) INFORMATION FOR SEQ ID NO: 1685:

(i) SEQUENCE CHARACTERISTICS:

(A) LENGTH:            50 base pairs
      (B) TYPE:              nucleic acid
      (C) STRANDEDNESS:      single
      (D) TOPOLOGY:          linear (xi) SEQUENCE DESCRIPTION: SEQ ID NO: 1685:

GCUGACAGAA GCAAACCAGA GAAACACACG UUGUGGUACA UUACCUGGUA        50

(2) INFORMATION FOR SEQ ID NO: 1686:

(i) SEQUENCE CHARACTERISTICS:

(A) LENGTH:            50 base pairs
      (B) TYPE:              nucleic acid
      (C) STRANDEDNESS:      single
      (D) TOPOLOGY:          linear (xi) SEQUENCE DESCRIPTION: SEQ ID NO: 1686:

UGUUCAAGAA GACGACCAGA GAAACACACG UUGUGGUACA UUACCUGGUA        50

(2) INFORMATION FOR SEQ ID NO: 1687:

(i) SEQUENCE CHARACTERISTICS:

(A) LENGTH:            50 base pairs
      (B) TYPE:              nucleic acid
      (C) STRANDEDNESS:      single
      (D) TOPOLOGY:          linear (xi) SEQUENCE DESCRIPTION: SEQ ID NO: 1687:

GUCCCAAGAA GUUUACCAGA GAAACACACG UUGUGGUACA UUACCUGGUA        50

(2) INFORMATION FOR SEQ ID NO: 1688:

(i) SEQUENCE CHARACTERISTICS:

(A) LENGTH:            50 base pairs
      (B) TYPE:              nucleic acid
      (C) STRANDEDNESS:      single
      (D) TOPOLOGY:          linear (xi) SEQUENCE DESCRIPTION: SEQ ID NO: 1688:

CCUUGCAGAA GUUUACCAGA GAAACACACG UUGUGGUACA UUACCUGGUA        50

(2) INFORMATION FOR SEQ ID NO: 1689:

(i) SEQUENCE CHARACTERISTICS:

```
            (A)  LENGTH:              50 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 1689:

GGCCCCAGAA GCCCACCAGA GAAACACACG UUGUGGUACA UUACCUGGUA            50

(2)  INFORMATION FOR SEQ ID NO: 1690:

(i)  SEQUENCE CHARACTERISTICS:

(A)  LENGTH:              50 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 1690:

UGCCUCAGAA GACAACCAGA GAAACACACG UUGUGGUACA UUACCUGGUA            50

(2)  INFORMATION FOR SEQ ID NO: 1691:

(i)  SEQUENCE CHARACTERISTICS:

(A)  LENGTH:              50 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 1691:

GCCUGAAGAA GGCAACCAGA GAAACACACG UUGUGGUACA UUACCUGGUA            50

(2)  INFORMATION FOR SEQ ID NO: 1692:

(i)  SEQUENCE CHARACTERISTICS:

(A)  LENGTH:              50 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 1692:

AGUGGGAGAA GUCAACCAGA GAAACACACG UUGUGGUACA UUACCUGGUA            50

(2)  INFORMATION FOR SEQ ID NO: 1693:

(i)  SEQUENCE CHARACTERISTICS:

(A)  LENGTH:              50 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 1693:

CUGCCGAGAA GGUCACCAGA GAAACACACG UUGUGGUACA UUACCUGGUA            50

(2)  INFORMATION FOR SEQ ID NO: 1694:

(i)  SEQUENCE CHARACTERISTICS:

(A)  LENGTH:              50 base pairs
            (B)  TYPE:                nucleic acid
            (C)  STRANDEDNESS:        single
            (D)  TOPOLOGY:            linear (xi)  SEQUENCE DESCRIPTION: SEQ ID NO: 1694:

GCCGGCAGAA GCGUACCAGA GAAACACACG UUGUGGUACA UUACCUGGUA            50
```

(2) INFORMATION FOR SEQ ID NO: 1695:

(i) SEQUENCE CHARACTERISTICS:

(A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO: 1695:

CAGUGCAGAA GUAGACCAGA GAAACACACG UUGUGGUACA UUACCUGGUA      50

(2) INFORMATION FOR SEQ ID NO: 1696:

(i) SEQUENCE CHARACTERISTICS:

(A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO: 1696:

UCGUUGAGAA GCCUACCAGA GAAACACACG UUGUGGUACA UUACCUGGUA      50

(2) INFORMATION FOR SEQ ID NO: 1697:

(i) SEQUENCE CHARACTERISTICS:

(A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO: 1697:

GCGAUGAGAA GGAUACCAGA GAAACACACG UUGUGGUACA UUACCUGGUA      50

(2) INFORMATION FOR SEQ ID NO: 1698:

(i) SEQUENCE CHARACTERISTICS:

(A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO: 1698:

ACCACCAGAA GCAAACCAGA GAAACACACG UUGUGGUACA UUACCUGGUA      50

(2) INFORMATION FOR SEQ ID NO: 1699:

(i) SEQUENCE CHARACTERISTICS:

(A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO: 1699:

UGAAGAAGAA GAUCACCAGA GAAACACACG UUGUGGUACA UUACCUGGUA      50

(2) INFORMATION FOR SEQ ID NO: 1700:

(i) SEQUENCE CHARACTERISTICS:

(A) LENGTH: 50 base pairs
      (B) TYPE: nucleic acid
      (C) STRANDEDNESS: single (D) TOPOLOGY:          linear (xi) SEQUENCE DESCRIPTION: SEQ ID NO: 1700:

UCCUGCAGAA GCCUACCAGA GAAACACACG UUGUGGUACA UUACCUGGUA          50

(2) INFORMATION FOR SEQ ID NO: 1701:

(i) SEQUENCE CHARACTERISTICS:

(A) LENGTH:            50 base pairs
            (B) TYPE:              nucleic acid
            (C) STRANDEDNESS:      single
            (D) TOPOLOGY:          linear (xi) SEQUENCE DESCRIPTION: SEQ ID NO: 1701:

GAUAGCAGAA GGAAACCAGA GAAACACACG UUGUGGUACA UUACCUGGUA          50

(2) INFORMATION FOR SEQ ID NO: 1702:

(i) SEQUENCE CHARACTERISTICS:

(A) LENGTH:            50 base pairs
            (B) TYPE:              nucleic acid
            (C) STRANDEDNESS:      single
            (D) TOPOLOGY:          linear (xi) SEQUENCE DESCRIPTION: SEQ ID NO: 1702:

CCAGCAAGAA GCACACCAGA GAAACACACG UUGUGGUACA UUACCUGGUA          50

(2) INFORMATION FOR SEQ ID NO: 1703:

(i) SEQUENCE CHARACTERISTICS:

(A) LENGTH:            50 base pairs
            (B) TYPE:              nucleic acid
            (C) STRANDEDNESS:      single
            (D) TOPOLOGY:          linear (xi) SEQUENCE DESCRIPTION: SEQ ID NO: 1703:

AUGCCCAGAA GGCGACCAGA GAAACACACG UUGUGGUACA UUACCUGGUA          50

(2) INFORMATION FOR SEQ ID NO: 1704:

(i) SEQUENCE CHARACTERISTICS:

(A) LENGTH:            50 base pairs
            (B) TYPE:              nucleic acid
            (C) STRANDEDNESS:      single
            (D) TOPOLOGY:          linear (xi) SEQUENCE DESCRIPTION: SEQ ID NO: 1704:

AGGUGAAGAA GAUGACCAGA GAAACACACG UUGUGGUACA UUACCUGGUA          50

(2) INFORMATION FOR SEQ ID NO: 1705:

(i) SEQUENCE CHARACTERISTICS:

(A) LENGTH:            50 base pairs
            (B) TYPE:              nucleic acid
            (C) STRANDEDNESS:      single
            (D) TOPOLOGY:          linear (xi) SEQUENCE DESCRIPTION: SEQ ID NO: 1705:

GGCAUGAGAA GCGUACCAGA GAAACACACG UUGUGGUACA UUACCUGGUA          50

(2) INFORMATION FOR SEQ ID NO: 1706:

-continued (i) SEQUENCE CHARACTERISTICS:

(A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1706:

GGAGGCAGAA GAAGACCAGA GAAACACACG UUGUGGUACA UUACCUGGUA          50

(2) INFORMATION FOR SEQ ID NO: 1707:

(i) SEQUENCE CHARACTERISTICS:

(A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1707:

CCAGGAAGAA GCCGACCAGA GAAACACACG UUGUGGUACA UUACCUGGUA          50

(2) INFORMATION FOR SEQ ID NO: 1708:

(i) SEQUENCE CHARACTERISTICS:

(A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1708:

CAGUUGAGAA GGUAACCAGA GAAACACACG UUGUGGUACA UUACCUGGUA          50

(2) INFORMATION FOR SEQ ID NO: 1709:

(i) SEQUENCE CHARACTERISTICS:

(A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1709:

UUUGCGAGAA GCACACCAGA GAAACACACG UUGUGGUACA UUACCUGGUA          50

(2) INFORMATION FOR SEQ ID NO: 1710:

(i) SEQUENCE CHARACTERISTICS:

(A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1710:

CCAAGCAGAA GUCCACCAGA GAAACACACG UUGUGGUACA UUACCUGGUA          50

(2) INFORMATION FOR SEQ ID NO: 1711:

(i) SEQUENCE CHARACTERISTICS:

(A) LENGTH:         50 base pairs
        (B) TYPE:           nucleic acid
        (C) STRANDEDNESS:   single
        (D) TOPOLOGY:       linear (xi) SEQUENCE DESCRIPTION: SEQ ID NO: 1711:

-continued

CCCAAAAGAA GUGAACCAGA GAAACACACG UUGUGGUACA UUACCUGGUA        50

(2) INFORMATION FOR SEQ ID NO: 1712:

(i) SEQUENCE CHARACTERISTICS:

(A) LENGTH:          50 base pairs
        (B) TYPE:            nucleic acid
        (C) STRANDEDNESS:    single
        (D) TOPOLOGY:        linear (xi) SEQUENCE DESCRIPTION: SEQ ID NO: 1712:

GCACCCAGAA GUUUACCAGA GAAACACACG UUGUGGUACA UUACCUGGUA        50

(2) INFORMATION FOR SEQ ID NO: 1713:

(i) SEQUENCE CHARACTERISTICS:

(A) LENGTH:          50 base pairs
        (B) TYPE:            nucleic acid
        (C) STRANDEDNESS:    single
        (D) TOPOLOGY:        linear (xi) SEQUENCE DESCRIPTION: SEQ ID NO: 1713:

CUCCCAAGAA GUCAACCAGA GAAACACACG UUGUGGUACA UUACCUGGUA        50

(2) INFORMATION FOR SEQ ID NO: 1714:

(i) SEQUENCE CHARACTERISTICS:

(A) LENGTH:          50 base pairs
        (B) TYPE:            nucleic acid
        (C) STRANDEDNESS:    single
        (D) TOPOLOGY:        linear (xi) SEQUENCE DESCRIPTION: SEQ ID NO: 1714:

GUUGGAAGAA GUAGACCAGA GAAACACACG UUGUGGUACA UUACCUGGUA        50

(2) INFORMATION FOR SEQ ID NO: 1715:

(i) SEQUENCE CHARACTERISTICS:

(A) LENGTH:          50 base pairs
        (B) TYPE:            nucleic acid
        (C) STRANDEDNESS:    single
        (D) TOPOLOGY:        linear (xi) SEQUENCE DESCRIPTION: SEQ ID NO: 1715:

UCAUCCAGAA GGGCACCAGA GAAACACACG UUGUGGUACA UUACCUGGUA        50

(2) INFORMATION FOR SEQ ID NO: 1716:

(i) SEQUENCE CHARACTERISTICS:

(A) LENGTH:          50 base pairs
        (B) TYPE:            nucleic acid
        (C) STRANDEDNESS:    single
        (D) TOPOLOGY:        linear (xi) SEQUENCE DESCRIPTION: SEQ ID NO: 1716:

GUACUCAGAA GCAUACCAGA GAAACACACG UUGUGGUACA UUACCUGGUA        50

(2) INFORMATION FOR SEQ ID NO: 1717:

(i) SEQUENCE CHARACTERISTICS:

(A) LENGTH:          50 base pairs
        (B) TYPE:            nucleic acid

```
            (C)  STRANDEDNESS:          single
            (D)  TOPOLOGY:              linear (xi)  SEQUENCE DESCRIPTION: SEQ ID NO: 1717:

UGGAGGAGAA GCUGACCAGA GAAACACACG UUGUGGUACA UUACCUGGUA                50

(2)  INFORMATION FOR SEQ ID NO: 1718:

(i)  SEQUENCE CHARACTERISTICS:

(A)  LENGTH:                50 base pairs
            (B)  TYPE:                  nucleic acid
            (C)  STRANDEDNESS:          single
            (D)  TOPOLOGY:              linear (xi)  SEQUENCE DESCRIPTION: SEQ ID NO: 1718:

AGGGGAAGAA GUGAACCAGA GAAACACACG UUGUGGUACA UUACCUGGUA                50

(2)  INFORMATION FOR SEQ ID NO: 1719:

(i)  SEQUENCE CHARACTERISTICS:

(A)  LENGTH:                50 base pairs
            (B)  TYPE:                  nucleic acid
            (C)  STRANDEDNESS:          single
            (D)  TOPOLOGY:              linear (xi)  SEQUENCE DESCRIPTION: SEQ ID NO: 1719:

UGAUGGAGAA GCUUACCAGA GAAACACACG UUGUGGUACA UUACCUGGUA                50

(2)  INFORMATION FOR SEQ ID NO: 1720:

(i)  SEQUENCE CHARACTERISTICS:

(A)  LENGTH:                50 base pairs
            (B)  TYPE:                  nucleic acid
            (C)  STRANDEDNESS:          single
            (D)  TOPOLOGY:              linear (xi)  SEQUENCE DESCRIPTION: SEQ ID NO: 1720:

GCAAGAAGAA GUCUACCAGA GAAACACACG UUGUGGUACA UUACCUGGUA                50

(2)  INFORMATION FOR SEQ ID NO: 1721:

(i)  SEQUENCE CHARACTERISTICS:

(A)  LENGTH:                50 base pairs
            (B)  TYPE:                  nucleic acid
            (C)  STRANDEDNESS:          single
            (D)  TOPOLOGY:              linear (xi)  SEQUENCE DESCRIPTION: SEQ ID NO: 1721:

GGUCUGAGAA GUAUACCAGA GAAACACACG UUGUGGUACA UUACCUGGUA                50

(2)  INFORMATION FOR SEQ ID NO: 1722:

(i)  SEQUENCE CHARACTERISTICS:

(A)  LENGTH:                50 base pairs
            (B)  TYPE:                  nucleic acid
            (C)  STRANDEDNESS:          single
            (D)  TOPOLOGY:              linear (xi)  SEQUENCE DESCRIPTION: SEQ ID NO: 1722:

UGUGGGAGAA GAGCACCAGA GAAACACACG UUGUGGUACA UUACCUGGUA                50

(2)  INFORMATION FOR SEQ ID NO: 1723:
```

(i) SEQUENCE CHARACTERISTICS:

(A) LENGTH: 50 base pairs
    (B) TYPE: nucleic acid
    (C) STRANDEDNESS: single
    (D) TOPOLOGY: linear (xi) SEQUENCE DESCRIPTION: SEQ ID NO: 1723:

GGAACGAGAA GGUUACCAGA GAAACACACG UUGUGGUACA UUACCUGGUA     50

(2) INFORMATION FOR SEQ ID NO: 1724:

(i) SEQUENCE CHARACTERISTICS:

(A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 1724:

UUUGGGAGAA GACUACCAGA GAAACACACG UUGUGGUACA UUACCUGGUA     50

(2) INFORMATION FOR SEQ ID NO: 1725:

(i) SEQUENCE CHARACTERISTICS:

(A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 1725:

AGAGCCAGAA GGCCACCAGA GAAACACACG UUGUGGUACA UUACCUGGUA     50

(2) INFORMATION FOR SEQ ID NO: 1726:

(i) SEQUENCE CHARACTERISTICS:

(A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 1726:

GUGAUAAGAA GGAUACCAGA GAAACACACG UUGUGGUACA UUACCUGGUA     50

(2) INFORMATION FOR SEQ ID NO: 1727:

(i) SEQUENCE CHARACTERISTICS:

(A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 1727:

UUCAGAAGAA GAUUACCAGA GAAACACACG UUGUGGUACA UUACCUGGUA     50

(2) INFORMATION FOR SEQ ID NO: 1728:

(i) SEQUENCE CHARACTERISTICS:

(A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 1728:

```
GGGCUGAGAA GUGUACCAGA GAAACACACG UUGUGGUACA UUACCUGGUA          50

(2) INFORMATION FOR SEQ ID NO: 1729:

(i) SEQUENCE CHARACTERISTICS:

(A) LENGTH:           50 base pairs
        (B) TYPE:             nucleic acid
        (C) STRANDEDNESS:     single
        (D) TOPOLOGY:         linear (xi) SEQUENCE DESCRIPTION: SEQ ID NO: 1729:

CAGGUGAGAA GGACACCAGA GAAACACACG UUGUGGUACA UUACCUGGUA          50

(2) INFORMATION FOR SEQ ID NO: 1730:

(i) SEQUENCE CHARACTERISTICS:

(A) LENGTH:           50 base pairs
        (B) TYPE:             nucleic acid
        (C) STRANDEDNESS:     single
        (D) TOPOLOGY:         linear (xi) SEQUENCE DESCRIPTION: SEQ ID NO: 1730:

GGGCAGAGAA GUCGACCAGA GAAACACACG UUGUGGUACA UUACCUGGUA          50

(2) INFORMATION FOR SEQ ID NO: 1731:

(i) SEQUENCE CHARACTERISTICS:

(A) LENGTH:           50 base pairs
        (B) TYPE:             nucleic acid
        (C) STRANDEDNESS:     single
        (D) TOPOLOGY:         linear (xi) SEQUENCE DESCRIPTION: SEQ ID NO: 1731:

CCAGUGAGAA GGGCACCAGA GAAACACACG UUGUGGUACA UUACCUGGUA          50

(2) INFORMATION FOR SEQ ID NO: 1732:

(i) SEQUENCE CHARACTERISTICS:

(A) LENGTH:           50 base pairs
        (B) TYPE:             nucleic acid
        (C) STRANDEDNESS:     single
        (D) TOPOLOGY:         linear (xi) SEQUENCE DESCRIPTION: SEQ ID NO: 1732:

CUGGUAAGAA GGGUACCAGA GAAACACACG UUGUGGUACA UUACCUGGUA          50

(2) INFORMATION FOR SEQ ID NO: 1733:

(i) SEQUENCE CHARACTERISTICS:

(A) LENGTH:           50 base pairs
        (B) TYPE:             nucleic acid
        (C) STRANDEDNESS:     single
        (D) TOPOLOGY:         linear (xi) SEQUENCE DESCRIPTION: SEQ ID NO: 1733:

AUUUUCAGAA GUGGACCAGA GAAACACACG UUGUGGUACA UUACCUGGUA          50

(2) INFORMATION FOR SEQ ID NO: 1734:

(i) SEQUENCE CHARACTERISTICS:

(A) LENGTH:           50 base pairs
```

```
        (B)  TYPE:            nucleic acid
        (C)  STRANDEDNESS:    single
        (D)  TOPOLOGY:        linear (xi) SEQUENCE DESCRIPTION: SEQ ID NO: 1734:

GAAAGAAGAA GGAUACCAGA GAAACACACG UUGUGGUACA UUACCUGGUA              50

(2) INFORMATION FOR SEQ ID NO: 1735:

(i) SEQUENCE CHARACTERISTICS:
        (A)  LENGTH:          50 base pairs
        (B)  TYPE:            nucleic acid
        (C)  STRANDEDNESS:    single
        (D)  TOPOLOGY:        linear (xi) SEQUENCE DESCRIPTION: SEQ ID NO: 1735:

AAACCAAGAA GUGGACCAGA GAAACACACG UUGUGGUACA UUACCUGGUA              50

(2) INFORMATION FOR SEQ ID NO: 1736:

(i) SEQUENCE CHARACTERISTICS:
        (A)  LENGTH:          50 base pairs
        (B)  TYPE:            nucleic acid
        (C)  STRANDEDNESS:    single
        (D)  TOPOLOGY:        linear (xi) SEQUENCE DESCRIPTION: SEQ ID NO: 1736:

UGGCUAAGAA GUGUACCAGA GAAACACACG UUGUGGUACA UUACCUGGUA              50

(2) INFORMATION FOR SEQ ID NO: 1737:

(i) SEQUENCE CHARACTERISTICS:
        (A)  LENGTH:          50 base pairs
        (B)  TYPE:            nucleic acid
        (C)  STRANDEDNESS:    single
        (D)  TOPOLOGY:        linear (xi) SEQUENCE DESCRIPTION: SEQ ID NO: 1737:

CCUUGAAGAA GAACACCAGA GAAACACACG UUGUGGUACA UUACCUGGUA              50

(2) INFORMATION FOR SEQ ID NO: 1738:

(i) SEQUENCE CHARACTERISTICS:
        (A)  LENGTH:          50 base pairs
        (B)  TYPE:            nucleic acid
        (C)  STRANDEDNESS:    single
        (D)  TOPOLOGY:        linear (xi) SEQUENCE DESCRIPTION: SEQ ID NO: 1738:

GUACCGAGAA GGCCACCAGA GAAACACACG UUGUGGUACA UUACCUGGUA              50

(2) INFORMATION FOR SEQ ID NO: 1739:

(i) SEQUENCE CHARACTERISTICS:
        (A)  LENGTH:          50 base pairs
        (B)  TYPE:            nucleic acid
        (C)  STRANDEDNESS:    single
        (D)  TOPOLOGY:        linear (xi) SEQUENCE DESCRIPTION: SEQ ID NO: 1739:

GGAAGGAGAA GAGUACCAGA GAAACACACG UUGUGGUACA UUACCUGGUA              50
```

-continued (2) INFORMATION FOR SEQ ID NO: 1740:

(i) SEQUENCE CHARACTERISTICS:
      (A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1740:

UGGUCCAGAA GUGGACCAGA GAAACACACG UUGUGGUACA UUACCUGGUA          50

(2) INFORMATION FOR SEQ ID NO: 1741:

(i) SEQUENCE CHARACTERISTICS:
      (A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1741:

AAACAAAGAA GUCUACCAGA GAAACACACG UUGUGGUACA UUACCUGGUA          50

(2) INFORMATION FOR SEQ ID NO: 1742:

(i) SEQUENCE CHARACTERISTICS:
      (A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1742:

GACAGGAGAA GCAUACCAGA GAAACACACG UUGUGGUACA UUACCUGGUA          50

(2) INFORMATION FOR SEQ ID NO: 1743:

(i) SEQUENCE CHARACTERISTICS:
      (A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1743:

CAGCAAAGAA GGGGACCAGA GAAACACACG UUGUGGUACA UUACCUGGUA          50

(2) INFORMATION FOR SEQ ID NO: 1744:

(i) SEQUENCE CHARACTERISTICS:
      (A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1744:

GCUGGAAGAA GAGUACCAGA GAAACACACG UUGUGGUACA UUACCUGGUA          50

(2) INFORMATION FOR SEQ ID NO: 1745:

(i) SEQUENCE CHARACTERISTICS:
      (A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1745:

AAUGUGAGAA GGAAACCAGA GAAACACACG UUGUGGUACA UUACCUGGUA          50

(2) INFORMATION FOR SEQ ID NO: 1746:

(i) SEQUENCE CHARACTERISTICS:

(A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1746:

AUUCUCAGAA GUGGACCAGA GAAACACACG UUGUGGUACA UUACCUGGUA          50

(2) INFORMATION FOR SEQ ID NO: 1747:

(i) SEQUENCE CHARACTERISTICS:

(A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1747:

AACAAAAGAA GUGUACCAGA GAAACACACG UUGUGGUACA UUACCUGGUA          50

(2) INFORMATION FOR SEQ ID NO: 1748:

(i) SEQUENCE CHARACTERISTICS:

(A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1748:

CAUUUCAGAA GAGCACCAGA GAAACACACG UUGUGGUACA UUACCUGGUA          50

(2) INFORMATION FOR SEQ ID NO: 1749:

(i) SEQUENCE CHARACTERISTICS:

(A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1749:

UUUCAGAGAA GCUUACCAGA GAAACACACG UUGUGGUACA UUACCUGGUA          50

(2) INFORMATION FOR SEQ ID NO: 1750:

(i) SEQUENCE CHARACTERISTICS:

(A) LENGTH:         50 base pairs
      (B) TYPE:           nucleic acid
      (C) STRANDEDNESS:   single
      (D) TOPOLOGY:       linear (xi) SEQUENCE DESCRIPTION: SEQ ID NO: 1750:

GGGGGCAGAA GACCACCAGA GAAACACACG UUGUGGUACA UUACCUGGUA          50

(2) INFORMATION FOR SEQ ID NO: 1751:

(i) SEQUENCE CHARACTERISTICS:

```
            (A) LENGTH:         50 base pairs
            (B) TYPE:           nucleic acid
            (C) STRANDEDNESS:   single
            (D) TOPOLOGY:       linear (xi) SEQUENCE DESCRIPTION: SEQ ID NO: 1751:

UUUGGGAGAA GCUGACCAGA GAAACACACG UUGUGGUACA UUACCUGGUA          50

(2) INFORMATION FOR SEQ ID NO: 1752:

(i) SEQUENCE CHARACTERISTICS:

(A) LENGTH:         50 base pairs
            (B) TYPE:           nucleic acid
            (C) STRANDEDNESS:   single
            (D) TOPOLOGY:       linear (xi) SEQUENCE DESCRIPTION: SEQ ID NO: 1752:

ACUCAAAGAA GAGAACCAGA GAAACACACG UUGUGGUACA UUACCUGGUA          50

(2) INFORMATION FOR SEQ ID NO: 1753:

(i) SEQUENCE CHARACTERISTICS:

(A) LENGTH:         50 base pairs
            (B) TYPE:           nucleic acid
            (C) STRANDEDNESS:   single
            (D) TOPOLOGY:       linear (xi) SEQUENCE DESCRIPTION: SEQ ID NO: 1753:

GGCCAGAGAA GUAAACCAGA GAAACACACG UUGUGGUACA UUACCUGGUA          50

(2) INFORMATION FOR SEQ ID NO: 1754:

(i) SEQUENCE CHARACTERISTICS:

(A) LENGTH:         50 base pairs
            (B) TYPE:           nucleic acid
            (C) STRANDEDNESS:   single
            (D) TOPOLOGY:       linear (xi) SEQUENCE DESCRIPTION: SEQ ID NO: 1754:

UAAAACAGAA GCAAACCAGA GAAACACACG UUGUGGUACA UUACCUGGUA          50

(2) INFORMATION FOR SEQ ID NO: 1755:

(i) SEQUENCE CHARACTERISTICS:

(A) LENGTH:         50 base pairs
            (B) TYPE:           nucleic acid
            (C) STRANDEDNESS:   single
            (D) TOPOLOGY:       linear (xi) SEQUENCE DESCRIPTION: SEQ ID NO: 1755:

UAACCAAGAA GGUUACCAGA GAAACACACG UUGUGGUACA UUACCUGGUA          50

(2) INFORMATION FOR SEQ ID NO: 1756:

(i) SEQUENCE CHARACTERISTICS:

(A) LENGTH:         50 base pairs
            (B) TYPE:           nucleic acid
            (C) STRANDEDNESS:   single
            (D) TOPOLOGY:       linear (xi) SEQUENCE DESCRIPTION: SEQ ID NO: 1756:

ACAAAGAGAA GCUGACCAGA GAAACACACG UUGUGGUACA UUACCUGGUA          50
```

(2) INFORMATION FOR SEQ ID NO: 1757:

(i) SEQUENCE CHARACTERISTICS:

(A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 1757:

ACUGUAAGAA GAAAACCAGA GAAACACACG UUGUGGUACA UUACCUGGUA     50

(2) INFORMATION FOR SEQ ID NO: 1758:

(i) SEQUENCE CHARACTERISTICS:

(A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO: 1758:

UGACUGAGAA GGGAACCAGA GAAACACACG UUGUGGUACA UUACCUGGUA     50

(2) INFORMATION FOR SEQ ID NO: 1759:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1759:

GCGCCGCCGC CGCC     14

(2) INFORMATION FOR SEQ ID NO: 1760:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1760:

CCGCCGCCGC CCAG     14

(2) INFORMATION FOR SEQ ID NO: 1761:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1761:

CCGCCGCCCA GACC     14

(2) INFORMATION FOR SEQ ID NO: 1762:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1762:

GCCCAGACCG GACG                                                        14

(2) INFORMATION FOR SEQ ID NO: 1763:

(i) SEQUENCE CHARACTERISTICS:
        (A) LENGTH:          14 base pairs
        (B) TYPE:            nucleic acid
        (C) STRANDEDNESS:    single
        (D) TOPOLOGY:        linear (xi) SEQUENCE DESCRIPTION: SEQ ID NO: 1763:

GACCGGACGA CAGG                                                        14

(2) INFORMATION FOR SEQ ID NO: 1764:

(i) SEQUENCE CHARACTERISTICS:
        (A) LENGTH:          14 base pairs
        (B) TYPE:            nucleic acid
        (C) STRANDEDNESS:    single
        (D) TOPOLOGY:        linear (xi) SEQUENCE DESCRIPTION: SEQ ID NO: 1764:

CGUCCGCCCG AGUC                                                        14

(2) INFORMATION FOR SEQ ID NO: 1765:

(i) SEQUENCE CHARACTERISTICS:
        (A) LENGTH:          14 base pairs
        (B) TYPE:            nucleic acid
        (C) STRANDEDNESS:    single
        (D) TOPOLOGY:        linear (xi) SEQUENCE DESCRIPTION: SEQ ID NO: 1765:

UCCCCGCCUC GCCG                                                        14

(2) INFORMATION FOR SEQ ID NO: 1766:

(i) SEQUENCE CHARACTERISTICS:
        (A) LENGTH:          14 base pairs
        (B) TYPE:            nucleic acid
        (C) STRANDEDNESS:    single
        (D) TOPOLOGY:        linear (xi) SEQUENCE DESCRIPTION: SEQ ID NO: 1766:

GCACGGCCCC CUGA                                                        14

(2) INFORMATION FOR SEQ ID NO: 1767:

(i) SEQUENCE CHARACTERISTICS:
        (A) LENGTH:          14 base pairs
        (B) TYPE:            nucleic acid
        (C) STRANDEDNESS:    single
        (D) TOPOLOGY:        linear (xi) SEQUENCE DESCRIPTION: SEQ ID NO: 1767:

CCCCUGACUC CGUC                                                        14

(2) INFORMATION FOR SEQ ID NO: 1768:

(i) SEQUENCE CHARACTERISTICS:

(A)  LENGTH:            14 base pairs
            (B)  TYPE:              nucleic acid
            (C)  STRANDEDNESS:      single
            (D)  TOPOLOGY:          linear (xi) SEQUENCE DESCRIPTION: SEQ ID NO: 1768:

ACUCCGUCCA GUAU                                                            14

(2)   INFORMATION FOR SEQ ID NO: 1769:

(i)  SEQUENCE CHARACTERISTICS:

(A)  LENGTH:            14 base pairs
            (B)  TYPE:              nucleic acid
            (C)  STRANDEDNESS:      single
            (D)  TOPOLOGY:          linear (xi) SEQUENCE DESCRIPTION: SEQ ID NO: 1769:

GGACGGCCGG GGCA                                                            14

(2)   INFORMATION FOR SEQ ID NO: 1770:

(i)  SEQUENCE CHARACTERISTICS:

(A)  LENGTH:            14 base pairs
            (B)  TYPE:              nucleic acid
            (C)  STRANDEDNESS:      single
            (D)  TOPOLOGY:          linear (xi) SEQUENCE DESCRIPTION: SEQ ID NO: 1770:

GCGCUGCUGG CUGC                                                            14

(2)   INFORMATION FOR SEQ ID NO: 1771:

(i)  SEQUENCE CHARACTERISTICS:

(A)  LENGTH:            14 base pairs
            (B)  TYPE:              nucleic acid
            (C)  STRANDEDNESS:      single
            (D)  TOPOLOGY:          linear (xi) SEQUENCE DESCRIPTION: SEQ ID NO: 1771:

GCUCUGCCCG GCGA                                                            14

(2)   INFORMATION FOR SEQ ID NO: 1772:

(i)  SEQUENCE CHARACTERISTICS:

(A)  LENGTH:            14 base pairs
            (B)  TYPE:              nucleic acid
            (C)  STRANDEDNESS:      single
            (D)  TOPOLOGY:          linear (xi) SEQUENCE DESCRIPTION: SEQ ID NO: 1772:

ACGCAGUUGG GCAC                                                            14

(2)   INFORMATION FOR SEQ ID NO: 1773:

(i)  SEQUENCE CHARACTERISTICS:

(A)  LENGTH:            14 base pairs
            (B)  TYPE:              nucleic acid
            (C)  STRANDEDNESS:      single
            (D)  TOPOLOGY:          linear (xi) SEQUENCE DESCRIPTION: SEQ ID NO: 1773:

UCUCAGCCUC CAGA                                                            14

(2) INFORMATION FOR SEQ ID NO: 1774:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1774:

CUGCAGAUCA UCAG                               14

(2) INFORMATION FOR SEQ ID NO: 1775:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1775:

UAGCAGUCUU AUCU                               14

(2) INFORMATION FOR SEQ ID NO: 1776:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1776:

AACCGGACUG AAGG                               14

(2) INFORMATION FOR SEQ ID NO: 1777:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1777:

GAGCUGCCCA UGAG                               14

(2) INFORMATION FOR SEQ ID NO: 1778:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1778:

GUGCGGUUCA GCAA                               14

(2) INFORMATION FOR SEQ ID NO: 1779:

(i) SEQUENCE CHARACTERISTICS:

(A) LENGTH: 14 base pairs
        (B) TYPE: nucleic acid
        (C) STRANDEDNESS: single (D)  TOPOLOGY:              linear (xi) SEQUENCE DESCRIPTION: SEQ ID NO: 1779:

ACCCUGCCCU GUGC                                                14

(2) INFORMATION FOR SEQ ID NO: 1780:

(i)  SEQUENCE CHARACTERISTICS:

(A)  LENGTH:                14 base pairs
                (B)  TYPE:                  nucleic acid
                (C)  STRANDEDNESS:          single
                (D)  TOPOLOGY:              linear (xi) SEQUENCE DESCRIPTION: SEQ ID NO: 1780:

GGGCAGCUGC CAAA                                                14

(2) INFORMATION FOR SEQ ID NO: 1781:

(i)  SEQUENCE CHARACTERISTICS:

(A)  LENGTH:                14 base pairs
                (B)  TYPE:                  nucleic acid
                (C)  STRANDEDNESS:          single
                (D)  TOPOLOGY:              linear (xi) SEQUENCE DESCRIPTION: SEQ ID NO: 1781:

AAGCUGUCCC AAUG                                                14

(2) INFORMATION FOR SEQ ID NO: 1782:

(i)  SEQUENCE CHARACTERISTICS:

(A)  LENGTH:                14 base pairs
                (B)  TYPE:                  nucleic acid
                (C)  STRANDEDNESS:          single
                (D)  TOPOLOGY:              linear (xi) SEQUENCE DESCRIPTION: SEQ ID NO: 1782:

GAGCUGCUGG GGUG                                                14

(2) INFORMATION FOR SEQ ID NO: 1783:

(i)  SEQUENCE CHARACTERISTICS:

(A)  LENGTH:                14 base pairs
                (B)  TYPE:                  nucleic acid
                (C)  STRANDEDNESS:          single
                (D)  TOPOLOGY:              linear (xi) SEQUENCE DESCRIPTION: SEQ ID NO: 1783:

AAACUGACCA AAAU                                                14

(2) INFORMATION FOR SEQ ID NO: 1784:

(i)  SEQUENCE CHARACTERISTICS:

(A)  LENGTH:                14 base pairs
                (B)  TYPE:                  nucleic acid
                (C)  STRANDEDNESS:          single
                (D)  TOPOLOGY:              linear (xi) SEQUENCE DESCRIPTION: SEQ ID NO: 1784:

GCGCUGCCGU GGCA                                                14

(2) INFORMATION FOR SEQ ID NO: 1785:

```
         (i)  SEQUENCE CHARACTERISTICS:

(A)  LENGTH:             14 base pairs
              (B)  TYPE:               nucleic acid
              (C)  STRANDEDNESS:       single
              (D)  TOPOLOGY:           linear (xi) SEQUENCE DESCRIPTION: SEQ ID NO: 1785:

UGACUGCUGC CACA                                                           14

(2)  INFORMATION FOR SEQ ID NO: 1786:

(i)  SEQUENCE CHARACTERISTICS:

(A)  LENGTH:             14 base pairs
              (B)  TYPE:               nucleic acid
              (C)  STRANDEDNESS:       single
              (D)  TOPOLOGY:           linear (xi) SEQUENCE DESCRIPTION: SEQ ID NO: 1786:

CGACUGCCUG GUCU                                                           14

(2)  INFORMATION FOR SEQ ID NO: 1787:

(i)  SEQUENCE CHARACTERISTICS:

(A)  LENGTH:             14 base pairs
              (B)  TYPE:               nucleic acid
              (C)  STRANDEDNESS:       single
              (D)  TOPOLOGY:           linear (xi) SEQUENCE DESCRIPTION: SEQ ID NO: 1787:

GGUCUGCCGC AAAU                                                           14

(2)  INFORMATION FOR SEQ ID NO: 1788:

(i)  SEQUENCE CHARACTERISTICS:

(A)  LENGTH:             14 base pairs
              (B)  TYPE:               nucleic acid
              (C)  STRANDEDNESS:       single
              (D)  TOPOLOGY:           linear (xi) SEQUENCE DESCRIPTION: SEQ ID NO: 1788:

CACCUGCCCC CCAC                                                           14

(2)  INFORMATION FOR SEQ ID NO: 1789:

(i)  SEQUENCE CHARACTERISTICS:

(A)  LENGTH:             14 base pairs
              (B)  TYPE:               nucleic acid
              (C)  STRANDEDNESS:       single
              (D)  TOPOLOGY:           linear (xi) SEQUENCE DESCRIPTION: SEQ ID NO: 1789:

UACCAGAUGG AUGU                                                           14

(2)  INFORMATION FOR SEQ ID NO: 1790:

(i)  SEQUENCE CHARACTERISTICS:

(A)  LENGTH:             14 base pairs
              (B)  TYPE:               nucleic acid
              (C)  STRANDEDNESS:       single
              (D)  TOPOLOGY:           linear (xi) SEQUENCE DESCRIPTION: SEQ ID NO: 1790:
```

```
AUACAGCUUU GGUG                                                14

(2) INFORMATION FOR SEQ ID NO: 1791:

(i) SEQUENCE CHARACTERISTICS:

(A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1791:

UGACAGAUCA CGGC                                                14

(2) INFORMATION FOR SEQ ID NO: 1792:

(i) SEQUENCE CHARACTERISTICS:

(A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1792:

UCACGGCUCG UGCG                                                14

(2) INFORMATION FOR SEQ ID NO: 1793:

(i) SEQUENCE CHARACTERISTICS:

(A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1793:

AUCCUGCCGG UGGC                                                14

(2) INFORMATION FOR SEQ ID NO: 1794:

(i) SEQUENCE CHARACTERISTICS:

(A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1794:

UUGCUGAUUC AGGC                                                14

(2) INFORMATION FOR SEQ ID NO: 1795:

(i) SEQUENCE CHARACTERISTICS:

(A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1795:

GGACGGACCU CCAU                                                14

(2) INFORMATION FOR SEQ ID NO: 1796:

(i) SEQUENCE CHARACTERISTICS:

(A) LENGTH:           14 base pairs
        (B) TYPE:             nucleic acid
```

```
            (C)  STRANDEDNESS:          single
            (D)  TOPOLOGY:              linear (xi) SEQUENCE DESCRIPTION: SEQ ID NO: 1796:

GGUCAGUUUU CUCU                                                         14

(2) INFORMATION FOR SEQ ID NO: 1797:

(i) SEQUENCE CHARACTERISTICS:

(A)  LENGTH:                14 base pairs
            (B)  TYPE:                  nucleic acid
            (C)  STRANDEDNESS:          single
            (D)  TOPOLOGY:              linear (xi) SEQUENCE DESCRIPTION: SEQ ID NO: 1797:

UUGCAGUCGU CAGC                                                         14

(2) INFORMATION FOR SEQ ID NO: 1798:

(i) SEQUENCE CHARACTERISTICS:

(A)  LENGTH:                14 base pairs
            (B)  TYPE:                  nucleic acid
            (C)  STRANDEDNESS:          single
            (D)  TOPOLOGY:              linear (xi) SEQUENCE DESCRIPTION: SEQ ID NO: 1798:

CGUCAGCCUG AACA                                                         14

(2) INFORMATION FOR SEQ ID NO: 1799:

(i) SEQUENCE CHARACTERISTICS:

(A)  LENGTH:                14 base pairs
            (B)  TYPE:                  nucleic acid
            (C)  STRANDEDNESS:          single
            (D)  TOPOLOGY:              linear (xi) SEQUENCE DESCRIPTION: SEQ ID NO: 1799:

AAACUGUUUG GGAC                                                         14

(2) INFORMATION FOR SEQ ID NO: 1800:

(i) SEQUENCE CHARACTERISTICS:

(A)  LENGTH:                14 base pairs
            (B)  TYPE:                  nucleic acid
            (C)  STRANDEDNESS:          single
            (D)  TOPOLOGY:              linear (xi) SEQUENCE DESCRIPTION: SEQ ID NO: 1800:

AAACAGCUGC AAGG                                                         14

(2) INFORMATION FOR SEQ ID NO: 1801:

(i) SEQUENCE CHARACTERISTICS:

(A)  LENGTH:                14 base pairs
            (B)  TYPE:                  nucleic acid
            (C)  STRANDEDNESS:          single
            (D)  TOPOLOGY:              linear (xi) SEQUENCE DESCRIPTION: SEQ ID NO: 1801:

GGGCUGCUGG GGCC                                                         14

(2) INFORMATION FOR SEQ ID NO: 1802:
```

(i) SEQUENCE CHARACTERISTICS:
        (A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1802:

UGUCAGCCGA GGCA                                                    14

(2) INFORMATION FOR SEQ ID NO: 1803:

(i) SEQUENCE CHARACTERISTICS:
        (A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1803:

UGCCUGCCUC AGGC                                                    14

(2) INFORMATION FOR SEQ ID NO: 1804:

(i) SEQUENCE CHARACTERISTICS:
        (A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1804:

UGACGGCCCC CACU                                                    14

(2) INFORMATION FOR SEQ ID NO: 1805:

(i) SEQUENCE CHARACTERISTICS:
        (A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1805:

GACCUGCCCG GCAG                                                    14

(2) INFORMATION FOR SEQ ID NO: 1806:

(i) SEQUENCE CHARACTERISTICS:
        (A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1806:

ACGCAGACGC CGGC                                                    14

(2) INFORMATION FOR SEQ ID NO: 1807:

(i) SEQUENCE CHARACTERISTICS:
        (A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1807:

```
CUACGGAUGC ACUG                                                           14

(2) INFORMATION FOR SEQ ID NO: 1808:

(i) SEQUENCE CHARACTERISTICS:
        (A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1808:

AGGCUGUCCA ACGA                                                           14

(2) INFORMATION FOR SEQ ID NO: 1809:

(i) SEQUENCE CHARACTERISTICS:
        (A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1809:

AUCCCGUCCA UCGC                                                           14

(2) INFORMATION FOR SEQ ID NO: 1810:

(i) SEQUENCE CHARACTERISTICS:
        (A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1810:

UUGCUGCUGG UGGU                                                           14

(2) INFORMATION FOR SEQ ID NO: 1811:

(i) SEQUENCE CHARACTERISTICS:
        (A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1811:

GAUCGGCCUC UUCA                                                           14

(2) INFORMATION FOR SEQ ID NO: 1812:

(i) SEQUENCE CHARACTERISTICS:
        (A) LENGTH:           14 base pairs
        (B) TYPE:             nucleic acid
        (C) STRANDEDNESS:     single
        (D) TOPOLOGY:         linear (xi) SEQUENCE DESCRIPTION: SEQ ID NO: 1812:

AGGCUGCUGC AGGA                                                           14

(2) INFORMATION FOR SEQ ID NO: 1813:

(i) SEQUENCE CHARACTERISTICS:

(A) LENGTH:           14 base pairs
```

```
            (B)  TYPE:              nucleic acid
            (C)  STRANDEDNESS:      single
            (D)  TOPOLOGY:          linear (xi)  SEQUENCE DESCRIPTION: SEQ ID NO: 1813:

UUCCCGUCGC UAUC                                                    14

(2)   INFORMATION FOR SEQ ID NO: 1814:

(i)   SEQUENCE CHARACTERISTICS:
            (A)  LENGTH:            14 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 1814:

GUGCCGCCUG CUGG                                                    14

(2)   INFORMATION FOR SEQ ID NO: 1815:

(i)   SEQUENCE CHARACTERISTICS:
            (A)  LENGTH:            14 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 1815:

CGCCUGCUGG GCAU                                                    14

(2)   INFORMATION FOR SEQ ID NO: 1816:

(i)   SEQUENCE CHARACTERISTICS:
            (A)  LENGTH:            14 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 1816:

CAUCUGCCUC ACCU                                                    14

(2)   INFORMATION FOR SEQ ID NO: 1817:

(i)   SEQUENCE CHARACTERISTICS:
            (A)  LENGTH:            14 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 1817:

ACGCAGCUCA UGCC                                                    14

(2)   INFORMATION FOR SEQ ID NO: 1818:

(i)   SEQUENCE CHARACTERISTICS:
            (A)  LENGTH:            14 base pairs
            (B)  TYPE:              nucleic acid
            (C)  STRANDEDNESS:      single
            (D)  TOPOLOGY:          linear (xi)  SEQUENCE DESCRIPTION: SEQ ID NO: 1818:

CUUCGGCUGC CUCC                                                    14
```

(2) INFORMATION FOR SEQ ID NO: 1819:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1819:

CGGCUGCCUC CUGG    14

(2) INFORMATION FOR SEQ ID NO: 1820:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1820:

UACCUGCUCA ACUG    14

(2) INFORMATION FOR SEQ ID NO: 1821:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1821:

GUGCAGAUCG CAAA    14

(2) INFORMATION FOR SEQ ID NO: 1822:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1822:

GGACCGUCGC UUGG    14

(2) INFORMATION FOR SEQ ID NO: 1823:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1823:

UCACAGAUUU UGGG    14

(2) INFORMATION FOR SEQ ID NO: 1824:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1824:

AAACUGCUGG GUGC                              14

(2) INFORMATION FOR SEQ ID NO: 1825:

(i) SEQUENCE CHARACTERISTICS:
        (A) LENGTH:        14 base pairs
        (B) TYPE:          nucleic acid
        (C) STRANDEDNESS:  single
        (D) TOPOLOGY:      linear (xi) SEQUENCE DESCRIPTION: SEQ ID NO: 1825:

UGACCGUUUG GGAG                              14

(2) INFORMATION FOR SEQ ID NO: 1826:

(i) SEQUENCE CHARACTERISTICS:
        (A) LENGTH:        14 base pairs
        (B) TYPE:          nucleic acid
        (C) STRANDEDNESS:  single
        (D) TOPOLOGY:      linear (xi) SEQUENCE DESCRIPTION: SEQ ID NO: 1826:

CUACAGACUC CAAC                              14

(2) INFORMATION FOR SEQ ID NO: 1827:

(i) SEQUENCE CHARACTERISTICS:
        (A) LENGTH:        14 base pairs
        (B) TYPE:          nucleic acid
        (C) STRANDEDNESS:  single
        (D) TOPOLOGY:      linear (xi) SEQUENCE DESCRIPTION: SEQ ID NO: 1827:

GCCCUGAUGG AUGA                              14

(2) INFORMATION FOR SEQ ID NO: 1828:

(i) SEQUENCE CHARACTERISTICS:
        (A) LENGTH:        14 base pairs
        (B) TYPE:          nucleic acid
        (C) STRANDEDNESS:  single
        (D) TOPOLOGY:      linear (xi) SEQUENCE DESCRIPTION: SEQ ID NO: 1828:

AUGCCGACGA GUAC                              14

(2) INFORMATION FOR SEQ ID NO: 1829:

(i) SEQUENCE CHARACTERISTICS:
        (A) LENGTH:        14 base pairs
        (B) TYPE:          nucleic acid
        (C) STRANDEDNESS:  single
        (D) TOPOLOGY:      linear (xi) SEQUENCE DESCRIPTION: SEQ ID NO: 1829:

CAGCAGCCCC UCCA                              14

(2) INFORMATION FOR SEQ ID NO: 1830:

(i) SEQUENCE CHARACTERISTICS:

```
          (A)  LENGTH:             14 base pairs
          (B)  TYPE:               nucleic acid
          (C)  STRANDEDNESS:       single
          (D)  TOPOLOGY:           linear (xi) SEQUENCE DESCRIPTION: SEQ ID NO: 1830:

UCACGGACUC CCCU                                                              14

(2) INFORMATION FOR SEQ ID NO: 1831:

(i) SEQUENCE CHARACTERISTICS:
          (A)  LENGTH:             14 base pairs
          (B)  TYPE:               nucleic acid
          (C)  STRANDEDNESS:       single
          (D)  TOPOLOGY:           linear (xi) SEQUENCE DESCRIPTION: SEQ ID NO: 1831:

AAGCUGUCCC AUCA                                                              14

(2) INFORMATION FOR SEQ ID NO: 1832:

(i) SEQUENCE CHARACTERISTICS:
          (A)  LENGTH:             14 base pairs
          (B)  TYPE:               nucleic acid
          (C)  STRANDEDNESS:       single
          (D)  TOPOLOGY:           linear (xi) SEQUENCE DESCRIPTION: SEQ ID NO: 1832:

AGACAGCUUC UUGC                                                              14

(2) INFORMATION FOR SEQ ID NO: 1833:

(i) SEQUENCE CHARACTERISTICS:
          (A)  LENGTH:             14 base pairs
          (B)  TYPE:               nucleic acid
          (C)  STRANDEDNESS:       single
          (D)  TOPOLOGY:           linear (xi) SEQUENCE DESCRIPTION: SEQ ID NO: 1833:

AUACAGCUCA GACC                                                              14

(2) INFORMATION FOR SEQ ID NO: 1834:

(i) SEQUENCE CHARACTERISTICS:
          (A)  LENGTH:             14 base pairs
          (B)  TYPE:               nucleic acid
          (C)  STRANDEDNESS:       single
          (D)  TOPOLOGY:           linear (xi) SEQUENCE DESCRIPTION: SEQ ID NO: 1834:

GCUCAGACCC CACA                                                              14

(2) INFORMATION FOR SEQ ID NO: 1835:

(i) SEQUENCE CHARACTERISTICS:
          (A)  LENGTH:             14 base pairs
          (B)  TYPE:               nucleic acid
          (C)  STRANDEDNESS:       single
          (D)  TOPOLOGY:           linear (xi) SEQUENCE DESCRIPTION: SEQ ID NO: 1835:

AACCAGUCCG UUCC                                                              14
```

(2) INFORMATION FOR SEQ ID NO: 1836:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1836:

AGUCCGUUCC CAAA                                14

(2) INFORMATION FOR SEQ ID NO: 1837:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1837:

GGCCCGCUGG CUCU                                14

(2) INFORMATION FOR SEQ ID NO: 1838:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1838:

AUCCUGUCUA UCAC                                14

(2) INFORMATION FOR SEQ ID NO: 1839:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1839:

AAUCAGCCUC UGAA                                14

(2) INFORMATION FOR SEQ ID NO: 1840:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1840:

ACACUGUCCA GCCC                                14

(2) INFORMATION FOR SEQ ID NO: 1841:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 1841:

GUCCAGCCCA CCUG                                                                14

(2) INFORMATION FOR SEQ ID NO: 1842:

(i) SEQUENCE CHARACTERISTICS:

(A) LENGTH:         14 base pairs
        (B) TYPE:           nucleic acid
        (C) STRANDEDNESS:   single
        (D) TOPOLOGY:       linear (xi) SEQUENCE DESCRIPTION: SEQ ID NO: 1842:

CGACAGCCCU GCCC                                                                14

(2) INFORMATION FOR SEQ ID NO: 1843:

(i) SEQUENCE CHARACTERISTICS:

(A) LENGTH:         14 base pairs
        (B) TYPE:           nucleic acid
        (C) STRANDEDNESS:   single
        (D) TOPOLOGY:       linear (xi) SEQUENCE DESCRIPTION: SEQ ID NO: 1843:

GCCCUGCCCA CUGG                                                                14

(2) INFORMATION FOR SEQ ID NO: 1844:

(i) SEQUENCE CHARACTERISTICS:

(A) LENGTH:         14 base pairs
        (B) TYPE:           nucleic acid
        (C) STRANDEDNESS:   single
        (D) TOPOLOGY:       linear (xi) SEQUENCE DESCRIPTION: SEQ ID NO: 1844:

ACCCUGACUA CCAG                                                                14

(2) INFORMATION FOR SEQ ID NO: 1845:

(i) SEQUENCE CHARACTERISTICS:

(A) LENGTH:         14 base pairs
        (B) TYPE:           nucleic acid
        (C) STRANDEDNESS:   single
        (D) TOPOLOGY:       linear (xi) SEQUENCE DESCRIPTION: SEQ ID NO: 1845:

CCACAGCUGA AAAU                                                                14

(2) INFORMATION FOR SEQ ID NO: 1846:

(i) SEQUENCE CHARACTERISTICS:

(A) LENGTH:         14 base pairs
        (B) TYPE:           nucleic acid
        (C) STRANDEDNESS:   single
        (D) TOPOLOGY:       linear (xi) SEQUENCE DESCRIPTION: SEQ ID NO: 1846:

AUCCAGACUC UUUC                                                                14

(2) INFORMATION FOR SEQ ID NO: 1847:

(i) SEQUENCE CHARACTERISTICS:

```
        (A) LENGTH:            14 base pairs
        (B) TYPE:              nucleic acid
        (C) STRANDEDNESS:      single
        (D) TOPOLOGY:          linear (xi) SEQUENCE DESCRIPTION: SEQ ID NO: 1847:

CCACAGACUG GUUU                                                          14

(2) INFORMATION FOR SEQ ID NO: 1848:

(i) SEQUENCE CHARACTERISTICS:

(A) LENGTH:            14 base pairs
        (B) TYPE:              nucleic acid
        (C) STRANDEDNESS:      single
        (D) TOPOLOGY:          linear (xi) SEQUENCE DESCRIPTION: SEQ ID NO: 1848:

ACACCGACUA GCCA                                                          14

(2) INFORMATION FOR SEQ ID NO: 1849:

(i) SEQUENCE CHARACTERISTICS:

(A) LENGTH:            14 base pairs
        (B) TYPE:              nucleic acid
        (C) STRANDEDNESS:      single
        (D) TOPOLOGY:          linear (xi) SEQUENCE DESCRIPTION: SEQ ID NO: 1849:

GUUCUGCUUC AAGG                                                          14

(2) INFORMATION FOR SEQ ID NO: 1850:

(i) SEQUENCE CHARACTERISTICS:

(A) LENGTH:            14 base pairs
        (B) TYPE:              nucleic acid
        (C) STRANDEDNESS:      single
        (D) TOPOLOGY:          linear (xi) SEQUENCE DESCRIPTION: SEQ ID NO: 1850:

GGCCGGAUCG GUAC                                                          14

(2) INFORMATION FOR SEQ ID NO: 1851:

(i) SEQUENCE CHARACTERISTICS:

(A) LENGTH:            14 base pairs
        (B) TYPE:              nucleic acid
        (C) STRANDEDNESS:      single
        (D) TOPOLOGY:          linear (xi) SEQUENCE DESCRIPTION: SEQ ID NO: 1851:

ACUCUGUCCC UUCC                                                          14

(2) INFORMATION FOR SEQ ID NO: 1852:

(i) SEQUENCE CHARACTERISTICS:

(A) LENGTH:            14 base pairs
        (B) TYPE:              nucleic acid
        (C) STRANDEDNESS:      single
        (D) TOPOLOGY:          linear (xi) SEQUENCE DESCRIPTION: SEQ ID NO: 1852:

CCACUGAUGG ACCA                                                          14
```

(2) INFORMATION FOR SEQ ID NO: 1853:

(i) SEQUENCE CHARACTERISTICS:
       (A) LENGTH:        14 base pairs
       (B) TYPE:          nucleic acid
       (C) STRANDEDNESS:  single
       (D) TOPOLOGY:      linear (xi) SEQUENCE DESCRIPTION: SEQ ID NO: 1853:

AGACUGACUU GUUU                                                          14

(2) INFORMATION FOR SEQ ID NO: 1854:

(i) SEQUENCE CHARACTERISTICS:
       (A) LENGTH:        14 base pairs
       (B) TYPE:          nucleic acid
       (C) STRANDEDNESS:  single
       (D) TOPOLOGY:      linear (xi) SEQUENCE DESCRIPTION: SEQ ID NO: 1854:

AUGCCGCCCC UGUC                                                          14

(2) INFORMATION FOR SEQ ID NO: 1855:

(i) SEQUENCE CHARACTERISTICS:
       (A) LENGTH:        14 base pairs
       (B) TYPE:          nucleic acid
       (C) STRANDEDNESS:  single
       (D) TOPOLOGY:      linear (xi) SEQUENCE DESCRIPTION: SEQ ID NO: 1855:

CCCCUGUCUU GCUG                                                          14

(2) INFORMATION FOR SEQ ID NO: 1856:

(i) SEQUENCE CHARACTERISTICS:
       (A) LENGTH:        14 base pairs
       (B) TYPE:          nucleic acid
       (C) STRANDEDNESS:  single
       (D) TOPOLOGY:      linear (xi) SEQUENCE DESCRIPTION: SEQ ID NO: 1856:

ACUCGGAUUC CAGC                                                          14

(2) INFORMATION FOR SEQ ID NO: 1857:

(i) SEQUENCE CHARACTERISTICS:
       (A) LENGTH:        14 base pairs
       (B) TYPE:          nucleic acid
       (C) STRANDEDNESS:  single
       (D) TOPOLOGY:      linear (xi) SEQUENCE DESCRIPTION: SEQ ID NO: 1857:

UUCCAGCCCA CAUU                                                          14

(2) INFORMATION FOR SEQ ID NO: 1858:

(i) SEQUENCE CHARACTERISTICS:
       (A) LENGTH:        14 base pairs
       (B) TYPE:          nucleic acid
       (C) STRANDEDNESS:  single (D) TOPOLOGY:          linear (xi) SEQUENCE DESCRIPTION: SEQ ID NO: 1858:

CCACAGCUGA GAAU                                                14

(2) INFORMATION FOR SEQ ID NO: 1859:

(i) SEQUENCE CHARACTERISTICS:
            (A) LENGTH:            14 base pairs
            (B) TYPE:              nucleic acid
            (C) STRANDEDNESS:      single
            (D) TOPOLOGY:          linear (xi) SEQUENCE DESCRIPTION: SEQ ID NO: 1859:

ACACCGCUUU UGUU                                                14

(2) INFORMATION FOR SEQ ID NO: 1860:

(i) SEQUENCE CHARACTERISTICS:
            (A) LENGTH:            14 base pairs
            (B) TYPE:              nucleic acid
            (C) STRANDEDNESS:      single
            (D) TOPOLOGY:          linear (xi) SEQUENCE DESCRIPTION: SEQ ID NO: 1860:

GCUCAGAUGA AAUG                                                14

(2) INFORMATION FOR SEQ ID NO: 1861:

(i) SEQUENCE CHARACTERISTICS:
            (A) LENGTH:            14 base pairs
            (B) TYPE:              nucleic acid
            (C) STRANDEDNESS:      single
            (D) TOPOLOGY:          linear (xi) SEQUENCE DESCRIPTION: SEQ ID NO: 1861:

AAGCUGCUCU GAAA                                                14

(2) INFORMATION FOR SEQ ID NO: 1862:

(i) SEQUENCE CHARACTERISTICS:
            (A) LENGTH:            14 base pairs
            (B) TYPE:              nucleic acid
            (C) STRANDEDNESS:      single
            (D) TOPOLOGY:          linear (xi) SEQUENCE DESCRIPTION: SEQ ID NO: 1862:

GGUCAGCUGC CCCC                                                14

(2) INFORMATION FOR SEQ ID NO: 1863:

(i) SEQUENCE CHARACTERISTICS:
            (A) LENGTH:            14 base pairs
            (B) TYPE:              nucleic acid
            (C) STRANDEDNESS:      single
            (D) TOPOLOGY:          linear (xi) SEQUENCE DESCRIPTION: SEQ ID NO: 1863:

CAGCUGCCCC CAAA                                                14

(2) INFORMATION FOR SEQ ID NO: 1864:

```
        (i) SEQUENCE CHARACTERISTICS:

(A) LENGTH:          14 base pairs
            (B) TYPE:            nucleic acid
            (C) STRANDEDNESS:    single
            (D) TOPOLOGY:        linear (xi) SEQUENCE DESCRIPTION: SEQ ID NO: 1864:

UCUCUGCCUU GAGU                                                         14

(2) INFORMATION FOR SEQ ID NO: 1865:

(i) SEQUENCE CHARACTERISTICS:

(A) LENGTH:          14 base pairs
            (B) TYPE:            nucleic acid
            (C) STRANDEDNESS:    single
            (D) TOPOLOGY:        linear (xi) SEQUENCE DESCRIPTION: SEQ ID NO: 1865:

UUACAGCUCU GGCC                                                         14

(2) INFORMATION FOR SEQ ID NO: 1866:

(i) SEQUENCE CHARACTERISTICS:

(A) LENGTH:          14 base pairs
            (B) TYPE:            nucleic acid
            (C) STRANDEDNESS:    single
            (D) TOPOLOGY:        linear (xi) SEQUENCE DESCRIPTION: SEQ ID NO: 1866:

UUGCAGAUGU UUUA                                                         14

(2) INFORMATION FOR SEQ ID NO: 1867:

(i) SEQUENCE CHARACTERISTICS:

(A) LENGTH:          14 base pairs
            (B) TYPE:            nucleic acid
            (C) STRANDEDNESS:    single
            (D) TOPOLOGY:        linear (xi) SEQUENCE DESCRIPTION: SEQ ID NO: 1867:

AACCUGACUG GUUA                                                         14

(2) INFORMATION FOR SEQ ID NO: 1868:

(i) SEQUENCE CHARACTERISTICS:

(A) LENGTH:          14 base pairs
            (B) TYPE:            nucleic acid
            (C) STRANDEDNESS:    single
            (D) TOPOLOGY:        linear (xi) SEQUENCE DESCRIPTION: SEQ ID NO: 1868:

CAGCAGUCCU UUGU                                                         14

(2) INFORMATION FOR SEQ ID NO: 1869:

(i) SEQUENCE CHARACTERISTICS:

(A) LENGTH:          14 base pairs
            (B) TYPE:            nucleic acid
            (C) STRANDEDNESS:    single
            (D) TOPOLOGY:        linear (xi) SEQUENCE DESCRIPTION: SEQ ID NO: 1869:
```

```
UUUCAGCCUA CAGU                                                            14

(2) INFORMATION FOR SEQ ID NO: 1870:

(i) SEQUENCE CHARACTERISTICS:

(A) LENGTH:          14 base pairs
        (B) TYPE:            nucleic acid
        (C) STRANDEDNESS:    single
        (D) TOPOLOGY:        linear (xi) SEQUENCE DESCRIPTION: SEQ ID NO: 1870:

UCCCAGAUCA GUCA                                                            14

(2) INFORMATION FOR SEQ ID NO: 1871:

(i) SEQUENCE CHARACTERISTICS:

(A) LENGTH:          11 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for any base
            The letter "H" stands for A, C or U.

(xi) SEQUENCE DESCRIPTION: SEQ ID NO: 1871:

NNNNUHNNNN N                                                               11

(2) INFORMATION FOR SEQ ID NO: 1872:

(i) SEQUENCE CHARACTERISTICS:

(A) LENGTH:          28 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for any base.

(xi) SEQUENCE DESCRIPTION: SEQ ID NO: 1872:

NNNNNCUGAN GAGNNNNNNC GAAANNNN                                             28

(2) INFORMATION FOR SEQ ID NO: 1873:

(i) SEQUENCE CHARACTERISTICS:

(A) LENGTH:          15 base pairs
        (B) TYPE:            nucleic acid
        (C) STRANDEDNESS:    single
        (D) TOPOLOGY:        linear (ix) FEATURE:

(D) OTHER INFORMATION:   The letter "N" stands for any base.
            The letter "Y" stands for C or U.
            The letter "H" stands for A, C or U.

(xi) SEQUENCE DESCRIPTION: SEQ ID NO: 1873:

NNNNNNNYNG HYNNN                                                           15

(2) INFORMATION FOR SEQ ID NO: 1874:

(i) SEQUENCE CHARACTERISTICS:

(A) LENGTH:          47 base pairs
```

```
            (B) TYPE:              nucleic acid
            (C) STRANDEDNESS:      single
            (D) TOPOLOGY:          linear (ix) FEATURE:

(D) OTHER INFORMATION: The letter "N" stands for any base.
                The letter "H" stands for A, C or U.

(xi) SEQUENCE DESCRIPTION: SEQ ID NO: 1874:

NNNNGAAGNN NNNNNNNNNA AAHANNNNNN NACAUUACNN NNNNNNN                  47

(2) INFORMATION FOR SEQ ID NO: 1875:

(i) SEQUENCE CHARACTERISTICS:

(A) LENGTH:            49 base pairs
            (B) TYPE:              nucleic acid
            (C) STRANDEDNESS:      single
            (D) TOPOLOGY:          linear (ix) FEATURE:

(D) OTHER INFORMATION: The letter "N" stands for any base.

(xi) SEQUENCE DESCRIPTION: SEQ ID NO: 1875:

CUCCACCUCC UCGCGGUNNN NNNNGGGCUA CUUCGGUAGG CUAAGGGAG                49

(2) INFORMATION FOR SEQ ID NO: 1876:

(i) SEQUENCE CHARACTERISTICS:

(A) LENGTH:            176 base pairs
            (B) TYPE:              nucleic acid
            (C) STRANDEDNESS:      single
            (D) TOPOLOGY:          linear (xi) SEQUENCE DESCRIPTION: SEQ ID NO: 1876:

GGGAAAGCUU GCGAAGGGCG UCGUCGCCCC GAGCGGUAGU AAGCAGGGAA CUCACCUCCA    60

AUUUCAGUAC UGAAAUUGUC GUAGCAGUUG ACUACUGUUA UGUGAUUGGU AGAGGCUAAG   120

UGACGGUAUU GGCGUAAGUC AGUAUUGCAG CACAGCACAA GCCCGCUUGC GAGAAU       176

(2) INFORMATION FOR SEQ ID NO: 1877:

(i) SEQUENCE CHARACTERISTICS:

(A) LENGTH:            37 base pairs
            (B) TYPE:              nucleic acid
            (C) STRANDEDNESS:      single
            (D) TOPOLOGY:          linear (ix) FEATURE:

(D) OTHER INFORMATION: The letter "N" stands for any base.
                The letter "H" stands for A, C or U.

(xi) SEQUENCE DESCRIPTION: SEQ ID NO: 1877:

NNNNNNNCUG AUGAGGCCGA AAGGCCGAAA NNNNNNH                             37
```

ENZYMATIC NUCLEIC ACID TREATMENT OF DISEASES OR CONDITIONS RELATED TO LEVELS OF EPIDERMAL GROWTH FACTOR RECEPTORS

CROSS REFERENCE TO RELATED APPLICATION

This application claims the benefit of Saghir Akhtar et al., U.S. Provisional Application 60/036,476, entitled "Enzymatic Nucleic Acid Treatment of Diseases or Conditions Related to Levels of Epidermal Growth Factor Receptors", filed Jan. 31, 1997, which is hereby incorporated herein by reference in its entirety, including any drawings and figures.

BACKGROUND OF THE INVENTION

The present invention concerns therapeutic compositions and methods for the treatment of cancer.

The present invention relates to therapeutic compositions and methods for the treatment or diagnosis of diseases or conditions related to EGFR expression levels, such as cancer. The following summary is not meant to be complete and is provided only for understanding of the invention that follows. This summary is not an admission that any of the work described below is prior art to the claimed invention.

The epidermal growth factor receptor (EGFR) is a 170 kDa transmembrane glycoprotein consisting of an extracellular 'ligand' binding domain, a transmembrane region and an intracellular domain with tyrosine kinase activity (Kung et al., 1994). The binding of growth factors to the EGFR results in down regulation of the ligand-receptor complex, autophosphorylation of the receptor and other protein substrates, leading ultimately to DNA synthesis and cell division. The external ligand binding domain is stimulated by EGF and also by TGFα, amphiregulin and some viral growth factors (Modjtahedi & Dean, 1994).

The EGFR gene (c-erbB1), is located on chromosone 7, and is homologous to the avian erythroblastosis virus oncogene (v-erbB), which induces malignancies in chickens. The v-erbB gene codes for a truncated product that lacks the extracellular ligand binding domain. The tyrosine kinase domain of the EGFR has been found to have 97% homology to the v-erbB transforming protein (Downward et al., 1984).

EGFR is overexpressed in a number of malignant human tissues when compared to their normal tissue counterparts (for review see Khazaie et al., 1993). The gene for the receptor is both amplified and overexpressed in a number of cancer cells. Overexpression of the EGFR is often accompanied by the co-expression of the growth factors EGF and TGFα, suggesting that an autocrine pathway for control of growth may play a major part in the progression of tumors (Sporn & Roberts, 1985).

Growth factors and their receptors may play a role in the development of human brain tumors. A high incidence of overexpression, amplification, deletion and structural rearrangement of the gene coding for the EGFR has been found in biopsies of brain tumors (Ostrowski et al., 1994). In fact the amplification of the EGFR gene in glioblastoma multiforme tumors is one of the most consistent genetic alterations known, with the EGFR being overexpressed in approximately 40% of malignant gliomas (Black, 1991). It has also been demonstrated that in 50% of glioblastomas, amplification of the EGFR gene is accompanied by the co-expression of mRNA for at least one or both of the growth factors EGF and TNFα (Ekstrand et al., 1991).

The amplified genes are frequently rearranged and associated with polymorphism leading to abnormal protein products (Wong et al., 1994). The rearrangements that have been characterized usually shown deletions of part of the extracellular domain, resulting in the production of an EGFR protein that is smaller is size. Three classes of deletion mutant EGF receptor genes have been identified in glioblastoma tumors. Type I mutants lack the majority of the external domain, including the ligand binding site, type II mutants have a deletion in the domain adjacent to the membrane but can still bind ligands and type III, which is the most common and found in 17% of glioblastomas, have a deletion of 267 amino acids spanning domains I and II of the EGFR.

In addition to glioblastomas, abnormal EGFR expression has also been reported in a number of squamous epidermoid cancers and breast cancers (reviewed in Kung et al, 1994; Modjtahedi & Dean, 1994). Many patients with tumors that overexpress the EGFR have a poorer prognosis than those who do not (Khazaie et al., 1993). Consequently, therapeutic strategies which can potentially inhibit or reduce the aberrant expression of the EGFR receptor are of great interest as potential anti-cancer agents.

SUMMARY OF THE INVENTION

This invention relates to ribozymes, or enzymatic nucleic acid molecules, directed to cleave RNA species that are required for cellular growth responses. In particular, applicant describes the selection and function of ribozymes capable of cleaving RNA encoded by the receptor of epidermal growth factor (EGFR). Such ribozymes may be used to inhibit the hyper-proliferation of tumor cells in one or more cancers.

In the present invention, ribozymes that cleave EGFR RNA are described. Those of ordinary skill in the art will understand that from the examples described that other ribozymes that cleave target RNAs required for cell proliferation may be readily designed and are within the invention. Such RNAs may have at least 90% homology to EGFR in humans with a normal EGFR gene.

By "inhibit" is meant that the activity of EGFR or level of RNAs encoded by EGFR is reduced below that observed in the absence of the nucleic acid, particularly, inhibition with ribozymes preferably is below that level observed in the presence of an inactive RNA molecule able to bind to the same site on the mRNA, but unable to cleave the RNA.

By "enzymatic nucleic acid molecule" it is meant a nucleic acid molecule which has complementarity in a substrate binding region to a specified gene target, and also has an enzymatic activity which is active to specifically cleave RNA in that target. That is, the enzymatic nucleic acid molecule is able to intermolecularly cleave RNA and thereby inactivate a target RNA molecule. This complementarity functions to allow sufficient hybridization of the enzymatic nucleic acid molecule to the target RNA to allow the cleavage to occur. One hundred percent complementarity is preferred, but complementarity as low as 50–75% may also be useful in this invention.

The term enzymatic nucleic acid is used interchangeably with phrases such as ribozymes, catalytic RNA, enzymatic RNA, catalytic DNA, nucleozyme, DNAzyme, RNA enzyme, endoribonuclease, minizyme, leadzyme, oligozyme or DNA enzyme, as used in the art. All of these terminologies describe nucleic acid molecules with enzymatic activity.

By "equivalent" RNA to EGFR is meant to include those naturally occurring RNA molecules associated with cancer in various animals, including human.

By "complementarity" is meant a nucleic acid that can form hydrogen bond(s) with another RNA sequence by either traditional Watson-Crick or other non-traditional types (for example, Hoogsteen type) of base-paired interactions.

Seven basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, since the concentration of ribozyme necessary to affect a therapeutic treatment is lower. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to completely eliminate catalytic activity of a ribozyme.

Nucleic acid molecules having an endonuclease enzymatic activity are able to repeatedly cleave other separate RNA molecules in a nucleotide base sequence-specific manner. Such enzymatic RNA molecules can be targeted to virtually any RNA transcript, and efficient cleavage achieved in vitro (Zaug et al., 324, *Nature* 429 1986; Uhlenbeck, 1987 *Nature* 328, 596; Kim at al., 84 *Proc. Natl. Acad. Sci. USA* 8788, 1987; Dreyfus, 1988, *Einstein Quart. J. Bio. Med.*, 6, 92; Haseloff and Gerlach, 334 *Nature* 585, 1988; Cech, 260 *JAMA* 3030, 1988; and Jefferies et al., 17 *Nucleic Acids Research* 1371, 1989).

Because of their sequence-specificity, trans-cleaving ribozymes show promise as therapeutic agents for human disease (Usman & McSwiggen, 1995*Ann. Rep. Med. Chem.* 30, 285–294; Christoffersen and Marr, 1995 *J. Med. Chem.* 38, 2023–2037). Ribozymes can be designed to cleave specific RNA targets within the background of cellular RNA. Such a cleavage event renders the RNA non-functional and abrogates protein expression from that RNA. In this manner, synthesis of a protein associated with a disease state can be selectively inhibited.

Ribozymes that cleave the specified sites in EGFR RNAs represent a novel therapeutic approach to treat diseases, such as cancer and other conditions. Applicant indicates that ribozymes are able to inhibit the activity of EGFR and that the catalytic activity of the ribozymes is required for their inhibitory effect. Those of ordinary skill in the art, will find that it is clear from the examples described that other ribozymes that cleave these sites in EGFR RNAs may be readily designed and are within the scope of this invention.

In one of the preferred embodiments of the inventions herein, the enzymatic nucleic acid molecule is formed in a hammerhead or hairpin motif, but may also be formed in the motif of a hepatitis δ virus, group I intron, group II intron or RNaseP RNA (in association with an RNA guide sequence) or Neurospora VS RNA. Examples of such hammerhead motifs are described by Dreyfus, supra, Rossi et al., 1992, *AIDS Research and Human Retroviruses* 8, 183; of hairpin motifs by Hampel et al., EP0360257, Hampel and Tritz, 1989 *Biochemistry* 28, 4929, Feldstein et al., 1989, *Gene* 82, 53, Haseloff and Gerlach, 1989, *Gene*, 82, 43, and Hampel et al., 1990 *Nucleic Acids Res.* 18, 299; of the hepatitis δ virus motif is described by Perrotta and Been, 1992 *Biochemistry* 31, 16; of the RNaseP motif by Guerrier-Takada et al., 1983 *Cell* 35, 849; Forster and Altman, 1990, *Science* 249, 783; Li and Altman, 1996, *Nucleic Acids Res.* 24, 835; Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799; Guo and Collins, 1995, *EMBO. J.* 14, 363); Group II introns are described by Griffin et al., 1995, *Chem. Biol.* 2, 761; Michels and Pyle, 1995, *Biochemistry* 34, 2965; Pyle et al., *International PCT Publication No. WO 96/22689*; and of the Group I intron by Cech et al., U.S. Pat. No. 4,987,071. These specific motifs are not limiting in the invention and those skilled in the art will recognize that all that is important in an enzymatic nucleic acid molecule (or multiple fragments of such molecules) of this invention is that is has a specific substrate binding site or arm(s) which is complementary to one or more of the target gene RNA regions, and that it have nucleotide sequences within or surrounding that substrate binding site which impart an RNA cleaving activity to the molecule (enzymatic portion).

By "enzymatic portion" is meant that part of the ribozyme essential for cleavage of an RNA substrate.

By "substrate binding arm" is meant that portion of a ribozyme which is complementary to (i.e., able to base-pair with) a portion of its substrate. Generally, such complementarity is 100%, but can be less if desired. For example, as few as 10 bases out of 14 may be base-paired. Such arms are shown generally in FIGS. 1–3 as discussed below. That is, these arms contain sequences within a ribozyme which are intended to bring ribozyme and target RNA together through complementary base-pairing interactions; e.g., ribozyme sequences with stems I and III of a standard hammerhead ribozyme make up the substrate-binding domain (see FIG. 1).

In a preferred embodiment the invention provides a method for producing a class of enzymatic cleaving agents which exhibit a high degree of specificity for the RNA of a desired target. The enzymatic nucleic acid molecule is preferably targeted to a highly conversed sequence region of a target mRNAs encoding EGFR proteins such that specific treatment of a disease or condition can be provided with either one or several enzymatic nucleic acids. Such enzymatic nucleic acid molecules can be delivered exogenously to specific cells as required. Alternatively, the ribozymes can be expressed from DNA/RNA vectors that are delivered to specific cells.

Synthesis of nucleic acids greater that 100 nucleotides in length is difficult using automated methods, and the therapeutic cost of such molecules is prohibitive. In this invention, small nucleic acid motifs (e.g., antisense oligonucleotides, hammerhead or the hairpin ribozymes) are used for exogenous delivery. The simple structure of these molecules increases the ability of the nucleic acid to invade targeted regions of the mRNA structure. However, these nucleic acid molecules can also be expressed within cells from eukaryotic promoters (e.g., Izant and Weintraub, 1985 *Science* 229, 345; McGarry and Lindquist, 1986 *Proc. Natl. Acad. Sci. USA* 83, 399; SullengerScanlon et al., 1991, *Proc. Natl. Acad. Sci. USA,* 88, 10591–5; Kashani-Sabet et al., 1992 *Antisense Res. Dev.,* 2, 3–15; Dropulic et al., 1992 *J. Virol.,* 66, 1432–41; Weerasinghe et al., 1991 *J. Virol,* 65, 5531–4; Ojwang et al., 1992 *Proc. Natl. Acad. Sci. USA* 89, 10802–6; Chen et al., 1992 *Nucleic Acids Res.,* 20, 4581–9; Sarver et al., 1990 *Science* 247, 1222–1225; Thompson et al., 1995 *Nucleic Acids Res.* 23, 2259). Those skilled in the art realize that any nucleic acid can be expressed in eukaryotic cells from the appropriate DNA/RNA vector. The activity of such nucleic acids can be augmented by their release from the primary transcript by a ribozyme (Draper et al., PCT WO93/23569, and Sullivan et al., PCT WO94/02595, both hereby incorporated in their totality by reference herein; Ohkawa et al., 1992 *Nucleic Acids Symp. Ser.,* 27, 15–6; Taira et al., 1991, *Nucleic Acids Res.,* 19, 5125–30; Ventura et al., 1993 *Nucleic Acids Res.,* 21, 3249–55; Chowrira et al., 1994 *J. Biol. Chem.* 269, 25856).

Such ribozymes are useful for the prevention of the diseases and conditions discussed above, and any other diseases or conditions that are related to the levels of EGFR activity in a cell or tissue.

By "related" is meant that the inhibition of EGFR RNAs and thus reduction in the level respective protein activity will relieve to some extent the symptoms of the disease or condition.

Ribozymes are added directly, or can be complexed with cationic lipids, packaged within liposomes, or otherwise delivered to target cells. The nucleic acid or nucleic acid complexes can be locally administered to relevant tissues ex vivo, or in vivo through injection, infusion pump or stent, with or without their incorporation in biopolymers. In preferred embodiments, the ribozymes have binding arms which are complementary to the sequences in Tables III and IV. Examples of such ribozymes are also shown in Table III and IV. Examples of such ribozymes consist essentially of sequences defined in these Tables.

By "consists essentially of" is meant that the active ribozyme contains an enzymatic center or core equivalent to those in the examples, and binding arms able to bind mRNA such that cleavage at the target site occurs. Other sequences may be present which do not interfere with such cleavage.

Thus, in a first aspect, the invention features ribozymes that inhibit gene expression and/or cell proliferation via cleavage of RNA expressed from the EGFR gene. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target mRNAs, preventing translation and protein accumulation. In the absence of the expression of the target gene, cell proliferation is inhibited.

In a preferred embodiment, the enzymatic RNA molecules cleave EGFR mRNA and inhibit cell proliferation. Such ribozymes are useful for the prevention and/or treatment of cancer. Ribozymes are added directly, or can be complexed with cationic lipids, packaged within liposomes, or otherwise delivered to smooth muscle cells. The RNA or RNA complexes can be locally administered to relevant tissues through the use of a catheter, infusion pump or stent, with or without their incorporation in biopolymers. The ribozymes, similarly delivered, also are useful for inhibiting proliferation of certain cancers associated with elevated levels of the EGFR, particularly glioblastoma multiforme. Using the methods described herein, other enzymatic RNA molecules that cleave EGFR and thereby inhibit tumor cell proliferation may be derived and used as described above. Specific examples are provided below in the Tables and figures.

In another aspect of the invention, ribozymes that cleave target molecules and inhibit EGFR activity are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell (for a review see Couture and Stinchcomb, 1986, *TIG.,* 12, 510).

By "patient" is meant an organism which is a donor or recipient of explanted cells or the cells themselves. "Patient" also refers to an organism to which enzymatic nucleic acid molecules can be administered. Preferably, a patient is a mammal or mammalian cells. More preferably, a patient is a human or human cells.

By "vectors" is meant any nucleic acid- and/or viral-based technique used to deliver a desired nucleic acid.

These ribozymes, individually, or in combination or in conjunction with other drugs, can be used to treat diseases or conditions discussed above. For example, to treat a disease or condition associated with EGFR levels, the patient may be treated, or other appropriate cells may be treated, as is evident to those skilled in the art.

In a further embodiment, the described ribozymes can be used in combination with other known treatments to treat conditions or diseases discussed above. For example, the described ribozymes could be used in combination with one of more known therapeutic agents to treat cancer.

In preferred embodiments, the ribozymes have binding arms which are complementary to the sequences in the tables III and IV (Seq ID NOs. 1–823 and 1759–1870. Examples of such ribozymes are also shown in Tables III and IV (Seq. ID Nos. 824–1758). Other sequences may be present which do not interfere with such cleavage.

Other features and advantages of the invention will be apparent from the following description of the preferred embodiments thereof, and from the claims.

DESCRIPTION OF THE PREFERRED EMBODIMENTS

The drawings will first briefly by described.

Drawings:

FIG. 1 is a diagrammatic representation of the hammerhead ribozyme domain known in the art. Stem II can be $\geq 2$ base-pair long.

FIG. 2a is a diagrammatic representation of the hammerhead ribozyme domain known in the art; FIG. 2b is a diagrammatic representation of the hammerhead ribozyme as divided by Uhlenbeck (1987, *Nature,* 327, 596–600) into a substrate and enzyme portion; FIG. 2c is a similar diagram showing the hammerhead divided by Haseloff and Gerlach (1988, *Nature,* 334, 585–591) into two portions; and FIG. 2d is a similar diagram showing the hammerhead divided by Jeffries and Symons (1989, *Nucl. Acids. Res.,* 17, 1371— 1371) into two portions.

FIG. 3 is a diagrammatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq$1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq$2 bases. The connecting loop can also be replaced with a non-nucleotide linker molecule. H refers to bases A, U, or C. Y refers to pyrimidine bases. " " refers to a covalent bond.

Figure 6A:
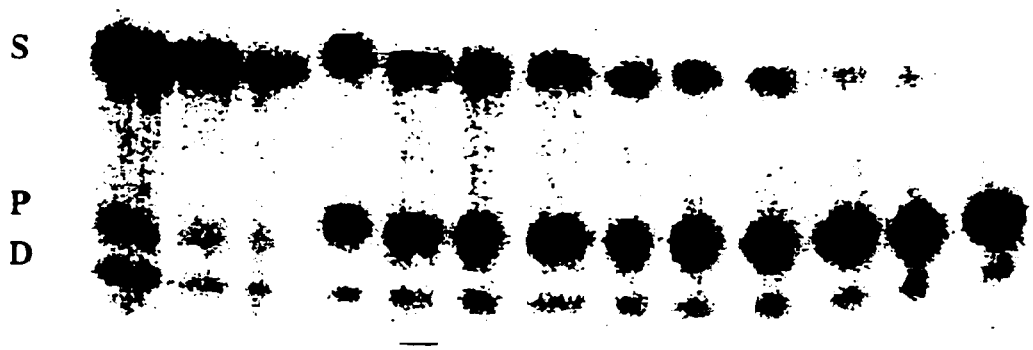
Figure 6B:
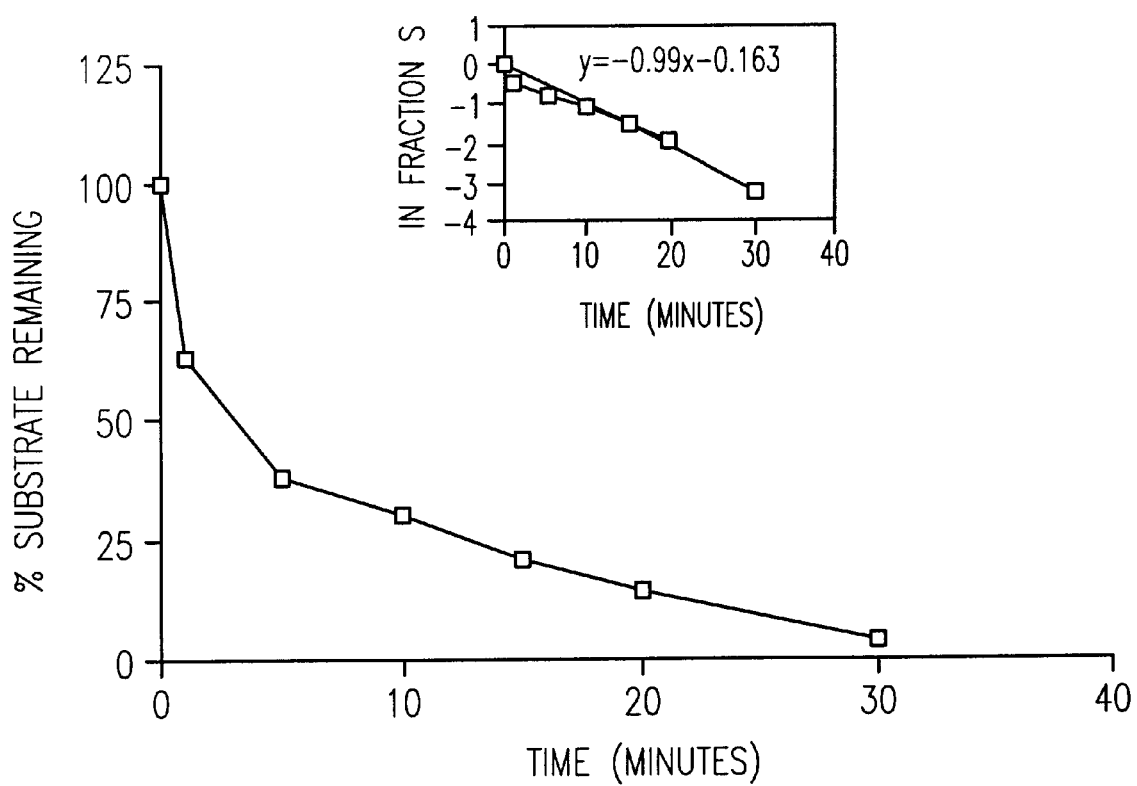
Figure 6C:
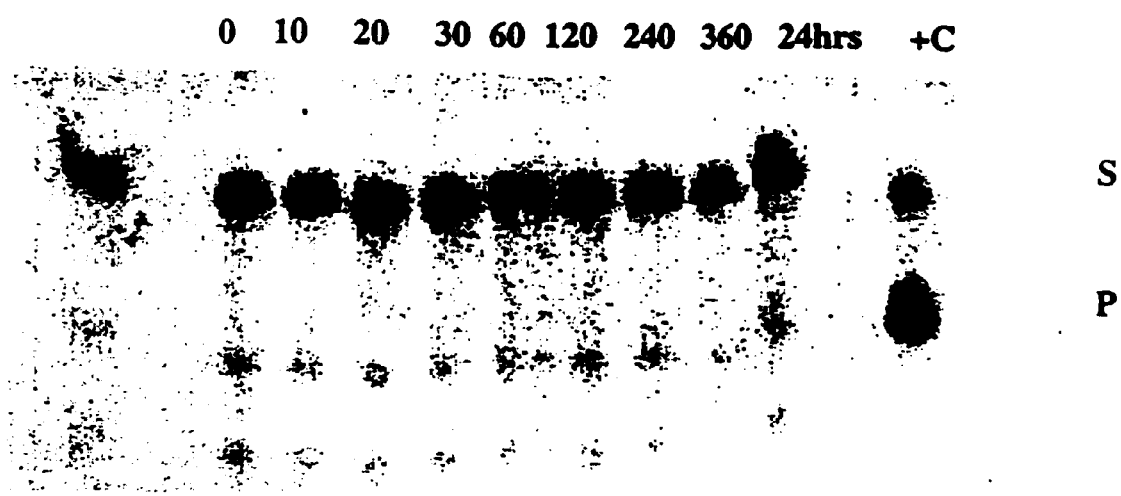

FIG. 6 shows in vitro RNA cleavage activity of Amino ribozymes tergeted against EGFR RNA. a Autoradiograph of the cleavage reaction. The reaction was performed in the presence of 50 mM Tris.HCl (pH 7.5), 10 mM MgCl$_2$ at 37° C. as described below. Times of the reaction in minutes are given above the lanes. S0 represents intact substrate in Tris.HCl buffer without the addition of ribozyme at time 0. S1 represents intact substrate in Tris.HCl buffer at time 60 min. +C represents a positive control of cleaved product only. Band S represents intact substrate, band P cleaved product and band D degradation; b Time course of cleavage. Bands from autoradiography were quantified by scanning densitometry and the fraction of substrate remaining plotted against time. inset. Semilog plots were used to determine the half life of the substrate ($t_{1/2}$=0.693/k); c Autoradiograph showing reaction of the EGFR ribozyme against a non complementary substrate RNA. 40 nM ribozyme was added to 1 nM substrate in the presence of 50 mM Tris.HCl (pH 7.5), 10 mM MgCl$_2$ at 37° C. Band S refers to intact substrate and band P is cleaved product. Reaction times are given in minutes (unless stated otherwise). C represents intact substrate without the addition of ribozyme. +C represents cleaved product.

Figure 7A:
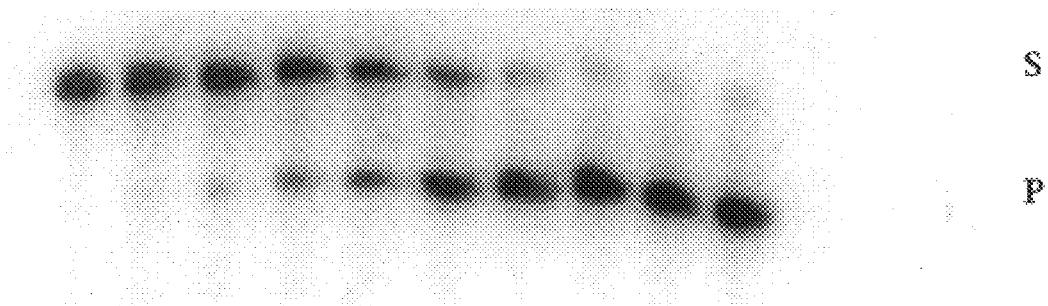
Figure 7B:
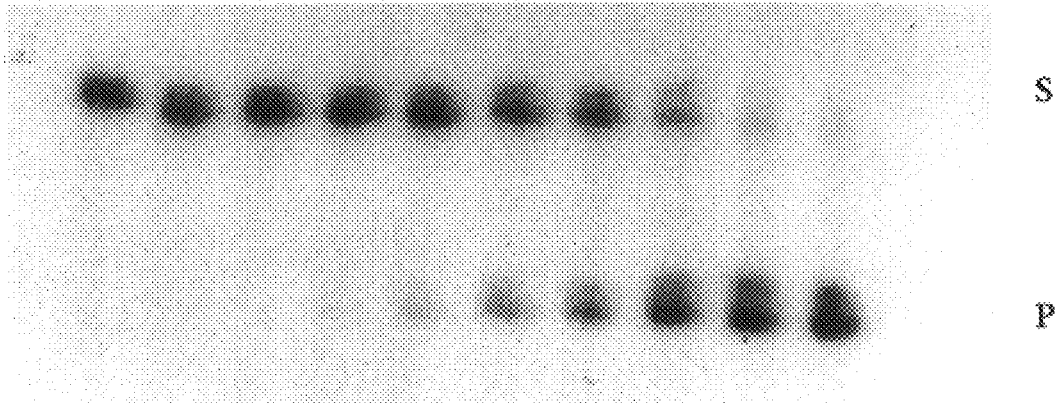
Figure 7C:
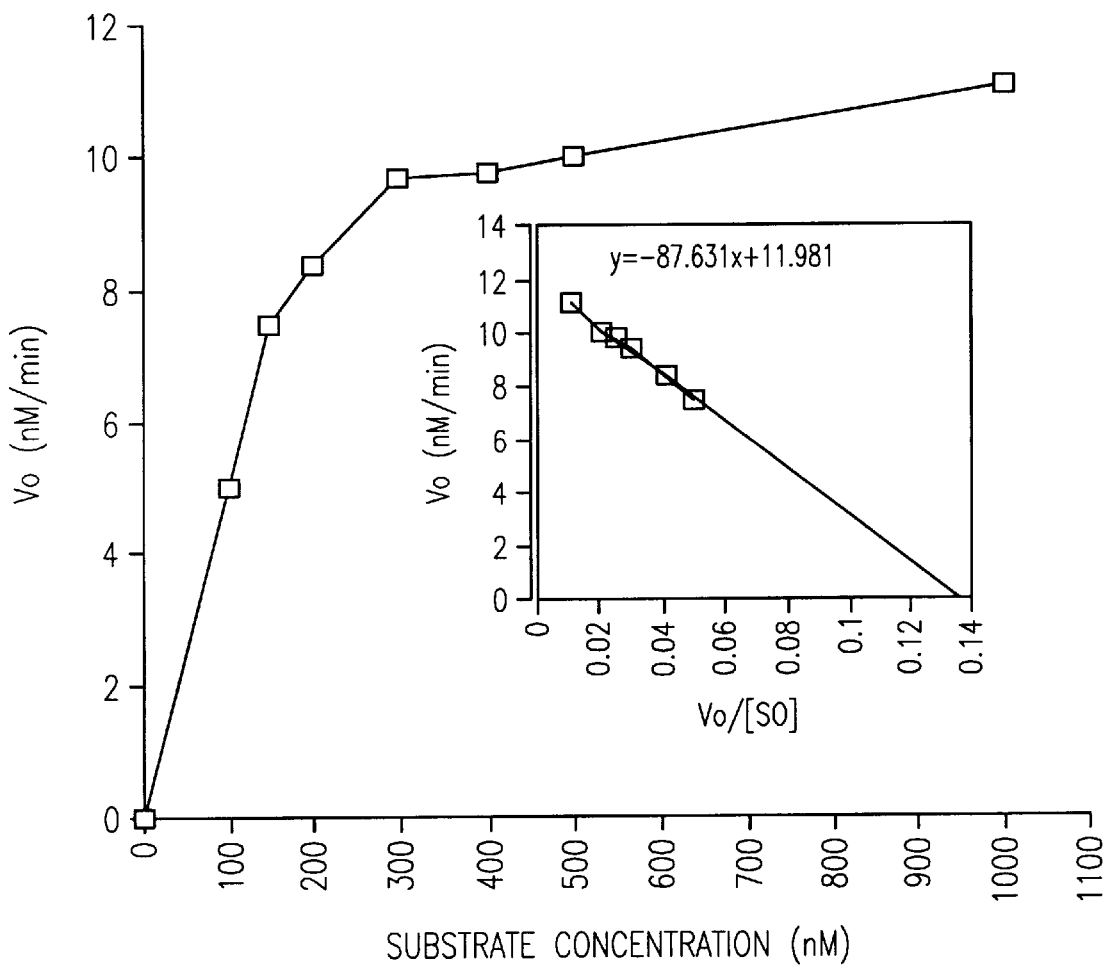

FIG. 7 Representative examples of autoradiographs depicting the time course of cleavage reactions exhibited by EGFR ribozyme against it's target substrate under multiple turnover reactions. a In vitro activity of 10 nM ribozyme with 300 nM of 5' [32P] labelled substrate RNA; b In vitro activity of 10 nM ribozyme with 1 $\mu$M of 5'[32P] labelled substrate RNA. Reactions were performed in the presence of 50 mM Tris.HCl (pH 7.5), 10 mM MgCl$_2$ at 37° C. as described below. Reaction times, in minutes, are given above the lanes. C represents intact substrate in Tris.HCl buffer without the addition of ribozyme. Band S refers to intact substrate and band P refers to cleaved product. c Kinetics of hammerhead cleavage reactions exhibited by the EGFR ribozyme. The initial rate of reaction (Vo,nM/min) is plotted versus substrate concentration. Ribozyme concentration was 10 nM while substrate concentration varied as indicated. inset Eadie-Hofstee plot of this data.

Figure 8:
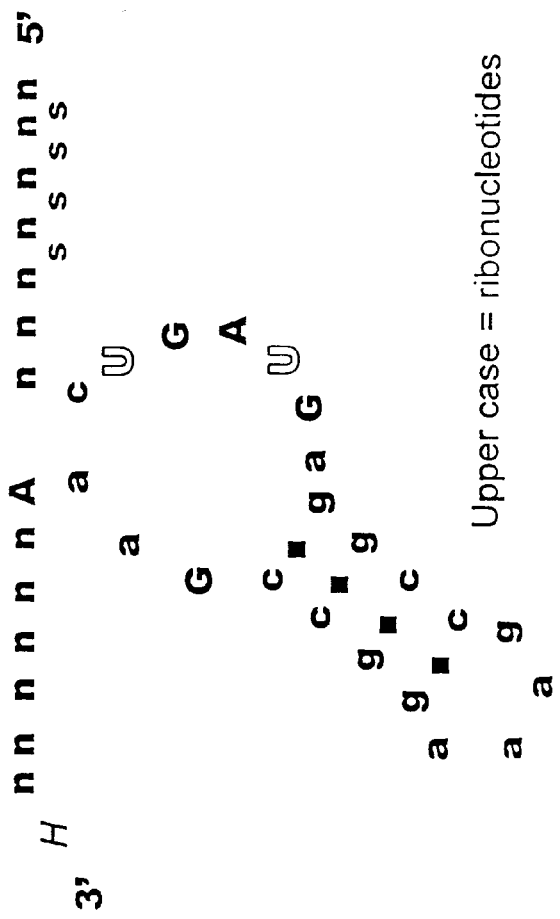

FIG. 8 shows a generic structure of chemically modified amino hammerhead ribozyme.

Figure 9:
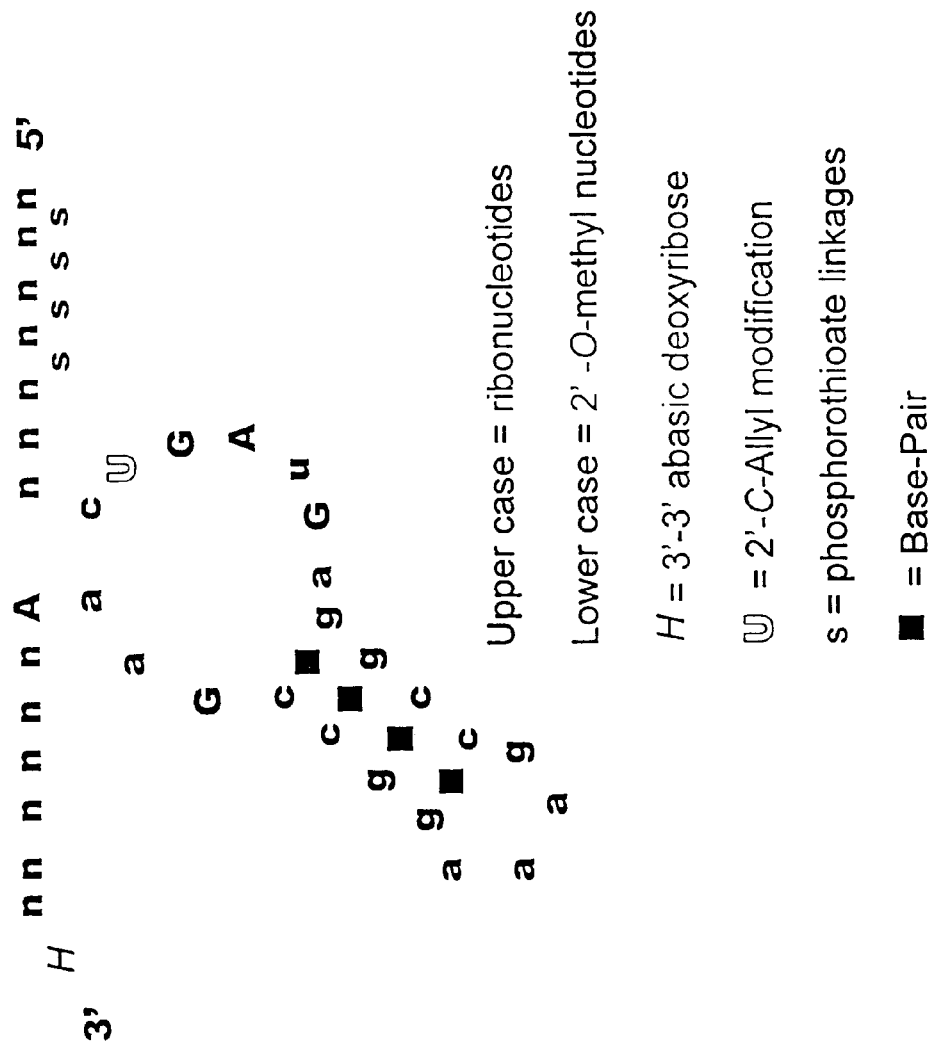

FIG. 9 shows a generic structure of chemically modified C-allyl hammerhead ribozyme.

TARGET SITES

Targets for useful ribozymes can be determined as disclosed in Draper et al., WO 93/23569; Sullivan et al., WO 93/23057; Thompson et al., WO 94/02595; Draper et al., WO 95/04818; McSwiggen et al., U.S. Pat. No. 5,525,468 and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein.

The sequence of human EGFR RNAs were screened for optimal ribozyme target sites using a computer folding algorithm. Hammerhead or hairpin ribozyme cleavage sites were identified. These sites are shown in Tables III and IV (All sequences are 5' to 3' in the tables) The nucleotide base position is noted in the Tables as that site to be cleaved by the designated type of ribozyme. The nucleotide base position is noted in the Tables as that site to be cleaved by the designated type of ribozyme.

Hammerhead or hairpin ribozymes were designed that could bind and were individually analyzed by computer folding (Jaeger et al., 1989 *Proc. Natl. Acad. Sci. USA,* 86, 7706) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Ribozymes of the hammerhead or hairpin motif were designed to anneal to various sites in the mRNA message. The binding arms are complementary to the target site sequences described above. The ribozymes were chemically synthesized. The method of synthesis used follows the procedure for normal RNA synthesis as described in Usman et al., 1987 *J. Am. Chem. Soc.,* 109, 7845; Scaringe et al., 1990 *Nucleic Acids Res.,* 18, 5433; and Wincott et al., 1995 *Nucleic Acids Res.* 23, 2677–2684 and makes use of common nucleic acid protecting and coupling groups, such as dimethoxytrityl at the 5'-end, and phosphoramidites at the 3'-end. Small scale synthesis were conducted on a 394 Applied Biosystems, Inc. synthesizer using a modified 2.5 $\mu$mol scale protocol with a 5 min coupling step for alkylsilyl protected nucleotides and 2.5 min coupling step for 2'-O-methylated nucleotides. Table II outlines the amounts, and the contact times, of the reagents used in the synthesis cycle. A 6.5-fold excess (163 $\mu$L of 0.1 M=16.3 $\mu$mol) of phosphoramidite and a 24-fold excess of S-ethyl tetrazole (238

μL of 0.25 M=59.5 μmol) relative to polymer-bound 5'-hydroxyl was used in each coupling cycle. Average coupling yields on the 394 Applied Biosystems, Inc. synthesizer, determined by colorimetric quantitation of the trityl fractions, were 97.5–99%. Other oligonucleotide synthesis reagents for the 394 Applied Biosystems, Inc. synthesizer: detrytilation solution was 2% TCA in methylene chloride (ABI); capping was performed with 16% N-methyl imidazole in THF (ABI) and 10% acetic anhydride/10% 2,6-lutidine in THF (ABI); oxidation was 16.9 mM $I_2$, 49 mM pyridine, 9% water in THF (Millipore). B & J Synthesis Grade acetonitrile was used directly from the reagent bottle. S-Ethyl tetrazole solution (0.25 M acetonitrile) was made up from the solid obtained from American International Chemical, Inc.

Deprotection of the RNA was performed as follows. The polymer-bound oligoribonucleotide, trityl-off, was transferred from the synthesis column to a 4 mL glass screw top vial and suspended in a solution of methylamine (MA) at 65° C. for 10 min. After cooling to −20° C., the supernatant was removed from the polymer support. The support was washed three times with 1.0 mL of EtOH:MeCN:$H_2O$/3:1:1, vortexed and the supernatant was then added to the first supernatant. The combined supernatants, containing the oligoribonucleotide, were dried to a white powder.

The base-deprotected oligoribonucleotide was resuspended in anhydrous TEA•HF/NMP solution (250 μL of a solution of 1.5 mL N-methyl-pyrrolidinone, 750 μL TEA and 1.0 mL TEA•3HF to provide a 1.4M HF concentration) and heated to 65° C. for 1.5 h. The resulting, fully deprotected, oligomer was quenched with 50 mM TEAB (9 mL) prior to anion exchange desalting.

For anion exchange desalting of the deprotected oligomer, the TEAB solution was loaded onto a Qiagen 500® anion exchange cartridge (Qiagen Inc.) that was prewashed with 50 mM TEAB (10 mL). After washing the loaded cartridge with 50 mM TEAB (10 mL), the RNA was eluted with 2 M TEAB (10 mL) and dried down to a white powder.

Inactive hammerhead ribozymes were synthesized by substituting a U for $G_5$ and a U for $A_{14}$ (numbering from Hertel, K. J., et al., 1992, Nucleic Acids Res., 20, 3252).

The average stepwise coupling yields were >98% (Wincott et al., 1995 Nucleic Acids Res. 23, 2677–2684).

Hairpin ribozymes are synthesized in two parts and annealed to reconstruct the active ribozyme (Chowrira and Burke, 1992 Nucleic Acids Res., 20, 2835–2840). Ribozymes are also synthesized from DNA templates using bacteriophage T7 RNA polymerase (Milligan and Uhlenbeck, 1989, Methods Enzymol. 180, 51).

Ribozymes are modified to enhance stability and/or enhance catalytic activity by modification with nuclease resistant groups, for example, 2'-amino, 2'-C-allyl, 2'-flouro, 2'-O-methyl, 2'-H, nucleotide base modifications (for a review see Usman and Cedegren, 1992 TIBS 17, 34; Usman et al., 1994 Nucleic Acids Symp. Ser. 31, 163; Burgin et al., 1996 Biochemistry 6, 14090). Ribozymes are purified by gel electrophoresis using general methods or are purified by high pressure liquid chromatography (HPLC; See Wincott et al., supra) the totality of which is hereby incorporated herein by reference) and are resuspended in water.

The sequences of the ribozymes that are chemically synthesized, useful in this study, are shown in Tables III–IV. Those in the art will recognize that these sequences are representative only of many more such sequences where the enzymatic portion of the ribozyme (all but the binding arms) is altered to affect activity. For example, stem-loop II sequence of hammerhead ribozymes can be altered (substitution, deletion, and/or insertion) to contain any sequences provided a minimum of two base-paired stem structure can form. Similarly, stem-loop IV sequence of hairpin ribozymes listed in Table IV (5'-CACGUUGUG-3') can be altered (substitution, deletion, and/or insertion) to contain any sequence, provided a minimum of two base-paired stem structure can form. Preferably, no more than 200 bases are inserted at these locations. The sequences listed in Tables III and IV may be formed of ribonucleotides or other nucleotides or non-nucleotides. Such ribozymes (which have enzymatic activity) are equivalent to the ribozymes described specifically in the Tables.

Optimizing Ribozyme Activity

Figure 1:
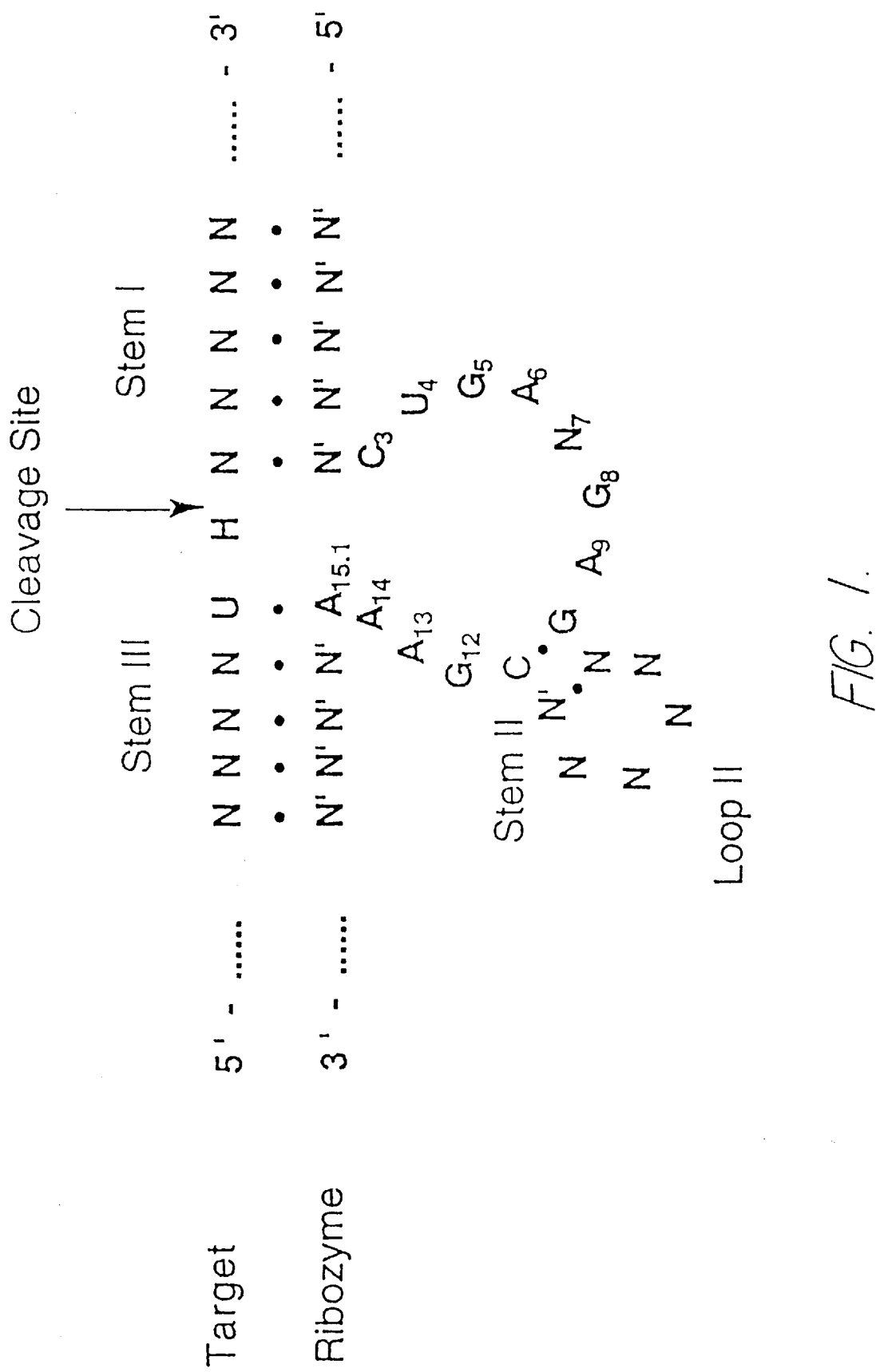
Figure 2A:
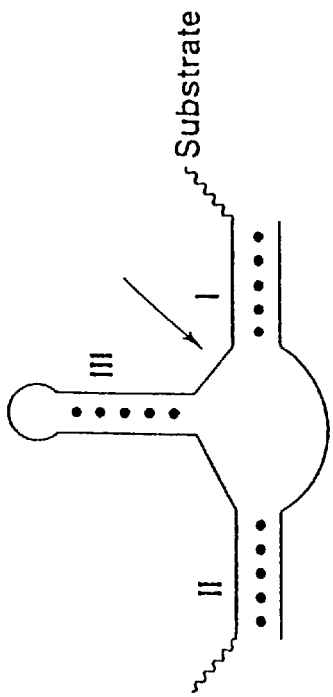
Figure 2B:
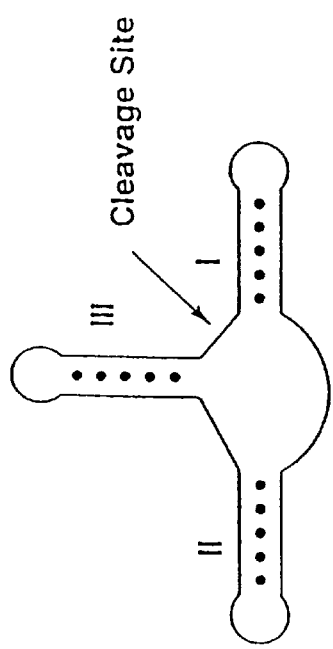
Figure 2C:
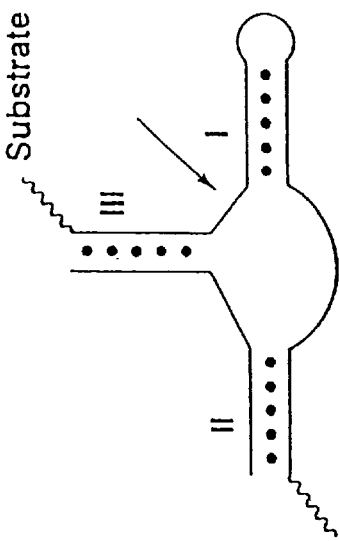
Figure 2D:
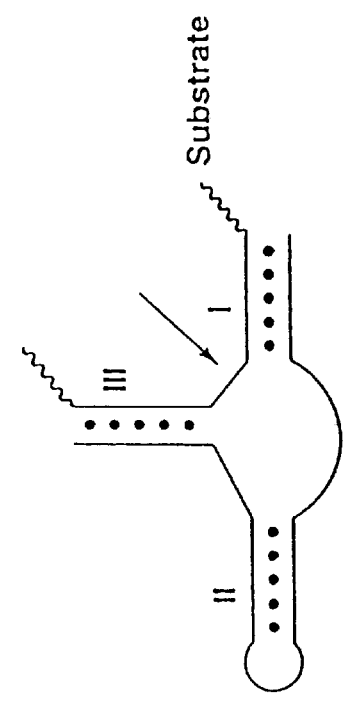

Ribozyme activity can be optimized as described by Draper et al., supra. The details will not be repeated here, but include altering the length of the ribozyme binding arms (stems I and III, see FIG. 2c), or chemically synthesizing ribozymes with modifications (base, sugar and/or phosphate) that prevent their degradation by serum ribonucleases and/or enhance their enzymatic activity (see e.g., Eckstein et. al., International Publication No. WO 92/07065; Perrault et al., 1990 Nature 344, 565; Pieken et al., 1991 Science 253, 314; Usman and Cedergren, 1992 Trends in Biochem. Sci. 17, 334; Usman et al., International Publication No. WO 93/15187; and Rossi et al., International Publication No. WO 91/03162; Sproat, U.S. Pat. No. 5,334, 711; and Burgin et al., supra; all of these describe various chemical modifications that can be made to the base, phosphate and/or sugar moieties of enzymatic RNA molecules). Modifications which enhance their efficacy in cells, and removal of stem II bases to shorten RNA synthesis times and reduce chemical requirements are desired. (All of these publications are hereby incorporated by reference herein.).

By "enhanced enzymatic activity" is meant to include activity measured in cells and/or in vivo where the activity is a reflection of both catalytic activity and ribozyme stability. In this invention, the product of these properties in increased or not significantly (less than 10 fold) decreased in vivo compared to an all RNA ribozyme.

The enzymatic nucleic acid having chemical modifications which maintain or enhances enzymatic activity is provided. Such nucleic acid is also generally more resistant to nucleases than unmodified nucleic acid. By "modified bases" in this aspect is meant nucleotide bases other than adenine, guanine, cytosine and uracil at 1' position or their equivalents; such bases may be used within the catalytic core of the enzyme as well as in the substrate-binding regions. In particular, the invention features modified ribozymes having a base substitution selected from pyridin-4-one, pyridin-2-one, phenyl, pseudouracil, 2, 4, 6-trimethoxy benzene, 3-methyluracil, dihydrouracil, naphthyl, 6-methyl-uracil and aminophenyl. As noted above, substitution in the core may decrease in vitro activity but enhances stability. Thus, in a cell and/or in vivo the activity may not be significantly lowered. As exemplified herein such ribozymes are useful in a cell and/or in vivo even if activity over all is reduced 10 fold. Such ribozymes herein are said to "maintain" the enzymatic activity on all RNA ribozyme.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres.

For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein.

Another means of accumulating high concentrations of a ribozyme(s) within cells is to incorporated the ribozyme-encoding sequences into a DNA or RNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA,* 87, 6743–7; Gao and Huang 1993 *Nucleic Acids Res.,* 21, 2867–72; Lieber et al., 1993 *Methods Enzymol.,* 217, 47–66; Zhou et al., 1990 *Mol. Cell. Biol.,* 10, 4529–37). Several investigators have demonstrated that ribozymes expressed from such promoters can function in mammalian cells (e.g. Kashani-Sabet et al., 1992 *Antisense Res. Dev.,* 2, 3–15; Ojwang et al., 1992 *Proc. Natl. Acad. Sci. USA,* 89, 10802–6; Chen et al., 1992 *Nucleic Acids Res.,* 20, 4581–9; Yu et al., 1993 *Proc. Natl. Acad. Sci. USA,* 90, 6340–4; L'Huillier et al., 1992 *EMBO J.* 11, 4411–8; Lisziewicz et al., 1993 *Proc. Natl. Acad. Sci. USA.,* 90, 8000–4; Thompson et al., 1995 *Nucleic Acids Res.* 23, 2259; Sullenger & Cech, 1993, *Science,* 262, 1566). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In a preferred embodiment of the invention, a transcription unit expressing a ribozyme that cleaves mRNAs encoded by EGFR is inserted into a plasmid DNA vector of an adenovirus or adeno-associated virus DNA viral vector or a retroviral RNA vector. Viral vectors have been used to transfer genes and lead to either transient or long term gene expression (Zabner et al., 1993 *Cell* 75, 207; Carter, 1992 *Curr. Opi. Biotech.* 3, 533). The adenovirus vector is delivered as recombinant adenoviral particles. The DNA may be delivered alone or complexed with vehicles (as described for RNA above). The recombinant adenovirus or AAV particles are locally administered to the site of treatment, e.g., through incubation or inhalation in vivo or by direct application to cells or tissues ex vivo. Retroviral vectors have also been used to express ribozymes in mammalian cells (Ojwang et al., 1992 supra; Thompson et al., 1995 supra; Couture and Stinchcomb, 1996; supra).

In another preferred embodiment, the ribozyme is administered to the site of EGFR expression (e.g., tumor cells) in an appropriate liposomal vesicle.

EXAMPLES

Example 1

Identification of Potential Ribozyme Cleavage Sites in Human EGFR RNA

The sequence of human EGFR RNA was screened for accessible sites using a computer folding algorithm. Regions of the mRNA that did not form secondary folding structures and potential hammerhead and/or hairpin ribozyme cleavage sites were identified. The sequences of these cleavage sites are shown in tables III and IV.

Example 2

Selection of Ribozyme Cleavage Sites in Human EGFR RNA

To test whether the sites predicted by the computer-based RNA folding algorithm corresponded to accessible sites in EGFR RNA, 20 hammerhead sites were selected for analysis. Ribozyme target sites were chosen by analyzing genomic sequences of human EGFR (GenBank Accession No. X00588) and prioritizing the sites on the basis of folding. Hammerhead ribozymes were designed that could bind each target (see FIG. 2C) and were individually analyzed by computer folding (Christoffersen et al., 1994 *J. Mol. Struc. Theochem.,* 311, 273; Jaeger et al., 1989, *Proc. Natl. Acad. Sci. USA,* 86, 7706) to assess whether the ribozyme sequences fold into the appropriate secondary structure. Those ribozymes with unfavorable intramolecular interactions between the binding arms and the catalytic core were eliminated from consideration. As noted below, varying binding arm lengths can be chosen to optimize activity. Generally, at least 5 bases on each arm are able to bind to, or otherwise interact with, the target RNA.

Example 3

Chemical Synthesis and Purification of Ribozymes for Efficient Cleavage of EGFR RNA Ribozymes of the hammerhead of hairpin motif were designed to anneal to various sites in the RNA message. The binding arms are complementary to the target site sequences described above. The ribozymes were chemically synthesized. The method of synthesis used followed the procedure for normal RNA synthesis as described in Usman et al., (1987 *J. Am. Chem. Soc.,* 109, 7845), Scaringe et al., (1990 *Nucleic Acids Res.,* 18, 5433) and Wincott et al., supra, and made use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from Hertel et al., 1992 *Nucleic Acids Res.,* 20, 3252). Hairpin ribozymes were synthesized in two parts and annealed to reconstruct the active ribozyme (Chowrira and Burke, 1992 *Nucleic Acids Res.,* 20, 2835– 2840). Ribozymes were also synthesized from DNA templates using bacteriophage T7 RNA polymerase (Milligan and Uhlenbeck, 1989, *Methods Enzymol.* 180, 51). All ribozymes were modified to enhance stability by modification with nuclease resistant groups, for example, 2'-amino, 2'-C-allyl, 2'-flouro, 2'-O-methyl, 2'-H (for a review see Usman and Cedergren, 1992 *TIBS* 17, 34). Ribozymes were purified by gel electrophoresis using general methods or were purified by high pressure liquid chromatography (HPLC; See Wincott et al., supra; the totality of which is hereby incorporated herein by reference) and were resuspended in water. The sequences of the chemically synthesized ribozymes used in this study are shown below in Table III and IV.

Example 4

Ribozyme Cleavage of EGFR RNA Target

Twenty hammerhead-type ribozymes targeted to the human EGFR RNA were designed and synthesized to test the cleavage activity in vitro. The target sequences and the nucleotide location within the EGFR mRNA are given in Table III. All hammerhead ribozymes were synthesized with binding arm (Stems I and III; see FIG. 2C) lengths of seven nucleotides. The relative abilities of a HH ribozyme to cleave human EGFR RNA is summarized in FIGS. 6 and 7.

Full-length or partially full-length, internally-labeled target RNA for ribozyme cleavage assay was prepared by in vitro transcription in the presence of [α-$^{32}$p] CTP, passed over a G 50 Sephadex column by spin chromatography and used as substrate RNA without further purification. Alternatively, substrates were 5'-$^{32}$P-end labeled using T4 polynucleotide kinase enzyme. Assays were performed by pre-warming a 2× concentration of purified ribozyme in ribozyme cleavage buffer (50 mM Tris.HCl, pH 7.5 at 37° C., 10 mM MgCl$_2$) and the cleavage reaction was initiated by adding the 2× ribozyme mix to an equal volume of substrate RNA (maximum of 1–5 nM) that was also pre-warmed in cleavage buffer. As an initial screen, assays were carried out for 1 hour at 37° C. using a final concentration of either 40 nM or 1 μM ribozyme, i.e., ribozyme excess. The reaction was quenched by the addition of an equal volume of 95% formamide, 20 mM EDTA, 0.05% bromophenol blue and 0.05% xylene cyanol after which the sample was heated to 95° C. for 2 minutes, quick chilled and loaded onto a denaturing polyacrylamide gel. Substrate RNA and the specific RNA cleavage products generated by ribozyme cleavage were visualized on an autoradiograph of the gel. The percentage of cleavage was determined by Phosphor Imager® quantitation of bands representing the intact substrate and the cleavage products.

Single Turnover Reaction: Alternatively, Cleavage reactions were carried out in 50 mM Tris.HCl, pH 7.5 and 10 mM MgCl$_2$ at 37° C. In order to disrupt aggregates that can form during storage, unlabelled ribozyme and 5'end labelled substrate were denatured and renatured separately in standard cleavage buffer (50 mM Tris.HCl, pH 7.5) by heating to 90° C. for 2 minutes and allowed to equilibrate to the reaction temperature of 37° C. for 15 minutes. Each RNA solution was then adjusted to a final concentration of 10 mM MgCl$_2$ and incubated at 37° C. for a further 15 minutes. Cleavage reactions were initiated by combining the ribozyme and the substrate samples to the required concentrations in a final volume of 100 μl. Ribozyme concentration was 40 nM and substrate concentration was 1 nM. The reaction was also repeated using double (2 nM) and half (0.5 nM) the concentration of substrate to verify that the reaction was indeed performed under single turnover conditions. Aliquots of 10 μl were removed at appropriate time intervals between 0 and 120 minutes and quenched by adding an equal volume of formamide loading buffer (9:1 (v:v) formamide:1× TBE) and frozen on dry ice. Product and substrate were separated by denaturing 20% polyacrylamide (7M urea) gel electrophoresis. To determine the fraction of cleavage, substrate and product bands were located by autoradiography of wet gels and quantified by densitometry of these autoradiograms. Autorads were scanned using an AGFA focus scanner connected to a Macintosh computer and images were saved as TIFF files. The programme NIH Image 1.58 (Division of Computing and Research Technology, NIH, Bethesda, USA) was used to plot and quantify the band intensities. In addition, the relevant bands were excised from the gel and quantified by scintillation counting of the slices cut from the gel (Packard Tricarb 2000 CA liquid scintillation analyser).

Reaction rate constants (k) were obtained from the slope of semilogarithmic plots of the amount of substrate remaining versus time. The activity half time t½ was calculated as 0.693/k. Each rate constant was determined from duplicate experiments.

In order to show the specificity of cleavage demonstrated under the above conditions, the experiment was repeated using a different substrate, relating to another site along the human EGFR mRNA. All conditions remained as described above except samples were taken over a longer time period i.e. at intervals spanning over 24 hours rather than over 2 hours.

Multiple Turnover Reactions: The kinetic characteristics of ribozyme RPI.4782 were determined from Eadie-Hofstee plots obtained from initial velocities with multiple turnovers done with 5' 32P labelled substrate. Cleavage reactions were carried out in 50 mM Tris.HCl, pH 7.5 and 10 mM MgCl$_2$ at 37° C. Stock solutions of 100 nM ribozyme and 500 nM–2 uM substrate RNA were prepared in 50 mM Tris.HCl, pH 7.5, preheated separately at 90° C. for 2 minutes and cooled to 37° C. for 15 minutes. After MgCl$_2$ was added to each of these solutions to a final volume of 10 mM, a further incubation period of 15 minutes at 37° C. took place. Cleavage reactions were performed in a final volume of 100 μl with a concentration of 10 nM ribozyme and concentrations of substrate between 100 nM and 1 μM. Reactions were initiated by the addition of ribozyme stock solution to substrate. Aliquots of 10 μl were taken at time intervals between 0 and 120 minutes, quenched by adding an equal volume of formamide loading buffer and frozen on dry ice. Intact substrate and products of cleavage were separated by electrophoresis on a 20% polyacrylamide/7M urea denaturing gel and were detected by autoradiography. The degree of cleavage at each time point was quantified by scanning densitometry of the resulting autoradiogram. Initial rates of reaction were measured at eight substrate concentrations and values of Kcat and Km were determined using Eadie-Hofstee plots.

As shown in FIGS. 6 and 7, Amino hammerhead ribozymes (RPI.4782) targeted against EGFR RNA cleaved their target RNAs in a sequence-specific manner the cleavage rates appeared to follow saturation kinetics with respect to concentration of substrate. Cleavage rates were first order at low substrate concentrations, however, as the concentration of substrate increased, the reactions rates levelled off suggesting that ribozymes were effectively saturated with substrate. These results indicate that the cleavage reactions were truly catalytic and were therefore amenable to analysis using Michaelis Menten rate equation. From a Eadie-Hofstee plot the kinetic parameters Km and Kcat were determined; ribozyme exhibited a Km valve of 87 nM and a Kcat value of 1.2 min$^{-1}$.

Under single turnover conditions, ribozyme RPI.4782 exhibited rapid cleavage of it's target sequence, the half life of the substrate being only 7 minutes. The high activity of this ribozyme is in agreement with the findings of Beigelman et al. (1995c). They reported that a ribozyme modified in the same manner as RPI.4782 exhibited almost wild type activity, with the half life of the substrate being only 3 minutes. Although cleavage was slightly slower than that demonstrated by Beigelman et al. (1995c), these findings clearly demonstrate that ribozyme RPI.4782 is able to cleave it's target in a highly efficient manner.

Figure 3:
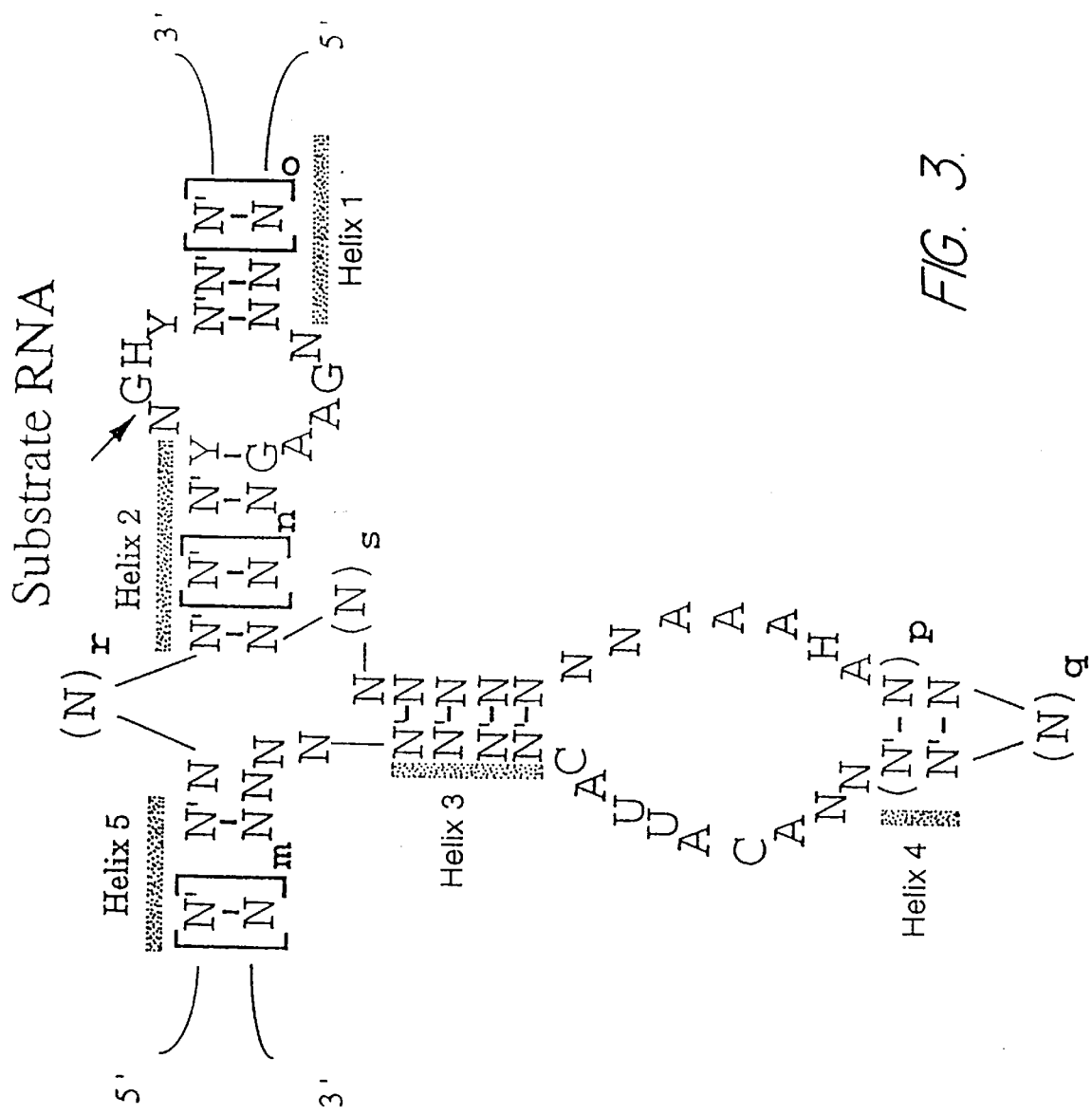
Figure 4:
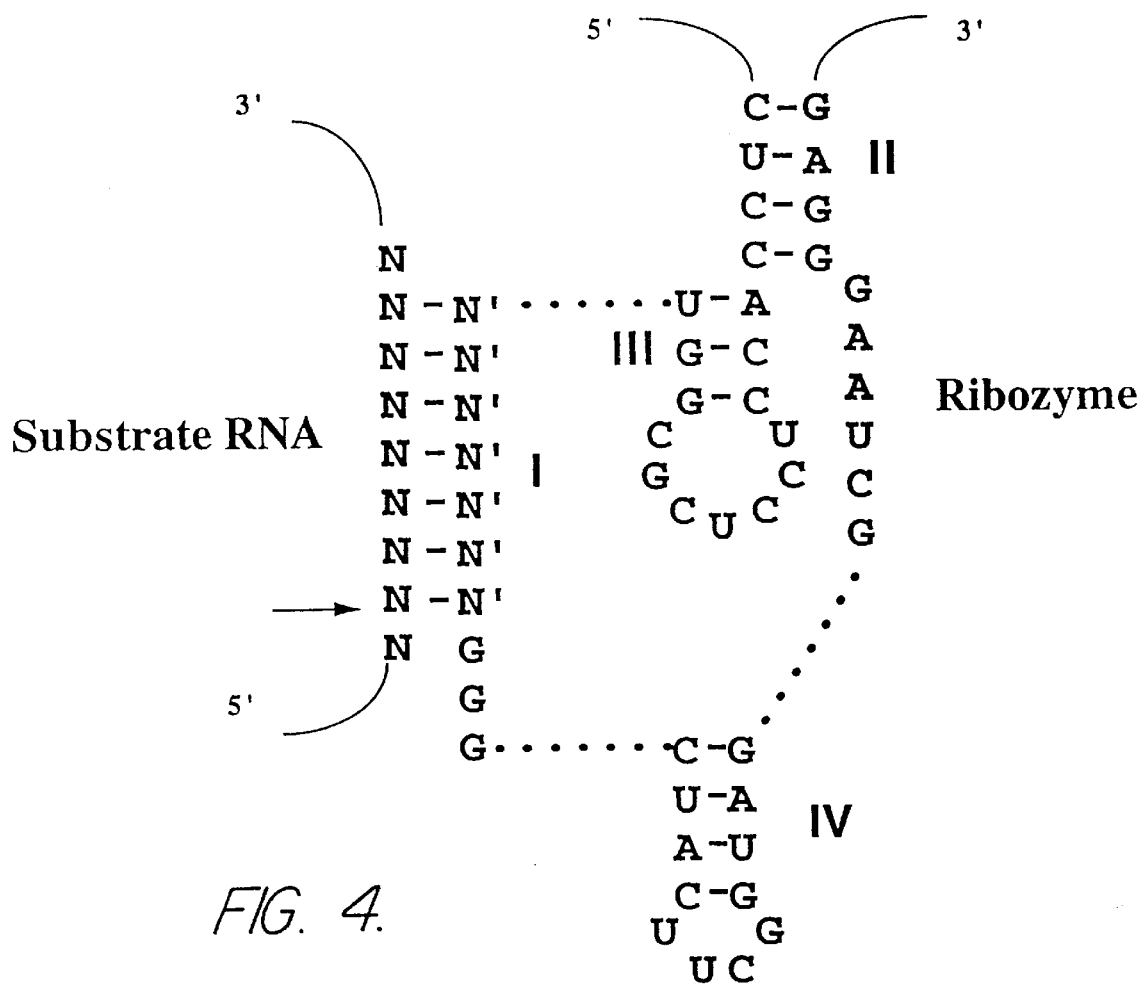
FIG. 4 is a representation of the general structure of the hepatitis delta virus ribozyme domain known in the art.
Figure 5:
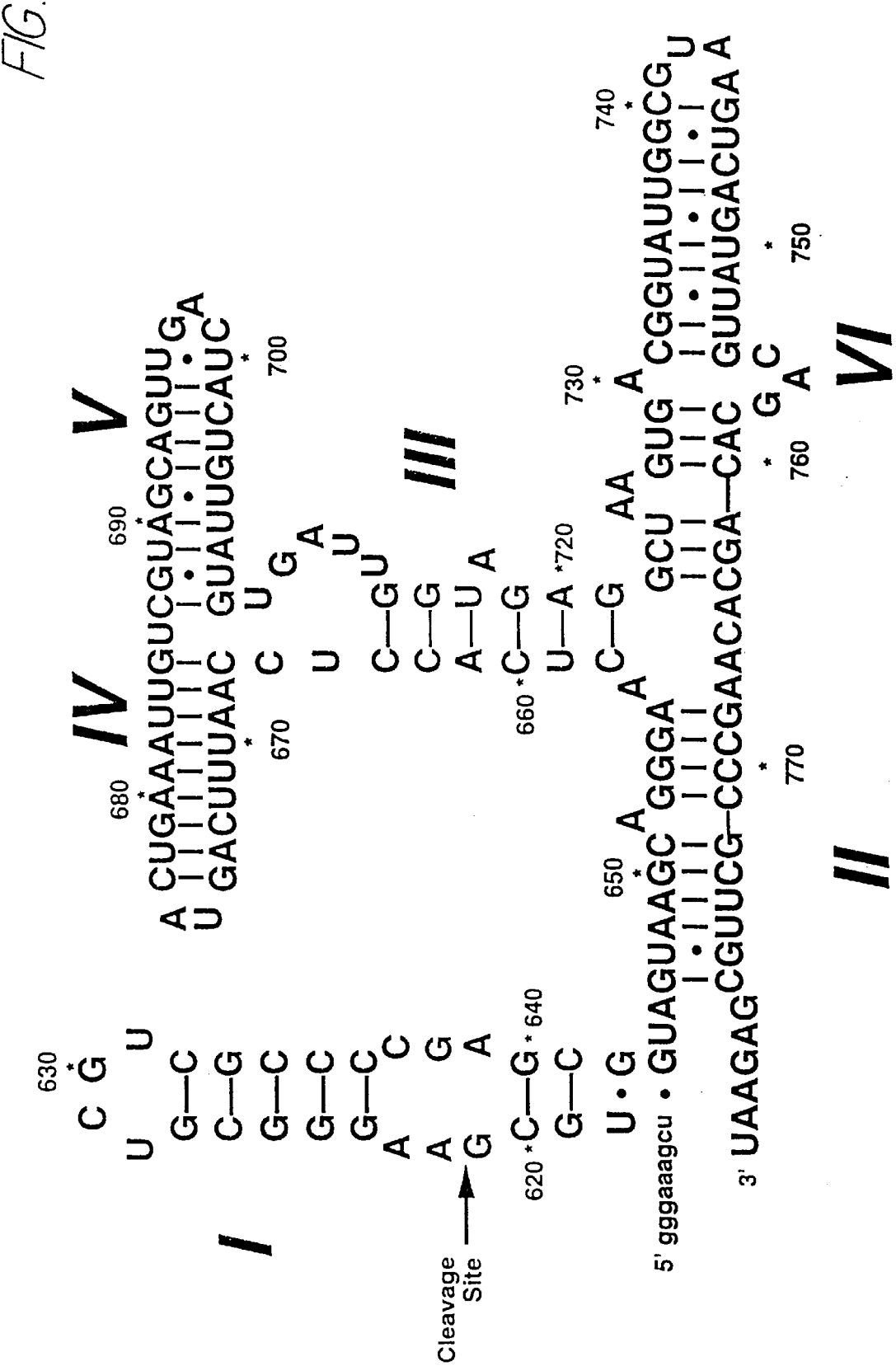
FIG. 5 is a representation of the general structure of the self-cleaving VS RNA ribozyme domain.

When the experiment was repeated using a different, non complementary, substrate sequence, no cleavage products were evident (FIG. 3.3), demonstrating the sequence specificity of this molecule.

To assess more precisely the activity of ribozyme Amino ribozyme (RPI.4782), the kinetic parameters $K_M$ and $k_{cat}$ were determined under multiple turnover conditions. The results indicate that the cleavage reaction was truly catalytic with a turnover rate ($K_{cat}$) of 1.2 min$^{-1}$ and a $K_M$ value of 87 nM (FIGS. 6 and 7). These results fall in line with typical values reported for the hammerhead ribozyme of 1–2 min$^{-1}$ and 20–200 nM for Kcat and Km respectively (Kumar et al, 1996). Direct comparisons are difficult, however, since many factors including base sequence, length of substrate binding arms and varying chemical modifications can have an effect on these kinetic parameters (Fedor & Uhlenbeck, 1992).

Example 5

Stability of EGFR Ribozymes in Fetal Calf Serum

To assess the stability of the chemically modified ribozyme, a comparative stability study was carried out in 100% foetal calf serum (Gibco, Paisley, U.K.) at 37° C. Degradation profiles of 5' and internally [$^{32}$P] labelled ribozyme were compared to those of 5'-end [$^{32}$P] labelled phosphoodiester (PO), phosphorothioate (PS) oligodeoxynucleotides and unmodified RNA.

Synthesis/labelling: 37mer PO and PS oligonucleotides were synthesized on an automated DNA synthesizer (model 392, Applied Biosystems, Warrington, U.K.) using standard phosphoramide chemistry (section 2.2.1). The chemically modified 37mer ribozyme (Amino Hammerhead Ribozyme; FIG. 8) and the 15mer unmodified all RNA substrate were synthesized as described above. Ribozymes and oligonucleotides were radiolabelled with [$^{32}$P] ATP and purified on 20% polyacrylamide gel as previously described.

Degradation study conditions: Radiolabelled ribozymes/oligonucleotides were incubated in 100 μl of FCS at 37° C. to give a final concentration of 200 nM. 10 μl aliquots were removed at timed intervals, mixed with a loading buffer containing 80% formamide, 10 mM EDTA (pH 8.0), 0.25% xylene cyanol, 0.25% bromophenol blue, and frozen at −20 C. prior to gel loading. Degradation profiles were analysed by 20% polyacrylamide (7M urea) gel electrophoresis and autoradiography.

A comparative stability study was undertaken in 100% fetal calf serum (FCS) to compare the degradation profiles of 5' end labelled and internally labelled amino ribozyme to those of 5'end labelled unmodified RNA substrate, phosphodiester (PO) and phosphorothioate (PS) oligodeoxynucleotides. The chemical modifications of the amino ribozyme resulted in a substantial increase in nuclease resistance over that of the unmodified substrate. The half life ($t_{50\%}$) of the internally labelled ribozyme was approximately 20 hours whereas the substrate was completely degraded within the time that it took to add the RNA to serum, mix and quench the reaction ($t_{50\%}$<1 min). It was interesting to note that although the patterns of degradation were clearly different for the internally labelled ribozyme (figure 3.6a) and the 5'end labelled ribozyme, the kinetics of degradation were strikingly similar. ($t_{50\%}$ of≈20 hours for both).

A comparison of ribozyme degradation and oligodeoxynucleotide degradation was also performed. The chemically modified ribozyme appeared to be more stable in FCS than either the PO oligonucleotide or the PS oligonucleotide; the approximate half lives being 10 minutes and 5 hours respectively. It must be noted, however, that the apparent degradation products migrated to the position of free phosphate. This suggests that dephosphorylation (removal of [$^{32}$P] label) occurred, resulting in a progressive increase in free phosphate concentration with time.

There is no doubt, however, that the findings of this study show that the chemical modifications applied to ribozyme result in an extremely stable structure. Under the conditions of this experiment amino ribozyme proved to be the most stable to nuclease mediated degradation in fetal calf serum.

Example 6

Ribozymes Uptake Studies

Cell Culture Techniques U87-MG cell line was purchased from the European Cell Culture Collection, Porton Down, U.K. These human glioblastoma astrocytoma cells were originally derived from a grade 3 malignant glioma by explant technique (Poten et al., 1968). A431 cells were derived from a vulval carcinoma and expresses the EGFR at levels 10 to 50 fold higher than seen in other cell lines (Ullrich et al., 1984).

The cell lines U87-MG and Raw 264.7 were maintained in Dulbecco's modified Eagle's media (DMEM) supplemented by 10% v/v foetal bovine serum (FBS), 1% penicillin/streptomycin and 1% v/v L-glutamine (all supplied from Gibco, Paisley, U.K.). The same media, without the addition of the foetal bovine serum, was used in the stability and uptake studies. A431 cells were maintained under the same conditions except glutamine was added to a final concentration of 2% v/v. CaCo-2 cells were kindly cultured and plated by Vanessa Moore in DMEM, 10% FBS, 1% non essential amino acids, 1% peniciilin/streptomycin, and 1% L-glutamine.

Cells were cultured in 75 cm$^3$ plastic tissue culture flasks (Falcon, U.K.) with 25 ml of the respective media. The cultures were incubated at 37° C. in a humidified (95%) atmosphere of 5% CO2 in air. Stock cultures were maintained by changing the media every 48 hours and passaged (1:5) when confluent (after approximately 4 days). Passaging was carried out using the following procedure:

The media was removed and the cells washed with 10 ml of phosphate-buffered saline solution (PBS). Following this, 5 ml of 2× Trypsin/EDTA (0.25% w/v trypsin, 0.2% disodium ethylenediamine tetraacetate in PBS, pH 7.2) was added and the flasks incubated at 37° C. for 5 minutes. The flasks were tapped to dislodge the cell monolayer from the bottom and fresh media was added to neutralise the trypsin. The cells were split as required and media added to a final volume of 25 ml.

For long term storage, frozen stock cultures were prepared in the following manner:

Stock cultures were trypsinised as described and neutralised with the addition of 10 ml of DMEM media. The cell suspension was then transferred to a 15 ml universal tube (Falcon, U.K.) and centrifuged for 3 minutes at 350 revolutions per minutes. The supernatant was decanted and the cell pellet was resuspnded in 1 ml of freezing media (10% DMSO, 90% heat inactivated foetal calf serum) and transferred to a 2 ml screw capped cryovial (Costar, U.K.). The ampule was then placed in the freezing head of a liquid nitrogen freezer for 4–6 hours before being transferred into liquid nitrogen (−196° C.) cell bank. When required, the cells were recovered by rapid thawing at 37° C. and gradual dilution with DMEM media before seeding in 25 cm$^3$ flasks (Falcon, U.K.).

The viable cell density of stock cultures was measured by haemocytometry using a trypan blue exclusion test. 100 μl of trypan blue (4 mg ml$^{-1}$) was mixed with 400 μl of cell suspension (1:1.25 dilution). A small amount of the trypan blue-cell suspension was transfered to the counting chamber of a Neubauer haemocytometer, with depth of 0.1 mm and area 1/440 mm² (Weber Scientific International Ltd, U.K.). The cells were counted in the 5 large squares of the haemocytometer using a light microscope. Since live cells do not take up the trypan blue dye, while dead cells do, the number of viable (unstained) cells were counted. The cell density was calculated using the following equation:

cells ml$^{-1}$=average count per square$\times 10^4 \times 1.25$ (dilution factor of trypan blue)

Cell Association Studies: A series of experiments were conducted to examine the mechanism of uptake of the ribozyme in the U87-MG glioblastoma cell line. The following general experimental procedure was used throughout these studies unless otherwise stated.

Synthesis/labelling: Prior to use in uptake studies, the 37mer ribozyme was internally labelled with 32P as previously described (section 2.3.2) and purified by 20% native polyacrylamaide gel electrophoresis. [14C] Mannitol specific activity 56mCi/mmol) was purchased from Amersham (Amersham, U.K.).

Uptake study procedure: U87-MG cells were cultured on plastic 24-well plates (Falcon, U.K.). Confluent stock cultures were trypsinised and the cell density of the stock suspension diluted to $0.5 \times 10^5$ cells ml$^{-1}$ with DMEM media. Each well was seeded with 2 ml of the diluted cell suspension to give a final concentration of $1 \times 10^5$ well-1. The plates were incubated at 37° C. in a humidified (95%) atmosphere of 5% $CO_2$ in air. After approximately 20–24 hours, the cell monolayers had reached confluency and were then ready for uptake experiments. The media was then removed and the monolayer carefully washed twice with PBS (2×1 ml×5 min) to remove any traces of serum. The washing solution was aspirated and replaced with 200 μl of serum free DMEM media containing the radiolabelled ribozyme. Both PBS and serum free media were equilibrated at 37 C. for 1 hour prior to use. The plates were incubated at 37° C., unless otherwise stated, in a dry environment for the duration of the experiment. Once incubated for the desired period of time, the apical media was carefully collected and their radioactive content assessed by liquid scintillation counting (LSC) The cells were then washed 3 times * (3×0.5 ml×5 min) with ice cold PBS/sodium azide (0.05% w/v NaN$_3$/PBS) to inhibit any further cellular metabolism and remove any ribozyme loosley associated with the cell surface. The washings were collected and their radioactive content determined by LSC. Cell monolayers were solubilised by shaking with 0.5 ml of 3% v/v Triton X100 (Aldrich Chemical Company, Gillingham, UK) in distilled water for 1 hour at room temperature. The wells were washed twice more (2×0.5 ml) with Triton X-100 to ensure that all the cells had been harvested and the radioactivity content of the cellular fraction determined by LSC. Unless otherwise indicated, all experiments were performed at a final concentration of 0.01 μM 32P internally labelled riboxyme and incubated for a period of 60 minutes.

The uptake of Amino ribozymes were compared in different cell lines. The results show that cellular association of these ribozymes ranged from 0.325±0.021 ng/10⁵ cells in intestinal epithelial cells to 1.09±0.207 ng/10⁵ cells in the macrophage cell line.

The ability of ribozymes to penetrate the cell membrane and the mechanism of entrance are important considerations in developing ribozymes as therapeutics. The mechanisms by which oligodeoxynucleotides enter cells has been well documented (for review see Akhtar & Juliano, 1991) and include the involvement of fluid phase, adsorptive and receptor mediated endocytosis. The mechanism and extent of uptake is dependent on many factors including oligonucleotide type and length and cell line studied. In contrast, however, no mechanism of cellular uptake has yet been described for ribozymes and robonucleotides. In order to investigate the means of uptake of ribozyme RPI.4782 in glioma cells, a series of cellular association studies were performed in the human glioma derived cell line, U87-MG.

The cellular association of robozyme RPI.4782 to U87-MG cells appeared to be biphasic, with a rapid initial phase continuing for approximately two hours followed by a slower second phase. The cellular association of oligonucleotides has been shown to be a dynamic process representing both uptake and efflux processes (jaroszewski & Cohen, 1990). Consequently, the plateauing seen in the second phase could represent an equilibrium of both uptake and exocytosis of ribozyme. The uptake of ribozyme RPI.4782 was strongly dependent on temperature, suggesting that an active process is involved. In addition, the metabolic inhibitors, sodium azide and 2-deoxyglucose significantly inhibited cellular association by 66%, demonstrating that ribozyme uptake was also energy dependent.

The energy and temperature dependency of cellular association of this ribozyme in U87-MG cells are characteristic of an active process, indicating that the mechanism of uptake is via endocytosis. These findings do not, however, distinguish whether fluid phase endocytosis or receptor mediated endocytosis is involved; since both mechanisms will be effected by these parameters (Beltinger et al., 1994). In order to evaluate the pathway of internalization, the uptake of a fluid phase marker, [14C] mannitol, was measured to determine the extent of pinocytosis in U87-MG cells. The basal rate of pinocytosis in these cells remained extremely low throughout the time period tested and it is unlikely, therefore, to account for a significant fraction of ribozyme uptake in this cell line.

To investigate whether ribozyme RPI.4782 is taken up into U87-MG cells by receptor mediated endocytosis a self competition study was conducted. Ribozyme uptake was found to be significantly inhibited by competition with unlabelled ribozyme. This demonstrates that cellular association was concentration dependent and suggests that the dominant uptake mechanism is via receptor mediated endocytosis.

Receptor mediated endocytosis involves the internalization of molecules via specific membrane protein, cell surface receptors. Consequently, a proteolytic enzyme such as trypsin or pronase® can be used to determine the extent to which membrane proteins mediate uptake (Beck et al., 1996; Shoji et al., 1991; Wu-pong et al., 1994). In a study investigating the cellular association of oligonucleotides in intestinal CaCo-2 cells, Beck et al. (1996) reported a 50% reduction of uptake upon cell surface washing with pronase, while 60% of oligonucleotide uptake was reported to be trypsin sensitive in Rauscher Red 5-1.5 ertythroleukemai cells (Wu-Pong et al., 1994). To further characterize ribozyme uptake, the effects of the endocytosis inhibitor, phenylarsine oxide and the endosomal alkalinizers, chloroquine and monensin could be studied (Loke et al., 1989; Wu-Pong et al., 1994).

To determine whether specific binding sites are involved in the uptake of ribozyme RPI.4782 in U87-MG cells, competition studies are required to evaluate the effect on ribozyme uptake by competitors such as oligonucleotides, ATP and other polyanions, such as dextran sulphate and heparin. The cellular association of ribozyme RPI.4782 to U87-MG cells was also found to be pH dependent. In fact a decrease in pH from pH 8 to pH 5 resulted in a significant increase in cellular association. The effect of pH on ribozyme partition coefficients had not as yet been undertaken in order to determine whether the increase in cellular association was due to an increase in the partition coefficient of the ribozyme, at low pH conditions. The increase of cellular association at low pH is in agreement with the work of Goodarzi et al (1991) and kitajima et al (1992) who found that cellular association of oligonucleotides also increased under acidic conditions. It has been postulated that enhanced binding could be due to the presence of a 34kDa membrane protein receptor that functions around pH 4.5 (Goodarzi et al., 1991). In addition, the α amino group of lysine, the guanidium group of arginine and protonated imidazole of histidine have been suggested to be possible oligonucleotide binding sites (Blackburn et al., 1990). Histidine, having a pKa of 6.5 is susceptible to protonation over a pH range of 7.2 to 5.0. Therefore, the enhanced affinity of ribozyme RPI.4782 to U87-MG cells at pH 5.0 could be due to protonation of histidine residues present at the binding site.

In general these observations suggest that the pathway of cellular uptake of ribozyme involves an active cellular process; indications are that the predominant mechanism of uptake is via receptor mediated endocytosis.

Example 7: Ribozyme stability in U87-MG Cells

In order to ensure that the results obtained from the uptake studies represented cell association of intact 37mer ribozyme and not degraded ribozyme or free [$^{32}$P] label, the stability of this ribozyme, when incubated with U87 cells, was examined.

U87-MG cells were seeded onto 24 well-plates as previously described and used approximately 24 hours post seeding. Internally [$^{32}$P] labelled ribozyme RPI.4782 was added to 200 μl of serum free media to give a final concentration of 10 nM. 10 μl aliquots of the apical solution were colleced at variable time points over a period of 4 hours, mixed with an equal volume of formamide loading buffer (9:1 v/v formamide: 1x TBE) and stored at −20 C. Prior to gel loading, the samples were heated to 100° C. for 5 minutes and separated on 7M urea/20% acrylamide gels; bands were detected by autoradiography of wet gels.

For comparative purposes, the stability profiles of 5' labelled ribozyme RPI.4782, 5' end labelled all RNA 15 mer substrate, and 5' end labelled 37 mer PO and PS oligodeoxynucleotides were also measured under the same conditions.

To ensure that any findings obtained from uptake studies represented the cellular association of intact 37 mer ribozyme and not that of shorter degraded fragments of free [$^{32}$P] label, the degradation of 5'-end and internally [$^{32}$P] labelled ribozyme was examined when exposed to U87-MG cells. For comparative purposes, the stability profile of an unmodified RNA substrate was also measured under the same conditions. The chemically modified ribozyme remained largely intact throughout a four hour incubation period. While no degradation was evident from the internally labelled sample, the 5'-end labelled ribozyme did exhibit some degradation after 120 minutes. This indicates that 5' dephosphorylation occured in the latter case. In contast, however, the unmodified RNA substrate was completely degraded within 10 minutes incubation with the U87-MG cell monolayer. The ribozyme was clearly protected from cellular nucleases by the chemical modifications previously described.

Optimizing Ribozyme Activity

Sullivan, et al., supra, describes the general methods for delivery of enzymatic RNA molecules. The data presented in Examples above indicate that different cationic lipids can deliver active ribozymes to smooth muscle cells. Experiments similar to those performed in above-mentioned Examples are used to determine which lipids give optimal delivery of ribozymes to specific cells. Other such delivery methods are known in the art and can be utilized in this invention.

The proliferation of smooth muscle cells can also be inhibited by the direct addition of chemically stabilized ribozymes. Presumably, uptake is mediated by passive diffusion of the anionic nucleic acid across the cell membrane. In this case, efficacy could be greatly enhanced by directly coupling a ligand to the ribozyme. The ribozymes are then delivered to the cells by receptor-mediated uptake. Using such conjugated adducts, cellular uptake can be increased by several orders of magnitude without having to alter the phosphodiester linkages necessary for ribozyme cleavage activity.

Alternatively, ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. The RNA/vehicle combination is locally delivered by direct injection or by use of a catheter, infusion pump or stent. Alternative routes of delivery include, but are not limited to, intramuscular injection, aerosol inhalation, oral (tablet or pill form), topical, systemic, ocular, intraperitoneal and/or intrathecal delivery. More detailed descriptions of ribozyme delivery and administration are provided in Sullivan, et al., supra and Draper, et al., supra which have been incorporated by reference herein.

Chemical modifications, ribozyme sequences and ribozyme motifs described in this invention are meant to be non-limiting examples, and those skilled in the art will recognize that other modifications (base, sugar and phosphate modifications) to enhance nuclease stability of a ribozyme can be readily generated using standard techniques and are hence within the scope of this invention.

Use of Ribozymes Targeting EGFR

Overexpression of the EGFR has been reported in a number of cancers (see above). Thus, inhibition of EGFR expression (for example using ribozymes) can reduce cell proliferation of a number of cancers, in vitro and in vivo and can reduce their proliferative potential.

Ribozymes, with their catalytic activity and increased site specificity (see above), are likely to represent a potent and safe therapeutic molecule for the treatment of cancer. In the present invention, ribozymes are shown to inhibit smooth muscle cell proliferation and stromelysin gene expression. From those practiced in the art, it is clear from the examples described, that the same ribozymes may be delivered in a similar fashion to cancer cells to block their proliferation. These ribozymes can be used in conjunction with existing cancer therapies.

Gliomas are the most common primary tumors arising from the brain, in fact each year malignant gliomas account for approximately 2.5% of the deaths from cancer (Bruner, 1994). These gliomas are morphologically and biologically heterogeneous and include neoplasms derived from several cell types. Astrocytomas form the largest single group among the primary tumors (75–90%) which also includes oligodendrogliomas, ependymomas and mixed gliomas (Bruner, 1994). Distinct histological features allow astrocytomas to be graded into levels of anaplasia, the most widely used today involves a three tiered grading system (Ringertz, 1950) dividing astrocytomas into low grade astrocytomas, anaplastic astrocytomas and glioblastomas The most malignant and frequently occurring form, glioblastoma multiforme (GBM), accounts for approximately one third of all primary brain tumors (Wong et al., 1994). This tumor is so undifferentiated that it cell of origin remains obscure, however most examples are generally thought to arise from astrocytes because glial fibrillary acidic protein (GFAP), a histological morphology of glioblastoma can be highly variable, confirming the name "multiforme".

The characteristic features of glioblastoma multiforme is tumor necrosis. The individual cells may be small with a high nuclear/cytoplasmic ratio or very large and bizarre with abundant eosinophilic cytoplasm. The small cells are the more proliferative ones and show a more aggressive course. In fact some glioblastomas are so highly cellular that the population of small anaplastic cells stimulates primitive neuroectodermal tumors such as medulloblastoma. These small cells often appear to condense around areas of tumor necrosis forming characteristic 'pseudopalisades". They also have the propensity to infiltrate the brain extensively, giving the appearance of multifocal gliomas.

Despite advances in many areas of cancer research and treatment, glioblastoma multiforme almost always proves fatal, with a median survival rate of less than one year and a 5 year survival rate of 5.5% or less (Martuza et al., 1991). At present, no therapeutic modality has substantially changed the outcome of patients with glioblastoma. Characteristics of this type of tumor, including it's invasive nature, it's ability to spread locally and distantly while avoiding recognition by the immune system, it's relative resistance to radiation and a high local recurrence rate, limit the success of conventional therapy. The effective treatment of glioblastoma multiforme, therefore, presents a tremendous challenge.

The current methods of treatment used in the management of malignant gliomas are briefly reviewed.

Surgery: The cornerstone of therapy for glioblastoma multiforme tumors has been surgery. The use of microsurgical techniques, intraoperative ultrasonic aspiration, electrophysiologic monitoring and lasers make the surgical procedure safe and accurate (Komblith et al., 1993). Although surgery does improve the survival of patients with glioblastoma multiforme, the inability to surgically remove eloquent areas of cerebral cortex invaded by the tumor render such ablative technologies of only modest value.

Radiotherapy: Malignant gliomas such as glioblastoma multiforme exhibit an extraordinary resistance to radiotherapy and as a consequence the effectiveness of this form of treatment is limited. the sensitivity of the surrounding, unaffected, brain limits the dose that can safely be delivered to 60 Gy (Leibel et al., 1994), which is well below the level required to completely eradicate the primary tumor in the majority of patients. In addition, whole brain radiotherapy does not prevent local tumor recurrence. The effective use of more localized forms of radiotherapy, such as radiosensitizers and radiosurgical techniques, are at present under review.

Chemotherapy: Chemotherapy has been shown to be effective adjuncts to surgery and radiotherapy in the treatment of cancer. Unfortunately, however, chemotherapy has had a limited impact on survival in patients with high grade astrocytomas. A report published in 1993 determined that adding chemotherapy to surgery and radiation improved the median survival duration in these patients from 9.4 to 12 months (Fine et al., 1993).

Generally, the relatively lipid soluble and non ionized nitrosourea drugs; e.g. carmustine, lomustine, semustine and nimustine, have proved to be the most active single chemotherapy agents for treating malignant astrocytomas (Lesser & Grossman, 1994). New drugs continue to enter clinical trials in patients with glioblastoma; none so far, however, have substantially prolonged a patient's life span. A myriad of physiological and biological factors such as the blood brain barrier, heterogeneous and resistant tumor cell populations and unacceptable toxicities have limited the efficacy of these agents.

Different routes of administration have been used to overcome the impenetrability of the blood brain barrier. A unique delivery system has been reported (Brem et al., 1991) which incorporates biodegradable polymers impregnated with chemotherapy agents. These polymers are placed topically at the resection site and slowly release the drugs as they degrade. Direct injection into tumors may also be useful as a means to deliver the highest dose to the tumor site without systemic exposure.

Immunotherapy: Glioblastoma multiforme is an appropriate target for immunological directed therapy. Studies have revealed that sera from patients with GBM stimulates little or no humoral response. A realistic approach, therefore, is to stimulate a stronger immune response in glioblastoma patients. Although this approach looks promising in theory, as yet no effective means of stimulating a clinically immune response has been identified. The most promising avenue, through the use of lymphokine activated killer (LAK) cells and interleukin -2, has been limited by lack of tumor specific cell homing and difficulties with LAK cell delivery and toxicity.

Advances in the understanding of the molecular basis of cancer has now made it possible to design molecules that specifically interact with cancer cells. The most promising modes of therapy for the treatment of GBM, therefore, may lie with molecular based technologies which employ genetic interventions to alter the properties or behaviour of specific cells.

In fact, glioblastoma multiforme tumors are ideal candidates for this type of therapy since they rarely metastasize, are accessible to direct delivery techniques and can be precisely monitored by MRI and CT scans. The tumor cells may also divide rapidly, which enables agents such as retroviruses to infect the cells and synthesize genes leading to tumor cell destruction. (Kornblith et al., 1993).

Many detailed cytogenetic studies have been performed on malignant gliomas and these reveal commonly occurring abnormalities (Bigner & Vogelstein, 1990). For example, approximately 80% of malignant gliomas have gains of one or more copies of chromosome 7 and approximately 60% show a loss of chromosome 10. In addition, one of the most consistent genetic abnormalities is the presence of double minute chromosomes (DMs). Double minute chromosomes refer to small portions of chromosomes which are paired but lack a centromere; they are the karyotypic manifestation of gene amplification. The presence of such DMs have been found in over 50% of glioblastomas, with some tumors possessing 50–100 copies of DMs per cell (Ostrowski et al., 1994). This indicates that gene amplification in a cancer cell is a key method of increasing a certain amount of protein.

References

Adams et al., (1994), *Tetrahedron Letters,* 35, 1597–1600.
Akhtar et al., (1992) *Trends In Cell Biology,* 2, 139–143.
Akhtar et al., (1996) *In Press.*

Akhtar et al., (1995) *Nature Medicine*, 1(4), 300–302.

Akhtar et al., (1991) *Life Sciences*, 49, 1793–1801.

Ali et al., (1994) *Gene Therapy*, 1, 367–384.

Altman (1993) *Proceedings Of The National Acadamy Of Sciences, USA.*, 90, 10898–10900.

Amiri et al., (1994) *Biochemistry*, 33, 13172–13177.

Aurup et al., (1995) In: Akhtar, S. Ed), *Delivery Strategies For Antisense Oligonucleotide Therapeutics*. London, Crc Press. P; 161–177.

Ayers et al., (1996) *Journal Of Controlled Release*, 38, 167–175.

Bacchetti et al., 1995 *International Journal Of Oncology*, 7, 423–432.

Barinaga (1993) *Science*, 262, 1512–1514.

Bassi et al., 1995 *Nat. Struct. Biol.*, 2, 45–55.

Beck et al., 1997 *Submitted*.

Beigelman et al., 1994 *Biorg. Med. Chem. Lett*, 4, 1715–1720.

Beigelman et al., 1995 *Nucleosides And Nucleotides*, 14, 895–899.

Beigelman et al., 1995 b *Nucleic Acids Research*, 23(21), 4434–4442.

Beigelman et al., 1995 C *Journal Of Biological Chemistry*, 270(43), 25701–25708.

Beltinger et al., 1995 *J. Clin. Invest.*, 95, 1814–1823.

Bertrand et al., 1994 *Embo Journal*, 73: 2904–2912.

Bertrand et al., 1996 *Nucleic Acids And Molecular Biology*, 10, 301–313.

Bertrand et al., 1994 *Nucleic Acids Research*, 22(3), 293–300.

Bigner et al., 1990 *Brain Pathol.*, 1, 12–18.

Black et al., 1991 *New England Journal Of Medicine*, 324, 1471–1476 & 1555–1564.

Bratty et al., 1993 *Biochimica Et Biophysica Acta.* 1216, 345–359.

Brem et al., 1991 *Journal Of Neurosurgery*, 74, 441–446.

Bruner, 1994 *Seminars in Oncology*, 21(2), 126–138.

Cech et al., 1986 *Annual Review of Biochemistry*, 55, 599–629.

Cech et al., 1994 *Nature*, 372, 39–40.

Cech et al., 1981 *Cell*, 27, 487–496.

Chadeneau et al., 1995 *Oncogene*, 11, 893–898.

Chen et al., 1996 *Cancer Gene Therapy*, 3(1), 18–23.

Crooke, 1992 *Annual Review of Pharmacology*, 32, 329–379.

Denman,. 1993 *Biocomputing*, 15(6), 1090–1094.

Denman, 1996 *Febs Letters*, 382, 116–120.

Downward 1984 *Nature*, 307, 521–527.

Dropulic et al., 1993 *Antisense Research And Development*, 3 87–94.

Elkins et al., 1995 In: Akhtar, S. *Delivery Stratergies For Antisense Oligonucleotide Therapeutics*, London, Crc Press. Pp 17–37.

Ellis et al., 1993 *Nucleic Acids Research.* 21(22), 5171–5178.

Eckstein, 1985 *Annual Review Of Biochemistry*, 54, 367–402.

Ekstrand et al., 1991 *Cancer Research*, 51, 2164–2172.

Fedor et al., 1990 *Proceedings Of The National Acadamy Of Sciences, USA*, 87, 1668–1672.

Fedor et al., 1992 *Biochemistry*, 31, 12042–12054.

Feigner et al., 1994 *Journal Of Biological Chemistry*, 269, 2550–2561.

Feng et al., 1995 *Science*, 69, 1236–1241.

Fine et al., 1993 *Cancer*, 71, 2585–2597.

Flory et al., 1996 *Proceedings Of The National Acadamy Of Sciences, USA*, 93, 754–758.

Foster et al., 1987 *Cell*, 49, 211–220.

Fu et al., 1992 *Proceedings Of The National Acadamy Of Sciences, USA*, 89, 3985–3989.

Gait et al., 1995 *Nucleosides And Nucleotides*, 14(3–5), 1133–1144.

Gish et al., 1989 *Trends In Biochemical Sciences*, 14, 97–100.

Goodarzi et al., 1991 *Biochem. Biophys. Res. Comm*, 181, 1343–1351.

Goodchild et al., 1990 *Nucleic Acids Research*, 20, 4607–4612.

Griffiths et al., 1987 *Nucleic Acids Research*, 15, 4145–4162.

Guerrier-Takda et al., 1983 *Cell*, 35, 849–857.

Gutierrez et al., 1992 *Lancet*, 339, 715–719.

Hampel, A. et al., 1990 *Nucleic Acids Research*, 18, 299–304.

Healy 1995 *Oncology Research* 7(3), 121–130.

Heidenreich et al., 1994 *Journal Of Biological Chemistry*, 269, 2131–2138.

Heidenreich et al., 1993 *Faseb Journal*, 7, 90–96.

Hendry et al., 1995 *Nucleic Acids Research*, 23(19), 3928–3936.

Herschlag et al., 1994 *Embo Journal*, 13, 2913–2924.

Hertel et al., 1992 *Nucleic Acids Research*, 20(12), 3252.

Hertel et al., 1994 *Biochemistry*, 33, 3374–3385.

Homann et al., 1994 *Nucleic Acids Research*, 22, 3951–3957.

Inoue, T. (1994) Time To Change Partners. *Nature*, 370, 99–100.

Jaeger, J. A. Turner, D. H., Zuker, M. (1989). Improved Predictions Of Secondary Structures For Rna, *Proceedings Of The National Acadamy For Sciences, USA*, 86, 7706–7710.

Jarvis et al., 1996 *RNA* 2, 419–428.

Juliano et al., 1992 *Antisense Research And Develpment*, 2, 165.

Kanazawa et al., 1996 *Biochemical An Biophysical Research Communication*, 225, 570–576.

Kariko et al., 1994 *Febs Letters*, 352, 41–44.

Khazaie et al., 1993 *Cancer And Mestastasis Review*, 12, 255–274.

Kiehntopf et al., 1995 a *Journal Of Molecular Medicine*, 73, 65–71.

Keihntopf, M., Esquivel, E. L., Brach, M. A., Hermann, F. (1995b) Clinical Applications Of Ribozymes. *The Lancet*, 345, 1027–1031.

Keihntopf et al., 1994 *Embo Journal*, 13, 4645–4652.

Kim et al., 1994 *Science*, 266, 2011–2015.

Kisich et al., 1995 *Journal Of Cellular Biochemistry*, 19a, 291.

Koizumi et al., 1993 *Biol. Pharm. Bull.*, 16, 879–883.

Kornblith et al., 1994 *Surg. Neurol*, 39, 538–43.

Kumar et al., 1996 *Nucleic Acids And Molecular Biology*, 10, 217–230.

Kung et al., 1994 In: Pretlow, T. G. & Pretlow, T. P. (Eds) *Biochemical And Molecular Aspects Of Selected Cancers, Volume 2*, San Diego, Academic Press, 19–45.

L'huillier et al., 1996 *Nucleic Acids And Molecular Biology*, 10, 283–299.

Lamond et al., 1993 *Febs Letters*, 325(1), 123–127.

Lange et al., 1994 *Leukemia*, 7(11), 1786–1794.

Leibel et al., 1994 *Seminars In Oncology*, 21(2), 198–219.

Leopold et al., 1995 *Blood*, 85, 2162–2170.

Lesser, G. L. & Grossman, S. (1994) *The Chemotherapy Of High Grade Astrocytomas. Seminars In Oncology*, 21(2), 220–235.

Lewis et al., 1995 *Journal Of Cellular Biochemistry*, 19a, 227.

Loke et al., 1989 *Proceedings Of The National Acadamy Of Sciences, USA*, 88, 3474–3478.

Lyngstadaas et al., 1995 *Embo Journal*, 14(21), 5224–5229.

Marshall et al., 1993 *Science*, 259, 1565–1569.

Marschall et al., 1994 *Cellular and Molecular Neurobiology*, 14(5), 523–538.

Martuza et al., 1991 *Science*, 252, 854–855.

Miller et al., 1991 *Virology*, 183, 711–720.

Milligan et al., 1993 *Journal Of Medicinal Chemistry*, 36(14) 1923–1937.

Modjtahedi et al., 1994 *International Journal Of Cancer*, 4, 277–296.

Morvan et al., 1994 *Tetrahedron Letters*, 31, 7149–7152.

Ohkawa et al., 1995 *Journal Of Biochemistry*, 118, 251–258.

Olsen et al., 1991 *Biochemistry*, 31, 9735–9741.

Ostrowski et al., 1994 In Human Malignant Glioma. In: Pretlow, T. G. & Pretlow, T. P. (Eds) *Biochemical And Molecular Aspects Of Selected Cancers*, San Diego, Academic Press, 143–168.

Paolella et al., 1992 *Embo Journal*, 11(5), 1913–1919.

Perreault et al., 1990 *Nature*, 334, 565–567.

Perriman et at., 1995 *Proceedings Of The National Academy Of Sciences, USA*, 92, 6175–6179.

Perriman et al., 1992 *Gene*, 113, 157–163.

Pieken et al., 1991 *Science*, 253, 314–317.

Pley, H. W., Flaherty, K. M. & Mckay, D. B. (1994) Three-Dimensional Structure Of A Hammerhead Ribozyme. *Nature*, 372, 68–74.

Ponten et al., 1968 *Acta Path. Microbiol. Scandinav*, 74, 465–486.

Puttaraju et al., 1993 *Nucleic Acids Research*, 21, 4253–4258.

Rawls 1996 *Chemical And Engineering News*, 74(5), 26–28.

Reddy 1996 *Drugs Of Today*, 32(2), 113–137.

Ringertz, 1950 *Acta. Pathol. Microbiol. Scand.*, 27, 51–64.

Rossi 1994 *Current Biology*, 4(5), 469–471.

Rossi 1995 *Tibtech*, 13, 301–305.

Rossi et al., 1991 *Aids Res. Hum. Retroviruses*, 8, 183–189.

Ruffner et al., 1990 *Nucleic Acids Research*, 18, 6025.

Ruffner, et al., 1990 *Biochemistry*, 29, 10695–10702.

Rhyu 1995 *Journal Of The national Cancer Institute*, 87(12), 884–894.

Sambrook 1989 *Molecular Cloning: A Laboratory Manual*, Second Edition, Vols 1, 2 & 3. Cold Srings Harbor, Laboratory Press.

Scaringe et al., 1990 *Nucleic Acids Research*, 18, 5433–5441.

Scott et al., 1995 *Cell*, 81, 991–1002.

Sczakiel 1996 *Nucleic Acids and Molecular Biology*, 10, 231–241.

Sczakiel et al., 1994 *Biol. Chem. Hoppe-Seyler*, 375, 745–746.

Sczakiel et al., 1993 *Antisense Research And Development*, 3, 45–52.

Shaw et al., 1991 *Nucleic Acids Research*, 19(4), 747–750.

Shibahara et al., 1986 *Nucleic Acids Research*, 17, 239–242.

Shimayama et al., 1993 *Nucleic Acids Research*, 21, 2605–2611.

Shimayama et al., 1995 *Biochemistry*, 34, 3649–3654.

Shoji et al., 1991 *Nucleic Acids Research*, 19(20), 5543–5550.

Shoji et al., 1996 *Antimicrobial Agents And Chemotherapy*, 40(7), 1670–1675.

Sioud et al., 1992 *Journal Of Molecular Biology*, 223, 831–835.

Snyder et al., 1993 *Blood*, 82, 600–605.

Sporn et al., 1985 *Nature*, 313, 745–747.

Sproat 1996 *Nucleic Acids And Molecular Biology*, 10, 265–281.

Stein et al., 1988 *Gene*, 72, 333–341.

Stein et al., 1993 *Science*, 261, 1004–1006.

Stein et al., 1993 *Biochemistry*, 32, 4855–4861.

Suh et al., 1993 *Febs Letters*, 326 (1,2,3), 158–162.

Sullinger et al., 1993 *Science*, 262, 1566–1569.

Sullivan, 1993 *A Comparison To Methods In Enzymology*, 5, 61–66.

Sullivan, 1994 *The Journal Of Investigative Dermatology*, 100(5), 85s–89s.

Symons, R. H. (1992) Small Catalytic Rnas. *Annual Review Of Biochemistry*, 61, 641–671.

Symon, 1994 *Current Biology*, 4, 322–330.

Szostak 1993 *Nature*, 361, 119–120.

Tayler et al., 1992 *Nucleic Acids Research*, 20(17), 4559–4565.

Thierry et al., 1995 In: Akhtar, S (Ed), Delivery Strategies For Antisnse Oligonucleotide Therapeutics, London, Crc Press.

Thomson et al., 1993 *Nucleic Acids Research*, 21, 5600–5603.

Thomson et al., 1996 *Nucleic Acids And Molecular Biology*, 19, 172–196

Thompson et al., 1995 *Nature Medicine*, 1(3), 277–278.

Tidd et al., 1989 *British Journal Of Cancer*, 60, 343–350.

Tsuchihashi et al., 1993 *Science*, 262, 99–102.

Tuschl et al., 1993 *Proceedings Of The National Acadamy Of Sciences, USA*, 90, 6991–6994.

Tuschl, T., Gohlke, C., Jovin, T. M., Westhof, E., Eckstein, F. (1995) A Three Dimentional Model For The Hammerhead Ribozyme Based On Fluorescence Measurements. *Science*, 266, 785–788.

Uhlenbeck, 1987 *Nature*, 328, 596–600.

Usman et al., 1992 *Trends In Biochemical Science*, 17, 334–339.

Usman et al., 1996 *Annual Reports In Medicinal Chemistry*, 30, 285–294.
Usman et al., 1996 *Nucleic Acids And Molecular Biology*, 10, 243–263.
Werner et al., 1995 *Nucleic Acids Research*, 23, 2092–2096.
Williams et al., 1992 *Proceedings Of The National Acadamy Of Science, USA*, 89, 918–921.
Wincott et al., 1995 *Nucleic Acids Research*, 23(14) 2677–2684.
Wong et al., 1994 *Seminars In Oncology*, 21(2), 139–148
Wu et al, 1989 *Proceeding Of The National Academy Of Sciences, USA*, 86, 18
Wu-Pong et al., 1994 *Antisense Research And Development*, 4, 155–163.
Yakubov et al., 1989 *Proceedings Of The National Academy Of Sciences, USA*, 86, 6454–6458.
Yang et al., 1992 *Biochemistry*, 31, 5005–5009.
Young et al., 1993 *Febs Letters*, 326, 158
Yu et al., 1993 *Proceedings Of Th National Academy Of Science, USA*, 90, 6340–6344.
Zuker et al., (1991) *Nucleic Acids Research*, 19(10), 2707–2714

Diagnostic Uses

Ribozymes of this invention may be used as diagnostic tools to examine genetic drift and mutations within diseased cells or to detect the presence of EGFR RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with EGFR related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., EGFR) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of naturally occurring ribozymes

Group I Introns

Size: ~150 to >1000 nucleotides.
Requires a U in the target sequence immediately 5' of the cleavage site.
Binds 4–6 nucleotides at the 5'-side of the cleavage site.
Reaction mechanism: attack by the 3'-OH of guanosine to generate cleavage products with 3'-OH and 5'-guanosine.
Additional protein cofactors required in some cases to help folding and maintainance of the active structure [1].
Over 300 known members of this class. Found as an intervening sequence in *Tetrahymena thermophila* rRNA, fungal mitochondria, chloroplasts, phage T4, blue-green algae, and others.
Major structural features largely established through phylogenetic comparisons, mutagenesis, and biochemical studies [2,3].
Complete kinetic framework established for one ribozyme [4,5,6,7].
Studies of ribozyme folding and substrate docking underway [8,9,10].
Chemical modification investigation of important residues well established [11,12].
The small (4–6 nt) binding site may make this ribozyme too non-specific for targeted RNA cleavage, however, the Tetrahymena group I intron has been used to repair a "defective" β-galactosidase message by the ligation of new β-galactosidase sequences onto the defective message [13].

RNAse P RNA (M1 RNA)

Size: ~290 to 400 nucleotides.
RNA portion of a ubiquitous ribonucleoprotein enzyme.
Cleaves tRNA precursors to form mature tRNA [14].
Reaction mechanism: possible attack by $M^{2+}$-OH to generate cleavage products with 3'-OH and 5'-phosphate.
RNAse P is found throughout the prokaryotes and eukaryotes. The RNA subunit has been sequenced from bacteria, yeast, rodents, and primates.
Recruitment of endogenous RNAse P fro therapeutic applications is possible through hybridization of an External Guide Sequence (EGS) to the target RNA [15,16]
Important phosphate and 2' OH contacts recently identified [17,18]

Group II Introns

Size: >1000 nucleotides.
Trans cleavage of target RNAs recently demonstrated [19,20].
Sequence requirements not fully determined.
Reaction mechanism: 2'-OH of an internal adenosine generates cleavage products with 3'-OH and a "lariat" RNA containing a 3'–5' and a 2'–5' branch point.
Only natural ribozyme with demonstrated participation in DNA cleavage [21,22] in addition to RNA cleavage and ligation.
Major structural features largely established through phylogenetic comparisons [23].
Important 2' OH contacts beginning to be identified [24]
Kinetic framework under development [25]

Neurospora VS RNA

Size: ~144 nucleotides.
Trans cleavage of hairpin target RNAs recently demonstrated [26].
Sequence requirements not fully determined.
Reaction mechanism: attack by 2'-OH 5' to the scissile bond to generate cleavage products with 2',3'-cyclic phosphate and 5'-OH ends.
Binding sites and structural requirements not fully determined.
Only 1 known member of this class. Found in Neurospora VS RNA.

Hammerhead Ribozyme (see text for references)
Size: ~13 to 40 nucleotides.
Requires the target sequence UH immediately 5' of the cleavage site.
Binds a variable number nucleotides on both sides of the cleavage site.
Reaction mechanism: attack by 2'-OH 5' to the scissle bond to generate cleavage products with 2',3'-cyclic phosphate and 5'-OH ends.

TABLE I-continued

Characteristics of naturally occurring ribozymes 14 known members of this class. Found in a number of plant pathogens (virusoids) that use RNA as the infectious agent.
Essential structural features largely defined, including 2 crystal structures [ ]
Minimal ligation activity demonstrated (for engineering through in vitro selection) [ ]
Complete kinetic framework established for two or more ribozymes [ ].
Chemical modification investigation of important residues well established [ ].

Hairpin Ribozyme

Size: ~50 nucleotides.
Requires the target sequence GUC immediately 3' of the cleavage site.
Binds 4–6 nucleotides at the 5'-side of the cleavage site and a variable number to the 3'-side of the cleavage site.
Reaction mechanism: attack by 2'-OH 5' to the scissle bond to generate cleavage products with 2',3'-cyclic phosphate and 5'-OH ends.
3 known members of this class. Found in three plant pathogen (satellite RNAs of the tobacco ringspot virus, arabis mosaic virus and chicory yellow mottle virus) which uses RNA as the infectious agent.
Essential structural features largely defined [27,28,29,30]
Ligation activity (in addition ot cleavage activity) makes ribozyme amenable to engineering through in vitro selection [31 ]
Complete kinetic framework established for one ribozyme [32 ].
Chemical modification investigation of important residues begun [33,34].

Hepatitis Delta Virus (HDV) Ribozyme

Size: ~60 nucleotides.
Trans cleavage of target RNAs demonstrated [35].
Binding sites and structural requirements not fully determined, although no sequences 5' of cleavage sites are required. Folded ribozyme contains a pseudoknot structure [36].
Reaction mechanism: attack by 2'-OH 5' to the scissile bond to generate cleavage products with 2',3'-cyclic phosphate and 5'-OH ends.
Only 2 known members of this class. Found in human HDV.
Circular form of HDV is active and shows increased nuclease stability [37]

1. Mohr, G.; Caprara, M. G.; Guo, Q.; Lambowitz, A. M. Nature, 370, 147–150 (1994).
2. Michel, Francois; Westhof, Eric. Slippery substrates. Nat. Struct. Biol. (1994), 1(1), 5–7.
3. Lisacek, Frederique; Diaz, Yolande; Michel, Francois. Automatic identification of group I intron cores in genomic DNA sequences. J. Mol. Biol. (1994), 235(4), 1206–17.
4. Herschlag, Daniel; Cech, Thomas R.. Catalysis of RNA cleavage by the Tetrahymena thermophila ribozyme. 1. Kinetic description of the reaction of an RNA substrate complementary to the active site. Biochemistry (1990), 29(44), 10159–71.
5. Herschlag, Daniel; Cech, Thomas R.. Catalysis of RNA cleavage by the Tetrahymena thermophila ribozyme. 2. Kinetic description of the reaction of an RNA substrate that forms a mismatch at the active site. Biochemistry (1990), 29(44), 10172–80.
6. Knitt, Deborah S.; Herschlag, Daniel. pH Dependencies of the Tetrahymena Ribozyme Reveal an Unconventional Origin of an Apparent pKa. Biochemistry (1996), 35(5), 1560–70.
7. Bevilacqua, Philip C.; Sugimoto, Naoki; Turner, Douglas H.. A mechanistic framework for the second step of splicing catalyzed by the Tetrahymena ribozyme. Biochemistry (1996), 35(2), 648–58.
8. Li, Yi; Bevilacqua, Philip C.; Mathews, David; Turner, Douglas H.. Thermodynamic and activation parameters for binding of a pyrene-labeled substrate by the Tetrahymena ribozyme: docking is not diffusion-controlled and is driven by a favorable entropy change. Biochemistry (1995), 34(44), 14394–9.
9. Banerjee, Aloke Raj; Turner, Douglas H.. The time dependence of chemical modification reveals slow steps in the folding of a group I ribozyme. Biochemistry (1995), 34(19), 6504–12.
10. Zarrinkar, Patrick P.; Williamson, James R., The P9.1–P9.2 peripheral extension helps guide folding of the Tetrahymena ribozyme. Nucleic Acids Res. (1996), 24(5), 854–8.
11. Strobel, Scott A.; Cech, Thomas R.. Minor groove recognition of the conserved G.cntdot.U pair at the Tetrahymena ribozyme reaction site. Science (Washington, D.C.) (1995), 267(5198), 675–9.
12. Strobel, Scott A.; Cech, Thomas R.. Exocyclic Amine of the Conserved G.cntfdot.U Pair at the Cleavage Site of the Tetrahymena Ribozyme Contributes to 5'-Splice Site Selection and Transition State Stabilization. Biochemistry (1996), 35(4), 1201–11.
13. Sullenger, Bruce A.; Cech, Thomas R.. Ribozyme-mediated repair of defective mRNA by targeted trans-splicing. Nature (London) (1994), 371 (6498), 619–22.
14. Robertson, H. D.; Altman, S.; Smith, J. D. J. Biol. Chem., 247, 5243–5251 (1972).
15. Forster, Anthony C.; Altman, Sidney. External guide sequences for an RNA enzyme. Science (Washington, D.C., 1883–) (1990), 249(4970), 783–6.
16. Yuan, Y.; Hwang, E. S.; Alman, S. Targeted cleavage of mRNA by human RNase P. Proc. Natl. Acad. Sci. USA (1992) 89, 8006–10.
17. Harris, Michael E.; Norman R.. Identification of phosphates involved in catalysis by the ribozyme RNase P RNA. RNA (1995), 1(2), 210–18.
18. Pan, Tao; Loria, Andrew; Zhong, Kun. Probing of tertiary interactions in RNA: 2'-hydroxyl-base contacts between the RNase P RNA and pre-tRNA. Proc. Natl. Acad. Sci. U.S.A. (1995), 92(26),12510–14.
19. Pyle, Anna Marie; Green, Justin B.. Building a Kinetic Framework for Group II Intron Ribozyme Activity: Quantitation of Interdomain Binding and Reaction Rate. Biochemistry (1994), 33(9), 2716–25.
20. Michels, William J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationships. Biochemistry (1995), 34(9), 2965–77.
21. Zimmerly, Steven; Guo, Huatao; Eskes, Robert; Yang, Jian; Perlman, Philip S.; Lambowitz, Alan M.. A group II intron RNA is a catalytic component of a DNA endonuclease involved in intron mobility. Cell (Cambridge, Mass.) (1995), 83(4), 529–38.
22. Griffin, Edmund A., Jr.; Qin, Zhifeng; Michels, Williams J., Jr.; Pyle, Anna Marie. Group II intron ribozymes that cleave DNA and RNA linkages with similar efficiency, and lack contacts with substrate 2'-hydroxyl groups. Chem. Biol. (1995), 2(11), 761–70.
23. Michel, Francois; Ferat, Jean Luc. Structure and activities of group II introns. Annu. Rev. Biochem. (1995), 64, 435–61.
24. Abramovitz, Dana L.; Friedman, Richard A.; Pyle, Anna Marie. Catalytic role of 2'-hydroxyl groups within a group II intron active site. Science (Washington, D.C.) (1996), 271(5254), 1410–13.
25. Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256 (1), 31–49.
26. Guo, Hans C. T.; Collins, Richard A.. Efficient trans-cleavage of a stem-loop RNA substrate by a ribozyme derived from Neurospora VS RNA. EMBO J. (1995), 14(2), 368–76.
27. Hampel, Arnold; Tritz, Richard; Hicks, Margaret; Cruz, Phillip. 'Hairpin' catalytic RNA model: evidence for helixes and sequence requirement for substrate RNA. Nucleic Acids Res. (1990), 18(2), 299–304.
28. Chowrira, Bharat M.; Berzal-Herranz, Alfredo; Burke, John M.. Novel guanosine requirement for catalysis by the hairpin ribozyme. Nature (London) (1991), 354(6351), 320–2.
29. Berzal-Herranz, Alfredo; Joseph, Simpson; Chowrira, Bharat M.; Butcher, Samuel E.; Burke, John M.. Essential nucleotide sequences and secondary structure elements of the hairpin ribozyme. EMBO J. (1993), 12(6), 2567–73.
30. Joseph, Simpson; Berzal-Herranz, Alfredo; Chowrira, Bharat M.; Buthcher, Samuel E.. Substrate selection rules for the hairpin ribozyme determined by in vitro selection, mutation, and analysis of mismatched substrates. Genes Dev. (1993), 7(1), 130–8.
31. Berzal-Herranz, Alfredo; Joseph, Simpson; Burke, John M.. In vitro selection of active hairpin ribozymes by sequential RNA-catalyzed cleavage and ligation reactions. Genes Dev. (1992), 6(1), 129–34.
32. Hegg, Lisa A.; Fedor, Martha J.. Kinetics and Thermodynamics of Intermolecular Catalysis by Hairpin Ribozymes. Biochemistry (1995), 34(48), 15813–28.
33. Grasby, Jane A.; Mersmann, Karin; Singh, Mohinder; Gait, Michael J.. Purine Functional Groups in Essential Residues of the Hairpin Ribozyme Required for Catalytic Cleavage of RNA. Biochemistry (1995), 34(12), 4068–76.
34. Schmidt, Sabine; Beigelman, Leonid; Karpeisky, Alexander; Usman, Nassim; Sorensen, Ulrik S.; Gait, Michael J.. Base and sugar requirements for RNA cleavage of essential nucleoside residues in internal loop B of the hairpin ribozyme: implications for secondary structure. Nucleic Acids Res. (1996), 24(4), 573–81.
35. Perrotta, Anne T.; Been, Michael D.. Cleavage of oligoribonucleotides by a ribozyme derived from the hepatitis .delta. virus RNA sequence. Biochemistry (1992), 31(1), 16–21.
36. Perrotta, Anne T.; Been, Michael D.. A pseudoknot-like structure required for efficient self-cleavage of hepatitis delta virus RNA. Nature (London) (1991), 350(6317), 434–6.
37. Puttaraju, M.; Perrotta, Anne T.; Been, Michael D.. A circular trans-acting hepatitis delta virus ribozyme. Nucleic Acids Res. (1993), 21(18), 4253–8.

TABLE II

2.5 µmol RNA Synthesis Cycle

| Reagent | Equivalents | Amount | Wait Time* |
|---|---|---|---|
| Phosphoramidites | 6.5 | 163 µL | 2.5 |
| S-Ethyl Tetrazole | 23.8 | 238 µL | 2.5 |
| Acetic Anhydride | 100 | 233 µL | 5 sec |
| N-Methyl Imidazole | 186 | 233 µL | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery.

TABLE III

Human EGF-R Hammerhead Ribozyme and Target Sequences

| nt. Position | Substrate | Seq. ID NOs. | Ribozyme | Seq. ID NOs. |
|---|---|---|---|---|
| 19 | GCCGGAGUC CCGAGCUA | 1 | UAGCUCGG CUGAUGA X GAA ACUCCGGC | 824 |
| 27 | CCCGAGCUA GCCCCGGC | 2 | GCCGGGGC CUGAUGA X GAA AGCUCGGC | 825 |
| 70 | GGCCACCUC GUCGGCGU | 3 | ACGCCGAC CUGAUGA X GAA AGGUGGCC | 826 |
| 73 | CACCUCGUC GGCGUCCG | 4 | CGGACGCC CUGAUGA X GAA ACGAGGUG | 827 |
| 79 | GUCGGCGUC CGCCCGAG | 5 | CUCGGGCG CUGAUGA X GAA ACGCCGAC | 828 |
| 89 | GCCCGAGUC CCCGCCUC | 6 | GAGGCGGG CUGAUGA X GAA ACUCGGGC | 829 |
| 97 | CCCCGCCUC GCCGCCAA | 7 | UUGGCGGC CUGAUGA X GAA AGGCGGGG | 830 |
| 137 | CCCUGACUC CGUCCAGU | 8 | ACUGGACG CUGAUGA X GAA AGUCAGGG | 831 |
| 141 | GACUCCGUC CAGUAUUG | 9 | CAAUACUG CUGAUGA X GAA ACGGAGUC | 832 |
| 146 | CGUCCAGUA UUGAUCGG | 10 | CCGAUCAA CUGAUGA X GAA ACUGGACG | 833 |
| 148 | UCCAGUAUU GAUCGGGA | 11 | UCCCGAUC CUGAUGA X GAA AUACUGGA | 834 |
| 152 | GUAUUGAUC GGGAGAGC | 12 | GCUCUCCC CUGAUGA X GAA AUCAAUAC | 835 |
| 172 | AGCGAGCUC UUCGGGGA | 13 | UCCCCGAA CUGAUGA X GAA AGCUCGCU | 836 |
| 174 | CGAGCUCUU CGGGGAGC | 14 | GCUCCCCG CUGAUGA X GAA AGAGCUCG | 837 |
| 175 | GAGCUCUUC GGGGAGCA | 15 | UGCUCCCC CUGAUGA X GAA AAGAGCUC | 838 |
| 197 | GCGACCCUC CGGGACGG | 16 | CCGUCCCG CUGAUGA X GAA AGGGUCGC | 839 |
| 219 | GCAGCGCUC CUGGCGCU | 17 | AGCGCCAG CUGAUGA X GAA AGCGCUGC | 840 |
| 240 | GCUGCGCUC UGCCCGGC | 18 | GCCGGGCA CUGAUGA X GAA AGCGCAGC | 841 |
| 253 | CGGCGAGUC GGGCUCUG | 19 | CAGAGCCC CUGAUGA X GAA ACUCGCCG | 842 |
| 259 | GUCGGGCUC UGGAGGAA | 20 | UUCCUCCA CUGAUGA X GAA AGCCCGAC | 843 |
| 276 | AAGAAAGUU UGCCAAGG | 21 | CCUUGGCA CUGAUGA X GAA ACUUUCUU | 844 |
| 277 | AGAAAGUUU GCCAAGGC | 22 | GCCUUGGC CUGAUGA X GAA AACUUUCU | 845 |
| 292 | GCACGAGUA ACAAGCUC | 23 | GAGCUUGU CUGAUGA X GAA ACUCGUGC | 846 |
| 300 | AACAAGCUC ACGCAGUU | 24 | AACUGCGU CUGAUGA X GAA AGCUUGUU | 847 |
| 308 | CACGCAGUU GGGCACUU | 25 | AAGUGCCC CUGAUGA X GAA ACUGCGUG | 848 |
| 316 | UGGGCACUU UUGAAGAU | 26 | AUCUUCAA CUGAUGA X GAA AGUGCCCA | 849 |
| 317 | GGGCACUUU UGAAGAUC | 27 | GAUCUUCA CUGAUGA X GAA AAGUGCCC | 850 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 318 | GGCACUUUU GAAGAUCA | 28 | UGAUCUUC CUGAUGA X GAA AAAGUGCC | 851 |
| 325 | UUGAAGAUC AUUUUCUC | 29 | GACAAAAU CUGAUGA X GAA AUCUUCAA | 852 |
| 328 | AAGAUCAUU UUCUCAGC | 30 | GCUGAGAA CUGAUGA X GAA AUGAUCUU | 853 |
| 329 | AGAUCAUUU UCUCAGCC | 31 | GGCUGAGA CUGAUGA X GAA AAUGAUCU | 854 |
| 330 | CAUCAUUUU CUCAGCCU | 32 | AGGCUGAG CUGAUGA X GAA AAAUGAUC | 855 |
| 331 | AUCAUUUUC UCAGCCUC | 33 | GAGGCUGA CUGAUGA X GAA AAAAUGAU | 856 |
| 333 | CAUUUUCUC AGCCUCCA | 34 | UGGAGGCU CUGAUGA X GAA AGAAAAUG | 857 |
| 339 | CUCAGCCUC CAGAGGAU | 35 | AUCCUCUG CUGAUGA X GAA AGGCUGAG | 858 |
| 350 | GAGGAUGUU CAAUAACU | 36 | AGUUAUUG CUGAUGA X GAA ACAUCCUC | 859 |
| 351 | AGGAUGUUC AAUAACUG | 37 | CAGUUAUU CUGAUGA X GAA AACAUCCU | 860 |
| 355 | UGUUCAAUA ACUGUGAG | 38 | CUCACAGU CUGAUGA X GAA AUUGAACA | 861 |
| 369 | GAGGUGGUC CUUGGGAA | 39 | UUCCCAAG CUGAUGA X GAA ACCACCUC | 862 |
| 372 | GUGGUCCUU GGGAAUUU | 40 | AAAUUCCC CUGAUGA X GAA AGGACCAC | 863 |
| 379 | UUGGGAAUU UGGAAAUU | 41 | AAUUUCCA CUGAUGA X GAA AUUCCCAA | 864 |
| 380 | UGGGAAUUU GGAAAUUA | 42 | UAAUUUCC CUGAUGA X GAA AAUUCCCA | 865 |
| 387 | UUGGAAAUU ACCAUGU | 43 | ACAUAGGU CUGAUGA X GAA AUUUCCAA | 866 |
| 388 | UGGAAAUUA CCUAUGUG | 44 | CACAUAGG CUGAUGA X GAA AAUUUCCA | 867 |
| 392 | AAUUACCUA UGUGCAGA | 45 | UCUGCACA CUGAUGA X GAA AGGUAAUU | 868 |
| 406 | AGAGGAAUU AUGAUCUU | 46 | AAGAUCAU CUGAUGA X GAA AUUCCUCU | 869 |
| 407 | GAGGAAUUA UGAUCUUU | 47 | AAAGAUCA CUGAUGA X GAA AAUUCCUC | 870 |
| 412 | AUUAUGAUC UUUCCUUC | 48 | GAAGGAAA CUGAUGA X GAA AUCAUAAU | 871 |
| 414 | UAUGAUCUU UCCUUCUU | 49 | AAGAAGGA CUGAUGA X GAA AGAUCAUA | 872 |
| 415 | AUGAUCUUU CCUUCUUA | 50 | UAAGAAGG CUGAUGA X GAA AAGAUCAU | 873 |
| 416 | UGAUCUUUC CUUCUUAA | 51 | UUAAGAAG CUGAUGA X GAA AAAGAUCA | 874 |
| 419 | UCUUUCCUU CUUAAAGA | 52 | UCUUUAAG CUGAUGA X GAA AGGAAAGA | 875 |
| 420 | CUUUCCUUC UUAAAGAC | 53 | GUCUUUAA CUGAUGA X GAA AAGGAAAG | 876 |
| 422 | UUCCUUCUU AAAGACCA | 54 | UGGUCUUU CUGAUGA X GAA AGAAGGAA | 877 |
| 423 | UCCUUCUUA AAGACCAU | 55 | AUGGUCUU CUGAUGA X GAA AAGAAGGA | 878 |
| 432 | AAGACCAUC CAGGAGGU | 56 | ACCUCCUG CUGAUGA X GAA AUGGUCUU | 879 |
| 448 | UGGCUGGUU AUGUCCUC | 57 | GAGGACAU CUGAUGA X GAA ACCAGCCA | 880 |
| 449 | GGCUGGUUA UGUCCUCA | 58 | UGAGGACA CUGAUGA X GAA AACCAGCC | 881 |
| 453 | GGUUAUGUC CUCAUUGC | 59 | GCAAUGAG CUGAUGA X GAA ACAUAACC | 882 |
| 456 | UAUGUCCUC AUUGCCCU | 60 | AGGGCAAU CUGAUGA X GAA AGGACAUA | 883 |
| 459 | GUCCUCAUU GCCCUCAA | 61 | UUGAGGGC CUGAUGA X GAA AUGAGGAC | 884 |
| 465 | AUUGCCCUC AACACAGU | 62 | ACUGUGUU CUGAUGA X GAA AGGGCAAU | 885 |
| 483 | GAGCGAAUU CCUUUGGA | 63 | UCCAAAGG CUGAUGA X GAA AUUCGCUC | 886 |
| 484 | AGCGAAUUC CUUUGGAA | 64 | UUCCAAAG CUGAUGA X GAA AAUUCGCU | 887 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 487 | GAAUUCCUU UGGAAAAC | 65 | GUUUUCCA CUGAUGA X GAA AGGAAUUC | 888 |
| 488 | AAUUCCUUU GGAAAACC | 66 | GGUUUUCC CUGAUGA X GAA AAGGAAUU | 889 |
| 504 | CUGCAGAUC AUCAGAGG | 67 | CCUCUGAU CUGAUGA X GAA AUCUGCAG | 890 |
| 507 | CAGAUCAUC AGAGGAAA | 68 | UUUCCUCU CUGAUGA X GAA AUGAUCUG | 891 |
| 517 | GAGGAAAUA UGUAGUAC | 69 | GUAGUACA CUGAUGA X GAA AUUUCCUC | 892 |
| 521 | AAAUAUGUA CUACGAAA | 70 | UUUCGUAG CUGAUGA X GAA ACAUAUUU | 893 |
| 524 | UAUGUACUA CGAAAAUU | 71 | AAUUUUCG CUGAUGA X GAA AGUACAUA | 894 |
| 532 | ACGAAAAUU CCUAUGCC | 72 | GGCAUAGG CUGAUGA X GAA AUUUUCGU | 895 |
| 533 | CGAAAAUUC CUAUGCCU | 73 | AGGCAUAG CUGAUGA X GAA AAUUUUCG | 896 |
| 536 | AAAUUCCUA UGCCUUAG | 74 | CUAAGGCA CUGAUGA X GAA AGGAAUUU | 897 |
| 542 | CUAUGCCUU AGCAGUCU | 75 | AGACUGCU CUGAUGA X GAA AGGCAUAG | 898 |
| 543 | UAUGCCUUA GCAGUCUU | 76 | AAGACUGC CUGAUGA X GAA AAGGCAUA | 899 |
| 549 | UUAGCAGUC UUAUCUAA | 77 | UUAGAUAA CUGAUGA X GAA ACUGCUAA | 900 |
| 551 | AGCAGUCUU AUCUAACU | 78 | AGUUAGAU CUGAUGA X GAA AGACUGCU | 901 |
| 552 | GCAGUCUUA UCUAACUA | 79 | UAGUUAGA CUGAUGA X GAA AAGACUGC | 902 |
| 554 | AGUCUUAUC UAACUAUG | 80 | CAUAGUUA CUGAUGA X GAA AUAAGACU | 903 |
| 556 | UCUUAUCUA ACUAUGAU | 81 | AUCAUAGU CUGAUGA X GAA AGAUAAGA | 904 |
| 560 | AUCUAACUA UGAUGCAA | 82 | UUGCAUCA CUGAUGA X GAA AGUUAGAU | 905 |
| 571 | AUGCAAAUA AAACGGGA | 83 | UCCGUUUU CUGAUGA X CAA AUUUGCAU | 906 |
| 604 | UGAGAAAUU UACAGGAA | 84 | UUCCUGUA CUGAUGA X GAA AUUUCUCA | 907 |
| 605 | GAGAAAUUU ACAGGAAA | 85 | UUUCCUGU CUGAUGA X GAA AAUUUCUC | 908 |
| 606 | AGAAAUUUA CAGGAAAU | 86 | AUUUCCUG CUGAUGA X GAA AAAUUUCU | 909 |
| 615 | CAGGAAAUC CUGCAUGG | 87 | CCAUGCAG CUGAUGA X GAA AUUUCCUG | 910 |
| 635 | CGUGCGGUU CAGCAACA | 88 | UGUUGCUG CUGAUGA X GAA ACCGCACG | 911 |
| 636 | GUGCGGUUC AGCAACAA | 89 | UUGUUGCU CUGAUGA X GAA AACCGCAC | 912 |
| 672 | GAGAGCAUC CAGUGGCG | 90 | CGCCACUG CUGAUGA X GAA AUGCUCUC | 913 |
| 687 | CGGGACAUA GUCAGCAG | 91 | CUGCUGAC CUGAUGA X GAA AUGUCCCG | 914 |
| 690 | GACAUAGUC AGCAGUGA | 92 | UCACUGCU CUGAUGA X GAA ACUAUGUC | 915 |
| 701 | CAGUGACUU UCUCAGCA | 93 | UGCUGAGA CUGAUGA X GAA AGUCACUG | 916 |
| 702 | AGUGACUUU CUCAGCAA | 94 | UUGCUGAG CUGAUGA X GAA AAGUCACU | 917 |
| 703 | CUGACUUUC UCAGCAAC | 95 | GUUGCUGA CUGAUGA X GAA AAAGUCAC | 918 |
| 705 | GACUUCUC AGCAACAU | 96 | AUGUUGCU CUGAUGA X GAA AGAAAGUC | 919 |
| 716 | CAACAUGUC GAUGGACU | 97 | AGUCCAUC CUGAUGA X GAA ACAUGUUG | 920 |
| 725 | GAUGGACUU CCAGAACC | 98 | GGUUCUGG CUGAUGA X GAA AGUCCAUC | 921 |
| 726 | AUGGACUUC CAGAACCA | 99 | UGGUUCUG CUGAUGA X GAA AAGUCCAU | 922 |
| 760 | AGUGUGAUC CAAGCUGU | 100 | ACAGCUUG CUGAUGA X GAA AUCACACU | 923 |
| 769 | CAAGCUGUC CCAAUGGG | 101 | CCCAUUGG CUGAUGA X GAA ACAGCUUG | 924 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 825 | ACCAAAAUC AUCUGUGC | 102 | GCACAGAU CUGAUGA X GAA AUUUUGGU | 925 |
| 828 | AAAAUCAUC UGUGCCCA | 103 | UGGGCACA CUGAUGA X GAA AUGAUUUU | 926 |
| 845 | GCAGUGCUC CGGGCGCU | 104 | AGCGCCCG CUGAUGA X GAA AGCACUGC | 927 |
| 866 | UGGCAAGUC CCCCAGUG | 105 | CACUGGGG CUGAUGA X GAA ACUUGCCA | 928 |
| 936 | UGCCUGGUC UGCCGCAA | 106 | UUGCGGCA CUGAUGA X GAA ACGAGGCA | 929 |
| 947 | CCGCAAAUU CCGAGACG | 107 | CGUCUCGG CUGAUGA X GAA AUUUGCGG | 930 |
| 948 | CGCAAAUUC CGAGACGA | 108 | UCGUCUCG CUGAUGA X GAA AAUUUGCG | 931 |
| 987 | CCCCCACUC AUGCUCUA | 109 | UAGAGCAU CUGAUGA X GAA AGUGGGGG | 932 |
| 993 | CUCAUGCUC UACAACCC | 110 | GGGUUGUA CUGAUGA X GAA AGCAUGAG | 933 |
| 995 | CAUGCUCUA CAACCCCA | 111 | UGGGGUUG CUGAUGA X GAA AGAGCAUG | 934 |
| 1010 | CACCACGUA CCAGAUGG | 112 | CCAUCUGG CUGAUGA X GAA ACGUGGUG | 935 |
| 1040 | GGGCAAAUA CAGCUUUG | 113 | CAAAGCUG CUGAUGA X GAA AUUUGCCC | 936 |
| 1046 | AUACAGCUU UGGUGCCA | 114 | UGGCACCA CUGAUGA X GAA AGCUGUAU | 937 |
| 1047 | UACAGCUUU GGUGCCAC | 115 | GUGGCACC CUGAUGA X GAA AAGCUGUA | 938 |
| 1072 | AGAAGUGUC CCCGUAAU | 116 | AUUACGGG CUGAUGA X GAA ACACUUCU | 939 |
| 1078 | GUCCCCGUA AUUAUGUG | 117 | CACAUAAU CUGAUGA X GAA ACGGGGAC | 940 |
| 1081 | CCCGUAAUU AUGGGUG | 118 | CACCACAU CUGAUGA X GAA AUUACGGG | 941 |
| 1082 | CCGUAAUUA UGUGGUGA | 119 | UCACCACA CUGAUGA X GAA AAUUACGG | 942 |
| 1096 | UGACAGAUC ACGGCUCG | 120 | CGAGCCGU CUGAUGA X GAA AUCUGUCA | 943 |
| 1103 | UCACGGCUC GUGCGUCC | 121 | GGACGCAC CUGAUGA X GAA AGCCGUGA | 944 |
| 1110 | UCGUGCGUC CGAGCCUG | 122 | CAGGCUCG CUGAUGA X GAA ACGCACGA | 945 |
| 1133 | CGACAGCUA UGAGAUGG | 123 | CCAUCUCA CUGAUGA X GAA AGCUGUCG | 946 |
| 1155 | GACGGCGUC CGCAAGUG | 124 | CACUUGCG CUGAUGA X GAA ACGCCGUC | 947 |
| 1165 | GCAAGUGUA AGAAGUGC | 125 | GCACUUCU CUGAUGA X GAA ACACUUGC | 948 |
| 1183 | AAGGGCCUU GCCGCAAA | 126 | UUUGCGGC CUGAUGA X GAA AGGCCCUU | 949 |
| 1198 | AAGUGUGUA ACGGAAUA | 127 | UAUUCCGU CUGAUGA X GAA ACACACUU | 950 |
| 1206 | AACGGAAUA GGUAUUGG | 128 | CCAAUACC CUGAUGA X GAA AUUCCGUU | 951 |
| 1210 | GAAUAGGUA UUGGUGAA | 129 | UUCACCAA CUGAUGA X GAA ACCUAUUC | 952 |
| 1212 | AUAGGUAUU GGUGAAUU | 130 | AAUUCACC CUGAUGA X GAA AUACCUAU | 953 |
| 1220 | UGGUGAAUU UAAAGACU | 131 | AGUCUUUA CUGAUGA X GAA AUUCACCA | 954 |
| 1221 | GGUGAAUUU AAAGACUC | 132 | GAGUCUUU CUGAUGA X GAA AAUUCACC | 955 |
| 1222 | GUGAAUUUA AAGACUCA | 133 | UGAGUCUU CUGAUGA X GAA AAAUUCAC | 956 |
| 1229 | UAAAGACUC ACUCUCCA | 134 | UGGAGAGU CUGAUGA X GAA AGUCUUUA | 957 |
| 1233 | GACUCACUC UCCAUAAA | 135 | UUUAUGGA CUGAUGA X GAA AGUGAGUC | 958 |
| 1235 | CUCACUCUC CAUAAAUG | 136 | CAUUUAUG CUGAUGA X GAA AGAGUGAG | 959 |
| 1239 | CUCUCCAUA AAUGCUAC | 137 | GUAGCAUU CUGAUGA X GAA AUGGAGAG | 960 |
| 1246 | UAAAUGCUA CGAAUAUU | 138 | AAUAUUCG CUGAUGA X GAA AGCAUUUA | 961 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 1252 | CUACGAAUA UUAAACAC | 139 | GUGUUUAA CUGAUGA X GAA AUUCGUAG | 962 |
| 1254 | ACGAAUAUU AAACACUU | 140 | AAGUGUUU CUGAUGA X GAA AUAUUCGU | 963 |
| 1255 | CGAAUAUUA AACACUUC | 141 | GAAGUGUU CUGAUGA X GAA AAUAUUCG | 964 |
| 1262 | UAAACACUU CAAAAACU | 142 | AGUUUUUG CUGAUGA X GAA AGUGUUUA | 965 |
| 1263 | AAACACUUC AAAAACUG | 143 | CAGUUUUU CUGAUGA X GAA AAGUGUUU | 966 |
| 1277 | CUGCACCUC CAUCAGUG | 144 | CACUGAUG CUGAUGA X GAA AGGUGCAG | 967 |
| 1281 | ACCUCCAUC AGUGGCGA | 145 | UCGCCACU CUGAUGA X GAA AUGGAGGU | 968 |
| 1291 | GUGGCGAUC UCCACAUC | 146 | GAUGGGGA CUGAUGA X GAA AUCGCCAC | 969 |
| 1293 | GGCGAUCUC CACAUCCU | 147 | AGGAUGUG CUGAUGA X GAA AGAUCGCC | 970 |
| 1299 | CUCCACAUC CUGCCGGU | 148 | ACCGGCAG CUGAUGA X GAA AUGUGGAG | 971 |
| 1313 | GGUGGCAUU UAGGGGUG | 149 | CACCCCUA CUGAUGA X GAA AUGCCACC | 972 |
| 1314 | GUGGCAUUU AGGGGUGA | 150 | UCACCCCU CUGAUGA X GAA AAUGCCAC | 973 |
| 1315 | UGGCAUUUA GGGGUGAC | 151 | GUCACCCC CUGAUGA X CAA AAAUGCCA | 974 |
| 1325 | GGGUGACUC CUUCACAC | 152 | GUGUGAAG CUGAUGA X GAA AGUCACCC | 975 |
| 1328 | UGACUCCUU CACACAUA | 153 | UAUGUGUG CUGAUGA X GAA AGGAGUCA | 976 |
| 1329 | GACUCCUUC ACACAUAC | 154 | GUAUGUGU CUGAUGA X GAA AAGGAGUC | 977 |
| 1336 | UCACACAUA CUCCUCCU | 155 | AGGAGGAG CUGAUGA X GAA AUGUGUCA | 978 |
| 1339 | CACAUACUC CUCCUCUG | 156 | CAGAGGAG CUGAUGA X GAA AGUAUGUG | 979 |
| 1342 | AUACUCCUC CUCUGGAU | 157 | AUCCAGAG CUGAUGA X GAA AGGAGUAU | 980 |
| 1345 | CUCCUCCUC UGGAUCCA | 158 | UGGAUCCA CUGAUGA X GAA AGGAGGAG | 981 |
| 1351 | CUCUGGAUC CACAGGAA | 159 | UUCCUGUG CUGAUGA X GAA AUCCAGAG | 982 |
| 1366 | AACUGGAUA UUCUGAAA | 160 | UUUCGAAA CUGAUGA X GAA AUCCAGUU | 983 |
| 1368 | CUGGAUAUU CUGAAAAC | 161 | GUUUUCAG CUGAUGA X CAA AUAUCCAG | 984 |
| 1369 | UGGAUAUUC UGAAAACC | 162 | GGUUUUCA CUGAUGA X GAA AAUAUCCA | 985 |
| 1380 | AAAACCGUA AGGAAAU | 163 | AUUUCCUU CUGAUGA X GAA ACGGUUUU | 986 |
| 1389 | AAGGAAAUC ACAGGGUU | 164 | AACCCUGU CUGAUGA X GAA AUUUCCUU | 987 |
| 1397 | CACAGGGUU UUUGCUGA | 165 | UCAGCAAA CUGAUGA X GAA ACCCUGUG | 988 |
| 1398 | ACAGGGUUU UUGCUGAU | 166 | AUCAGCAA CUGAUGA X GAA AACCCUGU | 989 |
| 1399 | CAGGGUUUU UGCUGAUU | 167 | AAUCAGCA CUGAUGA X GAA AAACCCUG | 990 |
| 1400 | AGGGUUUUU GCUGAUUC | 168 | GAAUCAGC CUGAUGA X GAA AAAACCCU | 991 |
| 1407 | UUGCUGAUU CAGGCUUG | 169 | CAAGCCUG CUGAUGA X GAA AUCAGCAA | 992 |
| 1408 | UGCUGAUUC AGGCUUGG | 170 | CCAAGCCU CUGAUGA X GAA AAUCAGCA | 993 |
| 1414 | UUCAGGCUU GGCCUGAA | 171 | UUCAGGCC CUGAUGA X GAA AGCCUGAA | 994 |
| 1437 | ACGGACCUC CAUGCCUU | 172 | AAGGCAUG CUGAUGA X GAA AGGUCCGU | 995 |
| 1445 | CCAUGCCUU UGAGAACC | 173 | GGUUCUCA CUGAUGA X GAA AGGCAUGG | 996 |
| 1446 | CAUGCCUUU GAGAACCU | 174 | AGGUUCUC CUGAUGA X GAA AAGGCAUG | 997 |
| 1455 | GAGAACCUA GAAAUCAU | 175 | AUGAUUUC CUGAUGA X GAA AGGUUCUC | 998 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 1461 | CUAGAAAUC AUACGCGG | 176 | CCGCGUAU CUGAUGA X GAA AUUUCUAG | 999 |
| 1464 | GAAAUCAUA CGCGGCAG | 177 | CUGCCGCG CUGAUGA X GAA AUGAUUUC | 1000 |
| 1489 | AACAUGGUC AGUUUUCU | 178 | AGAAAACU CUGAUGA X GAA ACCAUGUU | 1001 |
| 1493 | UGGUCAGUU UUCUCUUG | 179 | CAAGAGAA CUGAUGA X GAA ACUGACCA | 1002 |
| 1494 | GGUCAGUUU UCUCUUGC | 180 | GCAAGAGA CUGAUGA X GAA AACUGACC | 1003 |
| 1495 | GUCAGUUUU CUCUUGCA | 181 | UGCAAGAG CUGAUGA X GAA AAACUGAC | 1004 |
| 1496 | UCAGUUUUC UCUUGCAG | 182 | CUGCAAGA CUGAUGA X GAA AAAACUGA | 1005 |
| 1498 | AGUUUUCUC UUGCAGUC | 183 | GACUGCAA CUGAUGA X GAA AGAAAACU | 1006 |
| 1500 | UUUUCUCUU GCAGUCGU | 184 | ACGACUGC CUGAUGA X GAA AGAGAAAA | 1007 |
| 1506 | CUUGCAGUC GUCAGCCU | 185 | AGGCUGAC CUGAUGA X GAA ACUGCAAG | 1008 |
| 1509 | GCAGUCGUC AGCCUGAA | 186 | UUCAGGCU CUGAUGA X GAA ACGACUGC | 1009 |
| 1521 | CUGAACAUA ACAUCCUU | 187 | AAGGAUGU CUGAUGA X GAA AUGUUCAG | 1010 |
| 1526 | CAUAACAUC CUUGGGAU | 188 | AUCCCAAG CUGAUGA X GAA AUGUUAUG | 1011 |
| 1529 | AACAUCCUU GGGAUUAC | 189 | GUAAUCCC CUGAUGA X GAA AGGAUGUU | 1012 |
| 1535 | CUUGGGAUU ACGCUCCC | 190 | GGGAGCGU CUGAUGA X GAA AUCCCAAG | 1013 |
| 1536 | UUGGGAUUA CGCUCCCU | 191 | AGGGAGCG CUGAUGA X GAA AAUCCCAA | 1014 |
| 1541 | AUUACGCUC CCUCAAGG | 192 | CCUUGAGG CUGAUGA X GAA AGCGUAAU | 1015 |
| 1545 | CGCUCCCUC AAGGAGAU | 193 | AUCUCCUU CUGAUGA X GAA AGGGAGCG | 1016 |
| 1554 | AAGGAGAUA AGUGAUGG | 194 | CCAUCACU CUGAUGA X GAA AUCUCCUU | 1017 |
| 1572 | GAUGUGAUA AUUUCAGG | 195 | CCUGAAAU CUGAUGA X GAA AUCACAUC | 1018 |
| 1575 | GUGAUAAUU UCAGGAAA | 196 | UUUCCUGA CUGAUGA X GAA AUUAUGAC | 1019 |
| 1576 | UGAUAAUUU CAGGAAAC | 197 | GUUUCCUG CUGAUGA X GAA AAUUAUCA | 1020 |
| 1577 | GAUAAUUUC AGGAAACA | 198 | UGUUUCCU CUGAUGA X GAA AAAUUAUC | 1021 |
| 1591 | ACAAAAAUU UGUGCUAU | 199 | AUAGCACA CUGAUGA X GAA AUUUUUGU | 1022 |
| 1592 | CAAAAAUUU GUGCUAUG | 200 | CAUAGCAC CUGAUGA X GAA AAUUUUUG | 1023 |
| 1598 | UUUGUGCUA UGCAAAUA | 201 | UAUUUGCA CUGAUGA X GAA AGCACAAA | 1024 |
| 1606 | AUGCAAAUA CAAUAAAC | 202 | GUUUAUUG CUGAUGA X GAA AUUUGCAU | 1025 |
| 1611 | AAUACAAUA AACUGGAA | 203 | UUCCAGUU CUGAUGA X GAA AUUGUAUU | 1026 |
| 1628 | AAAACUGUU UGGGACCU | 204 | AGGUCCCA CUGAUGA X GAA ACAGUUUU | 1027 |
| 1629 | AAACUGUUU GGGACCUC | 205 | GAGGUCCC CUGAUGA X GAA AACAGUUU | 1028 |
| 1637 | UGGGACCUC CGGUCAGA | 206 | UCUGACCG CUGAUGA X GAA AGGUCCCA | 1029 |
| 1642 | CCUCCGGUC AGAAAACC | 207 | GGUUUUCU CUGAUGA X GAA ACCGGAGG | 1030 |
| 1656 | ACCAAAAUU AUAAGCAA | 208 | UUGCUUAU CUGAUGA X GAA AUUUUGGU | 1031 |
| 1657 | CCAAAAUUA UAAGCAAC | 209 | GUUGCUUA CUGAUGA X GAA AAUUUUGG | 1032 |
| 1659 | AAAAUUAUA AGCAACAG | 210 | CUGUUGCU CUGAUGA X GAA AUAAUUUU | 1033 |
| 1701 | GGCCAGGUC UGCCAUGC | 211 | GCAUGGCA CUGAUGA X GAA ACCUGGCC | 1034 |
| 1712 | CCAUGCCUU GUGCUCCC | 212 | GGGAGCAC CUGAUGA X GAA AGGCAUGG | 1035 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 1718 | CUUGUGCUC CCCCGAGG | 213 | CCUCGGGG CUGAUGA X GAA AGCACAAG | 1036 |
| 1758 | GACUGCGUC UCUUGCCG | 214 | CGGCAAGA CUGAUGA X GAA ACGCAGUC | 1037 |
| 1760 | CUGCGUCUC UUGCCGGA | 215 | UCCGGCAA CUGAUGA X GAA AGACGCAG | 1038 |
| 1762 | GCGUCUCUU GCCGGAAU | 216 | AUUCCGGC CUGAUGA X GAA AGAGACGC | 1039 |
| 1773 | CGGAAUGUC AGCCGAGG | 217 | CCUCGGCU CUGAUGA X GAA ACAUUCCG | 1040 |
| 1809 | UGCAAGCUU CUGGAGGG | 218 | CCCUCCAG CUGAUGA X GAA AGCUUGCA | 1041 |
| 1810 | GCAAGCUUC UGGAGGGU | 219 | ACCCUCCA CUGAUGA X GAA AAGCUUGC | 1042 |
| 1832 | AAGGGAGUU UGUGGAGA | 220 | UCUCCACA CUGAUGA X GAA ACUCCCUU | 1043 |
| 1833 | AGGGAGUUU GUGGAGAA | 221 | UUCUCCAC CUGAUGA X GAA AACUCCCU | 1044 |
| 1844 | GGAGAACUC UGAGUGCA | 222 | UGCACUCA CUGAUGA X GAA AGUUCUCC | 1045 |
| 1854 | GAGUGCAUA CAGUGCCA | 223 | UGGCACUG CUGAUGA X GAA AUGCACUC | 1046 |
| 1879 | GCCUGCCUC AGGCCAUG | 224 | CAUGGCCU CUGAUGA X GAA AGGCAGGC | 1047 |
| 1893 | AUGAACAUC ACCUGCAC | 225 | GUGCAGGU CUGAUGA X GAA AUGUUCAU | 1048 |
| 1924 | ACAACUGUA UCCAGUGU | 226 | ACACUGGA CUGAUGA X GAA ACAGUGGU | 1049 |
| 1926 | AACUGUAUC CAGUGUGC | 227 | GCACACUG CUGAUGA X GAA AUACAGUU | 1050 |
| 1940 | UGCCCACUA CAUUGACG | 228 | CGUCAAUG CUGAUGA X GAA AGUGGGCA | 1051 |
| 1944 | CACUACAUU GACGGCCC | 229 | GGGCCGUC CUGAUGA X GAA AUGUAGUG | 1052 |
| 1962 | CACUGCGUC AAGACCUG | 230 | CAGGUCUU CUGAUGA X GAA ACGCAGUG | 1053 |
| 1983 | GCAGGAGUC AUGGGAGA | 231 | UCUCCCAU CUGAUGA X GAA ACUCCUGC | 1054 |
| 2007 | ACCCUGGUC UGGAAGUA | 232 | UACUUCCA CUGAUGA X GAA ACCAGGGU | 1055 |
| 2015 | CUGGAAGUA CGCAGACG | 233 | CGUCUGCG CUGAUGA X GAA ACUUCCAG | 1056 |
| 2050 | UGUGCCAUC CAAACUGC | 234 | GCAGUUUG CUGAUGA X GAA AUGGCACA | 1057 |
| 2063 | CUGCACCUA CGGAUGCA | 235 | UGCAUCCG CUGAUGA X GAA AGGUGCAG | 1058 |
| 2083 | GGCCAGGUC UUGAAGGC | 236 | GCCUUCAA CUGAUGA X GAA ACCUGGCC | 1059 |
| 2085 | CCAGGUCUU GAAGGCUG | 237 | CAGCCUUC CUGAUGA X GAA AGACCUGG | 1060 |
| 2095 | AAGGCUGUC AACGAAU | 238 | AUUCGUUG CUGAUGA X GAA ACAGCCUU | 1061 |
| 2110 | AUGGGCCUA AGAUCCCG | 239 | CGGGAUCU CUGAUGA X GAA AGGCCCAU | 1062 |
| 2115 | CCUAAGAUC CCGUCCAU | 240 | AUGGACGG CUGAUGA X GAA AUCUUAGG | 1063 |
| 2120 | GAUCCCGUC CAUCGCCA | 241 | UGGCGAUG CUGAUGA X GAA ACGGGAUC | 1064 |
| 2124 | CCGUCCAUC GCCACUGG | 242 | CCAGUGGC CUGAUGA X GAA AUGGACGG | 1065 |
| 2148 | GGGGCCCUC CUCUUGCU | 243 | AGCAAGAG CUGAUGA X GAA AGGGCCCC | 1066 |
| 2151 | GCCCUCCUC UUGCUGCU | 244 | AGCAGCAA CUGAUGA X GAA AGGAGGGC | 1067 |
| 2153 | CCUCCUCUU GCUGCUGG | 245 | CCAGCAGC CUGAUGA X GAA AGAGGAGG | 1068 |
| 2178 | CUGGGGAUC GGCCUCUU | 246 | AAGAGGCC CUGAUGA X GAA AUCCCCAG | 1069 |
| 2184 | AUCGGCCUC UUCAUGCG | 247 | CGCAUGAA CUGAUGA X GAA AGGCCGAU | 1070 |
| 2186 | CGGCCUCUU CAUGCGAA | 248 | UUCGCAUG CUGAUGA X GAA AGAGGCCG | 1071 |
| 2187 | GGCCUCUUC AUGCGAAG | 249 | CUUCGCAU CUGAUGA X GAA AAGAGGCC | 1072 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 2205 | CGCCACAUC GUUCGGAA | 250 | UUCCGAAC CUGAUGA X GAA AUGUGGCG | 1073 |
| 2208 | CACAUCGUU CGGAAGCG | 251 | CGCUUCCG CUGAUGA X GAA ACGAUGUG | 1074 |
| 2209 | ACAUCGUUC GGAAGCGC | 252 | GCGCUUCC CUGAUGA X GAA AACGAUGU | 1075 |
| 2250 | AGGGAGCUU GUGGAGCC | 253 | GGCUCCAC CUGAUGA X GAA AGCUCCCU | 1076 |
| 2260 | UGGAGCCUC UUACACCC | 254 | GGGUGUAA CUGAUGA X GAA AGGCUCCA | 1077 |
| 2262 | GAGCCUCUU ACACCCAG | 255 | CUGGGUGU CUGAUGA X GAA AGAGGCUC | 1078 |
| 2263 | AGCCUCUUA CACCCAGU | 256 | ACUGGGUG CUGAUGA X GAA AAGAGGCU | 1079 |
| 2281 | GAGAAGCUC CCAACCAA | 257 | UUGGUUGG CUGAUGA X GAA AGCUUCUC | 1080 |
| 2293 | ACCAAGCUC UCUUGAGG | 258 | CCUCAAGA CUGAUGA X GAA AGCUUGGU | 1081 |
| 2295 | CAAGCUCUC UUGAGGAU | 259 | AUCCUCAA CUGAUGA X GAA AGAGCUUG | 1082 |
| 2297 | AGCUCUCUU GAGGAUCU | 260 | AGAUCCUC CUGAUGA X GAA AGAGAGCU | 1083 |
| 2304 | UUGAGGAUC UUGAAGGA | 261 | UCCUUCAA CUGAUGA X GAA AUCCUCAA | 1084 |
| 2306 | GAGGAUCUU GAAGGAAA | 262 | UUUCCUUC CUGAUGA X GAA AGAUCCUC | 1085 |
| 2321 | AACUGAAUU CAAAAAGA | 263 | UCUUUUUG CUGAUGA X GAA AUUCAGUU | 1086 |
| 2322 | ACUGAAUUC AAAAAGAU | 264 | AUCUUUUU CUGAUGA X GAA AAUUCAGU | 1087 |
| 2331 | AAAAAGAUC AAAGUGCU | 265 | AGCACUUU CUGAUGA X GAA AUCUUUUU | 1088 |
| 2345 | GCUGGGCUC CGGUGCGU | 266 | ACGCACCG CUGAUGA X GAA AGCCCAGC | 1089 |
| 2354 | CGGUGCGUU CGGCACGG | 267 | CCGUGCCG CUGAUGA X GAA ACGCACCG | 1090 |
| 2355 | GGUGCGUUC GGCACGGU | 268 | ACCGUGCC CUGAUGA X GAA AACGCACC | 1091 |
| 2366 | CACGGUGUA UAAGGGAC | 269 | GUCCCUUA CUGAUGA X GAA ACACCGUG | 1092 |
| 2368 | CGGUGUAUA AGGGACUC | 270 | GAGUCCCU CUGAUGA X GAA AUACACCG | 1093 |
| 2376 | AAGGGACUC UGGAUCCC | 271 | GGGAUCCA CUGAUGA X GAA AGUCCCUU | 1094 |
| 2382 | CUCUGGAUC CCAGAAGG | 272 | CCUUCUGG CUGAUGA X GAA AUCCAGAG | 1095 |
| 2400 | GAGAAAGUU AAAAUUCC | 273 | GGAAUUUU CUGAUGA X GAA ACUUUCUC | 1096 |
| 2401 | AGAAAGUUA AAAUUCCC | 274 | GGGAAUUU CUGAUGA X GAA AACUUUCU | 1097 |
| 2406 | GUUAAAAUU CCCGUCGC | 275 | GCGACGGG CUGAUGA X GAA AUUUUAAC | 1098 |
| 2407 | UUAAAAUUC CCGUCGCU | 276 | AGCGACGG CUGAUGA X GAA AAUUUUAA | 1099 |
| 2412 | AUUCCCGUC GCUAUCAA | 277 | UUGAUAGC CUGAUGA X GAA ACGGGAAU | 1100 |
| 2416 | CGGUCGCUA UCAAGGAA | 278 | UUCCUUGA CUGAUGA X GAA AGCGACGG | 1101 |
| 2418 | GUCGCUAUC AAGGAAUU | 279 | AAUUCCUU CUGAUGA X GAA AUAGCGAC | 1102 |
| 2426 | GAAGGAAUU AAGAGAAG | 280 | CUUCUCUU CUGAUGA X GAA AUUCCUUG | 1103 |
| 2427 | AAGGAAUUA AGAGAAGC | 281 | GCUUCUCU CUGAUGA X GAA AAUUCCUU | 1104 |
| 2441 | AGCAACAUC UCCGAAAG | 282 | CUUUCGGA CUGAUGA X GAA AUGUUGCU | 1105 |
| 2443 | CAACAUCUC CGAAAGCC | 283 | GGCUUUCG CUGAUGA X GAA AGAUGUUG | 1106 |
| 2463 | AAGGAAAUC CUCGAUGA | 284 | UCAUCGAG CUGAUGA X GAA AUUUCCUU | 1107 |
| 2466 | GAAAUCCUC GAUGAAGC | 285 | GCUUCAUC CUGAUGA X GAA AGGAUUUC | 1108 |
| 2477 | UGAAGCCUA CGUGAUGG | 286 | CCAUCACG CUGAUGA X GAA AGGCUUCA | 1109 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 2526 | CUGGGCAUC UGCCUCAC | 287 | GUGAGGCA CUGAUGA X GAA AUGCCCAG | 1110 |
| 2532 | AUCUGCCUC ACCUCCAC | 288 | GUGGAGGU CUGAUGA X GAA AGGCAGAU | 1111 |
| 2537 | CCUCACCUC CACCGUGC | 289 | GCACGGUG CUGAUGA X GAA AGGUGAGG | 1112 |
| 2550 | GUGCAACUC AUCACGCA | 290 | UGCGUGAU CUGAUGA X GAA AGUUGCAC | 1113 |
| 2553 | CAACUCAUC ACGCAGCU | 291 | AGCUGCGU CUGAUGA X GAA AUGAGUUG | 1114 |
| 2562 | ACGCAGCUC AUGCCCUU | 292 | AAGGGGAU CUGAUGA X GAA AGCUGCGU | 1115 |
| 2570 | CAUGCCCUU CGGCUGCC | 293 | GGCAGCCG CUGAUGA X GAA AGGGCAUG | 1116 |
| 2571 | AUGCCCUUC GGCUGCCU | 294 | AGGCAGCC CUGAUGA X GAA AAGGGCAU | 1117 |
| 2580 | GGCUGCCUC CUGGACUA | 295 | UAGUCCAG CUGAUGA X GAA AGGCAGCC | 1118 |
| 2588 | CCUGGACUA UGUCCGGG | 296 | CCCGGACA CUGAUGA X GAA AGUCCAGG | 1119 |
| 2592 | GACUAUGUC CGGGAACA | 297 | UGUUCCCG CUGAUGA X GAA ACAUAGUC | 1120 |
| 2611 | AAGACAAUA UUGGCUCC | 298 | GGAGCCAA CUGAUGA X GAA AUUGUCUU | 1121 |
| 2613 | GACAAUAUU GGCUCCCA | 299 | UGGGAGCC CUGAUGA X GAA AUAUUGUC | 1122 |
| 2618 | UAUUGGCUC CCAGUACC | 300 | GGUACUGG CUGAUGA X GAA AGCCAAUA | 1123 |
| 2624 | CUCCCAGUA CCUGCUCA | 301 | UGAGCAGG CUGAUGA X GAA ACUGGGAG | 1124 |
| 2631 | UACCUGCUC AACUGGUG | 302 | CACCAGUU CUGAUGA X GAA AGCAGGUA | 1125 |
| 2649 | GUGCAGAUC GCAAAGGG | 303 | CCCUUUGC CUGAUGA X GAA AUCUGCAC | 1126 |
| 2666 | CAUGAACUA CUUGCAGG | 304 | CCUCCAAG CUGAUGA X GAA AGUUCAUG | 1127 |
| 2669 | GAACUACUU GGAGGACC | 305 | GGUCCUCC CUGAUGA X GAA AGUAGUUC | 1128 |
| 2680 | AGGACCGUC GCUGGGUG | 306 | CACCAAGC CUGAUGA X GAA ACGGUCCU | 1129 |
| 2684 | CCGUCGCUU GGUGCACC | 307 | GGUGCACC CUGAUGA X GAA AGCGACGG | 1130 |
| 2715 | AGGAACGUA CUGGUGAA | 308 | UUCACCAG CUGAUGA X GAA ACGUUCCU | 1131 |
| 2739 | CAGCAUGUC AAGAUCAC | 309 | GUGAUCUU CUGAUGA X GAA ACAUGCUG | 1132 |
| 2745 | GUCAAGAUC ACAGAUUU | 310 | AAAUCUGU CUGAUGA X GAA AUCUUGAC | 1133 |
| 2752 | UCACAGAUU UGGGCUG | 311 | CAGCCCAA CUGAUGA X GAA AUCUGUGA | 1134 |
| 2753 | CACAGAUUU UGGGCUGG | 312 | CCAGCCCA CUGAUGA X GAA AAUCUCUG | 1135 |
| 2754 | ACAGAUUUU GGGCUGGC | 313 | GCCAGCCC CUGAUGA X GAA AAAUCUGU | 1136 |
| 2792 | GAAAGAAUA CCAUGCAG | 314 | CUGCAUGG CUGAUGA X GAA AUUCUUUC | 1137 |
| 2818 | AAGUGCCUA UCAAGUGG | 315 | CCACUUGA CUGAUGA X GAA AGGCACUU | 1138 |
| 2820 | GUGCCUAUC AAGUGGAU | 316 | AUCCACUU CUGAUCA X GAA AUAGGCAC | 1139 |
| 2834 | GAUGGCAUU GGAAUCAA | 317 | UUGAUUCC CUGAUGA X GAA AUGCCAUC | 1140 |
| 2840 | AUUGGAAUC AAUUUUAC | 318 | GUAAAAUU CUGAUGA X GAA AUUCCAAU | 1141 |
| 2844 | GAAUCAAUU UUACACAG | 319 | CUGUGUAA CUGAUGA X GAA AUUGAUUC | 1142 |
| 2845 | AAUCAAUUU UACACAGA | 320 | UCUGUGUA CUGAUGA X GAA AAUUGAUU | 1143 |
| 2846 | AUCAAUUUU ACACAGAA | 321 | UUCUGUGU CUGAUGA X GAA AAAUUGAU | 1144 |
| 2847 | UCAAUUUUA CACAGAAU | 322 | AUUCUGUG CUGAUGA X GAA AAAAUUGA | 1145 |
| 2856 | CACAGAAUC UAUACCCA | 323 | UGGGUAUA CUGAUGA X GAA AUUCUGUG | 1146 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 2858 | CAGAAUCUA UACCCACC | 324 | GGUGGGUA CUGAUGA X GAA AGAUUCUG | 1147 |
| 2860 | GAAUCUAUA CCCACCAG | 325 | CUGGUGGG CUGAUGA X GAA AUAGAUUC | 1148 |
| 2877 | AGUGAUGUC UGGAGCUA | 326 | UAGCUCCA CUGAUGA X GAA ACAUCACU | 1149 |
| 2885 | CUGGAGCUA CGGGGUGA | 327 | UCACCCCG CUGAUGA X GAA AGCUCCAG | 1150 |
| 2898 | GUGACCGUU UGGGAGUU | 328 | AACUCCCA CUGAUGA X GAA ACGGUCAC | 1151 |
| 2899 | UGACCGUUU GGGAGUUG | 329 | CAACUCCC CUGAUGA X GAA AACGGUCA | 1152 |
| 2906 | UUGGGAGUU GAUGACCU | 330 | AGGUCAUC CUGAUGA X GAA ACUCCCAA | 1153 |
| 2915 | GAUGACCUU UGGAUCCA | 331 | UGGAUCCA CUGAUGA X GAA AGGUCAUC | 1154 |
| 2916 | AUGACCUUU GGAUCCAA | 332 | UUGGAUCC CUGAUGA X GAA AAGGUCAU | 1155 |
| 2921 | CUUUGGAUC CAAGCCAU | 333 | AUGGCUUG CUGAUGA X GAA AUCCAAAG | 1156 |
| 2930 | CAAGCCAUA UGACGGAA | 334 | UUCCGUCA CUGAUGA X GAA AUGGCUUG | 1157 |
| 2940 | GACGGAAUC CCUGCCAG | 335 | CUGGCAGG CUGAUGA X GAA AUUCCGUC | 1158 |
| 2955 | AGCGAGAUC UCCUCCAU | 336 | AUGGAGGA CUGAUGA X GAA AUCUCGCU | 1159 |
| 2957 | CGAGAUCUC CUCCAUCC | 337 | GGAUGGAG CUGAUGA X GAA AGAUCUCG | 1160 |
| 2960 | GAUCUCCUC CAUCCUGG | 338 | CCAGGAUG CUGAUGA X GAA AGGAGAUC | 1161 |
| 2964 | UCCUCCAUC CUGGAGAA | 339 | UUCUCCAG CUGAUGA X GAA AUGGAGGA | 1162 |
| 2985 | GAACGCCUC CCUCAGCC | 340 | GGCUGAGG CUGAUGA X GAA AGGCGUUC | 1163 |
| 2989 | GCCUCCCUC AGCCACCC | 341 | GGGUGGCU CUGAUGA X GAA AGGGAGGC | 1164 |
| 3000 | CCACCCAUA UGUACCAU | 342 | AUGGUACA CUGAUGA X GAA AUGGGUGG | 1165 |
| 3004 | CCAUAUGUA CCAUCGAU | 343 | AUCGAUGG CUGAUGA X GAA ACAUAUGG | 1166 |
| 3009 | UGUACCAUC GAUGUCUA | 344 | UAGACAUC CUGAUGA X GAA AUGGUACA | 1167 |
| 3015 | AUCGAUGUC UACAUGAU | 345 | AUCAUGUA CUGAUGA X GAA ACAUCGAU | 1168 |
| 3017 | CGAUGUCUA CAUGAUCA | 346 | UGAUCAUG CUGAUGA X GAA AGACAUCG | 1169 |
| 3024 | UACAUGAUC AUGGUCAA | 347 | UUGACCAU CUGAUGA X GAA AUCAUGUA | 1170 |
| 3030 | AUCAUGGUC AAGUGCUG | 348 | CAGCACUU CUGAUGA X GAA ACCAUGAU | 1171 |
| 3045 | UGGAUGAUA GACGCAGA | 349 | UCUGCGUC CUGAUGA X GAA AUCAUCCA | 1172 |
| 3055 | ACGCAGAUA GUCGCCCA | 350 | UGGGCGAC CUGAUGA X GAA AUCUGCGU | 1173 |
| 3058 | CAGAUAGUC GCCCAAAG | 351 | CUUUGGGC CUGAUGA X GAA ACUAUCUG | 1174 |
| 3068 | CCCAAAGUU CCGUGAGU | 352 | ACUGACGG CUGAUGA X GAA ACUUUGGG | 1175 |
| 3069 | CCAAAGUUC CGUGAGUU | 353 | AACUCACG CUGAUGA X GAA AACUUUGG | 1176 |
| 3077 | CCGUGAGUU GAUCAUCG | 354 | CGAUGAUC CUGAUGA X GAA ACUCACGG | 1177 |
| 3081 | GAGUUGAUC AUCGAAUU | 355 | AAUUCGAU CUGAUGA X GAA AUCAACUC | 1178 |
| 3084 | UUGAUCAUC GAAUUCUC | 356 | GAGAAUUC CUGAUGA X GAA AUGAUCAA | 1179 |
| 3089 | CAUCGAAUU CUCCAAAA | 357 | UUUUGGAG CUGAUGA X GAA AUUCGAUG | 1180 |
| 3090 | AUCGAAUUC UCCAAAAU | 358 | AUUUUGGA CUGAUGA X GAA AAUUCGAU | 1181 |
| 3092 | CGAAUUCUC CAAAAUGG | 359 | CCAUUUUG CUGAUGA X GAA AGAAUUCG | 1182 |
| 3119 | CCAGCGCUA CCUUGUCA | 360 | UGACAAGG CUGAUGA X GAA AGCGCUGG | 1183 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 3123 | CGCUACCUU GUCAUUCA | 361 | UGAAUGAC CUGAUGA X GAA AGGUAGCG | 1184 |
| 3126 | UACCUUGUC AUUCAGGG | 362 | CCCUGAAU CUGAUGA X GAA ACAAGGUA | 1185 |
| 3129 | CUUGUCAUU CAGGGGGA | 363 | UCCCCCUG CUGAUGA X GAA AUGACAAG | 1186 |
| 3130 | UUGUCAUUC AGGGGGAU | 364 | AUCCCCCU CUGAUGA X GAA AAUGACAA | 1187 |
| 3151 | GAAUGCAUU UGCCAAGU | 365 | ACUUGGCA CUGAUGA X GAA AUGCAUUC | 1188 |
| 3152 | AAUGCAUUU GCCAAGUC | 366 | GACUUGGC CUGAUGA X GAA AAUGCAUU | 1189 |
| 3160 | UGCCAAGUC CUACAGAC | 367 | GUCUGUAG CUGAUGA X GAA ACUUGGCA | 1190 |
| 3163 | CAAGUCCUA CAGACUCC | 368 | GGAGUCUG CUGAUGA X GAA AGGACUUG | 1191 |
| 3170 | UACAGACUC CAACUUCU | 369 | AGAAGUUG CUGAUGA X GAA AGUCUGUA | 1192 |
| 3176 | CUCCAACUU CUACCGUG | 370 | CACGGUAG CUGAUGA X GAA AGUUGGAG | 1193 |
| 3177 | UCCAACUUC UACCGUGC | 371 | GCACGGUA CUGAUGA X GAA AAGUUGGA | 1194 |
| 3179 | CAACUUCUA CCGUGCCC | 372 | GGGCACGG CUGAUGA X GAA AGAAGUUG | 1195 |
| 3233 | CGACGAGUA CCUCAUCC | 373 | GGAUGAGG CUGAUGA X GAA ACUCGUCG | 1196 |
| 3237 | GAGUACCUC AUCCCACA | 374 | UGUGGGAU CUGAUGA X GAA AGGUACUC | 1197 |
| 3240 | UACCUCAUC CCACAGCA | 375 | UGCUGUGG CUGAUGA X GAA AUGAGGUA | 1198 |
| 3254 | GCAGGGCUU CUUCAGCA | 376 | UGCUGAAG CUGAUGA X GAA AGCCCUGC | 1199 |
| 3255 | CAGGGCUUC UUCAGCAG | 377 | CUGCUGAA CUGAUGA X GAA AAGCCCUG | 1200 |
| 3257 | GGGCUUCUU CAGCAGCC | 378 | GGCUGCUG CUGAUGA X GAA AGAAGCCC | 1201 |
| 3258 | GGCUUCUUC AGCAGCCC | 379 | GGGCUGCU CUGAUGA X GAA AAGAAGCC | 1202 |
| 3269 | CAGCCCCUC CACGUCAC | 380 | GUGACGUG CUGAUGA X GAA AGGGGCUG | 1203 |
| 3275 | CUCCACGUC ACGGACUC | 381 | GAGUCCGU CUGAUGA X GAA ACGUGGAG | 1204 |
| 3283 | CACGGACUC CCCUCCUG | 382 | CAGGAGGG CUGAUGA X GAA AGUCCGUG | 1205 |
| 3288 | ACUCCCCUC CUGAGCUC | 383 | GAGCUCAG CUGAUGA X GAA AGGGGAGU | 1206 |
| 3296 | CCUGAGCUC UCUGAGUG | 384 | CACUCAGA CUGAUGA X GAA AGCUCAGG | 1207 |
| 3298 | UGAGCUCUC UGAGUGCA | 385 | UGCACUCA CUGAUGA X CAA AGAGCUCA | 1208 |
| 3319 | GCAACAAUU CCACCGUG | 386 | CACGGUGG CUGAUGA X GAA AUUGUUGC | 1209 |
| 3320 | CAACAAUUC CACCGUGG | 387 | CCACGGUG CUGAUGA X GAA AAUUGUUG | 1210 |
| 3331 | CCGUGGCUU GCAUUGAU | 388 | AUCAAUGC CUGAUGA X GAA AGCCACGG | 1211 |
| 3336 | GCUUGCAUU GAUAGAAA | 389 | UUUCUAUC CUGAUGA X GAA AUGCAAGC | 1212 |
| 3340 | GCAUUGAUA GAAAUGGG | 390 | CCCAUUUC CUGAUGA X GAA AUCAAUGC | 1213 |
| 3361 | AAAGCUGUC CAUCAAG | 391 | CUUGAUGG CUGAUGA X GAA ACAGCUUU | 1214 |
| 3366 | UGUCCCAUC AAGGAAGA | 392 | UCUUCCUU CUGAUGA X GAA AUGGGACA | 1215 |
| 3380 | AGACAGCUU CUUGCAGC | 393 | GCUGCAAG CUGAUGA X GAA AGCUGUCU | 1216 |
| 3381 | GACAGCUUC UUGCAGCG | 394 | CGCUGCAA CUGAUGA X GAA AAGCUGUC | 1217 |
| 3383 | CAGCUUCUU GCAGCGAU | 395 | AUCGCUGC CUGAUGA X GAA AGAAGCUG | 1218 |
| 3392 | GCAGCGAUA CAGCUCAG | 396 | CUGAGCUG CUGAUGA X GAA AUCGCUGC | 1219 |
| 3398 | AUACAGCUC AGACCCCA | 397 | UGGGGUCU CUGAUGA X GAA AGCUGUAU | 1220 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 3416 | AGGCGCCUU GACUGAGG | 398 | CCUCAGUC CUGAUGA X GAA AGGCGCCU | 1221 |
| 3432 | GACAGCAUA GACGACAC | 399 | GUGUCGUC CUGAUGA X GAA AUGCUGUC | 1222 |
| 3443 | CGACACCUU CCUCCCAG | 400 | CUGGGAGG CUGAUGA X GAA AGGUGUCG | 1223 |
| 3444 | GACACCUUC CUCCCAGU | 401 | ACUGGGAG CUGAUGA X GAA AAGGUGUC | 1224 |
| 3447 | ACCUUCCUC CCAGUGCC | 402 | GGCACUGG CUGAUGA X GAA AGGAAGGU | 1225 |
| 3461 | GCCUGAAUA CAUAAACC | 403 | GGUUUAUG CUGAUGA X GAA AUUCAGGC | 1226 |
| 3465 | GAAUACAUA AACCAGUC | 404 | GACUGGUU CUGAUGA X GAA AUGUAUUC | 1227 |
| 3473 | AAACCAGUC CGUUCCCA | 405 | UGGGAACG CUGAUGA X GAA ACUGGUUU | 1228 |
| 3477 | CAGUCCGUU CCCAAAAG | 406 | CUUUUGGG CUGAUGA X GAA ACGGACUG | 1229 |
| 3478 | AGUCCGUUC CCAAAAGG | 407 | CCUUUUGG CUGAUGA X GAA AACGGACU | 1230 |
| 3497 | CGCUGGCUC UGUGCAGA | 408 | UCUGCACA CUGAUGA X GAA AGCCAGCG | 1231 |
| 3508 | UGCAGAAUC CUGUCUAU | 409 | AUAGACAG CUGAUGA X GAA AUUCUGCA | 1232 |
| 3513 | AAUCCUGUC UAUCACAA | 410 | UUGUGAUA CUGAUGA X GAA ACAGGAUU | 1233 |
| 3515 | UCCUGUCUA UCACAAUC | 411 | GAUUGUGA CUGAUGA X GAA AGACAGGA | 1234 |
| 3517 | CUGUCUAUC ACAAUCAG | 412 | CUGAUUGU CUGAUGA X GAA AUAGACAG | 1235 |
| 3523 | AUCACAAUC AGCCUCUG | 413 | CAGAGGCU CUGAUGA X GAA AUUGUGAU | 1236 |
| 3529 | AUGAGCCUC UGAACCCC | 414 | GGGGUUCA CUGAUGA X GAA AGGCUGAU | 1237 |
| 3560 | CCCACACUA CCAGGACC | 415 | GGUCCUGG CUGAUGA X GAA AGUGUGGG | 1238 |
| 3599 | CCCCGAGUA UCUCAACA | 416 | UGUUGAGA CUGAUGA X GAA ACUCGGGG | 1239 |
| 3601 | CCGAGUAUC UCAACACU | 417 | AGUGUUGA CUGAUGA X GAA AUACUCCG | 1240 |
| 3603 | GAGUAUCUC AACACUGU | 418 | ACAGUGUU CUGAUGA X GAA AGAUACUC | 1241 |
| 3612 | AACACUGUC CAGCCCAC | 419 | GUGGGCUG CUGAUGA X GAA ACAGUGUU | 1242 |
| 3627 | ACCUGUGUC AACAGCAC | 420 | GUGCUGUU CUGAUGA X GAA ACACAGGU | 1243 |
| 3638 | CAGCACAUU CGACAGCC | 421 | GGCUGUCG CUGAUGA X GAA AUGUGCUG | 1244 |
| 3639 | AGCACAUUC GACAGCCC | 422 | GGGCUGUC CUGAUGA X GAA AAUGUGCU | 1245 |
| 3681 | CACCAAAUU AGCCGGUA | 423 | UCCAGGCU CUGAUGA X GAA AUUUGGUG | 1246 |
| 3682 | ACCAAAUUA GCCUGGAC | 424 | GUCCAGGC CUGAUGA X GAA AAUUUGGU | 1247 |
| 3701 | CCCUGACUA CCAGCAGG | 425 | CCUGCUGG CUGAUGA X GAA AGUCAGGG | 1248 |
| 3713 | GCAGGACUU CUUUCCCA | 426 | UGGGAAAG CUGAUGA X GAA AGUCCUGC | 1249 |
| 3714 | CAGGACUUC UUUCCCAA | 427 | UUGGGAAA CUGAUGA X GAA AAGUCCUG | 1250 |
| 3716 | GGACUUCUU UCCCAAGG | 428 | CCUUGGGA CUGAUGA X GAA AGAAGUCC | 1251 |
| 3717 | GACUUCUUU CCCAAGGA | 429 | UCCUUGGG CUGAUGA X GAA AAGAAGUC | 1252 |
| 3718 | ACUUCUUUC CCAAGGAA | 430 | UUCCUUGG CUGAUGA X GAA AAAGAAGU | 1253 |
| 3744 | AAUGGCAUC UUUAAGGG | 431 | CCCUUAAA CUGAUGA X GAA AUGCCAUU | 1254 |
| 3746 | UGGCAUCUU UAAGGGCU | 432 | AGCCCUUA CUGAUGA X GAA AGAUGCCA | 1255 |
| 3747 | GGCAUCUUU AAGGGCUC | 433 | GAGCCCUU CUGAUGA X GAA AAGAUGCC | 1256 |
| 3748 | GCAUCUUUA AGGGCUCC | 434 | GGAGCCCU CUGAUGA X GAA AAAGAUGC | 1257 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 3755 | UAAGGGCUC CACAGCUG | 435 | CAGCUGUG CUGAUGA X GAA AGCCCUUA | 1258 |
| 3776 | UGCAGAAUA CCUAAGGG | 436 | CCCUUAGG CUGAUGA X GAA AUUCUGCA | 1259 |
| 3780 | GAAUACCUA AGGGUCGC | 437 | GCGACCCU CUGAUGA X GAA AGGUAUUC | 1260 |
| 3786 | CUAAGGGUC GCGCCACA | 438 | UGUGGCGC CUGAUGA X GAA ACCCUUAG | 1261 |
| 3806 | CAGUGAAUU UAUUGGAG | 439 | CUCCAAUA CUGAUGA X GAA AUUCACUG | 1262 |
| 3807 | AGUGAAUUU AUUGGAGC | 440 | GCUCCAAU CUGAUGA X GAA AAUUCACU | 1263 |
| 3808 | GUCAAUUUA UUGGAGCA | 441 | UGCUCCAA CUGAUGA X GAA AAAUUCAC | 1264 |
| 3810 | GAAUUUAUU GGAGCAUG | 442 | CAUGCUCC CUGAUGA X GAA AUAAAUUC | 1265 |
| 3831 | CGGAGGAUA GUAUGAGC | 443 | GCUCAUAC CUGAUGA X GAA AUCCUCCG | 1266 |
| 3834 | AGGAUAGUA UGAGCCCU | 444 | AGGGCUCA CUGAUGA X GAA ACUAUCCU | 1267 |
| 3843 | UGAGCCCUA AAAAUCCA | 445 | UGGAUUUU CUGAUGA X GAA AGGGCUCA | 1268 |
| 3849 | CUAAAAAUC CAGACUCU | 446 | AGAGUCUG CUGAUGA X GAA AUUUUUAG | 1269 |
| 3856 | UCCAGACUC UUUCGAUA | 447 | UAUCGAAA CUGAUGA X GAA AGUCUGGA | 1270 |
| 3858 | CAGACUCUU UCGAUACC | 448 | GGUAUCGA CUGAUGA X GAA AGAGUCUG | 1271 |
| 3859 | AGACUCUUU CGAUACCC | 449 | GGGUAUCG CUGAUGA X GAA AAGAGUCU | 1272 |
| 3860 | GACUCUUUC GAUACCCA | 450 | UGGGUAUC CUGAUGA X GAA AAAGAGUC | 1273 |
| 3864 | CUUUCGAUA CCCAGGAC | 451 | GUCCUGGG CUGAUGA X GAA AUCGAAAG | 1274 |
| 3888 | CAGCAGGUC CUCCAUCC | 452 | GGAUGGAG CUGAUGA X GAA ACCUGCUG | 1275 |
| 3891 | CAGGUCCUC CAUCCCAA | 453 | UUGGGAUG CUGAUGA X GAA AGGACCUG | 1276 |
| 3895 | UCCUCCAUC CCAACAGC | 454 | GCUGUUGG CUGAUGA X GAA AUGGAGGA | 1277 |
| 3915 | GCCCGCAUU AGCUCUUA | 455 | UAAGAGCU CUGAUGA X GAA AUGCGGGC | 1278 |
| 3916 | CCCGCAUUA GCUCUUAG | 456 | CUAAGAGC CUGAUGA X GAA AAUGCGGG | 1279 |
| 3920 | CAUUAGCUC UUAGACCC | 457 | GGGUCUAA CUGAUGA X GAA AGCUAAUG | 1280 |
| 3922 | UUAGCUCUU AGACCCAC | 458 | GUGGGUCU CUGAUGA X GAA AGAGCUAA | 1281 |
| 3923 | UAGCUCUUA GACCCACA | 459 | UGUGGGUC CUGAUGA X GAA AAGAGCUA | 1282 |
| 3939 | AGACUGGUU UUGCAACG | 460 | CGUUGCAA CUGAUGA X GAA ACCAGUCU | 1283 |
| 3940 | GACUCGUUU UGCAACCU | 461 | ACGUUGCA CUGAUGA X GAA AACCAGUC | 1284 |
| 3941 | ACUGGUUUU GCAACGUU | 462 | AACGUUGC CUGAUGA X GAA AAACCAGU | 1285 |
| 3949 | UGCAACGUU UACACCGA | 463 | UCGGUGUA CUGAUGA X GAA ACGUUGCA | 1286 |
| 3950 | GCAACGUUU ACACCGAC | 464 | GUCGGUGU CUGAUGA X GAA AACGUUGC | 1287 |
| 3951 | CAACGUUUA CACCGACU | 465 | AGUCGGUG CUGAUGA X GAA AAACGUUG | 1288 |
| 3960 | CACCGACUA GCCAGGAA | 466 | UUCCUGGC CUGAUGA X GAA AGUCGGUG | 1289 |
| 3971 | CAGGAAGUA CUUCCACC | 467 | GGUGGAAG CUGAUGA X GAA ACUUCCUG | 1290 |
| 3974 | GAAGUACUU CCACCUCG | 468 | CGAGGUGG CUGAUGA X GAA AGUACUUU | 1291 |
| 3975 | AAGUACUUC CACCUCGG | 469 | CCGAGGUG CUGAUGA X GAA AAGUACUU | 1292 |
| 3981 | UUCCACCUC GGGCACAU | 470 | AUGUGCCC CUGAUGA X GAA AGGUGGAA | 1293 |
| 3990 | GGGCACAUU UGGGAAG | 471 | CUUCCCAA CUGAUGA X GAA AUGUGCCC | 1294 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 3991 | GGCACAUUU UGGGAAGU | 472 | ACUUCCCA CUGAUGA X GAA AAUGUGCC | 1295 |
| 3992 | GCACAUUUU GGGAAGUU | 473 | AACUUCCC CUGAUGA X GAA AAAUGUGC | 1296 |
| 4000 | UGGGAAGUU GCAUUCCU | 474 | AGGAAUGC CUGAUGA X GAA ACUUCCCA | 1297 |
| 4005 | AGUUGCAUU CCUUUGUC | 475 | GACAAAGG CUGAUGA X GAA AUGCAACU | 1298 |
| 4006 | GUUGCAUUC CUUUGUCU | 476 | AGACAAAG CUGAUGA X GAA AAUGCAAC | 1299 |
| 4009 | GCAUUCCUU UGUCUUCA | 477 | UGAAGACA CUGAUGA X GAA AGGAAUGC | 1300 |
| 4010 | CAUUCCUUU GUCUUCAA | 478 | UUGAAGAC CUGAUGA X GAA AAGCAAUG | 1301 |
| 4013 | UCCUUUGUC UUCAAACU | 479 | AGUUUGAA CUGAUGA X GAA ACAAAGGA | 1302 |
| 4015 | CUUUGUCUU CAAACUGU | 480 | ACAGUUUG CUGAUGA X GAA AGACAAAG | 1303 |
| 4016 | UUUGUCUUC AAACUGUG | 481 | CACAGUUU CUGAUGA X GAA AAGACAAA | 1304 |
| 4031 | UGAAGCAUU UACAGAAA | 482 | UUUCUGUA CUGAUGA X GAA AUGCUUCA | 1305 |
| 4032 | GAAGCAUUU ACAGAAAC | 483 | GUUUCUGU CUGAUGA X GAA AAUGCUUC | 1306 |
| 4033 | AAGCAUUUA CACAAACG | 484 | CGUUUCUG CUGAUGA X GAA AAAUGCUU | 1307 |
| 4045 | AAACCCAUC CAGCAAGA | 485 | UCUUGCUG CUGAUGA X GAA AUGCGUUU | 1308 |
| 4056 | GCAAGAAUA UUGUCCCU | 486 | AGGGACAA CUGAUGA X GAA AUUCUUGC | 1309 |
| 4058 | AAGAAUAUU GUCCCUUU | 487 | AAAGGGAC CUGAUGA X GAA AUAUUCUU | 1310 |
| 4061 | AAUAUUGUC CCUUUGAG | 488 | CUCAAAGG CUGAUGA X GAA ACAAUAUU | 1311 |
| 4065 | UUGUCCCUU UGAGCAGA | 489 | UCUGCUCA CUGAUGA X GAA AGGGACAA | 1312 |
| 4066 | UGUCCCUUU GAGCAGAA | 490 | UUCUGCUC CUGAUGA X GAA AAGGGACA | 1313 |
| 4077 | GCAGAAAUU UAUCUUUC | 491 | GAAAGAUA CUGAUGA X GAA AUUUCUGC | 1314 |
| 4078 | CAGAAAUUU AUCUUUCA | 492 | UGAAAGAU CUGAUGA X GAA AAUUUCUG | 1315 |
| 4079 | AGAAAUUUA UCUUUCAA | 493 | UUGAAAGA CUGAUGA X GAA AAAUUUCU | 1316 |
| 4081 | AAAUUUAUC UUUCAAAG | 494 | CUUUGAAA CUGAUGA X GAA AUAAAUUU | 1317 |
| 4083 | AUUUAUCUU UCAAAGAG | 495 | CUCUUUGA CUGAUGA X GAA AGAUAAAU | 1318 |
| 4084 | UUUAUCUUU CAAAGAGG | 496 | CCUCUUUG CUGAUGA X GAA AAGAUAAA | 1319 |
| 4085 | UUAUCUUUC AAAGAGGU | 497 | ACCUCUUU CUGAUGA X GAA AAAGAUAA | 1320 |
| 4094 | AAAGAGGUA UAUUGAA | 498 | UUCAAAUA CUGAUGA X GAA ACCUCUUU | 1321 |
| 4096 | AGAGGUAUA UUGAAAA | 499 | UUUUCAAA CUGAUGA X GAA AUACCUCU | 1322 |
| 4098 | AGGUAUAUU UGAAAAAA | 500 | UUUUUUCA CUGAUGA X GAA AUAUACCU | 1323 |
| 4099 | GGUAUAUUU GAAAAAAA | 501 | UUUUUUUC CUGAUGA X GAA AAUAUACC | 1324 |
| 4118 | AAAAAGUA UAUGUGAG | 502 | CUCACAUA CUGAUGA X GAA ACUUUUUU | 1325 |
| 4120 | AAAAGUAUA UGUGAGGA | 503 | UCCUCACA CUGAUGA X GAA AUACUUUU | 1326 |
| 4130 | GUGAGGAUU UUUAUUGA | 504 | UCAAUAAA CUGAUGA X GAA AUCCUCAC | 1327 |
| 4131 | UGAGGAUUU UUAUUGAU | 505 | AUCAAUAA CUGAUGA X GAA AAUCCUGA | 1328 |
| 4132 | GAGGAUUUU UAUUGAUU | 506 | AAUCAAUA CUGAUGA X GAA AAAUCCUC | 1329 |
| 4133 | AGGAUUUUU AUUGAUUG | 507 | CAAUCAAU CUGAUGA X GAA AAAAUCCU | 1330 |
| 4134 | GGAUUUUUA UUGGAUUGG | 508 | CCAAUCAA CUGAUGA X GAA AAAAAUCC | 1331 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 4136 | AUUUUUAUU GAUUGGGG | 509 | CCCCAAUC CUGAUGA X GAA AUAAAAAU | 1332 |
| 4140 | UUAUUGAUU GGGGAUCU | 510 | AGAUCCCC CUGAUGA X GAA AUCAAUAA | 1333 |
| 4147 | UUGGGGAUC UUGGAGUU | 511 | AACUCCAA CUGAUGA X GAA AUCCCCAA | 1334 |
| 4149 | GGGGAUCUU GGAGUUUU | 512 | AAAACUCC CUGAUGA X GAA AGAUCCCC | 1335 |
| 4155 | CUUGGAGUU UUUCAUUG | 513 | CAAUGAAA CUGAUGA X GAA ACUCCAAG | 1336 |
| 4156 | UUGGAGUUU UUCAUUGU | 514 | ACAAUGAA CUGAUGA X GAA AACUCCAA | 1337 |
| 4157 | UGGAGUUUU UCAUUGUC | 515 | GACAAUGA CUGAUGA X GAA AAACUCCA | 1338 |
| 4158 | GGAGUUUUU CAUUGUCG | 516 | CGACAAUG CUGAUGA X GAA AAAACUCC | 1339 |
| 4159 | GAGUUUUUC AUUGUCGC | 517 | GCGACAAU CUGAUGA X GAA AAAAACUC | 1340 |
| 4162 | UUUUUCAUU GUCGCUAU | 518 | AUAGCGAC CUGAUGA X GAA AUGAAAAA | 1341 |
| 4165 | UUCAUUGUC GCUAUUGA | 519 | UGAAUAGC CUGAUGA X GAA ACAAUGAA | 1342 |
| 4169 | UUGUCGCUA UUCAUUUU | 520 | AAAAUCAA CUGAUGA X GAA AGCGACAA | 1343 |
| 4171 | GUCGCUAUU GAUUUUUA | 521 | UAAAAAUC CUGAUGA X GAA AUAGCGAC | 1344 |
| 4175 | CUAUUGAUU UUUACUUC | 522 | GAAGUAAA CUGAUGA X GAA AUCAAUAG | 1345 |
| 4176 | UAUUGAUUU UUACUUCA | 523 | UGAAGUAA CUGAUGA X GAA AAUCAAUA | 1346 |
| 4177 | AUUGAUUUU UACUUCAA | 524 | UUGAAGUA CUGAUGA X GAA AAAUCAAU | 1347 |
| 4178 | UUGAUUUUU ACUUCAAU | 525 | AUUGAAGU CUGAUGA X GAA AAAAUCAA | 1348 |
| 4179 | UGAUUUUUA CUUCAAUG | 526 | CAUUGAAG CUGAUGA X GAA AAAAAUCA | 1349 |
| 4182 | UUUUUACUU CAAUGCGC | 527 | GCCCAUUG CUGAUGA X GAA AGUAAAAA | 1350 |
| 4183 | UUUUACUUC AAUGGGCU | 528 | AGCCCAUU CUGAUGA X GAA AAGUAAAA | 1351 |
| 4192 | AAUGGGCUC UUCCAACA | 529 | UGUUGGAA CUGAUGA X GAA AGCCCAUU | 1352 |
| 4194 | UGGGCUCUU CCAACAAG | 530 | CUUGUUGG CUGAUGA X GAA AGAGCCCA | 1353 |
| 4195 | GGGCUCUUC CAACAAGG | 531 | CCUUCUUG CUGAUGA X GAA AAGAGCCC | 1354 |
| 4212 | AAGAAGCUU GCUGCUAG | 532 | CUACCAGC CUGAUGA X GAA ACCUUCUU | 1355 |
| 4219 | UUGCUGGUA GCACUUGC | 533 | GCAAGUGC CUGAUGA X GAA ACCAGCAA | 1356 |
| 4225 | GUAGCACUU GCUACCCU | 534 | AGGGUAGC CUGAUGA X GAA AGUGCUAC | 1357 |
| 4229 | CACUUGCUA CCCUGAGU | 535 | ACUCAGGG CUGAUGA X GAA AGCAACUG | 1358 |
| 4238 | CCCUGAGUU CAUCCAGC | 536 | CCUGGAUG CUGAUGA X GAA ACUCAGCG | 1359 |
| 4239 | CCUGAGUUC AUCCAGGC | 537 | GCCUGGAU CUGAUGA X GAA AACUCAGG | 1360 |
| 4242 | GAGUUCAUC CAGGCCCA | 538 | UGGGCCUG CUGAUGA X GAA AUGAACUC | 1361 |
| 4280 | CCACAAGUC UUCCAGAG | 539 | CUCUGGAA CUGAUGA X GAA ACUUGUGG | 1362 |
| 4282 | ACAAGUCUU CCAGAGGA | 540 | UCCUCUGG CUGAUGA X GAA AGAGUUGU | 1363 |
| 4283 | CAAGUCUUC CAGAGGAU | 541 | AUCCUCUG CUGAUGA X GAA AAGACUUG | 1364 |
| 4295 | AGGAUGCUU GAUUCCAG | 542 | CUGGAAUC CUGAUGA X GAA AGCAUCCU | 1365 |
| 4299 | UGCUUGAUU CCAGUGGU | 543 | ACCACUGG CUGAUGA X GAA AUCAAGCA | 1366 |
| 4300 | GCUUGAUUC CAGUGGUU | 544 | AACCACUG CUGAUGA X GAA AAUCAAGC | 1367 |
| 4308 | CCAGUGGUU CUGCUUCA | 545 | UGAAGCAG CUGAUGA X GAA ACCACUGG | 1368 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 4309 | CAGUGGUUC UGCUUCAA | 546 | UUGAAGCA CUGAUGA X GAA AACCACUG | 1369 |
| 4314 | GUUCUGCUU CAAGGCUU | 547 | AAGCCUUG CUGAUGA X GAA AGCAGAAC | 1370 |
| 4315 | UUCUGCUUC AAGGCUUC | 548 | GAAGCCUU CUGAUGA X GAA AAGCAGAA | 1371 |
| 4322 | UCAAGGCUU CCACUGCA | 549 | UGCAGUGG CUGAUGA X GAA AGCCUUGA | 1372 |
| 4323 | CAAGGCUUC CACUGCAA | 550 | UUGCAGUG CUGAUGA X GAA AAGCCUUG | 1373 |
| 4338 | AAAACACUA AAGAUCCA | 551 | UGGAUCUU CUGAUGA X GAA AGUGUUUU | 1374 |
| 4344 | CUAAAGAUC CAAGAAGG | 552 | CCUUCUUG CUGAUGA X GAA AUCUUUAG | 1375 |
| 4356 | GAAGGCCUU CAUGGCCC | 553 | GGGCCAUG CUGAUGA X GAA AGGCCUUC | 1376 |
| 4357 | AAGGCCUUC AUGGCCCC | 554 | GGGGCCAU CUGAUGA X GAA AAGGCCUU | 1377 |
| 4378 | GGCCGGAUC GGUACUGU | 555 | ACAGAACC CUGAUGA X GAA AUCCGGCC | 1378 |
| 4382 | GGAUCGGUA CUGUAUCA | 556 | UGAUACAG CUGAUGA X GAA ACCGAUCC | 1379 |
| 4387 | GGUACUGUA UCAAGUCA | 557 | UGACUUGA CUGAUGA X GAA ACAGUACC | 1380 |
| 4389 | UACUGUAUC AAGUCAUG | 558 | CAUGACUU CUGAUGA X GAA AUACAGUA | 1381 |
| 4394 | UAUCAAGUC AUGGCAGG | 559 | CCUGCCAU CUGAUGA X GAA ACUUGAUA | 1382 |
| 4404 | UGGCAGGUA CAGUAGGA | 560 | UCCUACUG CUGAUGA X GAA ACCUGCCA | 1383 |
| 4409 | GGUACAGUA GGAUAAGC | 561 | GCUUAUCC CUGAUGA X GAA ACUGUACC | 1384 |
| 4414 | AGUAGGAUA AGCCACUC | 562 | GAGUGGCU CUGAUGA X GAA AUCCUACU | 1385 |
| 4422 | AAGCCACUC UGUCCCUU | 563 | AAGGGACA CUGAUGA X GAA AGUGGCUU | 1386 |
| 4426 | CACUCUGUC CCUUCCUG | 564 | CAGGAAGG CUGAUGA X GAA ACAGAGUG | 1387 |
| 4430 | CUGUCCCUU CCUGGGCA | 565 | UGCCCAGG CUGAUGA X GAA AGGGACAG | 1388 |
| 4431 | UGUCCCUUC CUGGGCAA | 566 | UUGCCCAG CUGAUGA X GAA AAGGGACA | 1389 |
| 4462 | GGAUGAAUU CUUCCUUA | 567 | UAAGGAAG CUGAUGA X GAA AUUCAUCC | 1390 |
| 4463 | GAUGAAUUC UUCCUUAG | 568 | CUAAGGAA CUGAUGA X GAA AAUUCAUC | 1391 |
| 4465 | UGAAUUCUU CCUUAGAC | 569 | GUCUAAGG CUGAUGA X GAA AGAAUUCA | 1392 |
| 4466 | GAAUUCUUC CUUAGACU | 570 | AGUCUAAG CUGAUGA X GAA AAGAAUUC | 1393 |
| 4469 | UUCUUCCUU AGACUUAC | 571 | GUAAGUCU CUGAUGA X GAA AGGAAGAA | 1394 |
| 4470 | UCUUCCUUA GACUUACU | 572 | AGUAAGUC CUGAUGA X GAA AAGGAAGA | 1395 |
| 4475 | CUUAGACUU ACUUUUGU | 573 | ACAAAAGU CUGAUGA X GAA ACUCUAAG | 1396 |
| 4476 | UUAGACUUA CUUUUGUA | 574 | UACAAAAG CUGAUGA X GAA AAGUCUAA | 1397 |
| 4479 | GACUUACUU UUGUAAAA | 575 | UUUUACAA CUGAUGA X GAA AGUAAGUC | 1398 |
| 4480 | ACUUACUUU UGUAAAAA | 576 | UUUUUACA CUGAUGA X GAA AAGUAAGU | 1399 |
| 4481 | CUUACUUUU GUAAAAAU | 577 | AUUUUUAC CUGAUGA X GAA AAAGUAAG | 1400 |
| 4484 | ACUUUUGUA AAAAUGUC | 578 | GACAUUUU CUGAUGA X GAA ACAAAAGU | 1401 |
| 4492 | AAAAAUGUC CCACGGU | 579 | ACCGUGGG CUGAUGA X GAA ACAUUUUU | 1402 |
| 4501 | CCCACGGUA CUUACUCC | 580 | GGAGUAAG CUGAUGA X GAA ACCGUGGG | 1403 |
| 4504 | ACGGUACUU ACUCCCCA | 581 | UGGGGAGU CUGAUGA X GAA AGUACCGU | 1404 |
| 4505 | CGGUACUUA CUCCCCAC | 582 | GUCGGGAG CUGAUGA X GAA AAGUACCG | 1405 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 4508 | UACUUACUC CCCACUGA | 583 | UCAGUGGG CUGAUGA X GAA AGUAAGUA | 1406 |
| 4529 | CCAGUGGUU UCCAGUCA | 584 | UGACUGGA CUGAUGA X GAA ACCACUGG | 1407 |
| 4530 | CAGUGGUUU CCAGUCAU | 585 | AUGACUGG CUGAUGA X GAA AACCACUG | 1408 |
| 4531 | AGUGGUUUC CAGUCAUG | 586 | CAUGACUG CUGAUGA X GAA AAACCACU | 1409 |
| 4536 | UUUCCAGUC AUGAGCGU | 587 | ACGCUCAU CUGAUGA X GAA ACUGGAAA | 1410 |
| 4545 | AUGAGCGUU AGACUGAC | 588 | GUCAGUCU CUGAUGA X GAA ACGCUCAU | 1411 |
| 4546 | UGAGCGUUA GACUGACU | 589 | AGUCAGUC CUGAUGA X GAA AACGCUCA | 1412 |
| 4555 | GACUGACUU GUUUGUCU | 590 | AGACAAAC CUGAUGA X GAA AGUCAGUC | 1413 |
| 4558 | UGACUUCUU UGUCUUCC | 591 | GGAAGACA CUGAUGA X GAA AGAAGUCA | 1414 |
| 4559 | GACUUGUUU GUCUUCCA | 592 | UGGAAGAC CUGAUGA X GAA AACAAGUC | 1415 |
| 4562 | UUGUUUGUC UUCCAUUC | 593 | GAAUGGAA CUGAUGA X GAA ACAAACAA | 1416 |
| 4564 | CUUUGUCUU CCAUUCCA | 594 | UGGAAUGG CUGAUGA X GAA AGACAAAC | 1417 |
| 4565 | UUUGUCUUC CAUUCCAU | 595 | AUGGAAUG CUGAUGA X GAA AAGACAAA | 1418 |
| 4569 | UCUUCCAUU CCAUUGUU | 596 | AACAAUGG CUGAUGA X GAA AUGGAAGA | 1419 |
| 4570 | CUUCCAUUC CAUUGUUU | 597 | AAACAAUG CUGAUGA X GAA AAUGGAAG | 1420 |
| 4574 | CAUUCCAUU GUUUGAA | 598 | UUCAAAAC CUGAUGA X GAA AUGGAAUG | 1421 |
| 4577 | UCCAUUGUU UUGAAACU | 599 | AGUUUCAA CUGAUGA X GAA ACAAUGGA | 1422 |
| 4578 | CCAUUGUUU UGAAACUC | 600 | GAGUUUCA CUGAUGA X GAA AACAAUGG | 1423 |
| 4579 | CAUUGUUUU GAAACUCA | 601 | UGAGUUUC CUGAUGA X GAA AAACAAUG | 1424 |
| 4586 | UUGAAACUC AGUAUGCC | 602 | GGCAUACU CUGAUGA X GAA AGUUUCAA | 1425 |
| 4590 | AACUCAGUA UGCCGCCC | 603 | GGGCGGCA CUGAUGA X GAA ACUGAGUU | 1426 |
| 4603 | GCCCCUGUC UUGCUGUC | 604 | GACAGAAA CUGAUGA X GAA ACAGGGGC | 1427 |
| 4605 | CCCUGUCUU GCUGUCAU | 605 | AUGACAGC CUGAUGA X GAA AGACAGGG | 1428 |
| 4611 | CUUGCUGUC AUGAAAUC | 606 | GAUUUCAU CUGAUGA X GAA ACAGCAAG | 1429 |
| 4619 | CAUGAAAUC AGCAAGAG | 607 | CUCUUGCU CUGAUGA X GAA AUUUCAUG | 1430 |
| 4640 | UGACACAUC AAAUAAUA | 608 | UAUUAUUU CUGAUGA X GAA AUGUGUCA | 1431 |
| 4645 | CAUCAAAUA AUAACUCG | 609 | CGAGUUAU CUGAUGA X GAA AUUUGAUG | 1432 |
| 4648 | CAAAUAAUA ACUCGGAU | 610 | AUCCGAGU CUGAUGA X GAA AUUAUUUG | 1433 |
| 4652 | UAAUAACUC GGAUUCCA | 611 | UGGAAUCC CUGAUGA X GAA AGUUAUUA | 1434 |
| 4657 | ACUCGGAUU CCAGCCCA | 612 | UGGGCUGG CUGAUGA X GAA AUCCGAGU | 1435 |
| 4658 | CUCGGAUUC CAGCCCAC | 613 | GUGGGCUG CUGAUGA X GAA AAUCCGAG | 1436 |
| 4669 | GCCCACAUU GGAUUCAU | 614 | AUGAAUCC CUGAUGA X GAA AUGUGGGC | 1437 |
| 4674 | CAUUGGAUU CAUCAGCA | 615 | UGCUGAUG CUGAUGA X GAA AUCCAAUG | 1438 |
| 4675 | AUUGGAUUC AUCAGCAU | 616 | AUGCUGAU CUGAUGA X GAA AAUCCAAU | 1439 |
| 4678 | GGAUUCAUC AGCAUUUG | 617 | CAAAUGCU CUGAUGA X GAA AUGAAUCC | 1440 |
| 4684 | AUCAGCAUU UGGACCAA | 618 | UUGGUCCA CUGAUGA X GAA AUGCUGAU | 1441 |
| 4685 | UCAGCAUUU GGACCAAU | 619 | AUUGGUCC CUGAUGA X GAA AAUGCUGA | 1442 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 4694 | GGACCAAUA GCCCACAG | 620 | CUGUGGGC CUGAUGA X GAA AUUGGUCC | 1443 |
| 4718 | UGUGGAAUA CCUAAGGA | 621 | UCCUUAGG CUGAUGA X GAA AUUCCACA | 1444 |
| 4722 | GAAUACCUA AGGAUAAC | 622 | GUUAUCCU CUGAUGA X GAA AGGUAUUC | 1445 |
| 4728 | CUAAGGAUA ACACCGCU | 623 | AGCGGUGU CUGAUGA X GAA AUCCUUAG | 1446 |
| 4737 | ACACCGCUU UUGUUCUC | 624 | GAGAACAA CUGAUGA X GAA AGCGGUGU | 1447 |
| 4738 | CACCGGUUU UGUUCUCG | 625 | CGAGAACA CUGAUGA X GAA AAGCGGUG | 1448 |
| 4739 | ACCGCUUUU GUUCUCGC | 626 | GCGAGAAC CUGAUGA X GAA AAAGCGGU | 1449 |
| 4742 | GCUUUUGUU CUCGCAAA | 627 | UUUGCGAG CUGAUGA X GAA ACAAAAGC | 1450 |
| 4743 | CUUUUGUUC UCGCAAAA | 628 | UUUUGCGA CUGAUGA X GAA AACAAAAG | 1451 |
| 4745 | UUUGUUCUC GCAAAAAC | 629 | GUUUUUGC CUGAUGA X GAA AGAACAAA | 1452 |
| 4756 | AAAAACGUA UCUCCUAA | 630 | UUAGGAGA CUGAUGA X GAA ACGUUUUU | 1453 |
| 4758 | AAACGUAUC UCCUAAUU | 631 | AAUUAGGA CUGAUGA X GAA AUACGUUU | 1454 |
| 4760 | ACGUAUCUC CUAAUUUG | 632 | CAAAUUAG CUGAUGA X GAA AGAUACGU | 1455 |
| 4763 | UAUCUCCUA AUUUGAGG | 633 | CCUCAAAU CUGAUGA X GAA AGGAGAUA | 1456 |
| 4766 | CUCCUAAUU UGAGGCUC | 634 | GAGCCUCA CUGAUGA X GAA AUUAGGAG | 1457 |
| 4767 | UCCUAAUUU GAGGCUCA | 635 | UGAGCCUC CUGAUGA X GAA AAUUAGGA | 1458 |
| 4774 | UUGAGGCUC ACAUGAAA | 636 | UUUCAUCU CUGAUGA X GAA AGCCUCAA | 1459 |
| 4788 | AAAUGCAUC AGGUCCUU | 637 | AAGGACCU CUGAUGA X GAA AUGCAUUU | 1460 |
| 4793 | CAUCAGGUC CUUUGGGG | 638 | CCCCAAAG CUGAUGA X GAA ACCUGAUG | 1461 |
| 4796 | CAGGUCCUU UGGGGCAU | 639 | AUGCCCCA CUGAUGA X GAA AGGACCUG | 1462 |
| 4797 | AGGUCCUUU GGGGCAUA | 640 | UAUGCCCC CUGAUGA X GAA AAGGACCU | 1463 |
| 4805 | UGGGGCAUA GAUCAGAA | 641 | UUCUGAUC CUGAUGA X GAA AUGCCCCA | 1464 |
| 4809 | GCAUAGAUC AGAAGACU | 642 | AGUCUUCU CUGAUGA X GAA AUCUAUGC | 1465 |
| 4818 | ACAAGACUA CAAAAAUG | 643 | CAUUUUUG CUGAUGA X GAA AGUCUUCU | 1466 |
| 4835 | AAGCUGCUC UGAAAUCU | 644 | AGAUUUCA CUGAUGA X GAA AGCAGCUU | 1467 |
| 4842 | UCUGAAAUC UCCUUUAG | 645 | CUAAAGGA CUGAUGA X GAA AUUUCAGA | 1468 |
| 4844 | UGAAAUCUC CUUUAGCC | 646 | GGCUAAAG CUGAUGA X GAA AGAUUUCA | 1469 |
| 4847 | AAUCUCCUU UAGCCAUC | 647 | GAUGGCUA CUGAUGA X GAA AGGAGAUU | 1470 |
| 4848 | AUCUCCUUU AGCCAUCA | 648 | UGAUGGCU CUGAUGA X GAA AAGGAGAU | 1471 |
| 4849 | UCUCCUUUA GCCAUCAC | 649 | GUGAUGGC CUGAUGA X GAA AAAGGAGA | 1472 |
| 4855 | UUAGCCAUC ACCCCAAC | 650 | GUUGGGGU CUGAUGA X GAA AUGGCUAA | 1473 |
| 4874 | CCCAAAAUU AGUUGUG | 651 | CACAAACU CUGAUGA X GAA AUUUUGGG | 1474 |
| 4875 | CCAAAAUUA GUUGUGU | 652 | ACACAAAC CUGAUGA X GAA AAUUUUGG | 1475 |
| 4878 | AAAUUAGUU GUGUUAC | 653 | GUAACACA CUGAUGA X GAA ACUAAUUU | 1476 |
| 4879 | AAUUAGUUU GUGUUACU | 654 | AGUAACAC CUGAUGA X GAA AACUAAUU | 1477 |
| 4884 | GUUUGUGUU ACUUAUGG | 655 | CCAUAAGU CUGAUGA X GAA ACACAAAC | 1478 |
| 4885 | UUUGUGUUA CUUAUGGA | 656 | UCCAUAAG CUGAUGA X GAA AACACAAA | 1479 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 4888 | GUGUUACUU AUGGAAGA | 657 | UCUUCCAU CUGAUGA X GAA AGUAACAC | 1480 |
| 4889 | UGUUACUUA UGGAAGAU | 658 | AUCUUCCA CUGAUGA X GAA AAGUAACA | 1481 |
| 4898 | UGGAAGAUA GUUUUCUC | 659 | GAGAAAAC CUGAUGA X GAA AUCUUCCA | 1482 |
| 4901 | AAGAUAGUU UUCUCCUU | 660 | AAGGAAAA CUGAUGA X GAA ACUAUCUU | 1483 |
| 4902 | AGAUAGUUU UCUCCUUU | 661 | AAAGGAGA CUGAUGA X GAA AACUAUCU | 1484 |
| 4903 | GAUAGUUUU CUCCUUUU | 662 | AAAAGGAG CUGAUGA X GAA AAACUAUC | 1485 |
| 4904 | AUAGUUUUC UCCUUUUA | 663 | UAAAAGGA CUGAUGA X GAA AAAACUAU | 1486 |
| 4906 | AGUUUUCUC CUUUUACU | 664 | AGUAAAAG CUGAUGA X GAA AGAAAACU | 1487 |
| 4909 | UUUCUCCUU UUACUUCA | 665 | UGAAGUAA CUGAUGA X GAA AGGAGAAA | 1488 |
| 4910 | UUCUCCUUU UACUUCAC | 666 | GUGAAGUA CUGAUGA X GAA AAGGAGAA | 1489 |
| 4911 | UCUCCUUUU ACUUCACU | 667 | AGUGAAGU CUGAUGA X GAA AAAGGAGA | 1490 |
| 4912 | CUCCUUUUA CUUCACUU | 668 | AAGUGAAG CUGAUGA X GAA AAAAGGAG | 1491 |
| 4915 | CUUUUACUU CACUUCAA | 669 | UUGAAGUG CUGAUGA X GAA AGUAAAAG | 1492 |
| 4916 | UUUUACUUC ACUUCAAA | 670 | UUUGAAGU CUGAUGA X GAA AAGUAAAA | 1493 |
| 4920 | ACUUCACUU CAAAAGCU | 671 | AGCUUUUG CUGAUGA X GAA AGUGAAGU | 1494 |
| 4921 | CUUCACUUC AAAAGCUU | 672 | AAGCUUUU CUGAUGA X GAA AAGUGAAG | 1495 |
| 4929 | CAAAAGCUU UUUACUCA | 673 | UGAGUAAA CUGAUGA X GAA AGCUUUUG | 1496 |
| 4930 | AAAAGCUUU UUACUCAA | 674 | UUGAGUAA CUGAUGA X GAA AAGCUUUU | 1497 |
| 4931 | AAAGCUUUU UACUCAAA | 675 | UUUGAGUA CUGAUGA X GAA AAAGCUUU | 1498 |
| 4932 | AAGCUUUUU ACUCAAAG | 676 | CUUUGAGU CUGAUGA X GAA AAAAGCUU | 1499 |
| 4933 | AGCUUUUUA CUCAAAGA | 677 | UCUUUGAG CUGAUGA X GAA AAAAAGCU | 1500 |
| 4936 | UUUUUACUC AAAGAGUA | 678 | UACUCUUU CUGAUGA X GAA AGUAAAAA | 1501 |
| 4944 | CAAAGAGUA UAUGUUCC | 679 | GGAACAUA CUGAUGA X GAA ACUCUUUG | 1502 |
| 4946 | AAGAGUAUA UGUUCCCU | 680 | AGGGAACA CUGAUGA X GAA AUACUCUU | 1503 |
| 4950 | GUAUAUGUU CCCUCCAG | 681 | CUGGAGGG CUGAUGA X GAA ACAUAUAC | 1504 |
| 4951 | UAUAUGUUC CCUCCAGG | 682 | CCUGGAGG CUGAUGA X GAA AACAUAUA | 1505 |
| 4955 | UGUUCCCUC CAGGUCAG | 683 | CUGACCUG CUGAUGA X GAA AGGGAACA | 1506 |
| 4961 | CUCCGGGUC AGCUGCCC | 684 | GGGCAGCU CUGAUGA X GAA ACCUGGAG | 1507 |
| 4981 | AACCCCCUC CUUACGCU | 685 | AGCGUAAG CUGAUGA X GAA AGGGGGUU | 1508 |
| 4984 | CCCUCCUU ACGCUUUG | 686 | CAAAGCGU CUGAUGA X GAA AGGAGGGG | 1509 |
| 4985 | CCCUCCUUA CGCUUUGU | 687 | ACAAAGCG CUGAUGA X GAA AAGGAGGG | 1510 |
| 4990 | CUUACGCUU UGUCACAC | 688 | GUGUGACA CUGAUGA X GAA AGCGUAAG | 1511 |
| 4991 | UUACGCUUU GUCACACA | 689 | UGUGUGAC CUGAUGA X GAA AAGCGUAA | 1512 |
| 4994 | CGCUUUGUC ACAAAAA | 690 | UUUUGUGU CUGAUGA X GAA ACAAAGCG | 1513 |
| 5008 | AAAAGUGUC UCUGCCUU | 691 | AAGGCAGA CUGAUGA X GAA ACACUUUU | 1514 |
| 5010 | AAGUGUCUC UGCCUUGA | 692 | UCAAGGCA CUGAUGA X GAA AGACACUU | 1515 |
| 5016 | CUCUGCCUU GAGUCAUC | 693 | GAUGACUC CUGAUGA X GAA AGGCAGAG | 1516 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 5021 | CCUUGAGUC AUCUAUUC | 694 | GAAUAGAU CUGAUGA X GAA ACUCAAGG | 1517 |
| 5024 | UGAGUCAUC UAUUCAAG | 695 | CUUGAAUA CUGAUGA X GAA AUGACUCA | 1518 |
| 5026 | AGUCAUCUA UUCAAGCA | 696 | UGCUUGAA CUGAUGA X GAA AGAUGACU | 1519 |
| 5028 | UCAUCUAUU CAAGCACU | 697 | AGUGCUUG CUGAUGA X GAA AUAGAUGA | 1520 |
| 5029 | CAUCUAUUC AAGCACUU | 698 | AAGUGCUU CUGAUGA X GAA AAUAGAUG | 1521 |
| 5037 | CAAGCACUU ACAGCUCU | 699 | AGAGCUGU CUGAUGA X GAA AGUGCUUG | 1522 |
| 5038 | AAGCACUUA CAGCUCUG | 700 | CAGAGCUG CUGAUGA X GAA AAGUGCUU | 1523 |
| 5044 | UUACAGCUC UGGCCACA | 701 | UGUGGCCA CUGAUGA X GAA AGCUCUAA | 1524 |
| 5062 | CAGGGCAUU UUACAGCU | 702 | ACCUGUAA CUGAUGA X GAA AUGCCCUG | 1525 |
| 5063 | AGGGCAUUU UACAGGUG | 703 | CACCUGUA CUGAUGA X GAA AAUGCCCU | 1526 |
| 5064 | GGGCAUUUU ACAGGUGC | 704 | GCACCUGU CUGAUGA X GAA AAAUGCCC | 1527 |
| 5065 | GGCAUUUUA CAGGUGCG | 705 | CGCACCUG CUGAUGA X GAA AAAAUGCC | 1528 |
| 5083 | AUGACAGUA GCAUUAUG | 706 | CAUAAUGC CUGAUGA X GAA ACUGUCAU | 1529 |
| 5088 | AGUAGCAUU AUGAGUAG | 707 | CUACUCAU CUGAUGA X GAA AUGCUACU | 1530 |
| 5089 | GUAGCAUUA UGAGUAGU | 708 | ACUACUCA CUGAUGA X GAA AAUGCUAC | 1531 |
| 5095 | UUAUGAGUA GUGUGAAU | 709 | AUUCACAC CUGAUGA X GAA ACUCAUAA | 1532 |
| 5104 | GUGUGAAUU CAGGUAGU | 710 | ACUACCUG CUGAUGA X GAA AUUCACAC | 1533 |
| 5105 | UGUGAAUUC AGGUAGUA | 711 | UACUACCU CUGAUGA X GAA AAUUCACA | 1534 |
| 5110 | AUUCAGGUA GUAAAUAU | 712 | AUAUUUAC CUGAUGA X GAA ACCUGAAU | 1535 |
| 5113 | CAGGUAGUA AAUAUGAA | 713 | UUCAUAUU CUGAUGA X GAA ACUACCUG | 1536 |
| 5117 | UAGUAAAUA UGAAACUA | 714 | UAGUUUCA CUGAUGA X GAA AUUUACUA | 1537 |
| 5125 | AUGAAACUA GGGUUUGA | 715 | UCAAACCC CUGAUGA X GAA AGUUUCAU | 1538 |
| 5130 | ACUAGGGUU UGAAAUUG | 716 | CAAUUUCA CUGAUGA X GAA ACCCUAGU | 1539 |
| 5131 | CUAGGGUUU GAAAUUGA | 717 | UGAAUUUC CUGAUGA X GAA AACCCUAG | 1540 |
| 5137 | UUUGAAAUU GAUAAUGC | 718 | GCAUUAUC CUGAUGA X GAA AUUUCAAA | 1541 |
| 5141 | AAAUUGAUA AUGCUUUC | 719 | GAAAGCAU CUGAUGA X GAA AUCAAUUU | 1542 |
| 5147 | AUAAUGCUU UCACAACA | 720 | UGUUGUGA CUGAUGA X GAA AGCAUUAU | 1543 |
| 7775148 | UAAUGCUUU CACAACAU | 721 | AUGUUGUG CUGAUGA X GAA AAGCAUUA | 1544 |
| 5149 | AAUGCUUUC ACAACAUU | 722 | AAUGUUGU CUGAUGA X GAA AAAGCAUU | 1545 |
| 5157 | CACAACAUU UGCAGAUG | 723 | CAUCUGCA CUGAUGA X GAA AUGUUGUG | 1546 |
| 5158 | ACAACAUUU GCAGAUGU | 724 | ACAUCUGC CUGAUGA X GAA AAUGUUGU | 1547 |
| 5167 | GCAGAUGUU UUAGAAGG | 725 | CCUUCUAA CUGAUGA X GAA ACAUCUGC | 1548 |
| 5168 | CAGAUGUUU UAGAAGGA | 726 | UCCUUCUA CUGAUGA X GAA AACAUCUG | 1549 |
| 5169 | AGAUGUUUU AGAAGGAA | 727 | UUCCUUCU CUGAUGA X GAA AAACAUCU | 1550 |
| 5170 | GAUGUUUUA GAAGGAAA | 728 | UUUCCUUC CUGAUGA X GAA AAAACAUC | 1551 |
| 5184 | AAAAAGUU CCUUCCUA | 729 | UAGGAAGG CUCAUGA X GAA ACUUUUUU | 1552 |
| 5185 | AAAAGUUC CUUCCUAA | 730 | UUAGGAAG CUGAUGA X GAA AACUUUUU | 1553 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 5188 | AAGUUCCUU CCUAAAAU | 731 | AUUUUAGG CUGAUGA X GAA AGGAACUU | 1554 |
| 5189 | AGUUCCUUC CUAAAAUA | 732 | UAUUUUAG CUGAUGA X GAA AAGGAACU | 1555 |
| 5192 | UCCUUCCUA AAAUAAUU | 733 | AAUUAUUU CUGAUGA X GAA AGGAAGGA | 1556 |
| 5197 | CCUAAAAUA AUUUCUCU | 734 | AGAGAAAU CUGAUGA X GAA AUUUUAGG | 1557 |
| 5200 | AAAAUAAUU UCUCUACA | 735 | UGUAGAGA CUGAUGA X GAA AUUAUUUU | 1558 |
| 5201 | AAAUAAUUU CUCUACAA | 736 | UUGUAGAG CUGAUGA X GAA AAUUAUUU | 1559 |
| 5202 | AAUAAUUUC UCUACAAU | 737 | AUUGUAGA CUGAUGA X GAA AAAUUAUU | 1560 |
| 5204 | UAAUUUCUC UACAAUUG | 738 | CAAUUGUA CUGAUGA X GAA AGAAAUUA | 1561 |
| 5206 | AUUUCUCUA CAAUUGGA | 739 | UCCAAUUG CUGAUGA X GAA AGAGAAAU | 1562 |
| 5211 | UCUACAAUU GGAAGAUU | 740 | AAUCUUCC CUGAUGA X GAA AUUGUAGA | 1563 |
| 5219 | UGGAAGAUU GGAAGAUU | 741 | AAUCUUCC CUGAUGA X GAA AUCUUCCA | 1564 |
| 5227 | UGGAAGAUU CAGCUAGU | 742 | ACUAGCUG CUGAUGA X GAA AUCUUCCA | 1565 |
| 5228 | GGAAGAUUC AGCUAUUU | 743 | AACUAGCU CUGAUGA X GAA AAUCUUCC | 1566 |
| 5233 | AUUCAGCUA GUUAGGAG | 744 | CUCCUAAC CUGAUGA X GAA AGCUGAAU | 1567 |
| 5236 | CAGCUAGUU AGGAGCCC | 745 | GGGCUCCU CUGAUGA X GAA ACUAGCUG | 1568 |
| 5237 | AGCUAGUUA GGAGCCCA | 746 | UGGGCUCC CUGAUGA X GAA AACUAGCU | 1569 |
| 5247 | GAGCCCAUU UUUCCUA | 747 | UAGGAAAA CUGAUGA X GAA AUGGGCUC | 1570 |
| 5248 | AGCCCAUUU UUUCCUAA | 748 | UUAGGAAA CUGAUGA X GAA AAUGGGCU | 1571 |
| 5249 | GCCCAUUUU UUCCUAAU | 749 | AUUAGGAA CUGAUGA X GAA AAAUGGGC | 1572 |
| 5250 | CCCAUUUUU UCCUAAUC | 750 | GAUUAGGA CUGAUGA X GAA AAAAUGGG | 1573 |
| 5251 | CCAUUUUUU CCUAAUCU | 751 | AGAUUAGG CUGAUGA X GAA AAAAAUGG | 1574 |
| 5252 | CAUUUUUUC CUAAUCUG | 752 | CAGAUUAG CUGAUGA X GAA AAAAAAUG | 1575 |
| 5255 | UUUUUCCUA AUCUGUGU | 753 | ACACAGAU CUGAUGA X GAA AGGAAAAA | 1576 |
| 5258 | UUCCUAAUC UGUGUGUG | 754 | CACACACA CUGAUGA X GAA AUUAGGAA | 1577 |
| 5273 | UGCCCUGUA ACCUGACU | 755 | AGUCAGGU CUGAUGA X GAA ACAGGGCA | 1578 |
| 5285 | UGACUGGUU AACAGCAG | 756 | CUGCUGUU CUGAUGA X GAA ACCAGUCA | 1579 |
| 5286 | GACUGGUUA ACAGCAGU | 757 | ACUGCUGU CUGAUGA X GAA AACCAGUC | 1580 |
| 5295 | ACAGCAGUC CUUUGUAA | 758 | UUACAAAG CUGAUGA X GAA ACUGCUGU | 1581 |
| 5298 | GCAGUCCUU UGUAAACA | 759 | UGUUUACA CUGAUGA X GAA AGGACUGC | 1582 |
| 5299 | CAGUCCUUU GUAAACAG | 760 | CUGUUUAC CUGAUGA X GAA AAGGACUG | 1583 |
| 5302 | UCCUUUGUA AACAGUGU | 761 | ACACUGUU CUGAUGA X GAA ACAAAGGA | 1584 |
| 5311 | AACAGUGUU UUAAACUC | 762 | GAGUUUAA CUGAUGA X GAA ACACUGUU | 1585 |
| 5312 | ACAGUGUUU UAAACUCU | 763 | AGAGUUUA CUGAUGA X GAA AACACUGU | 1586 |
| 5313 | CAGUGUUUU AAACUCUC | 764 | GAGACUUU CUGAUGA X GAA AAACACUG | 1587 |
| 5314 | AGUGUUUUA AACUCUCC | 765 | GGAGAGUU CUGAUGA X GAA AAAACACU | 1588 |
| 5319 | UUUAAACUC UCCUAGUC | 766 | GACUAGGA CUGAUGA X GAA AGUUUAAA | 1589 |
| 5321 | UAAACUCUC CUAGUCAA | 767 | UUGACUAG CUGAUGA X GAA AGAGUUUA | 1590 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 5324 | ACUCUCCUA GUCAAUAU | 768 | AUAUUGAC CUGAUGA X GAA AGGAGAGU | 1591 |
| 5327 | CUCCUAGUC AAUAUCCA | 769 | UGGAUAUU CUGAUGA X GAA ACUAGGAG | 1592 |
| 5331 | UAGUCAAUA UCCACCCC | 770 | GGGGUGGA CUGAUGA X GAA AUUGACUA | 1593 |
| 5333 | GUCAAUAUC CACCCCAU | 771 | AUGGGGUG CUGAUGA X GAA AUAUUGAC | 1594 |
| 5342 | CACCCCAUC CAAUUUAU | 772 | AUAAAUUG CUGAUGA X GAA AUGGGGUG | 1595 |
| 5347 | CAUCCAAUU UAUCAAGG | 773 | CCUUGAUA CUGAUGA X GAA AUUGGAUG | 1596 |
| 5348 | AUCCAAUUU AUCAAGGA | 774 | UCCUUGAU CUGAUGA X GAA AAUUGGAU | 1597 |
| 5349 | UCCAAUUUA UCAAGGAA | 775 | UUCCUUGA CUGAUGA X GAA AAAUUGGA | 1598 |
| 5351 | CAAUUUAUC AAGGAAGA | 776 | UCUUCCUU CUGAUGA X GAA AUAAAUUG | 1599 |
| 5366 | GAAAUGGUU CAGAAAAU | 777 | AUUUUCUG CUGAUGA X GAA ACCAUUUC | 1600 |
| 5367 | AAAUGGUUC AGAAAAUA | 778 | UAUUUUCU CUGAUGA X GAA AACCAUUU | 1601 |
| 5375 | CAGAAAAUA UUUUCAGC | 779 | GCUGAAAA CUGAUGA X GAA AUUUUCUG | 1602 |
| 5377 | GAAAAUAUU UUCAGCCU | 780 | AGGCUGAA CUGAUGA X GAA AUAUUUUC | 1603 |
| 5378 | AAAAUAUUU UCAGCCUA | 781 | UAGGCUGA CUGAUGA X GAA AAUAUUUU | 1604 |
| 5379 | AAAUAUUUU CAGCCUAC | 782 | GUAGGCUG CUGAUGA X GAA AAAUAUUU | 1605 |
| 5380 | AAUAUUUUC AGCCUACA | 783 | UGUAGGCU CUGAUGA X GAA AAAAUAUU | 1606 |
| 5386 | UUCAGCCUA CAGUUAUG | 784 | CAUAACUG CUGAUGA X GAA AGGCUGAA | 1607 |
| 5391 | CCUACAGUU AUGUUCAG | 785 | CUGAACAU CUGAUGA X GAA ACUGUAGG | 1608 |
| 5392 | CUACAGUUA UGUUCAGU | 786 | ACUGAACA CUGAUGA X GAA AACUGUAG | 1609 |
| 5396 | AGUUAUGUU CAGUCACA | 787 | UGUGACUG CUGAUGA X GAA ACAUAACU | 1610 |
| 5397 | GUUAUGUUC AGUCACAC | 788 | GUGUGACU CUGAUGA X GAA AACAUAAC | 1611 |
| 5401 | UGUUCAGUC ACACACAC | 789 | GUGUGUGU CUGAUGA X GAA ACUGAACA | 1612 |
| 5412 | ACACACAUA CAAAAUGU | 790 | ACAUUUUG CUGAUGA X GAA AUGUCUGU | 1613 |
| 5421 | CAAAAUGUU CCUUUUGC | 791 | GCAAAAGG CUGAUGA X GAA ACAUUUUG | 1614 |
| 5422 | AAAAUGUUC CUUUUGCU | 792 | AGCAAAAG CUGAUGA X GAA AACAUUUU | 1615 |
| 5425 | AUGUUCCUU UUGCUUUU | 793 | AAAAGCAA CUGAUGA X GAA AGGAACAU | 1616 |
| 5426 | UGUUCCUUU UGCUUUUA | 794 | UAAAAGCA CUGAUGA X GAA AAGGAACA | 1617 |
| 5427 | GUUCCUUUU GCUUUUAA | 795 | UUAAAAGC CUGAUGA X GAA AAAGGAAC | 1618 |
| 5431 | CUUUUGCUU UAAAGUA | 796 | UACUUUAA CUGAUGA X GAA AGCAAAAG | 1619 |
| 5432 | UUUUGCUUU AAAGUAA | 797 | UUACUUUA CUGAUGA X GAA AAGCAAAA | 1620 |
| 5433 | UUUGCUUUU AAAGUAAU | 798 | AUUACUUU CUGAUGA X GAA AAAGCAAA | 1621 |
| 5434 | UUGCUUUUA AAGUAAUU | 799 | AAUUACUU CUGAUGA X GAA AAAAGCAA | 1622 |
| 5439 | UUUAAAGUA AUUUUUGA | 800 | UCAAAAAU CUGAUGA X GAA ACUUUAAA | 1623 |
| 5442 | AAGUAAUU UUUGACUC | 801 | GAGUCAAA CUGAUGA X GAA AUUACUUU | 1624 |
| 5443 | AAGUAAUUU UUGACUCC | 802 | GGAGUCAA CUGAUGA X GAA AAUUACUU | 1625 |
| 5444 | AGUAAUUUU UGACUCCC | 803 | GGGAGUCA CUGAUGA X GAA AAAUUACU | 1626 |
| 5445 | GUAAUUUUU GACUCCCA | 804 | UGGGAGUC CUGAUGA X GAA AAAAUUAC | 1627 |

TABLE III-continued

Human EGF-R Hammerhead Ribozyme and Target Sequences

| nt. Position | Substrate | Seq. ID NOs. | Ribozyme | Seq. ID NOs. |
|---|---|---|---|---|
| 5450 | UUUUGACUC CCAGAUCA | 805 | UGAUCUGG CUGAUGA X GAA AGUCAAAA | 1628 |
| 5457 | UCCCAGAUC AGUCAGAG | 806 | CUCUGACU CUGAUGA X GAA AUCUGGGA | 1629 |
| 5461 | AGAUCAGUC AGAGCCCC | 807 | GGGGCUCU CUGAUGA X GAA ACUGAUCU | 1630 |
| 5471 | GAGCCCCUA CACCAUUG | 808 | CAAUGCUG CUGAUGA X GAA AGGGGCUC | 1631 |
| 5478 | UACAGCAUU GUUAAGAA | 809 | UUCUUAAC CUGAUGA X GAA AUGCUGUA | 1632 |
| 5481 | AGCAUUGUU AAGAAAGU | 810 | ACUUUCUU CUGAUGA X GAA ACAAUGCU | 1633 |
| 5482 | GCAUUGUUA AGAAAGUA | 811 | UACUUUCU CUGAUGA X GAA AACAAUGC | 1634 |
| 5490 | AAGAAAGUA UUUGAUUU | 812 | AAAUCAAA CUGAUGA X GAA ACUUUCUU | 1635 |
| 5492 | GAAAGUAUU UGAUUUUU | 813 | AAAAAUCA CUGAUGA X GAA AUACUUUC | 1636 |
| 5493 | AAAGUAUUU GAUUUUUG | 814 | CAAAAAUC CUGAUGA X GAA AAUACUUU | 1637 |
| 5497 | UAUUUGAUU UUUGUCUC | 815 | GAGACAAA CUGAUGA X GAA AUCAAAUA | 1638 |
| 5498 | AUUUGAUUU UUGUCUCA | 816 | UGAGACAA CUGAUGA X GAA AAUCAAAU | 1639 |
| 5499 | UUUGAUUUU UGUCUCAA | 817 | UUGAGACA CUGAUGA X GAA AAAUGAAA | 1640 |
| 5500 | UUGAUUUUU GUCUCAAU | 818 | AUUGAGAC CUGAUGA X GAA AAAAUCAA | 1641 |
| 5503 | AUUUUUGUC UCAAUGAA | 819 | UUCAUUGA CUGAUGA X GAA ACAAAAAU | 1642 |
| 5505 | UUUUGUCUC AAUGAAAA | 820 | UUUUCAUU CUGAUGA X GAA AGACAAAA | 1643 |
| 5515 | AUGAAAAUA AAACUAUA | 821 | UAUAGUUU CUGAUGA X GAA AUUUUCAU | 1644 |
| 5521 | AUAAAACUA UAUUCAUU | 822 | AAUGAAUA CUGAUGA X GAA AGUUUUAU | 1645 |
| 5523 | AAAACUAUA UUCAUUUC | 823 | GAAAUGAA CUGAUGA X GAA AUAGUUUU | 1646 |

Where "X" represents stem II region of a HH ribozyme (Hertel et al., 1992 Nucleic Acids Res. 20 3252). The length of stem II may be ≥ 2 base-pairs.

TABLE IV

Human EGF-R Hairpin Ribozyme and Target Sequence

| nt. Position | Ribozyine | Seq. ID NOs. | Substrate | Seq. ID NOs. |
|---|---|---|---|---|
| 38 | GGCGGC AGAA GCGC ACCAGAGAAACACACGUUGUGGUACAUUACCUGGUA | 1647 | GCGCC GCC GCCGCC | 1759 |
| 41 | CUGGGC AGAA GCGG ACCAGAGAAACACACGUUGUGGUACAUUACCUGGUA | 1648 | CCGCC GCC GCCCAG | 1760 |
| 44 | GGUCUG AGAA GCGG ACCAGAGAAACACACGUUGUGGUACAUUACCUGGUA | 1649 | CCGCC GCC CAGACC | 1761 |
| 49 | CGUCCG AGAA GGGC ACCAGAGAAACACACGUUGUGGUACAUUACCUGGUA | 1650 | GCCCA GAC CGGACG | 1762 |
| 54 | CCUGUC AGAA GGUC ACCAGAGAAACACACGUUGUGGUACAUUACCUGGUA | 1651 | GACCG GAC GACAGG | 1763 |
| 80 | GACUCG AGAA GACG ACCAGAGAAACACACGUUGUGGUACAUUACCUGGUA | 1652 | CGUCC GCC CGAGUC | 1764 |
| 92 | CGGCGA AGAA GGGA ACCAGAGAAACACACGUUGUGGUACAUUACCUGGUA | 1653 | UCCCC GCC UCGCCG | 1765 |
| 125 | UCAGGG AGAA GUGC ACCAGAGAAACACACGUUGUGGUACAUUACCUGGUA | 1654 | GCACG GCC CCCUGA | 1766 |
| 132 | GACGGA AGAA GGGG ACCAGAGAAACACACGUUGUGGUACAUUACCUGGUA | 1655 | CCCCU GAC UCCGUC | 1767 |
| 138 | AUACUG AGAA GAGU ACCAGAGAAACACACGUUGUGGUACAUUACCUGGUA | 1656 | ACUCC GUC CAGUAU | 1768 |
| 204 | UGCCCC AGAA GUCC ACCAGAGAAACACACGUUGUGGUACAUUACCUGGUA | 1657 | GGACG GCC GGGGCA | 1769 |
| 227 | GCAGCC AGAA GCGC ACCAGAGAAACACACGUUGUGGUACAUUACCUGGUA | 1658 | GCGCU GCU GGCUGC | 1770 |
| 241 | UCGCCC AGAA GAGC ACCAGAGAAACACACGUUGUGGUACAUUACCUGGUA | 1659 | GCUCU GCC CGGCCA | 1771 |
| 305 | GUGCCC AGAA GCGU ACCAGAGAAACACACGUUGUGGUACAUUACCUGGUA | 1660 | ACGCA GUU GGGCAC | 1772 |
| 334 | UCUGGA AGAA GAGA ACCAGAGAAACACACGUUGUGGUACAUUACCUGGUA | 1661 | UCUCA GCC UCCAGA | 1773 |
| 500 | CUGAUG AGAA GCAG ACCAGAGAAACACACGUUGUGGUACAUUACCUGGUA | 1662 | CUGCA GAU CAUCAG | 1774 |
| 546 | AGAUAA AGAA GCUA ACCAGAGAAACACACGUUGUGGUACAUUACCUGGUA | 1663 | UAGCA GUC UUAUCU | 1775 |
| 577 | CCUUCA AGAA GGUU ACCAGAGAAACACACGUUGUGGUACAUUACCUGGUA | 1664 | AACCG GAC UGAAGG | 1776 |
| 590 | CUCAUG AGAA GCUC ACCAGAGAAACACACGUUGUGGUACAUUACCUGGUA | 1665 | GAGCU GCC CAUGAG | 1777 |
| 632 | UUGCUG AGAA GCAC ACCAGAGAAACACACGUUGUGGUACAUUACCUGGUA | 1666 | GUGCG GUU CAGCAA | 1778 |
| 648 | GCACAG AGAA GGGU ACCAGAGAAACACACGUUGUGGUACAUUACCUGGUA | 1667 | ACCCU GCC CUGUGC | 1779 |
| 742 | UUUGGC AGAA GCCC ACCAGAGAAACACACGUUGUGGUACAUUACCUGGUA | 1668 | GGGCA GCU GCCAAA | 1780 |
| 766 | CAUUGG AGAA GCUU ACCAGAGAAACACACGUUGUGGUACAUUACCUGGUA | 1669 | AAGCU GUC CCAAUG | 1781 |

TABLE IV-continued

Human EGF-R Hairpin Ribozyme and Target Sequence

| nt. Position | Ribozyme | Seq. ID NOs. | Substrate | Seq. ID NOs. |
|---|---|---|---|---|
| 781 | CACCCC AGAA GCUC ACCAGAGAAACACACGUUGUGGUACAUUACCUGGUA | 1670 | GAGCU GCU GGGGUG | 1782 |
| 815 | AUUUUG AGAA GUUU ACCAGAGAAACACACGUUGUGGUACAUUACCUGGUA | 1671 | AAACU GAC CAAAAU | 1783 |
| 853 | UGCCAC AGAA GCGC ACCAGAGAAACACACGUUGUGGUACAUUACCUGGUA | 1672 | GCGCU GCC GUGGCA | 1784 |
| 877 | UGUGGC AGAA GUCA ACCAGAGAAACACACGUUGUGGUACAUUACCUGGUA | 1673 | UGACU GCU GCCACA | 1785 |
| 928 | AGACCA AGAA GUCG ACCAGAGAAACACACGUUGUGGUACAUUACCUGGUA | 1674 | CGACU GCC UGGUCU | 1786 |
| 937 | AUUUGC AGAA GACC ACCAGAGAAACACACGUUGUGGUACAUUACCUGGUA | 1675 | GGUCU GCC GCAAAU | 1787 |
| 976 | GUGGGG AGAA GGUG ACCAGAGAAACACACGUUGUGGUACAUUACCUGGUA | 1676 | CACCU GCC CCCCAC | 1788 |
| 1013 | ACAUCC AGAA GGUA ACCAGAGAAACACACGUUGUGGUACAUUACCUGGUA | 1677 | UACCA GAU GGAUGU | 1789 |
| 1042 | CACCAA AGAA GUAU ACCAGAGAAACACACGUUGUGGUACAUUACCUGGUA | 1678 | AUACA GCU UUGGUG | 1790 |
| 1092 | GCCGUG AGAA GUCA ACCAGAGAAACACACGUUGUGGUACAUUACCUGGUA | 1679 | UGACA GAU CACGGC | 1791 |
| 1099 | CGCACG AGAA GUGA ACCAGAGAAACACACGUUGUGGUACAUUACCUGGUA | 1680 | UCACG GCU CGUGCG | 1792 |
| 1301 | GCCACC AGAA GGAU ACCAGAGAAACACACGUUGUGGUACAUUACCUGGUA | 1681 | AUCCU GCC GGUGGC | 1793 |
| 1403 | GCCUGA AGAA GCAA ACCAGAGAAACACACGUUGUGGUACAUUACCUGGUA | 1682 | UUGCU GAU UCAGGC | 1794 |
| 1431 | AUGGAG AGAA GUCC ACCAGAGAAACACACGUUGUGGUACAUUACCUGGUA | 1683 | GGACG GAC CUCCAU | 1795 |
| 1490 | AGAGAA AGAA GACC ACCAGAGAAACACACGUUGUGGUACAUUACCUGGUA | 1684 | GGUCA GUU UUCUCU | 1796 |
| 1503 | GCUGAC AGAA GCAA ACCAGAGAAACACACGUUGUGGUACAUUACCUGGUA | 1685 | UUGCA GUC GUCAGC | 1797 |
| 1510 | UGUUCA AGAA GACG ACCAGAGAAACACACGUUGUGGUACAUUACCUGGUA | 1686 | CGUCA GCC UGAACA | 1798 |
| 1625 | GUCCCA AGAA GUUU ACCAGAGAAACACACGUUGUGGUACAUUACCUGGUA | 1687 | AAACU GUU UGGGAC | 1799 |
| 1678 | CCUUGC AGAA GUUU ACCAGAGAAACACACGUUGUGGUACAUUACCUGGUA | 1688 | AAACA GCU GCAAGG | 1800 |
| 1729 | GGCCCC AGAA GCCC ACCAGAGAAACACACGUUGUGGUACAUUACCUGGUA | 1689 | GGGCU GCU GGGGCC | 1801 |
| 1774 | UGCCUC AGAA GACA ACCAGAGAAACACACGUUGUGGUACAUUACCUGGUA | 1690 | UGUCA GCC GAGGCA | 1802 |
| 1874 | GCCUGA AGAA GGCA ACCAGAGAAACACACGUUGUGGUACAUUACCUGGUA | 1691 | UGCCU GCC UCAGGC | 1803 |
| 1948 | AGUGGG AGAA GUCA ACCAGAGAAACACACGUUGUGGUACAUUACCUGGUA | 1692 | UGACG GCC CCCACU | 1804 |
| 1969 | CUGCCG AGAA GGUC ACCAGAGAAACACACGUUGUGGUACAUUACCUGGUA | 1693 | GACCU GCC CGGCAG | 1805 |
| 2019 | GCCGGC AGAA GCGU ACCAGAGAAACACACGUUGUGGUACAUUACCUGGUA | 1694 | ACGCA GAC GCCGGC | 1806 |
| 2065 | CAGUGC AGAA GUAG ACCAGAGAAACACACGUUGUGGUACAUUACCUGGUA | 1695 | CUACG GAU GCACUG | 1807 |
| 2092 | UCGUUG AGAA GCCU ACCAGAGAAACACACGUUGUGGUACAUUACCUGGUA | 1696 | AGGCU GUC CAACGA | 1808 |
| 2117 | GCGAUG AGAA GGAU ACCAGAGAAACACACGUUGUGGUACAUUACCUGGUA | 1697 | AUCCC GUC CAUCGC | 1809 |
| 2156 | ACCACC AGAA GCAA ACCAGAGAAACACACGUUGUGGUACAUUACCUGGUA | 1698 | UUGCU GCU GGUGGU | 1810 |
| 2179 | UGAAGA AGAA GAUC ACCAGAGAAACACACGUUGUGGUACAUUACCUGGUA | 1699 | GAUCG GCC UCUUCA | 1811 |
| 2231 | UCCUGC AGAA GCCU ACCAGAGAAACACACGUUGUGGUACAUUACCUGGUA | 1700 | AGGCU GCU CAGGA | 1812 |
| 2409 | GAUAGC AGAA GGAA ACCAGAGAAACACACGUUGUGGUACAUUACCUGGUA | 1701 | UUCCC GUC GCUAUC | 1813 |
| 2512 | CCAGCA AGAA GCAC ACCAGAGAAACACACGUUGUGGUACAUUACCUGGUA | 1702 | GUGCC GCC UGCUGG | 1814 |
| 2516 | AUGCCC AGAA GGCG ACCAGAGAAACACACGUUGUGGUACAUUACCUGGUA | 1703 | CGCCU GCU GGGCAU | 1815 |
| 2527 | AGGUGA AGAA GCCU ACCAGAGAAACACACGUUGUGGUACAUUACCUGGUA | 1704 | CAUCU GCC UCACCU | 1816 |
| 2558 | GGCAUG AGAA GCGU ACCAGAGAAACACACGUUGUGGUACAUUACCUGGUA | 1705 | ACGCA GCU CAUGCC | 1817 |
| 2572 | GGAGGC AGAA GAAG ACCAGAGAAACACACGUUGUGGUACAUUACCUGGUA | 1706 | CUUCG GCU GCCUCC | 1818 |
| 2575 | CCAGGA AGAA GCCG ACCAGAGAAACACACGUUGUGGUACAUUACCUGGUA | 1707 | CGGCU GCC UCCUGG | 1819 |
| 2627 | CAGUUG AGAA GGUA ACCAGAGAAACACACGUUGUGGUACAUUACCUGGUA | 1708 | UACCU GCU CAACUG | 1820 |
| 2645 | UUUGCG AGAA GCAC ACCAGAGAAACACACGUUGUGGUACAUUACCUGGUA | 1709 | GUGCA GAU CGCAAA | 1821 |
| 2677 | CCAAGC AGAA GUCC ACCAGAGAAACACACGUUGUGGUACAUUACCUGGUA | 1710 | GGACC GUC GCUUGG | 1822 |
| 2748 | CCCAAA AGAA GUGA ACCAGAGAAACACACGUUGUGGUACAUUACCUGGUA | 1711 | UCACA GAU UUUGGG | 1823 |
| 2768 | GCACCC AGAA GUUU ACCAGAGAAACACACGUUGUGGUACAUUACCUGGUA | 1712 | AAACU GCU GGGUGC | 1824 |
| 2895 | CUCCCA AGAA GUCA ACCAGAGAAACACACGUUGUGGUACAUUACCUGGUA | 1713 | UGACC GUU UGGGAG | 1825 |
| 3165 | GUUGGA AGAA GUAG ACCAGAGAAACACACGUUGUGGUACAUUACCUGGUA | 1714 | CUACA GAC UCCAAC | 1826 |
| 3188 | UCAUCC AGAA GGGC ACCAGAGAAACACACGUUGUGGUACAUUACCUGGUA | 1715 | GCCCU GAU GGAUGA | 1827 |
| 3225 | GUACUC AGAA GCAU ACCAGAGAAACACACGUUGUGGUACAUUACCUGGUA | 1716 | AUGCC GAC GAGUAC | 1828 |
| 3262 | UGGAGG AGAA GCUG ACCAGAGAAACACACGUUGUGGUACAUUACCUGGUA | 1717 | CAGCA GCC CCUCCA | 1829 |
| 3278 | AGGGGA AGAA GUGA ACCAGAGAAACACACGUUGUGGUACAUUACCUGGUA | 1718 | UCACG GAC UCCCCU | 1830 |
| 3358 | UGAUGG AGAA GCUU ACCAGAQAAACACGUUGUGGUACAUUACCUGGUA | 1719 | AAGCU GUC CCAUCA | 1831 |
| 3376 | GCAAGA AGAA GUCU ACCAGAGAAACACACGUUGUGGUACAUUACCUGGUA | 1720 | AGACA GCU UCUUGC | 1832 |
| 3394 | GGUCUG AGAA GUAU ACCAGAGAAACACACGUUGUGGUACAUUACCUGGUA | 1721 | AUACA GCU CAGACC | 1833 |
| 3399 | UGUGGG AGAA GAGC ACCAGAGAAACACACGUUGUGGUACAUUACCUGGUA | 1722 | GCUCA GAC CCCACA | 1834 |
| 3470 | GGAACG AGAA GGUU ACCAGAGAAACACACGUUGUGGUACAUUACCUGGUA | 1723 | AACCA GUC CGUUCC | 1835 |
| 3474 | UUUGGG AGAA GACU ACCAGAGAAACACACGUUGUGGUACAUUACCUGGUA | 1724 | AGUCC GUU CCCAAA | 1836 |
| 3489 | AGAGCC AGAA GGCC ACCAGAGAAACACACGUUGUGGUACAUUACCUGGUA | 1725 | GGCCC GCU GGCUCU | 1837 |
| 3510 | GUGAUA AGAA GGAU ACCAGAGAAACACACGUUGUGGUACAUUACCUGGUA | 1726 | AUCCU GUC UAUCAC | 1838 |
| 3524 | UUCAGA AGAA GAUU ACCAGAGAAACACACGUUGUGGUACAUUACCUGGUA | 1727 | AAUCA GCU UCUGAA | 1839 |
| 3609 | GGGCUG AGAA GUGU ACCAGAGAAACACACGUUGUGGUACAUUACCUGGUA | 1728 | ACACU GUC CAGCCC | 1840 |
| 3614 | CAGGUG AGAA GGAC ACCAGAGAAACACACGUUGUGGUACAUUACCUGGUA | 1729 | GUCCA GCC CACCUG | 1841 |
| 3643 | GGGCAG AGAA GUCG ACCAGAGAAACACACGUUGUGGUACAUUACCUGGUA | 1730 | CGACA GCC CUGCCC | 1842 |
| 3648 | CCAGUG AGAA GGGC ACCAGAGAAACACACGUUGUGGUACAUUACCUGGUA | 1731 | GCCCU GCC CACUGG | 1843 |
| 3696 | CUGGUA AGAA GGGU ACCAGAGAAACACACGUUGUGGUACAUUACCUGGUA | 1732 | ACCCU GAC UACCAG | 1844 |
| 3759 | AUUUUC AGAA GUGG ACCAGAGAAACACACGUUGUGGUACAUUACCUGGUA | 1733 | CCACA GCU GAAAAU | 1845 |
| 3851 | GAAAGA AGAA GGAU ACCAGAGAAACACACGUUGUGGUACAUUACCUGGUA | 1734 | AUCCA GUC UCUUUC | 1846 |
| 3931 | AAACCA AGAA GUGG ACCAGAGAAACACACGUUGUGGUACAUUACCUGGUA | 1735 | CCACA GAC UGGUUU | 1847 |
| 3955 | UGGCUA AGAA GUGU ACCAGAGAAACACACGUUGUGGUACAUUACCUGGUA | 1736 | ACACC GAC UAGCCA | 1848 |
| 4310 | CCUUGA AGAA GAAC ACCAGAGAAACACACGUUGUGGUACAUUACCUGGUA | 1737 | GUUCU GCU UCAAGG | 1849 |
| 4374 | GUACCG AGAA GGCC ACCAGAGAAACACACGUUGUGGUACAUUACCUGGUA | 1738 | GGCCG GAU CGGUAC | 1850 |
| 4423 | GGAAGG AGAA GAGU ACCAGAGAAACACACGUUGUGGUACAUUACCUGGUA | 1739 | ACUCU GUC CCUUCC | 1851 |
| 4514 | UGGUCC AGAA GUGG ACCAGAGAAACACACGUUGUGGUACAUUACCUGGUA | 1740 | CCACU GAU GGACCA | 1852 |
| 4550 | AAACAA AGAA GUCU ACCAGAGAAACACACGUUGUGGUACAUUACCUGGUA | 1741 | AGACU GAC UUGUUU | 1853 |
| 4594 | GACAGG AGAA GCAU ACCAGAGAAACACACGUUGUGGUACAUUACCUGGUA | 1742 | AUGCC GCC CCUGUC | 1854 |
| 4600 | CAGCAA AGAA GGGG ACCAGAGAAACACACGUUGUGGUACAUUACCUGGUA | 1743 | CCCCU GUC UUGCUG | 1855 |

TABLE IV-continued

Human EGF-R Hairpin Ribozyme and Target Sequence

| nt. Position | Ribozyme | Seq. ID NOs. | Substrate | Seq. ID NOs. |
|---|---|---|---|---|
| 4653 | GCUGGA AGAA GAGU ACCAGAGAAACACACGUUGUGGUACAUUACCUGGUA | 1744 | ACUCG GAU UCCAGC | 1856 |
| 4660 | AAUGUG AGAA GGAA ACCAGAGAAACACACGUUGUGGUACAUUACCUGGUA | 1745 | UUCCA GCC CACAUU | 1857 |
| 4701 | AUUCUC AGAA GUGG ACCAGAGAAACACACGUUGUGGUACAUUACCUGGUA | 1746 | CCACA GCU CAGAAU | 1858 |
| 4733 | AACAAA AGAA GUGU ACCAGAGAAACACACGUUGUGGUACAUUACCUGGUA | 1747 | ACACC GCU UUUGUU | 1859 |
| 4775 | CAUUUC AGAA GAGC ACCAGAGAAACACACGUUGUGGUACAUUACCUGGUA | 1748 | GCUCA GAU GAAAUG | 1860 |
| 4831 | UUUCAG AGAA GCUU ACCAGAGAAACACACGUUGUGGUACAUUACCUGGUA | 1749 | AAGCU GCU CUGAAA | 1861 |
| 4962 | GGGGGC AGAA GACC ACCAGAGAAACACACGUUGUGGUACAUUACCUGGUA | 1750 | GGUCA GCU GCCCCC | 1862 |
| 4965 | UUUGGG AGAA GCUG ACCAGAGAAACACACGUUGUGGUACAUUACCUGGUA | 1751 | CAGCU GCC CCCAAA | 1863 |
| 5011 | ACUCAA AGAA GAGA ACCAGAGAAACACACGUUGUGGUACAUUACCUGGUA | 1752 | UCUCU GCC UUGAGU | 1864 |
| 5040 | GGCCAG AGAA GUAA ACCAGAGAAACACACGUUGUGGUACAUUACCUGGUA | 1753 | UUACA GCU CUGGCC | 1865 |
| 5161 | UAAAAC AGAA GCAA ACCAGAGAAACACACGUUGUGGUACAUUACCUGGUA | 1754 | UUGCA GAU GUUUUA | 1866 |
| 5277 | UAACCA AGAA GGUU ACCAGAGAAACACACGUUGUGGUACAUUACCUGGUA | 1755 | AACCU GAC UGGUUA | 1867 |
| 5292 | ACAAAG AGAA GCUG ACCAGAGAAACACACGUUGUGGUACAUUACCUGGUA | 1756 | CAGCA GUC CUUUGU | 1868 |
| 5381 | ACUGUA AGAA GAAA ACCAGAGAAACACACGUUGUGGUACAUUACCUGGUA | 1757 | UUUCA GCC UACAGU | 1869 |
| 5453 | UGACUG AGAA GGGA ACCAGAGAAACACACGUUGUGGUACAUUACCUGGUA | 1758 | UCCCA GAU CAGUCA | 1870 |

We claim:

1. An enzymatic nucleic acid molecule which specifically cleaves RNA derived from an epidermal growth factor receptor (EGFR) gene encoding an EGFR with a functional extracellular domain and a functional intracellular domain.

2. The enzymatic nucleic acid molecule of claim 1, wherein said nucleic acid molecule is in a hairpin motif.

3. The enzymatic nucleic acid molecule of claim 1, wherein said nucleic acid molecule is in a hammerhead motif.

4. The enzymatic nucleic acid molecule of claim 3, wherein said nucleic acid molecule comprises a stem II region of length greater than or equal to 2 base pairs.

5. The enzymatic nucleic acid molecule of claim 3, wherein the binding arms of said nucleic acid molecule comprises sequences complementary to any of SEQ ID NOs 1–823.

6. The enzymatic nucleic molecule of claim 2, wherein the binding arms of said nucleic acid molecule comprises sequences complementary to any of SEQ ID NOs 1759–1870.

7. The enzymatic nucleic acid molecule of claim 2, wherein said nucleic haipin motif consists essentially of any ribozyme sequence shown as SEQ ID NOs 1647–1758.

8. The enzymatic nucleic molecule of claim 3, wherein said nucleic hammerhead motif consists essentially of any ribozyme sequence shown as SEQ ID NOs 824–1646.

9. The enzymatic nucleic acid molecule of claim 1, wherein said nucleic acid molecule is in a hepatitis delta virus, VS nucleic acid, group I intron, Group II intron, or RNase P nucleic acid motif.

10. The enzymatic nucleic acid molecule of claim 1, wherein said nucleic acid comprises between 12 and 100 bases complementary to said RNA.

11. The enzymatic nucleic acid molecule of claim 1, wherein said nucleic acid comprises between 14 and 24 bases complementary to said mRNA.

12. A mammalian cell including an enzymatic nucleic acid molecule of claim 1, wherein said mammalian cell is not a human.

13. The cell of claim 12, wherein said cell is a human cell.

14. An expression vector comprising nucleic acid sequence encoding at least one of the enzymatic nucleic acid molecule of claim 1, in a manner which allows expression of that enzymatic nucleic acid molecule.

15. A mammalian cell including an expression vector of claim 14, wherein said mammalian cell is not a human.

16. The cell of claim 15, wherein said cell is a human cell.

17. A composition comprising the enzymatic nucleic acid molecule of claim 1.

18. The enzymatic nucleic acid molecule of claim 3, wherein said nucleic acid molecule comprises at least five ribose residues, and wherein said nucleic acid comprises phosphorothioate linkages at at least three of the 5' terminal nucleotides, and wherein said nucleic acid comprises a 2'-C-allyl modification at position No. 4 of said nucleic acid, and wherein said nucleic acid comprises at least ten 2'-O-methyl modifications, and wherein said nucleic acid comprises a 3'- end modification.

19. The enzymatic nucleic acid of claim 18, wherein said nucleic acid comprises a 3'—3' linked inverted ribose moiety at said 3' end.

20. The enzymatic nucleic acid molecule of claim 3, wherein said nucleic acid molecule comprises at least five ribose residues, and wherein said nucleic acid molecule comprises phosphorothioate linkages at at least three of the 5' terminal nucleotides, and wherein said nucleic acid comprises a 2'-amino modification at position No. 4 and/or at position No. 7 of said nucleic acid molcule, wherein said nucleic acid molcule comprises at least ten 2'-O-methyl modifications, and wherein said nucleic acid comprises a 3'-end modification.

21. The enzymatic nucleic acid molecule of claim 3, wherein said nucleic acid molecule comprises at least five ribose residues, and wherein said nucleic acid molecule comprises phosphorothioate linkages at at least three of the 5' terminal nucleotides, and wherein said nucleic acid molecule comprises an abasic substitution at position No. 4 and/or at position No. 7 of said nucleic acid molecule, wherein said nucleic acid comprises at least ten 2'-O-methyl modifications, and wherein said nucleic acid molecule comprises a 3'-end modification.

22. The enzymatic nucleic acid molecule of claim 3, wherein said nucleic acid molecule comprises of at least five ribose residues, and wherein said nucleic acid comprises phosphorothioate linkages at at least three of the 5' terminal nucleotides, and wherein said nucleic acid molecule comprises a 6-methyl uridine substitution at position No. 4 and/or at position No. 7 of said nucleic acid molecule, wherein said nucleic acid molecule comprises at least ten 2'-O-methyl modifications, and wherein said nucleic acid molecule comprises a 3' end modification.

23. An enzymatic nucleic acid molecule which specifically cleaves RNA derived from an epidermal growth factor receptor (EGFR) gene encoding an EGFR which does not contain a deletion in its extracellular domain.

24. The enzymatic nucleic acid molecule of claim 23, wherein said nucleic acid molecule is in a hairpin motif.

25. The enzymatic nucleic acid molecule of claim 23, wherein said nucleic acid molecule is in a hammerhead motif.

26. The enzymatic nucleic acid molecule of claim 25, wherein said nucleic acid molecule comprises a stem II region of length greater than or equal to 2 base pairs.

27. The enzymatic nucleic acid molecule of claim 25, wherein the binding arms of said nucleic acid molecule comprises sequences complementary to any of SEQ ID Nos 1–823.

28. The enzymatic nucleic acid molecule of claim 24, wherein the binding arms of said nucleic acid molecule comprises sequences complementary to any of SEQ ID Nos 1759–1870.

29. The enzymatic nucleic acid molecule of claim 24, wherein said nucleic hairpin motif consists essentially of any ribozyme sequence shown as SEQ ID Nos 1647–1758.

30. The enzymatic nucleic acid molecule of claim 25, wherein said nucleic hammerhead motif consists essentially of any ribozyme sequence shown as SEQ ID Nos 824–1646.

31. The enzymatic nucleic acid molecule of claim 23, wherein said nucleic acid molecule is in a hepatitis delta virus, VS nucleic acid, Group I intron, Group II intron, or Rnase P nucleic acid motif.

32. The enzymatic nucleic acid molecule of claim 23, wherein said nucleic acid comprises between 12 and 100 bases complementary to said RNA.

33. The enzymatic nucleic acid molecule of claim 23, wherein said nucleic acid comprises between 14 and 24 bases complementary to said mRNA.

34. A mammalian cell including an enzymatic nucleic acid molecule of claim 23, wherein said mammalian cell is not a human.

35. The cell of claim 34, wherein said cell is a human cell.

36. An expression vector comprising nucleic acid sequence encoding at least one of the enzymatic nucleic acid molecule of claim 23, in a manner which allows expression of that enzymatic nucleic acid molecule.

37. A mammalian cell including an expression vector of claim 36, wherein said mammalian cell is not a human.

38. The cell of claim 37, wherein said cell is a human cell.

39. The enzymatic nucleic acid molecule of claim 25, wherein said nucleic acid comprises at least five ribose residues, and wherein said nucleic acid comprises phosphorothioate linkages at least three of the 5' terminal nucleotides, and wherein said nucleic acid comprises a 2'-C-ally modification at position No. 4 of said nucleic acid, and wherein said nucleic acid comprises at least ten 2'-O-methyl modifications, and wherein said nucleic acid comprises a 3'-end modification.

40. The enzymatic nucleic acid of claim 39, wherein said nucleic acid comprises a 3'–3' linked inverted ribose moiety at said 3' end.

41. The enzymatic nucleic acid molecule of claim 25, wherein said nucleic acid molecule comprises at least five ribose residues, and wherein said nucleic acid molecule comprises phosphorothioate linkages at least three of the 5' terminal nucleotides, and wherein said nucleic acid comprises 2'-amino modification at position No. 4 and/or at position No. 7 of said nucleic acid molecule, wherein said nucleic acid comprises a 2'-O-methyl modifications, and wherein said nucleic acid comprises a 3'-end modification.

42. The enzymatic nucleic acid molecule of claim 25, wherein said nucleic acid molecule comprises at least five ribose residues, and wherein said nucleic acid molecule comprises phosphorothioate linkages at least three of the 5' terminal nucleotides, and wherein said nucleic acid molecule comprises an abasic substitution at position No. 4 and/or at position No. 7 of said nucleic acid molecule, wherein said nucleic acid comprises at least ten 2'-O-methyl modifications, and wherein said nucleic acid molecule comprises a 3'-end modification.

43. The enzymatic nucleic acid molecule of claim 25, wherein said nucleic acid molecule comprises of at least five ribose residues, and wherein said nucleic acid comprises phosphorothioate linkages at least three of the 5' terminal nucleotides, and wherein said nucleic acid molecule comprises a 6-methyl uridine substitution at position No. 4 and/or position No. 7 of said nucleic acid molecule, wherein said nucleic acid molecule comprises at least ten 2'-O-methyl modifications, and wherein said nucleic acid molecule comprises a 3' end modification.

44. A composition comprising the enzymatic nucleic acid molecule of claim 23.

\* \* \* \* \*